(12) United States Patent
Piven et al.

(10) Patent No.: US 9,315,832 B2
(45) Date of Patent: *Apr. 19, 2016

(54) *CYANOBACTERIUM* SP. HOST CELL AND VECTOR FOR PRODUCTION OF CHEMICAL COMPOUNDS IN CYANOBACTERIAL CULTURES

(71) Applicant: Algenol Biofuels Inc., Ft. Myers, FL (US)

(72) Inventors: Irina Piven, Berlin (DE); Alexandra Friedrich, Berlin (DE); Ulf Dühring, Berlin (DE); Frank Uliczka, Berlin (DE); Kerstin Baier, Kleinmachnow (DE); Masami Inaba, Berlin (DE); Tuo Shi, San Diego, CA (US); Kui Wang, Qingdao (CN); Heike Enke, Berlin (DE); Dan Kramer, Berlin (DE)

(73) Assignee: Algenol Biotech LLC, Fort Myers, FL (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/297,294

(22) Filed: Jun. 5, 2014

(65) Prior Publication Data

US 2015/0017704 A1 Jan. 15, 2015

Related U.S. Application Data

(62) Division of application No. 14/041,122, filed on Sep. 30, 2013, now Pat. No. 8,846,369.

(60) Provisional application No. 61/741,000, filed on Dec. 21, 2012.

(51) Int. Cl.
*C12N 1/20* (2006.01)
*C12N 1/12* (2006.01)
*C12N 9/04* (2006.01)
*C12N 9/88* (2006.01)
*C12N 15/00* (2006.01)
*C12P 7/06* (2006.01)
*C12N 15/74* (2006.01)

(52) U.S. Cl.
CPC ............... *C12P 7/065* (2013.01); *C12N 9/0006* (2013.01); *C12N 9/88* (2013.01); *C12N 15/74* (2013.01); *C12Y 101/01001* (2013.01); *C12Y 401/01001* (2013.01); *Y02E 50/17* (2013.01)

(58) Field of Classification Search
CPC ........ C12N 15/74; C12N 9/0006; C12N 9/88; C12Y 401/01001; C12Y 101/01001; Y02E 50/17; C12P 7/065
USPC .......... 435/252.3, 257.2, 190, 232, 320.1, 161
See application file for complete search history.

(56) References Cited

U.S. PATENT DOCUMENTS 8,846,369 B2 * 9/2014 Piven ..................... C12N 15/74
435/161
2014/0178958 A1 * 6/2014 Piven ..................... C12P 7/065
435/161

\* cited by examiner

*Primary Examiner* — Ganapathirama Raghu
(74) *Attorney, Agent, or Firm* — Lawrence B. Ebert; Sam J. Barkley; David J. Lorenz

(57) ABSTRACT

A cyanobacterial host cell, *Cyanobacterium* sp., that harbors at least one recombinant gene for the production of a chemical compounds is provided, as well as vectors derived from an endogenous plasmid isolated from the cell.

3 Claims, 181 Drawing Sheets

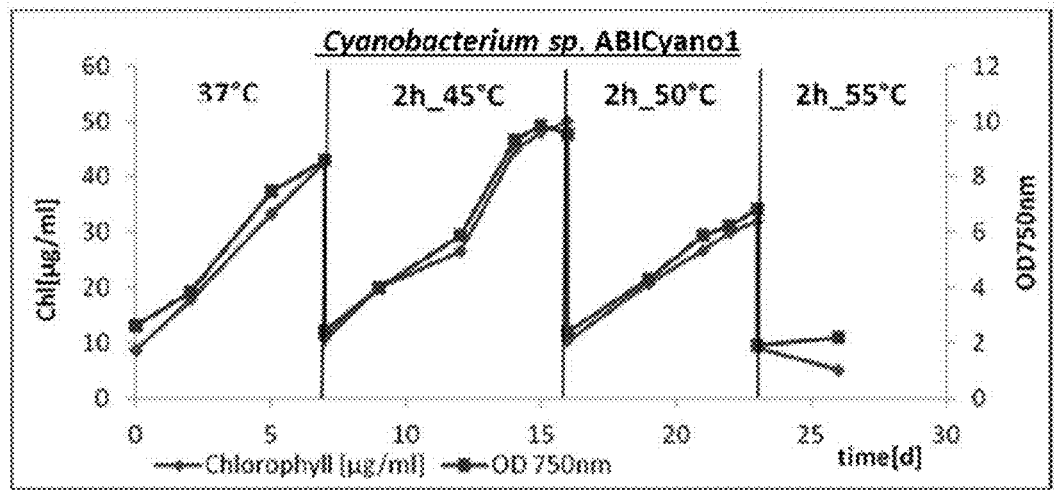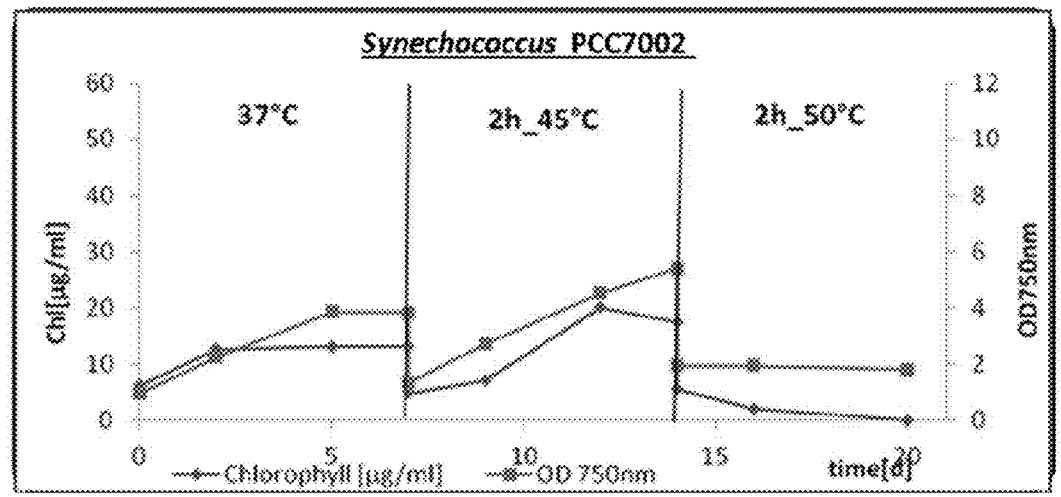
FIG. 2 A and 2 B

```
ID   pABICyanol-6.8  standard; circular DNA;    ; 6828 BP.
DE   Complementary copy of pABICyanol-6.8 and rc
CC   This file is created by Vector NTI
CC   http://www.invitrogen.com/
CC   ORIGDB|GenBank
CC   VNTDATE|640865706|
CC   VNTDBDATE|640865706|
CC   LSOWNER|
CC   VNTAUTHORNAME|Irina Piven|
FH   Key             Location/Qualifiers
FH
FT   primer          complement(1859..1883)
FT                   /vntifkey="27"
FT                   /label=FB3
FT   CDS             594..3779
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   CDS             5350..6036
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             3815..4000
FT                   /vntifkey="4"
FT                   /label=ORF\2
FT                   /note="orf2"
FT   CDS             complement(4260..5024)
FT                   /vntifkey="4"
FT                   /label=ORF\3
FT                   /note="orf3"
FT   CDS             6078..6341
FT                   /vntifkey="4"
FT                   /label=ORF\5
FT                   /note="orf5"
FT   CDS             6338..6586
FT                   /vntifkey="4"
FT                   /label=ORF\6
FT                   /note="orf6"
FT   rep_origin      3375..3408
FT                   /vntifkey="33"
FT                   /label=Rep_Origin_1
FT                   /note="active site motif of Rep protein"
SQ   Sequence 6828 BP; 2360 A; 1153 C; 1212 G; 2103 t;
     aatatttttc gtcagatacg caaaccttac aaacataatt aacaactgaa actattgata        60
     tgtctaggut ttagutctat cacaggttgt tagcacccct gtcatgtatc ttatatcatt       120
     tatttcacca tacggattaa gtgaaacota atgaaaatag tactttcgga gctttaactt       180
     taatgaaggt atgttttttt atagcatcg atgtctggtt taacaatagg aaaaagtagc        240
     taaactccc atgaattaaa gaataacaa ggtgtctaac aacctgttat taagaatgtt        300
     agaaaagact taacatttgt gttgagtttt tatagacatt ggtgtctaga catacggtag       360
     ataaggtttg ctcaaaaata aaataaaaaa agattggact aaaaaacatt taatttagta       420
```

FIG. 4A

```
caatttaatt agttattttt tcgtctcaaa ttttgctttg ttgagcagaa atttagataa    480
aaaaatcccc gtgatcagat tacaatgtcg ttcattgtac gatgtgtcga aaaatcttta    540
cgacactcta aactgaccac acgggggaaa aagaaaactg aactaataac atcatgatac    600
tcggaaaacc tagcaattct caaccoctaa acaaagaaa cttccaaaac cctgaccata     660
taaaggagtg gcaacaatca gcaatcagtc aagatttgat agcagaaaat cttgtatcgg    720
ttgctaatgg ttttgatgta ctatttatcg gcaataaata ccgaactaac acgggtgttc    780
tgtcacggca catattaaac tcctattctc atttagaaga tggtggttcg tatggtagaa    840
catttgaccc atttaccaat aaagaaatgc agtgggttca atttaaacg aatagaccaa     900
gaaaaggttc tactggtaag gtaatcaaat atgaatcgcc aaaaggtgaa cctacaagag    960
ttctaatgcc gtttgtgcct atgaaaatat ggcaacggat tagcgataag ttcggagtac   1020
cgattaatcc gaaaaagat actcactttt gggaatgggt aaagaataat ccatcgatac    1080
cgattgccat tacgaaagga ataaaaaag ctaattgcct attatcctat ggctatcctg    1140
ctattgcctt tgtaggcatt tggaacggat tagagaaact aaatgatttc tgaaggaaa    1200
agcagttaaa agaggatttg aaatggttgt tatccacgg caaccgaaat attaatatca    1260
tctttgacca agaccagaaa caaaaaactg taattaatgt aaacaaagct attttcgctt   1320
tatcttctct aataagtaga aatggtcata aagttaatat tgtgcaatgg ttgccgtcaa   1380
aaggtaaagg aatagatgat tatttggtag cttaccttt tgagaaaaga gaaaatcatt    1440
tagacaactt aattaaaatt gcaccatcat ttaattttg gtcaactaaa tacttattca    1500
agtgtcgtaa accagattta accgtaaatt gccgttattt gagcgatgca gtaaaagaat   1560
tacctcaaga ggatatagca ttaatagcac ctcacggcac gggtaaaact tcattagtag   1620
ctactcacgt taagaatcgg agttatcacg gaaggaaac tatttcattg gtgcatcttg    1680
aaagtttagc caaagctaat ggcaacgcac ttggattata ttaccgaacc gaaaataata   1740
ttgaaaagca atatcttgga tttagcttat gtgtagatag ttgccgtgat aagattaacg   1800
gcattacaac tgatattatt tcaggtcaag attattgcct tttcattgat gaaattgacc   1860
aagtaattcc acacatcctt aacagtgaaa ctgaagtaag taagtataga tgcaccatca   1920
ttgacaacttt ttctgaactg gtgagaaatg ctgaacaggt cattattgct gatgctgatt  1980
tatccgatgt gacgattgac ctaatagaaa acatcagagg taaaaaacta tatgtaatca   2040
agaatgaata tcagtatcag ggaatgactt ttaacgccgt tggttcacca ttagaaatga   2100
tgcaatgat gggaaaatcg gtgtcagaag gcaagaaatt atttattaac accacatccc   2160
aaaaggcaaa aagtaagtac ggcacaatcg ctcttgagtc ttatatttt ggtctaaata    2220
aagaagcaaa gatattaaga atagactctg aaaccactaa aaaccctgaa catccagcct   2280
ataaaatcat tgaccaagac ttaaataata tcctcaaaga ttatgattat gtcattgcct   2340
cacctgcct tcaaacaggt gtcagtatta cttaaaagg gcattttgac cagcaattta    2400
acttttcag tggaaacatt acacctcatt gcttttaca gcaaatgtgg cggttgaggg    2460
atgcagaaat tgaagattc tattatgtgc cgaactcatc taacctcaat ctcattggga   2520
ataagtcaag ttcaccatca gaccttctaa agagcaataa caagatggca acggcaacgg   2580
ttaaccttt gggtagaatc gactccgaat attccctaga gtatgaatcg cacggcattt   2640
ggcttgagac gtgggcaaaa ttatcagcac ggcataacag ttcaatgcgt tgttactctg   2700
aaattcttac ctatctaatt acgtctcaag ggcataaatt aaatatcaac attccctcac   2760
ctcttgcaga tattaagaag ctaaatgatg aggtaagtag taacagggaa aaggtaaaaa   2820
atgagagata ctctcagagg ttaaactcac cagatattaa cgatgcagaa gctaccatac   2880
tcgaatctaa agagcaaaaa atcggattga ctctcaatga gagatgcacc ctagaaaagc   2940
ataaagttaa gaagcggtat gggaatgtaa agatggatat tctcaccttt gatgatgatg   3000
gactataccc caaactcaga ctattttatt acctcaccat cggtaacct catctcaagg    3060
ctaatgacag aaaagctatt gccaaaatgg gcaatgacaa taaaggcaag attctatcaa   3120
aagcttagt taataaaact tactccgctc gtgtgaaggt cttagagatt cttaaactaa    3180
ctgactttat cgacaatctt agagatgaac tcttaataac tcccaataat ccagctatca   3240
ccgattttaa taatcttctg ctaagagcta agaaggattt aagagtatta ggagtcaaca   3300
tcggaaaata tccaatggcc aacattaatg ccgtacttac tctcattggt cacaaacttt   3360
ctgtaatgag agatgagttc ggaaaagaga aaaggataaa agtagatggt aaatcatacc   3420
gatgttatca acttgaaaca ttaccagatt ttaccaatga tactcttgac tactggttag   3480
```

FIG. 4A (continued)

```
aaatgatag ccaaaagaa gtaacagcaa cagaaaatta ctccgaaaat tttaaccctt  3640
caaatagcta caatccagac agtaagacac ttcagaggg tgcaatttc ctatatataa  3690
ataaagaaga attgcatcca aataaattgc acctagaaat aaaagaaggt gctgaacttt  3660
ttttattcgg ggtaaggtg attgtgaaag gaatcttgga cgggcagta actatattct  3720
ctatggtca agaatacgat ttatccctca atgaactaga ggggatgtta acatcatgaa  3780
ctttacaaga atcttttaa agggcgatcg caccatgtta aatgatggta catttgttca  3840
gatatttgat atttaccatg accacgcatt gggagtgacc cttgacctta agacagaaaa  3900
aattatttcc gatgatgtta gggtaattac tgtcaaagac ttattgttcg atggcactta  3960
taaagggta aaatctttta tgcccgataa tgcccgataa tgcccgattg atgctacaaa  4020
atcccataat cataagcgat aatccctaa tagcttgtaa ttcttgaacc gtagcgattt  4080
tagagtattc caaaagaag aaataaacac cgcaaaatgt cgtatttcac atatataaac  4140
caaggttttt tgccctaaaa tctttatgtt tgtagtgtga tgttgggtca aaatggtcag  4200
aaaagttgca aggtttttat ggatgcttac gcgcgcgagg ggtaagcatc cccaaatagt  4260
tacttatcc tagtccatgc ccatttattg ccgtcccgtt cggctttaaa aaagtgccaa  4320
aactcacaag gtgcaataaa aagttctgta cctttcgcaa ccctagataa tctttcaaca  4380
gttccttttt ttctattat ctggtacaa agttggcta gtttctcttt tccctctttt  4440
tcaatcaagc cttcttgtat gcccaactca ttgattaatc tctctatttt taccattatt  4500
tcccgttcag gtagtttatc ccctaaatct tcatggggg gcaatgtagg gcattctgaa  4560
ggggcttttt cttctgtctg gacattatct aatattgaag taaccaaact atcttcagtt  4620
tttctattc ctattaatc atattcggtt actgtatccg tatcaatatc cgaataacta  4680
tctttatccg tattagctat tcggttaagt ttatccgtta actcagaaac aagactatat  4740
agcggtttta gctttcttc tatcctgtta tctaatacgg ataagtttat acgttatca  4800
ttatccgtat tagtatcatt gggcttttt ggtagttcta ccctcata aaccgcttt  4860
attccaatt ccaacagact gataacagta tctttataa tgggttttt gctgatatgg  4920
tgaacttttg ccccttccat cattgcgata cttttctatct cactcatcaa cttatcgctt  4980
aagtgaatct cgtatctgtt taatccctta ctggttttat tcatatccgt ttacttt tatt  5040
cggttaacaa ttctatttta tacgaataaa atattatacg gtaacttta tacgtttaac  5100
tatcttatct atacggataa cagtaataag ttattcgtat tagttatacg tttacttt ta  5160
tccaaataaa attagtgcat ttaaactaaa agaatgattt tatcggagtt gatagcattg  5220
gattaaccta aagatgttta taagctatat ctgataagta ttaaggtta tttgttatt  5280
ctgtttattg acattatcag aataaaagaa tagaatataa ttgttgagag ataagaggtt  5340
taagtgatta tggttaagaa gttagttggt tatgtcaggg tcagtagtga atcgcaagag  5400
gataacacta gcttacagaa tcagatagag agaattgaag catattgtat ggcttttggt  5460
tatgagttgg taaaatatt caaagaggtt gccactggta caaaagcaga tattgaaacc  5520
cgtcctattt ttaatgaagc tatagaatac ttgaaacagg ataatgctaa tggaattatt  5580
gcttgaagc tagaccgaat cgcacggaat gcttagatg tattgcgttt ggttcgtgaa  5640
accttagaac cacaaaataa aatgttagtg ttactagata tcaaggtaga tacttcgaca  5700
ccttcaggaa aaatgatttt aactgtaatg agtgccgttg ctgaactcga aagagacatg  5760
atcatgatc gcactcaggg gggtagaaaa actaaagccc aaaagggcgg gtatgcctac  5820
gggaaaccta aatttggcta taagactgaa gaaaagcaac taaagaaga ttcagcacaa  5880
caggaaacta ttaaactaat taagagacac cgtaggtcag ggaaaagcta ccagaaaata  5940
gctgattatc tcatgccca aagtattccc actaaacaag gtaagaaatg gagttctagc  6000
gtagtctatc gaatctgtca ggaaaaagct ggttaagtct gtttatagat atttagaatt  6060
tattgaataa aaatagtatg aacaataaat atttatggac taaccaacgct cggaaacgtt  6120
taactgaacg atgggaaata aaagaatcat gggttattga taccatcgaa aatcctgaac  6180
gttcagaatt tattgttgat gagtcagggg aaaaatatca ttactataaa agatagcta  6240
agtttaagaa tagagtgtta gaagtgataa cttctgccaa ctcaacccc acaagaataa  6300
taacctttta ctttaaccgt aacatgagga aaaatttatg attgttactt acgataatga  6360
agttgacgca atttatttta agttaacgga aaataaatt gatagaacg aacctcaaac  6420
agacaggatt atcattgatt acgatgaaag taataatatt gttggcattg aggtattaga  6480
```

FIG. 4A (continued)

```
ttttaattat cttgtcaaga aaggtttaac cgttgctgat ttaccttttt ctgaagatga    6540
aagattaaca gcttctcaat attttaattt tcctgttgct atctaatcca gaagggcaa    6600
taatcccctt ctttcatcga gttagactta atatcacaaa agtcattttc attttaccgt    6660
ttcttttcca cagcgtccgt acgcccctcg ttaaatctca aaacgacaa tttatgatgt    6720
ttataaaaag ttactcactt taataagtat ttatactcat taaagggtta ttcttttttt    6780
gtagcctgat aggttgggaa ggaatatttc agattatcag atttgttg
```

FIG. 4A (continued)

orf1 rep ori binding protein

MILGKPSNSQPLNKRNFQNPDHIKEWQQSAISQDLIAENLVSVANGFDVLFIGNKYRTNTGVLSRHILNS
YSHLEDGGSYGRTFDPFTNKEMQWVQFKPNRPRKGSTGKVIKYESPKGEPTRVLMPFVPMKIWQRISDKF
GVPINPKKDTHFWEWVKNNPSIPIAITEGNKKANCLLSYGYPAIAFVGIWNGLEKINDFSKEKQLKEDLK
WLLSNGNRNINIIFDQDQKQKTVINVNKAIFALSSLISRNGHKVNIVQWLPSKGKGIDDYLVALPFEKRE
NHLDNLIKIAPSFNFWSTKYLFKCRKPDLTVNCRYLSDAVKELPQEDIALIAPHGTGKTSLVATHVKNRS
YHGRKTISLVHLESLAKANGNALGLYYRTENNIEKQYLGFSLCVDSCRDKINGITTDIISGQDYCLFIDE
IDQVIPHILNSETEVSKYRCTIIDTFSELVRNAEQVIIADADLSDVTIDLIENIRGKKLYVIKNEYQYQG
MTFNAVGSPLEMMAMMGKSVSEGKKLFINTTSQKAKSKYGTIALESYIFGLNKEAKILRIDSETTKNPEH
PAYKIIDQDLNNILKDYDYVIASPCLQTGVSITLKGHFDQQFNFSSGNITPHCFLQQMWRLRDAEIERFY
YVPNSSNLNLIGNKSSSPSDLLKSNNKMATATVNLLGRIDSEYSLEYESHGIWLETWAKLSARHNSSMRC
YSEILTYLITSQGHKLNINIPSPLADIKKLNDEVSSNREKVKNERYSQRLNSPDINDAEATILESKEQKI
GLTLNERCTLEKHKVKKRYGNVKMDILTFDDDGLYPKLRLFYYLTIGKPHLKANDRKAIAKMGNDNKGKI
LSKDLVNKTYSARVKVLEILKLTDFIDNLRDELLITPNNPAITDFNNLLLRAKKDLRVLGVNIGKYPMAN
INAVLTLIGRKLSVMRDEFGREKRIKVDGKSYRCYQLETLPDFTNDTLDYWLENDSQKEVTAPENYSENF
NPSNSYNPDSKTLSEGANFLYINKEELHPNKLHLEIKEGAELFLFGVKVIVKGILDGAVTIFSMGQEYDL
SLNELEGMLTS*

Fig. 4B orf2

MLNDGTFVQIFDIYHDHALGVTLDLKTEKIISDDVRVITVKDLLFDGTYKGVKSFMPDNAR

Fig. 4C orf3

MNKTSKGLNRYEIHLSDKLMSEIESIAMMEGAKVHHISKKPIIKDTVISLLELGIKAVYEGVELPKKPNDTNTDNDNRINLS
VLDNRIEEKLKPLYSLVSELTDKLNRIANTDKDSYSDIDTDTVTEYELIGIEKTEDSLVTSILDNVQTEEKAPSECPTLPPDEDL
GDKLPEREIMVKIERLINELGIQEGLIEKEGKEKLAKLCTEIIGKKVTVERLSRVAKGTELFIAPCEFWHFFKAERDGNKWA
WTRIK

Fig. 4D orf4

MVKKLVGYVRVSSESQEDNTSLQNQIERIEAYCMAFGYELVKIFKEVATGTKADIETRPIFNEAIEYLKQDNANGIIALKLD
RIARNALDVLRLVRETLEPQNKMLVLLDIQVDTSTPSGKMILTVMSAVAELERDMIYDRTQGGRKTKAQKGGYAYGKP
KFGYKTEEKELKEDSAQQETIKLIKRHRRSGKSYQKIADYLNAQSIPTKQGKKWSSSVVYRICQEKAG

Fig. 4E orf5

MNNKYLWTNHARKRLTERWEIKESWVIDTIENPERSEFIVDESGEKYHYYKRIAKFKNRVLEVITSANSTPTRIITFYFNRN
MRKNL

Fig. 4F orf6

MIVTYDNEVDAIYFKLTENKIDSTEPQTDRIIIDYDESNNIVGIEVLDFNYLVKKGLTVADLPFSEDERLTASQYFNFPV
AI

Fig. 4G

```
            1
Cyano10216  ---------- ---------- ---------- ---------- ----------
CyanoETS-03 ---------- ---------- ---------- --------GCA GCTACACATG
ABICyano2   AGAGTTTGAT CCTGGCTCAG GATGAACGCT GGCGGTATGC CTAACACATG
ABICyano1   AGAGTTTGAT CCTGGCTCAG GATGAACGCT GGCGGTATGC CTAACACATG
CyanoLLi5   ---------- ---------- GATGAACGCT GGCGGTATGC TTAACACATG
Cyano7202   ---------- ---------- ---------- ---------- ----------

51
Cyano10216  ---------- ---------- ---------- ---------- ----------
CyanoETS-03 CAAGTCGAAC GGGCTCTTCG G-AGCTAGTG GCGGACGGGT GAGGAACGCG
ABICyano2   CAAGTCGAAC GGGCTCTTCG G-AGCTAGTG GCGGACGGGT GAGGAACGCG
ABICyano1   CAAGTCGAAC GGTCTCTTCG G-AGATAGTG GCGGACGGGT GAGGAACGCG
CyanoLLi5   CAAGTCGAAC GGGCACTTCG G-TGATAGTG GCGCACGGGT GAGGAACACG
Cyano7202   ---------- -----CTTCG GATGATAGTG GCGGACGGGT GAGTAACACG 101
Cyano10216  -----ACCTG CCTCAAGGTC GGGGACAACA GTTGGAAACG ACTGCTAATA
CyanoETS-03 TGAGAACCTG CCTCAAGGTC GGGGACAACA GTTGGAAACG ACTGCTAATA
ABICyano2   TGAGAACCTG CCTCAAGGTC GGGGACAACA GTTGGAAACG ACTGCTAATA
ABICyano1   TGAGAACCTG CCTCAAGGTC GGGGACAACA GTTGGAAACG ACTGCTAATA
CyanoLLi5   TGAGAATCTG CCTCAAAGTC GGGGACAACA GTTGGAAACG ACTGCTAATA
Cyano7202   TGAGAATCTG CCCTTAGGTC GGGGACAACA GTTGGAAACG ACTGCTAATA 151
Cyano10216  CCGGATGAGC CGAATAGGTA AAAGATTTAT CGCCTTGAGA GGGGCTCGCG
CyanoETS-03 CCGGATGAGC CGAATAGGTA AAAGATTTAT CGCCTTGAGA GGGGCTCGCG
ABICyano2   CCGGATGAGC CGAATAGGTA AAAGATTTAT CGCCTTGAGA GGGGCTCGCG
ABICyano1   CCGGATGAGC CGAATAGGTA AAAGATTTAT CGCCTAGAGA GGGGCTCGCG
CyanoLLi5   CCGGATGAGC CGCA-AGGTA AAAGATTTAT CGCTTTGAGA GGAGCTCGCG
Cyano7202   CCGGATGAGC TGAA-AAGTA AAAGATTTAT CGCCTAGGGA AGAGCTCGCG 201
Cyano10216  TCTGATTAGC TAGATGGTGA GGTAAAGGCT TACCATGGCG ACGATCAGTA
CyanoETS-03 TCTGATTAGC TAGATGGTGA GGTAAAGGCT TACCATGGCG ACGATCAGTA
ABICyano2   TCTGATTAGC TAGATGGTGA GGTAAAGGCT TACCATGGCG ACGATCAGTA
ABICyano1   TCTGATTAGC TAGATGGTGA GGTAAAGGCT TACCATGGCG ACGATCAGTA
CyanoLLi5   TCTGATTAGC TAGATGGTGA GGTAAAGGCT TACCATGGCG ACGATCAGTA
Cyano7202   GCTGATTAGC TAGTTGGTAG TGTAAAGGAC AACCAAGGCA ACGATCAGTA 251
Cyano10216  GCTGGTCTGA GAGGATGAGC AGCCACACTG GGACTGAGAC ACGGCCCAGA
CyanoETS-03 GCTGGTCTGA GAGGATGAGC AGCCACACTG GGACTGAGAC ACGGCCCAGA
ABICyano2   GCTGGTCTGA GAGGATGAGC AGCCACACTG GGACTGAGAC ACGGCCCAGA
ABICyano1   GCTGGTCTGA GAGGATGAGC AGCCACACTG GGACTGAGAC ACGGCCCAGA
CyanoLLi5   GCTGGTCTGA GAGGATGAGC AGCCACACTG GGACTGAGAC ACGGCCCAGA
Cyano7202   GCTGGTCTGA GAGGATGAGC AGCCACACTG GGACTGAGAC ACGGCCCAGA
```

FIG. 5B

```
              301
Cyano10216    CTCCTACGGG AGGCAGCAGT GGGGAATTTT CCGCAATGGG CGAAAGCCTG
CyanoETS-03   CTCCTACGGG AGGCAGCAGT GGGGAATTTT CCGCAATGGG CGAAAGCCTG
ABICyano2     CTCCTACGGG AGGCAGCAGT GGGGAATTTT CCGCAATGGG CGAAAGCCTG
ABICyano1     CTCCTACGGG AGGCAGCAGT GGGGAATTTT CCGCAATGGG CGAAAGCCTG
CyanoLLi5     CTCCTACGGG AGGCAGCAGT GGGGAATTTT CCGCAATGGG CGAAAGCCTG
Cyano7202     CTCCTACGGG AGGCAGCAGT GGGGAATTTT CCGCAATGGG CGAAAGCCTG 351
Cyano10216    ACGGAGCAAT ACCGCGTGAG GGAGGAAGGC TCTTGGGTTG TAAACCTCAA
CyanoETS-03   ACGGAGCAAT ACCGCGTGAG GGAGGAAGGC TCTTGGGTTG TAAACCTCAA
ABICyano2     ACGGAGCAAT ACCGCGTGAG GGAGGAAGGC TCTTGGGTTG TAAACCTCAA
ABICyano1     ACGGAGCAAT ACCGCGTGAG GGAGGAAGGC TCTTGGGTTG TAAACCTCAA
CyanoLLi5     ACGGAGCAAT ACCGCGTGAG GGAGGAAGGC TCTTGGGTTG TAAACCTCAA
Cyano7202     ACGGAGCAAT ACCGCGTGAG GGAGGAAGGC TCTTGGGTTG TAAACCTCAA 401
Cyano10216    AACTTAGGGA AGAAAAAAAT GACGGTACCT AATGTAAGCA TCGGCTAACT
CyanoETS-03   AACTTAGGGA AGAAAAAAAT GACGGTACCT AATGTAAGCA TCGGCTAACT
ABICyano2     AACTTAGGGA AGAAAAAAAT GACGGTACCT AATGTAAGCA TCGGCTAACT
ABICyano1     AACTTAGGGA AGAAAAAAAT GACGGTACCT AATGTAAGCA TCGGCTAACT
CyanoLLi5     AACTTAGGGA AGAAGCAAGT GACGGTACCT AATATAAGCA TCGGCTAACT
Cyano7202     AACTCAGGGA AGAAGAAAGT GACGGTACCT GATATAAGCA TCGGCTAACT 451
Cyano10216    CCGTGCCAGC AGCCGCGGTA ATACGGAGGA TGCAAGCGTT ATCCGGAATC
CyanoETS-03   CCGTGCCAGC AGCCGCGGTA ATACGGAGGA TGCAAGCGTT ATCCGGAATC
ABICyano2     CCGTGCCAGC AGCCGCGGTA ATACGGAGGA TGCAAGCGTT ATCCGGAATC
ABICyano1     CCGTGCCAGC AGCCGCGGTA ATACGGAGGA TGCAAGCGTT ATCCGGAATC
CyanoLLi5     CCGTGCCAGC AGCCGCGGTA ATACGGAGGA TGCAAGCGTT ATCCGGAATC
Cyano7202     CCGTGCCAGC AGCCGCGGTA ATACGGAGGA TGCAAGCGTT ATCCGGAATC 501
Cyano10216    ATTGGGCGTA AAGAGTCCGT AGGTGGCACT TCAAGTCTGC TTTCAAAGAC
CyanoETS-03   ATTGGGCGTA AAGAGTCCGT AGGTGGCACT TCAAGTCTGC TTTCAAAGAC
ABICyano2     ATTGGGCGTA AAGAGTCCGT AGGTGGCACT TCAAGTCTGC TTTCAAAGAC
ABICyano1     ATTGGGCGTA AAGAGTCCGT AGGTGGCACT TCAAGTCTGC TTTCAAAGAC
CyanoLLi5     ATTGGGCGTA AAGCGTCCGT AGGTGGCATT TCAAGTCTGC TGTCAAAGAC
Cyano7202     ATTGGGCGTA AAGCGTCCGT AGGTGGCATT TCAAGTCTGC ATTCAAAGAC 551
Cyano10216    CGAAGCTCAA CTTCGGAAAG GGAGTGGAAA CTGAAGAGCT AGAGTATAGT
CyanoETS-03   CGAAGCTCAA CTTCGGAAAG GGAGTGGAAA CTGAAGAGCT AGAGTATAGT
ABICyano2     CGAAGCTCAA CTTCGGAAAG GGAGTGGAAA CTGAAGAGCT AGAGTATAGT
ABICyano1     CGAAGCTCAA CTTCGGAAAG GGAGTGGAAA CTGAAGAGCT AGAGTATAGT
CyanoLLi5     CGAAGCTCAA CTTCGGGCCG GCGGTGGAAA CTGAAAAGCT AGAGTGAAGT
Cyano7202     CGAGGCTCAA CCTCGGGCAG GGTGTGGAAA CTGAAAAGCT AGAGTACAGG
```

FIG. 5B (cont.)

```
             601
Cyano10216   AGGGG-TAGA  --GGGAATTC  CTAGTGTAGC  GGTGAAATGC  GTAGAGATTA
CyanoETS-03  AGGGGGTAGG  AGGGGAATTC  CTAGTGTAGC  GGTGAAATGC  GTAGAGATTA
ABICyano2    AGGGG-TAGA  --GGGAATTC  CTAGTGTAGC  GGTGAAATGC  GTAGAGATTA
ABICyano1    AGGGG-TAGA  --GGGAATTC  CTAGTGTAGC  GGTGAAATGC  GTAGAGATTA
CyanoLLi5    AGGGG-TAGA  --GGGAATTC  CTAGTGTAGC  GGTGAAATGC  GTAGAGATTA
Cyano7202    AGGGG-TAGA  --GGGAATTC  CTAGTGTAGC  GGTGAAATGC  GTAGAGATTA 651
Cyano10216   GGAAGAACAC  CAGTGGCGAA  GGCGCTCTAC  TGGGCATATA  CTGACACTGA
CyanoETS-03  GGAAGAACAC  CAGTGGCGAA  GGCGCTCTAC  TGGGCATATA  CTGACACTGA
ABICyano2    GGAAGAACAC  CAGTGGCGAA  GGCGCTCTAC  TGGGCATATA  CTGACACTGA
ABICyano1    GGAAGAACAC  CAGTGGCGAA  GGCGCTCTAC  TGGGCATATA  CTGACACTGA
CyanoLLi5    GGAAGAACAC  CAGTGGCGAA  GGCGCTCTAC  TGGACTTAAA  CTGACACTGA
Cyano7202    GGAAGAACAC  CAGTGGCGAA  GGCGCTCTAC  TGGACATGTA  CTGACACTGA 701
Cyano10216   GGGACGAAAG  CTAGGGGAGC  GAAAGGGATT  AGATACCCCT  GTAGTCCTAG
CyanoETS-03  GGGACGAAAG  CTAGGGGAGC  GAAAGGGATT  AGATACCCCT  GTAGTCCTAG
ABICyano2    GGGACGAAAG  CTAGGGGAGC  GAAAGGGATT  AGATACCCCT  GTAGTCCTAG
ABICyano1    GGGACGAAAG  CTAGGGGAGC  GAAAGGGATT  AGATACCCCT  GTAGTCCTAG
CyanoLLi5    GGGACGAAAG  CTAAGGGAGC  GAAAGGGATT  AGATACCCCT  GTAGTCTTAG
Cyano7202    GGGACGAAAG  CTAGGGTAGC  GAAAGGGATT  AGATACCCCT  GTAGTCTTAG 751
Cyano10216   CGGTAAACGA  TGGATACTAG  GCGTAGTGC-  TGTAAAAG-G  GACTGTGCCG
CyanoETS-03  CGGTAAACGA  TGGATACTAG  GCGTAGTGC-  TGTTAGAA-G  GACTGTGCCG
ABICyano2    CGGTAAACGA  TGGATACTAG  GCGTAGTGC-  TGTAAAAG-G  GACTGTGCCG
ABICyano1    CGGTAAACGA  TGGATACTAG  GCGTAGTGC-  TGTTAGAA-G  GACTGTGCCG
CyanoLLi5    CGGTAAACGA  TGGATACTAG  GTGTTGTCTG  TATCGACCCG  GACAGTGCCG
Cyano7202    CTGTAAACGA  TGGATACTAA  GTGTAGCGGG  TATAAACTCC  GGCTGTGCTG 801
Cyano10216   AAGCTAACGC  GTTAAGTATC  CCGCCTGGGG  AGTACGCACG  CAAGTGTGAA
CyanoETS-03  AAGCTAACGC  GTTAAGTATC  CCGCCTGGGG  AGTACGCACG  CAAGTGTGAA
ABICyano2    AAGCTAACGC  GTTAAGTATC  CCGCCTGGGG  AGTACGCACG  CAAGTGTGAA
ABICyano1    AAGCTAACGC  GTTAAGTATC  CCGCCTGGGG  AGTACGCACG  CAAGTGTGAA
CyanoLLi5    AAGCAAACGC  GTTAAGTATC  CCGCCTGGGG  AGTACGCACG  CAAGTGTGAA
Cyano7202    AAGCAAACGC  GTTAAGTATC  CCGCCTGGGG  AGTACGCACG  CAAGTGTGAA 851
Cyano10216   ACTCAAAGGA  ATTGACGGGG  ACCCGCACAA  GCGGTGGAGT  ATGTGGTTTA
CyanoETS-03  ACTCAAAGGA  ATTGACGGGG  ACCCGCACAA  GCGGTGGAGT  ATGTGGTTTA
ABICyano2    ACTCAAAGGA  ATTGACGGGG  ACCCGCACAA  GCGGTGGAGT  ATGTGGTTTA
ABICyano1    ACTCAAAGGA  ATTGACGGGG  ACCCGCACAA  GCGGTGGAGT  ATGTGGTTTA
CyanoLLi5    ACTCAAAGGA  ATTGACGGGG  ACCCGCACAA  GCGGTGGAGT  ATGTGGTTTA
Cyano7202    ACTCAAAGGA  ATTGACGGGG  ACCCGCACAA  GCGGTGGAGT  ATGTGGTTTA
```

FIG. 5B (cont.)

```
            901
Cyano10216    ATTCGATGCA ACGCGAAGAA CCTTACCAAG GCTTGACATC CTGCGAATCT
CyanoETS-03   ATTCGATGCA ACGCGAAGAA CCTTACCAAG GCTTGACATC CTGCGAATCT
ABICyano2     ATTCGATGCA ACGCGAAGAA CCTTACCAAG GCTTGACATC CTGCGAATCT
ABICyano1     ATTCGATGCA ACGCGAAGAA CCTTACCAAG GCTTGACATC CTGCGAATCT
CyanoLL15     ATTCGATGCA ACGCGAAGAA CCTTACCAAG GCTTGACATC CTGTGAATCT
Cyano7202     ATTCGATGCA ACGCGAAGAA CCTTACCAAG ACTTGACATC CGATGAATCT 951
Cyano10216    TGATGAAAGT TGAGAGTGCC TAAGGGAACG CAGAGACAGG TGGTGCATGG
CyanoETS-03   TGGAGAAATC TGAGAGTGCC TAAGGGAACG CAGAGACAGG TGGTGCATGG
ABICyano2     TGATGAAAGT TGAGAGTGCC TAAGGGAACG CAGAGACAGG TGGTGCATGG
ABICyano1     TGGAGAAATC TGAGAGTGCC TAAGGGAACG CAGAGACAGG TGGTGCATGG
CyanoLL15     CGATGAAAGT TGAGAGTGCC TTAGGGAACA CAGAGACAGG TGGTGCATGG
Cyano7202     TTTTGAAAGA AGAGAGTGCC TTAGGGAACA TCGTGACAGG TGGTGCATGG 1001
Cyano10216    CTGTCGTCAG CTCGTGTCGT GAGATGTTGG GTTAAGTCCC GCAACGAGCG
CyanoETS-03   CTGTCGTCAG CTCGTGTCGT GAGATGTTGG GTTAAGTCCC GCAACGAGCG
ABICyano2     CTGTCGTCAG CTCGTGTCGT GAGATGTTGG GTTAAGTCCC GCAACGAGCG
ABICyano1     CTGTCGTCAG CTCGTGTCGT GAGATGTTGG GTTAAGTCCC GCAACGAGCG
CyanoLL15     CTGTCGTCAG CTCGTGTCGT GAGATGTTGG GTTAAGTCCC GCAACGAGCG
Cyano7202     CTGTCGTCAG CTCGTGTCGT GAGATGTTGG GTTAAGTCCC GCAACGAGCG 1051
Cyano10216    CAACCCTCGT CCTTAGTTGC CAGCATTAAG TTGGGGACTC TAGGGAGACC
CyanoETS-03   CAACCCTCGT CCTTAGTTGC CAGCATTAAG TTGGGGACTC TAGGGAGACC
ABICyano2     CAACCCTCGT CCTTAGTTGC CAGCATTAAG TTGGGGACTC TAGGGAGACC
ABICyano1     CAACCCTCGT CCTTAGTTGC CAGCATTAAG TTGGGGACTC TAGGGAGACC
CyanoLL15     CAACCCTCGT CCTTAGTTGC CAGCATTAAG TTGGGGACTC TAGGGAGACT
Cyano7202     CAACCCTCGT CCTTAGTTGC CAGCATTAAG TTGGGGACTC TAGGGAGACC 1101
Cyano10216    GCCGGGGAGA ACTCGGAGGA AGGTGGGGAT GACGTCAAGT CAGCATGCCC
CyanoETS-03   GCCGGGGAGA ACTCGGAGGA AGGTGGGGAT GACGTCAAGT CAGCATGCCC
ABICyano2     GCCGGGGAGA ACTCGGAGGA AGGTGGGGAT GACGTCAAGT CAGCATGCCC
ABICyano1     GCCGGGGAGA ACTCGGAGGA AGGTGGGGAT GACGTCAAGT CAGCATGCCC
CyanoLL15     GCCGGGGAGA ACTCGGAGGA AGGTGGGGAT GACGTCAAGT CAGCATGCCC
Cyano7202     GCCGGGGAGA ACTCGGAGGA AGGTGGGGAT GACGTCAAGT CAGCATGCCC 1151
Cyano10216    CTTACGTCTT GGGCTACACA CGTACTACAA TGGTTGGGAC AAAGGGGAGC
CyanoETS-03   CTTACGTCTT GGGCTACACA CGTACTACAA TGGTTGGGAC AAAGGGGAGC
ABICyano2     CTTACGTCTT GGGCTACACA CGTACTACAA TGGTTGGGAC AAAGGGGAGC
ABICyano1     CTTACGTCTT GGGCTACACA CGTACTACAA TGGTTGGGAC AAAGGGGAGC
CyanoLL15     CTTACGTCTT GGGCTACACA CGTACTACAA TGGTAGGGAC AAAGGGAGGC
Cyano7202     CTTACGTCTT GGGCTACACA CGTACTACAA TGGTTGGGAC AAAGGGATGC
```

FIG. 5B (cont.)

```
            1201
Cyano10216  GAAGCCGCGA GGTGGAGCGA ATCTCATCAA ACCCAGCCAC AGTTCAGATT
CyanoETS-03 GAAACCGCGA GGTGGAGCGA ATCTCATCAA ACCCAGCCAC AGTTCAGATT
ABICyano2   GAAGCCGCGA GGTGGAGCGA ATCTCATCAA ACCCAGCCAC AGTTCAGATT
ABICyano1   GAAACCGCGA GGTGGAGCGA ATCTCATCAA ACCCAGCCAC AGTTCAGATT
CyanoLLi5   GAAACTGCGA AGTGGAGCGA ATCCTGTCAA ACCCTGCCCC AGTTCAGATT
Cyano7202   GAGACCGCAA GGTGGAGCGA AACCCATCAA ACCCAGCCCC AGTTCAGATC 1251
Cyano10216  GCAGGCTGAA ACTCGCCTGC ATGAAGGAGG AATCGCTAGT AATCGCAGGT
CyanoETS-03 GCAGGCTGAA ACTCGCCTGC ATGAAGGAGG AATCGCTAGT AATCGCAGGT
ABICyano2   GCAGGCTGAA ACTCGCCTGC ATGAAGGAGG AATCGCTAGT AATCGCAGGT
ABICyano1   GCAGGCTGAA ACTCGCCTGC ATGAAGGAGG AATCGCTAGT AATCGCAGGT
CyanoLLi5   GTAGGCTGAA ACTCGCCTAC ATGAAGGAGG AATCGCTAGT AATCGCAGGT
Cyano7202   GTCGGCTGAA ACTCGCCGAC GTGAAGGAGG AATCGCTAGT AATCGCAGGT 1301
Cyano10216  CAGCATACTG CGGTGAATCC GTTCCCGGGT CTTGTACACA CCGCCCGTCA
CyanoETS-03 CAGCATACTG CGGTGAATCC GTTCCCGGGT CTTGTACACA CCGCCCGTCA
ABICyano2   CAGCATACTG CGGTGAATCC GTTCCCGGGT CTTGTACACA CCGCCCGTCA
ABICyano1   CAGCATACTG CGGTGAATCC GTTCCCGGGT CTTGTACACA CCGCCCGTCA
CyanoLLi5   CAGCATACTG CGGTGAATCC GTTCCCGGGT CTTGTACACA CCGCCCGTCA
Cyano7202   CAGCATACTG CGGTGAATCC GTTCCCGGGT CTTGTACACA CCGCCCGTCA 1351
Cyano10216  CACCATGGAA GT-------- ---------- ---------- ----------
CyanoETS-03 CACCATGGAA GTTGGTCACG CCCGAAGTCG TTATTCTAAC CCAAG--GGA
ABICyano2   CACCATGGAA GTTGGTCACG CCCGAAGTCG TTATTCTAAC CCAAGTGGAA
ABICyano1   CACCATGGAA GTTGGTCACG CCCGAAGTCG TTATTCTAAC CCAAGTGGAA
CyanoLLi5   CACCATGGAA GTTGGTAACA TCCGAAGTCG TTACTCCAAC CCGCAAGGGG
Cyano7202   CACCATGGAA GTTGGTAACA TCCGAAGTCG TTACTCCAAC CATTTATGGA 1401
Cyano10216  ---------- ---------- ---------- ---------- ----------
CyanoETS-03 AGA-GACGCC AA--AGTGGG ACTAGTGACT GGGGTG---- ----------
ABICyano2   GGA-GACGCC GAAGGTGGGA CTAGTGACTG GGGTGAAGTC GTAACAAGGT
ABICyano1   GGA-GACGCC GAAGGTGGGA CTAGTGACTG GGGTGAAGTC GTAACAAGGT
CyanoLLi5   GGAGGATGCC GAAGGTGGGA CTAGTGACTG GGGTGAAGTC GTAACAAGGT
Cyano7202   GGAGATCTCT G------GA CTAGTGACTG GGGTG----- ----------

1451
Cyano10216  ---------- ---------- ---------- -----
CyanoETS-03 ---------- ---------- ---------- -----
ABICyano2   AGCCGTACCG GAAGGTGTGG CTGGATCACC T----
ABICyano1   AGCCGTACCG GAAGGTGTGG CTGGATCACC T----
CyanoLLi5   AGCCGTACCG GAAGGTGTGG CTGGATCACC TCCTT
Cyano7202   ---------- ---------- ---------- -----
```

FIG. 5B (cont.)

```
ID   pRL528     standard; circular DNA;    ; 16301 BP.
CC   This file is created by Vector NTI
CC   http://www.invitrogen.com/
CC   VNTDATE|584889451|
CC   VNTDBDATE|584895165|
CC   LSOWNER|
FH   Key             Location/Qualifiers
FH
FT   CDS             548..1996
FT                   /vntifkey="4"
FT                   /label=M.AvaI
FT   CDS             3006..4259
FT                   /vntifkey="4"
FT                   /label=M.Eco47II
FT   CDS             complement(15314..15955)
FT                   /vntifkey="4"
FT                   /label=Cm
SQ   Sequence 16301 BP; 4386 A; 3985 C; 3477 G; 4453 t;
     aagtcacggt actctccgga ggccttttc atatccggcg ggcctgacac ttccggatgc      60
     agcacacgaa aacagaagtc accggaacac gccattctga gaaaactgtc actaatctgt     120
     tttattccgc aaacagaaaa ccaccggata accggggtat aggaagtata aaccaccttt     180
     ttgggtatag gaagtataaa ccaccttttt gctcctcatc cgaagtatct tacctgaaat     240
     tccctcactc gtttaccgct caagcccaa ttttaactgc cggtccagcc taaaccgtc      300
     taataaggtt cgatttggcg gtaaaatctc tagcctgata gctcgagtc tagatatcga     360
     tgaattcgag ctcggtaccc tattcaatat ttaacttgat tactgtagaa gtataacaaa     420
     gtataatcag gttctasctg ttgtcaatta gtctataaaa aatagggttc aaatcttaag     480
     tgatagacga tagtgctttg tcctgataga atcttaagtt acctctttgt tacaagaaaa     540
     atataaaatg acttcatttg agcttgagag tcaatagaa ataagactg accgactga       600
     tcttgatcaa gagagtgatt cctttgtaca agaaatttct cgattcaata agcacttga      660
     gcaacgtttt agagataaga tgcgattgca tgaaagttta agtcgaaaaa tagttagttt     720
     tcaagctaat aagtcaaaac ctcagtatcg ctggtttaaa tataagaag cttttttcagt    780
     tgatttggta aatcagttaa tattcgagta cgagaaaaaa tcatttgaga ggattcttga    840
     ccccttcgca ggagcaggaa caatgctatt tgcctgtagt gatgccgta ttcaagcaga      900
     tggtatagaa gtgttaccta ttggtcaaga gattattgaa gtaaggaaaa taatccagcg    960
     acaattccgt cgagaagatt ttttgagatt gattgaatgg tacaaacaaa aaccttggaa   1020
     tcagcataat aatagaaaat atcttaatcg tttaagaatt actgacggag cttatcctcc   1080
     tgaaacagaa gcatcaatag agagattttt attttctata gaaaaagaga atattcttgt   1140
     gaaacaagtt ctccgttttg ctctattgtg tattcttgaa tctatcagct atacccgtaa   1200
     agatggacag tatctacgtt tggataaaag agcatttagg aaaagtggat cagataaatt   1260
     tgataaaggt aaaattctgg atttcgatga agcaattact gagcaaataa aattaattct   1320
     gaatgattcc tttgacttaa taagtaatcc attattttgt tatgggactc aagaagtgg    1380
     aattaattta tttaatgctt catgtcttaa aattctgcct gaatttgagc aagatttta    1440
     cgactgtatc attaccctct cacctattg taatcgttat gactatacac gtacataccg    1500
     tctagaatta gctctattag gtgtgggaga aagagatata gtacaacttta ggcaagatat    1560
     gctgagttgt actgttgaaa acaagaaaa gtctcttatt cacaattggc aggaagcatt    1620
     acgcatactt gataaacaag aattgttaca aagtatcttg cgctttcttg agcgagagct    1680
     tgaagaaaa aaacttaata ataacggtat tcctcgtatg ataaaggat atttctatga    1740
     aatggcttgc gttattatag aatgctttag agttttaaaa aatggctcac cttatttat     1800
     ggtaaatgat aatgttcgct atgcaggtat tgatatttcg gttgatttaa ttcttttctaa   1860
     tattgcagaa gaaattggtt ttaatgtgga gaaaattctt gtcttaccta ctggcaaagg   1920
     taacagtagc caacaaatgg ggacacatgg aagaagaca cttgcaaat gtgtgtatgt    1980
     ttggagaaaa ccctagtgcc atatcaatat catattcaaa gcaatgatga tcttgtgact   2040
```

FIG. 7

```
ccatatcaag aagtccgagc aggatttgtt gctttagctt tagaaagaaa tcgaaaagca      2100
acaccattcg ttgagcaggc aagagcatta aagatccgag taagccaaat tgaaagggg      2160
gatcctctag aagctttaat gcggtagttt atcacagtta aattgctaac gcagtcaggc      2220
accgtgtatg aaatctaaca atgcgctcat cgtcatcctc ggcaccgtca cctggatgc      2280
tgtaggcata ggcttggtta tgccggtact gccgggctc ttgcgggata tcgtccattc      2340
cgacagcatc gccagtcact atggcgtgct gctagcgcta tatgcgttga tgcaatttct      2400
atgcgcaccc gttctcggag cactgtccga ccgctttggc cgccgccag tctgctgcgc      2460
ttcgctactt ggagccacta tcgactacgc gatcatggcg accacaccg tcctgtggat      2520
cttctcaacg aagaagaag aatcatcgct gaggtgaaaa ataaatactc aacgttact      2580
ggcgggggatt tagcagataa atataaaggc ttagatgagt tggtatcacc gaaacatagc      2640
cgatttaagg attactgtgc gtactttgtt aatataatcc ctgtaaacc tatcagatat      2700
aacagcccct ttactcctt caataaaggt agtggtactc tgtgtccttc gaaccctaac      2760
attagaatca tgatggtgc gagtctctat gagcttgtca ctggcagacc agatgctctg      2820
caagaactcc atagtgctct ccctcacgca attgagtata ttttgagcga acgtcttggg      2880
cagcaaggtt ttccatccc tgataaagat agttttatta agtatttgg gctcgcttac      2940
ggctgataac catgatcaat gtttgacaaa gcacatgtaa acccatacag tagtaaccat      3000
gactaatgtt ggcatggtta ctaaatatgt taaaggaaga gttttcactt tcagaagttg      3060
cagacatttt gggcgtttca aaagaaactt taaggcgttg ggatactgct ggaaaattag      3120
tttctcaag aaatgacgaa aacactatc gatttataa aaagagcaa cttaaaaatt      3180
ttgaacaagc tcagtttta tttaaaagcc agtggctga tgagactaaa ataagcaata      3240
atgtttatac tgtattagag ttatttgctg gcgcagggg gatggcttta ggtttagaaa      3300
aagccggttt aaaatctgtt ttactaaatg aaattgactc ccatgcttgt aagacgttac      3360
gaaaaaatag gcctgaatgg aatgtggttg aagtgatgt gagccaagta gacttcaccc      3420
cttataggaa taccgttgat gtgctggctg gtggctttcc ttgccaggca ttctcttatg      3480
caggcaaaaa acttggtttt gaagatacac ggggcaccct tttctttgaa ttcgccgag      3540
ccgctaaaga aatcaatccg aaagtctctt tagcagagaa tgttcgaggg ttgctaaatc      3600
atgatgctgg acgaacttta gaaacaataa aaaatattat cacagacttg ggctacactt      3660
tatttgagcc aagagtgctt aaggctattt tctacaaagt gccgcaaaaa cgcgagcgtt      3720
tgatcattgt agctgtaaga aatgatcttg ctgatggcat cgattatgag tggccttctt      3780
cttacaataa aatattaacc cttaagatg cattaaaaaa gggagagctg tatgatacg      3840
acgtgccaga atctgaagga caaaaatatc ccaaaagaaa agcagagatc ctaagtatgg      3900
ttcctccggg tggctactgg agagatcttc ctgaagatat tcaaaagaa tacatgctca      3960
agagttttta cttaggtggg ggcaaaactg gtatggctcg tcgtttgtca tgggatgaac      4020
caagcctaac attaacatgc gccccagcac agaaacaaac agagcgttgc caccagaag      4080
aaacaagacc attaactgtg cgtgagtatg caagaataca gacttcccc gatgaatggg      4140
tatttgcagg ccaatgtca gcgaaatata agcaaatagg aaacgctgtt cctgttaatc      4200
tgtcatttgc tgttggcaaa tctgtggtac atctttaga taagataaat aaagataga      4260
ccctgtaaat aattctgtgt aattgctgcc atattaagg tgatcgctca ggcggtcacc      4320
gaactcgata ataaagcgac tcatcgcag ccgccagctc tggattggca tattccattt      4380
ttttgatgca tccttgatcg ccagagaaat gaccttccgc agcgagtcgt cagtcgggaa      4440
cactttacgc ttcttaatgg ccgcacggat cacgctgttc agcgattcga tagcgttcgt      4500
ggtgtagatg gccttgcgga tatcgggcga ataccgaag aacgtgttga tatttccca      4560
gtgcgcaacgc cagcttttgc tgatttgcgg gtatttatcg tccagacat tgggaactg      4620
ctccggtgcc actagcgcg cctcttctgt tggcgctga tacaccgtt ttaaccgcc      4680
agtgacggct ttgtagtcct tccaagatac gtatttcagg ctgttgcgca ccatatgaat      4740
gatgcaaac tggatgtgcg tctacggata cacgctgttt atgcatccg gaaagcttt      4800
cagacgtcc atgcaggcaa taggatatc ctgaagccc cgattcttaa gctctgtcag      4860
ccccccagc cagaacttgg cccttcgtt ctcggccagc cacatgccca gcaactcttt      4920
ctggcctccaa gtattaatac cgagtgcaag gaacaccgct tgttaattaa cggtgccacc      4980
ttgacgaact ttcaccacga tacagtcaag gtaaacaatg ggatacagtg catccagagg      5040
tcgatttgc cattctgcaa cctgctcttt gaccgcatca gtgactttac atatcagcgt      5100
```

FIG. 7 (continued)

```
gggtgacaca tctgcgtcgt acatctcttt gaaggtggcg acaatttcgc gggtagtcat   5160
atctttggcg tagagggata aaatctggct gtccatctgc gtaatgcgcg tctggtgctt   5220
cttaatcaac tgcggttcga aggtgttttc acggtcacgc gacgtgttca gttcgatcct   5280
ctacgccgga cgcatcgtgg ccggcatcac cggcgccaca ggtgcggttg ctgcgcccta   5340
tatcgccgac atcaccgatg gggaagatcg ggctcgccac ttcggctca tgagcgcttg   5400
tttcggcgtg gtatggtgg caggccccgt ggcggggga ctgttgggcg ccatctctt   5460
gcatgcacca ttccttgcgg cggcggtgct caacggctc aacctactac tgggctgctt   5520
cctaatgcag gagtcgcata agggagagcg tgactctag agtcgacctg cagcaatggc   5580
aacaacgttg cgcaaactat taactgggca actacttact ctagcttcc ggcaacaatt   5640
aatagactgg atggaggcgg ataagttgc aggaccactt ctgcgctcgg ccttccggc   5700
tggctggttt attgctgata aatctggagc cggtgagcgt ggatctcgcg gtatcattgc   5760
agcactgggg ccagatggta agccctcccg tatcgtagtt atctacacga cggggagtca   5820
ggcaactatg gatgaacgaa atagacagat cgctgagata ggtgcctcac tgattaagca   5880
ttggtaactg tcagaccaag tttactcata tatactttag attgatttaa aacttcattt   5940
ttaatttaaa aggatctagg tgaagatcct ttttgataat ctcatgacca aaatccctta   6000
acgtgagttt tcgttccact gagcgtcaga ccccgtacat cacgaatata gttgcttga   6060
catcctgaca agaataatat tgtaattaga aaaattatta ttttcatatt tctttccaac   6120
aaaagtaaaa atacttatgc atttaaaata ctacctacat aatttacctg aatcacttat   6180
accatggatt cttattttaa tatttaacga caatgataac actccttgt tatttatatt   6240
tatatcatca atacatgtat tgctatatcc atactctaaa ttaaccatat ctagatatat   6300
caaagaaaat acaaagttaa aaaagaacc ctggtactta tgcaagttat ctgcattgtt   6360
ttatttatta atggcaatcc cagtaggatt gccaagtttc atatattaca ctctaaagag   6420
aaattaaatc cctaacaact cattaagttt gtcaactca tcatccccta tgtaagaaga   6480
aacaatacct gtgacaattg caatccccca gaaaccaaga ggcaaccaa caataaaact   6540
aaacattaat gccacaattt ttgccacacc tacatcgacc gcacttttct ccagcgtgac   6600
aaacaaaggt cgccagttac cagttctat tgcatttta aaatcagaac cacatcata   6660
tagaaaagat actcgactgg tgattttaag cgactttgat atcttcgtta aattcttaga   6720
taactcatca taattaacag actctaacgc attaaaaata gcatcccgat caacttact   6780
gaatttctta tccagtacat tcttatactt ttcaaatgct gccagagctt catcaacacc   6840
ttgaattttc tttcctttag acttttccgc taaatcctga gcaattttg cgtatttttc   6900
tccatattgt tcggttatat attgataaaa tccaaccata gtttcaacag catctttat   6960
ctggctcttt tcaagagcat cctyagcttc ttttaattc tgctctgcct ctttaacctc   7020
agcggcctta ccatccctga cactaacagc attcttaatt tcattttcaa ctgcggagta   7080
ctcagcctgc ttagcttcaa gctgacgctg tagttttttc tgaacgtcac gccatccgg   7140
aaatccggag accttcacgt caacactctt ctgagcgttt tcaagctctc ctgcaactct   7200
ggaaacagta gcttgcttac tctgtacatc actttcagcc ttgccagtt cagtttcgc   7260
ctcagctaaa cgcttctctg cttccgccac cgcctgtttc tcttcattaa gagtttcatg   7320
ttcagcgacc tctgcatttt caccgagcct tcttcagct tcctctgtt tattcacatc   7380
accaatttta ctttgcaatg tattttata agaattaagt tgctaatat ctgcatcaag   7440
ctgatttgat tttttttgca actcatcaac atccctctca agatcagtga tacsatgata   7500
agaatgatgc ttgaatactt ttttcatctc ctcgatttc ttctgtttt cactaatctg   7560
tgtagcaatt ttattcttct gcttttgttt ttcattaatt acattactca ccaacttcga   7620
actcttatcc atatcactga cctgagcatt cgtggtgca gtattaactg agcagtgtt   7680
attgttgtta tttcctgagc tttctgcaaa aagtgatggc atatcactaa ttaaagaatt   7740
aagaactctg gagaccctc caaatggatt atcaccaga gttgaattct cttctgtcat   7800
aacaatacca ttcatcaccg gaaggccatc attattaatg acaacatcac cccacggagt   7860
cagatatgac tcacggtttt tcatcacagt tgatgtagaa ccagatgaat ttgaatttcc   7920
ctgaccacca ttattaccat gccagagcc accaccccag tgaacccac tattactatt   7980
attatttcca cctgctgat tcagattcgc ccctgttccc ccctagact cacccagcagt   8040
tggtccatat ccacttagtt ctttagccat aaattcctct tgataatta aacaataaa   8100
ttaaaaacaa tatactgtac atataaccac tggttttatg tacagtaaaa acctactact   8160
```

FIG. 7 (continued)

```
cagcattgtc catgtcaaga gcatggattt tcatttttgc aataaggatc acactatggg  8220
gaggcaggca ttgagaacgt cgaaacagaa cacggagca aatcaggatg agatataaaa  8280
ctgttggatc atgaaaaaac ggagaacgat gtgagcaaat caccccgcca taaactgaac  8340
aaaacagaca aacgacttct cgacaccctt gttgctgcg gatatgagca tgacaaagcc  8400
cgtgacctca tccagaaaca ggtttacacg ctgacactgg ctgatcagcg tcatgtggtc  8460
agtgaaatca gtaatggtgt gaatccacc caggctact cggcgtata ccaggcaaga  8520
cgcattcgcc tcgcccgtaa atatctgaac ggtaaaagg ttatggaaga aacggggaa  8580
aatacgccc catcagcgta aggatttctt ttgccgctcc agagactcca gttttttacg  8640
caaatcctct ctttttggg catctctggt gccagccagc tctgctctca actcatcgat  8700
ctgaagttgt atcttcagtc tattactgaa cattttctgt ctggcattaa catccgcaac  8760
aatgccgttt tttgtcttct cggccttttg ttgaaaaaca ttgctgtccg catgactggc  8820
aaccgaagca gaaagaacac taaaaagcag gactggcaca catttttca cgggattatt  8880
cctgactcat tgaccatcaa atcacattgg gagtaaaccg acgtatgata agagatactc  8940
ttcggagata taactccctg agtatcaaga ttaaaaacgc aaggagatgt ttatgagatc  9000
tgccgctgcc aggctgcttc tgataccttct gataacagca acaatagctc ttacaggatg  9060
cacaccaaag accagcctgg aacgacatac ccggcattat gtttatgctt cagatgatgg  9120
atttgatcct aacttctaca cccagaaagc agacaccata cgtatgatgc tccgttctt  9180
tcagcagttc cgggatatgg ggatgaaaga caaaccagcc ggagtatcag cagaaacggc  9240
acagcaacgt gtaaaagaat tccactcaga aaatttttt cactcactcc ggagcacaac  9300
agcctttgct ggcagaaaat acacaaacag cgatatgcct tcgccgaaaa aatgaaact  9360
aatggcagac accatttctg cggtttatct cgatggatac gagggcagac agtaaggat  9420
ttaccataat cccttaattg tacgcaccgc tgaaatgcgt tcagcgcgat cacggctgct  9480
gacaggtaaa aatggcaaca aaccaccga aagctgccg cgatcgcacc tgataaattt  9540
taacgtatg catagctatt cagccatgtg aataacgctg gttttgcctg cgtaaacctc  9600
atgacactgt ttttttttcca tcttttcagt tgatgacata cgcagacatc gcgggatgag  9660
gctgaggaat gagcgcgatc tggcaaagag gcaaaacaca gcaacaaaaa cgacacgcca  9720
gaatcgcgcc cggatgcgtt tttaacgcgt tccgtaccaa tctggcaacc tcccggaaca  9780
actcacgtc acatacctat tgacgggca cgccataccc gtgcttccg ttcctgctct  9840
tcatgcagg accgcgcacg ctccgttcc aggcgtgcct gctttcctg ttcatccctt  9900
atctgctgtt cgtgataaat aaccgactca agtggtccac ctgcccggct aatctctgca  9960
cctgctgact caagtcgtcg cactgttccc tcagttgccc gttctcctgt cgtgtcagct 10020
cgaacatatg ctgcaaatcc gtgaaggcgc tctcccagtc tttcagccgc tgcatatagt 10080
cctgctgcaa ttgctctaag gcgttcagta agtgcatttc cagctctgtc atactcactt 10140
actccctgac cagtcttact gcgttcttct tctccaccgt ccagttgttt tccccttca 10200
ccccggacgg caacactaga aatttcccgt tctgccctc gtgatacgtc acacccatg 10260
tttttccg gagttcgcc agcgtctctt cctggtccct gatagccagg atgttcgccg 10320
caatccggct ttcctgccac tgaatcagcc cccatgacg ccagaaaaat ccgcccgtg 10380
acgcagacg ccgtcagcga cgggtacagt atcgccctt tgaccagctt ccagagcagc 10440
tcttcctgcc gcgggccag ttgttctctc gtggcgtga actgcgcgtt cacggcactg 10500
ttcagcgtct ccagttgttc tttcaccgct gctgtgtgtg cgctgatagc gtctctgatt 10560
ttctgccgt ttaagttcag ttcctgtct acagacgctt cgagttcct gaactcgctg 10620
ttcagcatgt tctctgtaga gacggcacgc tctttcagtt tcttctcgaa gtctgtcccc 10680
atttgtaaaa gattgctcat acagcgccc tttcagcctg agattacgcc caccctcgg 10740
gtgggcgta ctgatactgc tcctggttgt cctcaccacc tcaaacctg ccgctgtaag 10800
cgcctcagtg acatcctgac gcgttttttag cgctccggca tggtaaagag cctccagtcc 10860
cctcgtaatc gcttctgcgg cctcctgttt cgctttcggc agattattcg gggtgacaag 10920
tgtccgcctg ttctccggtg cgttctgggtc gtgtcagccg taatggtgat tcaccagtgt 10980
ctgcagcga ttgattcgcg gacggtccgc tcggtcgtaa tagggctgga gcgttttcc 11040
gctcgccagc tccatattcg ggatgacaaa attcagctca agacgccct tgtcctggtg 11100
ctccacccac aggatgctgt actgattttt ttcaagaccg ggcatcagta cccgctcaaa 11160
gctctccatc accctttcac gctctccggt tggcagggtc tgctctgcaa aagacagaac 11220
cccgaggtg tatttttcg caaacggcgt ggcatcgatg agttccgca cctcttcggg 11280
```

FIG. 7 (continued)

```
agcacccgc agaactctcg cccttcccg gttacgtcc cggccagca ggtaatcaac    11340
cggaccactg ccacgcctt tcccctggc atgaaactta actatcatcc cgttctccct    11400
gtttacggac ctcatccctc agctcactca gttcacgtcc gatggccatc agtgcagcca    11460
ccaatgaac ccggtcatgc ccgaccact gtccgtgtt tatcttcgg gctatctgat    11520
tcaggttatt gccgaccgaa gcgaactggc gcaacagcgg cggtgccagt gtggaagac    11580
ctgacgtttt cgatggcggt gccccaggc agaccttacg catccatgac gcaagttgtt    11640
ttccctcaca acgtgccagc agccgcgcat gttcctcatc cgtgaccgt atcgtgagca    11700
tcctttcgcg tttcaccggt atcattaaaa acctccgaca gactcccac acatggagaa    11760
acagaactgt gactaaacag gaaaaacg cccttaacat ggcccgctc atcagaagcc    11820
agacgctgac cctgctggaa aaactgaatg aactggacgc cgacgaccag gctgacatct    11880
gcgaagcgct tcacgatcac gctgacgagc tttaccgcag ctgcctcgca cgcttcgggg    11940
ataacggtga aaactctga cacatgcagc tccggagac ggtcacagct ggcctgtgag    12000
cggatgccgg gagcagacaa gcccgtcagg gcgggtcagc gggttttagc gggtgtcggg    12060
gcgcagccat gacccagtca cgtagcgata gcggagtgta tactggctta atcatttggc    12120
atcagtgagg attgtatgaa aagtgcacca tgccgggtgt gaaatgccgc acagatgcgt    12180
aaggagaaaa tgctcgtcca ggcgctttc cgcttcctcg ctcactgact cgctccgctc    12240
ggtcgttcgg ctgcggcgag cggtatcagc tcactcaaag acggtaatgc ggttatccac    12300
agaatcaggg gataacgcca aagaacat gtgagcaaaa accagaacc cggaaaggc    12360
caggcagctg gcgttttcc ataggctcgg cccccttga cgagcatcac aaaaaacga    12420
cgctcaagtc agaggtggcg aaacccgaca ggacttaaag ataccaggcg tttccccctg    12480
gtggctccct cgtgcgctct cctgttccga cctgccgct taccggatac ctgtccgcct    12540
ttctcccttt gggaagcgtg gcgctttctc atagctcacg ctgttggtat ctcagttcgg    12600
tgtaggtcgt tgctccaag ctgggctgtg tgcacgaacc cccgttcag cccgaccgct    12660
gcgccttatc cggtaactat cgtcttgagt ccaacccggt aagacacgac ttaacgccac    12720
tggcagcagc cattggtaac tggatagtgg atttagatac gcagaactct tgaagttgaa    12780
gccttatagc ggctacactg gaaggacagc atttggtatc tgtgctccac taaagccagt    12840
tacccggtta agcagtcccc aactgactta accttcgact aaaccgcctc cccaggcggt    12900
tttttcgttt acaggcagca gattacgcgc agaaaaaaag gatctcaaga agatcctttg    12960
atctttccta ctgaacgcg atccccgtca gttcagaaga cgaagatggt gcaacggttc    13020
ctccttgtac aggggtctga cgctcagtgg aacgaaaact cacgttaagc aacgttttct    13080
aacctctgacg cctcttttaa tggtctcaga tgtcctttgg tcaccagttc tgccagcgtg    13140
aaggaataat ggccgagcat attgatatgt ccgtggcaaa gcggggagag gcgtgcgata    13200
tcttcatcat tcagtgtttc accttgcgcc cggagatgat ccaggctgc ctgcatatac    13260
atagtgttcc ataacacgac ggcgttagtg accagcccca gtgcgccag ttgatcttcc    13320
tgaccgtcgg tatatcgttt tcttatctca cctttttgac cgtgacagat ggctctggca    13380
acggcatggc ggctttctcc ccgattaagc tgggtcagaa tgccggcg gtaatcttca    13440
tcatcaatat aattaagcag atacagcgtt ttgttgatgc gccccacttc aatgattgcc    13500
tgagtcagtc cggaaggacg ttcactttc agcaatgaac ggaccagcac tgaagcctgt    13560
actttgccca gttcaaggga gccagcggtc cggatcattt cgtcccactg aaggactatt    13620
tttcggggat ctgattgccc tctgcaata tcattcagca cgccatagtt ggcatcatgg    13680
cccattcgcc agaaaacga agcacggca tcagccaggc gtgagaaaa ctggtatccc    13740
agcagccaga aaaggccaaa gacaagttcg ctggtacctg ctgtatcggt cataatttcg    13800
gttggattca gccggtctc ctgttccaga aggcttcca gcacaaagat agagtccctc    13860
agcgtcccg gtataacgat gccatgaaag ccggaatact gatcggacac aaagttgtac    13920
caggtgatcc ctctgttatt accaaagtat ttgcggttcg gtccggcatt gattgttctg    13980
actggcgtaa caaagcgcat tccatctgca gtccgcctca gcaatatcgg datagagcgc    14040
agggtcagga aatccttgga tatcgttcag gtagccacg ccgcgttga gcgcatagcg    14100
ctggttccc ggttggaagc tgtcgattga aacacggtgc atctgatcgg gcagggcgtc    14160
taagagcggc gcaatacgtc tgatctcatc ggcggcgat acaggcctcg cgtccggatg    14220
gctggcggcc ggtccgacat ccacgacgtc tgatccgact cgcagcattt cgatcgcgc    14280
ggtgacagcg ccggcgggt ctagccgccg gctctcatcg aagaaggagt cctcggtgag    14340
```

FIG. 7 (continued)

```
attcagaatg ccgaacaccg tcaccatggc gtcggcctcc gcagcgactt ccacgatggg    14400
gatcgggcga gcaaaaggc agcaattatg agcccatac ctacaaagcc ccacgcatca      14460
agcttttgcc catgaagcaa ccaggcaatg gctgtaatta tgacgacgcc gagtcccgac    14520
cagactgcat aagcaacacc gacagggatg gattcagaa ccagagaaca tgtcattgta    14580
ctggaaggcg cattacaact gcggctgggg gatgagtggc acaccgtttc tgccggggaa    14640
tccctgcgct tccatgcgga tatccgcac gcttacgcca atcccggtaa ggccattgtg     14700
acactgcata atctgatcca ttatccgcgc ccggcggaca aataaaaag cagggtataa     14760
taaatatacc ccgctttgac ttaacggatc gtcttactt atttgtaaaa taaaaccaaa     14820
ataaatatgt gttcagctta acttattata tatcatcctt ataccaaccg ggatgatatg    14880
tttatactga acagaaaagc atgccattca gaatactatc ttctgttata tatggcggtt    14940
tatttattgt ttaattacac acactcaggc atatcactat gctatcgtga tgttttcact    15000
ggtgttgtta ctactgcctt tacggcattt tggtgttgtt caaaatgact gtcgcagcag    15060
tctttctggt gtcttaaata ctattattat aactgcatct ggtgttgtta atattattgt    15120
tactgcttac tttattatta ttgctgtcag tcttgctgt tcttttttta ttaagggtat     15180
taccaaactg cggggcatt atcgtacagt gatcctgaac cagtctgaaa cgaaattaca    15240
gattacggtt aaaatataaa aaaagccac cattcctgcc ggatacggtg gcttaaatac    15300
agaattaatt aatttatttc agtatgttat cacacatcag ctgaagtgta ttaataaacc    15360
gtgctgcatg aaagccatca cagactgcat gatgaacctg tacagaaaca ggtaataata    15420
cgcggtcacc ttcctgctga aactttgcca tcgtaaaaac cggggcaaaa taatcatcat    15480
ttccggtgat gttcaggtta aatccgtcaa aactcaccca cggtaatgat gatatattca    15540
ggtgattctc cggtaaattt ccctgcggaa acaatctggt atcatgctga tattctgcg    15600
ttaccgcatt ataacctgcc ataaactcac tgagatccgg aaaataacgg caggacagtg    15660
cagagaatgt ttcggtttct ttatgaaaga cagtaagac cgggtctgac tggtccagt     15720
aaataagttc attgtctttc agtgccatcc ggaactccgg aaactgatta acagccggg    15780
agatcaggta aatcatcagc ggataaaact tataacctgt ctccgccagt gcggtacgca   15840
aagcggtaat atcgagttg gtggtcaggc tgaatccgca tttaatctgc tgacgataaa    15900
gggcaaagtg ttccctgcga ttccaggtat tcaggtcaat ccgggtaaaa ttcatggtta   15960
ttccttctga ttaatagtga aaatattaa taatcagaag gcagtctggt tgtctcaatg    16020
ggtaacattc cgtcctccgt aagctgtttg gtattcagta ataatacct atacgggctt    16080
aatctgtatt aagcccggct ttatttattc cggccaatca tcgcaaaca catagcggat    16140
cagttctgcg gattcacggt gcggtgctct cagcacatcc gccattaaat caatctccat    16200
ctgacaggtt tgcagcttgt cttccgccgg tacatacgga tcatccgtca ggaaactatc    16260
gccgtattta tccatcgacc cctgtatttg tgccgaaaat a                        16301
```

FIG. 7 (continued)

```
ID   TK225\pABICyano1-6.6_PnirAABICyano1-PDCmax-synADHmax-PrbcABICyano1-Km**-oriVT
     standard; circular DNA;    ; 12963 BP.
CC   This file is created by Vector NTI
CC   http://www.invitrogen.com/
CC   VNTDATE|625138593|
CC   VNTDBDATE|625140543|
CC   LSOWNER|
CC   VNTAUTHORNAME|Frank Uliczka|
FH   Key             Location/Qualifiers
FT   promoter        3574..4099
FT                   /vntifkey="30"
FT                   /label=PrbcLABICyano1
FT   CDS             4101..4916
FT                   /vntifkey="4"
FT                   /label=Km**
FT                   /note="maximal codon optimized kanamycin resistance gene"
FT   CDS             12473..12726
FT                   /vntifkey="4"
FT                   /label=ORF\6
FT                   /note="orf6"
FT   CDS             12218..12481
FT                   /vntifkey="4"
FT                   /label=ORF\5
FT                   /note="orf5"
FT   CDS             11490..12176
FT                   /vntifkey="4"
FT                   /label=ORF\4
FT                   /note="orf4 Integrase/Recombinase Similar to Site-specific
     recombinase of Bacillus thuringiensis serovar israelensis ATCC 35646"
FT   CDS             complement(10400..11164)
FT                   /vntifkey="4"
FT                   /label=ORF\3
FT                   /note="orf3"
FT   CDS             9955..10140
FT                   /vntifkey="4"
FT                   /label=ORF\2
FT                   /note="orf2"
FT   rep_origin      complement(9255..9272)
FT                   /vntifkey="33"
FT                   /label=Rep_Origin_1\(potential)
FT                   /note="potential rep origin; match pNostoc (Acc# M81381) nick
     site (358-375); on reverse strand"
FT   misc_feature    9515..9548
FT                   /vntifkey="21"
FT                   /label=Rep\motif
FT                   /note="Rep protein active site motif EXXKYXVKXXD"
FT   CDS             6734..9919
FT                   /vntifkey="4"
FT                   /label=ORF\1
FT                   /note="orf1  rep ori binding protein slr7037 homolog Similar to
     hypothetical protein slr7037 of plasmid pSYSA (103 kb)  of Synechocystis sp. PCC 6803"
FT   rep_origin      complement(5159..6217)
FT                   /vntifkey="33"
FT                   /label=OriVT
FT   insertion_seq   6224..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
```

FIG. 9

```
FT   terminator      3214..3369
FT                   /vntifkey="43"
FT                   /label=TrbcSABICyano1
FT   promoter        96..378
FT                   /vntifkey="30"
FT                   /label=PnirAABICyano1
FT   CDS             2203..3213
FT                   /vntifkey="4"
FT                   /label=synADHmax
FT   CDS             379..2085
FT                   /vntifkey="4"
FT                   /label=PDCmax
FT   gene            2203..3213
FT                   /vntifkey="60"
FT                   /note="ADH"
FT   gene            379..2085
FT                   /vntifkey="60"
FT                   /note="PDC"
SQ   Sequence 12968 BP; 4008 A; 2277 C; 2560 G; 4123 t;
     aatattttc  gtcagataog  caaacottac  aaacataatt  aacaactgaa  actattgata          60
     tgtctaggtt ttagctctat cacaggttgg atctgtcgac aattaataac ttcttcctgt         120
     acgggcgaat ggccatttgc tcctaactaa ctctgcggaa cgagcgtago                     180
     gaactctccg aattactaag ccttcatccc tgatagatgc aaaaaacgaa ttaaaattat         240
     gtgtaaaaag aaaatgtgtc tttatttagt agtcaaagtt acaaaatatt aagaatcaaa         300
     ttaataatgt attgggcagt taagtatata agtcttttaaa tatttatttg tattcaatat         360
     attaaccgag gataaattat gaattcttat acogtgggta cttatttagc cgaacgctta         420
     gtgcaaattg gtttaaaaca tcattttgcc gtggctgggg actataattt agtgttattg         480
     gataacttat tattaaataa aaacatggaa caagtgtatt gttgtaatga attaaattgt         540
     ggttttctg  ctgaaggtta tgctagagct aaagtgcag  ctgctgctgt tgttacttat         600
     tctgtgggtg ctttatctgc ttttgatgct attggtggtg cttatgccga aaattaccc          660
     gtgattttaa ttctggtgc  ccctaataat aatgatcatg ccgctggaca tgttttacat         720
     catgccttag gtaaacgga  ttatcattat caattagaaa tggccaaaaa tattactgct         780
     gctgccgaag ctatttatac tcctgaagaa gccctgcca  aaattgatca tgtgattaaa         840
     accgcttaac gggaaaaaa  accgtgtgat ttagaaattg cctgtaatat tgcttctatg         900
     ccttgtgctg ctcctgggcc tgcttctgct ttatttaatg atgaagccctc tgatgaagct         960
     agtttaaatg ctgccgtgga agaaaccttta aaatttattg ccaatacgcga taaagttgcc        1020
     gtgttagttg gttctaaatt aagagctgct ggtgtaagaa aagctgctgt taaattgct          1080
     gatgcttag  gtggtgcagt tgctactatg gctgctgcca aatcttttt  tccgaagaa          1140
     aatccccatt atattggaac tagttgggga gaagttcttt atcctgtgt  ggaaaaaact         1200
     atgaagaag  ccgacgctgt tattgcttta gcccctgtgt taatgatta  ttctaccact         1260
     ggttgactg  atattccga  tccaaaaaa  ctagttttag ccgaacctcg ttctgttgtt         1320
     gttaatggtg ttcgttcc  ctctgtgcat taaaagatt  attaaaccog cttagccaa          1380
     aaagtttcta aaaaactgg  tgccttagat tttttaaat ctttaaatgc gggtgaatta         1440
     aaaaagctg  ctcctgctga tcctctgct  cctttagtta atgctgaaat tgccgtcaa         1500
     gttgaagcct tattaaccgc taatactacc gttattgccg aaactggtga ttcttggtt          1560
     aatgcccaac gcatgcaatt cactaatggt gccgtgttg  aatatgaaat gcaatgggt          1620
     catattggtt ggtctgtacc tgctgctttt ggttatgctg ttgtgctcc  tgaacgtcgt         1680
     aatttttaa  tggtgggtga tggttctttt caattaactg ccaagaagt  tgccaaatg          1740
     gttcgcttaa aattacccgt tattattttt ttaataaata attatgttta taccattgaa         1800
     gtgatgattc atgatgggcc atataataat attaaaatt gggcttatgc gggtttaatg         1860
     gaagtgttta atgtaatgg  tgttatgat  tctggtgctg gtaaagtttt aaagccaaa          1920
     actggtggtg aattagtcga agctattaaa gttgcctag  ccaatactga tgggccaacc        1980
     ttaattgaat gtttattgg  ctcgaagat  tgtaccgaag aattagtaa  atgggtaaa          2040
     cgtgttgctg ctgctaattc tcgcaaaccc gtaataaat tattgtaatt tttggggatc        2100
     aattcgagct cggtacccaa actagtatgt agggtgaggt tatgctagc  gcttttaatt        2160
     aatccgcgga tttgtattca atatattaac cgaggacaac atatgattaa agcctatgct        2220
     gccttagaag ccaatgtaa  attacaaccc tttgaatatg atcctgtgc  tttaggtgcc        2280
     aatgaagtgg aaattgaagt gcaaatattgt ggtgtgtgtc attctgatt  atctatgatt        2340
```

FIG. 9 (continued)

```
aataatgaat gggqtatttc taattatccc ttagttcctg gtcatgaagt tgttggtact   2400
gttgctgcta tgggtgaagg tgttaatcat gtggaagtgg gtgatttagt tggtttaggt   2460
tggcattctg gttattgtat gacctgtcat tcttgtttat ctgttatca taatttatgt   2520
gccactgccg aatctactat tgtgggtcat tatggtggtt ttggtgatag agttcgtgct   2580
aaagtgttt ctgtggtgaa attaccaaa ggtattgatt tagcctctgc tgggccttta    2640
ttttgtggtg gtattacgt ttttctccc atggtggaat tatcttttaaa acctacggcc   2700
aaagttgctg ttattggtat tggtggttta ggtcatttag ccgttcaatt tttaagagcc   2760
tgggttgtg aagttactgc tttacctct tctgcccgta aacaaaccga agtttagaa     2820
ttaggtgccc atcatatttt agattctacc aatcctgaag ctattgcttc tgccgaaggt  2880
aaatttgatt atattatttc taccgtgaat ttaaaattag attggaattt atatatcagt  2940
aacttagccc ctcaaggtca ttttcatttt gttggtgtgg tgttagaacc cttggactta  3000
aacttatttc ccttattaat gggacaacgt tctgtttctg cttctcctgt tggtctcct   3060
gctactattg ccactatgtt agattttgcc gtgcgtcatg atattaaacc cgtggtggaa  3120
caattttctt ttgatcaaat taatgaagcc attgcccatt tagaatctgg taaagcccat  3180
tatcgcgtgg tgttatctca ttctaaaaat taataagatt aacttctaaa ctgaaacaaa  3240
tttgagggta ggcttcattg tctgcccta tttttttatt taggaaaagt gaacagacta   3300
aagagtgttg gtctatttgc tttgagtatg taaattaggc gttgctgaat taaggtatga  3360
ttttgacc cttctctctt ctgcagttac ctaggatttc tggcgaaagg gggatgtgct    3420
gcaaggcgat taagttgggt aacgccaggg ttttcccagt cacgacgttg taaaacgacg  3480
gccagtgagc gcgacgtaat acgactcact ataggcgaa ttggcggaag ccgtcaagg    3540
ccgcatggcg cgctacgta gacaattgtc gatgtaatta ttaactatct tattatagat   3600
gaggggagag ggagaaatta gttcggagag aacgctcgag cgctcgttcc gcaaagcggt  3660
acggagttag ttaggtgcta atgggcattc tccgtacag gaaagagtta gaagttatta   3720
attatcaaca attctccttt gcctagtgca tcgttacctt tttaattaaa acataaggaa  3780
aactaatat cgtaataatt taacctcaaa gtgtaaagaa atgtgaaatt ctgacttta    3840
taacgttaaa gaggaaaaa ttagcagttt aaaataccta gagaatagtc tggggtaagc   3900
atagagaatt agattagtta agtaatcaa attcagaaaa aataataatc gtaaatagtt   3960
aatctggggt tatagaaaat gatcccctta atgataagat ttaaactcga aaagcaaaag  4020
ccaaaaaact aacttccatt aaaagaagtt gttacatata acgctataaa gaaaatttat  4080
atatttggag gataccaacc atgtctcata ttcaacgtga aactagttgt tctcgtcctc  4140
gtttaaattc taatatggat gccgatttat atggttataa atgggctcgt gataatgttg  4200
gtcaatctgg tgctactatt tatcgtttat atggtaaacc tgatgctcct gaattattct  4260
tgaaacatgg taaaggttct gttgctaatg atgttactga tgaaatggtt cgtttaaact  4320
ggttgactga atttatgcct ttacctacta ttaaacattt tattcgtact ccgatgatg   4380
cttggttatt aactactgct attcctggta aaactgcttt tcaagtttta gaagaatatc  4440
ctgattctgg tgaaatatt gttgatgctt tagctgtttt tttacgtcgt ttacattcta   4500
ttcccgtttg taattgtcct tttaattctg atcgtgtttt tcgtttagct caagctcaat  4560
ctcgtatgaa taatggttta gttgatgctt ctgatttga tgatgaacgt aatggttggc   4620
ctgttgaaca agtttggaaa gaaatgcaca aattgttacc ttttctcct gattctgttg   4680
ttactactgg tgattttct ttagataatt tgatcttga tgaaggtaaa ttgattggtt    4740
gtattgatgt tggtcgtgtt ggtattgctg atcgttatca agatttagct atttttatgga  4800
attgtttagg tgaattttct ccttcttac agaaacgttt atttcagaaa tatggtattg   4860
ataatcctga tatgaacaag ttacaatttc atttaatgtt ggacgagttc ttttaagaat  4920
taattcatga ccaaaatccc ttaacgtgag ttttcgttcc actgagcgtc agacccgta   4980
gaaagatca aggatcttc ttgagatct ttttttctgc ggtaatctg ctgcctattat     5040
aattacgtac acgtgttatt acttgtgttaa cgacaattgt cttaattaac tgggcctcat  5100
gggccttcg ctcactgccc gctttccagt cgggaaacct gtcgtgccag ctctgcagat    5160
gaccgtgaaa acctctgaca catgcagctc ccggagacgg tcacagcttg tctgtaagcg   5220
gatgccggga gcagacaagc ccgtcaggc gcgtcagcgg gtgttggcgg gtgtcggggc    5280
gcagccatga ccccagtcacg tagcgatagc ggagtgtata ctggcttaac tatgcggcat   5340
cagagcagat tgtactgaga gtgcaccata tgcggtgtga ataccgcac agatgcgtaa    5400
ggagaaaata ccgcatcagg cgctcttccg cttcctcgct cactgactcg ctgcgctcgg   5460
tcgttcggct gcggcgagcg gtatcagctc actcaaaggc ggtaatacgg ttatccacag   5520
aatcagggga taacgcagga aaacatgt gagcaaaagg ccagcaaag gccaggaacc      5580
gtaaaaaggc cgcgttgctg gcgtttttcc ataggctccg cccccctgac gagcatcaca   5640
aaaatcgacg ctcaagtcag aggtggcgaa acccgacagg actataaaga taccaggcgt   5700
ttccccctgg aagctccctc gtgcgctctc ctgttccgac cctgccgctt accggatacc   5760
tgtccgcct tctcccttcg gaagcgtgg cgctttctca tagctcacgc tgtaggtatc     5820
tcagttcggt gtaggtcgtt cgctccaagc tgggctgtgt gcacgaaccc ccgttcagc    5880
ccgaccgctg cgccttatcc ggtaactatc gtcttgagtc caacccggta agacacgact   5940
```

FIG. 9 (continued)

```
tatcgccact ggcagcagcc actggtaaca ggattagcag agcgaggtat gtaggcggtg    6000
ctacagagtt cttgaagtgg tggcctaact acggctacac tagaaggaca gtatttggta    6060
tctgcgctct gctgaagcca gttaccttcg gaaaaagagt tggtagctct tgatccggca    6120
aacaaaccac cgctggtagc ggtggttttt ttgtttgcaa gcagcagatt acgcgcagaa    6180
aaaaaggatc tcaagaagat cctttgatct tttctactgc agaagcttgt tagcaaccct    6240
gtcatgtatt ttatattatt tatttcacca tacggattaa gtgaaccta atgaaaatag    6300
tactttcgga gctttaactt taatgaaggt atgttttttt atagacatcg atgtctggtt    6360
taacaatagg aaaagtagc taaactccc atgaattaaa gaaataacaa ggtgtctaac    6420
aacctgttat taagaatgtt agaaaagact taacatttgt gttgagtttt tatagacatt    6480
ggtgtctaga catacggtag ataaggtttg ctcaaaaata aaataaaaaa agattggact    6540
aaaaaacatt taatttagta caattcaatt agttattttt tcgtctcaaa ttttgctttg    6600
ttgagcagaa attagataa aaaaatcccc gtgatcagat tacaatgtcg ttcattgtac    6660
gatgtgtcga aaatcttta cgacactcta aactgaccac acggggggaaa aagaaaactg    6720
aactaataac atcatgatac tggaaaaacc tagcaattct caacccctaa acaaaagaaa    6780
cttccaaaac cctgaccata taaggagtg gcaaaaataca gcaatcagtc aagattgat    6840
agcagaaaat cttgctatcg ttgctaatgg ttttgatgta ctatttatcg gcaataaata    6900
ccgaactaac acgggtgttc tgtcacggca catattaaac tcctattctc atttagaaga    6960
tggtggttcg tatggtagaa cattgaccc atttaccaat aaagaaatgc agtgggttca    7020
atttaaaccg aatagaccaa gaaaggttc tactggtaag gtaatcaaat atgaatcgcc    7080
aaaaggtgaa cctacaagag ttctaatgcc gtttgtgcct atgaaaatat ggcaacggat    7140
tagcgataag ttcggagtac cgattaatcc gaaaaaagat actcacttt gggaatgggt    7200
aaagaataat ccatcgatac cgattgccat tacagaagga aataaaaag ctaattgcct    7260
attatcctat ggctatcctg ctattgcctt tgtaggcatt tggaacggat tagagaaaat    7320
aaatgatttc tcgaaggaaa agcagttaaa agaggatttg aaatggttgt tatccaacgg    7380
caaccgaaat attaatatca tctttgacca agaccagaaa caaaaaactg taattaatgt    7440
aaacaaagct atttttcgctt tatcttctct aataagtaga aatggtcata aagttaatat    7500
tgtgcaatgg ttgccgtcaa aaggtaaagg aatagatgat tatttggtag cttttacctt    7560
tgagaaaaga gaaaatcatt tagacaactt caattaaatt gcaccatcat ttaatttttg    7620
gtcaactaaa tactattca agtgtcgtaa accagattta acgtaaatt gccgttattc    7680
gagcgatgca gtaaaagaat taccctcaaga ggatatagca ttaatagcac ctcacggcac    7740
gggtaaaact tcattagtag ctactcacgt taagaatcgg agttatcacg gaaggaaaac    7800
tatttcattg gtgcatcttg aaagttagc caaagctaat ggcaacgcac ttggattata    7860
ttaccgaacc gaaaataata ttgaaaagca atatcttgga tttagcttac gtgtagatag    7920
ttgccgtgat aagattaacg gcattacaac tgatatatt tcaggtcaag attattgcct    7980
tttcattgat gaaattgacc aagtaattcc acacatcctt aacagtgaaa ctgaagtaag    8040
taagtataga tgcaccatca ttgacacttt ttctgaactg gtgagaaatg ctgaacaggt    8100
cattattgct gatgctgatt tatccgatgt gacgattgac ctaatagaaa acatcagagg    8160
taaaaaacta tatgtaatca agaatgaata tcagtatcag ggaatgactt taacgccgt    8220
tggttcacca ttagaaatga tggcaatgat gggaaaatcg gtgtcagaag gcaagaaatt    8280
atttattaac accacatcc aaaaggcaaa aagtaagtac ggcacatcc ctcttgagtc    8340
ttatatttt ggtctaaata aagaagcaaa gatattaaga ataactctg aaaccactaa    8400
aaacctgaa catccagcct ataaatcat tgaccaagac ttaaataata tcctcaaaga    8460
ttatgattat gtcattgcct cacctgcct tcaaacaggt gtcagtatta cttaaaagg    8520
gcatttgac cagcaattta actttccag tggaaacatt acacctcatt gcttttaca    8580
gcaaatgtgg cggttgaggg atgcagaaat tgaaagattc tattatgtgc cgaactcatc    8640
taacctcaat ctcattggga ataagtcaag ttaccatca gaccttctaa agagcaataa    8700
caagatggca acggcaacgg ttaacctttt gggtagaatc gactccgaat attccctaga    8760
gtatgaatcg cacggcattt ggcttgagac gtgggcaaaa ttatcagcac ggcataacag    8820
ttcaatgcgt tgttactctg aaattcttac ctatctaatt acgtctcaag ggcataaatt    8880
aaatatcaac attcctctac ctcttgcaga tattaagaag ctaaatgatg aggtaagtag    8940
taacaggga aaggtaaaaaa atgagagata ctctcagagg ttaaactcac cagatattaa    9000
cgatgcaaa gctaccatac tcgaatctaa agaaaatcggtat atcggtataa tctcaaatga    9060
gagatgcacc ctagaaaagc ataaagttaa gaagcggtat gggaatgtaa agatggatat    9120
tctcaacttt gatgatgatg gactataccc caaactcaga ctattttatt acctcaccat    9180
cggtaaacct catctcaagg ctaatgacag aaaagctatt gccaaatgg gcaatgacaa    9240
taaggcaag attctatcaa aagcttagt taataaaact tactccgctc gtgtgaaggt    9300
cttagagatt cttaaactaa ctgactttat cgcaatctt agagatgaac tcttaataac    9360
tcccaataat ccagctatca ccgactttaa taatcttctg ctaagagcta agaaggattt    9420
aagagtatta ggagtcaaca tcggaaaata tccaatggcc aacattaatg ccgtacttac    9480
```

FIG. 9 (continued)

```
tctcattggt cacaaacttt ctgtaatgag agatgagttc ggaaaagaga aaaggataaa      9540
agtagatggt aaatcatacc gatgttatca acttgaaaca ttaccagatt ttaccaatga      9600
tactcttgac tactggttag aaaatgatag ccaaaaagaa gtaacagcaa cagaaaatta      9660
ctccgaaaat tttaaccctt caaatagcta caatccagac agtaagcacc tttcagaggg      9720
tgcaaatttc ctatatataa ataaagaaga attgcatcca aataaattgc acctagaaat      9780
aaaagaaggt gctgaacttt ttttattcgg ggtaaaggtg attgtaaaga gaatcttgga      9840
cggggcagta actatattct ctatgggtca agaatacgat ttatccctca atgaactaga      9900
ggggatgtta acatcatgaa ctttacaaga atctttttaa agggcgatcg caccatgtta      9960
aatgatggta catttgttca gatatttgat atttaccatg accacgcatt gggagtgacc     10020
cttgacctta agacagaaaa aattatttcc gatgatgtta gggtaattac tgtcaaagac     10080
ttattgttcg atggcactta taaagggta aaatctttta tgcccgataa tgcccgataa     10140
tgcccgattg atgctacaaa atcccataat cataagcgat aatcccctaa tagcttgtaa     10200
ttcttgaacc gtagcgattt tagagtattc caaaagaag aaataaacac cgcaaaatgt      10260
cgtatttcac atatataaac caaggttttt tgccctaaaa tctttatgtt tgtagtgtga     10320
tgttgggtca aaatggtcag aaaagttgca aggttttat ggatgcttac gcgcgcgagg      10380
ggtaagcatc cccaaatagt tactttatcc tagtccatgc ccatttattg ccgtccgtt      10440
cggctttaaa aaagtgccaa aactcacaag gtgcaataaa aagttctgta cctttcgcaa     10500
ccctagataa tctttcaaca gttactttttt ttcctattat ctcggtacaa agtttggcta   10560
gtttctcttt tccctctttt tcaatcaagc cttcttgtat gcccaactca ttgattaatc     10620
tctctatttt taccattatt tcccgttcag gtagtttatc ccctaaatct tcatcggggg     10680
gcaatgtagg gcattctgaa ggggcttttt cttctgtctg gacattatct aatattgaag     10740
taaccaaact atcttcagtt ttttctattc ctattaattc atattcggtt actgtatccg     10800
tatcaatatc cgaataacta tctttatccg tattagctat tggttaagt ttatccgtta     10860
actcagaaac aagactatat agcggtttta gcttttcttc tatcctgtta tctaatacgg     10920
ataagtttat acggttatca ttatccgtat tagtatcatt gggcttttt ggtagttcta     10980
ccccctcata aaccgctttt attcccaatt ccaacagact gataacagta tcctttataa     11040
tgggtttttt gctgatatgg tgaacttttg cccctcccat cattcgata cttctatct      11100
cactcatcaa cttatcgctt aagtgaatct cgtatctgtt taatcccta ctggtttat      11160
tcatatccgt ttacttttatt cggttaacaa tttcatttt tacgaataaa atattatacg    11220
gttaacttta tacgtttaac tatttatct atacggataa cagtaatacg ttattcgtat    11280
tagttatacg tttactttta tccaaataaa attagtgcat ttaaactaaa agaatgattt    11340
tatcggagtt gatagcattg gattaaccta agatgtttaa taagtctatat ctgataagta  11400
tttaaggtta tttgttatt ctgtttatg acattatcag aataaaagaa tagaatataa      11460
ttgttgagag ataagaggtt taagtgatta tggttaagaa gttagttggt tatgtcaggg    11520
tcagtagtga atcgcaagag gataacacta gcttacagaa tcagtacagag agaattgaag   11580
catattgtat ggcttttggt tatgagttgg taaaaatatt caaagaggtt gccactggta    11640
caaagcaga tattgaaacc cgtcctattt ttaatgaagc tatagaatac ttgaaacagg     11700
ataatgctaa tggaattatt gccttgaagc tagacggaat cgcacggaat gctttagatg    11760
tattcgttt ggttcgtgaa accttagaac cacaaaataa aatgttagtg ttactagata    11820
ttcaggtaga tacttcgaca ccttcaggaa aaatgatttt aactgtaatg agtgccgttg    11880
ctgaactcga aagagcatg atctatgatc gcactcaggg gggtagaaag actaaagccc    11940
aaaagggcgg gtatgcctac gggaaaccta aatttggcta taagactgaa gaaaaggaac    12000
taaagaaga ttcagcacaa caggaaacta ttaaactaat taagagacac cgtaggtcag     12060
ggaaaagcta ccagaaaata gctgattatc tcaatgccca aagtattccc actaacacaag   12120
gtaagaaatg gagttctagc gtcgtctatc gaatctgtca ggaaaaagct ggttaagtct    12180
gtttatagat atttagaatt tattgaataa aaatagtatg aacaataat atttatggac    12240
taaccacgct cggaaacgtt taactgaacg atgggaaata aagaatcat gggttattga    12300
taccatcgaa aatcctgaac gttcagaatt tattgttgat gagtcagggg aaaaatatca    12360
ttactataaa agaatagcta agtttaagaa tagagtgtta gaagtgataa cttctgccaa    12420
ctcaacaccc acaagaataa taccttttta ctttaaccgt aacatgagga aaaatttatg    12480
attgttactt acgataatga agttgacgca atttatttta agttaacgga aaataaaatt    12540
gatagcaccg aacctcaaac agacaggatt atcattgatt acgatgaaag taataatatt    12600
gttggcattg aggtattaga ttttaattat cttgtcaaga aaggtttaac cgttgctgat    12660
ttacctttt ctgaagatga aagattaaca gcttctcaat atttaatttc tctgttgct     12720
atctaatcca gaagggcaa taatcccctt ctttcatcga gttagactta atatcacaaa    12780
agtcatttc atttatacgt ttcttttcca cagcgtccgt acgccctcg ttaaatctca     12840
aaacgacaa tttatgacgt ttataaaaag ttactcactt taataagtat ttatactcat    12900
taaagggtta ttcttttttt gtagcctgat aggttgggaa ggaatatttc agattatcag    12960
atttgttg                                                              12968
```

FIG. 9 (continued)

```
ID   TK293\pABICyano1-6.8_PnirAABICyano1-PGCmax-PrpeLABICyano1-synAQHmax-
     PrbcABICyano1-Km**-oriVT standard; circular DNA;     ; 13449 BP.
CC   This file is created by Vector NTI
CC   http://www.invitrogen.com/
CC   VNTDATE|620148318|
CC   VNTDBDATE|609812662|
CC   LSOWNER|
CC   VNTAUTHORNAME|Frank Oliczka|
FH   Key             Location/Qualifiers
FH
FT   promoter        4055..4580
FT                   /vntifkey="30"
FT                   /label=PrbcABICyano1
FT   CDS             4582..5397
FT                   /vntifkey="4"
FT                   /label=Km**
FT                   /note=" maximal codon optimized kanamycin resistance gene "
FT   CDS             12959..13207
FT                   /vntifkey="4"
FT                   /label=ORF\6
FT                   /note="orf6"
FT   CDS             12699..12962
FT                   /vntifkey="4"
FT                   /label=ORF\5
FT                   /note="orf5"
FT   CDS             11971..12657
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10881..11649)
FT                   /vntifkey="4"
FT                   /label=ORF\3
FT                   /note="orf3"
FT   CDS             10436..10631
FT                   /vntifkey="4"
FT                   /label=ORF\2
FT                   /note="orf2"
FT   rep_origin      complement(9736..9753)
FT                   /vntifkey="33"
FT                   /label=Rep_Origin_1\(potential)
FT                   /note="potential rep origin; match pNostoc (Acc# M81381) nick
site (358-375); on reverse strand"
FT   misc_feature    9996..10029
FT                   /vntifkey="21"
FT                   /label=Rep\motif
FT                   /note="Rep protein active site motif EXXKYKVKKKD"
FT   CDS             7215..10400
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
```

FIG. 11

```
FT   rep_origin      complement(5640..6698)
FT                   /vntifkey="33"
FT                   /label=OriVT
FT   insertion_seq   6705..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   promoter        2112..2680
FT                   /vntifkey="30"
FT                   /label=PrpsLABICyano1
FT   gene            379..2098
FT                   /vntifkey="60"
FT                   /note="PDC"
FT   gene            2684..3694
FT                   /vntifkey="60"
FT                   /note="ADH"
FT   CDS             379..2085
FT                   /vntifkey="4"
FT                   /label=PDCmax
FT   CDS             2694..3691
FT                   /vntifkey="4"
FT                   /label=synADHmax
FT   promoter        96..378
FT                   /vntifkey="30"
FT                   /label=PnirAABICyano1
FT   terminator      3695..3850
FT                   /vntifkey="43"
FT                   /label=TrbcABICyano1
SQ   Sequence 13449 BP; 4193 A; 2336 C; 2598 G; 4322 t;
     aatatttttc gtcagatacg caaaccttac aaacataatt aacaactgaa actattgata        60
     tgtctaggtt ttagctctat cacaggttgg atctgtcgac aattaataac ttcttcctgt       120
     acgggcgaat ggccatttgc tcctaactaa ctccgtactg ctttgcgaaa cgagcgtagc       180
     gaactctccg aattactaag ccttcatccc tgatagatgc aaaaaacgaa ttaaaattat       240
     gtgtaaaaag aaatgtgtc tttatttagt agtcaaagtt acaaaatatt aagaatcaaa        300
     ttaataatgt attgggcagt taagtatata agtctttaaa tatttatttg tattcaatat       360
     attaaccgag gacaaattat gaattcttat acgtgggta cttattagc cgaacgctta        420
     gtgcaaattg gtttaaaaca tcatttgcc gtggctgggg actataattt agtgttattg        480
     gataacttat tattaaataa aaacatgaaa caagtgtatt gttgtaatga attaaattgt       540
     ggttttttctg ctgaaggtta tgctagagct aaaggtgcag ctgctgctgt tgttacttat       600
     tctgtggtg ctttatctgc ttttgatgct attggtggtg cttatgccga aaatttaccc        660
     gtgatttaa ttctggtgc cctaataat aatgatcatg ccgctggaca tgttttacat        720
     catgccttag gtaaaaccga ttatcattat caattagaaa tggccaaaaa tattactgct       780
     gctgccgaag ctatttatac tcctgaagaa gccccctgcca aaattgatca tgtgattaaa       840
     accgcttac gcgaaaaaaa accgtgtat ttagaaattg cctgtaatat tgcttctatg         900
     ccttgtgctg ctcctgggcc tgcttctgct ttattaatg atgaagcctc tgatgaagct        960
     agtttaaatg ctgccgtgga agaaaccta aaattattg ccaatcgcga taagttgcc         1020
     gtgttagttg gttctaaatt aagagctgct ggtgctgaag aagctgctgt taaatttgct      1080
     gatgctttag gtggtgcagt tgctactatg gctgctgcca atcttttttt tccgaagaa       1140
     aatcccatt atattggaac tagttgggga gaagtttctt atctggttgt ggaaaaaact       1200
     atgaaagaag ccgacgctgt tattgcttta gcccctgtgt ttaatgatta ttctaccact     1260
```

FIG. 11(continued)

```
ggttggactg atattcccga tcccaaaaaa ttagttttag ccgaccctcg ttctgttgtt    1320
gttaatggtg ttcgctttcc ctctgtgcat ttaaaagatt atttaacccg cttagcccaa    1380
aaagtttcta aaaaactgtg tgccttagat tttttaaat ctttaaatgc gggtgaatta    1440
aaaaagctg ctcctgctga tccttctgct ccttagtta atgctgaaat tgcccgtcaa    1500
gttaagcct tattaacccc taatactacc gttattgccg aaactggtga ttcttggttt    1560
aatgcccaac gcatgaaatt acctaatggt gcccgtgttg aatatgaaat gcaatggggt    1620
catattggtt ggtctgtacc tgctgctttt ggttatgctg ttggtgctcc tgaacgtcgt    1680
aatattttaa tggtgggtga tggttctttt caattaactg cccaagaagt tgcccaaatg    1740
gttcgcttaa aattacccgt tattatttt ttaataaata attatggtta taccattgaa    1800
gtgatgattc atgatgggcc statataat attaaaaatt gggattatgc gggtttaatg    1860
gaagtgttta atggtaatgg tggttatgat tctggtgctg gtaaaggttt aaaagccaaa    1920
actggtgtg aattagctga agctattaaa gttgccttag ccaatactga tgggccaacc    1980
ttaattgaat gttttattgg tcgcgaagat tgtaccgaag aattagttaa atgggtaaa    2040
cgtgttgctg ctgctaattc tcgcaaaccc gtgaatacat tattgtaatt tttggggatc    2100
aattcgagct cctccgctta aaaaatttca ttttcgatc aaaaaagaca aattattact    2160
aattagctca tggcaataaa taatcagtag taatctgttt tcacatttta ttgttaattt    2220
ttattattgc taatatcaac ctttctact tctgcttaat attttattta tgtcaatgg    2280
gaaaatctga aataagattg agaacagtgt taccaataga agtatttaag gttaaagca    2340
tacctaaag ataacatttt tttttgaaa gagtcaaatt attttgaaa ggctgatatt    2400
tttgatattt actaatattt tatttatttc ttttccctt aaaataagag ctaaatctgt    2460
tttttattatc atttatcaag ctctattaat acctcaactt tttcaagaaa aaataataat    2520
aatttttccc tctattctca tgacctttta ggaaaattaa ttttagaaaa actattgaca    2580
aacccataaa aaatgagata agattataga ttgtcactgg tattttatac tagggcaaa    2640
ttatatttat atatacaaaa atgctgtata aaaaacatct catgattga aagcctatgc    2700
tgccttagaa gccaatggta aattacaacc ctttgaatat gatcctggtg ctttaggtgc    2760
caatgaagtg gaaattgaag tgcaatattg tggtgtgtgt cattctgatt tatctatgat    2820
taataatgaa tggggtattt ctaattatcc cttagttcct ggtcctgaag ttgttggtac    2880
tgttgctgct atgggtgaag gtgttaatca tgtggaagtg ggtgatttag ttggtttagg    2940
ttggcattct ggttattgta tgacctgtca ttcttgttta tctggttatc ataatttatg    3000
tgccactgcc gaatcactaa ttgtgggtca ttatggtggt tttggtgata gagttcgtgc    3060
taaaggtgtt tctgtggtga aattacccaa aggtattgat ttagcctctg ctgggccttt    3120
atttgtggt ggtattaccg ttttttctcc catggtggaa ttatctttaa acctaccgc    3180
caaagttgct gttattggta ttggtggttt aggtcattta gccgttcaat tttaagagc    3240
ctggggttgt gaagttactg cttttacctc ttctgcccgt aaacaaaccg aagttttaga    3300
attaggtgcc catcatattt tagattctac caatcctgaa gtattgctt ctgccgaggg    3360
taaatttgat tatattatt ctaccgtgaa tttaaaatta gattggaatt tatatatcag    3420
taccttagcc cctcaaggtc attttcattt tgttggtgtg gtgttagaac ccttggactt    3480
aaacttattt cccttattaa tgggacaacg ttctgtttct gcttctcctg ttggttctcc    3540
tgctactatt gccactatgt tagatttgc cgtgcgtcat gatattaaac ccgtggtgga    3600
acaattctct tttgatcaaa ttaatgaagc cattgcccat ttagaatctg gtaaagccaa    3660
ttatcgcgtg gtgttatctc attctaaaaa ttaataagat tacctctaa actgaaacaa    3720
atttgagggt aggcttcatt gtctgccctt atttttttat ttaggaaaag tgaacagact    3780
aaagagtgtt ggctctattg ctttgagtat gtaaattagg cgttgctgaa taaggtatg    3840
attttgacc ccttctctct tctgcagtta cctaggattt ctggcgaaag gggatgtgc    3900
tgcaaggcga ttaagttggg taacgccagg gttttcccag tcacgacgtt gtaaaacgac    3960
ggccagtgag cgcgacgtaa tacgactcac tatagggcga attggcgcga gccgtcaag    4020
gccgcatgc gcgcctacgt agacaattgt cgatgtaatt attaactatc ttattataga    4080
tgaggggaga gggagaaatt agttcggaga gaacgctcga ggctcgttc cgcaaagcgg    4140
tacggagtta gttagggct aatggcatt ctccgtaca ggaaagagtt agaagttatt    4200
aattatcaac aattctcctt tgcctagtgc atgttacct ttttaattaa aacataagga    4260
aaactaataa tcgtaataat ttaacctcaa agtgtaaaga aatgtgaaat tctgactttt    4320
```

FIG. 11(continued)

```
ataacgttaa agagggaaaa attagcagtt taaaatacct agagaatagt ctggggtaag    4380
catagagaat tagattagtt aagttaatca aattcagaaa aaataataat cgtaaatagt    4440
taatctgggt gtatagaaaa tgatcccctt catgataaga tttaaactcg aaaagcaaaa    4500
gccaaaaaac taacttccat taaaagaagt tgttacatat aacgctataa agaaaattta    4560
tatatttgga ggataccaac catgtctcat attcaacgtg aaactagttg ttctcgtcct    4620
cgtttaaatt ctaatatgga tgccgattta tatggttata aatgggctcg tgataatgtt    4680
ggtcaatctg gtgctactat ttatcgttta tatggtaaac ctgatgctcc tgaattattc    4740
ttgaaacatg gtaaggttc tgttgctaat gatgttactg atgaaatgt tcgtttaaac    4800
tggttgactg aatttatgcc tttactact attaaacatt ttattcgtac tcccgatgat    4860
gcttggttat taactactgc tattctggt aaaactgct ttcaagtttt agaagaatat    4920
cctgattctg gtgaaaatat tgttgatgct ttagctgttt tttacgtcg tttacattct    4980
attcccgttt gtaattgtc ttttaattct gatcgtgttt ttcgtttagc tcaagctcaa    5040
tctcgtatga ataatggttt agttgatgct tctgattttg atgatgaacg taatggttgg    5100
cctgttgaac aagtttggaa agaaatgcac aaattgttac cttttctcc tgattctgtt    5160
gttactcatg gtgattttc tttagataat ttgatctttg atgaaggtaa attgattggt    5220
tgtattgatg tggtcgtgt tgtattgct gatcgttatc aagatttagc tatttatgg    5280
aattgtttag gtgaatttc tccttcttta cagaaacgtt tatttcagaa atatggtatt    5340
gataatcctg atatgaacaa gttacaattt catttaatgt tggacgagtt cttttaagaa    5400
ttaattcctg accaaaatcc cttaacgtga gttttcgttc cactgagcgt cagacccgt    5460
agaaaagatc aaaggatctt cttgagatcc ttttttctg cgcgtaatct gctgctattt    5520
aaattacgta cacgtgttat tactttgtta acgacaattg tcttaattaa ctgggcctca    5580
tggccttcc gctcactgcc cgctttccag tcgggaaacc tgtcgtgcca gctctgcaga    5640
tgacggtgaa aacctctgac acatgcagct cccggagacg gtcacagctt gtctgtaagc    5700
ggatgccggg agcagacaag cccgtcaggg cgcgtcagcg ggtgttggcg ggtgtcgggg    5760
cgcagccatg accagtcac gtagcgatag cggagtgtat actggcttaa ctatgcggca    5820
tcagagcaga ttgtactgag agtgcaccat atgcggtgtg aaataccgca cagatgcgta    5880
aggagaaaat accgcatcag gcgctcttcc gcttcctcgc tcactgactc gctgcgctcg    5940
gtcgttcggc tgcggcgagc ggtatcagct cactcaaagg cggtaatacg gttatccaca    6000
gaatcagggg ataacgcagg aaagaacatg tgagcaaaag gccagcaaaa ggccaggaac    6060
cgtaaaaagg ccgcgttgct ggcgtttttc cataggctcc gcccccctga cgagcatcac    6120
aaaaatcgac gctcaagtca gaggtggcga aacccgacag gactataaag ataccaggcg    6180
tttccccctg gaagctccct cgtgcgctct cctgttccga cctgccgct taccggatac    6240
ctgtccgcct ttctcccttc gggaagcgtg gcgctttctc atagctcacg ctgtaggtat    6300
ctcagttcgg tgtaggtcgt tcgctccaag ctgggctgtg tgcacgaacc cccgttcag    6360
cccgaccgct gcgccttatc cggtaactat cgtcttgagt ccaacccggt aagacacgac    6420
ttatcgccac tggcagcagc cactggtaac aggattagca gagcgaggta tgtaggcggt    6480
gctacagagt tcttgaagtg gtggcctaac tacggctaca ctagaaggac agtatttggt    6540
atctgcgctc tgctgaagcc agttaccttc ggaaaaagag ttggtagctc ttgatccggc    6600
aaacaaacca ccgctggtag cggtggtttt tttgtttgca agcagcagat tacgcgcaga    6660
aaaaaaggat ctcaagaaga tcctttgatc ttttctactg agagcttg gtagacaccc    6720
tgtcatgtat tttatattat ttatttcacc atacggatta agtgaaacct aatgaaaata    6780
gtactttggg agcttaact taatgaagg tatgtttttt tatagacatc gatgtctggt    6840
ttaacaatag gaaaagtag ctaaaactcc catgaattaa agaataaca aggtgtctaa    6900
caacctgtta ttaagaatgt tagaaaagac ttaacatttg tgttgagttt ttatagacat    6960
tggtgtctag acatacggta gataaggttt gctcaaaaat aaaataaaaa agattggac    7020
taaaaaacat ttaatttagt acaatttaat tagttatttt ttcgtctcaa atttgctttt    7080
gttgagcaga aatttagata aaaaatccc cgtgatcaga ttacaatgtc gttcattgta    7140
cgatgtgtcg aaaaatcttt acgacactct aaactgacca cacgggtgaa aaagaaaact    7200
gaactaataa catcatgata ctcggaaaac ctagcaattc tcaacccta aacaaagaa    7260
acttccaaaa ccctgaccat ataaggagt ggcaacaatc agcaatcagt caagatttga    7320
tagcagaaaa tcttgtatcg gttgctaatg gttttgatgt actatttatc ggcaataaat    7380
```

FIG. 11(continued)

```
accgaactaa cacgggtgtt ctgtcaggc acatattaaa ctctattct catttagaag   7440
atggtggttc gtatggtaga acatttgacc catttaccaa taaagaaatg cagtgggttc   7500
aatttaaacc gaatagacca agaaaaggtt ctactggtaa ggtaatcaaa tatgaatcgc   7560
caaaaggtga acctacaaga gttctaatgc cgtttgtgcc tatgaaaata tggcaacgga   7620
ttagcgataa gttcggagta ccgattaatc cgaaaaaaga tactcacttt tgggaatggg   7680
taaagaataa tccatcgata ccgattgcca ttacagaagg aaataaaaaa gctaattgcc   7740
tattatccta tggctatcct gctattgcct ctgtaggcat ttggaacgga ttagagaaaa   7800
taaatgattt ctcgaaggaa aagcagttaa aagaggattt gaaatggttg ttatccaacg   7860
gcaaccgaaa tattaatatc atctttgacc aagaccagaa acaaaaaact gtaattaatg   7920
taaacaaagc tattttcgct ttatctctc taataagtag aaatggtcat aaagttaata   7980
ttgtgcaatg gttgccgtca aaggtaaag gaatagatga ttatttggta gctttaccctt   8040
ttgagaaaag agaaaatcat ttagacaact taattaaaat tgcaccatca tttaattttt   8100
ggtcaactaa atacttattc aagtgtcgta aaccagattt aacgtaaat tgccgttatt   8160
tgagcgatgc agtaaaagaa ttacctcaag aggatatagc attaatagca cctcacggca   8220
cgggtaaaac ttcattagta gctactcacg ttaagaatcg gagttatcac ggaaggaaaa   8280
ctatttcatt ggtgcatctt gaaagtttag ccaaagctaa tggcacgca cttggattat   8340
attaccgaac cgaaaataat attgaaagc aatatcttgg attagctta tgtgtagata   8400
gttgccgtga taagattaac ggcattacaa ctgatattat ttcaggtcaa gattattgcc   8460
ttttcattga tgaaattgac caagtaattc cacacatcct taacagtgaa actgaagtaa   8520
gtaagtatag atgcaccatc attgacactt tttctgaact ggtgagaaat gctgaacagg   8580
tcattattgc tgatgctgat ttatccgatg tgacgattga cctaatagaa aacatcagag   8640
gtaaaaaact atatgtaatc aagaatgaat atcagtatca gggaatgact tttaacgccg   8700
ttggttcacc attagaaatg atggcaatga tgggaaaatc ggtgtcagaa ggcaagaaat   8760
tatttattaa caccacatcc caaaaggcaa aaagtaagta cggcacaatc gctcttgagt   8820
cttatacttt tggtctaaat aaagaagcaa agatattaag aatagactct gaaaccactc   8880
aaaaccctga acatccagcc tataaaatca ttgaccaaga cttaaataat atcctcaaag   8940
attatgatta tgtcattgcc tcaccttgcc ttcaaacagg tgtcagtatt accttaaaag   9000
ggcatttttga ccagcaatt aacttttcca gtggaaacat tacacctcat tgcttttac   9060
agcaaatgtg gcggttgagg gatgcagaaa ttgaaagatt ctattatgtg ccgaactcat   9120
ctaacctcaa tctcattggg aataagtcaa gttcaccatc agacctttcta aagagcaata   9180
acaagatggc aacggcaacg gttaaccttt tgggtagaat cgactccgaa tattccctag   9240
agtatgaatc gcacggcatt tggcttgaga cgtgggcaaa attatcagca cggcataaca   9300
gttcaatgcg ttgttactct gaaattctta cctatctaat tacgtctcaa gggcataaat   9360
taaatatcaa cattccctca cctcttgcag atattaagaa gctaaatgat gaggtaagta   9420
gtaacaggga aaggtaaaa aatgagagat actctcagag gttaaactca ccagatatta   9480
acgatgcaga agctaccata ctcgaatcta aagagcaaaa aatcggattg actctcaatg   9540
agagatgcac cctagaaaag cataaagtta agaagcggta tgggaatgta aagatggata   9600
ttctcaacctt tgatgatgat ggactatacc ccaaactcag actatttat tacctcacca   9660
tcggtaaacc tcatctcaag gctaatgaca gaaagctat tgccaaaatg gcaatgaca   9720
ataaaggcaa gattctatca aaagacttag ttaataaaac ttactccgct cgtgtgaagg   9780
tcttagagat tcttaaacta actgacttta tcgacaatct tagagatgaa ctcttaataa   9840
ctcccaataa tccagctatc acgatttta ataatcttct gctaagagct aagaaggatt   9900
taagagtatt aggagtcaac atcggaaat atccaatggc caacattaat gccgtactta   9960
ctctcattgg tcacaaactt tctgtaatga gagatgagtt cggaaaagag aaaaggataa  10020
aagtagatgg taaatcatac cgatgttatc aacttgaaac attaccagat tttaccaatg  10080
atactcttga ctactggtta gaaaatgata gccaaaaaga gtaacagca acagaaaatt  10140
actccgaaaa ttttaaccct tcaaatagct acaatccaga cagtaagaca ctttcagagg  10200
gtgcaaattt cctatatata aataagaag aattgcatcc aaataaattg cacctagaaa  10260
taaagaagg tgctgaactt ttttattcg gggtaaaggt gattgtgaaa ggaatcttgg  10320
acggggcagt aactatattc tctatggtc aagaatacga tttatccctc aatgaactag  10360
agggatgtt aacatcatga actttacaag aatctttta aagggcgatc gcaccatgtt  10440
```

FIG. 11 (continued)

```
aaatgatggt acatttgttc agatatttga tatttaccat gaccacgcat tgggagtgac    10500
ccttgacctt aagacagaaa aaattatttc cgatgatgtt agggtaatta ctgtcaaaga    10560
cttattgttc gatggcactt ataaggggt aaatctttt atgccgata atgccgata        10620
atgccgatt gatgctacaa aatcccataa tcataagcga taatcccta atagcttgta      10680
attcttgaac cgtagcgatt ttagagtatt ccaaaagaa gaaataaaca ccgcaaaatg     10740
tcgtatttca catatataa ccaaggtttt ttgccctaaa atctttatgt ttgtagtgtg     10800
atgttgggtc aaaatggtca gaaagttgc aaggtttta tggatgctta cgcgcgcgag     10860
gggtaagcat ccccaaatag ttactttatc ctagtccatg cccatttatt gcgtccgt     10920
tcggctttaa aaaagtgcca aaactcacaa ggtgcaataa aagttctgt acctttcgca    10980
accctagata atcttcaac agttactttt tttccatta tctcgtaca aagtttggct      11040
agttctctt ttccctctt ttcaatcaag ccttcttgta tgccaactc attgattaat      11100
ctctctattt ttaccattat ttcccgttca ggtagtttat ccctaaatc ttcatcgggg    11160
ggcaatgtag ggcattctga aggggcttt tcttctgtct ggacattatc taatattgaa    11220
gtaaccaaac tatcttaagt tttttctatt cctattaatt catattcggt tactgtatcc   11280
gtatcaatat ccgaataact atctttatcc gtattagcta ttcggttaag tttatccgtt   11340
aactcagaaa caagactata tagcggtttt agctttctt ctatcctgtt atctaatcg    11400
gataagttta tacgttatc attatccgta ttagtatcat tggcttttt tgtagttct     11460
accccctcat aaaccgcttt tattcccaat tccaacagac tgataacagt atcctttata   11520
atgggttttt tgctgatatg gtgaactttt gcccttca tcattgcgat actttctatc    11580
tcactcatca acttatcgct taagtgaatc tgtatctgt ttaatcctt actggtttta    11640
ttcatatccg tttactttat tcggttaaca attctatttt ataccaataa aatattatac   11700
ggttaactt atacgttaa ctatttatc tatacggata acagtaataa gttattcgta     11760
ttagttatac gttactttt atccaataa aattagtgca tttaaactaa aagaatgatt    11820
ttatcggagt tgatagcatt ggattaacct aaagacgttt ataagctata tctgataagt   11880
atttaaggtt attttgttat tctgtttatt gacattatca gaataaaaga atagaatata   11940
attgttgaga gataagaggt ttaagtgatt atggttaaga agttagttgg ttatgtcagg   12000
gtcagtagtg aatcgcaaga ggataacact agcttacaga atcagataga gagaattgaa   12060
gcatattgta tggctttgg ttatgagttg gtaaaaatat tcaaagaggt tgccactggt   12120
acaaaagcag atattgaaac ccgtcctatt tttaatgaag ctatagaata cttgaacag    12180
gataatgcta atgaattat tgccttgaag ctagaccgaa tcgacggaa tgctttagat    12240
gtattgcgtt tggttcgtga aaccttagaa ccacaaaata aatgttagt gttactagat   12300
attcaggtag atacttcgac accttcagga aaaatgattt taactgtaat gagtgccgtt   12360
gctgaactcg aaagagacat gatctatgat cgcactcagg ggggtagaaa gactaaagcc   12420
caaaagggcg ggtatgccta cgggaaacct aaatttggct ataagactga agaaaaggaa   12480
ctaaaagaag attcagcaca acaggaaact attaaactaa ttaagagaca ccgtaggtca   12540
gggaaaagct accagaaaat agctgattat ctcaatgccc aaagtattcc cactaaacaa   12600
ggtaagaaat ggagttctag cgtcgtctat cgaatctgtc aggaaaaagc tggttaagtc   12660
tgtttataga tatttagaat ttattgaata aaaatagtat gaacaataaa tatttatgga   12720
ctaaccacgc tcggaaacgt ttaactgaac gatggaaat aaaagaatca tgggttattg   12780
ataccatcga aaatcctgaa cgttcagaat ttattgttga tgagtcaggg gaaaaatatc   12840
attactataa aagaatagct aagtttaaga atagagtgtt agaagtgata acttctgcca   12900
actcaacacc cacaagaata ataaccttt acttaaaccg taacatgagg aaaaatttat   12960
gattgttact tacgataatg aagttgacgc aatttatttt aagttaacgg aaaatacaaat  13020
tgatagcacc gaacctcaaa cagacaggat tatcactgat tacgatgaaa gtaataatat   13080
tgttggcatt gaggtattag atttaattta tcttgtcaag aaaggtttaa ccgttgctga   13140
tttacctttt tctgaagatg aaagattaac agcttctcaa tatttaatt ttcctgttgc    13200
tatctaatcc agaagggca ataatcccct tctttcatcg agttagactt aatatcacaa   13260
aagtcatttt catttaccg tttctttcc acagcgtccg tacgccctc gttaaatctc    13320
aaaaccgaca atttatgatg tttataaaaa gttactcact ttaataagta tttatactca   13380
ttaaagggtt attcttttt tgtagcctga taggtgggaa aggaatattt cagattatca    13440
gatttgttg                                                           13449
```

FIG. 11 (continued)

```
ID   TK295\pABICyano1-6.8_PnirAABICyano1-PDCmax-PpsbAABICyano1-synADHmax-
PrbcABICyano1-Km**-oriVT standard; circular DNA;    ; 13033 BP.
CC   This file is created by Vector NTI
CC   http://www.invitrogen.com/
CC   VNTDATE|620148482|
CC   VNTDBATE|620148482|
CC   LSOWNER|
CC   VNTAUTHORNAME|Frank Glicrka|
FH   Key             Location/Qualifiers
FH
FT   promoter        3639..4164
FT                   /vntifkey="30"
FT                   /label=PrbcABICyano1
FT   CDS             4166..4981
FT                   /vntifkey="4"
FT                   /label=Km**
FT                   /note=" maximal codon optimized kanamycin resistance gene "
FT   CDS             12543..12791
FT                   /vntifkey="4"
FT                   /label=ORF\6
FT                   /note="orf6"
FT   CDS             12283..12546
FT                   /vntifkey="4"
FT                   /label=ORF\5
FT                   /note="orf5"
FT   CDS             11555..12241
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10465..11229)
FT                   /vntifkey="4"
FT                   /label=ORF\3
FT                   /note="orf3"
FT   CDS             10020..10205
FT                   /vntifkey="4"
FT                   /label=ORF\2
FT                   /note="orf2"
FT   rep_origin      complement(9320..9337)
FT                   /vntifkey="33"
FT                   /label=Rep_Origin_1\(potential)
FT                   /note="potential rep origin; match pNostoc (Acc# M81381) nick
site (358-375) on reverse strand"
FT   misc_feature    9580..9613
FT                   /vntifkey="21"
FT                   /label=Rep\motif
FT                   /note="Rep protein active site motif EXXKYXVKXXD"
FT   CDS             6799..9984
FT                   /vntifkey="4"
FT                   /label=ORF\1
FT                   /note="orf1 rep ori binding protein slr7037 homolog Similar to
hypothetical protein slr7037 of plasmid pSYSA (103 kb) of Synechocystis sp. PCC 6803"
```

FIG. 13

```
FT   rep_origin      complement(5224..6282)
FT                   /vntifkey="33"
FT                   /label=OriV?
FT   insertion_seq   6289..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   promoter        2112..2264
FT                   /vntifkey="30"
FT                   /label=PpsbAABICyano1
FT   gene            379..2088
FT                   /vntifkey="60"
FT                   /note="PDC"
FT   gene            2268..3278
FT                   /vntifkey="60"
FT                   /note="ADH"
FT   CDS             379..2085
FT                   /vntifkey="4"
FT                   /label=PDCmaz
FT   CDS             2288..3275
FT                   /vntifkey="4"
FT                   /label=synADHmax
FT   promoter        96..378
FT                   /vntifkey="30"
FT                   /label=PnirAABICyano1
FT   terminator      3279..3434
FT                   /vntifkey="43"
FT                   /label=TrbcSABICyano1
SQ   Sequence 13033 BP; 4048 A; 2285 C; 2558 G; 4142 T;
     aatattttt  gtcajataaq caaaccttac aaacataatt aacaactgaa actattgata    60
     tgtctaggtt  ttagctctat cacaggttgg atctgtcgac aattaataac ttcttcctgt   120
     acgggcgaat  ggccatttgc tcctasctaa ctccgtactg ctttgcggaa cgagcgtagc   180
     gaactctccg  aattctcaag ccttcatccc tgatagatgc aaaaaacgaa ttaaaattat   240
     gtgtaaaaag  aaaatgtgtc tttatttagt agtcaaagtt acaaaatatt aagaatcaaa   300
     ttaataatgt  attggcagt  taagtatat  agtctttcaa tattatttg tattcaatat   360
     attaaccgag  gacaaattat gaattcttat accgtgggta cttatttagc cgaacgctta   420
     gtgcaaattg  gttaaaaaca tcattttgcc gtggctgggg actataattt agtgttattg   480
     gatcacttat  tattaactac aaacatggac caagtgtatt gttgtaatga attaaattgt   540
     ggtttttctg  ctgaaggtta tgctagagct aaagtgcag ctgctgctgt tgttacttat    600
     tctgtggggtg cttatatgc ttttgatgct attggtggtg cttatgccga aaatttaccc   660
     gtgatttaa   tttctggtgc ccctactaat aatgatcatg ccgctggaca tgtttacat   720
     catgcttag   gtaaaccgaa ttatcattat ccattagaaa tggccaaaaa tattactgct   780
     gctgccgaag  ctatttatac tcctgaagaa gcccctgcca aaattgatca tgtgattaaa   840
     accgccttac  gcgaaaaaaa accgtgtat ttagaaattg cctgtaatat tgcttctatg   900
     cctgtgctg   ctcctgggcc tgctctgct ttatttaatg atgaagctc tgatgaagct   960
     agttaaaatg  ctgccgtgga agaaacttaa aaatttattg ccaatcggga taaagttgcc  1020
     gtgttagttg  gttctaaatt aagagctgct ggtgcgaag aagctgctgt taaattgct   1080
     gatgctttag  gtgtgcagt tgctactgag gctgctgcca aatctttttt tcccgaagaa  1140
     aatccccatt  atattggaac tagttggga gaagtttctt atcctggtgt ggaaaaaact   1200
```

FIG. 13 (continued)

```
atgaagaag ccgacgctgt tattgcttta gccctgtgt ttaatgatta ttctaccact   1260
ggttggactg atattcccga tcccaaaaaa ttagttttag ccgaacctcg ttctgttgtt   1320
gttaatggtg ttcgttttcc ctctgtgcat ttaaagatt atttaaccg cttagcccaa   1380
aaagtttcta aaaaactgg tgcttagat ttttttaaat cttaaatgc gggtgaatta   1440
aaaaagctg ctcctgctga tccttctgct cctttagtta atgctgaaat tgcccgtcaa   1500
gttgaagcct tattaaccc taatactacc gttattgccg aaactggtga ttcttggttt   1560
aatgcccaac gcatgaaatt acctaatggt gccgtgttg aatatgaaat gcaatgggt   1620
catattggtt ggtctgtacc tgctgctttt ggttatgctg ttggtgctcc tgaacgtcgt   1680
aatattttaa tggtgggtga tggttctttt caattaactg cccagaagt tgcccaaatg   1740
gttcgcttaa aattacccgt tattattttt ttaataaata attatggtta taccattgaa   1800
gtgatgattc atgatgggcc atataataat attaaaatt gggattatgc gggtttaatg   1860
gaagtgttta atggtaatgg tggttatgat tctggtgctg gtaaaggttt aaaagccaaa   1920
actggtggtg aattagctga agctattaaa gttgccttag ccaatactga tgggccaacc   1980
ttaattgaat gttttattgg tcgcgaagat tgtaccgaag aattagttaa atgggggtaaa   2040
cgtgttgctg ctgctaattc tcgcaaaccc gtgaataaat tattgtaatt ttgggggatc   2100
aattcgagct cgccttacta taaacaaag ttatctgaga aataactata actattctga   2160
aaatatttga caaactttca caattttgtt atattagtaa gtgaggtgag caaatcaccc   2220
aaaatatata agtacctcga aaaattcata actgaaatca taagcatatg attaaagcct   2280
atgctgcctt agaagccaat ggtaaattac aacccttga atatgatcct ggtgctttag   2340
gtgccaatga agtggaaatt gaagtgcaat attgtggtgt gtgtcattct gatttatcta   2400
tgattaataa tgaatggggt atttctaatt atccttagt tcctggtcat gaagttgttg   2460
gtactgttgc tgctatgggt gaaggtgtta atcatgtgga agtgggtgat ttagttggtt   2520
taggttggca ttctggttat tgtatgacct gtcattcttg tttatctggt tatcataatt   2580
tatgtgccac tgccgaatct actattgtgg gtcattatgg tggttttggt gatagagttc   2640
gtgctaaagg tgtttctgtg gtgaaattac ccaaaggtat tgatttagcc tctgctgggc   2700
cttatttg tggtggtatt accgttttt ctcccatggt ggaattatct ttaaaaccta   2760
ccgccaaagt tgctgttatt ggtattggtg gtttaggtca tttagccgtt caatttttaa   2820
gagctgggg ttgtgaagtt actgctttta cctcttctgc ccgtaaacaa accgaagttt   2880
tagaattagg tgccatcat atttagatt ctaccaatcc tgaagctatt gcttctgccg   2940
aaggtaaatt tgattatatt atttctaccg tgaatttaaa attagattgg aatttatata   3000
tcagtacctt agcccctcaa ggtcatttc atttttgttgg tgtggtgtta aaccccttgg   3060
actaaaactt atttcccctta ttaatgggac aacgttctgt ttctgcttct cctgttggtt   3120
ctcctgctac tattgccact atgttagatt ttgccgtgcg tcatgatatt aaaccgtgg   3180
tggaacaatt ttcttttgat caaattaatg aagccattgc ccattagaa tctgtaaag   3240
cccattatcg cgtggtgtta tctcattcta aaaattaata agattaactt ctaaactgaa   3300
acaaatttga gggtaggctt cattgtctgc ccttatttt ttatttagga aaagtgaaca   3360
gactaaagag tgttggctct attgctttga gtatgtaaat taggcgttgc tgaattaagg   3420
tatgatttt gaccccttct ctcttctgca gttacctagg attttctggcg aaagggggat   3480
gtgctgcaag gcgattaagt gggtaacgc cagggttttc ccagtcacga cgttgtaaaa   3540
cgacggccag tgagcgcgac gtaatacgac tcactatagg gcgaattggc ggaaggcgt   3600
caaggccgca tgccgcgcct acgtagacaa ttgtcgatgt aattattaac tatcttatta   3660
tagatgaggg gagaggagaa attagttcg gagagaacgc tcgagcgctc gttccgcaaa   3720
gcggtacgga gttagttagg gctaatgggg cattctcccg tacaggaaag agttagaagt   3780
tattaattat caacaattct cctttgccta gtgcatcgtt acctttttaa ttaaaacata   3840
aggaaacta ataatcgtaa taatttaacc tcaaagtgta aagaaatgtg aaattctgac   3900
ttttataacg ttaaagaggg aaaattagc agtttaaaat acctagagaa tagtctgggg   3960
taagcataga gaattagatt agttaagtta atcaaattca gaaaaataa taatcgtaaa   4020
tagttcatct gggtgtatag aaaatgatcc ccttcatgat aagatttaaa ctcgaaagc   4080
aaaagccaaa aaactaactt ccattaaaag aagttgttac atataacgct ataagaaaa   4140
tttatatatt tggaggatcc caaccatgtc tcatattcaa cgtgaaacta gttgttctcg   4200
tcctgtttta aattctaata tggatgccga tttatatggt tataaatggg ctcgtgataa   4260
```

FIG. 13 (continued)

```
tgttggtcaa tctggtgcta ctatttatcg tttatatggt aaacctgatg ctcctgaatt   4320
attcttgaaa catggtaaag gttctgttgc taatgatgtt actgatgaaa tggttcgttt   4380
aaactggttg actgaattta tgcctttacc tactattaaa catttattc gtactcccga    4440
tgatgcttgg ttattaacta ctgctattcc tggtaaaact gcttttcaag ttttagaaga   4500
atatcctgat tctggtgaaa atattgttga tgctttagct gttttttac gtcgtttaca    4560
ttctattccc gtttgtaatt gtccttttaa ttctgatcgt gttttttcgtt tagctcaagc  4620
tcaatctcgt atgaataatg gttagttga tgcttctgat tttgatgatg aacgtaatgg    4680
ttggcctgtt gaacaagttt ggaagaaat gcacaaattg ttaccttttt ctcctgattc    4740
tgttgttact catggtgatt tttctttaga taatttgatc tttgatgaag gtaaattgat   4800
tggttgtatt gatgttggtc gtgttggtat tgctgatcgt tatcaagatt tagctatttt   4860
atggaattgt ttagtgaat tttctcctte tttacagaaa cgtttattc agaaatatgg    4920
tattgataat cctgatatga acaagttaca atttcattta atgttggacg agttctttta   4980
agaattaatt catgaccaaa atcccttaac gtgagtttc gttccactga gcgtcagacc    5040
ccgtagaaaa gatcaaagga tcttcttgag atcctttttt tctgcgcgta atctgctgct   5100
atttaaatta cgtacacgtg ttattacttt gttaacgaca attgtcttaa ttaactgggc   5160
ctcatgggcc ttccgctcac tgcccgcttt ccagtcggga aacctgtcgt gccagctctg   5220
cagatgacgg tgaaaacctc tgacacatgc agctcccgga gacggtcaca gcttgtctgt   5280
aagcggatgc cgggagcaga caagcccgtc agggcgcgtc agcgggtgtt ggcgggtgtc   5340
ggggcgcagc catgacccag tcacgtagcg atagcggagt gtatactggc ttaactatgc   5400
ggcatcagag cagattgtac tgagagtgca ccatatgcgg tgtgaaatac cgcacagatg   5460
cgtaaggaga aaataccgca tcaggcgctc ttccgcttcc tcgctcactg actcgctgcg   5520
ctcggtcgtt cggctgcggc gagcggtatc agctcactca aaggcggtaa tacggttatc   5580
cacagaatca ggggataacg caggaaagaa catgtgagca aaaggccagc aaaaggccag   5640
gaaccgtaaa aaggccgcgt tgctggcgtt tttccatagg ctccgccccc ctgacgagca   5700
tcacaaaaat cgacgctcaa gtcagaggtg gcgaaacccg acaggactat aaagatacca   5760
ggcgtttccc cctggaagct ccctcgtgcg ctctcctgtt ccgaccctgc cgcttaccgg   5820
atacctgtcc gcctttctcc cttcgggaag cgtggcgctt tctcatagct cacgctgtag   5880
gtatctcagt tcggtgtagg tcgttcgctc caagctgggc tgtgtgcacg aaccccccgt   5940
tcagcccgac cgctgcgcct tatccggtaa ctatcgtctt gagtccaacc cggtaagaca   6000
cgacttatcg ccactggcag cagccactgg taacaggatt agcagagcga ggtatgtagg   6060
cggtgctaca gagttcttga agtggtggcc taactacggc tacactagaa ggacagtatt   6120
tggtatctgc gctctgctga agccagttac cttcggaaaa agagttggta gctcttgatc   6180
cggcaaacaa accaccgctg gtagcggtgg ttttttgtt tgcaagcagc agattacgcg   6240
cagaaaaaaa ggatctcaag aagatccttt gatcttttct actgcagaag cttgttagac   6300
acctgtcat gtattttata ttatttattt caccatacgg attaagtgaa acctaatgaa    6360
aatagtactt tcggagcttt aactttaatg aaggtatgtt ttttatagaa catcgatgtc   6420
tggtttaaca ataggaaaaa gtagctaaaa ctccatgaaa ttaaagaaat aacaaggtgt   6480
ctaacaacct gttattaaga atgttagaaa agacttaaca tttgtgttga gttttatag    6540
acattggtgt ctagacatac ggtagataag gtttgctcaa aaatataaat aaaaaagatt   6600
ggactaaaaa acatttaatt tagtacaatt taattagtta tttttttcgtc tcaaattttg   6660
ctttgttgag cagaaattta gataaaaaa tcccgtgat cagattacaa tgtcgttcat     6720
tgtacgatgt gtcgaaaaat cttacgaca ctctaaactg accacacggg ggaaaagaa     6780
aactgaacta ataacatcat gatactcgga aaactagca attctcaacc ctaaacaaa     6840
agaaacttcc aaaacctga ccatataaag gagtggcaac aatcagcaat cagtcaagat    6900
ttgatagcag aaaatcttgt atcggttgct aatggtttg atgtactatt tatcggtaat    6960
aaataccgaa ctacacggg tgttctgtca cggcacatat taaactccta ttctcattta    7020
gaagatggtg gttcgtatgg tagaacattt gaccattta ccaataaaga aatgcagtgg    7080
gttcaattta aaccgaatag accaagaaag ggttctactg gtaaggtaat caaatatgaa   7140
tgccaaaag gtgaacctac aagagttcta atgccgtttg tgcctatgaa aatatggcaa    7200
cggattagcg ataagttcgg agtaccgatt aatccgaaaa aagatactca cttttgggaa   7260
tgggtaaaga ataatccatc gataccgatt gccattacag aaggaataa aaaagctaat    7320
tgcctattat cctatggcta tcctgctatt gccttgtag gcatttggaa cggattagag   7380
```

```
aaaataaatg atttctcgaa ggaaaagcag ttaaaagagg atttgaaatg gttgttatcc  7440
aacggcaacc gaaatattaa tatcatcttt gaccaagacc agaaacaaaa aactgtaatt  7500
aatgtaaaca aagctatttt cgctttatct tctctaataa gtagaaatgg tcataaagtt  7560
aatattgtgc aatggttgcc gtcaaaaggt aaaggaatag atgattattt ggtagcttta  7620
cctttttgaa aaagagaaaa tcatttagac aacttaatta aaattgcacc atcatttaat  7680
ttttggtcaa ctaaatactt attcaagtgt cgtaaaccag atttaaccgt aaattgccgt  7740
tatttgagcg atgcagtaaa agaattacct caagaggata tagcattaat agcacctcac  7800
ggcacgggta aaacttcatt agtagctact cacgttaaga atcggagtta tcacggaagg  7860
aaaactatt  cattggtgca tcttgaaagt ttagccaaag ctaatggcaa cgcacttgga  7920
ttatattacc gaaccgaaaa taatattgaa aagcaatatc tggatttag  cttatgtta   7980
gatagttgcc gtgataagat tacggcatt  acaactgata ttatttcagg tcaagattat  8040
tgccttttca ttgatgaaat tgaccaagta attccacaca tccttaacag tgaaactgaa  8100
gtaagtaagt atagatgcac catcattgac actttctctg aactggtgag aaatgctgaa  8160
caggtcatta ttgctgatgc tgatttatcc gatgtgacga ttgcctcat  agaaacatc   8220
agaggtaaaa aactatatgt aatcaagaat gaatatcagt atcaggaat  gacttttaac  8280
gccgttgtt  caccattaga aatgatggca atgatgggaa aatcggtgtc agaggcaag   8340
aaattattta ttaacaccac atcccaaaag gcaaaagta  agtacggcac aatcgctctt  8400
gagtcttata tttttggtct aaataaagaa gcaagatat  taagaataga ctctgaaacc  8460
actaaaaacc ctgaacatcc agcctataaa atcattgacc aagacttaaa taatatccto  8520
aaagattatg attatgtcat tgcctcacct tgccttcaaa caggtgtcag tattaccta   8580
aaaggcatt  ttgaccagca atttaacttt tccagtggaa acattacac  tcattgcttt  8640
ttacagcaaa tgtggcggtt gagggatgca gaaattgaaa gattctatta tgtgccgaac  8700
tcatctaacc tcaatctcat tgggaataag tcaagttcac catcagacct totaaagacc  8760
aataacaga tggcaacggc aacgttaacc ctttgggta gaatcgactc cgaatattcc   8820
ctagagtatg aatcgcacgg catttggctt gagacgtggg caaattatc agcacggcat   8880
aacagttcaa tgcgttgtta ctctgaaatt cttacctatc taattaacgtc tcaaggcat   8940
aaattaaata tcaacattcc ctcacctctt gcagatatta agaagctaaa tgatgaggta  9000
agtagtaaca gggaaaaggt aaaaaatgag agatactctc agaggttcaa ctcaccagat  9060
attaacgatg cagaagctac catactcgaa tctaaagagc aaaaaatcgg attgactctc  9120
aatgagagat gcacctaga  aaagcataaa gttaagaagc ggtatgggaa tgtaaagatg  9180
gatattctca ccttgatga  tgatggacta taccccaaac tcagactatt ttattaccte  9240
accatcggta aacctcatct caaggctaat gacagaaaag ctattgccaa aatgggcaat  9300
gacaataaag gcaagattct atcaaaagac ttagttaata aaacttactc cgctcgtgtg  9360
aaggtcttag agattcttaa actaactgac tttatcgaca atcttagaga tgaactctta  9420
ataactccca ataatccagc tatcacgat ttaataatc ttctgctaag agctaagaag  9480
gatttaagag tattaggagt caacatcgga aaatatccaa tggcaacat  taatgccgta  9540
cttactctca ttggtcacaa actttctgta atgagagatg agttcggaaa agagaaaagg  9600
ataaaagtag atggtaaatc atacgatgt  tatcaacttg aaacattacc agattttacc  9660
aatgatactc ttgactactg gttagaaaat gatagccaaa agaagtaac agcaacagaa  9720
aattactccg aaaattttaa cccttcaaat agctacaatc cagacagtaa gacactttca  9780
gagggtgcaa atttcctata tataaataaa gaagaattgc atccaaataa attgcaccta  9840
gaaatataaag aaggtgctga acttttttta ttcggggtaa aagtgattgt gaaaggaatc  9900
ttggacgggg cagtaactat attctctatg ggtcaagaat acgatttatc cctcaatgaa  9960
ctagagggga tgttaacatc atgaactta  caagaatctt ttaaaggcc gatcgcacca  10020
tgttaaatga tggtacattt gttcagatat ttgatattta ccatgaccac gcattgggag 10080
tgaccettga cctaagaca  gaaaaaatta tttccgatga tgttagggta attactgtca 10140
aagcttatt  gttcgatggc acttataag  gggtaaaatc tttatgccc  gataatgccc 10200
gataatgccc gattgatgct acaaaatccc ataatcataa gcgataatcc cctaatagct 10260
tgtaattctt gaaccgtagc gattttagag tattccaaaa agaagaaata aacaccgcaa 10320
aatgtcgtat ttcacatata taaaccaagg ttttttgccc taaaatcttt atgtttgtag 10380
tgtgatgttg ggtcaaaatg gtcagaaaag ttgcaaggtt tttatggatg cttacgcgcg 10440
```

FIG. 13 (continued)

```
cgaggggtaa ggatcoccaa atagttactt tatcctagtc catgccatt tattgccgtc    10500
ccgttcggct ttaaaaaagt gccaaaactc acaaggtgca ataaaaagtt ctgtaccttt    10560
cgcaaccota gataatcttt caacagttac ttttttcct attatctcgg tacaaagttt    10620
ggctagttta tcttttccct cttttcaat caagccttct tgtatgccca actcattgat    10680
taatctctct attttacca ttatttccg ttaggtagt ttatccccta aatcttcatc    10740
gggggcaat gtagggcatt ctgaagggc ttttcttct gtctggacat tatctaatat    10800
tgaagtaacc aaactatctt cagtttttc tattccatt aattcatatt cggttactgt    10860
atccgtatca atatccgaat aactatcttt atccgtatta gctattcggt taagtttatc    10920
cgttaactca gaaacaagac tatatacgg tttttagcttt tcttctatcc tgttatctaa    10980
tacggataag tttatacggt tatcattatc cgtattagta tcattggct tttttggtag    11040
ttctaccccc tcataaaccg cttttatcc caattccaac agactgataa cagtatcctt    11100
tataatgggt ttttgctga tatggtgaac ttttgccct tccatcattg cgatactttc    11160
tatctcactc atcaacttat cgcttaagtg aatctgtat ctgttaatc ccttactggt    11220
tttattcata tccgtttact ttattcggtt aacaattcta tttatacga ataaatatt    11280
atacggttaa ctttatacgt ttaactattt tatctatacg gataacagta ataagttatt    11340
cgtattagtt atacgtttac ttttatccaa ataaaattag tgcatttaaa ctaaaagaat    11400
gattttatcg gagttgatag cattggatta acctaaagat gtttataagc tatatctgat    11460
aagtatttaa ggttattttg ttattctgtt tattgacatt atcagaataa aagaatagaa    11520
tataattgtt gagagataag aggtttaagt gattatggtt aagaagttag ttggttatgt    11580
cagggtcagt agtgaatcgc aagaggataa cactagctta cagaatcaga tagagagaat    11640
tgaagcatat tgtatggctt ttggttatga gttggtaaaa atattcaaag aggttgccac    11700
tggtacaaaa gcagatatatt aaacccgtcc tattttttaat gaagctatag aatacttgaa    11760
acaggataat gctaatggaa ttattgcctt gaagctagac cgaatcgcac ggaatgcttt    11820
agatgtattg cgtttggttc gtgaaacctt agaaccacaa aataaaatgt tagtgttact    11880
agatattcag gtagatactt cgacacctc aggaaaatg attttaactg taatgagtgc    11940
cgttgctgaa ctcgaaagag acatgatcta tgatcgcact cagggggta gaaagactaa    12000
agcccaaaag ggcggtatg cctacggaa acctaaattt ggctataaga ctgaagaaaa    12060
ggaactaaaa gaagattcag cacaacagga aactattaaa ctaattaaga gacaccgtag    12120
gtcagggaaa agctaccaga aaatagctga ttatctcaat gcccaaagta ttcccactaa    12180
acaaggtaag aaatggagtt ctagcgtcgt ctatcgaatc tgtcaggaaa aagctggtta    12240
agtctgttta tagatattta gaatttattg aataaaaata gtatgaacaa taaatattta    12300
tggactaacc acgctcggaa acgttaact gaacgatggg aaataaaaga atcatgggtt    12360
attgatacca tcgaaaatcc tgaacgttca gaatttattg ttgatgagtc aggggaaaaa    12420
tatcattact ataaaagaat agctaagttt aagaatagag tgttagaagt gataacttct    12480
gccaactcaa caccacaag aatastaacc ttttacttta accgtaacat gaggaaaaat    12540
ttatgattgt tacttacgat aatgaagttg acgcaattta tttaagtta acggaaaata    12600
aaattgatag cacgaacct caaacagaca ggattatcat tgattacgat gaaagtaata    12660
atattgttgg cattgaggta ttagatttta ttatcttgt caagaaaggt ttaaccgttg    12720
ctgattacc tttttctgaa gatgaaagat taacagctcc tcaatatttt aattttcctg    12780
ttgctatcta atccagaagg ggcaataatc ccttctttc atcgagttag acttaatatc    12840
acaaaagtca ttttcatttt accgttcttt ttccacagcg tccgtacgcc cctcgttaaa    12900
tctcaaaacc gacaatttat gatgttata aaagttact cactttaata agtattttata    12960
ctcattaaag ggttattctt tttttgtagc ctgataggtt gggaaggaat atttcagatt    13020
atcagatttg ttg                                                       13033
```

FIG. 13 (continued)

TK229 pABICyano1-6.8 PpetEABICyano1-PDCmax-synADHmax-PrbcABICyano1-Km**-oriVT

```
ID   TK229\pABICyano1-6.8_PpetEABICyano1-PDCmax-synADHmax-PrbcABICyano1-Km**-oriVT
standard; circular DNA;    ; 13081 BP.
DT   25-JAN-2012
CC
CC   This file is created by Vector NTI
CC   http://www.invitrogen.com/
CC   ORIGDB|GenBank
CC   VNTDATE|621691376|
CC   VNTDBDATE|621691376|
CC   LSOWNER|
CC   VNTAUTHORNAME|Frank Oliczka|
CC   SSBMSPEC|3|NONE|GenBank|0
FH   Key             Location/Qualifiers
FH
FT   promoter        3687..4212
FT                   /vntifkey="30"
FT                   /label=PrbcLABICyano1
FT   CDS             4214..5029
FT                   /vntifkey="4"
FT                   /label=Km**
FT                   /note=" maximal codon optimized kanamycin resistance gene "
FT   CDS             12591..12839
FT                   /vntifkey="4"
FT                   /label=ORF\6
FT                   /note="orf6"
FT   CDS             12331..12594
FT                   /vntifkey="4"
FT                   /label=ORF\5
FT                   /note="orf5"
FT   CDS             11603..12289
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10513..11277)
FT                   /vntifkey="4"
FT                   /label=ORF\3
FT                   /note="orf3"
FT   CDS             10068..10293
FT                   /vntifkey="4"
FT                   /label=ORF\2
FT                   /note="orf2"
FT   rep_origin      complement(9368..9385)
FT                   /vntifkey="33"
FT                   /label=Rep_Origin_1\(potential)
FT                   /note="potential rep origin; match pNostoc (Acc# M81381) nick
site (358-379); on reverse strand"
FT   misc_feature    9628..9661
FT                   /vntifkey="21"
FT                   /label=Rep\motif
FT                   /note="Rep protein active site motig EXKKYXVEKKD"
FT   CDS             6847..10032
```

FIG. 15

```
FT                      /vntifkey="4"
FT                      /label=ORF\1
FT                      /note="orf1  rep ori binding protein slr7037 homolog Similar to
hypothetical protein slr7037 of plasmid pSYSA (103 kb)  of Synechocystis sp. PCC 6803"
FT      rep_origin      complement(5072..6338)
FT                      /vntifkey="33"
FT                      /label=OriVT
FT      insertion_seq   6337..89
FT                      /source="pABICyano1-6HindIIIBamHI"
FT                      /type="Custom cloned insert"
FT                      /vntifkey="14"
FT                      /label=pABICyano1-6HindIIIBamHI
FT                      /note="Unknown feature type;insert"
FT      CDS             2316..3323
FT                      /vntifkey="4"
FT                      /label=synADH
FT      CDS             494..2198
FT                      /vntifkey="4"
FT                      /label=PDC
FT      gene            2316..3326
FT                      /vntifkey="60"
FT                      /note="ADH"
FT      gene            494..2201
FT                      /vntifkey="60"
FT                      /note="PDC"
FT      promoter        101..493
FT                      /vntifkey="30"
FT                      /label=PpetEABICyano1
SQ      Sequence 13081 BP; 4061 A; 2280 C; 2573 G; 4167 t;
        aatattttc  gtcagataog  caaaccttac  aaacataatt  aacaactgaa  actattgata     60
        tgtctaggtt  ttagctctat  cacaggttgg  atctgtcgac  gagaagggga  acagggaaaa    120
        gtatttataa  ttgatacaaa  ctgtggttca  acttatttta  aagacatttt  tctccattta    180
        atgattattt  cggggaaaat  tttgaggatt  tttgattctt  aaattgacga  tatttttgtca   240
        ctaacacaac  gtgagcggta  aattatata   tagacctaaa  acctttacta  taagtgttat    300
        atatttaaat  cgctaagtat  atagttaaag  tgtagccaat  aattaactta  taacaagtga    360
        ttacggttaa  gtccttaat   ttatcactac  aagctaaaac  aaattttttca attagatatg    420
        acattaggtc  aaagttcata  gtatgatagt  aaaaaataaa  atttgacgat  ctgtaaaaat    480
        aaaaaaacac  aatgaattct  tatacagtgg  gtacttattt  agccgaacgc  ttagtgcaaa    540
        tggtttcaaa  acatcatttt  gccgtggctg  gggactataa  tttagtgtts  ttggataact    600
        tattattcaa  taaaaacatg  gaacaagtgt  attgttgtaa  tguattaaat  tgtggttttt    660
        ctgctgaagg  ttatgctaga  gctaaaggtg  cagctgctgc  tgttgttact  tattctgtgg    720
        gtgcttatc   tgcttttgat  gctattggtg  gtgcttatgc  cgaaaattta  cccgtgactt    780
        teattctgg   tgccctcat   aataatgatc  atgccgctgg  acatgtttta  catcatgcct    840
        taggtaaaac  cgcttatcat  tatcaattag  aaatgcccaa  aaatattact  gctgctgccg    900
        aagctattta  tactcctgaa  gaagcccctg  ccaaaattga  tcatgtgatt  aaaaccgcct    960
        tacgcgaaaa  aaaacccgtg  tatttagaaa  ttgcctgtaa  tattgcttct  atgccttgtg   1020
        ctgctcctgg  gcctgcttct  gctttattta  atgatgaagc  ctctgatgaa  gctagtttaa   1080
        atgctgccgt  ggaagaaacc  ttaaaattta  ttgccaatcg  cgataaagtt  gccgtgttag   1140
        ttggttctaa  attaagagct  gctggtgctg  aagaagctgc  tgttaaattt  gctgatgctt   1200
        taggtggtgc  agttgctact  atggctgctg  ccaaatcttt  ttttcccgaa  gaaaaatccc   1260
        attatattgg  aactagttgg  gggagaagttt ctttatcctgt tgtggaaaaa  actatgaaag   1320
```

FIG. 15 (continued)

```
aagccgacgc tgttattgct ttagccctg tgtttaatga ttattctacc actggttgga      1380
ctgatattcc cgatcccaaa aaattagttt tagccgaacc tcgttctgtt gttgttaatg      1440
gtgttcgctt tccctctgtg catttaaaag attatttaac ccgttagcc caaaaagttt      1500
ctaaaaaaac tggtgcctta gattttttta aatctttaaa tgcgggtgaa ttaaaaaaag      1560
ctgctcctgc tgatccttct gctcctttag ttaatgctga aattgccgt caagttgaag      1620
ccttattaac ccctaatact accgttattg ccgaaactgg tgattcttgg tttaatgccc      1680
aacgcatgaa attacctaat ggtgccgtt tgaatatga aatgcaatgg ggtcatattg      1740
gttggtctgt acctgctgct tttggttatg ctgttggtgc tcctgaacgt cgtaatattt      1800
taatggtggg tgatggttct tttcaattaa ctgcccaaga agttgccca atggttcgct      1860
taaaattacc cgttattatt ttttaataa ataattatgg ttataccatt gaagtgatga      1920
ttcatgatgg gccatataat aatattaaaa attgggatta tgcgggttta atggaagtgt      1980
ttaatggtaa tggtggttat gattctggtg ctggtaaagg tttaaaagcc aaaactggtg      2040
gtgaattagc tgaagctatt aaagttgcct tagccaatac tgatgggcca accttaattg      2100
aatgttttat tggtcgcgaa gattgtaccg aagaattagt taaatggggt aaacgtgttg      2160
ctgctgctaa ttctcgcaaa cccgtgaata aattattgta attttgggg atcaattcga      2220
gctcggtacc caaactagta tgtagggtga ggttatagct agcgcttta ttaatccgc      2280
ggatttgtat tcaatatatt aaccgaggac aacatatgat taaagcctat gctgccttag      2340
aagccaatgg taaattacaa cccttgaat atgatcctgg tgctttaggt gccaatgaag      2400
tggaaattga agtgcaatat tgtggtgtgt gtcattctga tttatctatg attaataatg      2460
aatggggtat ttctaattat cccttagttc ctggtcatga agttgttggt actgttgctg      2520
ctatgggtga aggtgttaat catgtggaag tgggtgattt agttggttta ggttggcatt      2580
ctggttattg tatgacctgt catcttgtt tatctgtta tcataattta tgtgccactg      2640
ccgaatctac tattgtgggt cattatggtg gttttggtga tagagttcgt gctaaaggtg      2700
tttctgtggt gaaattaccc aaaggtattg atttagcctc tgctgggcct ttatttgtg      2760
gtgtattac cgttttttct cccatggtgg aattatcttt aaaacctacc gccaaagttg      2820
ctgttattgg tattggtggt ttaggtcatt tagccgttca attttaaga gcctggggtt      2880
gtgaagttac tgcttttacc tcttctgccc gtaaacaaac cgaagtttta gaattaggtg      2940
cccatcatat tttagattct accaatcctg aagctattgc ttctgccgaa ggtaaatttg      3000
attatattat ttctacggtg aatttaaat tagattggaa tttatatatc agtaccttag      3060
ccctcaaggg tcattttcat tttgttggtg tggtgttaga acccttggac ttaaacttat      3120
ttcccttatt aatgggacaa cgttctgttt ctgcttctcc tgttggttct cctgctacta      3180
ttgccactat gttagatttt gccgtgcgtc atgatattaa accgtggtg gaacaatttt      3240
ctttttgatca aattaatgaa gccattgccc attagaatc tggtaaagcc cattatcgcg      3300
tggtgttatc tcattctaaa aattaataag attaacttct aaactgaaac aaatttgagg      3360
gtaggcttca ttgtctgccc ttattttttt atttaggaaa agtgaacaga ctaaagagtg      3420
ttggctctat tgctttgagt atgtaaatta ggcgttgctg aattaaggta tgattttga      3480
ccccttctct cttctgcagt tacctaggat ttctggcgaa aggggatgt gctgcaaggc      3540
gattaagttg ggtaacgcca gggttttccc agtcacgacg ttgtaaaacg acggccagtg      3600
agcgcgacgt aatacgactc actatagggc gaattgcggg aaggcgtca aggccgcatg      3660
gcgcgctac gtagacaatt gtcgatgtaa ttattaacta tcttattata gatgagggga      3720
gaggagaaa ttagttcgga gagaacgctc gagcgctgt tccgcaagc ggtacggagt      3780
tagttagggg ctaatgggca ttctcccgta caggaaagag ttagaagtta ttaattatca      3840
acaattctcc tttgcctagt gcatcgttac cttttaatt aaaacataag gaaaactaat      3900
aatcgtaata atttaacctc aaagtgtaaa gaatgtgaa attctgactt ttataacgtt      3960
aaagagggaa aaattagcag tttaaaatac ctagagaata gtctgggta agcatagaga      4020
attagattag ttaagttaat caaattcaga aaaataata atcgtaaata gttaatctgg      4080
gtgtatagaa aatgatcccc ttcatgataa gattaaact cgaaagcaa aagccaaaaa      4140
actaacttcc attaaaagaa gttgttacat ataacgctat aaagaaaatt tatatatttg      4200
gaggatacca accatgtctc atattcaacg tgaactagt tgttctgtc ctgtttaaa      4260
ttctaatatg gatgccgatt tatatggtta taatgggct cgtgataatg ttggtcaatc      4320
tggtgctact atttatcgtt tatatggtaa acctgatgct cctgaattat tcttgaaaca      4380
tggtaaaggt tctgttgcta atgatgttac tgatgaaatg gttcgtttaa actggttgac      4440
```

FIG. 15 (continued)

```
tgaatttatg cctttaccta ctattaaaca ttttattcgt actcccgatg atgcttggtt    4500
attaactact gctattcctg gtaaaactgc ttttcaagtt ttagaagaat atcctgattc    4560
tggtgaaaat attgttgatg ctttagctgt ttttttacgt cgtttacatt ctattcccgt    4620
ttgtaattgt ccttttaatt ctgatcgtgt ttttcgttta gctcaagctc aatctcgtat    4680
gaataatggt ttagttgatg cttctgattt tgatgatgaa cgtaatggtt ggcctgttga    4740
acaagtttgg aaagaaatgc acaaattgtt aacttttttct cctgattctg ttgttactca    4800
tggtgatttt tctttagata atttgatctt tgatgaaggt aaattgattg ttgtattga    4860
tgttggtcgt gttggtattg ctgatcgtta tcaagattta gctatttat ggaattgttt    4920
aggtgaattt tctccttctt tacagaaacg tttatttcag aaatatggta ttgataatcc    4980
tgatatgaac aagttacaat ttcatttaat gttggacgag ttcttttaag aattaattca    5040
tgaccaaaat cccttaacgt gagttttcgt tccactgagc gtcagacccc gtagaaaaga    5100
tcaaaggatc ttcttgagat cctttttttc tgcgcgtaat ctgctgctat ttaaattacg    5160
tacacgtgtt attactttgt taacgacaat tgtcttaatt aactgggcct catggccttt    5220
ccgctcactg cccgctttcc agtcgggaaa cctgtcgtgc cagctctgca gatgacggtg    5280
aaaacctctg acacatgcag ctcccggaga cggtcacagc ttgtctgtaa gcggatgccg    5340
ggagcagaca agcccgtcag ggcgcgtcag cgggtgttgg cgggtgtcgg ggcgcagcca    5400
tgacccagtc acgtagcgat agcggagtgt atactggctt aactatgcgg catcagagca    5460
gattgtactg agagtgcacc atatgcggtg tgaaataccg cacagatgcg taaggagaaa    5520
ataccgcatc aggcgctctt ccgcttcctc gctcactgac tcgctgcgct cggtcgttcg    5580
gctgcggcga gcggtatcag ctcactcaaa ggcggtaata cggttatcca cagaatcagg    5640
ggataacgca ggaaagaaca tgtgagcaaa aggccagcaa aaggccagga accgtaaaaa    5700
ggccgcgttg ctggcgtttt tccataggct ccgcccccct gacgagcatc acaaaaatcg    5760
acgctcaagt cagaggtggc gaaacccgac aggactataa agataccagg cgtttccccc    5820
tggaagctcc ctcgtgcgct ctcctgttcc gaccctgccg cttaccggat acctgtccg    5880
cttttctccct tcgggaagcg tggcgcttt catagctca cgctgtaggt atctcagttc    5940
ggtgtaggtc gttcgctcca agctgggctg tgtgcacgaa ccccccgttc agcccgaccg    6000
ctgcgcctta tccggtaact atcgtcttga gtccaacccg gtaagacacg acttatcgcc    6060
actggcagca gccactggta acaggattag cagagcgagg tatgtaggcg gtgctacaga    6120
gttcttgaag tggtggccta actacggcta cactagaagg acagtatttg gtatctgcgc    6180
tctgctgaag ccagttacct tcggaaaaag agttggtagc tcttgatccg gcaaacaaac    6240
caccgctggt agcggtggtt tttttgtttg caagcagcag attacgcgca gaaaaaaggg    6300
atctcaagaa gatcctttga tcttttctac tgcagaagct tgttagacac cctgtcatgt    6360
attttatatt atttattcca ccatacggat taagtgaaac ctaatgaaaa tagtactttc    6420
ggagctttaa ctttaatgaa ggtatgtttt tatagaca tcgatgtctg gtttaacaat    6480
aggaaaaagt agctaaaact cccatgaatt aaagaaataa caaggtgtct aacaacctgt    6540
tattaagaat gttagaaaag acttaacatt tgtgttgagt tttatagac attggtgtct    6600
agacatacgg tagataaggt ttgctcaaaa ataaaataaa aaagattgg actaaaaaac    6660
atttaattta gtacaattta attagttatt ttttcgtctc aaatttgct tgttgagca    6720
gaaatttaga taaaaaatc cccgtgatca gattacaatg tgttcattg tacgatgtgt    6780
cgaaaaatct ttacgacact ctaaactgac cacacgggg aaaagaaaa ctgaactaat    6840
aacatcatga tactcggaaa acctagcaat tctcaacccc taaacaaaag aaacttccaa    6900
aaccctgacc atataagga gtggcaacaa tcagcaatca gtcaagattt gatagcagaa    6960
aatcttgtat cggttgctaa tggttttgat gtactattta tcggcaataa ataccgaact    7020
aacacgggtg ttctgtcacg gcacatatta actcctatt ctcatttaga agatggtggt    7080
tgtatggta gaacattga cccatttacc aataaagaaa tgcagtgggt tcaatttaaa    7140
ccgaatagac caagaaagg ttctactggt aagtaatca aatatgaatc gccaaaggt    7200
gaacctacaa gagttctaat gccgtttgtg cctatgaaaa tatggcaacg gattagcgat    7260
aagttcggag tacgattaa tcgaaaaaa gatactcact tttgggaatg gtaaagaat    7320
aatccatcga tacgattgc cattacagaa ggaaataaaa agctaattg cctattatcc    7380
tatggctatc ctgctattgc ctttgtaggc atttggaacg gattagagaa aataaatgat    7440
ttctcgaagg aaaagcagtt aaaagaggat tgaaatggt tgttatccaa cggcaaccga    7500
```

FIG. 15 (continued)

```
aatattaata tcatctttga ccaagaccag aaacaaaaaa ctgtaattaa tgtaaacaaa   7560
gctatttcg ctttatcttc tctaataagt agaaatggtc ataaagttaa tattgtgcaa    7620
tggttgccgt caaaaggtaa aggaatagat gattatttgg tagcttacc ttttgagaaa    7680
agagaaaatc atttagacaa cttaattaaa attgcaccat catttaattt ttggtcaact   7740
aaatacttat tcaagtgtcg taaaccagat ttaaccgtaa attgccgtta tttgagcgat   7800
gcagtaaaag aattacctca agaggatata gcattaatag cacctcacgg cacgggtaaa   7860
acttcattag tagctactca cgttaagaat cggagttatc acggaaggaa aactatttca   7920
ttggtgcatc ttgaaagttt agccaaagct aatggcaacg cacttggatt atattaccga   7980
accgaaaata atattgaaaa gcaatatctt ggatttagct tatgtgtaga tagttgccgt   8040
gataagatta acggcattac aactgatatt atttcaggtc aagattattg ccttttcatt   8100
gatgaaattg accaagtaat tccacacatc cttaacagtg aaactgaagt aagtaagtat   8160
agatgcacca tcattgacac ttttctgaa ctggtgagaa atgctgaaca ggtcattatt    8220
gctgatgctg attatccga tgtgacgatt gacctaatag aaaacatcag aggtaaaaaa    8280
ctatatgtaa tcaagaatga atatcagtat cagggaatga cttttaacgc cgttggttca   8340
ccattagaaa tgatggcaat gatgggaaaa tcgtgtcag aagcaagaa attatttatt     8400
aacaccacat cccaaaaggc aaaaagtaag tacggcacaa tcgtctcttga gtcttatatt   8460
tttggtctaa ataaagaagc aaagatatta agaatagact ctgaaaccac taaaaaccct   8520
gaacatccag cctataaaat cattgaccaa gacttaaata atatcctcaa agattatgat   8580
tatgtcattg cctcaccttg ccttcaaaca ggtgtcagta ttaccttaaa agggcatttt   8640
gaccagcaat ttaacttttc cagtggaaac attacacctc attgctttt acagcaaatg    8700
tggcggttga gggatgcaga aattgaaaga ttctattatg tgccgaactc atctaaactc    8760
aatctcattg ggaataagtc aagttcacca tcagaccttc taaagagcaa taacaagctg   8820
gcaacggcaa cggttaaccct tttgggtaga atcgactccg aatattccct agagtatgaa   8880
tgcaacggca tttggcttga gacgtgggca aaattatcag cacggcataa cagttcaatg    8940
cgttgttact ctgaaattct tacctatcta attacgtctc aagggcataa attaaatatc    9000
aacattccct cacctcttgc agatattaag aagctaaatg atgaggtaag tagtaacagg   9060
gaaaaggtaa aaaatgagag atactctcag aggttaaact caccagatat taacgatgca   9120
gaagctacca tactcgaatc taaagagcaa aaaatcggat tgactctcaa tgagagatgc   9180
accctagaaa agcataaagt taagaagcgg tatgggaatg taaagatgga tattctcacc   9240
tttgatgatg atggactata ccccaaactc agactatttt attacctcac catcggtaaa   9300
cctcatctca aggctaatga cagaaaagct attgccaaaa tgggcaatga caataaaggc   9360
aagattctat caaaagactt agttaataaa acttactccg ctcgtgtgaa ggtcttagag   9420
attcttaaac taactgactt tatcgacaat cttagagatg aactcttaat aactcccaat   9480
aatccagcta tcaccgattt taatcatctt ctgctaagag ctaagaagga tttaagagta   9540
ttaggagtca acatcggaaa atatccaatg gccaacatta atgccgtact tactctcatt   9600
ggtcacaaac tttctgtaat gagagatgag ttcggaaaag agaaaaggat aaaagtagat   9660
ggtaaatcat accgatgtta tcaacttgaa acattaccag attttaccaa tgatactctt   9720
gactactgt tagaaaatga tagccaaaa gaagtaacag caacagaaaa ttactccgaa      9780
aattttaacc cttcaaatag ctacaatcca gacagtaaga cactttcaga gggtgcaaat   9840
ttcctatatc taaatacaga agaattgcat ccaaataaat tgcactaga aataaagac      9900
ggtgctgaac ttttttatt cggggtaaag gtgattgtga aaggaatctt ggacgggca     9960
gtaactatat tctctatggg tcaagaatac gatttatccc tcaatgaact agaggggatg  10020
ttaacatcat gaactttaca agaatctttt taagggcga tcgcaccatg ttaaatgatg   10080
gtacatttgt tcagatattt gatatttacc atgaccacgc attgggagtg accttgacc   10140
ttaagacaga aaaattatt tccgatgatg ttaggtaat tactgtcaaa gacttattgt    10200
tcgatggcac ttataaaggg gtaaaatctt ttatgccgga taatgccga taatgccga   10260
ttgatgctac aaaatcccat aatcataagc gataatcccc taatagcttg taattcttga  10320
accgtagcga tttagagta ttccaaaaag aagaaataaa caccgcaaaa tgtcgtattt    10380
cacatatata aaccaaggtt ttttgccct aaatctttat gtttgtagtg tgatgttggg   10440
tcaaaatggt cagaaagtt gcaaggtttt tatggatgct tacgcgcgcg agggtaagc    10500
atcccaaat agttacttta tcctagtcca tgccattta ttgccgtccc gttcggcttt   10560
```

FIG. 15 (continued)

```
aaaaaagtgc caaaactcac aaggtgcaat aaaaagttct gtaactttcg caacectaga   10620
taatctttca acagttactt ttttcctat  tatctcggta caaagtttgg ctagtttctc   10680
ttttccctct ttttcaatca agccttcttg tatgccaac  tcattgatta atctctctat   10740
ttttaccatt atttccgtt  caggtagttt atccctaaa  tcttcatcgg gggcaatgt    10800
agggcattct gaagggctt  ttcttctgt  ctggacatta tctaatattg aagtaaccaa   10860
actatcttca gttttttcta ttcctattaa ttcatattcg gttactgtat ccgtatcaat   10920
atccgaataa ctatctttat ccgtattagc tattcggtta agtttatccg ttaactcaga   10980
aacaagacta tatagcggtt ttagctttc  ttctatcctg ttatctaata cggataagtt   11040
tataacggtta tcattatccg tattagtatc attgggcttt ttggtagtt  ctacccccc   11100
ataaaccgct tttattccca attccaacag actgataaca gtatcctta  taatgggttt   11160
tttgctgata tggtgaactt ttgcccttc  catcattgcg atactttcta tctcactcat   11220
caacttatcg cttaagtgaa tctcgtatct gtttaatccc ttactggttt tattcatatc   11280
cgtttacttt attcggttaa caattctatt ttatacgaat aaaatattat acggttaact   11340
ttatacgttt aactatttta tctatacgga taacagtaat aagttattcg tattagttat   11400
acgtttactt ttatccaaat aaaattagtg catttaaact aaaagaatga ttttatcgga   11460
gttgatagca ttggattaac ctaaagatgt ttataagcta tatctgataa gtatttaagg   11520
ttatttgtt  attctgttta ttgacattat cagaataaaa gaatagaata taattgttga   11580
gagataagag gttaagtga  ttatgttaa  gaagttagtt ggttatgtca gggtcagtag   11640
tgaatcgcaa gaggataaca ctagcttaca gaatcagata gagagaattg aagcatattg   11700
tatggctttt ggttatgagt tggtaaaaat attccaaagag gttgccactg gtacaaaagc   11760
agatattgaa accgtccta  tttttaatga agctatagaa tacttgaaac aggataatgc   11820
taatgaatt  attgccttga agctagaccg aatcgcacgg aatgctttag atgtattgcg   11880
tttggttcgt gaaaccttag aaccacaaaa taaaatgtta gtgttactag atattcaggt   11940
agatacttcg acaccttcag gaaaaatgat tttaactgta atgagtgccg ttgctgaact   12000
cgaaagagac atgatctatg atcgcactca gggggtaga  aagactaaag cccaaaaggg   12060
cgggtatgcc tacgggaaac ctaaattggg ctataagact gaagaaaagg aactaaaaga   12120
agattcagca caacaggaaa ctattaaact aattaagagt caccgtaggt caggaaaag    12180
ctaccagaaa atagctgatt atctcaatgc ccaaagtatt cccactaaac aagtaagaa    12240
atggagttct agcgtcgtct atcgaatctg tcaggaaaaa gctggttaag tctgttata    12300
gatatttaga atttattgaa taaaaatagt atgaacaata atatatttatg gactaaccac   12360
gctcggaaac gtttaactga acgatgggaa ataaaagaat catgggttat tgataccatc   12420
gaaaatcctg aacgttcaga atttattgtt gatgagtcag gggaaaaata tcattactat   12480
aaaagaatag ctaagtttaa gaatagagtg ttagaagtga taacttctgc caactcaaca   12540
ccccacaagaa taataacctt ttactttaac cgtaacatga ggaaaaattt atgattgtta   12600
cttacgataa tgaagttgac gcaatttatt ttaagttaac ggaaaataaa attgatagca   12660
ccgaacctca aacagacagg attatcatty attacgatga agtaataat  attgttggca   12720
ttgaggtatt agattttaat tatcttgtca agaaaggttt aaccgttgct gattaccttt   12780
tttctgaaga tgaagatta  acagcttctc aatatttaa  ttttcctgtt gctatctaat   12840
ccagaagggg caataatccc cttctttcat cgagttagac ttaatatcac aaaagtcatt   12900
ttcatttac  cgtttctttt cccacagcgtc cgtacgccc  tcgttaaatc tcaaaaccga   12960
caatttatga tgtttataaa aagttactca ctttaataag tatttatact cattaaaggg   13020
ttattctttt tttgtagcct gataggttgg gaaggaatat ttcagattat cagatttgtt   13080
g                                                                    13081
```

```
ID   TK368\pABICyano1-6.8_PpetEABICyano1-PDCmax-PrpsLABICyano1-synADHmax-
     PrbcABICyano1-Km**-oriVT standard; circular DNA;     ; 13562 BP.
CC   This file is created by Vector NTI
CC   http://www.invitrogen.com/
CC   VNTDATE|630061176|
CC   VNTDBDATE|630061267|
CC   LSOWNER|
CC   VNTAUTHORNAME|Frank Uliczka|
FH   Key             Location/Qualifiers
FH
FT   terminator      3806..3963
FT                   /vntifkey="43"
FT                   /label=TrbcSABICyano1
FT   CDS             2797..3804
FT                   /vntifkey="4"
FT                   /label=synADHmax
FT   gene            2797..3807
FT                   /vntifkey="60"
FT                   /note="ADH"
FT   promoter        2225..2793
FT                   /vntifkey="30"
FT                   /label=PrpsLABICyano1
FT   insertion_seq   6818..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   misc_difference 4137..4140
FT                   /vntifkey="85"
FT                   /label=TA\in\pMA\data
FT   rep_origin      complement(5753..6811)
FT                   /vntifkey="33"
FT                   /label=OriVT
FT   CDS             7328..10513
FT                   /vntifkey="4"
FT                   /label=ORF\1
FT                   /note="orf1 rep ori binding protein slr7037 homolog Similar to
     hypothetical protein slr7037 of plasmid pSYSA (103 kb) of Synechocystis sp. PCC 6803"
FT   misc_feature    10109..10142
FT                   /vntifkey="21"
FT                   /label=Rep\motif
FT                   /note="Rep protein active site motif EKXKYXVFKKD"
FT   rep_origin      complement(9849..9866)
FT                   /vntifkey="33"
FT                   /label=Rep_Origin_1\(potential)
FT                   /note="potential rep origin; match pNostoc (Acc# M81381) nick
     site (358-375); on reverse strand"
FT   CDS             10549..10734
FT                   /vntifkey="4"
FT                   /label=ORF\2
FT                   /note="orf2"
```

```
taggtggtgc agttgctact atggctgctg ccaaatcttt ttttcccgaa gaaaatcccc        1260
           attatattgg aactagttgg ggagaagttt cttatcctgg tgtggaaaaa actatgaaag   1320
           aagccgacgc tgttattgct ttagccoctg tgtttaatga ttattctacc actggttgga   1380
           ctgatattcc cgatcccaaa aaattagttt tagccgaacc tcgttctgtt gttgttaatg   1440
           gtgttcgctt tccctctgtg catttaaaag attatttaac ccgcttacc caaaaagttt    1500
           ctaaaaaaac tgtgccctta gatttttta aatctttaaa tgcgggtgaa ttaaaaaaag    1560
           ctgtcctgc tgatcctct gctcctttag ttaatgctga aattgcccgt caagttgaag     1620
           ccttattaac ccctaatact acccgttattg ccgaactgg tgattcttgg tttaatgccc    1680
           aacgcatgaa attacctaat ggtgccgtg ttgaatatga aatgcaatgg ggtcatattg     1740
           gttggtctgt acctgctgct tttgttatg ctgttggtgc tcctgaacgt cgtaatattt     1800
           taatggtggg tgatggttct tttcaattaa ctgcccaaga gttgccaa atggttcgct     1860
           taaaattacc cgttattatt tttttaataa ataattatgg ttataccatt gaagtgatga    1920
           ttcatgatgg gccatataat aatattaaaa attgggatta tgcgggttta atggaagtgt    1980
           ttaatggtaa tggtggttat gattctggtg ctggtaaagg tttaaaagcc aaaactggtg    2040
           gtgaattagc tgaagctatt aaagttgcct tagccaatac tgatgggcca accttaattg    2100
           aatgttttat tggtcgcgaa gattgtaccg aagaattagt taaatggggt aaacgtgttg    2160
           ctgctgctaa ttctcgcaaa cccgtgaata aattattgta attttggggg atcaattcga    2220
           gctcctccgc ttaaaaaatt tcattttttcg atcaaaaag acaaattatt actaattagc    2280
           tcatggcaat aaataatcag tagtaatctg tttcacatt ttattgttaa ttttattat     2340
           tgctaatatc aacctttcct acttctgctt aatatttat ttatgctcaa tgggaaaatc    2400
           tgaataagaa ttgagaacag tgttaccaat agaagtattt aagttaaa gcatacctta    2460
           aagataacat ttttttttga aaagagtcaa attattttg aaaggctgat attttgata   2520
           tttactaata ttttatttat ttcttttcc cttaaaataa gagctaaatc tgttttatt    2580
           atcatttatc aagctctatt aatacctcaa cttttcaag aaaaaataat aataattttt    2640
           ccctctactc tcatgaccttt taggaaaat taattttaga aaaactattg acaaacccat   2700
           aaaaatgag ataagattat agattgtcac tggtatttta tactagaggc aaattatatt   2760
           tatatataca aaaatgctgt ataaaaaca tctcatatga ttaaagccta tgctgcctta   2820
           gaagccaatg gtaaattaca acccttgaa tatgatcctg tgctttaggg tgccaatgaa    2880
           gtggaaattg aagtgcaata ttgtggtgtg tgtcattctg atttatctat gattaataat   2940
           gaatggggta tttctaatta tcccttagtt cctggtcatg aagttgttgg tactgttgct   3000
           gctatgggtg aaggtgttaa tcatgtggaa gtgggtgatt tagttggttt aggttggcat   3060
           tctggttatt gtatgacctg tcattcttgt ttatctggtt atcataattt atgtgccact   3120
           gccgaatcta ctattgtggg tcattatggt ggttttggtg atagagttcg tgctaaaggt   3180
           gtttctgtgg tgaaattacc caaaggtatt gatttagcct ctgctgggcc tttatttttgt  3240
           ggtggtatta ccgttttttc tcccatggtg gaattatctt taaaacctac cgccaaagtt    3300
           gctgttactg gtattggtgg tttaggtcat ttagccgttc aatttctaag agcctgggt    3360
           tgtgaagtta ctgcttttac ctcttctgcc cgtaaacaaa ccgaagtttt agaattaggt    3420
           gcccatcata tttagattc taccaatcct gaagctattg cttctgccga aggtaaattt    3480
           gattatatta tttctaccgt gaatttaaaa ttagattgga atttatatat cagtacctta   3540
           gcccctcaag gtcattttca ttttgttggt gtgtgttag aacccttgga cttaaactta    3600
           tttcccttat taatgggaca acgttctgtt tctgcttctc ctgttggttc tcctgctact   3660
           attgccacta tgttagattt tgccgtggt catgatatta aacccgtggt ggaacaattt    3720
           tcttttgatc aaattaatga agccattgcc cattagaat ctggtaaagc ccattatcgc    3780
           gtggtgttat ctcattctaa aaattaataa gattaacttc taaactgaaa caaatttgag    3840
           ggtaggcttc attgtctgcc cttattttt tatttaggaa aagtgaacag actaaagagt     3900
           gttggctcta ttgctttgag tatgtaaatt aggcgttgct gaattaaggt atgatttttg   3960
           acccttctc tcttctgcag ttacctagga tttctggcga aaggggatg tgctgcaagg     4020
           cgattaagtt gggtaacgcc aggttttcc cagtcacgac gttgtaaaac gacggccagt    4080
           gagcgcgacg taatacgact cactataggg cgaattggcg gaaggccgtc aagcgcgcat    4140
           ggcgcgccta cgtagacaat tgtcgatgta attattaact atcttattat agatgagggg    4200
           agagggagaa attagttcgg agagaacgct cgagcgctcg ttccgcaaag cggtacggag    4260
```

FIG. 17 (continued)

```
ttagttaggg gctaatgggc attctcccgt acaggaaaga gttagaagtt attaattatc    4320
aacaattctc ctttgcctag tgcatcgtta cctttttaat taaaacataa ggaaaactaa    4380
taatcgtaat aatttaacct caaagtgtaa agaaatgtga aattctgact tttataacgt    4440
taaagaggga aaaattagca gtttaaaata cctagagaat agtctggggt aagcatagag    4500
aattagatta gttaagttaa tcaaattcag aaaaaataat aatcgtaaat agttaatctg    4560
ggtgtataga aaatgatccc cttcatgata agatttaaac tcgaaaagca aagccaaaa    4620
aactaacttc cattaaaaga agttgttaca tataacgcta taaagaaaat ttatatattt    4680
ggaggatacc aaccatgtct catattcaac gtgaaactag ttgttctcgt cctcgtttaa    4740
attctaatat ggatgccgat ttatatggtt ataaatgggc tcgtgataat gttggtcaat    4800
ctggtgctac tatttatcgt ttatatggta aacctgatgc tcctgaatta ttcttgaaac    4860
atggtaaagg ttctgttgct aatgatgtta ctgatgaaat ggttcgttta aactggttga    4920
ctgaatttat gcctttacct actattaaac attttattcg tactcccgat gatgcttggt    4980
tattaactac tgctattcct ggtaaaactg cttttcaagt tttagaagaa tatcctgatt    5040
ctggtgaaaa tattgttgat gcttagctg tttttttacg tcgtttacat tctattcccg    5100
tttgtaattg tccttttaat tctgatcgtg tttttcgttt agctcaagct caatctcgta    5160
tgaataatgg tttagttgat gcttctgatt ttgatgatga acgtaatggt tggcctgttg    5220
aacaagttg gaaagaaatg cacaaattgt taccttttc tcctgattct gttgttactc    5280
atggtgattt ttcttagat aatttgatct ttgatgaagg taaattgatt ggttgtattg    5340
atgttggtcg tgttggtatt gctgatcgtt atcaagattt agctattta tggaattgtt    5400
taggtgaatt ttctccttct ttacagaaac gtttatttca gaaatatggt attgataatc    5460
ctgatatgaa caagttacaa tttcatttaa tgttggacga gttcttttaa gaattaattc    5520
atgaccaaaa tcccttaacg tgagttttcg ttccactgag cgtcagaccc cgtagaaaag    5580
atcaaaggat cttcttgaga tcctttttt ctgcgcgtaa tctgctgcta tttaaattac    5640
gtacacgtgt tattactttg ttaacgacaa ttgtcttaat taactgggcc tcatgggcct    5700
tccgctcact gcccgctttc cagtcgggaa acctgtcgtg ccagctctgc agatgacggt    5760
gaaaacctct gacacatgca gctcccggag acggtcacag cttgtctgta agcggatgcc    5820
gggagcagac aagcccgtca gggcgcgtca gcgggtgttg gcgggtgtcg ggcgcagcc    5880
atgacccagt cacgtagcga tagcggagtg tatactggct taactatgcg gcatcagagc    5940
agattgtact gagagtgcac catatgcggt gtgaaatacc gcacagatgc gtaaggagaa    6000
aataccgcat caggcgctct tccgcttcct cgctcactga ctcgctgcgc tcggtcgttc    6060
ggctgcggcg agcggtatca gctcactcaa aggcggtaat acggttatcc acagaatcag    6120
gggataacgc aggaaagaac atgtgagcaa aaggccagca aaaggccagg aaccgtaaaa    6180
aggccgcgtt gctggcgttt ttccataggc tccgcccccc tgacgagcat cacaaaaatc    6240
gacgctcaag tcagaggtgg cgaaacccga caggactata aagataccag gcgtttcccc    6300
ctggaagctc cctcgtgcgc tctcctgttc cgaccctgcc gcttaccgga tacctgtccg    6360
cctttctccc ttcgggaagc gtggcgcttt ctcatagctc acgctgtagg tatctcagtt    6420
cggtgtaggt cgttcgctcc aagctgggct gtgtgcacga accccccgtt cagcccgacc    6480
gctgcgcctt atccggtaac tatcgtcttg agtccaaccc ggtaagacac gacttatcgc    6540
cactggcagc agccactggt aacaggatta gcagagcgag gtatgtaggc ggtgctacag    6600
agttcttgaa gtggtggcct aactacggct acactagaag gacagtattt ggtatctgcg    6660
ctctgctgaa gccagttacc ttcggaaaaa gagttggtag ctcttgatcc ggcaaacaaa    6720
ccaccgctgg tagcggtggt ttttttgttt gcaagcagca gattacgcgc agaaaaaag    6780
gatctcaaga agatcctttg atcttttcta ctgcagaagc ttgttagaca cctgtcatg    6840
tattttatat tatttattc accatacgga ttaagtgaaa cctaatgaaa atagtacttt    6900
cggagcttta acttaatga aggtatgttt tttatagac atcgatgtct ggtttaacaa    6960
taggaaaag tagctaaaac tccatgaat taagaaata acaaggtgtc taacaacctg    7020
ttattaagaa tgttagaaaa gacttaacat ttgtgttgag ttttataga cattggtgtc    7080
tagacatacg gtagataagg tttgctcaaa aataaaataa aaaagattg gactaaaaaa    7140
catttaattt agtacaattt aattagttat ttttcgtctt caaatttgc tttgttgagc    7200
agaaatttag ataaaaaaat cccgtgatc agattacaat gtcgttcatt gtacgatgtg    7260
tcgaaaatc tttacgacac tctaaactga ccacacgggg gaaaaagaaa actgaactaa    7320
taacatcatg atactcggaa aacctagcaa ttctcaaccc ctaaacaaaa gaaacttcca    7380
```

FIG. 17 (continued)

```
aaacoctgac catataaagg agtggcaaca atcagcaatc agtcaagatt tgatagcaga      7440
aaatcttgta toggttgcta atggttttga tgtactattt atcggcaata aataccgaac      7500
taacacgggt gttctgtcac ggcacatatt aaactcctat tctcatttag aagatggtgg      7560
ttcgtatggt agaacatttg accoatttac caataaagaa atgcagtggg ttcaatttaa      7620
accgaataga ccaagaaaag gttctactgg taaggtaatc aaatatgaat cgccaaaagg      7680
tgaacctaca agagttctaa tgccgtttgt gcctatgaaa atatggcaac ggattagcga      7740
taagttcgga gtaccgatta atccgaaaaa agatactcac ttttgggaat gggtaaagaa      7800
taatccatcg ataccgattg ccattacaga aggaaataaa aaagctaatt gcctattatc      7860
ctatggctat cctgctattg cctttgtagg catttggaac ggattagaga aataaaatga      7920
tttctcgaag gaaaagcagt taaagagga tttgaaatgg ttgttatcca acggcaaccg      7980
aaatattaat atcatctttg accaagacca gaaacaaaaa actgtaatta atgtaaacaa      8040
agctatttc gcttatctt ctctaataag tagaaatggt cataaagtta atattgtgca       8100
atggttgccg tcaaaggta aggaataga tgattatttg gtagctttac cttttgagaa       8160
aagagaaaat catttagaca acttaattaa aattgcacca tcatttaatt tttggtcaac      8220
taaatactta ttcaagtgtc gtaaaccaga tttaccgta aattgccgtt atttgagcga      8280
tgcagtaaaa gaattaccct aagaggatat agcattaata gcacctcacg gcacgggtaa     8340
aacttcatta gtagctactc acgttaagaa tcggagttat cacggaagga aaactatttc     8400
attggtgcat cttgaaagtt tagccaaagc taatggcaac gcacttggat tatattaccg     8460
aaccgaaaat aatattgaaa agcaatatct tggatttagc ttatgtgtag atagttgccg     8520
tgataagatt aacggcatta caactgatat tatttcaggt caagattatt gccttttcat     8580
tgatgaaatt gaccaagtaa ttccacacat ccttaacagt gaaactgaag taagtaagta     8640
tagatgcacc atcattgaca ctttttctga actggtgaga aatgctgaac aggtcattat     8700
tgctgatgct gatttatccg atgtgacgat tgacctaata gaaaacatca gaggtaaaaa     8760
actatatgta atcaagaatg aatatcagta tcagggaatg acttttaacg ccgttggttc     8820
accattagaa atgatggcaa tgatgggaaa atggtgtca gaaggcaaga aattatttat       8880
taacaccaca tcccaaaagg caaaagtaa gtacggcaca atcgctcttg agtcttatat       8940
ttttggtcta aataaagaag caaagatatt aagaatagac tctgaaacca ctaaaaaccc      9000
tgaacatcca gcctataaaa tcattgacca agcttaaat aatatcctca aagattatga       9060
ttatgtcatt gcctcacctt gccttcaaac aggtgtcagt attaccttaa aagggcattt      9120
tgaccagcaa tttaactttt ccagtggaaa cattacacct cattgcttt tacagcaaat       9180
gtggcggttg aggatgcag aaattgaaag attctattat gtgccgaact catctaacct       9240
caatctcatt gggaataagt caagttcacc atcagacctt ctaaagagca ataacaagat      9300
ggcaacggca acggttaacc ttttgggtag aatcgactcc gaatattccc tagagtatga     9360
atcgcacggc atttggcttg agacgtgggc aaaattatca gcacggcata acagttcaat     9420
gcgttgttac tctgaaattc ttacctatct aattacgtct caagggcata aattaaatat      9480
caacattccc tcacctcttg cagatattaa gaagctaaat gatgaggtaa gtagtaacag      9540
ggaaaaggta aaaaatgaga gatactctca gaggttaaac tcaccagata ttaacgatgc      9600
agaagctacc atactcgaat ctaaagagca aaaaatcgga ttgactctca atgagagatg     9660
caccctagaa aagcataaag ttaagaagcg gtatgggaat gtaaagatgg atattctcac     9720
ctttgatgat gatggactat acccccaaact cagactattt tattacctca ccatggtaa      9780
acctcatctc aaggctaatg acagaaaagc tattgccaaa atgggcaatg acaataaagg     9840
caagattcta tcaaaagact tagttaataa aacttactcc gctcgtgtga aggtcttaga    9900
gattcttaaa ctaactgact ttatcgacaa tcttagagat gaactcttaa taactccaa      9960
taatccagct atcaccgatt ttaataatct tctgctaaga gctaagaagg atttaagagt    10020
attaggagtc aacatcggaa aatatccaat ggccaacatt aatgccgtac ttactctcat    10080
tgtcacaaa cttctgtaa tgagagatga gttcggaaaa gagaaaagga taaaagtaga     10140
tgtaaatca tacgatgtt atcaacttga aacattacca gattttacca atgatactct     10200
tgactactgg ttagaaaatg atagccaaaa agaagtaaca gcaacagaaa attactccga    10260
aaattttaac ccttcaaata gctacaatcc agacagtaag acacttcag agggtgcaaa    10320
ttcctatatc ataaataag aagaattgca tccaaataaa ttgcacctag aaatataaga    10380
aggtgctgaa ctttttttat tcggggtaaa ggtgattgtg aaaggaatct tggacgggc    10440
```

FIG. 17 (continued)

```
agtaactata ttctctatgg gtcaagaata cgatttatcc ctcaatgaac tagagggat    10500
gttaacatca tgaacttkac aagaatctct ttaaagggcg atcgcaccat gttaaatgat   10560
ggtacatttg ttcagatatt tgatatttac catgaccacg cattgggagt gaccottgac   10620
cttaagacag aaaaaattat ttccgatgat gttagggtaa ttactgtcaa agacttattg   10680
ttcgatggca cttataaagg ggtaaaatct tctatgcccg ataatgcccg ataatgcccg   10740
attgatgcta caaatccca taatcataag cgtaatccc ctaatagctt gtaattcttg     10800
aaccgtagcg attttagagt attccaaaaa gagaaataa acaccgcaaa atgtcgtatt    10860
tcacatatat aaaccaaggt tttttgccct aaaatcttta tgtttgtagt gtgatgttgg   10920
gtcaaaatgg tcagaaaagt tgcaaggttt ttatggatgc ttacgcgcgc gagggtaag    10980
catcccaaa tagttacttt atcctagtcc atgcccattt attgcgtcc cgttcggctt    11040
taaaaaagtg ccaaactca caaggtgcaa taaaaagttc tgtacctttc gaaccctag    11100
ataatctttc aacgttact ttttttccta ttatctcggt acaaagtttg gctagtttct   11160
cttttccctc tttttcaatc aagccttctt gtatgcccaa ctcattgatt aatctctcta  11220
tttttaccat tatttcccgt tcaggtagtt tatccctaa atcttcatcg ggggcaatg    11280
tagggcattc tgaagggct tttctttctg tctggacatt atctaatatt gaagtaacca   11340
aactatcttc agttttttct attcctatta attcatattc ggttactgta tccgtatcaa  11400
tatccgaata actatcttta tccgtattag ctattcggtt aagtttatcc gttaactcag  11460
aaacaagact atataagcgt tttagctttt cttctatcct gttatctaat acggataagt   11520
ttatacggtt atcattatcc gtattagtat catggggctt ttttggtagt tctaccccct  11580
cataaaccgc ttttattccc aattccaaca gactgataac agtatccttt ataatgggtt  11640
ttttgctgat atggtgaact ttgcccctt ccatcattgc gatactttct atctcactca   11700
tcaacttatc gcttaagtga atctcgtatc tgtttaatcc cttactggtt ttattcatat   11760
ccgtttactt tattcggtta acaattctat tttatacgaa taaaatatta tacgttaac    11820
tttatacgtt taactatttt atcctatacgg ataacagtaa taagttattc gtattagtta  11880
tacgttact tttatccaaa taaaattagt gcatttaaac taaaagaatg attttatcgg    11940
agttgatagc attggattaa cctaaagatg tttataagct atatctgata agtatttaag   12000
gttattttgt tattctgttt attgacatta tcagaataaa agaatagaat ataattgttg  12060
agagataaga ggtttaagtg attatggtta agaagttagt tggttatgtc agggtcagta   12120
gtgaatcgca agaggataac actagcttac agaatcagat agagagaatt gaagcatatt  12180
gtatggcttt tggttatgag ttggtaaaaa tattcaaaga ggttgccact ggtacaaaag  12240
cagatattga aaccgtcct atttttaatg aagctataga atacttgaaa caggataatg  12300
ctaatggaat tattgccttg aagctagacc gaatcgcacg gaatgcttta gatgtattgc   12360
gtttggttcg tgaaaccttga gaaccacaaa ataaaatgtt agtgttacta gatattcagg   12420
tagatacttc gacaccttca ggaaaaatga ttttaactgt aatgagtgcc gttgctgaac   12480
tcgaaagaga catgatctat gatcgcactc agggggtag aaagactaaa gcccaaaagg   12540
ggggtatgc ctacggaaa cctaaatttg gctataagac tgaagaaaag gaactaaag     12600
aagattcagc acaacaggaa actattaaac taattaagag acacgtagg tcagggaaaa   12660
gctaccagaa aatagctgat tatctcaatg cccaaagtat tccactaaa caaggtaaga   12720
aatggagttc tagcgtcgtc tatcgaatct gtcaggaaaa agctggttaa gtctgtttat   12780
agatatttag aatttattga ataaaaatag tatgaacaat aaatatttat ggactaacca   12840
cgctcggaaa cgttaactg aacgatggga aataaaagaa tcatgggtta ttgatacctat  12900
cgaaaatcct gaacgttcag aatttattgt tgatgagtca ggggaaaaat atcattacta   12960
taaaagaata gctaagttta agaatagagt gttagaagtg ataacttctg ccaactcaac  13020
acccacaaga ataataaccct tttactttaa ccgtaacatg aggaaaaatt tatgattgtt   13060
acttacgata atgaagttga cgcaatttat tttaagttaa cggaaaataa aattgatagc   13140
accgaacctc aaacagacag gattatcatt gattacgatg aaagtaataa tattgttgcc   13200
attgaggtat tagatttaa ttatcttgtc aagaaaggtt taaccgttgc tgatttacct    13260
ttttctgaag atgaaagatt aacagcttct caatatttta attttcctgt tgctatctaa  13320
tccagaaggg gcaataatcc ccttctttca tcgagttaga cttaatatca caaagtcat   13380
tttcattta ccgtttcttt tccacagcgt ccgtacgcc ctgttaaat ctcaaaccg      13440
acaatttatg atgtttataa aaagttactc acttttaataa gtatttatac tcattaaagg  13500
gttattcttt tttttgtagcc tgataggttg ggaaggaata tttcagatta tcagatttgt  13560
tg                                                                   13562
```

FIG. 17 (continued)

```
ID   #1495\pABICyano1-6.8::PnirAABICyano1-zmPDCABICyano1(opt3)-PrpsLABICyano1-
     ADHABICyano1(opt3)_ter-PrbcABICyano1-Km** standard; circular DNA;   ; 13119 BP.
CC   This file is created by Vector NTI
CC   http://www.invitrogen.com/
CC   VNTDATE|624110553|
CC   VNTDBDATE|626784563|
CC   LSOWNER|
FH   Key             Location/Qualifiers
FH
FT   gene            2581..3591
FT                   /vntifkey="60"
FT                   /note="SycADHopti"
FT   terminator      3604..3648
FT                   /vntifkey="43"
FT                   /label=Terminator_1
FT                   /note="Ter_B0011"
FT   CDS             2581..3588
FT                   /vntifkey="4"
FT                   /label=SynADHABICyano1(opt3)
FT   promoter        2009..2577
FT                   /vntifkey="30"
FT                   /label=PrpsLABICyano1
FT   promoter        1..283
FT                   /vntifkey="30"
FT                   /label=PnirAABICyano1
FT   insertion_seq   6280..13113
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   rep_origin      complement(5215..6273)
FT                   /vntifkey="33"
FT                   /label=OriVT
FT   CDS             6790..9975
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   misc_feature    9571..9604
FT                   /vntifkey="21"
FT                   /label=Rep\motif
FT                   /note="Rep protein active site motif EXXKYXVKXXD"
FT   rep_origin      complement(9311..9328)
FT                   /vntifkey="33"
FT                   /label=Rep_Origin_1\(potential)
FT                   /note="potential rep origin; match pNostoc (Acc# 881381) nick
site (358-375); on reverse strand"
FT   CDS             10011..10196
FT                   /vntifkey="4"
FT                   /label=ORF\2
FT                   /note="orf2"
```

FIG. 19

```
FT   CDS             complement(10456..11220)
FT                   /vntifkey="4"
FT                   /label=ORF\3
FT                   /note="orf3"
FT   CDS             11546..12232
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             12274..12537
FT                   /vntifkey="4"
FT                   /label=ORF\5
FT                   /note="orf5"
FT   CDS             12534..12782
FT                   /vntifkey="4"
FT                   /label=ORF\6
FT                   /note="orf6"
FT   CDS             4157..4972
FT                   /vntifkey="4"
FT                   /label=Km**
FT                   /note=" maximal codon optimized kanamycin resistance gene "
FT   CDS             284..1990
FT                   /vntifkey="4"
FT                   /label=zmPDCABICyano1(opt3)
FT   promoter        3692..4155
FT                   /vntifkey="30"
FT                   /label=PrbcLABICyano1
SQ   Sequence 13119 BP; 4182 A; 2307 C; 2512 G; 4118 t;
     tgacaatta ataacttctt cctgtacggg cgaatggcca tttgctccta actaactccg     60
     tactgctttg cggaacgagc gtagcgaact ctccgaatta ctaagcctcc atccctgata    120
     gatgcaaaaa acgaattaaa attatgtgta aaaagaaaat gtgtctttat ttagtagtca    180
     aagttacaaa atattaagaa tcaaattaat aatgtattgg gcagttaagt atataagtct    240
     ttaaatattt atttgtattc aatatattaa ccgaggacaa attatgaatt cttacactgt    300
     tggaacctat ttagcagaac gttagttcca aattggtctc aaacaccatt ttgcagtagc    360
     tggtgattat aatttagttt tattggataa cttattgtta aataagaata tgaacaagt    420
     gtattgttgt aatgaattaa actgtggttt ttctgctgag ggatatgctc gtgcaaaagg    480
     tgctgccgca gcagttgtta cttattctgt tggagcatta agtgctttg acgctattgg    540
     aggtgcttat gcagaaaatt tacctgtaat cttaatctct ggtgcaccca ataacaacga    600
     tcacgctgct ggtcatgtat tgcatcatgc tttaggtaaa accgattatc attaccaatt    660
     agaaatggca aaaaatatta ccgtgccgc agaagctatt tatactcccg aagaagcacc    720
     tgctaagatc gatcacgtaa ttaaaaccgc tctccgtgag aaaaaaccg tatatttaga    780
     aatcgcttgc aatatcgctt ctatgccttg tgcagctcct ggacctgcta gtgcttatt    840
     taacgatgaa gcatctgatg aggctagttt aaatgccgct gttgaagaaa ctttgaaatt    900
     tattgctaat cgtgataaag tagctgtttt agttggttct aaactccgtg ccgctggtgc    960
     agaagaacgc gctgtaaaat tcgcagatgc cttaggaggt gctgttgcca caatggcagc   1020
     cgctaaagtt ttttccccg aagaaaatcc tcattscatt ggtacttctt ggggtgaggt   1080
     atcttaccct ggtgtagaaa aaccatgaa ggaagctgat gcagtaattg cattagctcc   1140
     tgtttttcaat gattactcta ccactggttg gactgatatt ccagaccca aaaaattagt   1200
     tttagcagaa cctcgtctgt tagttgtgaa tggtgttaga tttcccagtg tacatctcaa   1260
     agattattta actgtttag ctcaaaaagt gagtaaaaag actggcgcac tgattctt   1320
     taaatctttt aatgctggtg aattaaagaa agagctcct gctgatccca gtgctcctt   1380
     agtgaatgcc gaaatcgcaa gacaagttga agccttgtta actcctaaca ctaccgttat   1440
```

FIG. 19 (continued)

```
tgccgagact ggtgatagtt ggttcaatgc tcaacgcatg aaattaccca atggtgctcg   1500
tgttgagtat gaaatgcaat gggtcacat tggatggtct gttcctgctg catttggata    1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacgt aatggtggat acgacagtgg    1800
agcaggtaaa ggattaaaag ctaaacagg agtgagtta gctgaagcaa ttaaagtagc     1860
tttagccaat acagatggtc ctaccttaat cgaatgtttc attggacgtg aagattgtac   1920
tgaagagtta gtaaatggg gaaagcgtgt tgccgctgca aattctcgta aacctgtaaa    1980
caaactcttg tagttaggat ccgagctcct ccgcttaaaa aatttcattt ttcgatcaaa    2040
aaagacaaat tattactaat tagctcatgg caataaataa tcagtagtaa tctgttttca   2100
catttattg ttatttttta ttattgctaa tatcaaccTt ttctacttct gttaatatt    2160
ttatttatgc tcaatgggaa aatctgaaat aagattgaga acagtgttac caatagaagt   2220
atttaaggtt taaagcatac cttaaagata acatttttt ttgaaaagag tcaaattatt    2280
tttgaaaggc tgatattttt gatatttact aatatttat ttatttcttt ttcccttaaa    2340
ataagagcta aatctgtttt tattatcatt tatcaagctc tattaatacc tcaacttttt   2400
caagaaaaaa taataataat ttttccctct attctcatga cctttaggga aaattaattt    2460
tagaaaaact attgacaaac ccataaaaaa tgagataaga ttatagattg tcactggtat   2520
tttatactag aggcaaatta tatttatata tacaaaatg ctgtataaaa aacatctcat    2580
atgattaagg cttatgctgc attagaagct aatggtaaat tacaacctt tgaatacgat    2640
cccggtgctt taggtgcaaa tgaagtagaa attgaggttc agtattgtgg tgtatgtcat   2700
tctgatttat ctatgattaa caacgaatgg ggaatttcca attatccctt agttcctgga   2760
caccaagttg ttggtactgt agcagctatg ggagaaggag ttaatcatgt tgaagtaggt   2820
gacttagtag gttgggatg gcattctggt tactgtatga cctgtcatag ttgtttatct   2880
ggttatcaca acttatgtgc aactgctgaa agtaccattg ttggtcatta cggtggtttt   2940
ggtgatagag taagagctaa aggagttagt gttgtaaat taccaaaagg tatcgactta    3000
gcaagtgcag gtcctctctt ttgtggggt attactgttt ttagtcctat ggttgaatta    3060
agtttaaagc caactgcaaa agtagccgtc attggtattg gaggattggg acacttagct   3120
gttcaattc tccgtgcatg gggatgtgaa gttactgcct ttacttctag tgctcgtaaa    3180
caaacgagg tattagaatt aggagcacac catatcttag attccaccaa cctgaagct    3240
atcgctagtg cagagggaaa attcgattat attattagta ctgttaattt gaaattagat   3300
tggaacctct acatctctac tttagctccc caaggtcatt ttcactttgt tggagttgta   3360
ttagaacccc tcgatttaaa cttattccct ttattaatgg gacaacgttc tgttagtgca   3420
tctcctgttg gatctcccgc tactattgct accatgttag attttgcagt acgtcacgat   3480
attaaacctg tagtagaaca attctctttc gatcaaatca acgaagctat tgctcattta   3540
gaaagtggta aggctcatta ccgtgttgtt ttatctcact ctaaaaacta actagatctc   3600
tgcagagaat ataaaagcc agattattaa tccggctttt ttattattta aatactgtgc   3660
acgatcctgc aggatcatct tgctgaaaaa ctcgagcgct cgttccgcaa agcggtacgg   3720
agttagttag gggctaatgg gcattctccc gtacaggaaa gagttagaag ttattaatta   3780
tcaacaattc tcctttgcct agtgcatcgt tacctttta attaaaacat aaggaaaact    3840
aataatcgta ataatttaac ctcaaagtgt aaagaaatgt gaaattctga cttttataac   3900
gttaaagagg gaaaattag cagtttaaaa tacctagaga atagtctggg gtaagcatag    3960
agaattagat tagttaagtt aatcaaattc agaaaaaata ataatcgtaa atagttaatc   4020
tgggtgtata gaaaatgatc ccttcatga taagacttaa actgaaaag caaaagccaa     4080
aaaactaact tccattaaaa gaagttgtta catataacgc tataagaaa atttatatat    4140
ttgaaggata ccaaccatgt ctcatattca acgtgaaact agttgttctc gccctcgttt   4200
aaattctaat atggatgccg atttatatgg ttataatgg gctcgtgata atgttggtca    4260
atctggtgct actatttatc gtttatatgg taaacctgat gctcctgaat tattcttgaa   4320
acatggtaaa ggttctgttg ctaatgatgt tactgatgaa atggttcgtt taaactggtt   4380
gactgaattt atgccttac ctactattaa acatttatt cgtactcccg atgatgcttg     4440
gttattaact actgctattc ctggtaaaac tgcttttcaa gtttagaag aatatcctga    4500
```

FIG. 19 (continued)

```
ttctggtgaa aatattgttg atgctttagc tgttttttta cgtcgtttac attctattcc    4560
cgtttgtaat tgtccttttta attctgatcg tgttttttgt ttagctcaag ctcaatctcg   4620
tatgaataat ggtttagttg atgcttctga ttttgatgat gaacgtaatg gttggcctgt    4680
tgaacaagtt tggaaagaaa tgcacaaatt gttacctttt tctcctgatt ctgttgttac    4740
tcatggtgat ttttctttag ataatttgat ctttgatgaa ggtaaattga ttggttgtat    4800
tgatgttggt cgtgttggta ttgctgatcg ttatcaagat ttagctattt tatggaattg    4860
tttaggtgaa ttttctcctt ctttacagaa acgttatttt cagaaatatg gtattgataa    4920
tcctgatatg aacaagttac aatttcattt aatgttggac gagttctttt aagaattaat    4980
tcatgatcaa aatccttaa cgtgagtttt cgttccactg agcgtcagac ccgtagaaa      5040
agatcaaagg atcttcttga gatcctttt ttctgcgcgt aatctgctgc tatttaaatt     5100
acgtacacgt gttattactt tgttaacgac aattgtctta attaactggg cctcatgggc    5160
cttccgctca ctgcccgctt tccagtcggg aaacctgtcg tgccagctct gcagatgacg    5220
gtgaaaacct ctgacacatg cagctcccgg agacggtcac agcttgtctg taagcggatg    5280
ccggagcag acaagcccgt cagggcgcgt cagcgggtgt tggcggtgt cggggcgcag      5340
ccatgaccca gtcacgtagc gatagcggag tgtatactgg cttaactatg cggcatcaga    5400
gcagattgta ctgagagtgc accatatgcg gtgtgaaata ccgcacagat gcgtaaggag    5460
aaaataccgc atcaggcgct cttccgcttc ctcgctcact gactcgctgc gctcggtcgt    5520
tcggctgcgg cgagcggtat cagctcactc aaaggcggta atacggttat ccacagaatc    5580
aggggataac gcaggaaaga acatgtgagc aaaaggccag caaaaggcca ggaaccgtaa    5640
aaaggccgcg ttgctggcgt ttttccatag gctccgcccc cctgacgagc atcacaaaaa    5700
tcgacgctca agtcagaggt ggcgaaaccc gacaggacta taaagatacc aggcgtttcc    5760
ccctggaagc tccctcgtgc gctctcctgt tccgaccctg ccgcttaccg gatacctgtc    5820
cgcctttctc ccttcggaa gcgtggcgct ttctcatagc tcacgctgta ggtatctcag    5880
ttcggtgtag gtcgttcgct ccaagctggg ctgtgtgcac gaaccccccg ttcagcccga    5940
ccgctgcgcc ttatccggta actatcgtct tgagtccaac ccggtaagac acgacttatc    6000
gccactggca gcagccactg gtaacaggat tagcagagcg aggtatgtag gcggtgctac    6060
agagttcttg aagtggtggc ctaactacgg ctacactaga aggacagtat ttggtatctg    6120
cgctctgctg aagccagtta ccttcggaaa aagagttggt agctcttgat ccggcaaaca    6180
aaccaccgct ggtagcggtg gtttttttgt ttgcaagcag cagattacgc gcagaaaaaa    6240
aggatctcaa gaagatcctt tgatcttttc tactgcagaa gcttgttaga caccctgtca    6300
tgtatttttat attatttatt tcaccatacg gattaagtga aacctaatga aaatagtact    6360
ttcggagctt taactttaat gaaggtatgt tttttatag acatcgatgt ctggtttaac     6420
aataggaaaa agtagctaaa actcccatga attaaagaaa taacaaggtg tctaacaacc    6480
tgttattaag aatgttagaa aagacttaac atttgtgttg agttttata gacattggtg     6540
tctagacata cggtagataa ggtttgctca aaatataat aaaaaagat tggactaaaa       6600
aacatttaat ttagtacaat ttaattagtt attttttcgt ctcaaatttt gctttgttga    6660
gcagaaattt agataaaaaa atccccgtga tcagattaca atgtcgttca ttgtacgatg    6720
tgtcgaaaaa tctttacgac actctaaact gaccacacgg gggaaaaaga aactgaact     6780
aataacatca tgatactcgg aaaacctagc aattctcaac cctaaacaa aagaaacttc    6840
caaaacctg accatataaa ggagtgcaa caatcagcaa tcgtcaaga tttgatgcaa        6900
gaaaatcttg tatcggttgc taatggtttt gatgtactat ttatcggcaa taaataccga    6960
actaacacgg gtgttctgtc acggacata ttaaactcct attctcattt agaagatggt       7020
ggttcgtatg gtagaacatt tgacccattt accaataaag aaatgcagtg gttcaattt     7080
aaaccgaata gaccaagaaa aggttctact ggtaaggtaa tcaaatatga atcgccaaaa    7140
ggtgaaccta caagagttct aatgccgttt gtgcctatga aaatatggca acgattagc     7200
gataagttcg gagtaccgat taatccgaaa aaagatactc acttttggga atgggtaaag    7260
aataatccat cgataccgat tgccattaca gaaggaaata aaaagctaa ttgcctatta     7320
tcctatggct atcctgctat tgcctttgta ggcatttgga acggattaga gaaaataaat    7380
gattctctga aggaaaagca gttaaaagag gatttgaaat ggttgttatc caacggcaac    7440
cgaaatatta atatcatctt tgaccaagac cagaaacaaa aaactgtaat taatgtaaac    7500
aaagctattt tcgctttatc ttctctaata agtagaaatg gtcataaagt taatattgtg   7560
```

FIG. 19 (continued)

```
caatggttgc cgtcaaaagg taaaggaata gatgattatt tggtagcttt acctttgag    7620
aaaagagaaa atcatttaga caacttaatt aaaattgcac catcatttaa ttttggtca    7680
actaaatact tattcaagtg tcgtaaacca gatttaaccg taaattgccg ttatttgagc   7740
gatgcagtaa aagaattacc tcaagaggat atagcattaa tagcaccica cggcacggt   7800
aaaacttcat tagtagctac tcacgttaag aatcggagtt atcacggaag gaaaactatt   7860
tcattggtgc atcttgaaag tttagccaaa gctaatggca acgcacttgg attatattac   7920
cgaaccgaaa ataatattga aaagcaatat cttggattta gttatgtgt agatagttgc    7980
cgtgataaga ttaacggcat tacaactgat attatttcag gtcaagatta ttgccttttc   8040
attgatgaaa ttgaccaagt aattccacac atccttaaca gtgaaactga agtaagtaag   8100
tatagatgca ccatcattga cactttttct gaactggtga gaaatgctga acaggtcatt   8160
attgctgatg ctgatttatc cgatgtgacg attgacctaa tagaaaacat cagagagtaaa  8220
aaactatatg taatcaagaa tgaatatcag tatcagggaa tgacttttaa cgccgttggt   8280
tcaccattag aaatgatggc aatgatggga aaatcggtgt cagaaggcaa gaaattattt   8340
attaacacca catccaaaa ggcaaaaagt aagtacggca caatcgctct tgagtcttat    8400
attttggtc taaataaaga agcaaagata ttaagaatag actctgaaac cactaaaaac    8460
cctgaacatc cagcctataa aatcattgac caagacttaa ataatatcct caaagattat   8520
gattatgtca ttgcctcacc ttgccttcaa acaggtgtca gtattaccit aaaagggcat   8580
tttgaccagc aatttaactt ttccagtgga aacattacac ctcattgctt ttacagcaa    8640
atgtggcggt tgagggatgc agaaattgaa agattctatt atgtgccgaa ctcatctaac   8700
ctcaatctca ttggaataa gtcaagttca ccatcagacc ttctaaagag caataacaag    8760
atggcaaggg caacggttaa ccttttgggt agaatcgact ccgaatattc cctagagtat   8820
gaatcgcacg gcatttggct tgagacgtgg gcaaaattat cagcacggca taacagttca   8880
atgcgttgtt actctgaaat tcttacctat ctaattacgt ctcaagggca taaattaaat   8940
atcaacattc cctcacctct tgcagatatt aagaagctaa atgatgaggt aagtagtaac   9000
agggaaaagg taaaaaatga gagatactct cagaggttaa actcaccaga tattaacgat   9060
gcagaagcta ccatactcga atctaaagag caaaaaatcg gattgactct caatgagaga   9120
tgcaccctag aaaagcataa agttaagaag cggtatggga atgtaaagat ggatattctc   9180
acctttgatg atgatggact ataccccaaa ctcagactat tttattacct caccatcggt   9240
aaacctcatc tcaaggctaa tgacagaaaa gctattgcca aaatgggcaa tgacaataaa   9300
ggcaagattc tatcaaaaga cttagttaat aaaacttact ccgctcgtgt gaaggtctta   9360
gagattctta aactaactga ctttatcgac aatcttagag atgaactctt aataactccc   9420
aataatccag ctatcaccga ttttaataat cttctgctaa gagctaagaa ggatttaaga   9480
gtattaggag tcaacatcgg aaaatatcca atggccaaca ttaatgccgt acttactctc   9540
attggtcaca aactttctgt aatgagagat gagttcggaa aagagaaaag gataaaagta   9600
gatggtaaat catacgatg ttatcaactt gaaacattac cagattttac caatgatact   9660
cttgactact ggttagaaaa tgatagccaa aaagaagtaa cagcaacaga aaattactcc   9720
gaaaatttta acccttcaaa tagctacaat ccagacagta agacctttc agagggtgca   9780
aatttcctat atatasataa agaagaattg catccaaata aattgcacct agaaataaaa   9840
gaaggtgctg aacttttttt attcggggta aaggtgattg tgaaaggaat cttggacggg   9900
gcagtaacta tattctctat gggtcaagaa tacgatttat ccctcaatga actagagggg  9960
atgttaacat catgaacttt acaagaatct tttaaagggg cgatcgcacc atgttaaatg  10020
atggtacatt tgttcagata tttgatattt accatgacca cgcattggga gtgaccottg   10080
aacttaagac agaaaaaatt atttccgatg atgttagggt aattactgtc aaagacttat   10140
tgttcgatgg cacttataaa ggggtaaaat cttttatgcc cgataatgcc cgataatgcc   10200
cgattgatgc tacaaaatcc cataatcata atcgataatc ccctaatagc ttgtaattct   10260
tgaaccgtag cgattttaga gtattccaaa aagaagaaat aaacaccgca aaatgtcgta   10320
tttcacatat ataaaccaag gtttttttgcc ctaaaatctt tatgtttgta gtgtgatgtt   10380
gggtcaaaat ggtcagaaaa gttgcaaggt tttatggat gcttacgcgc gcgagggta    10440
agcatcccca aatagttact ttatcctagt ccatgcccat ttattgcgt ccgttcggc    10500
tttaaaaaag tgccaaaact cacaaggtgc aataaaaagt tctgtacctt tgcaaccct   10560
agataatctt tcaacagtta cttttttttcc tattatctcg gtacaaagtt tggctagttt  10620
ctcttttccc tcttttcaa tcaagcctto ttgtatgccc aactcattga ttaatctctc   10680
```

FIG. 19 (continued)

```
tatttttacc attatttccc gttcaggtag tttatcccct aaatcttcat cggggggcaa    10740
tgtagggcat tctgaagggg ctttttcttc tgtctggaca ttatctaata ttgaagtaac    10800
caaactatct tcagtttttt ctattcctat taattcatat tcggttactg tatccgtatc    10860
aatatccgaa taactatctt tatccgtatt agctattcgg ttaagtttat ccgttaactc    10920
agaaacaaga ctatatagcg gttttagctt ttcttctatc ctgttatcta atacggataa    10980
gtttatacgg ttatcattat ccgtattagt atcattgggc ttttttggta gttctacccc    11040
ctcataaacc gctttattc ccaattccaa cagactyata acagtatcct ttataatggg     11100
tttttgctg atatggtgaa cttttgcccc ttccatcatt gcgatactt ctatctcact      11160
catcaactta tcgttaagt gaatctcgta tctgtttaat ccctactgg tttattcat       11220
atccgttac tttattcggt taacaattct attttatacg aataaaatat tatacgttaa     11280
actttatacg tttaactatt ttatctatac ggataacagt aataagttat tcgtattagt    11340
tatacgttta cttttatcca aataaaatta gtgcatttaa actaaagaa tgatttatc      11400
ggagttgata gcattggatt aacctaaaga tgtttataag ctatatctga taagtacttta  11460
aggttatttt gttattctgt ttattgacat tatcagaata aagaataga atataattgt    11520
tgagagataa gaggtttaag tgattatggt taagaagtta gttggttatg tcagggtcag   11580
tagtgaatcg caagaggata acactagctt acagaatcag atagagagaa ttgaagcata   11640
ttgtatggct tttggttatg agttggtaaa aatattcaaa gaggttgcca ctggtacaaa   11700
agcagatatt gaaaccggtc ctattttttaa tgaagctata gaatacttga aacaggataa  11760
tgctaatgga attattgcct tgaagctaga ccgaatcgca cggaatgctt tagatgtatt   11820
gcgtttggtt cgtgaaacct tagaaccaca aaataaaatg ttagtgttac tagatattca   11880
ggtagatact tcgacacctt caggaaaaat gatttaact gtaatgagtg ccgttgctga    11940
actcgaaaga gacatgatct atgatcgcac tcaggggggt agaaagacta agcccaaaa    12000
gggcgggtat gcctacggga aacctaaatt tggctataag actgaagaaa aggaactaaa   12060
agaagattca gcacaacagg aaactattaa actattaag agacaccgta ggtcagggaa    12120
aagctaccag aaaatagctg attatctcaa tgcccaaagt attcccacta aacaaggtaa   12180
gaaatggagt tctagcgtcg tctatcgaat ctgtcaggaa aaagctggtt aagtctgttt   12240
atagatattt agaatttatt gaataaaaat agtatgaaca ataaatattt atggactaac   12300
cacgctcgga aacgtttaac tgaacgatgg gaaataaaag aatcatgggt tattgatacc   12360
atcgaaaatc ctgaacgttc agaatttatt gttgatgagt cagggaaaa atatcattac   12420
tataaaagaa tagctaagtt taagaataga gtgttagaag tgataacttc tgccactca   12480
acacccacaa gaataataac cttttacttt aaccgtaaca tgaggaaaaa tttatgattg   12540
ttacttacga taatgaagtt gacgcaattt attttaagtt aacggaaaat aaaattgata   12600
gcaccgaacc tcaaacagac aggattatca ttgattacga tgaaagtaat aatattgttg   12660
gcattgaggt attagatttt aattatcttg tcaagaaagg tttaaccgtt gctgatttac   12720
cttttctgaa agatgaaaga ttaacagctt ctcaatattt taattttcct gttgctatct   12780
aatccagaag gggcaataat ccccttcttt catcgagtta gactaatat cacaaaagtc    12840
atttcattt taccgtttct tttccacagc gtccgtacgc cctcgttaa atctcaaaac    12900
cgacaattta tgatgtttat aaaaagttac tcactttaat aagtatttat actcattaaa   12960
gggttattct tttttgtag cctgataggt tgggaaggaa tatttcagat tatcagattt    13020
gttgaatatt ttcgtcaga tacgaaacc ttacaacat aattaacacc tgaaactatt      13080
gatatgtcta ggttttagct ctatcacagg ttggatctg                           13119
```

FIG. 19 (continued)

1578 pABICyano1-6.S::PnirAABICyano1-zmPDCABICyano1(opt3)-dsrA-Prbc*(optRBS)-synADHoop-PrbcABICyano1-Km**

```
ID      #1578\pABICyanol-6.8::PnirAABICyanol-zmPDCABICyanol(opt3)-derA-Prbc*(optRBS)-
        synADH\oop-PrbcABICyanol-Km** standard; circular DNA;      ; 12648 BP.
CC      This file is created by Vector NTI
CC      http://www.invitrogen.com/
CC      VNTDATE|634296508|
CC      VNTDBDATE|634296508|
CC      LSOWNER|
FH      Key             Location/Qualifiers
FH
FT      promoter        46..136
FT                      /vntifkey="30"
FT                      /label=Prbc*(optRBS)
FT      insertion_seq   2..47
FT                      /vntifkey="14"
FT                      /label=dsrA\ter
FT      CDS             117..1127
FT                      /vntifkey="4"
FT                      /label=synADH
FT      terminator      1157..1187
FT                      /vntifkey="43"
FT                      /label=oop\terminator
FT      promoter        1214..1677
FT                      /vntifkey="30"
FT                      /label=PrbcABICyanol
FT      CDS             10925..12631
FT                      /vntifkey="4"
FT                      /label=zmPDCABICyanol(opt3)
FT      CDS             1679..2494
FT                      /vntifkey="4"
FT                      /label=Km**
FT                      /note=" maximal codon optimised kanamycin resistance gene "
FT      CDS             10056..10304
FT                      /vntifkey="4"
FT                      /label=ORF\6
FT                      /note="orf6"
FT      CDS             9796..10059
FT                      /vntifkey="4"
FT                      /label=ORF\5
FT                      /note="orf5"
FT      CDS             9068..9754
FT                      /vntifkey="4"
FT                      /label=ORF\4
FT                      /note="orf4 Integrase/Recombinase Similar to Site-specific
recombinase of Bacillus thuringiensis serovar israelensis ATCC 35646"
FT      CDS             complement(7978..8742)
FT                      /vntifkey="4"
FT                      /label=ORF\3
FT                      /note="orf3"
FT      CDS             7533..7718
FT                      /vntifkey="4"
FT                      /label=ORF\2
FT                      /note="orf2"
```

FIG. 21

```
FT   rep_origin      complement(6833..6850)
FT                   /vntifkey="33"
FT                   /label=Rsp_Origin_1\(potential)
FT                   /note="potential rep origin; match pNostoc (Acc# M81381) nick
site (358-375); on reverse strand"
FT   misc_feature    7093..7126
FT                   /vntifkey="21"
FT                   /label=Rep\motif
FT                   /note="Rep protein active site motig EXXKYKVKXXG"
FT   CDS             4312..7487
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(2737..3795)
FT                   /vntifkey="33"
FT                   /label=OriVT
FT   insertion_seq   3802..10635
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type;insert"
FT   promoter        10642..10924
FT                   /vntifkey="30"
FT                   /label=PnirAABICyano1
SQ   Sequence 12648 BP; 3928 A; 2331 C; 2557 G; 3832 t;
     cagcaagttt catcccgacc ccctcagggt cgggattttt ttattgtact agttgacata        60
     agtaaaggca tccctgcgt gatataatta cctcagttt aaggaggtat acacatatga        120
     ttaaagccta cgctgccctg gaagccaacg gaaaactcca acccttgaa tacgacccg         180
     gtgcctggg tgctaatgag gtggagattg aggtgcagta ttgtgggtg tgccacagtg         240
     atttgtccat gattaataac gaatgggca tttcaatta cccctagtg cgggtcatg          300
     aggtggtggg tactgtggcc gccatgggcg aagggtgaa ccatgttgag gtggggatt         360
     tagtggggct gggttggcat tcgggctact gcatgacctg ccatagttgt ttatctggct       420
     accacaacct ttgtgccacg gcgaaatcga ccattgtggg ccactacggt ggctttgtg        480
     atcgggttcg ggccaaggga gtcagcgtgg tgaaattacc taaaggcatt gacctagcca       540
     gtgccgggcc ccttttctgt ggaggaatta ccgttttcag tcctatggtg gaactgagtt       600
     taaagcccac tgcaaaagtg gcagtgatcg gcattggggg cttgggccat ttagcggtgc       660
     aatttctccg ggcctgggc tgtgaagtga ctgccttac ctccagtgcc aggaagcaaa         720
     cggcagtgtt ggaattggc gtcatcaca tactagatta caccaatcaa gagcgatcg          780
     ccagtgcgga aggcaaattt gactatatta tctccactgt gaacctgaag cttgactgga       840
     acttatacat cagcaccctg gcgcccaggg gacatttcca ctttgttggg gtggtgttgg       900
     agcctttgga tctaaatttt ttccccttt tgatgggaca cgctccgtt tctgcctcc          960
     cagtgggtag tcccgccacc attgccacca tgttggactt tgctgtgcgc catgacatta      1020
     aaccgtgt ggaacaattt agcttgatc agatcaacga ggcgatgcc catctagaaa         1080
     gcggcaaagc ccattatcgg gtagtgctca gccatagtaa aaattagctc tgcaaggtt       1140
     gcttctggt ccgtggaacg ctcggttgcc gccgggcgtt tttattcct gcaggatcat       1200
     cttgctgaaa aactcgagcg ctcgttccgc aaagcggtac ggagttagtt agggctaat       1260
     gggcattctc ccgtacagga aagagttaga agttattaat tatcaacaat tctcctttgc      1320
     ctagtgcatc gttaccttt taattaaaac ataagaaaa ctaataacg taataattta        1380
     acctcaaagt gtaaagaaat gtgaaattct gacttttata acgttaaaga gggaaaaatt      1440
```

FIG. 21 (continued)

```
agcagtttaa aataccctaga gaatagtctg gggtaagcat agagaattag attagttaag      1500
           ttaatcaaat tcagaaaaaa taataatcgt aaatagttaa tctgggtgta tagaaaatga 1560
           tcccttcat gataagattt aaactgaaa agcaaaagcc aaaaaactaa cttccattaa  1620
           aagaagttgt tacatataac gctataaaga aatttatat atttgagga taccaaccat  1680
           gtctcatatt caacgtgaaa ctagttgttc tcgccctcgt ttaaattcta atatggatgc 1740
           cgatttatat ggttataaat gggctcgtga taatgttggt caatcgtgtg ctactattta 1800
           tcgtttatat ggtaaacctg atgctcctga attattcttg aaacatggta aaggttctgt 1860
           tgctaatgat gttactgatg aaatggttcg tttaactgg ttgactgaat ttatgccttt   1920
           aactactatt aaacattta ttcgtactcc cgatgatgct tggttattaa ctactgctat  1980
           tcctggtaaa actgcttttc aagttttaga agaatatcct gattctggtg aaaatattgt 2040
           tgatgcttta gctgttttt tacgtcgttt acattctatt ccgtttgta attgtcctt   2100
           taattctgat cgtgttttc gtttagctca agctcaatct cgtatgaata atggtttagt 2160
           tgatgcttct gattttgatg atgaacgtaa tggttggcct gttgaacaag tttgaaaga  2220
           aatgcacaaa ttgttacctt ttctcctga ttctgttgtt actcatggta ttttttcttt   2280
           agataatttg atctttgatg aagtaaaatt gattggttgt attgatgttg gtcgtgttgg 2340
           tattgctgat cgttatcaag atttagctat ttatggaat tgtttaggtg aattttctcc   2400
           ttcttttacag aaacgtttat ttcagaaata tggtattgat aatctgata tgaacaagtt 2460
           acaatttcat ttaatgttgg acgagttctt ttaagaatta attcatgacc aaaatccctt  2520
           aacgtgagtt ttcgttccac tgagcgtcag acccgtaga aagatcaaa ggatcttctt   2580
           gagatccttt ttttctgcgc gtaatctgct gcttgcaaa ttacgtacac gtgttattac   2640
           tttgttaacg acaattgtct taattaactg ggcctcatgg gccttccgct cactgcccgc 2700
           ttccagtcg ggaaacctgt cgtgccagct gcagatga cggtgaaaac ctctgacaca   2760
           tgcagctcc ggagacgtc acagcttgtc tgtaagcgga tgccgggagc agacaagcc   2820
           gtcagggcgc gtcagcgggt gttgcgggt gtcgggcgc agccatgacc cagtcacgta   2880
           gcgatagcgg agtgtatact ggcttaacta tgcggcatca gagcagattg tactgagagt 2940
           gcaccatatg cggtgtgaaa taccgcacag atgcgtaagg agaaaatacc gcatcaggcg 3000
           ctcttccgct tcctcgctca ctgactcgct gcgctcggtc gttcggctgc ggcgagcggt 3060
           atcagctcac tcaaaggcgg taatacggtt atccacagaa tcaggggata acgcaggaaa 3120
           gaacatgtga gcaaaaggcc agcaaaaggc caggaaccgt aaaaaggccg cgttgctggc 3180
           gtttttccat aggctccgcc ccctgacga gcatcacaaa aatcgacgct caagtcagag 3240
           gtggcgaaac ccgacaggac tataaagata ccaggcgttt ccccctggaa gctccctcgt 3300
           gcgctctcct gttccgaccc tgccgcttac cggatacctg tccgcctttc tcccttcggg 3360
           aagcgtgggg ctttctcata gctcacgctg taggtatctc agttcggtgt aggtcgttcg 3420
           ctccaagctg ggctgtgtgc acgaaccccc cgttcagccc gaccgctgcg ccttatccgg 3480
           taactatcgt cttgagtcca acccggtaag cacgactta tgccactgg cagcagccac  3540
           tggtaacagg attagcagag cgaggtatgt aggcggtgct acagagttct tgaagtggtg 3600
           gcctaactac ggctacacta agaagacagt atttggtatc tgcgctctgc tgaagccagt 3660
           taccttcgga aaaagagttg gtagctcttg atccggcaaa caaaccaccg ctggtagcgg 3720
           tggtttttt gtttgcaagc agcagattac gcgcagaaaa aaggatctc aagaagatcc  3780
           tttgatcttt tctactgcag aagcttgtta gacaccctgt catgtatttt atattattta 3840
           tttcaccata cggattaagt gaaacctaat gaaatagta ctttcggagc tttaacttta  3900
           atgaaggtat gttttttat agacatcgat gtctggttta acataggaa aagtagcta   3960
           aaactcccat gaattaaaga aataacaagg tgtctaacaa cctgttatta agaatgttag 4020
           aaaagactta acatttgtgt tgagttttta tagacattgg tgtctagaca tacggtagat 4080
           aagtttgct caaaataaa ataaaaaag attggactaa aaacatttta atttagtaca    4140
           atttaattag ttatttttc gtctcaaatt ttgcttgtt gagcagaaat ttagataaaa   4200
           aaatcccgt gatcagatta caatgtcgtt cattgtacga tgtgtcgaaa aatctttacg  4260
           acactctaaa ctgaccacac ggggaaaaa gaaactgaa ctaataacat catgatactc   4320
           ggaaaaccta gcaattctca acccctaaac aaaagaaact tccaaaaccc tgaccatata 4380
           aaggagtggc aacaatcagc aatcagtcaa gatttgatag cagaaaatct tgtatcggtt 4440
           gctaatggtt ttgatgtact atttatcggc aataaatacc gaactaacac gggtgttctg 4500
```

FIG. 21 (continued)

```
tcaggcaca tattaaactc ctattctcat ttagaagatg gtggttcgta tggtagaaca    4560
tttgaccat ttaccaataa agaaatgcag tgggttcaat ttaaaccgaa tagaccaaga    4620
aaaggttcta ctggtaaggt aatcaaatat gaatcgccaa aaggtgaacc tacaagagtt    4680
ctaatgccgt ttgtgcctat gaaaatatgg caacggatta gcgataagtt cggagtaccg    4740
attaatccga aaaagatac tcactttggg gaatgggtaa agaataatcc atcgatacg     4800
attgccatta cagaaggaaa taaaaagct aattgcctat tatcctatgg ctatcctgct    4860
attgcctttg taggcatttg gaacggatta gagaaataa atgatttctc gaaggaaaag    4920
cagttaaaag aggatttgaa atggttgtta tccaacggca accgaaatat taatatcatc    4980
tttgaccaag accagaaaca aaaaactgta attaatgtaa acaaagctat tttcgcttta    5040
tcttctctaa taagtagaaa tggtcataaa gttaatattg tgcaatggtt gccgtcaaaa    5100
ggtaaaggaa tagatgatta tttggtagct ttaccttttg agaaaagaga aaatcattta    5160
gacaacttaa ttaaaattgc accatcattt aattttggt caactaaata cttattcaag    5220
tgtcgtaaac cagatttaac cgtaaattgc cgttatttga gcgatgcagt aaaagaatta    5280
cctcaagagg atatagcatt aatagcacct cacggacgg gtaaaacttc attagtagct    5340
actcaagtta agaatcggag ttatcacgga aggaaaacta tttcattggt gcatcttgaa    5400
agtttagcca aagctaatgg caacgcactt ggattatatt accgaaccga aaataatatt    5460
gaaaagcaat atcttggatt tagcttatgt gtagatagtt gccgtgataa gattaacggc    5520
attacaactg atattatttc aggtcaagat tattgcctt tcattgatga aattgaccaa    5580
gtaattccac acatccttaa cagtgaaact gaagtaagta agtatagatg caccatcatt    5640
gacactttt ctgaactggt gagaaatgct gaacaggtca ttattgctga tgctgattta    5700
tccgatgtga cgattgacct aatagaaaac atcagggta aaaactata tgtaatcaag    5760
aatgaatatc agtatcaggg aatgactttt aacgcgttg gttcaccatt agaaatgatg    5820
gcaatgatgg gaaaatcggt gtcagaaggc aagaaattat ttattaacac cacatcccaa    5880
aaggcaaaaa gtaagtacgg cacaatcgct cttgagtctt atatttttgg tctaaataaa    5940
gaagcaaaga tattaagaat agactctgaa accactaaaa accctgaaca tccagcctat    6000
aaaatcattg accaagactt aaataatatc ctcaaagatt atgattatgt cattgcctca    6060
ccttgcttc aaacaggtgt cagtattacc ttaaaggc attttgacca gcaatttaac    6120
ttttccagtg gaaacattac acctcattgc tttttacagc aaatgtggcg gttgagggat    6180
gcagaaattg aaagattcta ttatgtgccg aactcatcta acctcaatct cattgggaat    6240
aagtcaagtt caccatcaga ccttcaaaag agcaataaca agatggcaac ggcaacggtt    6300
aaccttttgg gtagaatcga ctcgaatat tccctagagt atgaatcgca cggcatttgg    6360
cttgagacgt gggcaaaatt atcagcacgg cataacagtt caatgcgttg ttactctgaa    6420
attcttacct atctaattac gtctcaaggg cataaattaa atatcaacat tccctcacct    6480
cttgcagata ttaagaagct aaatgatgag gtaagtagta acaggaaaaa ggtaaaaaat    6540
gagagatact ctcagaggtt aaactcacca gatattaacg atgcagagc taccatactc    6600
gaatctaaag agcaaaaaat cggattgact ctcaatgaga gatgcaccct agaaaagcat    6660
aaagtaaga agcggtatgg gaatgtaaag atggatattc tcacctttga tgatgatgga    6720
ctataccca aactcagact attttattac ctcaccatcg gtaaacctca tctcaaggct    6780
aatgacagaa aagctattgc caaaatgggc aatgacaata aggcaagat tctatcaaaa    6840
gacttagtta ataaaactta ctccgctcgt gtgaaggtct tagagattct taaactaact    6900
gacttatcg acaatcttag agatgaactc ttaataactc ccaataatcc agctatcacc    6960
gatttaata atcttctgct aagagctaag aaggatttaa gagtattagg agtcaacatc    7020
ggaaaatatc aatggcaa cattaatgcc gtacttactc tcattggtca caaactttct    7080
gtaatgagag atgagttcgg aaaagagaaa aggataaaag tagatggtaa atcatacgga    7140
tgttatcaac ttgaaacatt accagatttt accaatgata ctcttgacta ctggttagaa    7200
aatgatagcc aaaaagaagt aacagcaaca gaaattact ccgaaattt taacccttca    7260
aatagctaca atccagacag taagacactt tcagagggtg caaatttcct atatataaat    7320
aaagaagaat tgcatccaaa taaattgcac ctagaaataa aagaaggtgc tgaacttttt    7380
ttattcgggg taaagtgat tgtgaacgga atcttggacg gggcagtaac tatattctct    7440
atgggtcaag aatacgattt atccctcaat gaactagagg ggatgttaac atcatgaact    7500
ttacaagaat cttttaaag ggcgatcgca ccatgttaaa tgatggtaca tttgttcaga    7560
tatttgatat ttaccatgac caacgcattgg gagtgaccct tgaccttaag acagaaaaaa    7620
```

FIG. 21 (continued)

```
ttatttccga tgatgttagg gtaattactg tcaaagactt attgttcgat ggcacttata   7680
aagggtaaa atctttatg ccgataatg ccgataatg ccgattgat gtacaaaat        7740
cccataatca taagcgataa tcccctaata gcttgtaatt cttgaaccgt agcgatttta   7800
gagtattcca aaaagaagaa ataaacaccg caaatgtcg tatttcacat atataaacca   7860
aggttttttg cctaaaatc tttatgtttg tagtgtgatg ttgggtcaaa atggtcagaa   7920
aagttgcaag gtttttatgg atgcttacgc gcgcgagggg taagcatccc caaatagtta  7980
ctttatccta gtccatgcc atttattgcc gtcccgttcg gctttaaaaa agtgccaaaa   8040
ctcacaaggt gcaataaaaa gttctgtacc tttcgcaacc ctagataatc tttcaacagt   8100
tactttttt cctattatct cggtacaaag tttggctagt ttctcttttc cctctttttc   8160
aatcaagcct tcttgtatgc ccaactcatt gattaatctc tctatttta ccattatttc    8220
ccgttcaggt agttatccc ctaaatcttc atcggggggc aatgtagggc attctgaagg   8280
ggcttttct tctgtctgga cattatctaa tattgaagta accaaactat cttcagtttt   8340
ttctattcct attaattcat attcggttac tgtatccgta tcaatatccg ataactatc   8400
tttatccgta ttagctattc ggttaagttt atccgttaac tcagaaacaa gactatatag   8460
cggttttagc tttcttcta tcctgttatc taatacggat aagtttatac ggttatcatt   8520
atccgtatta gtatcattgg gctttttgg tagttctacc ccctcataaa ccgcttttat    8580
tcccaattcc aacagactga taacagtatc ctttataatg ggttttttgc tgatatggtg   8640
aacttttgcc ccttccatca ttgcgatact ttctatctca ctcatcaact tatcgcttaa   8700
gtgaatctgg tatctgttta atcccttact ggttttattc atatccgttc actttattcg   8760
gttaacaatt ctatttata cgaataaaat attatacggt taactttata cgttaacta   8820
ttttatctat acggataaca gtaataagtt attcgtatta gttatacgtt tactttatc    8880
caaataaaat tagtgcattt aaactaaaag aatgatttta tcggagttga tagcattgga   8940
ttaacctaaa gatgtttata agctatatct gataagtatt taaggttatt ttgttattct   9000
gtttattgac attatcagaa taaaagaata gaatataatt gttgagagat aagaggttta   9060
agtgattatg gttaagaagt tagttggtta tgtcagggtc agtagtgaat cgcaagagga   9120
taacactagc ttacagaatc agatagagag aattgaagca tattgtatgg cttttggtta   9180
tgagttggta aaaatattca aagaggttgc cactggtaca aaagcagata ttgaaaccgc   9240
tcctattttt aatgaagcta tagaatactt gaaacaggat aatgctaatg gaattattgc   9300
cttgaagcta gaccgaatcg cacggaatgc tttagatgta ttcgtttgg ttcgtgaaac    9360
cttagaacca caaaataaaa tgttagtgtt actagatatt caggtagata cttcgacacc   9420
ttcaggaaaa atgattttaa ctgtaatgag tgccgttgct gaactcgaaa gagacatgat   9480
ctatgatcgc actcagggg gtagaaagac taaagcccaa aagggcgggt atgcctacgg   9540
gaaacctaaa tttggctata agactgaaga aaaggaacta aagaagatt cagcacaaca   9600
ggaaactatt aaactaatta agagacaccg taggtcaggg aaaagctacc agaaaatagc   9660
tgattatctc aatgcccaaa gtattcccac taaacaaggt aagaaatgga gttctagcgt   9720
cgtctatcga atctgtcagg aaaagctgg ttaagtctgt ttatagatat ttgaattta    9780
ttgaataaaa atagtatgaa caataaatat ttatggacta accacgctcg gaaacgttta   9840
actgaacgat gggaaataaa agaatcatgg gttattgata ccatcgaaaa tcctgaacgt   9900
tcagaattta ttgttgatga gtcagggaa aaatatcatt actataaaag aatagctaag   9960
tttaagaata gagtgttaga agtgataact tctgccaact caacaccgac aagaataata  10020
acctttact ttaaccgtaa catgaggaaa aattatgat tgttacttac gataatgaag   10080
ttgacgcaat ttatttaag ttaacggaaa ataaaattga tagcaccgaa cctcaaacag    10140
acaggattat cattgattac gatgaaagta ataatattgt tggcattgag gtattagatt   10200
ttaattatct tgtcaagaaa ggtttaaccg ttgctgattt acttttttct gaagatgaaa   10260
gattaacagc ttctcaatat tttaattttc ctgttgctat ctaatccaga agggggaata  10320
atccccttct ttcatcgagt tagacttaat atcacaaaag tcatttcat ttaccgttt    10380
ctttttccaca gcgtccgtac gcccctcgtt aaatctcaaa accgacaatt tatgatgttt   10440
ataaaagtt actcacttta ataagtattt atactcatta aagggttatt ctttttttgt    10500
agcctgatag gttgggaagg aatatttcag attatcagat tgttgaata tttctcgtca    10560
gatacgcaaa ccttacaaac ataattaaca actgaaacta ttgatatgtc taggttttag   10620
ctctatcaca ggttggatct gtcgacaatt aataacttct tcctgtacgg gcgaatggcc   10680
```

FIG. 21 (continued)

```
atttgctcct aactaactcc gtactgcttt gcggaacgag cgtagcgaac tctccgaatt   10740
actaagcctt catccctgat agatgcaaaa aacgaattaa aattatgtgt aaaaagaaaa   10800
tgtgtcttta tttagtagtc aaagttacaa aatattaaga atcaaattaa taatgtattg   10860
ggcagttaag tatataagtc tttaaatatt tatttgtatt caatatatta accgaggaca   10920
aattatgaat tcttacactg ttggaaccta tttagcagaa cgtttagttc aaattggtct   10980
caaacaccat tttgcagtag ctggtgatta taatttagtt ttattggata acttattgtt   11040
aaataagaat atggaacaag tgtattgttg taatgaatta aactgtggtt tttctgctga   11100
gggatatgct cgtgcaaaag gtgctgccgc agcagttgtt acttattctg ttggagcatt   11160
aagtgctttt gacgctattg gaggtgctta tgcagaaaat ttacctgtaa tcttaatctc   11220
tggtgcacc aataacaacg atcacgctgc tggtcatgta ttgcatcatg ctttaggtaa   11280
aaccgattat cattaccaat tagaaatggc aaaaaatatt accgctgccg cagaagctat   11340
ttatactccc gaagaagcac ctgctaagat cgatcacgta attaaaaccg ctctccgtga   11400
gaaaaaaccc gtatatttag aaatcgcttg caatatcgct tctatgcctt gtgcagctcc   11460
tggacctgct agtgctttat ttaacgatga agcatctgat gaggctagtt taaatgccgc   11520
tgttgaagaa actttgaaat ttattgctaa tcgtgataaa gtagctgttt tagttggttc   11580
taaactcgt gccgctggtg cagaagaagc ggctgtaaaa ttgcagatg ccttaggagg   11640
tgctgttgcc acaatggcag ccgctaaaag ttttttcccc gaagaaaatc ctcattacat   11700
tggtacttct tggggtgagg tatcttaccc tggtgtagaa aaaaccatga aggaagctga   11760
tgcagtaatt gcattagctc ctgttttcaa tgattactct accactggtt ggactgatat   11820
tccagacccc aaaaaattag tttagcaga acctgctct gtagttgtga atggtgttag   11880
atttcccagt gtacatctca aagattattt aactcgttta gctcaaaaag tgagtaaaaa   11940
gactggcgca ctcgatttct ttaaatcttt aaatgctggt gaattaaaga agcagctcc   12000
tgctgatccc agtgctctt tagtgaatgc cgaaatcgca agacaagttg aagccttgtt   12060
aactcctaac actaccgtta ttgccgagac tggtgatagt tggttcaatg ctcaacgcat   12120
gaaattaccc aatggtgctc gtgttgagta tgaaatgcaa tggggtcaca ttggatggtc   12180
tgttcctgct gcatttggat atgcagttgg agcacctgag cgtagaaaca ttttaatggt   12240
aggtgatggt tctttccaac tcactgctca agaagttgca caaatggtac gtttaaaatt   12300
gcctgttatt atctttctca ttaacaacta tggttacacc attgaagtta tgattcatga   12360
tggtccttat aataacatta agaattggga ttacgcaggt ttaatggagg tatttaacgg   12420
taatggtgga tacgacagtg gagcaggtaa aggattaaaa gctaaacag gaggtgagtt   12480
agctgaagca attaaagtag ctttagccaa tacagatggt cctaccttaa tcgaatgttt   12540
cattggacgt gaagattgta ctgaagagtt agttaaatgg ggaaagcgtg ttgccgctgc   12600
aaattctcgt aaacctgtaa acaaactctt gtagttagga tccgagct                12648
```

FIG. 21 (continued)

```
ID   #1581\pABICyanol-6.8::PnirAABICyanol-zmPDCABICyanol(opt3)-dsrA-PrpsLABICyanol-
     ADHABICyanol(opt3) ter-PrbcABICyanol-Km** standard; circular DNA;   ; 13165 BP.
CC   This file is created by Vector NTI
CC   http://www.invitrogen.com/
CC   VNTDATE|634480119|
CC   VNTDBDATE|634484179|
CC   LSOWNER|
FH   Key             Location/Qualifiers
FH
FT   promoter        1741..2204
FT                   /vntifkey="30"
FT                   /label=PrbcLABICyanol
FT   CDS             11452..13158
FT                   /vntifkey="4"
FT                   /label=zmPDCABICyanol(opt3)
FT   CDS             2206..3021
FT                   /vntifkey="4"
FT                   /label=Km**
FT                   /note=" maximal codon optimized kanamycin resistance gene "
FT   CDS             10583..10831
FT                   /vntifkey="4"
FT                   /label=ORF\6
FT                   /note="orf6"
FT   CDS             10323..10586
FT                   /vntifkey="4"
FT                   /label=ORF\5
FT                   /note="orf5"
FT   CDS             9595..10281
FT                   /vntifkey="4"
FT                   /label=ORF\4
FT                   /note="orf4 Integrase/Recombinase Similar to Site-specific
     recombinase of Bacillus thuringiensis serovar israelensis ATCC 35646"
FT   CDS             complement(8505..9269)
FT                   /vntifkey="4"
FT                   /label=ORF\3
FT                   /note="orf3"
FT   CDS             8060..8245
FT                   /vntifkey="4"
FT                   /label=ORF\2
FT                   /note="orf2"
FT   rep_origin      complement(7360..7377)
FT                   /vntifkey="33"
FT                   /label=Rep_Origin_1\(potential)
FT                   /note="potential rep origin; match pNostoc (Acc# M81381) nick
     site (358-375); on reverse strand"
FT   misc_feature    7620..7653
FT                   /vntifkey="21"
FT                   /label=Rep\motif
FT                   /note="Rep protein active site motiq EXKKYKVKXXD"
FT   CDS             4839..8024
FT                   /vntifkey="4"
FT                   /label=ORF\1
```

FIG. 23

```
FT                    /note="orf1  rep ori binding protein slr7037 homolog Similar to
hypothetical protein slr7037 of plasmid pSYSA (103 kb)  of Synechocystis sp. PCC 6803"
FT   rep_origin       complement(3264..4322)
FT                    /vntifkey="33"
FT                    /label=OriVT
FT   insertion_seq    4329..11162
FT                    /source="pABICyano1-6HindIIIBamHI"
FT                    /type="Custom cloned insert"
FT                    /vntifkey="14"
FT                    /label=pABICyano1-6HindIIIBamHI
FT                    /note="Unknown feature type:insert"
FT   promoter         11169..11451
FT                    /vntifkey="30"
FT                    /label=PnirAABICyano1
FT   promoter         58..626
FT                    /vntifkey="30"
FT                    /label=PrpsLABICyano1
FT   CDS              630..1637
FT                    /vntifkey="4"
FT                    /label=SynADH(ABICyano1opt3)
FT   terminator       1653..1698
FT                    /vntifkey="43"
FT                    /label=Terminator_1
FT                    /note="Ter_B0011"
FT   gene             630..1640
FT                    /vntifkey="60"
FT                    /note="SycADHopti"
FT   terminator       1..56
FT                    /vntifkey="43"
FT                    /label=dsrA
SQ   Sequence 13165 BP; 4190 A; 2319 C; 2522 G; 4134 t;
     gatccagcaa gtttcatccc gacccctca gggtcgggat ttttttattg tgagctctc        60
     cgcttaaaaa attttcatttt tcgatcaaaa aagacaaatt attactaatt agctcatggc   120
     aataaataat cagtagtaat ctgttttcac attttattgt taatttttat tattgctaat   180
     atcaaccttc tctacttctg cttaatattt tatttatgct caatgggaaa atctgaatca   240
     agattgagaa cagtgttcac aatagaagta ttaagtgtt aagcatact tcaaagataa     300
     catttttttt tgaaagagt caaattattt tgaaaggct gatatttg atatttacta       360
     atatttctatt tattctttt tcccttaaaa taagagctaa atctgttttt attatcattt   420
     atcaagctct attaatacct caacttttt aagaaaaaat aataataatt tttccctcta    480
     ttctcatgac cttttaggaa aattaatttt agaaaaacta ttgacaaacc cataaaaaat   540
     gagataagat tatagattgt cactggtatt ttactagaa ggcaaattat attttatatat   600
     acaaaaatgc tgtataaaaa acatctcata tgattaaggc ttatgctgca ttagaagcta   660
     atggtaaatt acacactttt gaatacgatc ccggtgcttt aggtgcaaat gaagtgaaa    720
     ttgaggttca gtattgtggt gtatgtcatt ctgatttatc tatgattaac aacgaatggg   780
     gaatttccaa ttatccctta gttcctggac acgaagttgt tggtactgta gcagctatgg   840
     gagaaggagt taatcatgtt gaagtaggtg acttagtagg tttgggatgg cattctggtt   900
     actgtatgac ctgtcatagt tgtttatctg gttatcacaa cttatgtgca actgctgaaa   960
     gtaccattgt tggtcattac ggtggttttg gtgatagagt aagagctaaa ggagttagtg  1020
     ttgttaaatt accaaaaggt atcgactag caagtgcagg tcctctctctt tgtgggtca    1080
     ttactgtttt tagtcctatg gttgaattaa gttaaagcc aactgcaaaa gtagccgtca   1140
     ttggtattgg aggattggga cacttagctg ttcaattct ccgtgcatgg ggatgtgaag    1200
     ttactgcctt tacttctagt gctcgtaaac aaaccgaggt attagaatta ggagcacacc  1260
```

FIG. 23 (continued)

```
atatcttaga ttccaccaac cctgaagcta tcgctagtgc agagggaaaa ttcgattata  1320
ttattagtac tgttaatttg aaattagatt ggaacctcta catctctact ttagctcccc  1380
aagtgtcattt tcactttgtt ggagttgtat tagaaccct cgatttaaac ttattccctt  1440
tattaatggg acaacgttct gttagtgcat ctcctgttgg atctcccgct actattgcta  1500
ccatgttaga ttttgcagta cgtcacgata ttaacctgt agtagaacaa ttctctttcg  1560
atcaaatcaa cgaagctatt gctcatttag aaagtgtaa ggtcattac cgtgttgttt  1620
tatctcactc taaaaactaa ctagatctct gcagagaata taaaaagcca gattattaat  1680
ccggcttttt tattatttaa atactgtgca cgatcctgca ggatcatctt gctgaaaaac  1740
tcgagcgtc gttccgcaaa gcggtacgga gttagttagg ggctaatggg cattctccg  1800
tacaggaaag agttagaagt tattaattat caacaattct cctttgccta gtgcatcgtt  1860
acctttttaa ttaaacata aggaaaacta ataatcgtaa taatttaacc tcaaagtgta  1920
aagaaatgtg aaattctgac ttttataacg ttaaagaggg aaaaattagc agtttaaaat  1980
acctagagaa tagtctgggg taagcataga gaattagatt agttaagtta atcaaattca  2040
gaaaaataa taatcgtaaa tagttaatct gggtgtatag aaaatgatcc cctccatgat  2100
aagatttaaa ctcgaaaagc aaaagccaaa aactaactt ccattaaaag aagttgttac  2160
atataacgct ataaagaaaa tttatatatt tggaggatac caaccatgtc tcatattcaa  2220
cgtgaaacta gttgttctcg ccctcgttta aattctaata tggatgccga tttatatggt  2280
tataaatggg ctcgtgtaaa tgttggtcaa tctggtgcta ctatttatcg tttatatggt  2340
aaacctgatg ctcctgaatt attcttgaaa catggcaaag gttctgttgc taatgatgtt  2400
actgatgaaa tggttcgttt aaactggttg actgaattta tgcctttacc tactattaaa  2460
catttattc gtactccga tgatgcttgg ttattaacta ctgctattcc tggtaaaact  2520
gcttttcaag ttttagaaga atatcctgat tctggtgaaa atattgttga tgctttagct  2580
gttttttac gtgtttaca ttctattccc gtttgtaatt gtccttttaa ttctgatcgt  2640
gtttttcgtt tagctcaagc tcaatctcgt atgaataatg gtttagttga tgcttctgat  2700
tttgatgatg aacgtaatgg ttggcctgtt gaacaagttt ggaaagaaat gcacaaattg  2760
ttaccttttt ctcctgatct tgttgttact catggtgatt tttctttaga taatttgatc  2820
tttgatgaag gtaaattgat tggttgtatt gatgtcggtc gtgttggtat tgctgatcgt  2880
tatcaagatt tagctatttt atggaattgt ttaggtgaat tttctcctc tttacagaaa  2940
cgtttatttc agaaatatgg tattgataat cctgatatga acaagttaca attcatta  3000
atgttggacg agtctttta agaattaatt catgaccaaa atcccttaac gtgagttttc  3060
gttccactga gcgtcagacc ccgtagaaaa gatcaaagga tcttcttgag atcctttttt  3120
tctgcgcgta atctgctgct atttaaatta cgtacacgtg ttattacttt gttacgaca  3180
attgtcttaa ttaactgggc ctcatgggcc ttccgctcac tgcccgcttt ccagtcggga  3240
aacctgtcgt gccagctctg cagatgacgg tgaaacctc tgacacatgc agctcccgga  3300
gacggtcaca gcttgtctgt aagcggatgc cgggagcaga caagcccgtc agggcgcgtc  3360
agcgggtgtt ggcgggtgtc gggcgcagc catgacccag tcacgtagcg atagcggagt  3420
gtatactggc ttaactatgc ggcatcagag cagattgtac tgagagtgca ccatatgcgg  3480
tgtgaaatac cgcacagatg cgtaaggaga aaataccgca tcaggcgctc ttccgcttcc  3540
tcgctcactg actcgctgcg ctcggtcgtt cggctgcggc gagcggtatc agctcactca  3600
aaggcggtaa tacggttatc cacagaatca ggggataacg caggaaagaa catgtgagca  3660
aaaggccagc aaaaggccag gaaccgtaaa aaggccgcgt tgctggcgtt tttccatagg  3720
ctccgcccc ctgacgagca tcacaaaaat cgacgctcaa gtcagaggtg cgaaacccg  3780
acaggactat aaagatacca ggcgtttccc cctggaagct ccctcgtgcg ctctcctgtt  3840
ccgaccctgc cgcttaccgg atacctgtcc gcctttctcc cttcgggaag cgtggcgctt  3900
tctcatagct cacgctgtag gtatctcagt tcggtgtagg tcgttcgctc caagctgggc  3960
tgtgtgcacg aaccccccgt tcagcccgac cgctgcgcct tatccggtaa ctatcgtctt  4020
gagtccaacc cggtaagaca cgacttatcg ccactggcag cagccactgg taacaggatt  4080
agcagagcga ggtatgtagg cggtgctaca gagttcttga agtggtggcc taactacggc  4140
tacactagaa ggacagtatt tggtatctgc gctctgctga agccagttac cttcggaaaa  4200
agagttggta gctcttgatc cggcaaacaa accaccgctg gtagcggtgg tttttttgtt  4260
tgcaagcagc agattacgcg cagaaaaaaa ggatctcaag aagatccttt gatcttttct  4320
```

FIG. 23 (continued)

```
actgcagaag cttgttagac accctgtcat gtatttata ttatttattt caccatacgg    4380
attaagtgaa acctaatgaa aatagtactt tcggagcttt aactttaatg aaggtatgtt    4440
tttttataga catcgatgtc tggtttaaca ataggaaaaa gtagctaaaa ctccatgaa     4500
ttaaagaaat aacaaggtgt ctaacaacct gttattaaga atgttagaaa agacttaaca    4560
tttgtgttga gttttatag  acattggtgt ctagacatac ggtagataag gtttgctcaa    4620
aaataaata  aaaaagatt  ggactaaaaa acatttaatt tagtacaatt taattagtta    4680
ttttttcgtc tcaaattttg ctttgttgag cagaaattta gataaaaaa  tcccgtgat     4740
cagattacaa tgtcgttcat tgtacgatgt gtcgaaaaat ctttacgaca ctctaaactg    4800
accacacggg ggaaaagaa  aactgaacta ataacatcat gatactggga aaacctagca    4860
attctcaacc cctaaacaaa agaaacttcc aaaaccctga ccatataaag gagtggcaac    4920
aatcagcaat cagtcaagat ttgatagcag aaaatcttgt atcggttgct aatggttttg    4980
atgtactatt tatcggcaat aaatacgaa  ctaacacggg tgttctgtcc cggcacatat    5040
taaactccta ttctcattta gaagatggtg gttcgtatgg tagaacattt gacccattta    5100
ccaataaaga aatgcagtgg gttcaattta aaccgaatag accaagaaaa ggttctactg    5160
gtaaggtaat caaatatgaa tcgccaaaag gtgaacctac aagagttcta atgccgtttg    5220
tgcctatgaa aatatggcaa cggattagcg ataagttcgg agtaccgatt aatccgaaaa    5280
aagatactca ctttttgggaa tgggtaaaga ataatccatc gatacogatt gccattacag    5340
aaggaaataa aaaagctaat tgcctattat cctatggcta tcctgctatt gcctttgtag    5400
gcatttggaa cggattagag aaaatgaaat g attttctcgaa ggaaaagcag ttaaaagagg    5460
atttgaaatg gttgttatcc aacggcaacc gaaatattaa tatcatcttt gaccaagacc    5520
agaaacaaaa aactgtaatt aatgtaaaca aagctatttt cgcttatct  tctctaataa    5580
gtagaaatgg tcatcaaagtt aatattgtgc aatggttgcc gtcaaaaggt aaggaatag    5640
atgattattt ggtagcttta ccttttgaga aagagaaaaa tcatttagac aacttaatta    5700
aaattgcacc atcatttaat ttttggtcaa ctaaatactt attcaagtgt cgtaaaccag    5760
atttaaccgt aaattgccgt tatttgagcg atgcagtaaa agaattacct caagaggata    5820
tagcattaat agcacctcac ggcacgggta aaacttcatt agtagctact cacgttaaga    5880
atcggagtta tcacggaagg aaaactattt cattggtgca tcttgaaagt ttagccaaag    5940
ctaatggcaa cgcacttgga ttatattacc gaaccgaaaa taatattgaa aagcaatatc    6000
ttggatttag cttatgtgta gatagttgcc gtgataagat taacggcatt acaactgata    6060
ttatttcagg tcaagattat tgcctttca  ttgatgaaat tgaccaagta attccacaca    6120
tccttaacag tgaaactgaa gtaagtaagt atagatgcac catcattgac acttttctg     6180
aactggtgag aaatgctgaa caggtcatta ttgctgatgc tgatttatcc gatgtgacga    6240
ttgacctaat agaaaacatc agaggtaaaa aactatatgt aatcaagaat gaatatcagt    6300
atcagggaat gacttttaac gccgttggtt caccattaga aatgatggca atgatgggaa    6360
aatcggtgtc agaggcaag  aaattattta ttaacaccac atcccaaaag gcaaaaagta    6420
agtacggcac aatcgctctt gagtcttata ttttggtct  aaataaagaa gcaaagatat    6480
taagaataga ctctgaaacc actaaaaacc ctgaacatcc agcctataaa atcattgacc    6540
aagcttaaa  taatatcctc aaagattatg attatgtcat tgcctcacct tgccttcaaa    6600
caggtgtcag tattaccttta aaagggcatt ttgaccagca atttaacttt tccagtggaa    6660
acattacacc tcattgcttt ttacagacaaa tgtggcggtt gagggatgca gacattgaaa    6720
gattctatta tgtgccgaac tcatctaacc tcaatctcat tgggaataag tcaagttcac    6780
catcagacct tctaaagagc aataacaaga tgcaacgc  aacggttaac cttttgggta    6840
gaatcgactc cgaatattcc ctagtgtatg aatcgcacgg catttggctt gagacgtggg    6900
caaattatc  agcacggcat aacagttcaa tgcgttgtta ctctgaaatt cttacctatc    6960
taattacgtc tcagggcat  aaattaaata tcaacattcc ctcacctctt gcagatatta    7020
agaagctaaa tgatgaggta agtagtaaca gggaaaaggt aaaaaatgag agatactctc    7080
agaggttaaa ctaccagat  attaacgatg cagaagctac catactggaa tctaaagagc    7140
aaaaaatcgg attgactctc aatgagagat gcaccctaga aagcataaaa gttaagaagc    7200
ggtatgggaa tgtaaagatg gatattctca acttgatga tgatggacta tacccaaac    7260
tcagactatt ttattaccta accatcggta aacctcatct caaggctaat gacagaaaag    7320
ctattgccaa aatgggcaat gacaataaag gcaagattct atcaaaagac ttagttaata    7380
```

FIG. 23 (continued)

```
aaacttactc cgctcgtgtg aaggtcttag agattcttaa actaactgac tttatcgaca    7440
atcttagaga tgaactctta ataactccca ataatccagc tatcaccgat tttaataatc    7500
ttctgctaag agctaagaag gatttaagag tattaggagt caacatcgga aaatatccaa    7560
tggccaacat taatgccgta cttactctca ttggtcacaa actttctgta atgagagatg    7620
agttcggaaa agagaaaagg ataaaagtag atggtaaatc ataccgatgt tatcaacttg    7680
aaacattacc agattttacc aatgatactc ttgactactg gttagaaaat gatagccaaa    7740
aagaagtaac agcaacagaa aattactccg aaaatttttaa ccttcaaat agctacaatc    7800
cagacagtaa gacactttca gagggtgcaa atttcctata tataaataaa gaagaattgc    7860
atccaaataa attgcaccta gaaataaaag aaggtgctga acttttttta ttcggggtaa    7920
aggtgattgt gaaaggaatc ttggacgggg cagtaactat attctctatg ggtcaagaat    7960
acgatttatc cctcaatgaa ctagagggga tgttaacatc atgaactttta caagaatctt    8040
tttaaagggc gatcgcacca tgttaaatga tggtacattt gttcagatat ttgatattta    8100
ccatgaccac gcattgggag tgaccottga ccttaagaca gaaaaaatta tttccgatga    8160
tgttagggta attactgtca aagacttatt gttcgatggc acttataaag gggtaaaatc    8220
ttttatgccc gataatgccc gataatgccc gattgatgct acaaaatccc ataatcataa    8280
gcgataatcc cctaatagct tgtaattctt gaaccgtagc gatttagag tattccaaaa    8340
agaagaaata aacaccgcaa aatgtcgtat tcacatata taaaccaagg ttttttgccc    8400
taaaatcttt atgtttgtag tgtgatgttg ggtcaaaatg gtcagaaaag ttgcaaggtt    8460
tttatggatg cttacgcgcg cgaggggtaa gcatcccaa atagttactt tatcctagtc    8520
catgcccatt tattgccgtc ccgttcggct ttaaaaagt gccaaaactc acaaggtgca    8580
ataaaagtt ctgtaccttt cgcaacccta gataatcttt caacagttac tttttttcct    8640
attatctcgg tacaaagttt ggctagtttc tcttttcccct cttttcaat caagcttct    8700
tgtatgccca actcattgat taatctctct atttttacca ttatttcccg ttcaggtagt    8760
ttatccccta aatcttcatc gggggggcaat gtagggcatt ctgaagggc ttttttcttct    8820
gtctggacat tatctaatat tgaagtaacc aaactatctt cagtttttc tattcctatt    8880
aattcatatt cggttactgt atccgtatca atatccgaat aactatcttt atccgtatta    8940
gctattcggt taagtttatc cgttaactca gaaacaagac tatatagcgg tttagcttt    9000
tcttctatcc tgttatctaa tacggataag tttatacggt tatcattatc cgtattagta    9060
tcattgggct ttttgggtag ttctacccca tcataaaccg cttttattcc caattccaac    9120
agactgataa cagtatcctt tataatgggt ttttgctga tatgtgaac ttttgccct    9180
tccatcattg cgatactttc tatctcactc atcaacttat cgcttaagtg aatctcgtat    9240
ctgtttaatc ccttactggt tttattcata tccgttact ttattcggtt aacaattcta    9300
ttttatacga ataaaatatt atacggttaa ctttatacgt ttaactattt tatctatacg    9360
gataacagta ataagttatt cgtattagtt atacgtttac ttttatccaa ataaaattag    9420
tgcatttaaa ctaaaagaat gattttatcg gagttgatag cattggatta acctaaagat    9480
gtttataagc tatatctgat aagtatttaa ggttattttg ttattctgtt tattgacatt    9540
atcagaataa aagaatagaa tataattgtt gagagataag aggtttaagt gattatggtt    9600
aagaagttag ttggttatgt cagggtcagt agtgaatcgc aagaggataa cactagctta    9660
cagaatcaga tagagagaat tgaagcatat tgtatggctt ttggttatga gttggtaaaa    9720
atattcaaag aggttgccac tggtacaaaa gcagatattg aaaccgtcc tatttttaat    9780
gaagctatag aatacttgaa acaggataat gctaatggaa ttattgcctt gaagctagac    9840
cgaatcgcac ggaatgcttt agatgtattg cgtttggttc gtgaaacctt agaaccacaa    9900
aataaaatgt tagtgttact agatattcag gtagatactt cgacaccttc aggaaaaatg    9960
attttaactg taatgagtgc cgttgctgaa ctcgaaagag acatgatcta tgatcgcact   10020
cagggggta gaagactaa agcccaaaag ggcgggtatg cctacggaa acctaaattt   10080
ggctataaga ctgaagaaaa ggaactaaaa gaagattcag cacaacagga aactattaaa   10140
ctaattaaga gacaccgtag gtcagggaaa agctaccaga aaatagctga ttatctcaat   10200
gcccaaagta ttcccactaa acaagtaaag aaatggagtt ctagcgtcgt ctatcgaatc   10260
tgtcaggaaa aagctggtta agtctgttta tagatattta gaatttattg aataaaaata   10320
gtatgaacaa taaatattta tggactaacc acgctcggaa acgtttaact gaacgatggg   10380
aaataaaaga atcatgggtt attgatacca tcgaaaatcc tgaacgttca gaatttattg   10440
ttgatgagtc agggggaaaaa tatcattact ataaaagaat agctaagttt aagaatagag   10500
```

FIG. 23 (continued)

```
tgttagaagt gataacttct gcaactcaa cacccacaag aataataacc ttttacttta    10560
accgtaacat gaggaaaaat ttatgattgt tacttacgat aatgaagttg acgcaattta    10620
ttttaagtta acggaaaata aaattgatag cacegaacct caaacagaca ggattatcat    10680
tgattacgat gaaagtaata atattgttgg cattgaggta ttagatttta attatcttgt    10740
caagaaaggt ttaaccgttg ctgatttacc tttttctgaa gatgaaagat taacagcttc    10800
tcatattttt aattttcctg ttgctatcta atcagaagg ggcaataatc ccttctttc     10860
atcgagttag acttaatatc acaaaagtca ttttcatttt accgttctt ttccacagcg     10920
tccgtacgcc cctcgttaaa tctcaaaacc gacaatttat gatgtttata aaaagttact    10980
cactttaata agtatttata ctcattaaag ggttattctt ttttgtagc ctgataggtt     11040
gggaaggaat atttcagatt atcagatttg ttgaatattt ttgtcagat acgcaaacct    11100
tacaaacata attaacaact gaaactattg atatgtctag gttttagctc tatcacaggt    11160
tggatctgtc gacaattaat aacttcttcc tgtacgggcg aatggccatt tgctcctaac    11220
taactccgta ctgctttgcg gaacgagcgt agcgaactct ccgaattact aagccttcat    11280
ccctgataga tgcaaaaaac gaattaaaat tatgtgtaaa aagaaaatgt gtctttattt    11340
agtagtcaaa gttacaaaat attaagaatc aaattaataa tgtattgggc agttaagtat    11400
ataagtcttt aaatatttat ttgtattcaa tatattaacc gaggacaaat tatgaattct    11460
tacactgttg gaacctattt agcagaacgt ttagttcaaa ttggtctcaa acaccatttt    11520
gcagtagctg gtgattataa tttagtttta ttggataact tattgttaaa taagaatatg    11580
gaacaagtgt attgttgtaa tgaattaaac tgtggttttt ctgctgaggg atatgctcgt    11640
gcaaaaggtg ctgccgcagc agttgttact tattctgttg gagcattaag tgcttttgac    11700
gctattggag gtgcttatgc agaaaattta cctgtaatct taatctctgg tgcacccaat    11760
aacaacgatc acgctgctgg tcatgtattg catcatgctt taggtaaaac cgattatcat    11820
taccaattag aaatggcaaa aaatattacc gctgccgcag aagctattta tactcccgaa    11880
gaagcacctg ctaagatcga tcacgtaatt aaaaccgctc tccgtgagaa aaaacccgta    11940
tatttagaaa tcgcttgcaa tatcgcttct atgccttgtg cagctcctgg acctgctagt    12000
gctttattta acgtgaagc atctgatgag gctagtttaa atgccgctgt tgaagaaact    12060
ttgaaattta ttgctaatcg tgataaagta gctgttttag ttggttctaa actccgtgcc    12120
gctggtgcag aagaagcggc tgtaaaattc gcagatgcct taggaggtgc tgttgccaca    12180
atggcagccg ctaaaagttt tttccccgaa gaaaatcctc attacattgg tacttcttgg    12240
ggtgaggtat cttaccctgg tgtagaaaaa accatgaagg aagctgatgc agtaattgca    12300
ttagctcctg ttttcaatga ttactctacc actggttgga ctgatattcc agaccccaaa    12360
aaattagttt tagcagaacc tcgctctgta gttgtgaatg tgttagatt tccagtgta     12420
catctcaaag attatttaac tcgtttagct caaaagtga gtaaaagac tggcgcactc    12480
gatttctta aatctttaaa tgctggtgaa ttaagaaag cagctcctgc tgatcccagt    12540
gctcctttag tgaatgccga aatcgaaga caagttgaag cctgttaac tcctaacact     12600
accgttattg ccgagactgg tgatagttgg ttcaatgctc aacgcatgaa attacccaat    12660
ggtgctcgtg ttgagtatga aatgcaatgg ggtcacattg gatggtctgt tcctgctgca    12720
tttggatatg cagttggagc acctgagcgt agaaacattt taatggtagg tgatggttct    12780
ttccaactca ctgctcaaga agttgcacaa atggtacgtt taaaattgcc tgttattatc    12840
tttctcatta acaactatgg ttacaccatt gaagttatga ttcatgatgg tccttataat    12900
aacattaaga attgggatta cgcaggttta atggaggtat ttaacgtaa tggtgatac     12960
gacagtggag caggtaaagg attaaagct aaacaggag gtgagttagc tgaagcaatt    13020
aaagtagctt tagccaatac agatggtcct accttaatcg aatgtttcat tggacgtaa    13080
gattgtactg aagagttagt taatgggga aagcgtgttg ccgctgcaaa ttctctgtaaa    13140
cctgtaaaca aactcttgta gttag                                         13165
```

FIG. 23 (continued)

```
ID    #1606\\pABICyano1::PnirA-zmPDC(opt1)_dsrA-Prbc*(optRBS)-synADH(opt1)_ter
standard; circular DNA;       ; 12760 BP.
CC    This file is created by Vector NTI
CC    http://www.invitrogen.com/
CC    VNTDATE|645465372|
CC    VNTDBDATE|645465372|
CC    LSOWNER|
CC    VNTAUTHORNAME|Ulf Duehring|
FH    Key             Location/Qualifiers
FH
FT    promoter        2063..2131
FT                    /vntifkey="30"
FT                    /label=Prbc*(optRBS)
FT    promoter        1..283
FT                    /vntifkey="30"
FT                    /label=PnirAABICyano1
FT    rep_origin      complement(4858..5916)
FT                    /vntifkey="33"
FT                    /label=OriVT
FT    primer_bind     4903..4934
FT                    /vntifkey="28"
FT                    /label=Bom-R
FT    primer_bind     complement(5221..5252)
FT                    /vntifkey="28"
FT                    /label=Bom-F
FT    CDS             6433..9618
FT                    /vntifkey="4"
FT                    /label=ORF\1
FT                    /note="orf1 rep ori binding protein slr7037 homolog Similar to
hypothetical protein slr7037 of plasmid pSYSA (103 kb)  of Synechocystis sp. PCC 6803"
FT    misc_feature    9214..9247
FT                    /vntifkey="21"
FT                    /label=Rep\motif
FT                    /note="Rep protein active site motif EXXEYXVKXXD"
FT    rep_origin      complement(8954..8971)
FT                    /vntifkey="33"
FT                    /label=Rep_Origin_1
FT                    /note="potential rep origin; match pNostoc (Acc# M81381) nick
site (358-375); on reserse strand"
FT    CDS             9654..9839
FT                    /vntifkey="4"
FT                    /label=ORF\2
FT                    /note="orf2"
FT    CDS             complement(10099..10863)
FT                    /vntifkey="4"
FT                    /label=ORF\3
FT                    /note="orf3"
FT    CDS             11189..11875
FT                    /vntifkey="4"
FT                    /label=ORF\4
FT                    /note="orf4 Integrase/Recombinase Similar to Site-specific
recombinase of Bacillus thuringiensis serovar israelensis ATCC 35646"
FT    CDS             11917..12180
FT                    /vntifkey="4"
FT                    /label=ORF\5
FT                    /note="orf5"
FT    CDS             12177..12425
FT                    /vntifkey="4"
FT                    /label=ORF\6
FT                    /note="orf6"
FT    misc_marker     3800..4615
```

FIG. 25

```
FT                   /vntifkey="22"
FT                   /label=Km**
FT                   /note="Km**"
FT    promoter       3335..3798
FT                   /vntifkey="30"
FT                   /label=PrbcABICyano1
FT    terminator     3143..3298
FT                   /vntifkey="43"
FT                   /label=TrbcSABICyano1
FT    CDS            2132..3139
FT                   /vntifkey="4"
FT                   /label=synADHABICyano1(opt1)
FT    gene           2132..3142
FT                   /vntifkey="69"
FT                   /note="ADH"
FT    insertion_seq  2017..2062
FT                   /vntifkey="14"
FT                   /label=dsrA
FT                   /note="dsr terminator from E.coli"
FT    CDS            264..1990
FT                   /vntifkey="4"
FT                   /label=zmPDCABICyano1(opt1)
SQ    Sequence 12762 BP; 3950 A; 2245 C; 2488 G; 4079 t;
      tcgacaatta ataacttctt cctgtacggg cgaatggcca tttgctccta actaactccg       60
      tactgctttg cggaacgagc gtagcgaact ctccgaatta ctaagccttc atccctgata      120
      gatgcaaaaa acgaattaaa attatgtgta aaaagaaaat gtgtctttat ttagtagtca      180
      aagttacaaa atattaagaa tcaaattaat aatgtattgg gcagttaagt ataagtct       240
      ttaatatttt attgtattc aaatatatta ccgagagaca attatgaatt cttataccgt      300
      gggtacttat ttagccgaac gcttagtgca aattggttta aaacatcatt ttgccgtggc      360
      tgggactat aatttagtgt tattggatca cttattatta aataaaaaca tggaacaagt      420
      gtattgttgt aatgaattaa attgtgttt ttctgctgaa ggttatgcta gagctaaagg      480
      tgcagctgct gctgttgcta cttattctgt gggtgcttta tctgcttttg atgccattgg      540
      tgtgcttat gccgaaaatt taccgtgat tttaattct ggtgccccta ataataatga      600
      tcatgccgct ggacatgttt tacatcatgc cttaggtaaa acgattatc attatcatt      660
      agaaatggcc aaaaatatta ctgctgtgc cgaagctatt tatactcctg aagaagcccc      720
      tgccaaaatt gatcatgtga ttaaaaccgc cttacgcgaa aaaaaccccg tgtatttaga      780
      aattgcctgt aatattgctt ctatgccttg tgtgctcct gggctgctt ctgcttatt      840
      taatgatgaa gcctctgatg aagctagttt aaatgctgcc gtggaagaaa ccttaaaatt      900
      tattgccaat cgcgataaag ttgccgtgtt agttggttct aaattaagag ctgctggtgc      960
      tgaagaagct gctgttaaat ttgctgatgc tttaggtgt gcagttgcta ctatggctgc     1020
      tgccaaatct tttttttccg aagaaaatcc ccattatatt ggaactagtt gggagaagt     1080
      ttcttatcct ggtgtggaaa aactatgaa agaagccgac gctgttattg cttagcccc     1140
      tgtgtttaat gattatttta ccactggttg gactgatatt ccgatccca aaaaattagt     1200
      tttagccgaa cctgttctg tgttgttga tggtgttcgc tttccctctg tgcatttaaa     1260
      agattattta accgcttag cccaaaaagt ttctaaaaaa actgtgctt tagattttt     1320
      taaatctttta aatgcgggtg aattaaaaaa agctgctcct gctgatcctt ctgctcctt     1380
      agttaatgct gaaattgccc gtcaagttga agccttatta accctaata ctaccgttat     1440
      tgccgaaact ggtgattctt ggtttaatgc ccaacgcatg aaattacct atggtgcccg     1500
      tgttgaatat gaaatgcaat gggtcatat tggttgtct gtactgctg ctttggta     1560
      tgctgttggt gctcctgaac gtggtaaatt tctcaatggtg ggtgatgtt cttttcaatt     1620
      aactgcccaa gaagttgccc aaatgttcg cttaaaatta ccgttatta tttttaat     1680
      aaataattat ggttataccat tgaagtgat gattcatgat gggccatata ataatattaa     1740
      aaattgggat tatgcgggtt taatggaagt gtttaatggt aatggtggtt atgattctgg     1800
      tgctggtaaa ggtttaaaag ccaaaactgg tgctgaatta gctgaagcta ttaaagttgc     1860
      cttagccaat actgatgggc caacttaat tgaatgtttt attggtcgcg aagattgtac     1920
      cgaagaatta gttaaatggg gtaaacgtgt tgctgctgct aattctcgca aaccgtgaa     1980
      taaattattg taattttgg ggatcaattc gagctcagca gtttcatcc cgacccctc     2040
      agggtcggga tttttttatt gtactagttg acataagtaa aggcatccc tgcgtgatat     2100
      aattaccttc agtttaagga ggtataaca tatgattaaa gcctatgctg ccttagaagc     2160
      caatgtaaa ttacaaccct ttgaatatga tcctggtgct ttaggtgcca atgaagtgga     2220
```

FIG. 25 (continued)

```
aattgaagtg caatattgtg gtgtgtgtca ttctgattta tctatgatta ataatgaatg    2280
gggtatttct aattatccct tagttcctgg tcatgaagtt gttggtactg ttgctgctat    2340
gggtgaaggt gttaatcatg tggaagtggg tgatttagtt ggtttaggtt ggcattctgg    2400
ttattgtatg acctgtcatt cttgtttatc tggttatcat aatttatgtg ccactgccga    2460
atctactatt gtgggtcatt atggtggttt tggtgataga gttcgtgcta aaggtgtttc    2520
tgtggtgaaa ttacccaaag gtattgattt agcctctgct gggcctttat ttgtggtgg    2580
tattaccgtt ttttctccca tggtggaatt atctttaaaa cctaccgcca aagttgctgt    2640
tattggtatt ggtggtttag gtcatttagc cgttcaattt ttaagagcct ggggttgtga    2700
agttactgct tttaccctct ctgccgtaa acaaaccgaa gttttagaat taggtgccca    2760
tcatattta gattctacca atcctgaagc tattgcttct gccgaaggta aatttgatta    2820
tattatttct accgtgaatt taaaattaga ttggaattta tatatcagta cctagcccc    2880
tcaaggtcat tttcatttg ttggtgtggt gttagaaccc ttggacttaa acttatttcc    2940
cttattaatg ggacaacgtt ctgttctgc ttctcctgtt ggttctcctg ctactattgc    3000
cactatgtta gattttgccg tgcgtcatga tattaaaccc gtggtggaac aatttttctt    3060
tgatcaaatt aatgaagcca ttgccattt agaatctggt aaagcccatt atcgcgtggt    3120
gttatctcat tctaaaaatt aataagatta acttctaaac tgaaacaaat ttgagggtag    3180
gcttcattgt ctgcccttat tttttatt aggaaaagtg aacagactaa agagtgttgg    3240
ctctattgct ttgagtatgt aaattaggcg ttgctgaatt aaggtatgat ttttgacccc    3300
ttctctcttc tgcaggatca tcttgctgaa aaactctgag gctcgttccg caaagcggta    3360
cggagttagt tagggctaa tgggcattct cccgtacagg aaagagttag aagttattaa    3420
ttatcaacaa ttctcctttg cctagtgcat cgttaccttt ttaattaaaa cataaggaaa    3480
actaataatc gtaataattt aacctcaaag tgtaaagaaa tgtgaaattc tgactttat    3540
aacgttaaag agggaaaaat tagcagttta aaataccctag agaatagtct ggggtaagca    3600
tagagaatta gattagttaa gttaatcaaa ttcagaaaaaa ataataatcg taaatagtta    3660
atctgggtgt atagaaaatg atcccttca tgataagatt taaactcgaa aagcaaaagc    3720
caaaaaacta acttccatta aaagaagttg ttacatataa cgctataaag aaaatttata    3780
tatttggagg ataccaacca tgtctcatat tcaacgtgaa actagttgtt ctcgccctcg    3840
tttaaattct aatatggatg ccgatttata tggttataaa tgggctcgtg ataatgttgg    3900
tcaatctggt gctactattt atcgtttata tggtaaacct gatgctcctg aattattctt    3960
gaaacatggt aaaggttctg ttgctaatga tgttactgat gaaatggttc gtttaaactg    4020
gttgactgaa tttatgcctt tacctactat taaacatttt attcgtactc ccgatgatgc    4080
ttggttatta actactgcta ttcctggtaa aactgctttt caagttttag aagaatatcc    4140
tgattctggt gaaaatattg ttgatgcttt agctgttttt ttagtcgtt tacattctat    4200
tcccgtttgt aattgtcctt ttaattctga tcgtgttttt tcgtttagctc aagctcaatc    4260
tcgtatgaat aatggttag ttgatgcttc tgattttgat gatgaacgta atgttggcc    4320
tgttgaacaa gtttggaaag aaatgcacaa attgttacct tttttctctg atctcgttgt    4380
tactcatgat gattttctt tagataattt gatctttgat gaaggtaaat tgattggttg    4440
tattgatgtt ggtcgtgttg gtattgctga tcgttatcaa gattagctca ttttatggaa    4500
ttgtttaggt gaatttctc cttctttaca gaaacgttta tttcagaaat atggtattga    4560
taatcctgat atgaacaagt tacaatttca tttaatgttg gacgagttct tttaagaatt    4620
aattcatgac caaaatccct taacgtgagt tttcgttcca ctgagcgtca gaccccgtag    4680
aaaagatcaa aggatcttct tgagatcctt ttttctgcg cgtaatctgc tgctatttaa    4740
attacgtaca cgtgttatta ctttgttaac gacaattgtc ttaattaact gggcctcatg    4800
ggccttccgc tcactgcccg ctttccagtc gggaaacctg tcgtgccagc tgcagatg    4860
acggtgaaaa cctctgacac atgcagctcc cggagacggt cacagcttgt ctgtaagcgg    4920
atgccgggag cagacaagcc cgtcaggcg cgtcagcggg tgttggcggg tgtcggggcg    4980
cagccatgac ccagtcacgt agcgatagcg gagtgtatac tggcttaact atgcggcatc    5040
agagcagatt gtactgagag tgcaccatat gcggtgtgaa ataccgcaca gatgcgtaag    5100
gagaaaatac cgcatcaggc gctcttccgc ttcctcgctc actgactcgc tgcgctcggt    5160
cgttcggctg cggcgagcgg tatcagctca ctcaaaggcg gtaatacggt tatccacaga    5220
atcaggggat aacgcaggaa agaacatgtg agcaaaaggc cagcaaaagg ccaggaaccg    5280
taaaaaggcc gcgttgctgg cgtttttcca taggctccgc ccccctgacg agcatcacaa    5340
aaatcgacgc tcaagtcaga ggtggcgaaa cccgacagga ctataaagat accaggcgtt    5400
tccccctgga agctccctcg tgcgctctc tgttccgacc ctgccgctta ccggatacct    5460
gtccgccttt ctcccttcg gaagcgtggc gctttctcat agctcacgct gtaggtatct    5520
cagttcggtg taggtcgttc gctccaagct gggctgtgtg cacgaacccc cgttcagcc    5580
cgaccgctgc gccttatccg gtaactatcg tcttgagtcc aacccggtaa gacacgactt    5640
atcgccactg gcagcagcca ctggtaacag gattagcaga gcgaggtatg taggcggtgc    5700
```

FIG. 25 (continued)

```
tacagagttc ttgaagtggt ggcctaacta cggctacact agaaggacag tatttggtat   5760
ctgcgctctg ctgaagccag ttaccttcgg aaaaagagtt ggtagctctt gatccggcaa   5820
acaaaccacc gctggtagcg gtggtttttt tgtttgcaag cagcagatta cgcgcagaaa   5880
aaaaggatct caagaagatc ctttgatctt ttctactgca gaagcttgtt agacaccctg   5940
tcatgtattt tatattattt atttcaccat acggattaag tgaaacctaa tgaaaatagt   6000
actttcggag ctttaacttt aatgaaggta tgtttttta tagacatcga tgtctggttt   6060
aacaatagga aaaagtagct aaaactccca tgaattaaag aataacaag gtgtctaaca   6120
acctgttatt aagaatgtta gaaaagactt aacatttgtg ttgagttttt atagacattg   6180
gtgtctagac atacggtaga taaggtttgc tcaaaaataa aataaaaaaa gattggacta   6240
aaaaacattt aatttagtac aatttaatta gttattttt cgtctcaaat tttgctttgt   6300
tgagcagaaa tttagataaa aaaatcccg tgatcagatt acaatgtcgt tcattgtacg   6360
atgtgtcgaa aaatctttac gacactctaa actgaccaca cggggcaaaa agaaaactga   6420
actaataaca tcatgatact cggaaaacct agcaattctc aacccctaaa caaaagaaac   6480
ttccaaaacc ctgaccatat aaaggagtgg caacaatcag caatcagtca agatttgata   6540
gcagaaaatc ttgtatcggt tgctaatggt tttgatgtac tatttatcgg caataaatac   6600
cgaactaaca cgggtgttct gtcacggcac atattaaact cctattctca tttagaagat   6660
ggtggttcgt atggtagaac atttgaccca tttaccaata aagaaatgca gtgggttcaa   6720
tttaaacgga atagaccaag aaaaggttct actggtaagg taatcaaata tgaatcgcca   6780
aaaggtgaac ctacaagagt tctaatgccg tttgtgccta tgaaaatatg gcaacggatt   6840
agcgataagt tcggagtacc gattaatccg aaaaagata ctcacttttg ggaatgggta   6900
aagaataatc catcgatacc gattgccatt acagaaggaa ataaaaaagc taattgccta   6960
ttatcctatg gctatcctgc tattgccttt gtaggcattt ggaacggatt agagaaaata   7020
aatgatttct cgaaggaaaa gcagtaaaaa gaggatttga atggttgtt atccaacggc   7080
aaccgaaata ttaatatcat ctttgaccaa gaccagaaac aaaaaactgt aattaatgta   7140
aacaaagcta ttttcgcttt atcttctcta ataagtagaa atggtcataa agttaatatt   7200
gtgcaatggt tgccgtcaaa aggtaaagga atagatgatt atttggtagc tttaccttt   7260
gagaaaagag aaaatcattt agacaactta attaaaattg caccatcatt taattttttgg   7320
tcaactaaat actattcaa gtgtcgtaaa ccagatttaa ccgtaaattg ccgttatttg   7380
agcgatgcag taaaagaatt acctcaagag gatatagcat taatgcacc tcacggcacg   7440
ggtaaaactt cattagtaga tactcacgtt aagaatcgga gttatcacgg aaggaaaact   7500
atttcattgg tgcatcttga aagtttagcc aaagctaatg gcaacgcact tggattatat   7560
taccgaaccg aaaataatat tgaaaagcaa tatcttggat ttagcttatg tgtagatagt   7620
tgccgtgata agattaacgg cattacaact gatattattt caggtcaaga ttattgcctt   7680
ttcattgatg aaattgacca agtaattcca cacatcctta acagtgaaac tgaagtaagt   7740
aagtatagat gcaccatcat tgacactttt tctgaactgg tgagaaatgc tgaacaggtc   7800
attattgctg atgctgattt atcgatgtg acgattgacc taatagaaaa catcagaggt   7860
aaaaaactat atgtaatcaa gaatgaatat cagtatcagg gaatgacttt taacgccgtt   7920
ggttcaccat tagaaatgat ggcaatgatg ggaaaatcgg tgtcagaagg caagaaatta   7980
ttattaaca ccacatccca aaaggcaaaa agtaagtacg gcacaatcgc tcttgagtct   8040
tatatttttg gtctaaataa agaagcaaag atattaagaa tagactctga aaccactaaa   8100
aaccctgaac atccagccta taaaatcatt gaccaagact aaataatat cctcaaagat   8160
tatgattatg tcattgcctc accttgcctt caaacaggtg tcagtattac cttaaaaggg   8220
catttgacc agcaatttaa cttttccagt ggaaacatta cacctcattg cttttttacag   8280
caaatgtggc ggttgaggga tgcagaaatt gaaagattct attatgtgcc gaactcatct   8340
aacctcaatc tcattggaa taagtcaagt tcaacctaaa accttctaaa gagcaataac   8400
aagatggcaa cggcaacggt taaacttttg ggtagaatcg actccgaata ttccctagag   8460
tatgaatcgc acggcatttg gcttgagacg tgggcaaaat tatcagcacg gcataacgt   8520
tcaatgcgtt gttactctga aattcttacc tatctaatta cgtctcaagg gcataaatta   8580
aatatcaaca ttcctcacc tcttgcagat attaagaagc taaatgatga ggtaagtagt   8640
aacagggaaa aggtaaaaaa tgagagatac tctcagaggt taaactcacc agatattaac   8700
gatgcagaag ctaccatact cgaatctaaa gagcaaaaaa tcggattgac tctcaatgag   8760
agatgcaccc tagaaaagca taaagttaag aagcggtatg ggaatgtaaa gatggatatt   8820
ctcaccttg atgatgatgg actataccc aaactcagac tatttatta cctcaccatc   8880
ggtaaacctc atctcaaggc taatgacaga aaagctattg ccaaaatggg caatgacaat   8940
aaaggcaaga ttctatcaaa agacttagtt aataaaactt actccgctcg tgtgaaggtc   9000
ttagagattc ttaaactaac tgactttatc gacaatctta gagtgaact cttaataact   9060
cccaataatc cagctatcac cgattttaat aatcttctgc taagagctaa gaaggattta   9120
agagtattag gagtcaacat cggaaatat ccaatggcca acattaatgc cgtacttact   9180
ctcattggtc acaaactttc tgtaatgaga gatgagttcg gaaagagaa aaggataaaa   9240
gtagatggta aatcataccg atgttatcaa cttgaaacat taccagattt taccaatgat   9300
```

FIG. 25 (continued)

```
actcttgact actggttaga aaatgatagc caaaagaag taacagcaac agaaaattac      9360
tccgaaaatt ttaaccctto aaatagctac aatccagaca gtaagacact ttcagagggt     9420
gcaaatttcc tatatataaa taaagaagaa ttgcatccaa ataaattgca cctagaaata     9480
aaagaaggtg ctgaacttt tttattcggg gtaaggtga ttgtgaaagg aatcttggac       9540
ggggcagtaa ctatattctc tatgggtcaa gaatacgatt tatccctcaa tgaactagag    9600
gggatgttaa catcatgaac tttacaagaa tcttttaaa gggcgatcgc accatgttaa     9660
atgatggtac atttgttcag atatttgata ttaccatga ccacgcattg ggagtgaccc     9720
ttgaccttaa gacagaaaaa attatttccg atgatgttag ggtaattact gtcaaagact    9780
tattgttcga tggcacttat aaaggggtaa aatcttttat gcccgataat gcccgataat   9840
gcccgattga tgctacaaaa tcccataatc ataagcgata atccctaat agcttgtaat    9900
tcttgaaccg tagcgatctt agagtattcc aaaagaaga ataaacacc gcaaaatgtc     9960
gtatttcaca tatataaacc aaggttttt gccctaaaat ctttatgttt gtagtgtgat    10020
gttgggtcaa aatggtcaga aaagttgcaa ggttttatg gatgcttacg cgcgcgaggg   10080
gtaagcatcc ccaaatagtt actttatcct agtccatgcc cattattgc cgtcccgttc    10140
ggctttaaaa aagtgccaaa actcacaagg tgcaataaaa agttctgtac ctttcgcaac   10200
cctagataat ctttcaacag ttactttttt tcctattatc tggtacaaa gtttggctag    10260
tttctctttt ccctcttttt caatcaagcc ttcttgtatg cccaactcat tgattaatct   10320
ctctattttt accattattt cccgttcagg tagtttatcc cctaaatctt catcggggg    10380
caatgtaggg cattctgaag gggcttttc ttctgtctgg acattatcta atattgaagt   10440
aaccaaacta tcttcagttt tttctattcc tattaattca tattcggtta ctgtatccgt   10500
atcaatatcc gaataactat ctttatccgt attagctatt cggttaagtt tatccgttaa  10560
ctcagaaaca agactatata gcggttttag cttttcttct atcctgttat ctaatacgga  10620
taagtttata cggttatcat tatccgtatt agtatcattg gcttttttg gtagttctac   10680
ccctcataa acgcttta ttcccaattc caacagactg ataacagtat cctttataat     10740
gggtttttg ctgatatggt gaacttttgc ccttccatc attgcgatac tttctatctc   10800
actcatcaac ttatcgctta agtgaatctc gtatcgttt aatcccttac tggtttatt    10860
catatccgtt tactttatc ggttaacaat tctatttat acgaataaaa tattatacgg   10920
ttaactttat acgttaact attttatcta tacggataac agtaataagt tattcgtatt   10980
agttatacgt ttacttttat ccaaataaaa ttagtgcatt taaactaaaa gaatgatttt  11040
atcggagttg atagcattgg attaacctaa agatgtttaa aagctatatc tgataagtat  11100
ttaaggttat tttgttattc tgtttattga cattatgaa ataaaagaat agaatataat   11160
tgttgagaga taagaggttt aagtgattat ggttaagaag ttagttggtt atgtcagggt  11220
cagtagtgaa tcgcaagagg ataacactag cttacagaat cagatagaga gaattgaagc  11280
atattgtatg gcttttggtt atgagttgt aaaaatattc aaagagggttg ccactggtac  11340
aaaagcagat attgaaaccc gtcctatttt taatgaagct atagaatact tgaaacagga  11400
taatgctaat ggaattattg ccttgaagct agaccgaatc gcacggaatg ctttagatgt  11460
attgcgttg gttcgtgaaa cctagaaacc acaaaataaa atgttagtgt tactagatat   11520
tcaggtagat acttcgacac cttcaggaaa aatgatttta actgtaatga gtgccgttgc  11580
tgaactcgaa agagacatga tctatgatcg cactcagggg ggtagaaaga ctaaagccca  11640
aaagggcggg tatgcctacg ggaaacctaa atttggctat aagactgaag aaaaggaact  11700
aaaagaagat tcagcacaac aggaaactat taaactaatt aagagacacc gtaggtcagg  11760
gaaaagctac cagaaaatag ctgattatct caatgcccaa agtattccca ctaaacaagg  11820
taagaaatgg agttctagcg tcgtctatcg aatctgtcag gaaaaagctg ttaagtctg   11880
tttatagata tttagaattt attgaataaa aatagtatga acaataaata tttatggact  11940
aaccacgctc ggaaacgttt aactgaacga tgggaaataa aagaatcatg ggttattgat  12000
accatgaaa atcctgaacg ttcagaattt attgttgatg agtcagggga aaatatcat   12060
tactataaaa gaatagctaa gtttaagaat agagtgttag aagtgataac ttctgccaac  12120
tcaacaccca caagaataat aaccttttac tttaaccgta acatgaggaa aaatttatga  12180
ttgttactta cgataatgaa gttgacgcaa tttatttaa gttaacggaa aataaaattg   12240
atagcaccga acctcaaaca gacaggatta tcattgatta cgatgaaagt aataatattg  12300
ttggcattga ggtattagat tttaattatc ttgtcaagaa aggtttaacc gttgctgatt  12360
taccttttc tgaagatgaa agattaacag cttctcaata ttttaatttt cctgttgcta  12420
tctaatccag aagggcaat aatccccttc tttcatcgag ttagacttaa tatcacaaaa  12480
gtcattttca ttttcacgtt tctttttccac agcgtccgta cgcccctcgt taaatctcaa  12540
aaccgacaat ttatgatgtt tataaaaagt tactcactt aataagtatt tatactcatt   12600
aaagggttat tcttttttg tagcctgata ggttggaag gaatattca gattatcaga    12660
tttgttgaat attttttcgtc agataccgca accttacaaa cataattaac aactgaaact  12720
attgatatgt ctaggtttta gctctatcac aggttggatc tg                      12762
```

FIG. 25 (continued)

TK471 pABICyano1::pilT-PrbcLABICyano1_Km**pilC-sacB-oriVT

```
ID   TK471\ pABICyano1::pilT-PrbcLABICyano1_Km**pilC-sacB-oriVT standard; circular
DNA;    ; 13354 BP.
CC   This file is created by Vector NTI
CC   http://www.invitrogen.com/
CC   VNTDATE|641221300|
CC   VNTDBDATE|645294711|
CC   LSOWNER|
CC   VNTAUTHORNAME|Irina Piven|
FH   Key             Location/Qualifiers
FH
FT   insertion_seq   6610..89
FT                   /source="pABICyano-6BindIIIBamHI"
FT                   /type="Custom cloned insert"
FT                   /vntifkey="14"
FT                   /label=pABICyano1-6.8
FT                   /note="Unknown feature type:insert"
FT   rep_origin      complement(5545..6693)
FT                   /vntifkey="33"
FT                   /label=OriVT
FT   CDS             7120..10305
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   CDS             10341..10526
FT                   /vntifkey="4"
FT                   /label=ORF\2
FT                   /note="orf2"
FT   CDS             complement(10786..11550)
FT                   /vntifkey="4"
FT                   /label=ORF\3
FT                   /note="orf3"
FT   CDS             11876..12562
FT                   /vntifkey="4"
FT                   /label=ORF\4
FT                   /note="orf4 integrase/Recombinase Similar to Site-specific
recombinase of Bacillus thuringiensis serovar israelensis ATCC 35646"
FT   CDS             12604..12867
FT                   /vntifkey="4"
FT                   /label=ORF\5
FT                   /note="orf5"
FT   CDS             12864..13112
FT                   /vntifkey="4"
FT                   /label=ORF\6
FT                   /note="orf6"
FT   3'UTR           4649..5402
FT                   /vntifkey="50"
FT                   /label=pilT-flank
FT   3'UTR           2105..2872
FT                   /vntifkey="50"
FT                   /label=pilC-flank
FT   promoter        complement(3924..4383)
```

FIG. 27

```
FT                      /vntifkey="30"
FT                      /label=PrbcLASICyano
FT          CDS         complement(3108..3923)
FT                      /vntifkey="4"
FT                      /label=Km**
FT          promoter    101..563
FT                      /vntifkey="30"
FT                      /label=PsacB
FT          CDS         564..1985
FT                      /vntifkey="4"
FT                      /label=sacB
SQ          Sequence 13354 BP; 4435 A; 2630 C; 2459 G; 3830 t;
     aatattttc gtcagataug caaaucttac aascataatt aacaactgaa actattgata        60
     tgtctaggtt ttagctctat cacaggttgg atctgtcgac gatcctttt aacccatcac       120
     atataccgc cgttcactat tatttagtga aatgagatat tatgatattt tctgaattgt       180
     gattaaaaag gcaactttat gcccatgcaa cagaaactat aaaaaataca gagaatgaaa       240
     agaaacagat agattttta gttctttagg cccgtagtct gcaatctctt ttatgatttt       300
     ctatcaaaca aaagaggaaa atagaccagt tgcaatccaa aggagagtct aatagaatga       360
     ggtcgaaaag taaatcgcgc gggtttgtta ctgataaagc aggcaagacc taaaatgtgt       420
     aagggcaaa gtgtatactt tggcgtcacc ccttacatat tttaggtctt ttttattgt        480
     gcgtaactaa cttgccatct tcaaacagga gggctggaag aagcagaccg ctaacacagt       540
     acataaaaaa ggagacatga acgatgaaca tcaaaagtt tgcaaacaa gcaacagtat        600
     taacctttac taccgcactg ctgcaggag gcgcaactca agcgttgcg aaagaaacga       660
     accaaaagcc atataaggaa acatacggca tttcccatat tacacgccat gatatgctgc       720
     aaatccctga acagcaaaaa atgaaaaat atcaagttcc tgaattcgat tgtccacaa        780
     ttaaaaatat ctcttctgca aaaggcctgg aggttggga cagctggcca ttacaaaacg       840
     ctgacggcac tgtcgcaaac tatcacggct accacatcgt ctttgcatta gcggagatc       900
     ctaaaaatgc ggatgacaca tgatttaca tgttctatca aaagtcggc gaaacttcta       960
     ttgacagctg aaaaaacgct ggccgcgtct ttaagacag cgacaaattc gatgcaaatg      1020
     attctatcct aaagaccaa acaaagaat ggtcaggttc agccacattt acatctgacg       1080
     gaaaaatccg tttattctac actgattct ccgtaaaca ttacggcaaa caaacactga      1140
     caactgcaca agttaacgta tcagcatcag acagctcttt gaacatcaac ggtgtagagg      1200
     attataaatc aatctttgac ggtgacgaa aascgtatcc aaatgtacag cagttcatcg      1260
     atgaagcaa ctacagctca ggcacaacc atacgctgag agatcctcac tacgtagaag      1320
     ataaaggcca caaatactta gtatttgaag caaacactgg aactgaagat ggctaccaag      1380
     gcgaagaatc tttatttaac aaagcatact atggcaaaag cacatcattc ttccgtcaag      1440
     aaagtcaaaa acttctgcaa agcgataaaa aacgcacggc tgagttagca acggcgctc      1500
     tcggtatgat tgagctaaac gatgattaca cactgaaaa agtgatgaaa ccgctgattg      1560
     catctaacac agtaacagat gaaattgaac gcgcaacgt ctttaaaatg aacggcaaat      1620
     ggtacctgtt cactgcctcc acggatcaa aatgacgat tgacggcatt aacgtctacg      1680
     atattacat gcttggttat gttctaatt ctttaactgg cccatacaag ccgctgaaca      1740
     aaactggcct tgtgttaaaa atggatcttg atcctaacga tgtaacctt acttactcac      1800
     acttcgctgt acctcaagcg aaggaaaca atgtcgtgat tacaagctat atgacaaaca      1860
     gaggattcta cgcagacaaa aatcaaacgt tgcgcaaag cttcctgctg aacatcaaag      1920
     gcaagaaaac atctgttgtc aaagacagca tcctgaaca aggacaatta acagttaaca      1980
     aataaaaacg caaagaaaa tgccgatatc ctattggcat ttctttat ttcttatcaa       2040
     cataaaggtg aatccatat gaactatgga tggcgcagc atgctccgg cgccatcac         2100
     tagtgctcga tgacgctggt taatgcctta actgcttgtt ctacttcatc ttcataaaaa      2160
     tctgcaactt tcatcatcat tgcatctaat tcccgttt cttcaccaat catcatcatt      2220
     tgaattgcca tagagggaaa aaccttcttt tccgagatcg caacacttaa catcctcct      2280
     tctaaaatag aatcttttgc ggcgccaatg gcattagaaa ttactttatt agggatagtc      2340
```

FIG. 27 (continued)

```
tcttgagata tttctaaaca ttgtaagata ggcacaccag aacgggttaa agtaccaaaa    2400
atacgacaaa aacgagcaac agcacttttt tcatttaagt ccccaaaaat gggagcttta    2460
agtgcgatcg tatctatttg taaacgtcca gcaggagttt tataatattg acggaaggca    2520
aaaacaaccc caataatcac accacggga ataattgctt tcagctacg caaaaaatca    2580
ctaagagtaa ccatacttg agtcaagcc ggcattctg caccaattg gtcgaaata        2640
ccagcaaata caggaatcaa gaaatggtc ataccaaaa aagcaatgac cgcaaaaata     2700
ccaacagtga caggataagc cattgctgat ttaatttggt tttgcaaacg agcaacatct    2760
tcgagaagtt tagcaagacg attcatgact tcgtctaaaa cccccctgt ttctcccgct     2820
tctaccatac tcacatatag cctatcaaaa cagtcgggat gctttgccat tgcttcagat    2880
aaattaaccc cctgttgaac atcctctcca atagtagtta gagccttctt aaatttagga    2940
tttcctgatt gctctgccaa tactgacaaa gagcggccgc atttaaatag cagcagatta    3000
cgcgcagaaa aaaggatct caagaagatc ctttgatctt ttctacgggg tctgacgctc     3060
agtggaacga aaactcacgt taagggattt tggtcatgaa ttaattctta aagaactcg     3120
tccaacatta aatgaaattg taacttgttc atatcaggat tatcaatacc atatttctga    3180
aataaacgtt tctgtaaaga aggagaaaat tcacctaaac aattccataa aatagctaaa    3240
tcttgataac gatcagcaat accaacacga ccaacatcaa tacaaccaat caatttacct    3300
tcatcaaaga tcaaattatc taaagaaaaa tcaccatgag taacaacaga atcaggagaa    3360
aaaggtaaca atttgtgcat ttctttccaa acttgttcaa caggccaacc attacgttca    3420
tcatcaaaat cagaagcatc aactaaacca ttattcatac gagattgagc ttgagctaaa    3480
cgaaaaacac gatcagaatt aaaaggacaa ttcaaaacgg gaatagaatg taaacgacgt    3540
aaaaaaacag ctaaagcatc aacaatattt tcaccagaat caggatattc ttctaaaact    3600
tgaaaagcag ttttaccagg aatagcagta gttaataacc aagcatcatc gggagtacga    3660
ataaaatgtt taatagtagg taaaggcata aattcagtca accagtttaa acgaaccatt    3720
tcatcagtaa catcattagc aacagaacct ttaccatgtt tcaagaataa ttcaggagca    3780
tcaggtttac catataaacg ataaatagta gcaccayatt gaccaacatt atcacgagcc    3840
catttataac catataaatc ggcatccata ttgaattta aacgaggacg agaacaacta    3900
gtttcacgtt gaatatgaga catggttggt atcctccaaa tatataaatt ttctttatag    3960
cgttatatgt aacaacttct tttaatggaa gttagttttt tggcttttgc ttttcgagtt    4020
taaatcttat catgaagggg atcatttct atacacccag attaactatt tacgattatt    4080
atttttttctg aatttgatta acttaactaa tctaattctc tatgcttacc ccagactatt    4140
ctctaggtat tttaaactgc taatttttcc ctcttaacg ttataaaagt cagaatttca      4200
cattctttta cacttgagg ttaaattatt acgattatta gttttcctta tgttttaatt      4260
aaaaaggtaa cgatgcacta ggcaaggag aattgttgat aattaataac ttctaactct      4320
ttcctgtacg ggagaatgcc cattagcccc taactaactc cgtacgctt tgcggaacga     4380
gcgctcgagc gttctctccg aactaatttc tccctctcc ctcatctata ataagatagt      4440
taataattac atcgacaatt gtctacgtag gcgcgcatg cggccttgac ggccttccgc     4500
caattcgccc tatagtgagt cgtattacgt cgcgctcact ggccgtcgtt ttacaacgtc     4560
gtgactggga aaaccctggc gttacccaac ttaatcgcct tgcagcacat cccccctttcg    4620
ccagctgcgc cggatcctg caggtcgacg atcgcaggtg tcaatcat gatttcttga       4690
gccattgccc taccaaattc gccggtttg ggattttct tttagcaa agtttgagca        4740
aatactgcca ataaagagtt agataacatt gctctaattt gggcttgttc tgccgaagga    4800
aatacatcaa taatacgatc aattgttccc gccgcagagc tagtatgtaa agtaccaaag    4860
acaaggtgtc cagtttccgc cgccgtaatc gccaaagaaa tggtttctaa gtcgcgcatc    4920
tcacccacta gaataatatc tggatcttcc cttaacgccg ctttttaagg cattggcaaa     4980
ctttagtat cttctccttt ttgacgttgg tgaaatagac tgttaatatt gggaaaaaca      5040
tactcgatcg gatcttctac tgttaagatg tgttctgcac gagtgcggtt aattaagtcc     5100
aacattgccg ctaagtagt agttttcca gaacctgtct gcctgtcac taaaatcata       5160
cccctaggc gttcggacat ctccttgaca atatctggta agcctaattg atcaaaattg     5220
ggaattttgg aagataaagc ccttaaacaa gggcataac aaccccttc cttataaaca      5280
tttacacgaa atcgagccaa gccttttacc ccgtaggaac agtctaactc ccattcttgc    5340
tctaatgttt tacgttgagt attattgagc atactaaaaa ttaattttg gcactcttga    5400
```

FIG. 27 (continued)

```
gcattaaggg gttcatctcc aatgcaaaat tacgtacacg tgttattact ttgttaacga    5460
caattgtctt aattaactgg cctcatgggc cttccgctca ctgcccgctt tccagtcggg    5520
aaacctgtcg tgccagctct gcagatgacg gtgaaacct  ctgacacatg cagctcccgg    5580
agaggtcac  agcttgtctg taagcggatg ccgggagcag acaagcccgt caggcgcgt    5640
cagcgggtgt tgcgggtgt  cgggcgcag  ccatgaccca gtcacgtagc gatagcggag    5700
tgtatactgg cttaactatg cggcatcaga gcagattgta ctgagagtgc accatatgcg    5760
gtgtgaaata ccgcacagat gcgtaaggag aaaataccgc atcaggcgct cttccgcttc    5820
ctcgctcact gactcgctgc gctcggtcgt tcggctgcgg cgagcggtat cagctcactc    5880
aaaggcggta atacggttat ccacagaatc aggggataac gcaggaaaga catgtgagc    5940
aaaaggccag caaaaggcca ggaaccgtaa aaaggccgcg ttgctggcgt ttttccatag    6000
gctccgcccc cctgacgagc atcacaaaaa tcgacgctca gtcagaggt  ggcgaaaccc    6060
gacaggacta taaagatacc aggcgtttcc ccctggaagc tccctcgtgc gctctcctgt    6120
tccgaccctg ccgcttaccg gatacctgtc cgcctttctc ccttcgggaa gcgtggcgct    6180
ttctcaatgc tcacgctgta ggtatctcag ttcggtgtag gtcgttcgct ccaagctggg    6240
ctgtgtgcac gaaccccccg ttcagcccga ccgctgcgcc ttatccggta actatcgtct    6300
tgagtccaac ccggtaagac acgacttatc gccactggca gcagccactg gtaacaggat    6360
tagcagagcg aggtatgtag gcggtgctac agagttcttg aagtggtggc ctaactacgg    6420
ctacactaga aggacagtat ttggtatctg cgctctgctg aagccagtta ccttcggaaa    6480
aagagttggt agctcttgat ccggcaaaca accaccgct  ggtagcggtg gtttttttgt    6540
ttgcaagcag cagattacgc gcagaaaaaa aggatctcaa gaagatcctt tgatcttttc    6600
tactgcagaa gcttgttaga caccctgtca tgtattttat attatttatt tcaccatacg    6660
gattaagtga aacctaatga aaatagtact ttcggagctt taactttaat gaaggtatgt    6720
ttttttatag acatcgatgt ctggtttaac aataggaaaa agtagctaaa actcccatga    6780
attaaagaaa taacaaggtg tctaacaacc tgttattaag aatgttagaa aagacttaac    6840
atttgtgttg agttttata  gacattggtg cctagacata cggtagataa ggtttgctca    6900
aaaataaat  aaaaaagat  tggctaaaa  aacatttaat ttagtacaat ttaattagtt    6960
atttttcgt  ctcaaatttt gctttgttga gcagaaattt agataaaaaa atccccgtga    7020
tcagattaca atgtcgttca ttgtacgatg tgtcgaaaaa tctttacgac actctaaact    7080
gaccacacgg gggaaaaaga aaactgaact aataacatca tgatactcgg aaaacctagc    7140
aattctcaac ccctaaacaa aagaaacttc caaaaccctg accatataaa ggagtggcaa    7200
caatcagcaa tcgtcaaga  tttgatagca gaaaatcttg tatcggttgc taatggtttt    7260
gatgtactat ttatcggcaa taaatacgga actaacacgg tgttctgtc  acggcacata    7320
ttaaactcct attctcattt agaagatggt ggttcgtatg gtagaacatt tgacccattt    7380
accaataaag aaatgcagtg ggttcaattt aaaccgaata gaccaagaaa aggttctact    7440
ggtaaggtaa tcaaatatga atcgccaaaa ggtgaaccta caagagttct aatgccgttt    7500
gtgcctatga aaatatggca acggattagc gataagttcg gagtaccgat taatccgaaa    7560
aaagatactc actttggga  atgggtaaag aataatccat cgataccgat tgccattaca    7620
gaaggaaata aaaagctaa  ttgcctatta tcctatgget atcctgctat tgcctttgta    7680
ggcatttgga acggattaga gaaatataat gatttctcga aggaaaagca gttaaaagag    7740
gatttgaaat ggttgttatc caacggcaac cgaaatatta atatcatctt tgaccaagac    7800
cagaacaaa  aactgtaat  taatgtaaac aagctatttt tcgtttatc  ttctctaata    7860
agtagaaatg gtcataaagt taatattgtg caatggttgc cgtcaaaagg taaaggaata    7920
gatgattatt tggtagcttt acctttgag  aaaagagaaa atcatttaga caacttaatt    7980
aaaattgcac catcatttaa tttttgtca  actaaatact tattcaagtg tcgtaaacca    8040
gatttaaccg taaattgcg  ttatttgagc gatgcagtaa aagaattacc tcaagaggat    8100
atagcattaa tagcacctca cggcacggt  aaaacttcat tagtagctac tcacgttaag    8160
aatcggagtt atcacggaag gaaaactatt tcattggtgc atcttgaaag tttagccaaa    8220
gctaatggca acgcacttgg attatattac cgaaccgaaa ataatattga aaagcaatat    8280
cttggattta gcttatgtgt agatagttgc cgtgataaga ttaacggcat tacaactgat    8340
attatttcag gtcaagatta ttgcctttc  attgatgaaa ttgaccaagt aattccacac    8400
atccttaaca gtgaaactga agtaagtaag tatagatgca ccatcattga cacttttct    8460
gaactggtga gaaatgctga acaggtcatt attgctgatg ctgatttatc cgatgtgacg    8520
```

```
attgacctaa tagaaaacat cagaggtaaa aaactatatg taatcaagaa tgaatatcag    8580
tatcagggaa tgacttttaa cgccgttggt tcaccattag aaatgatggc aatgatggga    8640
aaatcggtgt cagaaggcaa gaaattattt attaacacca catcccaaaa ggcaaaaagt    8700
aagtacggca caatcgctct tgagtcttat attttggtc taaataaaga agcaaagata    8760
ttaagaatag actctgaaac cactaaaaac cctgaacatc cagcctataa aatcattgac    8820
caagacttaa ataatatcct caaagattat gattatgtca ttgcctcacc ttgccttcaa    8880
acaggtgtca gtattacctt aaaagggcat tttgaccagc aatttaactt ttccagtgga    8940
aacattacac ctcattgctt tttacagcaa atgtggcggt tgagggatgc agaaattgaa    9000
agattctatt atgtgccgaa ctcatctaac ctaatctca ttgggaataa gtcaagttca     9060
ccatcagcc ttctaaagag caataacaag atggcaacgg caacggttaa ccttttgggt     9120
agaatcgact ccgaatattc cctagagtat gaatcgcacg gcatttggct tgagacgtgg    9180
gcaaaattat cagcacggca taacagttca atgcgttgtt actctgaaat tcttacctat    9240
ctaattacgt ctcaagggca taattaaat atcaacattc cctcacctct tgcagatatt     9300
aagaagctaa atgatgaggt aagtagtaac agggaaaagg taaaaaatga gagatactct    9360
cagaggttaa actcaccaga tattaacgat gcagaagcta ccatactcga atctaaagag    9420
caaaaaatcg gattgactct caatgagaga tgcaccctag aaaagcataa agttaagaag    9480
cggtatggga atgtaaagat ggatattctc accttgatg atgatggact atacccaaa     9540
ctcagactat tttattacct caccatcggt aaacctcatc tcaaggctaa tgacagaaaa    9600
gctattgcca aaatgggcaa tgacaataaa ggcaagattc tatcaaaaga cttagttaat    9660
aaaacttact ccgctcgtgt gaaggtctta gagattctta aactaactga ctttatcgac    9720
aatcttagag atgaactctt aataactccc aataatccag ctatcaccga ttttaataat    9780
cttctgctaa gagctaagaa ggatttaaga gtattaggag tcaacatcgg aaaatatcca    9840
atggccaaca ttaatgccgt acttactctc attggtcaca aactttctgt aatgagagat    9900
gagttcggaa aagagaaaag gataaaagta gatggtaaat cataccgatg ttatcaactt    9960
gaaacattac cagattttac caatgatact cttgactact ggttagaaaa tgatagccaa   10020
aaagaagtaa cagcaacaga aaattactcc gaaaatttta accttcaaa tagctacaat    10080
ccagacagta agacacttc agaggtgca aatttcctat atataaataa agaagaattg     10140
catccaaata aattgcacct agaaataaaa gaaggtgctg aacttttttt attcggggta   10200
aaggtgattg tgaaaggaat cttggacggg gcagtaacta tattctctat gggtcaagaa   10260
tacgatttat ccctcaatga actagagggg atgttaacat catgaacttt acaagaatct   10320
ttttaaaggg cgatcgcacc atgttaaatg atggtacatt tgttcagata tttgatattt   10380
accatgacca cgcattggga gtgaccttg accttaagac agaaaaaatt atttccgatg   10440
atgttagggt aattactgtc aaagacttat tgttcgatgg cacttataaa gggtaaaat    10500
cttttatgcc cgataatgcc cgataatgcc cgattgatgc tacaaaatcc cataatcata   10560
agcgataatc ccctaatagc ttgtaattct tgaaccgtag cgattttaga gtattccaaa   10620
aagaagaaat aaacaccgca aaatgtcgta tttcacatat ataaaccaag gttttttgcc   10680
ctaaaatctt tatgttgta gtgtgatgtt gggtcaaaat ggtcagaaaa gttgcaaggt    10740
ttttatggat gcttacgcgc gcgagggta agcatccca aatagttact ttatcctagt     10800
ccatgccat ttattgccgt ccgttcggc tttaaaaaag tgccaaaact cacaaggtgc     10860
aataaaaagt tctgtaacctt tgcaaccct agataatctt tcaacagtta cttttttcc    10920
tattatctcg gtacaaagtt tggctagttt ctctttttcc tcttttcaa tcagccttc     10980
ttgatgccc aactcattga ttaatctctc tatttttacc attatttccc gttcaggtag    11040
tttatccct aaatcttcat cgggggcaa tgtagggcat tctgaagggg cttttttctc     11100
tgtctggaca ttatctaata ttgaagtaac caaactatct tcagttttt ctattcctat    11160
taattcatat tcggttactg tatccgtatc aatatccgaa taactatctt tatccgtatt   11220
agctattcgg ttaagtttat ccgttaactc agaaacaaga ctatatagcg gttttagctt   11280
ttcttctatc ctgttatcta atacggataa gttatacgg ttatcattat ccgtattagt    11340
atcattgggc ttttttggta gttctacccc ctcataaacc gttttattc ccaattccaa    11400
cagactgata acagtatcct ttataatggg ttttgctg atatggtgaa cttttgcccc    11460
ttccatcatt gcgatacttt ctatctcact catcaactta tgcttaagt gaatctgta     11520
tctgtttaat cccttactgg ttttattcat atccgtttac tttattcggt taacaattct   11580
```

FIG. 27 (continued)

```
attttatacg aataaaatat tatacggtta actttatacg tttaactatt ttatctatac   11640
ggataacagt aataagttat tcgtattagt tatacgttta cttttatcca aataaaatta   11700
gtgcatttaa actaaaagaa tgattttatc ggagttgata gcattggatt aacctaaaga   11760
tgtttataag ctatatctga taagtattta aggttatttt gttattctgt ttattgacat   11820
tatcagaata aaagaataga atataattgt tgagagataa gaggtttaag tgattatggt   11880
taagaagtta gttggttatg tcagggtcag tagtgaatcg caagaggata acactagctt   11940
acagaatcag atagagagaa ttgaagcata ttgtatggct tttggttatg agttggtaaa   12000
aatattcaaa gaggttgcca ctgtacaaa agcagatatt gaaacccgtc ctattttaa    12060
tgaagctata gaatacttga aacaggataa tgctaatgga attattgcct tgaagctaga   12120
ccgaatcgca cggaatgctt tagatgtatt gcgtttggtt cgtgaaacct tagaaccaca   12180
aaataaaatg ttagtgttac tagatattca ggtagatact tgacaccttt caggaaaaat   12240
gattttaact gtaatgagtg ccgttgctga actcgaaaga gacatgatct atgatcgcac   12300
tcaggggggt agaaagacta aagcccaaaa gggcgggtat gcctacggga aacctaaatt   12360
tggctataag actgaagaaa aggaactaaa agaagattca gcacaacagg aaactattaa   12420
actaattaag agacaccgta ggtcaggaa aagctaccag aaaatagctg attatctcaa   12480
tgcccaaagt attcccacta aacaagtgaa gaaatggagt tctagcgtcg tctatcgaat   12540
ctgtcaggaa aaagctggtt aagtctgttt atagatactt agaatttatt gaataaaaat   12600
agtatgaaca ataaatattt atggactaac cacgctcgga aacgtttaac tgaacgatgg   12660
gaaataaaag aatcatggt tattgatacc atcgaaaatc ctgaacgttc agaatttatt   12720
gttgatgagt caggggaaaa atatcattac tataaaagaa tagctaagtt taagaataga   12780
gtgttagaag tgataacttc tgccaactca acaccacaa gaataataac cttttacttt   12840
aaccgtaaca tgaggaaaaa tttatgattg ttacttacga taatgaagtt gacgcaattt   12900
attttaagtt aacggaaaat aaaattgata gcaccgaacc tcaaacagac aggattatca   12960
ttgattacga tgaagtaat aatatgttg gcattgaggt attagatttt aattatcttg   13020
tcaagaaaagg tttaaccgtt gctgattac ctttttctga agatgaaaga ttaacagctt    13080
ctcaatattt taattttcct gttgctatct aatccagaag gggcaataat cccttctttt   13140
catcgagtta gacttaatat cacaaaagtc attttcattt tacgtttct tttccacagc   13200
gtccgtacgc ccctcgttaa atctcaaaac cgacaattta tgatgtttat aaaaagttac   13260
tcactttaat aagtatttat actcattaaa gggttattct ttttttgtag cctgataggt   13320
tgggaaggaa tatttcagat tatcagattt gttg                              13354
```

FIG. 27 (continued)

```
ID   #1629\\pABICyano1::PnirA(opt2)-zmPDC(opt1)_dsrA-Prbc*(optRBS)-synADH(opt1)_ter
standard; circular DNA;    ; 12763 BP.
CC   This file is created by Vector NTI
CC   http://www.invitrogen.com/
CC   VNTDATE|645468904|
CC   VNTDBDATE|645468924|
CC   LSOWNER|
CC   VNTAUTHORNAME|Ulf Duehring|
FH   Key             Location/Qualifiers
FH
FT   insertion_seq   2913..2063
FT                   /vntifkey="14"
FT                   /label=dsrA
FT                   /note="dsr terminator from E.coli"
FT   gene            2133..3143
FT                   /vntifkey="60"
FT                   /note="ADH"
FT   CDS             2133..3140
FT                   /vntifkey="4"
FT                   /label=synADH(opt1)
FT   terminator      3144..3299
FT                   /vntifkey="43"
FT                   /label=TrbcSABICyano1
FT   promoter        3336..3739
FT                   /vntifkey="30"
FT                   /label=PrbcABICyano1
FT   CDS             3801..4616
FT                   /vntifkey="4"
FT                   /label=Km**
FT                   /note="Km**"
FT   CDS             12178..12426
FT                   /vntifkey="4"
FT                   /label=ORF\6
FT                   /note="orf6"
FT   CDS             11918..12181
FT                   /vntifkey="4"
FT                   /label=ORF\5
FT                   /note="orf5"
FT   CDS             11190..11876
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10100..10864)
FT                   /vntifkey="4"
FT                   /label=ORF\3
FT                   /note="orf3"
FT   CDS             9655..9840
FT                   /vntifkey="4"
FT                   /label=ORF\2
FT                   /note="orf2"
FT   rep_origin      complement(8955..8972)
FT                   /vntifkey="33"
FT                   /label=Rep_Origin_1
FT                   /note="potential rep origin; match pNostoc (Acc# M81381) nick
site (358-375); on reverse strand"
FT   misc_feature    9215..9248
FT                   /vntifkey="21"
FT                   /label=Rep\motif
FT                   /note="Rep protein active site motiq EXKKYXVEXXD"
```

FIG. 29

```
FT   CDS             6434..9619
FT                   /vntifkey="4"
FT                   /label=ORF\1
FT                   /note="orfI  rep ori binding protein slr7037 homolog Similar to
hypothetical protein slr7037 of plasmid pSYSA (103 kb)  of Synechocystis sp. PCC 6803"
FT   primer_bind     complement(5222..5253)
FT                   /vntifkey="28"
FT                   /label=Bom-F
FT   primer_bind     4904..4935
FT                   /vntifkey="28"
FT                   /label=Bom-R
FT   rep_origin      complement(4859..5917)
FT                   /vntifkey="33"
FT                   /label=OriVT
FT   promoter        2064..2132
FT                   /vntifkey="30"
FT                   /label=Prbc*(optRBS)
FT                   /note="improved version of the rbcL promoter from PCC6803"
FT   promoter        1..287
FT                   /vntifkey="30"
FT                   /label=PnirA*2
FT                   /note="improved version of nirA promoter"
FT   CDS             285..1991
FT                   /vntifkey="4"
FT                   /label=zmPDC(opt1)
SQ   Sequence 12763 BP; 3948 A; 2245 C; 2490 G; 4080 t;
     tcgacaatta ataacttctt cctgtacggg cgaatggcca tttgctccta actactccg        60
     tactgctttg cggaacgagc gtagcgaact ctccgaatta ctaagccttc atccctgata       120
     gatgcaaaaa acgaattaaa attatgttat aaaagaaaat gtgtctttat ttagtagtca       180
     aagttacaaa atattaagaa tcaaattaat aatgtattgg gcagttaagt atataagtct       240
     ctaaatattt attgtattc aatatattaa ggaggatcag cttatgaat tcttatacg          300
     tgggtactta tttagccgaa cgcttagtgc aaattggttt aaaacatcat tttgcgtgg        360
     ctggggacta taatttagtg ttattggata acttattatt aaataaaaac atggaacaag      420
     tgtattgttg taatgaatta aattgtggtt ttctgctga aggttatgct agagctaaag       480
     gtgcagctgc tgctgttgtt acttattctg tgggtgcttt atctgctttt gatgctattg      540
     gtggtgctta tgccgaaaat ttaaccgtga tttaatttc tggtgcccct aataacaatg       600
     atcatgccgc tggacatgtt ttacatcatg ccttaggtaa aaccgattat cattatcaat      660
     tagaaatggc caaaaatatt actgctgctg ccgaagctat ttatactcct gaagaagcc       720
     ctgccaaaat tgatcatgtg attaaaaccg ccttacgcga aaaaaaaccc gtgtatttag      780
     aaattgcctg taatattgct tctatgcctt gtgctgctcc tgggctgct tctgcttat       840
     ttaatgatga agcctctgat gaagctagtt taaatgctgc cgtggaagaa aaccttaaaat   900
     ttattgccaa tcgcgataaa gttgccgtgt tagttggttc taattaaga gctgctggtg     960
     ctgaagaagc tgctgttaaa tttgctgatg cttaggtgg tgcagttgct actatggctg    1020
     ctgccaaatc tttttttccc gaagaaaatc cccattatat tggaactagt tggggagaag    1080
     tttcttatcc tggtgtggaa aaaactatga aagaagccga cgctgttatt gctttagccc    1140
     ctgtgtttaa tgactattct accactggtt ggactgatat tccggatccc aaaaaattag    1200
     ttttagccga acctcgttct gtgttgtta atggtgttcg ctttccctct gtgcatttca    1260
     aagattattt aaccccgctta gcccaaaaag tttctaaaaa aactggtgcc ttagattttt    1320
     ttaaatcttt aaatgcgggt gaattaaaaa agctgctcc tgctgatcct tctgctcctt    1380
     tagttaatgc tgaaattgcc cgtcaagttg aagcctatt aacccctaat actacggta     1440
     ttgccgaaac tggtgattct tggtttaatg cccaagcat gaaattacct aatggtgcc     1500
     gtgttgaata tgaaatgcaa tcgggtcatc ttggttggtc tgtacctgct gcttttggtt    1560
     atgctgttgg tgctcctgaa cgtcgtaata tttaatggt gggtgatggt tcttttcaat    1620
     taactgccca agaagttgcc caaatggttc gcttaaaatt accggttatt attttttaa    1680
     taataacta tgttatatcc atgaagtga tgattcatga tgggccatat aataatatta     1740
     aaaattggga ttatgcggtt ttaatggaag tgtttaatgg taatggtggt tatgattctg    1800
     gtgctgtaa aggttaaaa gccaaaactg gtggtgaatt agctgaagct attaaagttg    1860
     ccttagccaa tactgatggg ccaaccttaa ttgaatgttt tattggtcgc gaagattgta    1920
     ccgaagaatt agttaaatgg ggtaaaacgta ttgctgtgc taattctgct aaaccggtga   1980
     ataaattatt gtaattttg gggatcaatt cgagctcagc aagttcatc ccgaccccct     2040
     caggtcggg atttttttat tgtactagtt gacataagta aaggcatccc ctgcgtgata    2100
```

FIG. 29 (continued)

```
taattacctt cagtttaagg aggtatacac atatgattaa agcctatgct gccttagaag    2160
ccaatggtaa attacaaccc tttgaatatg atcctggtgc tttaggtgcc aatgaagtgg    2220
aaattgaagt gcaatattgt ggtgtgtgtc attctgattt atctatgatt aataatgaat    2280
ggggtatttc taattatccc ttagttcctg gtcatgaagt tgttggtact gttgctgcta    2340
tgggtgaagg tgttaatcat gtggaagtgg gtgatttagt tggtttaggt tggcattctg    2400
gttattgtat gacctgtcat tcttgtttat ctgttatca taatttatgt gccactgccg    2460
aatctactat tgtgggtcat tatggtggtt ttggtgatag agttcgtgct aaaggtgttt    2520
ctgtggtgaa attacccaaa ggtattgatt tagcctctgc tgggcctttta ttttgtggtg    2580
gtattaccgt tttttctccc atggtggaat tatctttaaa acctaccgcc aaagttgctg    2640
ttattggtat tggtggttta ggtcatttag ccgttcaatt tttaagagcc tggggttgtg    2700
aagttactgc ttttacctct tctgccgta aacaaaccga agttttagaa ttaggtgccc    2760
atcatatttt agattctacc aatcctgaag ctattgcttc tgccgaaggt aaatttgatt    2820
atattatttc taccgtgaat ttaaaattag attggaattt atatatcagt accttagccc    2880
ctcaaggtca ttttcatttt gttggtgtgg tgttagaacc cttggactta aacttatttc    2940
ccttattaat gggacaacgt tctgtttctg cttctctgt tggttctcct gctactattg    3000
ccactatgtt agattttgcc gtgcgtcatg atattaaacc cgtggtgaa caatttttctt    3060
ttgatcaaat taatgaagcc attgccatt tagaatctgg taaagcccat tatcgcgtgg    3120
tgttatctca ttctaaaaat taataagatt aacttctaaa ctgaaacaaa tttgagggta    3180
ggcttcattg tctgcccta tttttttatt taggaaaagt gaacagacta aagagtgttg    3240
gctctattgc tttgagtatg taaattaggc gttgctgaat taaggtatga tttttgaccc    3300
cttctctctt ctgcaggatc atcttgctga aaaactcgag cgctcgttcc gcaaagcggt    3360
acggagttag ttaggggcta atgggcattc tccgtacag gaaagagtta gaagttatta    3420
attatcaaca attctccttt gcctagtgca tcgttacctt ttaattaaa acataaggaa    3480
aactaataat cgtaataatt taacctcaaa gtgtaaagaa atgtgaaatt ctgacttta    3540
taacgttaaa gagggaaaaa ttagcagttt aaaatacccta gagaatagtc tggggtaagc    3600
atagagaatt agattagtta agttaatcaa attcagaaaa aataataatc gtaaatagtt    3660
aatctgggtg tatagaaaat gatcccttc atgataagat ttaaactcga aaagcaaaag    3720
ccaaaaact aacttccatt aaaagaagtt gttacatata acgctataaa gaaaatttat    3760
atatttggag gataccaacc atgtctcata tcaacgtga aactagttgt tctcgccctc    3840
gtttaaattc taatatggat gccgatttat atggttataa atgggctcgt gataatgttg    3900
gtcaatctgg tgctactatt tatcgtttat atggtaaacc tgatgctcct gaattattct    3960
tgaaacatgg taaaggttct gttgctaatg atgttactga tgaaatggtt cgtttaaact    4020
ggttgactga atttatgcct ttacctacta ttaaacattt tattcgtact cccgatgatg    4080
cttggttatt aactactgct attcctggta aaactgcttt tcaagtttta gaagaatatc    4140
ctgattctgg tgaaatatt gttgatgctt tagctgtttt tttacgtcgt ttacattcta    4200
ttcccgtttg taattgtctt tttaattctg atgtgttttt tgtttagct caagctcaat    4260
ctcgtatgaa taatggttta gttgatgctt ctgatttga tgatgaacgt aatggttggc    4320
ctgttgaaca agtttggaaa gaaatgcaca aattgttacc ttttctcct gattctgttg    4380
ttactcatgg tgattttct ttagataatt tgatcttga tgaaggtaaa ttgattggtt    4440
gtattgatgt tggtcgtgtt ggtattgctg atcgttatca agatttagct attttatgga    4500
attgttaggt tgaattttct ccttcttac agaaacgttt atttcagaaa tatggtattg    4560
ataatcctga tatgaaatcaag ttacaatttc atttaatgtt ggacgagttc ttttaagaat    4620
taattcatga ccaaaatccc ttaacgtgag tttcgttcc actgagcgtc agacccgta    4680
gaaaagatca aaggatcttc ttgttcctct gcgtaattcg ctgctatttta    4740
aattacgtac acgtgttatt actttgttaa cgacaattgt cttaattaac tggcctcat    4800
gggccttccg ctcactgccc ggtttccagt cgggaaacct gtgtgcag ctctcagat    4860
gacggtgaaa acctctgaca catgcagctc ccggagacgg tcagcttg tctgtaagcg    4920
gatgcggga gcagacaagc ccgtcaggc ggtcagcgg gtgttggcgg gtgtcggggc    4980
gcagccatga cccagtcacg tagcgatagc ggagtgtata ctggcttaac tatgcggcat    5040
cagagcagat tgtactgaga gtgcaccata tgggtgtga ataccgcac agatgcgtaa    5100
ggagaaaata ccgcatcagg cgctcttccg cttcctcgct cactgactcg ctgcgctcgg    5160
tcgttcggct gcggcgagcg gtatcagctc actcaaaggc ggtaatacgg ttatccacag    5220
aatcagggga taacgcagga aagaacatgt gagcaaaagg ccagcaaaag gccaggaacc    5280
gtaaaaaggc cgcgttgctg gcgtttttcc ataggctccg cccccctgac gagcatcaca    5340
aaaatcgacg ctcaagtcag aggtggcgaa acccgacagg actataaaga taccaggcgt    5400
ttccccctgg aagctccctc gtgcgctctc ctgttccgac cctgccgctt accggatacc    5460
tgtccgcctt tctcccttcg ggaagcgtgg cgctttctca tagctcacgc tgtaggtatc    5520
tcagttcggt gtaggtcgtt cgctccaagc tgggctgtgt gcacgaaccc ccgttcagc    5580
ccgaccgctg cgccttatcc ggtaactatc gtcttgagtc caacccggta agacacgact    5640
tatcgccact ggcagcagcc actggtaaca ggattagcag agcgaggtat gtaggcggtg    5700
```

FIG. 29 (continued)

```
ctacagagtt cttgaagtgg tggcctaact acggctacac tagaaggaca gtatttggta    5760
tctgcgctct gctgaagcca gttaccttcg gaaaagagt tggtagctct tgatccggca    5820
aacaaaccac cgctggtagc ggtggttttt tgtttgcaa gcagcagatt acgcgcagaa    5880
aaaaggatc tcaagaagat cctttgatct tttctactgc agaagcttgt tagacaccct    5940
gtcatgtatt ttatattatt tattcaccca tacggattaa gtgaaccta atgaaaatag    6000
tactttcgga gctttaactt taatgaaggt atgttttttt atagcatcg atgtctggtt    6060
taacaataag aaaaagtagc taaaactccc atgaataacaa ggtgtctaac    6120
aacctgttat taagaatgtt agaaaagact taacatttgt gttgagtttt tatagacatt    6180
ggtgtctaga catacggtag ataaggtttg ctcaaaaata aaataaaaaa agattggact    6240
aaaaaacatt taatttagta caatttaatt agttattttt tcgtctcaaa ttttgctttg    6300
ttgagcagaa atttagataa aaaaatccc gtgatcagat tacaatgtcg ttcattgtac    6360
gatgtgtcga aaaatcttta cgacactcta aactgaccac acggggaaa agaaaactg    6420
aactaataac atcatgatac tcggaaaacc tagcaattct caaccoctaa acaaaagaaa    6480
cttccaaaac cctgaccata taaggagtg gcaacaatca gcaatcagtc aagatttgat    6540
agcagaaaat cttgtatcgg ttgctaatgg tttttgatgta ctatttatcg gcaataaata    6600
ccgaactaac acgggtgttc tgtcacggca catattaaac tcctattctc atttagaaga    6660
tggtggttcg tatggtagaa catttgaccc atttaccaat aaagaaatgc agtgggttca    6720
atttaaaccg aatagaccaa gaaaaggttc tactggtaag gtaatcaaat atgaatcgcc    6780
aaaaggtgaa cctacaagag ttctaatgcc gtttgtgcct atgaaaatat ggcaacggat    6840
tagcgataag ttcggagtac cgattaatcc gaaaaaagat actcactttt gggaatgggt    6900
aaagaataat ccatcgatac cgattgccat tacagaagga aataaaaag ctaattgcct    6960
attatcctat ggctatcctg ctattgcctt tgtaggcatt tggaccggat tagagaaaat    7020
aaatgatttc tcgaaggaaa agcagttaaa agaggatttg aaatggttgt tatccaacgg    7080
caaccgaaat attaatatca tctttgacca agacacagaaa caaaaaactg taattaatgt    7140
aaacaaagct attttcgctt tatcttctct aataagtaga aatggtcata aagttaatat    7200
tgtgcaatgg ttgccgtcaa aaggtaaagg aatagatgat tatttggtag ctttaccttt    7260
tgagaaaaga gaaaatcatt tagacaactt aattaaaatt gcaccatcat ttaattttg    7320
gtcaactaaa tactattcca agtgtcgtaa accagattta accgtaaatt gccgttattt    7380
gagcgatgca gtaaagaat tacctcaaga ggatatagca ttaatagcac ctcacggcac    7440
gggtaaaact tcattagtag ctactcacgt taagaatcgg agttatcacg gaaggaaaac    7500
tatttcattg gtgcatcttg aaagtttagc caagctaat ggcaacgac ttggattata    7560
ttaacgaacc gaaaataata ttgaaaagca atatcttgga tttagcttat gtgtagatag    7620
ttgccgtgat aagattaacg gcattacaac tgatattatt tcaggtcaag attattgcct    7680
tttcattgat gaaattgacc aagtaattcc acacatcctt aacagtgaaa ctgaagtaag    7740
taagtataga tgaccatca ttgacactt ttctgaactg gtgagaaatg ctgaacaggt    7800
cattattgct gatgctgatt tatccgatgt gacgattgac ctaatagaaa acatcagagg    7860
taaaaacta tatgtaatca agaatgaata tcagtatcag ggaatgactt taacgccgt    7920
tggttcaaca ttagaatga tggcaaatga gggaaatcg gtgtcaagca gcaaaaatt    7980
atttattaac accacatccc aaaagcaaa aagtaagtac ggcacaatcg ctcttgagtc    8040
ttatatttt ggtctaaata agaagcaaa gatattaaga atagactctg aaaccactaa    8100
aaacctgaa catccagcct ataaatcat tgaccaagac ttaaataata tcctcaaaga    8160
ttatgattat gtaattgcct cacctgcct tcaaacaggt gtcagtatta ccttaaaagg    8220
gcattttgac cagcaattta actttccag tggaaacatt acacctcatt gcttttaca    8280
gcaaatgtgg ccgttgaggg atgcagaaat tgaaagattc tattatgtgc cgaactcatc    8340
taacctcaat ctcattggga ataagtcaag ttcaccatca gaccttctaa agagcaataa    8400
caagatgca acggcaacgg ttaaccttt gggtagaatc gactcgaat attccctaga    8460
gtatgaatcg cacggcattt ggcttgagac gtgggcaaaa ttatcagcac ggcataacag    8520
ttcaatgcgt tgttactctg aaattcttac ctatctaatt acgtctcaag ggcataaatt    8580
aaatatcaac attccctcac ctcttgcaga tattaagaag ctaaatgatg aggtaagtag    8640
taacagggaa aagtaaaaa atgagagata ctctcagagg ttaaactcac cagatattaa    8700
cgatgcagaa gctaccatac tcgaatctaa agagcaaaaa atcggattga ctctcaatga    8760
gagatgcacc ctagatgagc ataagttaa gaagcggtat gggaatgtaa agatggatat    8820
tctcaccttt gatgatgtg gactacacc caaactcaga ctattttatt acctcaccat    8880
cggtaaacct catctcaagg ctaatgcag aaaagctatt gccaaaatgg gcaatgacaa    8940
taaaggcaag attctatcaa aagacttagt taataaaact tactccgtc gtgtgaaggt    9000
cttagagatt cttaaactaa ctgactttat cgacaatctt agagatgaac tcttaataac    9060
tccaataat ccagctatca ccgatttaa taatcttctg ctaagagcta agaaggattt    9120
aagagtatta ggagtcaaca tggaaaata tccaatggcc aacattaatg ccgtacttac    9180
tctccattggt cacaaacttt ctgtaatgag agatgagttc ggaaaagaga aaagggataaa    9240
```

FIG. 29 (continued)

```
agtagatggt aaatcataco gatgttatca acttgaaaca ttaccagatt ttaccaatga    9300
tactcttgac tactggttag aaaatgatag ccaaaaagaa gtaacagcaa cagaaaatta    9360
ctccgaaaat tttaaccctt caaatagcta caatccagac agtaagacac tttcagaggg    9420
tgcaaatttc ctatatataa ataaagaaga attgcatcca aataaattgc acctagaaat    9480
aaaagaaggt gctgaacttt ttttattcgg ggtaaaggtg attgtgaaag gaatcttgga    9540
cggggcagta actatattct ctatgggtca agaatacgat ttatccctca atgaactaga    9600
gggatgtta acatcatgaa ctttacaaga atcttttaa agggcgatcg caccatgtta     9660
aatgatggta catttgttca gatatttgat atttaccatg accagcatt gggagtgacc     9720
cttgacctta agacagaaaa aattatttcc gatgatgtta gggtaattac tgtcaaagac    9780
ttattgttcg atggcactta aaagggta aaatcttta tgcccgataa tgcccgataa      9840
tgcccgattg atgctacaaa atccataat cataagcgat aatccctaa tagcttgtaa      9900
ttcttgaacc gtagcgattt tagagtattc caaaaagaag aaataaacac cgcaaaatgt   9960
cgtatttcac atatataaac caaggtttt tgccctaaaa tctttatgtt tgtagtgtga    10020
tgttgggtca aaatggtcag aaaagttgca aggtttat ggatgcttac gcgcgcgagg     10080
ggtaagcatc cccaaatagt tactttatcc tagtccatgc ccatttattg ccgtcccgtt   10140
cggctttaaa aaagtgcaa aactcacaag gtgcaataaa aagttctgta ccttcgcaa     10200
ccctagataa tctttcaaca gttactttt ttcctattat ctcggtacaa agtttggcta    10260
gtttctcttt tccctctttt tcaatcaagc cttcttgtat gcccaactca ttgattaatc   10320
tctctatttt taccattatt tcccgttcag gtagtttatc ccctaaatct tcatcggggg   10380
gcaatgtagg gcattctgaa ggggcttttt cttctgtctg gacattatct aatattgaag   10440
taaccaaact atcttcagtt ttttctattc ctattaattc atattcgtt actgtatccg    10500
tatcaatatc cgaataacta tctttatccg tattagctat tcggttaagt ttatccgtta   10560
actcagaaac aagactatat agcggtttta gcttttcttc tatcctgtta tctaatacgg   10620
ataagtttat acggttatca ttatccgtat tagtatcatt gggctttttt ggtagtccta   10680
cccctcata aaccgctttt attcccaatt ccaacagact gataacagta tcctttataa    10740
tgggtttttt gctgatatgg tgaacttttg cccttccat cattgcgata ctttctatct    10800
cactcatcaa cttatcgctt aagtgaatct cgtatctgtt taatcccta ctggttttat    10860
tcatatccgt ttactttatt cggttaacaa ttctatttta tacgaataaa atattatacg   10920
gttaacttta tacgttaac tattttatct atacggataa cagtaataag ttattcgtat    10980
tagttatacg tttacttta tccaataaa attagtgcat ttaaactaaa agaatgattt     11040
tatcggagtt gatagcattg gattaaccta aagatgttta taagctatat ctgataagta   11100
tttaaggtta ttttgttatt ctgttattg acattatcag aataaaagaa tagaatataa   11160
tgtttgagag ataagaggtt taagtgatta tggttaagaa gttagttggt tatgtcaggg   11220
tcagtagtga atgcaagag gataacacta gcttaagaa tcagatagag agaattgaag    11280
catattgtat ggcttttgt tatgagttgg taaaaatatt caaagagtt gccactgta     11340
caaaagcaga tattgaaacc cgtcctattt ttaatgaagc tatagaatac ttgaaacagg    11400
ataatgctaa tggaattatt gcttgaagc tagaccgaat cgcacggaat gctttagatg   11460
tattgcgttt ggttcgtgaa acttagaac cacaaaataa aatgttagtg ttactagata   11520
ttcaggtaga tactttcaca ccttcaggaa aaatgatttt aactgtaatg agtgccgttg   11580
ctgaactcga aagagacatg atctatgatc gcactcaggg gggtagaaaa actaaagccc   11640
aaaagggcgg gtatgcctac gggaaaccta aatttggcta taagactgaa gaaaaggaac   11700
taaaagaaga ttcagcacaa caggaaacta ttaaactaat taagagacac cgtaggtcag   11760
ggaaaagcta ccagaaaata gctgattatc tcaatgccca aagtattccc actaaacaag   11820
gtaagaaatg gagttctagc gtcgtctatc gaatctgtca ggaaaaagct ggttaagtct   11880
gtttatagat atttagaatt tattgaataa aaatagtatg aacaataaat attatggac   11940
taaccacgct cggaaacgtt taactgaacg atgggaaata aagaatcat gggttattga   12000
taccatgaa aatcctgaac gttcagaatt tattgttgat gagtcaggg aaaaatatca    12060
ttactataaa agaatagcta agtttaagaa tagagtgtta gaagtgataa cttctgccaa    12120
ctcaacacc acaagataaa taacctttca ctttaaccgt aacatgagga aaaatttatg   12180
attgttactt acgataataa agttagttca atttatttta agttaacgga aataaaaatt   12240
gatagcaccg aacctcaaac agacaggatt atcattgatt acgataaag taataaatatt    12300
gttggcattg agtattaga ttttaattat ctgtcaagaa aagtttaaac cgttgctgat     12360
ttaccttttt ctgaagatga aagattaaca gcttctcaat atttttaattt tcctgttgct   12420
atctaatcca gaagggcaa taatcccctt ctttcatcga gttagactta atatccacaa    12480
agtcattttc attttacgtt ttcttttcca cagqtccqt acqccctcg ttaaatctca     12540
aaaccgacaa tttatgatgt ttataaaaag ttactcactt taataagtat ttatactcat   12600
taaagggtta ttctttttt gtagctgat aggttgggaa ggaatattc agattatcag      12660
atttgttgaa tattttcgt cagatacgca aaccttacaa acataattaa caactgaaac    12720
tattgatatg tctaggtttt agctctatca caggttggat ctg                     12763
```

FIG. 29 (continued)

```
ID   #1636\\pABICyano1::PnirA(opt3)-zmPDC(opt1)_dsrA-Prbc*(optRBS)-synADH(opt1)_ter
standard; circular DNA;    ; 12762 BP.
CC   This file is created by Vector NTI
CC   http://www.invitrogen.com/
CC   VNTDATE|645469353|
CC   VNTDBDATE|645469353|
CC   LSOWNER|
CC   VNTAUTHORNAME|Ulf Duehring|
FH   Key             Location/Qualifiers
FH
FT   CDS             284..1990
FT                   /vntifkey="4"
FT                   /label=zmPDC(opt1)
FT   promoter        6..283
FT                   /vntifkey="30"
FT                   /label=PnirA*3
FT                   /note="improved version of nirA promoter"
FT   insertion_seq   2017..2062
FT                   /vntifkey="14"
FT                   /label=dsrA
FT                   /note="dsrA terminator from E.coli"
FT   gene            2132..3142
FT                   /vntifkey="60"
FT                   /note="ADH"
FT   CDS             2132..3139
FT                   /vntifkey="4"
FT                   /label=synADH(opt1)
FT   terminator      3143..3298
FT                   /vntifkey="43"
FT                   /label=TrbcSABICyano1
FT   promoter        3335..3798
FT                   /vntifkey="30"
FT                   /label=PrbcABICyano1
FT   CDS             3800..4615
FT                   /vntifkey="4"
FT                   /label=Km**
FT                   /note="Km**"
FT   CDS             12177..12425
FT                   /vntifkey="4"
FT                   /label=ORF\6
FT                   /note="orf6"
FT   CDS             11917..12180
FT                   /vntifkey="4"
FT                   /label=ORF\5
FT                   /note="orf5"
FT   CDS             11189..11875
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10899..10863)
FT                   /vntifkey="4"
FT                   /label=ORF\3
FT                   /note="orf3"
FT   CDS             9654..9839
FT                   /vntifkey="4"
FT                   /label=ORF\2
FT                   /note="orf2"
FT   rep_origin      complement(8954..8971)
FT                   /vntifkey="33"
```

FIG. 31

```
FT                      /label=Rep_Origin_1
FT                      /note="potential rep origin; match pNostoc (Acc# M81381) nick
site (358-375); on reverse strand"
FT   misc_feature       9214..9247
FT                      /vntifkey="21"
FT                      /label=Rep\motif
FT                      /note="Rep protein active site motig EXXKYXVKXXD"
FT   CDS                6433..9618
FT                      /vntifkey="4"
FT                      /label=ORF\1
FT                      /note="orf1 rep ori binding protein slr7037 homolog Similar to
hypothetical protein slr7037 of plasmid pSYSA (103 kb) of Synechocystis sp. PCC 6803"
FT   primer_bind        complement(5221..5252)
FT                      /vntifkey="28"
FT                      /label=Bom-F
FT   primer_bind        4903..4934
FT                      /vntifkey="28"
FT                      /label=Bom-R
FT   rep_origin         complement(4858..5916)
FT                      /vntifkey="33"
FT                      /label=OriVT
FT   promoter           2063..2131
FT                      /vntifkey="30"
FT                      /label=PrbcL*(optRBS)
FT                      /note="improved version of rbcL promoter from PCC6803"
SQ   Sequence 12762 BP; 3948 A; 2248 C; 2485 G; 4081 t;
     tcgacaatta ataacttctt cctgtacggg cgaatggcca tttgctccta actaactccg        60
     tactgctttg cggaacgagc gtagcgaact ctccgaatta ctaagccttc atcctgata       120
     gatgcaaaaa acgcattaaa attatgcgta aaaagcatat ttgtctttat ttagtaatca       180
     aagttacaaa ttattaagaa tcaaattaat aatatattgg gcagttaagt atataagtct       240
     ttaaatattt atttgtattc aatatattaa ccgaggacaa attatgatt ctttatacgt       300
     gggtacttat ttagcgaac gcttagtgca aattgcttta aaacatcatt ttgccgtggc       360
     tgggactat aattagtgt tattggataa cttattatta aataaaaaca tggaacaagt       420
     gtattgttgt aatgaattaa attgtggttt tctgctgaa ggttatgcta gagctaaagg       480
     tgcagctgct gctgttgtta cttattctgt gggtgcttta tctgcttttg atgctattgg       540
     tggtgcttat gccgaaaatt taccgtgat tttaattct ggtgcccta ataataatga       600
     tcatgccgct ggacatgttt tacatcatgc cttaggtaaa accgattatc attatcaatt       660
     agaaatggcc aaaaatatta ctgctgctgc cgaagctatt tatactcctg aagaagcccc       720
     tgccaaaatt gatcatgtga ttaaaaacgc cttaagaaaa aaaaaccg tgtatttaga       780
     aattgcctgt aatattgctt ctatgcctta tgctgctcct gggcctgctt ctgctttatt       840
     taatgatgaa gcctctgatg aagctagttt aaatgctgcc gtggaagaaa ccttaaaatt       900
     tattgccaat cgcgataaag ttgccgtgtt agttggttct aaattaagag ctgctggtgc       960
     tgaagaagct gctgttaaat ttgctgatgc cttaggtggt gcagttgcta ctatggctgc      1020
     tgccaaatct tttttccg aagaaaatcc ccattatatt ggaactagtt ggggagaagt      1080
     ttcttatcct ggtgtggaaa aaactatgaa agaagcggac gctgttattg ctttagccc      1140
     tgtgtttaat gattattcta ccactggttg gactgatatt ccgatccca aaaaattagt      1200
     ttagccgaa cctcgttctg ttgttgttaa tggtcctcg ttccctctg tgatttaga      1260
     agattattta accgcttag cccaaaagt ttctaaaaaa actgctgcct tagatttttt      1320
     taaatctta aatgcgggtg aattaaaaaa agctgctcct gctgatcctt ctgtcctttt      1380
     agttaatgct gaaattgccc gtcagttga agcttatta acccctaata ctaccgttat      1440
     tgccgaaact gtgattctt ggtttaatgc ccacgcatg aaattacta atggtgcccg      1500
     tgttgaatat gaaatgcaat ggggtcatat tggttggtct gtacctgtg cttttggtta      1560
     tgctgttgg gctcctgaac gtggtaatat tttaatggtg ggtgatggtt cttttcaatt      1620
     aactgcccaa gaagttgccc aaatggttcg cttaaaatta ccgttatta tttttttaat      1680
     aaataattga ggttccgtga gattcatgat gggccatata ataatattaa      1740
     aaattgggat tatgcgggtt aatgaaagt gttaatggt aatggttgt atgattctgg      1800
     tgctggtaaa ggtttaaaag ccaaactgg tggtgaatta gctgaagcta ttaaagttgc      1860
     cttagccaat actgatggc caaccttaat tgaatgtttt attggtgcg aagattgtac      1920
     cgaagaatta gttaaatggg gtaaacgtgt tgctgctgct aattctcgca aacccgtgaa      1980
```

FIG. 31 (continued)

```
taaattattg taattttgg ggatcaattc gagctcagca agtttcatcc cgacccctc   2040
agggtcggga ttttttatt gtactagttg acataagtaa aggcatcccc tgcgtgatat   2100
aattaccttc agtttaagga ggtatacaca tatgattaaa gcctatgctg cottagaagc   2160
caatggtaaa ttacaaccct ttgaatatga tcctggtgct taggtgcca atgaagtgga   2220
aattgaagtg caatattgtg gtgtgtgtca ttctgattta tctatgatta ataatgaatg   2280
gggtatttct aattatccct tagttcctgg tcatgaagtt gttggtactg ttgctgctat   2340
gggtgaaggt gttaatcatg tggaagtggg tgatttagtt ggtttaggtt ggcattctgg   2400
ttattgtatg acctgtcatt cttgtttatc tggttatcat aatttatgtg ccactgccga   2460
atctactatt gtgggtcatt atggtggttt tggtgataga gttcgtgcta aaggtgtttc   2520
tgtggtgaaa ttaccaaaag gtattgattt agcctctgct gggccttat ttgtggtgg   2580
tattaccgtt ttttctccca tggtggaatt atctttaaaa cctaccgcca aagttgctgt   2640
tattggtatt ggtggtttag gtcatttagc cgttcaattt ttaagagcct gggttgtga   2700
agttactgct tttacctctt ctgccgtaa acaaaccgaa gttttagaat taggtgccca   2760
tcatatttta gattctacca atcctgaagc tattgcttct gccgaaggta aatttgatta   2820
tattatttct accgtgaatt taaaattaga ttggaattta tatatcagta ccttagcccc   2880
tcaaggtcat tttcattttg ttggtgtggt gttagaaccc ttggacttaa acttatttcc   2940
cttattaatg ggacaacgtt ctgtttctgc ttctcctgtt ggttctcctg ctactattgc   3000
cactatgtta gattttgccg tgctgtcatga tattaaaccc gtggtggaac aatttttctt   3060
tgatcaaatt aatgaagcca ttgcccattt agaatctggt aaagcccatt atcgcgtggt   3120
gttatctcat tctaaaaatt aataagatta acttctaaac tgaaacaaat ttgagggtag   3180
gcttcattgt ctgcccttat ttttttattt aggaaaagtg aacagactaa agagtgttgg   3240
ctctattgct ttgagtatgt aaattaggcg ttgctgaatt aagtatgat ttttgaccoc   3300
ttctctcttc tgcaggatca tcttgctgaa aaactcgagc gctcgttccg caaagcggta   3360
cggagttagt tagggctaa tgggcattct cccgtacagg aaagagttag aagttattaa   3420
ttatcaacaa ttctcctttg cctagtgcat cgttaccttt taattaaaa cataaggaaa   3480
actaataatc gtaataattt aacctcaaag tgtaaagaaa tgtgaaattc tgacttttat   3540
aacgttaaag agggaaaaat tagcagttta aaatacctag agaatagtct ggggtaagca   3600
tagagaatta gattagttaa gttaatcaaa ttcagaaaaa ataataatcg taaatagtta   3660
atctgggtgt atagaaaatg atcccttca tgataagatt taaactcgaa aagcaaaagc   3720
caaaaaacta acttccatta aaagaagttg ttacatataa cgctataaag aaaatttata   3780
tatttggagg ataccaacca tgtctcatat tcaacgtgaa actagttgtt ctgccctcg   3840
tttaaattct aatatggatg ccgatttata tggttataaa tgggctcgtg ataatgttgg   3900
tcaatctggt gctactattt atcgtttata tggtaaacct gatgctcctg aattattctt   3960
gaaacatggt aaaggttctg ttgctaatga tgttactgat gaaatggttc gtttaaactg   4020
gttgactgaa tttatgcctt tacctactat taaacatttt attcgtactc ccgatgatgc   4080
ttggttatta actactgcta ttcctggtaa aactgctttt caagtttag aagaatatcc   4140
tgattctggt gaaaatattg ttgatgcttt agctgttttt ttacgtcgtt tacattctat   4200
tcccgtttgt aattgtcctt ttaattctga tcgtgttttt cgtttagctc aagctcaatc   4260
tctgtatgaat aatggtttag ttgatgcttc tgattttgat gatgaacgta atggttggcc   4320
tgttgaacaa gtttgaaaag aaatgcacaa attgttacct ttttctcctg attctgttgt   4380
tactcatggt gatttttctt tagataattt gatctttgat gaaggtaaat tgattggttg   4440
tattgatgtt ggtcgtgttg gtattgctga tcgttatcaa gatttagcta ttttatggaa   4500
ttgtttaggt gaatttctc cttctttaca gaaacgttta tttcagaaat atggtattga   4560
taatcctgat atgaacaagt tacaatttca tttaatgttg gacgagttct tttaagaatt   4620
aattcatgac caaaatccct taacgtgagt tttcgttcca ctgagcgtca gacccctag   4680
aaaagatcaa aggatcttct tgagatcctt ttttttctgcg cgtaatctgc tgcttttaa   4740
attacgtaca cgtgttatta ctttgttaac gacaattgtc ttaattaact ggcctcatg   4800
ggccttccgc tcactgcccg ctttccagtc gggaaacctg tcgtgccagc tgcagatg   4860
acgttgaaaa cctctgacac atgcagctcc cggagacggt cacagcttgt ctgtaagcgg   4920
atgccgggag cagacaagcc cgtcaggcg cgtcagcggg tgttggcggg tgtcggggcg   4980
cagccatgac ccagtcacgt agcgatagcg gagtgtatac tggcttaact atgcggcatc   5040
agagcagatt gtactgagag tgcaccatat gcggtgtgaa ataccgcaca gatgcgtaag   5100
gagaaaatac cgcatcaggc gctcttccgc ttcctcgctc actgactcgc tgcgctcggt   5160
cgttcggctg cggcgagcgg tatcagctca ctcaaaggcg gtaatacggt tatccacaga   5220
atcaggggat aacgcaggaa agaacatgtg agcaaaaggc cagcaaaagg ccaggaaccg   5280
taaaaaggcc gcgttgctgg cgtttttcca taggctccgc cccctgacg agcatcacaa   5340
aaatcgacgc tcaagtcaga ggtggcgaaa cccgacagga ctataaagat accaggcgtt   5400
tccccctgga agctccctcg tgcgctctcc tgttccgacc ctgccgctta ccggatacct   5460
gtccgccttt ctcccttcgg gaagcgtggc gctttctcat agctcacgct gtaggtatct   5520
cagttcggtg taggtcgttc gctccaagct gggctgtgtg cacgaacccc cgttcagcc   5580
cgaccgctgc gccttatccg gtaactatcg tcttgagtcc aacccggtaa gacacgactt   5640
```

FIG. 31 (continued)

```
atcgccactg gcagcagcca ctggtaacag gattagcaga gcgaggtatg tagacggtgc    5700
tacagagttc ttgaagtggt ggcctaacta cggctacact agaaggacag tatttggtat    5760
ctgcgtctg ctgaagccag ttaccttcgg aaaaagagtt ggtagctctt gatccgcaa     5820
acaaaccacc gctggtagcg gtggttttt tgtttgcaag cagcagatta cgcgcagaaa    5880
aaaaggatct caagaagatc ctttgatctt ttctactgca gaagcttgtt agacaccctg    5940
tcatgtattt tatattattt atttcaccat acggattaag tgaacctaa tgaaaatagt     6000
actttcggag ctttaacttt aatgaaggta tgttttttta tagacatcga tgtctggttt    6060
aacaatagga aaagtagct aaactccca tgaattaaag aaataacaag gtgtctaaca      6120
acctgttatt aagaatgtta gaaaagactt aacatttgtg ttgagttttt atagacattg    6180
gtgtctagac atacggtaga taaggtttgc tcaaaataa ataaaaaaa gattggacta      6240
aaaacattt aatttagtac aatttaatta gttattttt cgtctcaaat tttgcttgt       6300
tgagcagaaa ttagataaa aaatcccg tgatcagatt acaatgtcgt tcattgtacg       6360
atgtgtcgaa aaatctttac gacactctaa actgaccaca cggggaaaa agaaaactga    6420
actaataaca tcatgatact cggaaaacct agcaattctc aacccctaaa caaaagaaac    6480
ttccaaaacc ctgaccatat aaaggagtgg caacaatcag caatcagtca agatttgata    6540
gcagaaaatc ttgtatcggt tgctaatggt ttgatgtac tatttatcgg caataaatac     6600
cgaactaaca cgggtgttct gtcacggcac atattaaact cctattctca tttagaagat    6660
ggtggttcgt atggtagaac atttgaccca tttaccaata agaaatgca gtgggttcaa     6720
ttaaaccga atagaccaag aaaaggttct actggtaagg taatcaaata tgaatcgcca     6780
aaaggtgaac ctacaagagt tctaatgccg tttgtgccta tgaaaatatg gcaacggatt    6840
agcgataagt tcggagtacc gattaatccg aaaaaagata ctcacttttg ggaattggta    6900
aagaataaca catcgataac gattgccatt acagaaggaa ataaaaagc taattgccta    6960
ttatcctatg gctatcctgc tattgccttt gtaggcattt ggaacggatt agagaaaata    7020
aatgatttct cgaaggaaaa gcagttaaaa gaggatttga aatggttgtt atccaacggc    7080
aacgaaata ttaatatcat ctttgaccaa gaccagaaac aaaaaactgt aattaatgta     7140
aacaaagcta tttcgctt atcttctcta ataagtagaa atggtcataa agttaatatt      7200
gtgcaatggt tgccgtcaaa aggtaaagga atagatgatt atttggtagc tttacctttt    7260
gagaaagag aaaatcattt agacaactta attaaaattg caccatcatt taattttgg     7320
tcaactaaat acttattcaa gtgtcgtaaa ccagatttaa ccgtaaattg ccgttattg    7380
agcgatgcag taaaagaatt acctcaagag gatatagcat taatagcacc tcacggcacg   7440
ggtaaaactt cattagtagc tactcacgtt aagaatcgga gttatcacgg aaggaaaact    7500
atttcattgg tgcatcttga aagtttagcc aaagctaatg gcaacgcact tggattatat    7560
taccgaaccg aaaataatat tgaaaagcaa tatcttggat ttagcttatg tgtagatagt    7620
tgccgtgata agattaacgg cattacaact gatattattt caggtcaaga ttattgcctt    7680
ttcattgatg aaattgacca agtaattcca cacatcctta acagtgaaac tgaagtaagt    7740
aagtatagat gcaccatcat tgacactttt tctgaactgg tgagaaatgc tgaacaggtc    7800
attattgctg atgctgattt atccgatgtg acgattgacc taatagaaaa catcagaggt    7860
aaaaactat atgtaatcaa gaatgaatat cagtatcagg gaatgacttt taacgccgtt    7920
ggttcaccat tagaaatgat ggcaatgatg ggaaaatcgg tgtcagaagg caagaaatta    7980
tttattaaca ccacatccca aaaggcaaaa agtaacatacg gcacaactgc tcttgagtct    8040
tatatttttg gtctaaataa agaagcaaag atattaagaa tagactctga aaccactaaa    8100
aacctgaac atccagccta taaatcatt gaccaagact aaaataatat cctcaaagat      8160
tatgattatg tcattgcctc accttgcctt caaacaggtg tcagtattac cttaaaaggg    8220
cattttgacc agcaatttaa cttttccagt ggaaacatta cacctcattg cttttacag     8280
caaatgtggc ggttgaggga tgcagaaatt gaaagattct attatgtgcc gaactcatct    8340
aacctcaatc tcattggaa taagtcaagt tcaccatcag accttctaaa gagcaataac    8400
aagatggcaa cggcaacggt taacctttg ggtagaatcg actccgaatc ttccctagag    8460
tatgaatcgc acggcatttg gcttgagacg tgggcaaaat tatcagcacg gcataacagt    8520
tcatgcgtt gttactctga aattcttacc tatctaatta cgtctcaagg gcataaatta    8580
aatatcaaca ttccctcacc tcttgcagat attaagaagc taaatgatga ggtaagtagt    8640
aacagggaaa aggtaaaaa tgagagatac tctcagaggt taaactcacc agatattaac    8700
gatgcagaag ctaccatact cgaatctaaa gagcaaaaa tcggattgac tctcaatgag   8760
agatgcaccc tagaaaagca taaagttaag aagcggtatg ggaatgtaaa gatggatatt    8820
ctcaccttg atgatgatgg actatacccc aaactcagac tatttatta cctcaccatc    8880
ggtaaacctc atctcaaggc taatgacaga aaagctattg ccaaatgggg caatgacaat    8940
aaaggcaaga ttctatcaaa agacttagtt aataaaactt actccgctcg tgtgaaggtc    9000
ttagagattc ttaaactaac tgactttatc gacaatctta gagatgaact cttaataact    9060
cccaataatc cagctatcac cgattttaat aatcttctgc taagagctaa gaaggattta    9120
agagtattag gagtcaaacat cggaatatat ccaatggcca acattaatgc cgtacttact   9180
ctcattggtc acaaacttc tgtgttatcaa gatgagttcg gaaagagaa aaggataaaa    9240
gtagatggta aatcatacg atgttatcaa cttgaaacat taccagattt taccaatgat    9300
```

FIG. 31 (continued)

```
actcttgact actggttaga aaatgatagc caaaaagaag taacagcaac agaaaattac    9360
tccgaaaatt ttaaccsttc aaatagctac aatccagaca gtaagacact ttcagagggt    9420
gcaaatttcc tatatataaa taaagaagaa ttgcatccaa ataasttgca cctagaaata    9480
aaagaaggtg ctgaactttt tttattcggg gtaaggtga ttgtgaaagg aatcttggac    9540
gggcagtaa ctatattctc tatgggtcaa gaatacgatt tatccctcaa tgaactagag    9600
gggatgttaa catcatgaac tttacaagaa tcttttttaaa gggcgatcgc accatgttaa    9660
atgatggtac atttgttcag atatttgata tttaccatga ccacgcattg ggagtgaccc    9720
ttgaccttaa gacagaaaaa attatttccg atgatgttag ggtaattact gtcaaagact    9780
tattgttcga tggcacttat aaaggggtaa aatcttttat gcccgataat gcccgataat    9840
gcccgattga tgctacaaaa tcccataatc ataagcgata atccctaat agcttgtaat    9900
tcttgaaccg tagcgatttt agagtattcc aaaaagaaga aataaacacc gcaaaatgtc    9960
gtatttcaca tatataaacc aaggttttt gccctaaaat ctttatgttt gtagtgtgat   10020
gttgggtcaa aatggtcaga aaagttgcaa ggttccatg gatgttattc cgcgcgaggg   10080
gtaagcatcc ccaaatagtt actttatcct agtcaatgcc catttattgc cgtcccgttc   10140
ggctttaaaa aagtgcaaa actcacaagg tgcaataaaa agttctgtac ctttcgcaac   10200
cctagataat ctttcaacag ttactttttt tcctattatc tggtacaaa gtttggctag   10260
tttctctttt ccctctttt caatcaagcc ttcttgtatg cccaactcat tgattaatct   10320
ctctatttt accattattt ccgttcagg tagtttatcc cctaaatctt catcggggg   10380
caatgtaggg cattctgaag gggcttttt ttctgtctgg acattatcta atattgaagt   10440
aaccaaacta tcttcagttt tttctattcc tattaattca tattcggtta ctgtatccgt   10500
atcaatatcc gaataactat ctttatccgt attagctatt cggttaagtt tatccgttaa   10560
ctcagaaaca agactatata gggttttag cttttcttct atcctgttat ctaatacgga   10620
taagtttata cggttatcat tatccgtatt agtatcattg ggctttttg gtagttctac   10680
ccctcataa acggctttta ttcccaattc caacagactg ataacagtat cctttataat   10740
gggttttttg ctgatatggt gaactttgc ccttccatc attgcgatac tttctatctc   10800
actcatcaac ttatcgctta agtgaatctc gtatctgttt aatccttac tggtttttatt  10860
catatccgtt tactttattc ggttaacaat tctattttat acgaataaaa tattatacgg   10920
ttaactttat acgtttaact attttatcta tacggataac agtaataagt tattcgtatt   10980
agttatacgt ttacttttat ccaaataaaa ttagtgcatt taaactaaaa gaatgatttt   11040
atcggagttg atagcattgg attaactaa agatgtttat aagctatatc tgataatat   11100
ttaaggttat tttgttattc tgtttattga cattatcaga ataaaagaat agaatataat   11160
tgttgagaga taagagggtt aagtgattat ggttaagaag ttagttggtt atgtcagggt   11220
cagtagtgaa tcgcaagagg ataacactag cttacagaat cagatagaga gaattgaagc   11280
atattgtatg gcttttggtt atgagttggt aaaaatattc aaagaggttg ccactggtac   11340
aaaagcagat attgaaaccc gtcctatttt taatgaagct atagaatact gaaacagga    11400
taatgctaat ggaattattg ccttgaagct agaccgaatc gcaggaatg ctttagatgt    11460
attgcgtttg gttcgtgaaa ccttagaacc acaaaataaa atgttagtgt tactagatat   11520
tcaggtagat actcgacac cttcaggaa aatgatttta actgtaatga gtgccgttgc    11580
tgaactcgaa agagacatga tctatgatcg cactcagggg ggtagaaga ctaaagccca    11640
aaagggcggg tatgcctacg ggaaacctaa attggctat aagctgaag aaaaggaact    11700
aaaagaagat tcagcacaac aggaaactat taaactaatt aagagacacc gtaggtcagg   11760
gaaaagctac cagaaaatag ctgattatct caatgcccaa agtattccca ctaaacaagg   11820
taagaaatgg agttctagcg tgtctatcg aatctgcag gaaaaagctg gttaagtctg    11880
tttatagata tttagaattt attgaataaa aatagtatga acaataaata tttatggact   11940
aaccacgtc ggaaacgttt aactgaacga tggaaataa aagaatcatg ggttattgat    12000
accatcgaaa atcctgaacg ttcagaattt ctcaggtatg agtcagggga aaatatcat   12060
tactctaaaa gaatagctaa gttcaagaat agagtgttag aagtgataac ttctgccaac   12120
tcaacagcca caagaataat aaccttttac tttaaccgta acatgaggaa aaatttatga   12180
ttgttactta cgataatgaa gttgacgcaa tttatttaa gttaacggaa aataaaattg   12240
atagcaccga acctcaaaca gacaggatta tcattgatta cgatgaaagt aataatattg   12300
ttggcattga ggtattagat tttaattatc ttgtcaagaa aggttaacc gttgctgatt   12360
taccttttc tgaagatgaa agattaacag cttctcaata ttttaatttt cctgttgcta   12420
tctaatcag aagggcaat aatcccttc tttcatcgag ttagcttaa tatcacaaaa   12480
gtcattttca ttttaccgtt tctttccac agcgtccgta cgccctcgt taaatctcaa   12540
aacgcacaat ttatgatgtt tataaaaagt tactcacttt aataagtatt tatactcatt   12600
aaagggttat tctttttttg tagcctgata ggttgggaag gaatattcca gattatcaga   12660
tttgttgaat atttttcgtc agatacgcaa acctacaaa cataattaac aactgaaact   12720
attgatatgt ctaggtttta gctctatcac aggttggatc tg                      12762
```

FIG. 31 (continued)

```
ID   #1630\\pABICyano1::corR-PcorT*1-zmPDC(opt1)_darA-Prbc*(optRBS)-synADH(opt1)_ter
standard; circular DNA;    ; 13726 BP.
CC   This file is created by Vector NTI
CC   http://www.invitrogen.com/
CC   VNTDATE|645469723|
CC   VNTDBDATE|645469723|
CC   LSOWNER|
CC   VNTAUTHORNAME|Ulf Duehring|
FH   Key             Location/Qualifiers
FH
FT   insertion_seq   2981..3026
FT                   /vntifkey="14"
FT                   /label=darA
FT                   /note="dsr terminator from E.coli"
FT   gene            3096..4106
FT                   /vntifkey="60"
FT                   /note="ADH"
FT   CDS             3096..4103
FT                   /vntifkey="4"
FT                   /label=synADH(opt1)
FT   terminator      4107..4262
FT                   /vntifkey="43"
FT                   /label=TrbcSABICyano1
FT   promoter        4293..4762
FT                   /vntifkey="30"
FT                   /label=PrbcABICyano1
FT   CDS             4764..5579
FT                   /vntifkey="4"
FT                   /label=Km**
FT                   /note="Km**"
FT   CDS             13141..13389
FT                   /vntifkey="4"
FT                   /label=ORF\6
FT                   /note="orf6"
FT   CDS             12881..13144
FT                   /vntifkey="4"
FT                   /label=ORF\5
FT                   /note="orf5"
FT   CDS             12153..12839
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11063..11827)
FT                   /vntifkey="4"
FT                   /label=ORF\3
FT                   /note="orf3"
FT   CDS             10618..10803
FT                   /vntifkey="4"
FT                   /label=ORF\2
FT                   /note="orf2"
FT   rep_origin      complement(9918..9935)
FT                   /vntifkey="33"
FT                   /label=Rep_Origin_1
FT                   /note="potential rep origin; match pNostoc (Acc# M81381) nick
site (358-375); on reverse strand"
FT   misc_feature    10178..10211
FT                   /vntifkey="21"
FT                   /label=Rep\motif
FT                   /note="Rep protein active site motig EKXKYXVKKXD"
FT   CDS             7397..10562
```

FIG. 33

```
FT                      /vntifkey="4"
FT                      /label=ORF\1
FT                      /note="orf1 rep ori binding protein alr7037 homolog Similar to
hypothetical protein alr7037 of plasmid pSYSA (103 kb) of Synechocystis sp. PCC 6803"
FT      primer_bind     complement(6186..6216)
FT                      /vntifkey="28"
FT                      /label=Bom-F
FT      primer_bind     5867..5898
FT                      /vntifkey="28"
FT                      /label=Bom-R
FT      rep_origin      complement(5822..6880)
FT                      /vntifkey="33"
FT                      /label=OriVT
FT      promoter        3027..3095
FT                      /vntifkey="30"
FT                      /label=PrbcL*(optRBS)
FT                      /note="improved version of rbcL promoter from PCC6803"
FT      CDS             complement(54..1166)
FT                      /vntifkey="4"
FT                      /label=corR
FT      promoter        1168..1247
FT                      /vntifkey="30"
FT                      /label=PcorT*1
FT                      /note="improved version of corT promoter from PCC6803"
FT      CDS             1248..2954
FT                      /vntifkey="4"
FT                      /label=zmPDC(opt1)
SQ      Sequence 13726 BP; 4163 A; 2504 C; 2756 G; 4306 t;
        tcgaccatgc gtccaaaact ttcaccatcc tttccctatc aacctttact gcactaaaga      60
        caagtgagat agcagtggca atctggcttt gcaatcaatg tttccactaa agcgtttagc     120
        gttactgcgg ctagaagtcc tccaccgagg ctcccctgaa tggtgatatg gggaatgcgg     180
        ctgtcatca gtcgtcgttt tgccccggca gcatgactaa aacgatcgg cattccgatc     240
        acaagagccg gctgaatatg ttgttgctct atcagcttac agcagtgag taaaacagaa      300
        ggggcatagc cgatcgccag cacacatcct tggggaatct gttgtaaccg ctgttgccaa     360
        tggtcatggt gccaaaaagc ttgctcggct tcctaagcc ctgtgatgtg agggtcgtcc      420
        atcagcgttt taaccgtaca tcctaaatga gctaaccgag tttgatcaag agccgcagcc     480
        acaaccggaa catcggtgac gactgcgacac cctgctttca gtgcatctcg tgccgaggcg     540
        atcgctccct gactcaatcg aacggcgttt accaagcgaa catcaccacc ggcgcagcct     600
        aattgatgta gtaagtgaat ggtaattca gagtaagccc ataaatcggg tagcaggtgt      660
        ttgagggatt cctgaaaggc ttctggatga gttgttgtct ccgcatctag gttcgtcaac     720
        aactgatcga gttttcctaa ccctcctgg acatccacat caagctgttt cagttgggcc     780
        agagcttccg cttgggtaat ctgcaaactc tggtcgcgtc ccagtaatcc ttctaaagca     840
        gatgcggttt ggcggagtcg agtaatctgc tgaatcacag cctgatattg ctgttgcaac     900
        tgcaccatta gggtgggatc aaggctctct tcagaatgac tatccgcag ttgccgaata      960
        tgagacaact gaaagccctg ctgtttgagg gcaatgactc gttggagcg ttgtacgtcc     1020
        tgctgagtat aacgcggta gttgccctct gagcgttgaa cggggggaag caatccgagg     1080
        gtgtggtaat ggcgcaccat cgcgaggcgta acgccacctc ccatgcatc tgtgaagttct     1140
        ttaatcgtta agtgattagt cttcatgact ttagtttact caaaacctg acattgacac     1200
        taatgttaag gttaggcgtc agaaggtaaa aatcgaggat aaaagcatg aattcttata     1260
        ccgttgggtac ttattcagcc gaacgcttag tgcaaattgg tttaaaacat cattttgcg     1320
        tggctgggga ctataattta gtgttattgg ataacttatt attaaataaa aacatgaaac     1380
        aagtgtactg ttgtaatgaa ttaaattgtg gttttctgc tgaaggttat gctagagcta     1440
        aaggtgcagc tgctgctgtt gttacttatt ctgtgggtgc tttatctgct tttgatgcta     1500
        ttggtggtgc ttatgccgaa aatttacccg tgattttaat ttctgtgcc cctaataata     1560
        atgatcatgc cgctggacat gttttacatc atgccttagg taaaaccgat tatcattatc     1620
        aattagaaat ggccaaaaat attactgtg ctgccgaagc tatttatact cctgaagaag     1680
        cccctgccaa aattgatcat gtgattaaaa ccgaataaaa ccggtgtatt                1740
        tagaaattgc ctgtaatatt gcttctatgc cttgtctgc tcctgggcct gcttctgctt     1800
        tatttaatga tgaagcctct gatgaagcta gtttaaatgc tgccgtgaa gaaaccttaa      1860
        aatttattgc caatcgcgat aaagttgccg tgttagttgg ttctaaatta agagctgctg     1920
```

FIG. 33 (continued)

```
gtgctgaaga agctgctgtt aaatttgctg atgctttagg tggtgcagtt gctactatgg    1980
ctgctgccaa atcttttttt ccgaagaaa atcccatta tattggaact agttgggag      2040
aagtttctta tcctggtgtg gaaaaaacta tgaagaagc cgacgctgtt attgctttag   2100
ccctgtgtt taatgattat tctaccactg gttggactga tattcccgat cccaaaaaat  2160
tagttttagc cgaacctcgt tctgttgttg ttaatggtgt tgctttccc tctgtgcatt   2220
taaaagatta tttaaccgc ttagcccaaa aagtttctaa aaaaactggt gccttagatt    2280
tttttaaatc tttaaatgcg ggtgaattaa aaaagctgc tcctgctgat ccttctgctc    2340
ctttagttaa tgctgaaatt gcccgtcaag ttgaacccct attaacccct aatactaccg   2400
ttattgccga aactggtgat tcttggttta tgccaacg catgaaatta cctaatggtg    2460
cccgtgttga atatgaaatg caatggggtc atattggttg gtctgtaccct gctgcttttg   2520
gttatgctgt tggtgctcct gaacgtcgta atattttaat ggtgggtgat ggttcttttc    2580
aattaactgc ccaagaagtt gcccaaatgg ttcgttaaa attacccgtt attattttt    2640
taataaataa ttatggttat accattgaag tgatgattca tgatgggcca tataataata    2700
ttaaaaattg ggattatgcg ggtttaatgg aagtgtttaa tgtaatggt ggttatgatt     2760
ctggtgctgg taaaggttta aaagccaaaa ctggtggtga attagctgaa gctattaaag    2820
ttgccttagc caatactgat gggccaacct taattgaatg ttttattggt cgcgaagatt    2880
gtaccgaaga attagttaaa tggggtaaac gtgttgctgc tgctaattct cgcaaacccg    2940
tgaataaatt attgtaattt tggggatca attcgagctc agcaagtttc atcccgaccc    3000
cctcagggtc gggattttt tattgtacta gttgacataa gtaaggcat ccctgcgtg     3060
atataattac cttcagttta aggaggtata cacatatgat taaagcctat gctgccttag   3120
aagccaatgg taaattacaa ccctttgaat atgatcctgg tgctttaggt gccaatgaag    3180
tggaaattga agtgcaatat tgtggtgtgt gtcattctga tttatctatg attaataatg    3240
aatggggtat ttctaattat cccttagttc ctggtcatga agttgttggt actgttgctg    3300
ctatgggtga aggtgttaat catgtggaag tgggtgattt agttggttta ggttggcatt    3360
ctggttattg tatgacctgt cattctgtt tatctggtta tcataattta tgtgccactg    3420
ccgaatctca tattgtgggt cattatggtg ttttggtga tagagttcgt gctaaaggtg    3480
tttctgtggt gaaattaccc aaaggtattg atttagcctc tgctggcct ttattttgtg    3540
gtggtattac cgtttttttct cccatggtgg aattatcttt aaaacctacc gccaaagttg    3600
ctgttattgg tattggtggt ttaggtcatt tagccgttca attttaaga gctggggtt     3660
gtgaagttac tgcttttacc tcttctgccc gtaaacaaac cgaagtttta gaattaggtg    3720
cccatcatat tttagattct accaatcctg aagctattgc ttctgccgaa ggtaaattg    3780
attatattat ttctaccgtg aatttaaaat tagattggaa tttatatatc agtaccttag    3840
ccctcaagg tcattttcat tttgttggtg tggtgttaga acccttggac ttaaacttat    3900
ttcccttatt aatgggacaa cgttctgttt ctgcttctcc tgttggttct cctgctacta    3960
ttgccactat gttagatttt gccgtgcgtc atgatattaa accgtggtg gaacaatttt     4020
cttttgatca aattaatgaa gccattgccc atttagaatc tggtaaagcc cattatcgcg   4080
tggtgttatc tcattctaaa aattaataag attaacttct aaactgaaac aaatttgagg    4140
gtaggcttca ttgtctgccc ttatttttt atttaggaaa agtgaacaga ctaaagagtg    4200
ttggctctat tgctttgagt atgtaaatta ggcgttgctg aattaaggta tgattttga    4260
cccttctct cttctgcagg atcatcttgc tgaaaactc gagcgctgt tccgcaaagc     4320
ggtacggagt tagttagggg ctaatgggca ttctcccgta caggaaagag ttagaagtta    4380
ttaattatca acaattctcc tttgctagt gcatgttac cttttaatt aaaacataag   4440
gaaactaat aatcgtaata atttaaccct aaagtgtaaa gaaatgtgaa attctgactt    4500
ttataaggga aaatagcag ttaaaaata ctagaagaata gtctgggta                4560
agcatagaga attagattag ttaagttaat caaattcaga aaaaataata atcgtaaata   4620
gttaatctgg gtgtatagaa aatgatcccc ttcatgataa gattttaaact cgaaaagcaa   4680
aagccaaaa actaacttcc attaaaagaa gttgttacat ataacgctat aaagaaaatt    4740
tatatatttg gaggtatcca accatgtctc atattcaacg tgaaactagt tgttctcgcc    4800
ctcgtttaaa ttctaatatg gatgccgatt tatatggtta taatgggct cgtgataatgt   4860
ttggtcaatc tggtgctact atttatcgtt tatatggtaa acctgatgct cctgaattat    4920
tcttgaaaca tggtaaaggt tctgttgcta atgatgttac tgatgaaatg gttcgtttaa    4980
actggttgac tgaatttatg cctttaaccta ctattaaaca ttttattcgt actcccgatg    5040
atgcttggtt attaactact gctattcctg gtaaactgg ttttcaagtt ttagaagaat    5100
atcctgattc tggtgaaaat attgttgatg ctttagctgt ttttttacgt cgtttacatt    5160
ctattcccgt ttgtaattgt ccttttaatt ctgatcgtgt tttcgtta gtcaagctc    5220
aatctcgtat gaataatggt ttagttgatg cttctgattt tgatgatgaa cgtaatgtt   5280
ggcctgttga acaagtttgg aaagaaatgc acaaattgtt acctttttct cctgattctg    5340
ttgttactca tggtgatttt tctttagata atttgatctt tgatgaaggt aaattgattg    5400
gttgtattga tgttggtcgt gttggtattg ctgatcgtta tcaagattta gctattttat    5460
ggaattgttt aggtgaattt tctccttcct tacagaaacg tttatttcag aaatatggta    5520
```

FIG. 33 (continued)

```
ttgataatcc tgatatgaac aagttacaat ttcatttaat gttggacgag ttcttttaag    5580
aattaattca tgaccaaaat cccttaacgt gagttttcgt tccactgagc gtcagacccc    5640
gtagaaaaga tcaaaggatc ttcttgagat cctttttttc tgcgcgtaat ctgctgctat    5700
ttaaattacg tacacgtgtt attactttgt taacgacaat tgtcttaatt aactgggcct    5760
catgggcctt ccgctcactg ccgctttcc agtcgggaaa cctgtcgtgc cagctctgca    5820
gatgcggtg aaaacctctg acacatgcay ctcccggaaa cggtcacagc ttgtctgtaa    5880
gcggatgccg ggagcagaca gccgtcag ggcggtcag cgggtgttgg cgggtgtcgg    5940
ggcgcagcca tgacccagtc acgtagcgat agcggagtgt atactggctt aactatgcgg    6000
catcagagca gattgtactg agagtgcacc atatgcggtg tgaaataccg cacagatgcg    6060
taaggagaaa ataccgcatc aggcgctctt ccgcttcctc gtcactgac tcgctgcgct    6120
cggtcgttcg gctgcggcga gcggtatcag ctcactcaaa ggcggtaata cggttatcca    6180
cagaatcagg ggataaagca ggaaagaaca tgtgagcaaa aggccagcaa aaggccagga    6240
accgtaaaaa ggccgcgttg ctggcgtttt tccataggct ccgccccct gacgagcatc    6300
acaaaaatcg acgctcaagt cagaggtggc gaaacccgac aggactataa agataccagg    6360
cgtttccccc tggaagctcc ctcgtgcgct ctcctgttcc gaccctgccg cttaccggat    6420
acctgtccgc ctttctccct tgggaagcg tggcgcttc tcatagctca cgctgtaggt    6480
atctcagttc ggtgtaggtc gttcgctcca agctgggctg tgtgcacgaa ccccccgttc    6540
agcccgaccg ctgcgcctta tccggtaact atcgtcttga gtccaacccg gtaagacacg    6600
acttatcgcc actggcagca gccactggta acaggattag cagagcgagg tatgtaggcg    6660
gtgctacaga gttcttgaag tggtggccta actacggcta cactagaagg acagtatttg    6720
gtatctgcgc tctgctgaag ccagttacct tcggaaaaag agttggtagc tcttgatccg    6780
gcaaacaaac caccgctgt agcggtggtt ttttgtttg caagcagcag attacgcgca    6840
gaaaaaagg atctcaagaa gatcctttga tcttttctac tgcagagcgt tgttagacac    6900
cctgtcatgt attttatatt atttatttca ccatacggat taagtgaaac ctaatgaaaa    6960
tagtactttc ggagctttaa ctttaatgaa ggtatgtttt tttatagaca tcgatgtctg    7020
gttaacaat aggaaaaagt agctaaaact cccatgaatt aaagaaataa caaggtgtct    7080
aacaacctgt tattaagaat gttagaaaag acttaacatt tgtgttgagt tttatagac    7140
attggtgtct agacatacgg tagataagt ttgctcaaaa ataaaataaa aaaagattgg    7200
actaaaaaac atttaattta gtacaattta attagttatt ttttcgtctc aaattttgct    7260
ttgttgagca gaaatttaga taaaaaaatc cccgtgatca gattacaatg tcgttcattg    7320
tacgatgtgt cgaaaatct ttacgacact ctaaactgac cacacggggg aaaaagaaaa    7380
ctgaactaat aacatcatga tactcggaaa aactagcaat tctcaacccc taaacaaaag    7440
aaacttccaa aaccctgacc atataaagga gtggcaacaa tcagcaatca gtcaagattt    7500
gatagcagaa aatcttgtat cggttgctaa tggttttgat gtactattta tcggcaataa    7560
ataccgaact aacacgggtg ttctgtcacg gcacatatta aactcctatt ctcatttaga    7620
agatggtggt tcgtatggta gaacatttga cccatttacc aataaagaaa tgcagtgggt    7680
tcaatttaaa ccgaatagac caagaaaagg ttctactggt aaggtaatca aatatgaatc    7740
gccaaaaggt gaacctacaa gagttctaat gccgtttgtg cctatgaaaa tatggcaacg    7800
gattagcgat aagttcggag tacgattaa tccgaaaaaa gatactcact tttgggaatg    7860
ggtaaagaat aatccatcga taccgattgc cattacagaa ggaaataaaa aagctaattg    7920
cctattatcc tatggctatc ctgctattgc ctttgtaggc atttggaacg gattagagaa    7980
aataaatgat ttctcgaagg aaaagcagtt aaaagaggat ttgaaatggt tgttatccaa    8040
cggcaaccga atattaata tcatctttga ccaagaccag aaacaaaaaa ctgtaattaa    8100
tgtaaacaaa gctatttcg ctttatcttc tctaataagt agaaatggtc ataaagttaa    8160
tattgtgcaa tggttgccgt caaaaggtaa aggaatagat gattatttgg tagctttacc    8220
ttttgagaaa agagaaatc atttagacaa cttaattaaa attgcaccat catttaattt    8280
ttggtcaact aaatacttat tcaagtgtcg taaaccagat ttaaccgtaa attgccgtta    8340
tttgagcgat gcagtaaaag aattacctca agaggatata gcattaatag caactcacgg    8400
cacgggtaaa acttcattag tagctactca cgttaagaat cggagttatc acggaaggaa    8460
aactatttca ttggtgcatc ttgaaagttt agccaaagct aatggcaacg cacttggatt    8520
atattaccga accgaaaata atattgaaaa gcaatatctt ggatttagct tatgtgtaga    8580
tagttgccgt gataagatta acggcattac aactgatatt atttcaggtc aagattattg    8640
ccttttcatt gatgaaattg accaagtaat tccacacatc cttaacagtg aaactgaagt    8700
aagtaagtat agatgcacca tcattgacac ttttctgaa ctggtgagaa atgctgaaca    8760
ggtcattatt gctgatgctg atttatccga tgtgacgatt gacctaatag aaaacatcag    8820
aagtgaaaaa ctatatgtaa tcaagaatga atatcagtat caggatga cttttaacgc    8880
cgttgttca ccattgaaaa tgtggcaat gatgggaaaa tcggtgtcag aaggcagaa    8940
attatttatt aacaccacat ccaaaggc aaaagtaag tacggcacaa tcgtcttga    9000
gtcttatatt tttggtctaa ataaagaagc aaagatatta agaatagact ctgaaaccac    9060
```

FIG. 33 (continued)

```
taaaaaccct gaacatccag cctataaaat cattgaccaa gacttaaata atatcctcaa    9120
agattatgat tatgtcattg cctcaccttg ccttcaaaca ggtgtcagta ttaccttaaa    9180
agggcttttt gaccagcaat ttaactttc cagtggaaac attacaccto attgcttttt    9240
acagcaaatg tggcggttga gggatgcaga aattgaaaga ttctattatg tgccgaacto    9300
atctaacctc aatctcattg aagtcaacc tcagccttc taaagagcaa    9360
taacaagatg gcaacggcaa cggttaacct tttgggtaga atgactccg aatattcct    9420
agagtatgaa tcgcacggca tttggcttga gacgtgggca aaattatcag cacggcataa    9480
cagttcaatg cgttgttact ctgaaattct tacctatcta attacgtctc aagggcataa    9540
attaaatatc aacattccct cacctcttgc agatattaag aagctaaatg atgaggtaag    9600
tagtaacagg gaaaaggtaa aaaatgagag atactctcag aggttaaact caccagatat    9660
taacgatgca gaagctacca tactcgaatc taaagagcaa aaaatggat tgactctcaa    9720
tgagagatgc acctagaaa agcataaagt taagaagcgg tatgggaatg taaagatgga    9780
tattctcacc tttgatgatg atggactata ccccaaactc agactatttt attacctcac    9840
catcggtaaa cctcatctca aggctaatga cagaaaagct attgccaaaa tgggcaatga    9900
caataaaggc aagattctat caaagactt agttaataaa acttactccg ctcgtgtgaa    9960
ggtcttagag attcttaaac taactgactt tatcgacaat cttagagatg aactcttaat   10020
aactcccaat aatccagcta tcaccgattt taataatctt ctgctaagag ctaagaagga   10080
tttaagagta ttaggagtca acatcggaaa atatccaatg gccaacatta atgccgtact   10140
tactctcatt ggtcacaaac tttctgtaat gagagatgag ttcggaaaag agaaaaggat   10200
aaaagtagat ggtaaatcat accgatgtta tcaacttgaa acattaccag attttaccaa   10260
tgatactctt gactactggt tagaaatga tagccaatcca gaagtacag caacagaaaa   10320
ttactccgaa aatttcaacc cttcaatag ctacaatcca gacagtaaga cactttcaga   10380
gggtgcaaat ttcctatata taaataaaga agaattgcat ccaaataaat tgcacctaga   10440
aataaaagaa ggtgctgaac tttttttatt cgggtaaag gtgattgtga aaggaatctt   10500
ggacggggca gtactatat tctctatggg tcaagaatac gatttatccc tcaatgaact   10560
agaggggatg ttaacatcat gaactttaca agaatctttt taaaggcga tgcaccatg   10620
ttaaatgatg gtacatttgt tcagatattt gatatttacc atgaccaagc attgggagtg   10680
acccttgacc ttaagacaga aaaaattatt tccgatgatg ttagggtaat tactgtcaaa   10740
gacttattgt tcgatggcac ttataaaggg gtaaaatctt ttatgcccga taatgcccga   10800
taatgcccga ttgatgctac aaaatccat aatcataagc gataatcccc taatagcttg   10860
taattcttga acagtagcga ttttagagta ttcaaaaag aagaaataaa caccgcaaaa   10920
tgtcgtattt caacatatata aaccaaggtt ttttgccta aaatctttat gtttgtagtg   10980
tgatgttggg tcaaaatggt cagaaaagtt gcaaggtttt tatggatgct tacgcgcgcg   11040
agggtaagc atccccaaat agttacttta tcctagtcca tgcccattta ttgccgtccc   11100
gttcggcttt aaaaaagtgc caaaactcac aaggtgcaat aaaaagttct gtacctttcg   11160
caacccctaga taatctttca acagttactt ttttcctat tatctggta caaagtttgg   11220
ctagtttctc ttttccctct tttcaatca agcttcttg tatgccaac tcattgatta   11280
atctctctat ttttaccatt atttcccgtt caggtagttt atccctaaa tcttcatcgg   11340
gggcaatgt agggcattct gaaggggctt tttcttctgt ctggacatta tctaatattg   11400
aagtaaccaa actatcttca gttttttcta ttcctattaa ttcatatcc gttactgtat   11460
ccgtatcaat atccgaataa ctatctttat ccgtattagc tattcggtta agtttatccg   11520
ttaactcaga aacaagacta tatagcggtt ttagcttttc ttctatcctg ttatctaata   11580
cggataagtt tatccggtta tcattatccg tattagtatc attgggcttt tttggtagtt   11640
ctaccccctc ataaaccgct ttattccca attcaacag actgataaca gtatcctta    11700
taatgggttt tttgctgata tggtgaactt ttgcccttc catcattgcg atactttcta   11760
tctcactcat caacttatcg cttaagtgaa tctcgtatct gtttaatccc ttactggttt   11820
tattccatatc cgttactttt attcggttaa caattctatt ttatacgaat aaaatattct   11880
acggttaact ttatacgttt aactattta tctatacgga taacagtaat aagttattcg   11940
tattagttat acgtttactt ttatccaaat aaaattagtg catttaaact aaaagaatga   12000
ttttatcgga gttgatagca ttggattaac ctaaagatgt ttataagcta tatctgataa   12060
gtatttaagg ttattttgtt attctgttta ttgacattat cagaataaaa gaatagaata   12120
taattgttga gagataagag gtttaagtga ttatggttaa gaagttagtt ggttatgtca   12180
gggtcagtag tgaatcgcaa gaggataaca ctagcttaca gatcagata gagagaattg   12240
aagcatattg tatggctttt ggttatgagt tggaaaaat attcaaagag gttgcactg    12300
gtacaaaagc agatattgaa accgtccta tttttaatga agctatagaa tacttgaaac   12360
aggatattgc taatggaatt attgccttga agctagaccg aatgcacgg aatgctttag   12420
atgtattgcg tttggttcgt gaaaccttag aaccaataaa taagttgag tgttactag   12480
atattcaggt agatacttcg acacccttag caaaatgat tttaactgta atgagtccg   12540
ttgctgaact cgaaactgag actgatctatg atcgcactca gggggtaga aagactccg   12600
cccaaaaggg cgggtatgcc tacgggaaac ctaaatttgg ctataagact gaagaaaagg   12660
aactaaaaga agattcagca caacaggaaa ctattaaact aattaagaga caccgtaggt   12720
```

FIG. 33 (continued)

```
cagggaaaag ctaccagaaa atagctgatt atctcaatgc ccaaagtatt cccactaaac  12780
aaggtaagaa atggagttct agcgtcgtct atcgaatctg tcaggaaaaa gctggttaag  12840
tctgtttata gatatttaga atttattgaa taaaaatagt atgaacaata aatatttatg  12900
gactaaccac gctcggaaac gtttaactga acgatgggaa ataaaagaat catgggttat  12960
tgataccatc gaaaatcctg aacgttcaga atttattgtt gatgagtcag gggaaaaata  13020
tcattactat aaaagaatag ctaagtttaa gaatagagtg ttagaagtga taacttctgc  13080
caactcaaca cccacaagaa taataacctt ttactttaac cgtaacatga ggaaaaattt  13140
atgattgtta cttacgataa tgaagttgac gcaatttatt ttaagttaac ggaaaataaa  13200
attgatagca ccgaacctca aacagacagg attatcattg attacgatga aagtaataat  13260
attgttggca ttgaggtatt agattttaat tatcttgtca agaaaggttt aacgttgct   13320
gatttacctt ttctgaaga tgaagatta acagcttctc aatattttaa ttttcctgtt  13380
gctatctaat ccagaagggg caataatccc cttctttcat cgagttagac ttaatatcac  13440
aaaagtcatt ttcatttac cgtttctttt ccacagcgtc cgtacgcccc tgttaaatc   13500
tcaaaaccga caatttatga tgtttataaa aagttactca ctttaataag tatttatact  13560
cattaaaggg ttattctttt tttgtagcct gataggttgg gaaggaatat ttcagattat  13620
cagatttgtt gaatattttt cgtcagatac gcaaacctta caaacataat taacaactga  13680
aactatcgat atgtctaggt tttagctcta tcacaggttg gatctg                13726
```

FIG. 33 (continued)

```
ID    #1631\\pABICyano1::corR-PcorT*2-zmPDC(opt1)_dsrA-Prbc*(optRBS)-synADH(opt1)_ter
standard; circular DNA;    ; 13726 BP.
CC    This file is created by Vector NTI
CC    http://www.invitrogen.com/
CC    VNTDATE|645470812|
CC    VNTDBDATE|645470812|
CC    LSOWNER|
CC    VNTAUTHORNAME|Ulf Duehring|
FH    Key              Location/Qualifiers
FH
FT    insertion_seq    2981..3026
FT                     /vntifkey="14"
FT                     /label=dsrA
FT                     /note="dsrA terminator from E.coli"
FT    gene             3096..4106
FT                     /vntifkey="60"
FT                     /note="ADH"
FT    CDS              3096..4103
FT                     /vntifkey="4"
FT                     /label=synADH(opt1)
FT    terminator       4107..4262
FT                     /vntifkey="43"
FT                     /label=TrbcSABICyano1
FT    promoter         4299..4762
FT                     /vntifkey="30"
FT                     /label=PrbcABICyano1
FT    CDS              4764..5579
FT                     /vntifkey="4"
FT                     /label=Km**
FT                     /note="Km**"
FT    CDS              13141..13389
FT                     /vntifkey="4"
FT                     /label=ORF\6
FT                     /note="orf6"
FT    CDS              12881..13144
FT                     /vntifkey="4"
FT                     /label=ORF\5
FT                     /note="orf5"
FT    CDS              10153..12839
FT                     /vntifkey="4"
FT                     /label=ORF\4
FT                     /note="orf4 Integrase/Recombinase Similar to Site-specific
recombinase of Bacillus thuringiensis serovar israelensis ATCC 35646"
FT    CDS              complement(11963..11827)
FT                     /vntifkey="4"
FT                     /label=ORF\3
FT                     /note="orf3"
FT    CDS              10618..10803
FT                     /vntifkey="4"
FT                     /label=ORF\2
FT                     /note="orf2"
FT    rep_origin       complement(9918..9935)
FT                     /vntifkey="33"
FT                     /label=Rep_Origin_1
FT                     /note="potential rep origin; match pNostoc (Acc# M81381) nick
site (358-375); on reverse strand"
FT    misc_feature     10178..10211
FT                     /vntifkey="21"
FT                     /label=Rep\motif
FT                     /note="Rep protein active site motif EXKKIXVKKXO"
FT    CDS              7397..10582
```

FIG. 35

```
FT                      /vntifkey="4"
FT                      /label=ORF\1
FT                      /note="orf1  rep ori binding protein slr7037 homolog Similar to
hypothetical protein slr7037 of plasmid pSYSA (103 kb)  of Synechocystis sp. PCC 6803"
FT       primer_bind    complement(6185..6216)
FT                      /vntifkey="28"
FT                      /label=Bom-F
FT       primer_bind    5867..5898
FT                      /vntifkey="28"
FT                      /label=Bom-R
FT       rep_origin     complement(5822..6880)
FT                      /vntifkey="33"
FT                      /label=OriVT
FT       promoter       3027..3095
FT                      /vntifkey="30"
FT                      /label=PrbcL*(optRBS)
FT                      /note="improved version of rbcL promoter from PCC6803"
FT       CDS            complement(54..1166)
FT                      /vntifkey="4"
FT                      /label=corR
FT       promoter       1169..1247
FT                      /vntifkey="30"
FT                      /label=PcorT*2
FT                      /note="improved version of corT promoter from PCC6803"
FT       CDS            1248..2954
FT                      /vntifkey="4"
FT                      /label=zmPDC(opt1)
SQ       Sequence 13726 BP; 4162 A; 2504 C; 2753 G; 4307 t;
         tcgaccatgc gtccaaaact ttcaccatcc tttcctatc aacctttact gcactaaaga        60
         caagtgagat agcagtggca atctggcttt gcaatcaatg tttccactaa agcgtttagc       120
         gttactgcgg ctagaagtcc tccaccgagg ctccctgaa tggtgtatatg gggaatggga       180
         ctgtcatca gtcgtcgttt tgcccccgga catgactaa aaccgatcgg cattccgatc         240
         acaagagccg gctgaatatg ttgttgctct atcagcttac aggcagtgag taaaacagaa       300
         gggcatagc cgatcgcag cacacatcct tgggaatct gttgtaaccg ctgttgcaa           360
         tggtcatggt gccaaaaagc ttgtcaggct tccctaagcc ctgtgatgtg agggtcgtca       420
         atcagcgttt taacgtaca tcctasatga gctaaccgaa tttgatcaag agccgcagcc        480
         acaaccggaa catcggtgac gactggacac cctgcttca gtgcatctcg tgccgaggcg       540
         atggtcct gactcaatgc aacggcgttt accagctaa catcaccaca ggcagcact            600
         aattgatgta atagtgaat ggtaattca gagtaagccg ataaatccg tagcagtgt           660
         ttgagggatt cctgaaaggc ttctggatga gttgttgtct ccgcatctag gttcgtccac       720
         aactgatcga gttttcctaa ccctcctgg acatccacat caagctgttt cagttgggcc       780
         agagcttccg cttggctaat ctgccaactc tgttcgcgtc ccagtaatcc ttctaaagca       840
         gatgcggttt ggcggagtcg agtaatctgc tgaatcacag cctgatattg ctgttgcaac       900
         tgcaccatta gggtgggatc aaggctctct tcagaatgc tatccagcag ttgccgaata        960
         tgaagacaact gaaagcccctg ctgtttgagg gcaatgactc gttggagccg ttgtacgtcc    1020
         tgctgagtat aaagcggta gttgccctct gagcgttgaa cggggggaag caatcccagg       1080
         gtgtggtaat ggcgcaccat gtgaggcgta acgccacctc ccactgcatc tgtgagttct     1140
         ttaatcgtta agtgattagt cttcatgact ttagttact caaaaccttg acattgacc         1200
         taatgttaag gtttagaatg agaaggtaaa aatccaagtt aaaagcatg aattcttata        1260
         ccgtgggtac ttatttagcc gaaacgcttag tgcaaattgg tttaaaacat cattttgccg     1320
         tggctgggga ctataattta gtgttattgg ataacttatc attaaataaa aacatggaac      1380
         aagtgtattg ttgtaatgaa ttaaattgtt gttttctgc tgaaggtta gctagagcta         1440
         aagtgcagc tgctgctgtt gttacttatt ctgtgggtac tttatctgct tttgatgcta       1500
         ttggtgtgc ttatgccgaa aattaccccg tgattttaat ttctgtgcc cctaataata         1560
         atgatcatgc cgctggacat gtttacatc atgccttagg taaaacgat tatcattatc        1620
         aattagaaat ggccaaaat attactgctg ctgccgaagc tatttatact cctgaagaag       1680
         ccctgcaa atttgatcat gtgattaaa ccgcttacg cgaaaaaaa ccgtgtatt             1740
         tagaaattgc ctgtaatatt gcttctatgc cttgtgtgc tcctgggct gttctgttt         1800
         tatttaatga tgaagcctct gatgaagcta gtttaaatgc tgccgtggaa gaaaccttaa     1860
         aatttattgc caatcgcgat aaagtgcgc tgttagttgg ttctaaatta agagctgctg      1920
```

FIG. 35 (continued)

```
gtgctgaaga agctgctgtt aaatttgctg atgcttagg tggtgcagtt gctactatgg    1980
ctgtgccaa atcttttttt cccgaagaaa atcccatta tattggaact agttggggag    2040
aagtttctta tcctggtgtg gaaaaacta tgaagaagc cgacgctgtt attgctttag    2100
ccctgtgtt taatgattat tctaccactg gttggactga tattcccgat ccaaaaaat    2160
tagtttagc cgaacctcgt tctgttgttg ttaatggtgt tgctttccc tctgtgcatt    2220
taaaagatta tttaaccggc ttagcccaaa aagtttctaa aaaaactggt gcttagatt    2280
ttttaaatc tttaaatgcg ggtgaattaa aaaagctgc tcctgctgat ccttctgctc    2340
ctttagttaa tgctgaaatt gccgtcaag ttgagcctt attaacccct aatactaccg    2400
ttattgccga aactggtgat tcttggttta atgcccaacg catgaaatta cctaatgttg    2460
cccgtgttga atatgaaatg caatggggtc atattggttg gtctgtacct gctgctttg    2520
gttatgctgt tggtgctcct gaacgtcgta atattttaat ggtgggtgat ggttctttc    2580
aattaactgc ccaagaagtt gcccaaatgg ttcgcttaaa attacccgtt attattttt    2640
taataaataa ttatggttat accattgaag tgatgattca tgatgggcca tataataata    2700
ttaaaaattg ggattatgcg ggttaatgg aagtgtttaa tggtaatggt ggttatgatt    2760
ctggtgctgg taaaggttta aaagccaaaa ctgtggtga attagctgaa gctattaaag    2820
ttgccttagc caatactgat gggccaacct taattgaatg tttattggt cgcgaagatt    2880
gtaccgaaga attagttaaa tgggtaaac gtgttgctgc tgctaattct cgcaaaccg    2940
tgaataaatt attgtaattt ttggggatca attcgagctc agcaagttc atccgaccc    3000
cctcagggtc gggattttt tattgtacta gttgacataa gtaaaggcat ccctgcgtg    3060
atataattac cttcagttta aggaggtata cacatatgat taaagcctat gctgccttag    3120
aagccaatga taaattacaa ccctttaagt atgatccgtg tgcttaggt gcaatgaag    3180
tggaaattga agtgcaatat tgtggtgtgt gtcattctga tttatctatg attaataatg    3240
aatgggtat ttctaattat cccttagttc ctggtcatga agttgttggt actgttgctg    3300
ctatgggtga aggtgttaat catgtgaag tgggtgattt agttggttta ggttggcatt    3360
ctggttattg tatgacctgt catcttgtt tatctggtta tcataattta tgtgccactg    3420
ccgaatctac tattgtgggt cattatggtg gttttggtga tagagttcgt gctaaaggtg    3480
tttctgtggt gaaattaccc aaaggtattg atttagcctc tgctgggcct ttattttgtg    3540
gtggtattac cgttttttct cccatggtgg aattatcttt aaaacctacc gccaaagttg    3600
ctgttattgg tattggtggt ttaggtcatt tagccgttca attttaaga gcctggggtt    3660
gtgaagttac tgcttttacc tcttctgccc gtaaacaaac cgaagtttta gaattaggtg    3720
cccatcatat tttagattct accaatcctg aagctattgc ttctgccgaa ggtaaatttg    3780
attatattat ttctaccgtg aatttaaaat tagattggaa tttatatatc agtaccttag    3840
cccctcaagg tcattttcat tttgttggtg tggtgttaga accttggac ttaaacttat    3900
ttcccttatt aatgggacaa cgttctgttt ctgcttctcc tgttggttct cctgctacta    3960
ttgccactat gttagattta gccgtgcgtc atgatattaa accgtggtg gaacaattt    4020
cttttgatca aattaatgaa gccattgccc atttagaatc tggtaaagcc cattatcgcg    4080
tggtgttatc tcattctaaa aattaataag attaacttct aaactgaaac aaatttgagg    4140
gtaggcttca ttgtctgccc ttatttttt atttaggaaa agtgaacaga ctaaagagtg    4200
ttggctctat tgctttgagt atgtaaatta ggcgttgctg aattaagtca tgattttga    4260
cccttctct cttctgcagg atcatcttgc tgaaaaactc gagcgctgt tccgcaaagc    4320
ggtacggagt tagttagggg ctaatgggca ttctcccgta caggaaagag ttagaagtta    4380
ttaattatca acaattctcc tttgcctagt gcatcgttac cttttaatt aaaacataag    4440
gaaaactaat aatcgtaata atttaacctc aaagtgtaaa gaaatgtgaa attctgactt    4500
ttataacgtt aaagagggaa aaattagcag tttaaaatac ctagagaata gtctggggta    4560
agcatagaga attagattag ttaagttaat caaattcaga aaaataata atcgtaaata    4620
gttaatctgg gtgtatagaa aatgatccc ttcatgataa gatttaaact cgacaagcaa    4680
aagccaaaaa actaacttcc attaaaagaa gttgttacat ataacgctat aagaaaatt    4740
tatatatttg gaggatacca accatgtctc atattcaacg tgaaactagt tgttctcgcc    4800
ctcgtttaaa ttctaatatg gatgccgatt tatatggtta taatggct cgtaagtaatg    4860
ttggtcaatc tggtgctact attttatcgtt tatatgtaa acctgatgct cctgaattat    4920
tcttgaaaca tggtaaaggt tctgttgcta atgatgttac tgatgaaatg gttcgtttaa    4980
actggttgac tgaatttatg cctttaccta ctattaaaca tttattcgt actcccgatg    5040
atgcttggtt attaactact gctattcctg gtaaaactgc tttcaagtt ttagaagaat    5100
atcctgattc tggtgaaaat attgttgatg cttagctgt ttttacgt cgttacatt    5160
ctattcccgt ttgtaattgt ccttttaatt ctgatcgtgt ttttcgttta gctcaagctc    5220
aatctcgtat gaatgatggt tttagttgatg cttctgattt tgatgatgaa cgtaatggtt    5280
ggcctgttga acaagtttgg aaagaaatgc acaaattgtt accttttct cctgattctg    5340
ttgtactca tggtgatttt tctttagata atttgatctt tgatgaaggt aaattgattg    5400
gttgtattga tgttggtcgt gttggtattg ctgatcgtta tcaagattta gctattttat    5460
```

FIG. 35 (continued)

```
ggaattgttt aggtgaattt tctccttctt tacagaaacg tttatttcag aaatatggta    5520
ttgataatcc tgatatgaac aagttacaat ttcatttaat gttggacgag ttcttttaag    5580
aattaattca tgaccaaaat cccttaacgt gagttttcgt tccactgagc gtcagacccc    5640
gtagaaaaga tcaaggatc ttcttgagat ccttttttc tgcggtaat ctgctgctat       5700
ttaaattacg tacacgtgtt attactttgt taacgacaat tgtcttaatt aactgggcct    5760
catggccttt ccgctcactg cccgctttcc agtcgggaaa cctgtcgtgc cagctctgca    5820
gatgacgtg aaaacctctg acacatgcag ctccgggaga cggtcacagc ttgtctgtaa     5880
gcggatgccg ggagcagaca agcccgtcag ggcgcgtcag gggtgttgg cggtgtcgg      5940
ggcgcagcca tgacccagtc acgtagcgat agcggagtgt atactggctt aactatgcgg    6000
catcagagca gattgtactg agagtgcacc atatgcggtg tgaaataccg cacagatgcg    6060
taaggagaaa ataccgcatc aggcgctctt ccgcttcctc gctcactgac tcgtgcgct    6120
cggtcgttcg gctgcggcga gcggtatcag ctcactcaaa ggcggtaata cggttatcca    6180
cagaatcagg ggataacgca ggaaagaaca tgtgagcaaa aggccagcaa aaggccagga    6240
accgtaaaaa ggccgcgttg ctggcgtttt tccataggct ccgcccccct gacgagcatc    6300
acaaaaatcg acgctcaagt cagaggtggc gaaacccgac aggactataa agataccagg    6360
cgtttccccc tggaagctcc ctcgtgcgct ctctgttcc gaccctgccg cttaccggat     6420
acctgtccgc cttctccct cgggaagcg tggcgcttt tcatagctca cgctgtaggt       6480
atctcagttc ggtgtaggtc gttcgctcca agctgggctg tgtgcacgaa ccccccgttc    6540
agcccgaccg ctgcgcctta tccggtaact atcgtcttga gtccaaccc gtaagacacg     6600
acttatcgcc actggcagca gccactggta acaggattag cagagcgagg tatgtaggcg    6660
gtgctacaga gttcttgaag tggtggccta actacggcta cactagaagg acagtatttg    6720
gtatctgcgc tctgctgaag ccagttacct tcggaaaaag agttggtagc tcttgatccg    6780
gcaaacaaac caccgctggt agcggtggtt ttttgtttg caagcagcag attacgcgca     6840
gaaaaaaggg atctcaagaa gatcctttga tcttttctac tgcagaagct tgttagacac    6900
cctgtcatgt attttatatt attttattca ccatacggat taagtgaaac ctaatgaaaa    6960
tagtactttc ggagctttaa ctttaatgaa ggtatgtttt tttatagaca tcgatgtctg    7020
gtttaacaat aggaaaagt agctaaaact cccatgaatt aaagaaataa caaggtgtct     7080
aacaacctgt tattaagaat gttagaaag acttaacatt tgtgttgagt tttatagac     7140
attggtgtct agacatacgg tagataaggt ttgctcaaaa ataaaataaa aaagattgg    7200
actaaaaaac atttaattta gtacaattta attagttatt ttttgtctc aaattttgct   7260
ttgttgagca gaaatttaga taaaaaaatc cccgtgatca gattacaatg tcgttcattg   7320
tacgatgtgt cgaaaaatct ttacgacact ctaaactgac cacacggggt aaaaagaaaa   7380
ctgaactaat aacatcatga tactcggaaa acctagcaat tctcaaccc taaacaaaag    7440
aaacttccaa aaccctgacc atataaagga gtggcaacaa tcagcaatca gtcaagattt    7500
gatagcagaa aatcttgtat cggttgctaa tggttttgat gtactattta tcggcaataa    7560
ataccgaact aacacgggtg ttctgtcacg gcacatatta aactcctatt ctcatttaga    7620
agatggtggt tcgtatggta gaacatttga cccatttacc aataaagaaa tgcagtgggt    7680
tcaatttaaa ccgastagac caagaaaagg ttctactgg aaggtaatca aatatgaatc     7740
gccaaaagg gaacctacaa gagttctaat gccgtttgtg cctatgaaaa tatggcaacg    7800
gattagcgat aagttcggag taccgattaa tccgaaaaaa gatactcact tttgggaatg    7860
ggtaaagaat aatccatcga tacgattgc cattacagaa ggaaataaaa agctaattg      7920
cctattatcc tatggctatc ctgctattgc ctttgtaggc atttgaacg gattagagaa    7980
aataaatgat ttctcgaagg aaaagcagtt aaaagaggat ttgaaatggt tgttatccaa    8040
cggcaaccga aatattaata tcatctttga ccaagaccca aaacaaaaac ctgaattaa     8100
tgtaaacaaa gctatttcg ctttatcttc tctaataagt agaaatggtc ataaagttaa    8160
tattgtgcaa tggttgccgt caaaaggtaa aggaatagat gattatttgg tagctttacc   8220
ttttgagaaa agagaaatc atttagacaa cttaattaaa attgcaccat catttaattt    8280
ttggtcaact aaatacttat tcaagtgtcg taaaccagat ttaacgtaa attgccgtta    8340
tttgagcgat gcagtaaaag aattacctca agaggatata gcattaatag cacctcacgg   8400
cacgggtaaa acttcattag tagctactca cgttaagaat cggagttatc acggaaggaa    8460
aactatttca ttggtgcatc ttgaaagttt agccaaagct aatggcaacg cacttggatt    8520
atattaccga accgaaaata atattgaaaa gcaatatctt ggattcgct tatgtgtaga    8580
tagttgccgt gataagatta acggcattac aactgatatt atttcaggtc aagattattg    8640
ccttttcatt gatgaaattg accaagtaat tccacacatc ttaacagtg aaactgaagt    8700
aagtaagtat agatgcacca tcattgacac ttttctgaa ctgtgagaa atgctgaaca     8760
ggtcattatt gctgatgctg atttatccga tgtgacgatt gacctaatag aaaacatcag    8820
aggtaaaaaa ctatatgtaa tcaagaatga atatcagtat cagggaatga cttttaaacgc   8880
cgttggttca ccattagaaa tgatgcaat gatgggaaaa tcggtgtcag aaggcaagaa    8940
attatttatt aacaccacat cccaaaaggc aaaaagtaag tacggcacaa tcgtctttga   9000
gtcttatatt tttggtctaa ataagaagc aaagatatta agaatagact ctgaaaccac    9060
taaaaaccct gaacatccag cctataaaat cattgaccaa gacttaaata atatcctcaa    9120
```

FIG. 35 (continued)

```
agattatgat tatgtcattg cctcaccttg ccttcaaaca ggtgtcagta ttaccttaaa    9180
agggcatttt gaccagcaat ttaacttttc cagtggaaac attacacctc attgcttttt    9240
acagcaaatg tggcggttga gggatgcaga aattgaaaga ttctattatg tgccgaactc    9300
atctaacctc aatctcattg gaataagtc aagttcacca tcagaccttc taaagagcaa    9360
taacaagatg gcaacggcaa cggttaacct tttgggtaga atcgactccg aatattcct    9420
agagtatgaa tcgcacggca tttggcttga gacgtgggca aaattatcag cacggcataa    9480
cagttcaatg cgttgttact ctgaaattct tacctatcta attacgtctc aagggcataa    9540
attaaatatc aacattccct cacctcttgc agatattaag aagctaaatg atgaggtaag    9600
tagtaacagg gaaaaggtaa aaaatgagag atactctcag aggtaaaact caccagatat    9660
taacgatgca gaagctacca tactcgaatc taaagagcaa aaaatcggat tgactctcaa    9720
tgagagatgc accctagaaa agcataaagt taagaagcgg tatgggaatg taaagatgga    9780
tattctcacc tttgatgatg atggactata ccccaaactc agactatttt attacctcac    9840
catcggtaaa cctcatctca aggctaatga cagaaagct attgccaaaa tgggcaatga    9900
caataaaggc aagattctat caaaagactt agttaataaa acttactccg ctcgtgtgaa    9960
ggtcttagag atcctcaaa taactgactt tatcgacaat cttagagatg aactcttaat   10020
aactcccaat aatccagcta tcacctgattt taataatctt ctgctaagag ctaagaagga   10080
tttaagagta ttaggagtca acatcggaaa atatccaatg gccaacatta atgccgtact   10140
tactctcatt ggtcacaaac tttctgtaat gagagatgag ttcggaaaag agaaaaggat   10200
aaaagtagat ggtaaatcat accgatgtta tcaacttgaa acattaccag attttaccaa   10260
tgatactctt gactactggt tagaaaatga tagccaaaaa gaagtaacag caacagaaaa   10320
ttactccgaa aattttaacc cttcaaatag ctacaatcca gacagtaaga cactttcaga   10380
gggtgcaaat ttcctatata taaataaaga agaattgcat ccaaataaat tgcacctaga   10440
aataaaagaa ggtgctgaac ttttttttatt cggggtaaag gtgattgtga aaggaatctt   10500
ggacggggca gtaactatat tctctatggg tcaagaatac gatttatccc tcaatgaact   10560
agaggggatg ttaacatcat gaactttaca agaatctttt taaagggcga tgcaccatg   10620
ttaaatgatg gtacatttgt tcagatattt gatatttacc atgaccacgc attgggagtg   10680
acccttgacc ttaagacaga aaaaattatt tccgatgatg ttagggtaat tactgtcaaa   10740
gacttattgt tcgatggcac ttataaaggg gtaaaatctt ttatgcccga taatgcccga   10800
taatgcccga ttgatgctac aaaatcccat aatcataagc gataatcccc taatagcttg   10860
taattcttga accgtagcga tttagagta ttccaaaag aagaaataaa cacgcaaaa   10920
tgtcgtattt cacatatata aaccaaggtt ttttgcccta aaatctttat gtttgtagtg   10980
tgatgttggg tcaaaatggt cagaaaagtt gcaaggtttt tatggatgct tacgcgcgcg   11040
agggtaagc atcccaaat agttacttta tcctagtcca tgccattta ttgccgtccc   11100
gttcggcttt aaaaaagtgc caaaactcac aaggtgcaat aaaaagttct gtacctttcg   11160
caaccctaga taatctttca acagttactt ttttttcctat tatctcggta caaagtttgg   11220
ctagtttctc ttttccctct tttcaatca agcttcttg tatgccaac tcattgatta   11280
atctctctat ttttaccatt atttcccgtt caggtagttt atcccctaaa tcttcatcgg   11340
gggcaatgt agggcattct gaagggggctt ttcttctgt ctggacatta tctaatattg   11400
aagtaaccaa actatcttga gttttttcta ttcctattaa ttcatattcg gttactgtat   11460
ccgtatcaat atccgaataa ctatctttat ccgtattagc tattcggtta agtttatccg   11520
ttaactcaga aacaagacta tatagcggtt ttagctttt ttctatcctg ttatctaata   11580
cggataagtt tataccggta tcattatccg tattagtatc attgggcttt tttggtagtt   11640
ctaccccctc ataaaccgct tttattccca attccaacag actgataaca gtatcctta   11700
taatgggttt tttgctgata tggtgaactt ttgcccttc catcattgcg atactttcta   11760
tctcactcat caacttatcg cttaagtgaa tctcgtatct gtttaatccc ttactggttt   11820
tattcatatc ccgttacttt attcggttaa caattctatt ttatacgaat aaaatattat   11880
acggttaact ttatacgttt aactattta tctatacgga taacagtaat aagttattcg   11940
tattagttat acgttacttt ttatccaaat aaaattagtg catttaaact aaaagaatga   12000
tttatcgga gttgatagca ttggattaac ctaaagatgt ttataagcta tatctgataa   12060
gtatttaagg ttattttgtt attctgttta ttgacattat cagaataaaa gaatagaata   12120
taattgttga gagataagag gtttaagtga ttatggttaa gaagttagtt ggttatgtca   12180
gggtcagtag tgaatcgcaa gaggataaca ctagcttaca gatcagata gagagaattg   12240
aagcatattg tatggctttt ggttatgagt tggtaaaaat attcaaagag gttgccactg   12300
gtacaaaagc agatattgaa accgtcctta ttttaatga agctatagaa tacttgaaac   12360
aggataatgc taatggaatt attgccttga agctagccg aatgcacgg aatgctttag   12420
atgtattgcg tttggttcgt gaaaccttag aaccacaaaa taaatgtta gtgttactag   12480
atattcaggt agatacttcg acaccttcag gaaaaatgat tttaactgta atgagtgccg   12540
ttgctgaact cgaaagagac atgatctatg atgcactca gggggtaga aagactaaag   12600
```

FIG. 35 (continued)

```
cccaaaaggg cgggtatgcc tacgggaaac ctaaatttgg ctataagact gaagaaaagg     12660
aactaaaaga agattcagca caacaggaaa ctattaaact aattaagaga cacogtaggt     12720
cagggaaaag ctaccagaaa atagctgatt atctcaatgc ccaaagtatt cccactaaac     12780
aaggtaagaa atggagttct agcgtcgtct atcgaatctg tcaggaaaaa gctggttaag     12840
tctgtttata gatatttaga atttattgaa taaaaatagt atgascaata aatatttatg     12900
gactaaccac gctcggaaac gtttaactga acgatgggaa ataaaagaat catgggttat     12960
tgataccatc gaaaatcctg aacgttcaga atttattgtt gatgagtcag gggaaaaata     13020
tcattactat aaaagaatag ctaagtttaa gaatagagtg ttagaagtga taacttctgc     13080
caactcaaca cccacaagaa taataacctt ttactttaac cgtaacatga ggaaaaattt     13140
atgattgtta cttacgataa tgaagttgac gcaatttatt ttaagttaac ggaaaataaa     13200
attgatagca ccgaacctca aacagacagg attatcattg attacgatga aagtaataat     13260
attgttggca ttgaggtatt agattttaat tatcttgtca agaaaggttt aaccgttgct     13320
gatttacctt tttctgaaga tgaaagatta acagcttctc aatatttttaa ttttcctgtt     13380
gctatctaat ccagaagggg caataatccc cttctttcat cgagttagac ttaatatcac     13440
aaaagtcatt ttcattttac cgtttctttt ccacagcgtc cgtacgcccc tcgttaaatc     13500
tcaaaacgca caatttatga tgtttataaa aagttactca ctttaataag tatttatact     13560
cattaaaggg ttattctttt tttgtagcct gataggttgg gaaggaatat ttcagattat     13620
cagatttgtt gaatattttt cgtcagatac gcaaaccttca caaacataat taacaactga     13680
aactattgat atgtctaggt tttagctcta tcacaggttg gatctg               13726
```

FIG. 35 (continued)

```
ID   #1632\\pABICyanol::corR-PcorT*3-zmPDCABICyanol(opt1)_dsrA-Prbc*(optRBS)-
     synADH(opt1)_ter standard; circular DNA;     ; 13726 BP.
CC   This file is created by Vector NTI
CC   http://www.invitrogen.com/
CC   VNTDATE|845696278|
CC   VNTDBDATE|645696292|
CC   LSOWNER|
CC   VNTAUTHORNAME|Ulf Duehring|
FH   Key             Location/Qualifiers
FH
FT   insertion_seq   2981..3026
FT                   /vntifkey="14"
FT                   /label=dsrA
FT                   /note="dsrA terminator from E.coli"
FT   gene            3096..4106
FT                   /vntifkey="60"
FT                   /note="ADH"
FT   CDS             3096..4103
FT                   /vntifkey="4"
FT                   /label=synADH(opt1)
FT   terminator      4107..4262
FT                   /vntifkey="43"
FT                   /label=TrbcSABICyanol
FT   promoter        4299..4762
FT                   /vntifkey="30"
FT                   /label=PrbcABICyanol
FT   CDS             4764..5579
FT                   /vntifkey="4"
FT                   /label=Km**
FT                   /note="Km**"
FT   CDS             13141..13389
FT                   /vntifkey="4"
FT                   /label=ORF\6
FT                   /note="orf6"
FT   CDS             12881..13144
FT                   /vntifkey="4"
FT                   /label=ORF\5
FT                   /note="orf5"
FT   CDS             12153..10839
FT                   /vntifkey="4"
FT                   /label=ORF\4
FT                   /note="orf4 Integrase/Recombinase Similar to Site-specific
     recombinase of Bacillus thuringiensis serovar israelensis ATCC 35646"
FT   CDS             complement(11063..11827)
FT                   /vntifkey="4"
FT                   /label=ORF\3
FT                   /note="orf3"
FT   CDS             10618..10803
FT                   /vntifkey="4"
FT                   /label=ORF\2
FT                   /note="orf2"
FT   rep_origin      complement(9918..9935)
FT                   /vntifkey="33"
FT                   /label=Rep_Origin_1
FT                   /note="potential rep origin; match pNostoc (Acc# M81381) nick
     site (358-375); on reverse strand"
FT   misc_feature    10178..10211
FT                   /vntifkey="21"
FT                   /label=Rep\motif
FT                   /note="Rep protein active site motif EXKKIXVKXXD"
FT   CDS             7397..10582
```

FIG. 37

```
FT                      /vntifkey="4"
FT                      /label=ORF\1
FT                      /note="orf1  rep ori binding protein slr7037 homolog Similar to
hypothetical protein slr7037 of plasmid pSYSA (103 kb)  of Synechocystis sp. PCC 6803"
FT      primer_bind     complement(6185..6216)
FT                      /vntifkey="28"
FT                      /label=Bom-F
FT      primer_bind     5867..5898
FT                      /vntifkey="28"
FT                      /label=Bom-R
FT      rep_origin      complement(5822..6880)
FT                      /vntifkey="33"
FT                      /label=OriVT
FT      promoter        3027..3095
FT                      /vntifkey="30"
FT                      /label=Prbc*(optRB3)
FT                      /note="improved version of rbcL promoter from PCC6803"
FT      promoter        1169..1247
FT                      /vntifkey="30"
FT                      /label=PcorT*3
FT                      /note="improved version of corT promoter from PCC6803"
FT      CDS             complement(54..1166)
FT                      /vntifkey="4"
FT                      /label=corR
FT      CDS             1248..2954
FT                      /vntifkey="4"
FT                      /label=zmPDC(opt1)
SQ      Sequence 13726 BP; 4162 A; 2503 C; 2755 G; 4306 t;
        tgaccatgc gtccaaaact ttcaccatcc tttccctatc aacctttact gcactaaaga       60
        caagtgagat agcagtggca atctggcttt gcaatcaatg tttccactaa agcgtttagc     120
        gttactgcgg ctagaagtcc tccaccgagg ctccctgaa tggtgatatg gggaatggga      180
        ctgtcatca gtcgtcgttt tgcccccgga gcatgactaa aacgatcgg cattccgatc       240
        acaagagccg gctgaatatg ttgttgctct atcagcttac aggcagtgag taaaacagaa     300
        gggcatagc cgatcgccag cacacatcct tgggaattca gttgtaaccg ctgttgccaa      360
        tggtcatggt gccaaaaagc ttgctcggct tccctaagcc ctgtcatgtg agggtcgtca     420
        atcagcgttt taaccgtaca tcctaaatga gctaaccgag tttgatcaag agccgcagcc     480
        acaaccggaa catcggtgac gactggacac cctgtttca gtgcatctcg tgccgaggcg      540
        atcgctcct gactcaatgc aacggcgttt accaagctaa catcaccaca ggccagcact      600
        aattgatgta gtaagtgaat ggtaatttca gagtaagccg ataaatccgg tagcaggtgt     660
        ttgagggatt cctgaaaggc ttctggatga gtkgttgtct ccgcatctag gttcgtccac     720
        aactgatcga gttttcctca cccctcctgg acatccacat caagctgttt cagttgggcc     780
        agagcttccg cttgggtaat ctggcaactc tggtcgcgtc ccagtaatcc ttctaaagcs    840
        gatgcggttt ggcgagtcg agtaatctgc tgaatcacag cctgatattg ctgttgcaac     900
        tgcaccatta gggtgggatc aaggtctctct tcagaatggc tatccagcag ttgccgaata    960
        tgaaccaact gaaagccctg ctgtttgagg gcaatgactc gttggagccg ttgtacgtcc   1020
        tgctgagtat aaaggcggta gttgccctct gagcgttgaa cgggggcaag caatcccagg   1080
        gtgtggtaat ggcgcaccat gcgagcgta acgccacctc ccactgcatc tgtgagttcc    1140
        ttaatcgtta agtgattagt cttcatgact ttagtttact caaaaccttg acattgcacc   1200
        taatgttaag gtttagaatg agaaggtaaa aatcgagcat aaaagcatg aattcttata     1260
        ccgtgggtac ttatttagcc gaaacgcttag tgcaaattgg tttaaaacat cattttgccg    1320
        tggctgggga ctataattta gtgttattgg ataacttatt attaaataaa aacatggaac    1380
        aagtgtattg ttgtaatgaa ttaaattgtg gttttctgc tgaaggttat gctagagcta     1440
        aagtgcagc tgctgctgtt gttacttatt ctgtggggtgc tttatctgct tttgatgcta    1500
        ttggtggtgc ttatgccgaa aatttaccog tgatttaat ttctggtgcc cctaataata    1560
        atgatcatgc cgctggacat gttttacatc atgccttagg taaaacgat tatcattatc    1620
        aattagaaat ggccaaatgc attactgctg ctgccgaagc tatttatact cctgaagaag   1680
        cccctgccaa aattgatcat gtgattaaaa cccgcctacg cgaaaacaaa cccgtgtatt    1740
        tagaaattgc ctgtaatatt gcttctatgc cttgtgctgc tcctgggcct gcttctgctt   1800
        tatttaatga tgaagcctct gatgaagcta gtttaaatgc tgccgtggaa gaaacctaa    1860
```

FIG. 37 (continued)

```
aatttattgc caatcgcgat aaagttgccg tgttagttgg ttctaaatta agagctgctg  1920
gtgctgaaga agctgctgtt aaatttgctg atgctttagg tggtgcagtt gctactatgg  1980
ctgctgccaa atctttttt  cccgaagaaa atcccatta  tattggaact agttggggag  2040
aagtttctta tcctggtgtg gaaaaacta  tgaagaagc  cgacgctgtt attgctttag  2100
ccctgtgtt  taatgattat tctaccactg gttggactga tattccgat  cccaaaaaat  2160
tagttttagc cgaacctcgt tctgttgttg ttaatggtgt tcgcttccc  tctgtgcatt  2220
taaaagatta tttaaccgc  ttagccaaa  aagtttctaa aaaaactggt gccttagatt  2280
tttttaaatc tttaaatgcg ggtgaattaa aaaagctgc  tcctgctgat ccttctgctc  2340
ctttagttaa tgctgaaatt gcccgtcaag ttgaagcctt attaaccct  aatactaccg  2400
ttattgccga aactggtgat tcttggttta atgcccaacg catgaaatta cctaatggtg  2460
cccgtgttga atatgaaatg caatggggtc atattggttg gtctgtacct gctgcttttg  2520
gttatgctgt tggtgctcct gaacgtcgta atatttaat  ggtgggtgat ggttctttc  2580
aattaactgc ccaagaagtt gcccaaatgg ttcgcttaaa attacccgtt attattttt   2640
taataaataa ttatggttat accattgaag tgatgattca tgatggggca tataataata  2700
ttaaaaattg ggattatgcg ggtttaatgg aagtgtttaa tggtaatggt ggttatgatt  2760
ctggtgctgg taaaggttta aaagccaaaa ctggtggtga attagctgaa gctattaaag  2820
ttgccttagc caatactgat gggccaacct taattgaatg ttttattggt cgcgaagatt  2880
gtaccgaaga attagttaaa tgggtaaac  gtgttgctgc tgctaattct cgcaaacccg  2940
tgaataaatt attgtaattt ttggggatca attcgagctc agcaagtttc atcccgaccc  3000
cctcagggtc gggattttt  tattgtacta gttgacataa gtaaaggcat ccctgcgtg   3060
atataattac cttcagttta aggaggtata cacatatgat taaagcctat gctgccttag  3120
aagccaatgg taaattacaa cccttgaat  atgatctgg  tgctttagt  gccaatgaag  3180
tggaaattga agtgcaatat tgtggtgtgt gtcattctga tttatctatg attaataatg  3240
aatggggtgt ttctaattat ccccttagttc ctggtcatga agttgttggt actgttgctg  3300
ctatgggtga aggtgttaat catgtggaag tgggtgattt agttggttta ggttggcatt  3360
ctggttattg tatgacctgt cattctgtt  tatctggtta tcataattta tgtgccactg  3420
ccgaatctac tattgtgggt cattatggtg gttttggtga tagagttcgt gctaaaggtg  3480
tttctgtggt gaaattaccc aaagtattg  attagcctc  tgctgggcct ttattttgtg  3540
gtggtattac cgttttttct cccatggtgg aattatcttt aaaacctacc gccaaagttg  3600
ctgttattgg tattggtggt ttaggtcatt tagccgttca attttaaga  gcctggggtt  3660
gtgaagttac tgcttttacc tcttctgccc gtaaacaaac cgaagtttta gaattaggtg  3720
cccatcatat tttagattct accaatcctg aagctattgc ttctgccgaa ggtaaatttg  3780
attatattat ttctaccgtg aatttaaaat tagattggaa tttatatatc agtaccttag  3840
ccccctcaagg tcattttcat ttgttggtg  tggtgttaga accttggac  ttaaacttat  3900
ttccttatt  aatgggacaa cgttctgttt ctgcttctcc tgttggttct cctgctacta  3960
ttgccactat gttagatttt gccgtgcgtc atgatattaa acccgtggtg gaacaatttt  4020
cttttgatca aattaatgaa gccattgccc atttagaatc tggtaaagcc cattatcgcg  4080
tggtgttatc tcattctaaa aattaataag attaacttct aaactgaaac aaatttgagg  4140
gtaggttca  ttgtctgccc ttatttttt atttaggaaa agtgaacaga ctaaagagtg  4200
ttggctctat tgcttgagt atgtaattaa gggttgctg  aattaaggta tgattttga   4260
cccttctct  cttctgcagg atcatcttgc tgaaaactc  gagcgctcgt tcgcaaagc   4320
ggtacggagt tagttagggg ctaatgggca ttctcccgta caggaaagag ttagaagtta  4380
ttaattatca acaattccc  tttgcctagt gcatcgttac ccttttaatt aaaacataag  4440
gaaaactaat aatcgtaata attttaacctc aaagtgtaaa gaaatgtgaa attctgactt  4500
ttataacgtt aaagagggaa aaattagcag tttaaaatac ctagagaata gtctggggta  4560
agcatagaga attagattag ttaagttaat caaattcaga aaaaataata atcgtaaata  4620
gttaatctgg gtgtatagaa aatgatccc  ttcatgataa gatttaaact cgaaagcaa   4680
aagccaaaaa actaacttcc attaaaagaa gttgttacat ataacgctat aaagaaaatt  4740
tatatacttg gaggatacca accatgtctc atattcaacg tgaaactagt tgttctcgcc  4800
ctgtttaaa  ttctaatatg gatgccgatt tatatggtta taaactgggct cgtgataatg  4860
ttggtcaatc tggtgctact atttatcgtt tatatggtaa acctgatgct cctgaattat  4920
tcttgaaaca tggtaaaggt tctgttgcta atgatgttac tgatgaaatg gttcgtttaa  4980
actggttgac tgaatttatg cctttaccta ctattaaaca ttttattcgt actcccgatg  5040
atgcttggtt attaactact gctattcctg gtaaaactgc ttttcaagtt ttagaagaat  5100
atcctgattc tggtgaaaat attgttgatg cttagctgt  ttttttacgt cgtttacatt  5160
ctattcccgt ttgtaattgt ccttttaatt ctgatcgtgt tttcgtttta gctcaagctc  5220
aatctcgtat gaataatggt ttagttgatg cttctgatttt tgatgatgaa cgtaatggtt  5280
ggcctgttga acaagtttgg aaagaaatgc acaaattgtt acctttttct cctgatctgt  5340
ttgttactca tggtgatttt tctttagata atttgatctt tgatgaaggt aaattgattg  5400
gttgtattga tgttggtcgt gttggtattg ctgatcgtta tcaagattta gctatttat   5460
ggaattgttt aggtgaactt tctcctcctt tacagaaacg tttatttcag aaatatggta  5520
```

FIG. 37 (continued)

```
ttgataatcc tgatatgaac aagttacaat ttcatttaat gttggacgag ttcttttaag    5580
aattaattca tgaccaaaat cccttaacgt gagtttttgt tccactgagc gtcagacccc    5640
gtagaaaaga tcaaaggatc ttcttgagat cctttttttc tgcgcgtaat ctgctgctat    5700
ttaaattacg tacacgtgtt attactttgt taacgacaat tgtcttaatt aactggcct    5760
catgggcctt ccgctcactg cccgctttcc agtcgggaaa cctgtcgtgc cagctctgca    5820
gatgacggtg aaaacctctg acacatgcag ctcccggaga cggtcacagc ttgtctgtaa    5880
gcggatgccg ggagcagaca agcccgtcag gcgcgtcag cgggtgttgg cgggtgtcgg    5940
ggcgcagcca tgacccagtc acgtagcgat agcggagtgt atactggctt aactatgcgg    6000
catcagagca gattgtactg agagtgcacc atatgcggtg tgaaataccg cacagatgcg    6060
taaggagaaa ataccgcatc aggcgctctt ccgcttcctc gctcactgac tcgctgcgct    6120
cggtcgttcg gctgcggcga gcggtatcag ctcactcaaa ggcggtaata cggttatcca    6180
cagaatcagg ggataacgca ggaaagaaca tgtgagcaaa aggccagcaa aaggccagga    6240
accgtaaaaa ggccgcgttg ctggcgtttt tccataggct ccgcccccct gacgagcatc    6300
acaaaaatcg acgctcaagt cagaggtggc gaaacccgac aggactataa agataccagg    6360
cgtttccccc tggaagctcc ctcgtgcgct ctcctgttcc gaccctgccg cttaccggat    6420
acctgtccgc cttctccct tcgggaagcg tggcgctttc tcatagctca cgctgtaggt    6480
atctcagttc ggtgtaggtc gttcgctcca agctgggctg tgtgcacgaa ccccccgttc    6540
agcccgaccg ctgcgcctta tccggtaact atcgtcttga gtccaacccg gtaagacacg    6600
acttatcgcc actggcagca gccactggta acaggattag cagagcgagg tatgtaggcg    6660
gtgctacaga gttcttgaag tggtggccta actacggcta cactagaagg acagtatttg    6720
gtatctgcgc tctgctgaag ccagttacct tcggaaaaag agttggtagc tcttgatccg    6780
gcaaacaaac cacgctggt agcggtggtt ttttgtttg caagcagcag attacgcgca    6840
gaaaaaaagg atctcaagaa gatcctttga tcttttctac tgcagaagct tgttagacac    6900
cctgtcatgt attttatatt atttattca ccatacggat taagtgaaac ctaatgaaaa    6960
tagtactttc ggagctttaa ctttaatgaa ggtatgtttt tttatagaca tcgatgtctg    7020
gtttaacaat aggaaaagt agctaaaact cccatgaatt aagaaataa caaggtgtct    7080
aacaacctgt tattaagaat gttagaaaag acttaacatt tgtgttgagt tttatagac    7140
attggtgtct agacatacgg tagataaggt ttgctcaaaa ataaaataaa aaaagattgg    7200
actaaaaaac atttaattta gtacaattta attagttatt tttgtctc aaatttgct    7260
ttgttgagca gaaatttaga taaaaaatc cccgtgatca gattacaatg tcgttcattg    7320
tacgatgtgt cgaaaaatct ttacgacact ctaaactgac cacacggggg aaaaagaaaa    7380
ctgaactaat aacatcatga tactcggaaa acctagcaat tctcaaccc taaacaaaag    7440
aaacttccaa aaccctgacc atataaagga gtggcaacaa tcagcaatca gtcaagattt    7500
gatagcagaa atcttgtat cggttgctaa tggttttgat gtactattta tcggcaataa    7560
ataccgaact aacacgggtg ttctgtcacg gcacatatta aactcctatt ctcatttaga    7620
agatggtgt tcgtatggta gaacatttga cccatttacc aataaagaaa tgcagtgggt    7680
tcaatttaaa ccgaatagac caagaaaagg ttctactggt aagtaatca aatatgaatc    7740
gccaaaaggt gaacctacaa gagttctaat gccgtttgtg cctatgaaaa tatggcaacg    7800
gattagcgat aagttcggag tacgattaa tccgaaaaaa gatactcact tttgggaatg    7860
ggtaaagaat aatccatcga tacgattgc cattacagaa ggaaataaaa aagctaattg    7920
cctattatcc tatggctatc ctgctattgc ctttgtaggc atttggaacg gattagagaa    7980
aataaatgat ttctcgaagg aaaagcagtt aaaagaggat ttgaaatggt tgttatccaa    8040
cggcaaccga aatattaata tcatctttga ccaagaccag aaacaaaaaa ctgtaattaa    8100
tgtaaacaaa gctattttcg ctttatcttc tctaataagt agaaatggtc ataaagttaa    8160
tattgtgcaa tggttgccgt caaaggtaa aggaatagat gattatttgg tagctttacc    8220
ttttgagaaa agagaaaatc atttagacaa cttaattaaa attgcaccat catttaattt    8280
ttggtcaact aaatacttat tcaagtgtcg taaaccagat taaccgtaa attgccgtta    8340
tttgagcgat gcagtaaaag aattacctca agaggatata gcattaatag cacctcacgg    8400
cacgggtaaa acttcattag tagctactca cgttaagaat cggagttatc acggaaggaa    8460
aactatttca ttggtgcatc ttgaaagttt agccaaagct aatggcaacg cacttggatt    8520
atattaccga accgaaaata atattgaaaa gcatatctt ggatttagct tatgtgtaga    8580
tagttgccgt gataagatta acgattaca aactgtattt atttcaggtc aagattattg    8640
ccttttcatt gatgaaattg accaagtaat tccacacatc cttaacgtg aaactgaagt    8700
aagtaagtat agatgcacca tcattgacac ttttctgaa ctggtgagaa atgctgaaca    8760
ggtcattatt gctgatgctg atttatccga tgtgacgatt gactaatag aaaacatcag    8820
aggtaaaaaa ctatatgtaa tcaagaatga atatcagtat caggaatga cttttaacgc    8880
cgttggttca ccattagaaa tgatggcaat gatgggaaaa tcggtgtcag aaggcaagaa    8940
attatttatt aacaccacat cccaaaaggc aaaaagtaag tacggcacaa tgctcttga    9000
gtcttatatt tttggtctaa ataaagaagc aaagatatta agaatagact ctgaaaccac    9060
```

FIG. 37 (continued)

```
taaaaaccct gaacatccag cctataaaat cattgaccaa gacttaaata atatcctcaa    9120
agattatgat tatgtcattg cctcaccttg ccttcaaaca ggtgtcagta ttaccttaaa    9180
agggcatttt gaccagcaat ttaacttttc cagtgaaaac attacacctc attgcttttt    9240
acagcaaatg tggcggttga gggatgcaga aattgaaaga ttctattatg tgccgaactc    9300
atctaacctc aatctcattg ggaataagtc aagttcacca tcagccttc taaagagcaa    9360
taacaagatg gcaacggcaa cggttaacct tttgggtaga atcgactccg aatattccct    9420
agagtatgaa tcgcacggca tttggcttga gacgtgggca aaattatcag cacggcataa    9480
cagttcaatg cgttgttact ctgaaattct tacctatcta attacgtctc aagggcataa    9540
attaaatatc aacattcct cacctcttgc agatattaag aagctaaatg atgaggtaag    9600
tagtaacagg gaaaaggtaa aaaatgagag atactctcag aggttaaact caccagatat    9660
taacgatgca gaagctacca tactcgaatc taaagagcaa aaaatcggat tgactctcaa    9720
tgagagatgc acctagaaa agcataaagt taagaagcgg tatgggaatg taaagatgga    9780
tattctcacc tttgatgatg atggactata cccaaactc agactatttt attacctcac    9840
catcggtaaa cctcatctca aggctaatga cagaaaagct attgccaaaa tgggcaatga    9900
caataaaggc aagattctat caaagacttc agttaataaa acttactccg ctcgtgtgaa    9960
ggtcttagag attcttaaac taactgactt tatcgacaat cttagagatg aactcttaat   10020
aactcccaat aatccagcta tcaccgattt taataatctt ctgctaagag ctaagaagga   10080
tttaagagta ttaggagtca acatcggaaa atatccaatg gccaacatta atgccgtact   10140
tactctcatt ggtcacaac tttctgtaat gagagatgag ttcgaaaag agaaaaggat   10200
aaaagtagat ggtaaatcat accgatgtta tcaacttgaa acattaccag atttaccaa   10260
tgatactctt gactactggt tagaaaatga tagccaaaaa gaagtaacag caacagaaaa   10320
ttactccgaa aattttaacc cttcaaatag ctacaatcca gacagtaaga cactttcaga   10380
gggtgcaaat ttcctatata taaataaga agaattgcat ccaaataaat tgcacctaga   10440
aataaagaa ggtgctgaac tttttttatt cgggtaaag gtgattgtga aaggaatctt   10500
ggacgggca gtaactatat tctctatggg tcaagaatac gatttatccc tcaatgaact   10560
agagggggatg ttaacatcat gaactttaca agaatctttt taagggcga tgcaccatg   10620
ttaaatgatg gtacatttgt tcagatattt gatattacc atgaccacgc attgggagtg   10680
accttgacc ttaagacaga aaaaattat tccgatgatg ttagggtaat tactgtcaaa   10740
gactattgt tcgatggcac ttataaaggg gtaaaatctt ttatgcccga taatgcccga   10800
taatgcccga ttgatgctac aaaatcccat aatcataagc gataatcccc taatagcttg   10860
taattcttga accgtagcga ttttagagta ttccaaaaag aagaaataaa caccgcaaaa   10920
tgtcgtattt cacatatata aaccaaggtt ttttgcccta aaatcttat gtttgtagtg   10980
tgatgttggg tcaaaatggt cagaaaagtt gcaaggtttt tatggatgct tacgcgcgcg   11040
agggtaagc atccccaaat agttacttta tcctagtcca tgcccattta ttgccgtccc   11100
gttcggcttt aaaasagtgc caaaactcac aaggtgcaat aaaagttct gtaccttcg   11160
caaccctaga taatctttca acagttactt ttttcctat tatctcggta caagtcttgg   11220
ctagtttctc ttttccctct ttttcaatca agccttcttg tatgcccaac tcattgatta   11280
atctctctat ttttaccatt atttcccgtt caggtagttt atccctaaa tcttcatcgg   11340
ggggcaatgt agggcattct gaaggggctt tttcttctgt ctggacatta tctaatattg   11400
aagtaaacaa actatcttca gttttttcta ttcctattaa ttcatattg gttactgtat   11460
ccgtatcaat atccgaataa ctatctttat ccgtattagc tattcggtta agtttatccg   11520
ttaactcaga aacaagacta tatacggtt ttagctttc tctatcctg ttatctaata   11580
cggataagtt tatacggtta tcattatccg tattgtatc attgggcttt tttggtagtt   11640
ctaccccctc ataaaccgct tttattccca attcaacag actgataaca gtatccttta   11700
taatgggttt tttgctgata tggtgaactt ttgcccttc catcattgcg atactttcta   11760
tctcactcat caacttatcg cttaagtgaa tctcgtatct gttaatccc ttactggttt   11820
tattccatatc cgttactt attcggttaa caattctatt ttatcgaat aaaatattat   11880
acggttaact ttatacgttt aactatttta tctatacgga taacagtaat aagttattcg   11940
tattagttat acgtttactt ttatccaaat aaaattagtg catttaaact aaaagaatga   12000
ttttatcgga gttgatagca tggattaac ctaaagatgt ttataagcta tatctgataa   12060
gtatttaagg ttatttttgt attctgttta ttgacattat cagaataaa gaatagaata   12120
taattgttga gagataagag gttaagtga ttatggttaa aagttagtt ggttatgtca   12180
gggtcagtag tgaatcgcaa gaggataaca ctagcttaca gaatcagata gagagaattg   12240
aagcatattg tatggctttt ggttatgagt tgtaaaaat attcaaagag gttgccactg   12300
gtacaaaagc agatattgaa acccgtccta tttttaatga agctatagaa tacttgaaac   12360
aggataatgc taatggaatt attgccttga gctagaccg aatcgcacgg aatgctttag   12420
atgtattgcg tttggttcgt gaaaccttag aaccacaaaa taaaatgtta gtgttactag   12480
atattcaggt agatacttca acacttcag gaaaatgat tttaactgta atgagtgcg   12540
ttgctgaact cgaaagagac atgatctatg atcgcactca gggggtaga aagactaaag   12600
cccaaaaggg cgggtatgcc tacgggaaac ctaaatttgg ctataagact gaagaaaagg   12660
aactaaaaga agattcagca caacagaaaa ctattaaact aattaagaga cacgtaggt   12720
```

FIG. 37 (continued)

```
cagggaaaag ctaccagaaa atagctgatt atctcaatgc ccaaagtatt cccactaaac   12780
aaggtaagaa atggagttct agcgtcgtct atcgaatctg tcaggaaaaa gctggttaag   12840
tctgtttata gatatttaga atttattgaa taaaaatagt atgaacaata aatatttatg   12900
gactaaccac gctcggaaac gtttaactga acgatgggaa ataaaagaat catgggttat   12960
tgataccatc gaaaatcctg aacgttcaga atttattgtt gatgagtcag gggaaaaata   13020
tcattactat aaaagaatag ctaagtttaa gaatagagtg ttagaagtga taacttctgc   13080
caactcaaca cccacaagaa taataacctt ttactttaac cgtaacatga ggaaaaattt   13140
atgattgtta cttacgataa tgaagttgac gcaatttatt ttaagttaac ggaaaataaa   13200
attgatagca ccgaacctca aacagacagg attatcattg attacgatga aagtaataat   13260
attgttggca ttgaggtatt agattttaat tatcttgtca agaaaggttt aaccgttgct   13320
gattacctt tttctgaaga tgaaagatta acagcttctc aatattttaa ttttcctgtt   13380
gctatctaat ccagaagggg caataatccc cttctttcat cgagttagac ttaatatcac   13440
aaaagtcatt tcattttac cgtttctttt ccacagcgtc cgtacgcccc tgttaaatc   13500
tcaaaaccga caatttatga tgtttataaa aagttactca ctttaataag tatttatact   13560
cattaaaggg ttattctttt tttgtagcct gataggttgg gaaggaatat ttcagattat   13620
cagatttgtt gaatatttt cgtcagatac gcaaacctta caaacataat taacaactga   13680
aactattgat atgtctaggt tttagctcta tcacaggttg gatctg                 13726
```

FIG. 37 (continued)

```
ID    #1635\pABICyanol::smtB-PsmtA-zmPDC(opt1)_dsrA-Prbc*(optRBS)-synADH(opt1)_ter
standard; circular DNA;    ; 12973 BP.
CC    This file is created by Vector NTI
CC    http://www.invitrogen.com/
CC    VNTDATE|645699239|
CC    VNTDBDATE|645699239|
CC    LSOWNER|
CC    VNTAUTHORNAME|Ulf Duehring|
FH    Key             Location/Qualifiers
FH
FT    CDS             582..2288
FT                    /vntifkey="4"
FT                    /label=zmPDC(opt1)
FT    CDS             complement(153..479)
FT                    /vntifkey="4"
FT                    /label=smtB
FT                    /note="smtB gene from Synechococcus PCC7002"
FT    promoter        480..581
FT                    /vntifkey="30"
FT                    /label=PsmtA
FT                    /note="smtA promoter from Synechococcus PCC7002"
FT    insertion_seq   2315..2360
FT                    /vntifkey="14"
FT                    /label=dsrA
FT                    /note="dsrA terminator from E.coli"
FT    gene            2430..3440
FT                    /vntifkey="60"
FT                    /note="ADH"
FT    CDS             2430..3437
FT                    /vntifkey="4"
FT                    /label=synADH(opt1)
FT    terminator      3441..3596
FT                    /vntifkey="43"
FT                    /label=TrbcABICyanol
FT    promoter        3633..4096
FT                    /vntifkey="30"
FT                    /label=PrbcABICyanol
FT    CDS             4098..4913
FT                    /vntifkey="4"
FT                    /label=Km**
FT                    /note="Km**"
FT    CDS             12475..12723
FT                    /vntifkey="4"
FT                    /label=ORF\6
FT                    /note="orf6"
FT    CDS             12215..12478
FT                    /vntifkey="4"
FT                    /label=ORF\5
FT                    /note="orf5"
FT    CDS             11487..12173
FT                    /vntifkey="4"
FT                    /label=ORF\4
FT                    /note="orf4 Integrase/Recombinase Similar to Site-specific
recombinase of Bacillus thuringiensis serovar israelensis ATCC 35646"
FT    CDS             complement(10397..11161)
FT                    /vntifkey="4"
FT                    /label=ORF\3
FT                    /note="orf3"
FT    CDS             9952..10137
FT                    /vntifkey="4"
FT                    /label=ORF\2
```

FIG. 39

```
FT                         /note="orf2"
FT    rep_origin           complement(9252..9369)
FT                         /vntifkey="33"
FT                         /label=Rep_Origin_1
FT                         /note="potential rep origin; match pNostoc (Acc# M81381) nick
site (358-375); on reserse strand"
FT    misc_feature         9512..9545
FT                         /vntifkey="21"
FT                         /label=Rep\motif
FT                         /note="Rep protein active site motif EXXKYXVKXXD"
FT    CDS                  6731..9916
FT                         /vntifkey="4"
FT                         /label=ORF\1
FT                         /note="orf1  rep ori binding protein slr7037 homolog Similar to
hypothetical protein slr7037 of plasmid pSYSA (103 kb)  of Synechocystis sp. PCC 6803"
FT    primer_bind          complement(5519..5550)
FT                         /vntifkey="28"
FT                         /label=Bom-F
FT    primer_bind          5201..5232
FT                         /vntifkey="28"
FT                         /label=Bom-R
FT    rep_origin           complement(5156..6214)
FT                         /vntifkey="33"
FT                         /label=OriVT
FT    promoter             2361..2429
FT                         /vntifkey="30"
FT                         /label=Prbc*(optRBS)
FT                         /note="improver version of rbcL promoter from PCC6803"
SQ    Sequence 12973 BP; 3970 A; 2324 C; 2561 G; 4118 t;
      tcgtcagata cgcaaacctt acaaacataa ttaacaactg aaactattga tatgtctagg         60
      ttttagctct atcacaggtt ggatctgtcg acgggcaaac tttatgaagc agatcaagcc        120
      tatatccgcc aagcaaccgg cagccgcgtt gattagtggg tgtgtccatc ctctggttcc        180
      tctaggtgct ccgaagcgtc acgatagaga ttaagaatgt ggtgatcctt gaggcgataa        240
      atcacattcc gccccttcct gcgatagctc actaaacgtg ctgtgcgcag ggttcttagt        300
      tggtgagaga cagccgatte actcatttca acggacggcg cgagttccgc cacccgatc         360
      tctccagtgg ccagggccga aagaatacgc cagcggttgg catcccccsa gacaccaaaa        420
      aattcggcca tccgttgggc cttggcttgg ttcagstttt tgccactgtg gtctgtcatt        480
      gttgctgat ctaaacaata cctgaataat tgttcatgtg ttaatctaaa aatgtgaaca         540
      atcgttcaac tatttaagac aatacctttgg aggtttaaac catgaattct tataccgtgg       600
      gtacttattt agccgaacgc ttagtgcaaa ttggtttaaa acatcatttt gccgtggctg        660
      gggactataa tttagtgtta ttggataact tattattaaa taaaaacatg gaacaagtgt        720
      attgttgtaa tgaattaaat tgtcgtgttt ctgctgaagg ttatgctaga gctaaaggtt        780
      cagtgtgctgc tgttgttact tattctgtgg gtgctttatc tgcttttgat gctattggtg       840
      gtgcttatgc cgaaaattta cccgtgattt taatttctgg tgccctaat aataatgatc         900
      atgccgctgg acatgtttta catcatgcct taggtaaaac cgattatcat tatcaattag        960
      aaatggccaa aaatattact gctgctgccg aagctattta tactcctgaa gaagccctg        1020
      ccaaaattga tcatgtgatt aaaaccgcct tacgcgaaaa aaaaccgtg tatttagaaa        1080
      ttgcctgtaa tattgcttct atgccttgtg ctgctcctgg gctgcttct gctttattta       1140
      atgatgaagc ctctgatgaa gctagtttaa atgctgccgt ggaagaacc ttaaaattta        1200
      ttgccaatcg cgataaagtt gccgtgttag ttgctgaa attaagagct gctggctgctg       1260
      aagaagctgc tgttaaattt gctgatgctt taggtggtgc agttgctact atggctgctg       1320
      ccaaatcttt ttttccgaa gaaaatcccc attatattgg aactagttgg ggagaagttt        1380
      cttatcctgg tgtggaaaaa actatgaaag aagccgacgc tgttattgct ttagccctg        1440
      tgtttaatga ttattctacc actggttgga ctgatattcc cgatcccaaa aaattagttg        1500
      tagccgaacc tcgttctgtt gttgttaatg gtgttcgctt tccctctgtg catttaaag        1560
      attattttaac ccgcttagcc caaaaagttt ctaaaaaaac tggtgcctta gattttttta        1620
      aatctttaaa tgcgggtgaa ttaaaaaaag ctgctcctgc tgatccttct gctcctttag        1680
      ttaatgctga aattgcccgt caagttgaag ccttattaac cctaaatact accgttattg        1740
      ccgaaactga tgtccttgc tttaatgcc acgtgaag attacctaat ggtgccgtg              1800
      ttgaatatga aatgcaatgg ggtcatattg gttggtctgt acctgctgct tttggttatg        1860
      ctgttggtgc tcctgaacgt cgtaatattt tastggtggg tgatggttct tttcaattaa        1920
```

FIG. 39 (continued)

```
ctgcccaaga agttgcccaa atggttcgct taaaattacc cgttattatt tttttaataa    1980
ataattatgg ttataccatt gaagtgatga ttcatgatgg gccatataat aatattaaaa    2040
attgggatta tgcgggttta atggaagtgt taatggtaa tggtggttat gattctggtg    2100
ctggtaaagg tttaaaagcc aaaactggtg gtgaattagc tgaagctatt aaagttgcct    2160
tagccaatac tgatgggcca accttaattg aatgttttat tggtcgcgaa gattgtaccg    2220
aagaattagt taaatggggt aaacgtgttg ctgctgctaa ttctcgcaaa cccgtgaata    2280
aattattgta attttgggg atcaattcga gctcagcaag tttcatcccg accccctcag    2340
ggtcgggatt ttttattgt actagttgac ataagtaaag gcatccctg cgtgatataa    2400
ttaccttcag tttaaggagg tatacacata tgattaaagc ctatgctgcc ttagaagcca    2460
atggtaaatt acaacccttt gaatatgatc ctggtgcttt aggtgccaat gaagtggaaa    2520
ttgaagtgca atattgtggt gtgtgtcatt ctgatttatc tatgattaat aatgaatggg    2580
gtatttctaa ttatccctta gttcctggtc atgaagttgt tggtactgtt gctgctatgg    2640
gtgaaggtgt taatcatgtg gaagtgggtg atttagttgg tttaggtggg cattctggtt    2700
attgtatgac ctgtcattct tgtttatctg gttgataagt tttatgtgcc actgccgaat    2760
ctactattgt ggtgcattat ggtggttttg gtgatagagt tcgtgctaaa ggtgtttctg    2820
tggtgaaatt acccaaaggt attgatttag cctctgctgg gcctttattt tgtggtggta    2880
ttaccgtttt ttctcccatg gtggaattat ctttaaaacc taccgccaaa gttgctgtta    2940
ttggtattgg tggtttaggt cattagccg ttcaattttt aagagcctgg ggttgtgaag    3000
ttactgcttt taccctcttct gcccgtaaac aaaccgaagt tttagaatta ggtgccccatc    3060
atattttaga ttctaccaat cctgaagcta ttgcttctgc cgaagtaaa tttgattata    3120
ttatttctac cgtgaattta aaattagatt ggaatttata tatcagtacc ttagccccctc    3180
aaggtcattt tcatttgtt ggtgtggtgt tagaacccctt ggacttaaac ttatttccct    3240
tattaatggg acaacgttct gtttctgctt ctcctgttgg ttctcctgct actattgcca    3300
ctatgttaga ttttgccgtg cgtcatgata ttaaacccgt ggtggaacaa tttttctttg    3360
atcaaattaa tgaagccatt gcccatttag aatctggtaa agcccattat cgcgtggtgt    3420
tatctcattc taaaaattaa taagattaac ttctaaactg aaacaaattt gagggtaggc    3480
ttcattgtct gcccttatt tttatttag gaaaagtgaa cagactaaag agtgttggct    3540
ctattgcttt gagtatgtaa attaggcgtt gctgaattaa ggtatgattt ttgacccctt    3600
ctctcttctg caggatcatc ttgctgaaaa actcgagcgc tcgttccgca aagcggtacg    3660
gagttagtta ggggctaatg ggcattctcc cgtacaggaa agagttagaa gttattaatt    3720
atcaacaatt ctccttttgcc tagtgcatcg ttaccttttt aattaaaaca taaggaaaac    3780
taataatcgt aataatttaa cctcaaagtg taagaaatg tgaaattctg acttttataa    3840
cgttaaagag ggaaaaatta gcagtttaaa ataccctagag aatagtctgg ggtaagcata    3900
gagaattaga ttagttaagt taatcaaatt cagaaaaaat aataatcgta aatagttaat    3960
ctgggtgtat agaaaatgat ccccttcatg ataagattta aactcgaaaa gcaaagcca    4020
aaaaactaac ttccattaaa agaagttgtt acatataacg ctataaagaa aatttatata    4080
tttggaggat accaaccatg tctcatattc aacgtgaaac tagttgttct cgccctgtt    4140
taaattctaa tatggatgcc gatttatatg gttataaatg ggctcgtgat aatgttggtc    4200
aatctggtgc tactattat cgtttatatg gtaaaccctga tgctcctgaa ttattcttga    4260
aacactgaa aggttctgtt gctaatgagt ttactgatga aatggttcgt ttaaactggt    4320
tgactgaatt tatgcctttta cctactatta aacatttat tcgtactccc gatgatgctt    4380
ggttattaac tactgctatt cctggtaaaa ctgcttttca agttttagaa gaatatcctg    4440
attctggtga aaatattgtt gatgctttag ctgttttttt acgtcgttta cattctattc    4500
ccgtttgtaa ttgtcttttt aatctgatc gtgtttttcg tttagctcaa gctcaatctc    4560
gtatgaataa tggtttagtt gatgcttctg attttgatga tgaacgtaat ggttggcctg    4620
ttgaacaagt ttggaaagaa atgcacaaat tgttaccttt ttctcctgat tctgttgtta    4680
stcatggtga ttttttttat gataatttga tctttgatga aggtaaattg attggttgta    4740
ttgatgttgg tcgtgttggt attgctgatc gttatcaaga tttagctatt ttatggaatt    4800
gtttaggtga attttctcct tctttacaga aacgttatt tcagaaatat ggtattgata    4860
atctgatat gaacaagtta caattcatt taatgttgga cgagttcttt taagaattaa    4920
ttcatgacca aaatccctta acgtgagttt tcgttccact gagcgtcaga cccgtagaa    4980
aagatcaaag gatcttcttg agatccttt tttctgcgcg taatctgctg ctatttaaat    5040
tacgtacacg tgttattact tgttaacga caattgtctt aattaactgg gcctcatggg    5100
ccttccgctc actgcccgct ttccagtcgg gaaacctgtc gtgccagctg cgacagatgac    5160
ggtgaaaacc tctgacacat gcagctccg gagacggtca gcttgtct gtaagcggat    5220
gccgggagca gacaagcccg tcagggcgcg tcagcgggtg ttggcgggtg tcggggcgca    5280
gccatgaccc agtcacgtag cgatagcgga gtgtatactg gcttaactat gcggcatcag    5340
agcagattgt actgagagtg caccatatgc ggtgtgaaat accgcacaga tgcgtaagga    5400
gaaatacgg catcaggcgc tcttccgctt cctcgctcac tgactcgctg cgctcggtcg    5460
ttcggctgcg gcgagcggta tcagctcact caaaggcggt aatacggtta tccacagaat    5520
cagggataa cgcaggaaag aacatgtgag caaaaggcca gcaaaggcc aggaaccgta    5580
```

FIG. 39 (continued)

```
aaaaggccgc gttgctgggg ttttttccata ggctccgccc ccctgacgag catcacaaaa     5640
atcgacgctc aagtcagagg tggcgaaacc cgacaggact ataaagatac caggcgtttc     5700
ccctggaag  ctccctcgtg cgctctcctg ttccgaccct gccgcttacc ggatacctgt     5760
ccgcctttct ccttcggga  agcgtggcgc tttctcatag ctcacgctgt aggtatctca     5820
gttcggtgta ggtcgttcgc tccaagctgg gctgtgtgca cgaacccccc gttcagcccg     5880
accgctgcgc cttatccggt aactatcgtc ttgagtccaa cccggtaaga cacgacttat     5940
cgccactggc agcagccact ggtaacagga ttagcagagc gaggtatgta ggcggtgcta     6000
cagagttctt gaagtggtgg cctaactacg gctacactag aaggacagta tttggtatct     6060
gcgctctgct gaagccagtt accttcggaa aaagagttgg tagctcttga tccggcaaac     6120
aaaccaccgc tggtagcggt ggttttttg  tttgcaagca gcagattacg cgcagaaaaa     6180
aaggatctca agaagatcct ttgatctttt ctactgcaga agcttgttag acaccctgtc     6240
atgtatttta tattatttat ttcaccatac ggattaagtg aaacctaatg aaaatagtac     6300
tttcggagct ttaactttaa tgaaggtatg tttttttata gacatcgatg tctggtttaa     6360
caatagaaaa aagtagctaa aactcccatg aattaaagaa ataacaaggt gtctaacaac     6420
ctgttattaa gaatgttaga aaagacttaa catttgtgtt gagtttttat agacattggt     6480
gtctagacat acgtagata  aggtttgctc aaaaataaaa taaaaaaaga ttggactaaa     6540
aaacatttaa tttagtacaa tttaattagt tatttttcg  tctcaaattt tgctttgttg     6600
agcagaaatt tagataaaaa aatcccgtg  atcagattac aatgtcgttc attgtacgat     6660
gtgtcgaaaa atctttacga cactctaaac tgaccacacg ggggaaaag  aaaactgaac     6720
taataacatc atgatactcg gaaaacctag caattctcaa ccctaaaca  aaagaaactt     6780
ccaaaaccct gaccatatag aggagtggca acaatcagca atcagtcaag atttgatagc     6840
agaaaatctt gtatcggttg ctaatggttt tgatgtacta tttatcggca ataaatacgg     6900
aactaacacg ggtgttctgt cacggcacat attaaactcc tattctcatt tagaagatgg     6960
tggttcgtat ggtagaacat ttgacccatt taccaataaa gaaatgcagt gggttcaatt     7020
taaaccgaat agaccaagaa aaggttctac tggtaaggta atcaaatatg aatcgccaaa     7080
aggtgaacct acaagagttc taatgccgtt tgtgcctatg aaaatatggc aacggattag     7140
cgataagttc ggagtaccga ttaatcgaa  aaaagatact cacttttggg aatgggtaaa     7200
gaataatcca tcgatacga  ttgccattac agaaggaaat aaaaaagcta attgcctatt     7260
atcctatggc tatcctgcta ttgcctttgt aggcatttgg aacggattag agaaaataaa     7320
tgatttctcg aaggaaaagc agttaaaaga ggattgaaa  tggttgttat ccaacggcaa     7380
ccgaaatatt aatatcatct ttgaccaaga ccagaaacaa aaaactgtaa ttaatgtaaa     7440
caaagctatt ttgctttat  cttctctaat aagtagaaat ggtcataaag ttaatattgt     7500
gcaatggttg ccgtcaaaag gtaaaggaat agatgattat ttggtagctt taccttttga     7560
gaaagagaa  aatcatttag acaacttaat taaattgca  ccatcattta ttttttggtc     7620
aactaaatac ttattcaagt gtcgtaaacc agatttaacc gtaaattgcc gttatttgag     7680
cgatgcagta aaagaattac ctcaagagga tatagcatta atagcacctc acggcacggg     7740
taaaacttca ttagtagcta ctcacgttaa gaatcggagt tatcacggaa ggaaaactat     7800
ttcattggtg catcttgaaa gttagccaaa agctaatggc aacgcacttg gattatatta     7860
ccgaaccgaa aataatattg aaaagcaata tcttggattt agcttatgtg tagatagttg     7920
ccgtgataag attaacggca ttacaactga tattattttca ggtcaagatt attgccttttt    7980
cattgatgaa attgaccaag taattccaca catccttaac agtgaaactg aagtaagtaa     8040
gtatagatgc accatcattg acacttttttc tgaactggtg agaaatgctg aacaggtcat     8100
tattgctgat gctgatttat ccgatgtgac gattgaccta ataagaaaca tcagaggtaa     8160
aaaactatat gtaatcaaga atgaatatca gtatcaggga atgactttta acgccgttgg     8220
ttcaccatta gaaatgatgg caatgatggg aaaatcggtg tcagggca agaaattatt     8280
tattaacacc acatcccaaa aggcaaaag  taagtacggc acaatcgctc ttgagtctta     8340
tattttggt  ctaaataaag aagcaaagat attaagaata gactctgaaa ccactaaaaa     8400
ccctgaacat ccagcctata aaatcattga ccaagactta aataatatcc tcaaagatta     8460
tgattatgtc attgcctcac cttgccttca aacaggtgtc agtattacct aaaagggca     8520
ttttgaccag caatttaact tttccagtgg aaacattaca cctcattgct ttttcagca     8580
aatgtggcgg ttgagggatg cagaaattga aagattctat tatgtgccga actcatctaa     8640
cctcaatctc attggaata  agtcaagttc accatcagac cttctaaaga gcaataacaa     8700
gatggaacg  gcaacggtta accttttggg tagaatcgac tccgaatatt ccctagagta     8760
tgaatcgaac ggcatttggc ttgagacgtg ggcaaaatta tcagcacggc ataacagttc     8820
aatgcgttgt tactctgaaa ttcttaccta tctaattacg tctcaagggc ataaattaaa     8880
tatcaacatt ccctcacctc ttgcagatat aagaagcta  aatgatgagg taagtagtaa     8940
cagggaaaag gtaaaaaatg agagatactc tcagaggtta aactcaccag atattaacga     9000
tgcagaagct accatactcg aatcaagaga gcggtatgac ggattgactc tcaatgagag    9060
atgcacccta gaaaacgcata aagttaagaa gcggtatggg aatgaagaa  tggatatttct   9120
cacctttgat gatgatggac tataacagaaa agctattgcc tttttattacc tcaccatcgg    9180
taaacctcat ctcaaggcta atgacagtca agctattgcc aaaatgggca atgacaataa    9240
```

FIG. 39 (continued)

```
aggcaagatt ctatcaaaag acttagttaa taaaacttac tccgctcgtg tgaaggtctt    9300
agagattctt aaactaactg actttatcga caatcttaga gatgaactct taataactcc    9360
caataatcca gctatcaccg attttaataa tcttctgcta agagctaaga aggatttaag    9420
agtattagga gtcaacatcg gaaaatatcc aatggccaac attaatgccg tacttactct    9480
cattggtcac aaactttctg taatgagaga tgagttcgga aaagagaaaa ggataaaagt    9540
agatggtaaa tcataccgat gttatcaact tgaaacatta ccagatttta ccaatgatac    9600
tcttgactac tggttagaaa atgatagcca aaaagaagta acagcaacag aaaattactc    9660
cgaaaatttt aaccottcaa atagctacaa tccagacagt aagacactt cagagggtgc    9720
aaatttccta tatataaata aagaagaatt gcatccaaat aaattgcacc tagaaataaa    9780
agaaggtgct gaactttttt tattcggggt aaaggtgatt gtgaaggaa tcttggacgg    9840
ggcagtaact atattctcta tgggtcaaga atacgattta tccctcaatg aactagaggg    9900
gatgttaaca tcatgaactt tacaagaatc tttttaaagg gcgatcgcac catgttaaat    9960
gatggtacat ttgttcagat atttgatatt taccatgacc acgcattggg agtgaccctt   10020
gaccttaaga cagaaaaaat tatttccgat gatgttaggg taattactgt caaagactta   10080
ttgttcgatg gcacttataa agggtaaaa tcttttatgc ccgataatgc ccgataatgc   10140
ccgattgatg ctacaaaatc ccataatcat aagcgataat ccctaatag cttgtaattc   10200
ttgaaccgta gcgatttag agtattccaa aagaagaaa taaacaccg aaaatgtcgt   10260
atttcacata tataaaccaa ggttttttgc cctaaaatct ttatgtttgt agtgtgatgt   10320
tgggtcaaaa tgtcagaaa agttgcaagg ttttatgga tgcttacgcg cgcgagggt   10380
aagcatcccc aaatagttac tttatcctag tccatgccca tttattgccg tcccgttcgg   10440
cttaaaaaaa gtgccaaaac tcacaaggtg caataaaaag ttcgtgacct ttcgcaaccc   10500
tagataatct tcaacagtt acttttttc ctatatctc ggtacaaagt ttggctagtt   10560
tctcttttcc ctcttttca atcaagcctt cttgtatgcc caactcattg attaatctct   10620
ctattttac cattatttcc cgttcaggta gtttatcccc taaatcttca tcgggggca   10680
atgtagggca ttctgaaggg gcttttttctt ctgtctggac attatctaat attgaagtaa   10740
ccaaactatc ttcagttttt tctattccta ttaattcata ttcggttact gtatccgtat   10800
caatatccga ataactatct ttatccgtat tagctattcg gttaagttta tcgttaact   10860
cagaaacaag actatatagc ggttttagct ttcttctat cctgttatct aatacggata   10920
agtttatacg gttatcatta tccgtattag tatcattggg cttttttggt agttctaccc   10980
cctcataaac cgcttttatt cccaattcca acagactgat aacagtatcc tttataatgg   11040
gttttttgct gatatggtga actttgccc cttccatcat tgcgatactt tctatctcac   11100
tcatcaactt atcgcttaag tgaatctcgt atcgtttaa tcccttactg gtttatttca   11160
tatccgttta ctttattcgg ttaacaattc tattttatac gaataaaata ttatacggtt   11220
aactttatac gttaactat tttatctata cggataacag taataagtta ttcgtattag   11280
ttatacgttt actttatcc aaataaaatt agtgcattta aactaaaaga atgatttat   11340
cggagttgat agcattggat taacctaaag atgtttataa gctatatctg ataagtattt   11400
aaggttatct tgttattctg tttattgaca ttatcagaat aaaagaatag aatataattg   11460
ttgagagata agaggtttaa gtgattatgg ttaagaagtt agttggttat gtcagggtca   11520
gtagtgaatc gcaagaggat aaacactagct tacagaatca gatagagaga attgaagcat   11580
attgtatgc ttttggttat gagttggtaa aaatattcaa agaggttgcc actgtacaa   11640
aagcagatat tgaaaccgt cctattttta atgaagctat agaatacttg aaacaggata   11700
atgctaatgg aattattgcc ttgaagctag accgaatcgc acggaatgct ttagatgtat   11760
tgcgtttgt tgtgaaacc ttagaaccac aaaataaaat gttagtgtta ctagatattc   11820
aggtagatac ttcgacaccct tcaggaaaaa tgatttttaac tgtaatgagt gccgttgctg   11880
aactcaggaa agacatgatc tatgatcgca ctcaggggg tagaaagaact aaagcccaaa   11940
agggcgggta tgcctacggg aaacctaaat ttggctataa gactgaagaa aaggaactaa   12000
aagaagattc agcacaacag gaaactatta aactaattaa gagacaccgt aggtcaggga   12060
aaagctacca gaaaatagct gattatctca atgcccaaag tattcccact aaacaaggta   12120
agaaatggag ttctagcgtc gtctatcgaa tctgtcagga aaagctggt taagtctgtt   12180
tatagatatt tagaatttat tgaataaaaa tagtatgaac aataaatatt tatggactaa   12240
ccagctcgg aaacgtttaa ctgaacgatg ggaaataaaa gaatcatggg ttattgatac   12300
catcgaaaat cctgaacgtt cagaatttat tgttgatgag tcaggggaaa aatatcatta   12360
ctataaaga atagctaagt taagaatag agtgttagaa gtgataactt ctgccaactc   12420
aacacccaca agaataataa ccttttactt taaccgtaac atgaggaaaa atttatgatt   12480
gttacttacg ataatgaagt tgacgcaatt tattttaagt taacggaaaa taaaattgat   12540
agcaccgaac ctcaaacaga caggattatc attgattacg atgaagtaa taatattgtt   12600
ggcattgagg tattagattt taattatctt gtcaagaaag gtttaaccgt tgctgattta   12660
ccttttttctg aagatgaaag attaacagct tctcaatatt ttaattttcc tgttgctatc   12720
taatccagaa ggggcaataa tcccottctt tcatcgagtt agacttaata tcacaaagt   12780
```

FIG. 39 (continued)

```
cattttcatt ttaccgtttc ttttccacag cgtccgtacg ccccttgtta aatctcaaaa    12840
ccgacaatt  atgatgttta taaaaagtta ctcactttaa taagtattta tactcattaa    12900
agggttattc ttttttgta  gcctgatagg ttgggaagga atatttcaga ttatcagatt    12960
tgttgaatat ttt                                                       12973
```

FIG. 39 (continued)

```
ID   #1639\\pABICyano1::smtB-PsmtA*1-zmPDC(opt1)_dsrA-Prbc*(optRBS)-synADH(opt1)_ter
standard; circular DNA;      ; 12973 BP.
CC   This file is created by Vector NTI
CC   http://www.invitrogen.com/
CC   VNTDATE|645696805|
CC   VNTDBDATE|645697025|
CC   LSOWNER|
CC   VNTAUTHORNAME|Ulf Duehring|
FH   Key             Location/Qualifiers
FH
FT   insertion_seq   2228..2073
FT                   /vntifkey="14"
FT                   /label=dsrA
FT                   /note="dsrA terminator from E.coli"
FT   gene            2343..3353
FT                   /vntifkey="60"
FT                   /note="ADH"
FT   CDS             2343..3350
FT                   /vntifkey="4"
FT                   /label=synADH(opt1)
FT   terminator      3354..3509
FT                   /vntifkey="43"
FT                   /label=TrbcSABICyano1
FT   promoter        3546..4009
FT                   /vntifkey="30"
FT                   /label=PrbcABICyano1
FT   CDS             4011..4826
FT                   /vntifkey="4"
FT                   /label=Km**
FT                   /note="Km**"
FT   CDS             12388..12636
FT                   /vntifkey="4"
FT                   /label=ORF\6
FT                   /note="orf6"
FT   CDS             12128..12391
FT                   /vntifkey="4"
FT                   /label=ORF\5
FT                   /note="orf5"
FT   CDS             11400..12086
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10310..11074)
FT                   /vntifkey="4"
FT                   /label=ORF\3
FT                   /note="orf3"
FT   CDS             9865..10050
FT                   /vntifkey="4"
FT                   /label=ORF\2
FT                   /note="orf2"
FT   rep_origin      complement(9165..9182)
FT                   /vntifkey="33"
FT                   /label=Rep_Origin_1
FT                   /note="potential rep origin; match pNostoc (Acc# M81381) nick
site (359-375); on reserve strand"
FT   misc_feature    9425..9458
FT                   /vntifkey="21"
FT                   /label=Rep\motif
FT                   /note="Rep protein active site motif EXXKYXVKXXD"
FT   CDS             6644..9829
```

FIG. 41

```
FT                      /vntifkey="4"
FT                      /label=ORF\1
FT                      /note="orf1  rep ori binding protein slr7037 homolog Similar to
hypothetical protein slr7037 of plasmid pSYSA (103 kb)  of Synechocystis sp. PCC 6803"
FT   primer_bind        complement(5432..5463)
FT                      /vntifkey="28"
FT                      /label=Bom-F
FT   primer_bind        5114..5145
FT                      /vntifkey="28"
FT                      /label=Bom-R
FT   rep_origin         complement(5069..6107)
FT                      /vntifkey="33"
FT                      /label=OriVT
FT   promoter           2274..2342
FT                      /vntifkey="30"
FT                      /label=Prbc* (optRBS)
FT                      /note="improved version of rbcL promoter from PCC6803"
FT   CDS                593..2201
FT                      /vntifkey="4"
FT                      /label=zmPDC(opt1)
FT   CDS                complement(69..392)
FT                      /vntifkey="4"
FT                      /label=smtB
FT                      /note="smtB gene from Synechococcus PCC7002"
FT   promoter           394..494
FT                      /vntifkey="30"
FT                      /label=PsmtA*1
FT                      /note="improved version of smtA promoter from PCC7002"
SQ   Sequence 12973 BP; 3974 A; 2324 C; 2562 G; 4113 t;
     tcgacgggca aactttatga agcagatcaa gactatatcc gccaagcaac cggcagccgc         60
     gttgattagt gggtgtgtcc atcctctggt tcgtctaggt gctccgaagc gtcacgatag        120
     agattaagaa tgtggtgatc cttgaggcga taaatcacat tccgcccttc cttgcgatag        180
     ctcactaaac gtgctgtgcg caggqttctt agttqqtqaq agacagccga ttcactcatt        240
     tcaacgqcqq cqqaqagttc ccccaccccqc atctctccaq tqqccaqqqc cqaaaqaata        300
     cgccaqcqqt tgqcatcccc caaqacaccc aaaaattcqq ccatccqttq qqccttqqct        360
     tgqttcaaqa ttttqccact gtqqtctqtc attqttcqct qatctaaaca ataccqaat         420
     aattqttcat gtqttaatct aaaaaatqtqa acaatqqtc aactattqaa qacaatacca         480
     aqqaqqtqat aaccatqaat tcttataccq tqqqtacttq tttaqccqaa cqcttaqtqc         540
     aaattqqttt aaaacatcat tttqccqtqq ctqcqqqacta caattctaqt ttattqqata         600
     acttattatt aaataaaaac atqqaacaaq tqtattqttq taatqaatta aattqtqqtt         660
     tttctqctqa aqqttatqct aqaqctaaaq qtqcaqctqc tqctqttqtt acttattctq         720
     tqqqtqcttt atctqcttt qatqctattq qtqqtqctta tqccqaaaat ttaccqqtqa         780
     ttttaatttc tqqtqcccct aataactatq atcatqcqqa tqqacatqtt ttacatcatq         840
     ccttaqqtaa aaccqattat cattatcaat taqaaatqqc caaaaatatt actqctqctq         900
     ccqaaqctat ttatactcct qaaqaaqccc ctqccaaaat tqatcatqtq attaaaaccq         960
     ccttaacqcqa aaaaaaccc qtqtatttaq aaattqcctq taatattqct tctatqccct        1020
     gtgctgctcc tgggcctgct tctgctttat taatgatga gcctctgat gaagctagtt        1080
     taaattgctgc cgtggaagaa accttaaaat ttattgccaa tcgcgataaa gttgccgtgt        1140
     tagttggttc taaattaaga gctgctggtg ctgaagaagc tgctgttaas tttgtgatg        1200
     ctttaggtgg tgcagttgct actatggctg ctgccaaatc tttttttccc gaagaaatc        1260
     cccattctat tggaactgtt tggggagaag tttcttatcc tggtgtggaa aaaactatga        1320
     aagaagccga cgctgttatt gctttagccc ctgtgtttaa tgattattct accactggtt        1380
     ggactgatat tcccgatccc aaaaaattag ttttagccga acctcgttct gttgttgtta        1440
     atggtgttcg ctttccctct gtgcatttaa aagattattt aaccgcgtta gccaaaaag        1500
     ttttctaaaa aactggtgcc ttagattttt ttaaatcgggt gaattaaaga        1560
     aagctgctcc tgctgatcct tctgctcctt tagttaatgc tgaaattgcc cgtcaagttg        1620
     aagcttatt aaccctaat actaccgtta ttgcgaaaac tggtgattct tggtttaatg        1680
     cccaacgcat gaaattgccc aatggtgccc gtgttgaata tgaaatgcaa tggggtcata        1740
```

FIG. 41 (continued)

```
ttggttggtc tgtacctgct gcttttggtt atgctgttgg tgctcctgaa cgtcgtaata   1800
ttttaatggt gggtgatggt tcttttcaat taactgccca agaagttgcc caaatggttc   1860
gcttaaaatt accgttatt attttttaa taaataatta tggttatacc attgaagtga    1920
tgattcatga tgggccatat aataatatta aaaattggga ttatgcgggt ttaatggaag   1980
tgtttaatgg taatggtggt tatgattctg ggtgttaaa aggtttaaaa ggcaaaactg   2040
gtggtgaatt agctgaagct attaaagttg cctagccaa tactgatggg ccaaccttaa    2100
ttgaatgttt tattggtcgc gaagattgta ccgaagaatt agttaaatgg ggtaaacgtg   2160
ttgctgtgc taattctgc aaaccgtga ataaattatt gtaattttg gggatcaatt      2220
cgagctcagc aagtttcatc ccgaccccct caggggtcggg attttttttat tgtactagtt  2280
gccataagta aaggcatccc ctgcgtgata taattacctt cagtttaagg aggtatacac   2340
atatgattaa agcctatgct gccttagaag ccaatggtaa attacaaccc tttgaatatg   2400
atcctggtgc tttaggtgcc aatgaagtgg aaattgaagt gcaatattgt ggtgtgtgtc   2460
attctgattt atctatgatt aataatgaat ggggtatttc taattatccc ttagttcctg   2520
gtcatgaagt tgttggtact gttgctgcta tgggtgaagg tgttaatcat gtggaagtgg   2580
gtgatttagt tggtttaggt tggcattctg gttattgtat gacctgtcat tcttgtttat   2640
ctggttatca taatttatgt gccactgccg aatctactat tgtgggtcat tatggtggtt   2700
ttggtgatag agttcgtgct aaaggtgttt ctgtggtgaa attacccaaa ggtattgatt   2760
tagcctctgc tgggcttta ttttgtggtg gtattaccgt tttttctccc atggtggaat   2820
tatctttaaa acctaccgcc aaagttgctg ttattggtat tggtggttta ggtcatttag   2880
ccgttcaatt tttaagagcc tggggttgtg aagttactgc ttttacctct tctgcccgta   2940
aacaaaccga agtttagaa ttaggtgccc atcattttt agattccacc aatcctgaag    3000
ctattgcttc tgccgaaggt aaatttgatt atattattc taccgtgaat ttaaaattag   3060
attggaattt atatatcagt accttagccc ctcaaggtca ttttcatttt gttggtgtgg   3120
tgttagaacc cttggactta aactatttc ccttattaat gggacaacgt tctgtttctg    3180
cttctcctgt tggttctcct gctactattg ccactatgtt agattttgcc gtgcgtcatg   3240
atattaaacc cgtggtggaa caatttttctt ttgatcaaat taatgaagcc attgcccatt   3300
tagaatctgg taaagcccat tatcgcgtgg tgttatctca ttctaaaaat aataagatt    3360
aacttctaaa ctgaaacaaa tttgagggta ggcttcattg tctgcccctta ttttttttatt  3420
taggaaaagt gaacagacta aagagtgttg gtctattgc tttgagtatg taaattaggc   3480
gttgctgaat taaggtatga ttttgacc cttctctctt ctgcaggatc atcttgctga    3540
aaaactcgag cgctcgttcc gcaaagcggt acggagttag ttaggggcta atgggcattc   3600
tcccgtacag gaaagagtta gaagttatta attatcaaca attctccttt gcctagtgca   3660
tcgttacctt tttaattaaa acataaggaa aactaataat cgtaataatt taacctcaaa   3720
gtgtaaagaa atgtgaaatt ctgacttta taacgttaaa gaggggaaaaa ttagcagttt   3780
aaaatccta gagaatagtc tgggtaagc atagagaatt agattagtta agttaatcaa   3840
attcagaaaa aataataatc gtaaatagtt aatctgggtg tatagaaaat gatcccctc   3900
atgataagat ttaaactcga aaagcaaaag ccaaaaaact aacttccatt aaaagaagtt   3960
gttacatata acgctataaa gaaaatttat atattggag gatacaaacc atgtctcata   4020
ttcaacgtga aactagttgt tctcgccctc gtttaaattc taatatggat gccgatttat   4080
atggttataa atgggctcgt gataatgttg gtcaatctgg tgctactatt tatcgtttat   4140
atggtaaacc tgatgctcct gaattattct tgaaacatgg taaagttct gttgctaatg   4200
atgttactga tgaaatggtt cgtttaaact ggttgactga atttatgcct ttacctacta   4260
ttaaacattt tattcgtact cccgatgatg cttggttatt aactactgct attcctggta   4320
aaactgcttt tcaagttta gaagaatatc ctgattctgg tgaaatatt gttgatgctt    4380
tagctgtttt ttacgtcgt ttacattcta ttccgtttg taattgtcct tttaattctg    4440
atcgtgtttt tcgtttagct caagctcaat ctgtatgaa taatggttta gttgatgctt    4500
ctgattttga tgatgaacgt aatggttggc ctgttaaaca agtttggaaa gaaatgcaca   4560
aattgttacc ttttctcct gattctgtt ttactcatgg tgattttct ttagataatt     4620
tgatctttga tgaaggtaaa ttgattggtt gtattgatgt tggtcgtgtt ggtattgctg   4680
atcgttatca agatttagct atttatggga attgttaagg tgaattttct ccttctttac   4740
agaaacgttt atttcagaaa tatggtatt ataatcctga tatgaacaag ttacaatttc    4800
atttaatgtt ggacgagttc ttttaagaat taattcatga ccaaaatccc ttaacgtgag   4860
ttttcgttcc actgagcgtc agacccgta gaaagatca aaggatcttc ttgagatcct    4920
ttttttctgc gcgtaatctg ctgcttttta aattaccgtac acgtgttatt actttgttaa   4980
cgacaattgt cttaattaac tgggctcat gggcttccg ctcactgccc gctttccagt    5040
cgggagacct gtcgtgccag ctctgcagat gcgtcgaaa acctctgaca catgcagctc    5100
ccggagaccgg tcacagcttg tctgtaagcg gatgccggga gcagacaagc ccgtcagggc   5160
gcgtcagcgg gtgttggcgg gtgtcggggc gcagccatga cccagtcacg tagcgatagc   5220
ggagtgtata ctggcttaac tatgcggcat cagagcagat tgtactgaga gtgcaccata   5280
tgcggtgtga aataccgcac agatgcgtaa ggagaaaata ccgcatcagg cgctcttccg   5340
cttcctcgct cactgactcg ctgcgctcgg tcgttcggct gcggcgagcg gtatcagctc   5400
```

```
actcaaaggc ggtaataogg ttatccacag aatcagggga taacgcagga aagaacatgt  5460
gagcaaaagg ccagcaaaag gccaggaacc gtaaaaaggc gcgttgctg gcgttttcc   5520
ataggctccg ccccctgac gagcatcaca aaaatcgacg ctcaagtcag aggtggcgaa  5580
acccgacagg actataaaga taccaggcgt ttccccctgg aagctccct gtcgctctc   5640
ctgttccgac cctgccgctt accggatacc tgtccgcctt tctccttcg ggaagcgtgg  5700
cgctttctca tagctcacgc tgtaggtatc tcagttcggt gtaggtcgtt cgctccaagc  5760
tgggctgtgt gcacgaaccc cccgttcagc ccgaccgctg cgccttatcc ggtaactatc  5820
gtcttgagtc caacccggta agacacgact tatcgccact ggcagcagcc actggtaaca  5880
ggattagcag agcgaggtat gtaggcggtg ctacagagtt cttgaagtgg tggcctaact  5940
acggctacac tagaaggaca gtatttggta tctgcgctct gctgaagcca gttaccttcg  6000
gaaaaagagt tggtagctct tgatccggca aacaaccac cgctggtagc ggtggttttt   6060
ttgttgcaa gcagcagatt acgcgcagaa aaaaaggatc tcaagaagat cctttgatct   6120
tttctactgc agaagcttgt tagacaccct gtcatgtatt ttatattatt tatttcacca  6180
tacggattaa gtgaaaccta atgaaaatag tactttcgga gctttaactt taatgaaggt   6240
atgtttttt atagacatcg atgtctggtt taacaatagg aaaaagtagc taaaactccc    6300
atgaattaaa gaaataacaa ggtgtctaac aacctgttat taagaatgtt agaaaagact  6360
taacatttgt gttgagtttt tatagacatt ggtgtctaga catacggtag ataaggttg    6420
ctcaaaaata aaataaaaaa agattggact aaaaaacatt taatttagta caatttaatt  6480
agttatttt tcgtctcaaa ttttgctttg ttgagcagaa atttagataa aaaaatcccc    6540
gtgatcagat tacaatgtcg ttcattgtac gatgtgtcga aaaatcttta cgacactcta  6600
aactgaccaa acggggggaaa aagaaaactg aactaataac atcatgatac tggaaaacc   6660
tagcaattct caaccctaa acaaagaaa cttccaaaac cctgaccata taaggagtg     6720
gcaacaatca gcaatcagtc aagatttgat agcagaaaat cttgtatcgg ttgctaatgg  6780
ttttgatgta ctatttatcg gcaatasata ccgaactaac acgggtgttc tgtcacggca   6840
catattaaac toctattctc atttagaaga tggtggttcg tatggtagaa catttgaccc  6900
atttaccaat aaagaaatgc agtgggttca atttaaaccg aatagaccaa gaaaaggttc  6960
tactggtaag gtaatcaaat atgaatcgcc aaaaggtgaa cctacaagag ttctaatgcc  7020
gtttgtgcct atgaaaatat ggcaacggat tagcgataag ttcggagtac cgattaatcc  7080
gaaaaaagat actcacttt gggaatgggt aaagaataat ccatcgatac cgattgccat    7140
tacagaagga aataaaaaag ctaattgcct attatcctat ggctatcctg ctattgcctt   7200
tgtaggcctt tggaacggat tagagaaaat aaatgattc tgaaggaaa agcagttaaa     7260
agaggatttg aaatggttgt tatccaacgg caacgaaat attaatatca tctttgacca   7320
agaccattga caaaaactg taattaatgt aaacaaagct attttcgctt tatcttctct   7380
aataagtaga aatggtcata aagttaatat tgtgcaatgg ttgccgtcaa aaggtaaagg  7440
aatagatgat tatttggtag ctttaccttt tgagaaaaga gaaaatcatt tagacaactt  7500
aattaaaatt gcaccatcat ttaattttg gtcaactaaa tacttattca agtgtcgtaa   7560
accagattta accgtaaatt gccgttattt gagcgatgca gtaaaagaat tacctcaaga   7620
ggatatagca ttaatagcac ctcacggcac gggtaaaact tcattagtag ctactcacgt   7680
taagaatcgg agttatcacg gaaggaaaac tatttcattg gtgcatcttg aaagtttagc   7740
caaagctaat ggcaacgcac ttgattata ctaccgaacc gaaaataata ttgaaagca    7800
atatcttgga tttagcttat gtgtagatag ttgccgtgat aagattaacg gcattacaac   7860
tgatatattt tcagtcaag attattgct tttcattgat gaaattgacc aagtaattcc    7920
acacatcctt aacagtgaaa ctgaagtaag taagtataga tgcaccatca gtgacacttt   7980
ttctgaactg gtgagaaatg ctgaacaggt cattattgct gatgctgatt tatccgatgt   8040
gacgattgac ctaatagaaa acatcagagg taaaaaacta tatgtaatca agaatgaata   8100
tcagtatcag ggaatgactt taacgccgt tggttcacca ttagaaatga tggcaatgat   8160
gggaaaatcg gtgtcagaag gcaagaaatt atttattaac accacatccc aaaaggcaaa  8220
aagtaagtac ggcacaatcg ctcttgagtc ttatattttt ggtctaaata aagaagcaaa   8280
gatattaaga atagactctg aaaccactaa aaaccctgaa catccagcct ataaaatcat   8340
tgaccaagac ttaaataata tcctcaaaga ttatgattat gtcattgcct cacttgcct    8400
tcaaacaggt gtcagtatta ccttaaaagg gcatttgac cagcaattta cttttccag    8460
tggaaacatt acacctcatt gcttttaca gcaaatgtgg cggttgaggg atgcagaaat   8520
tgaaagattc tattatgtgc cgaactcatc taacctcaat ctcattggga ataagtcaag  8580
ttcaccatca gaccttctaa agagcaataa caagatggca acggcaacgg ttaaccttt   8640
gggtagaatc gactccgaat attccctaga gtatgaatcg cacggcattt ggcttgagac  8700
gtgggcaaaa ttatcagcac ggcataacag ttcaatgcgt tgttactctg aaattcttac  8760
ctatctaatt acgtctcaag ggcatasatt aaatatcaac attccctcac ctcttgcaga  8820
tattaagaag ctaaatgatg aggtaagtag taacagggaa aaggtaaaaa atgagagata  8880
```

FIG. 41 (continued)

```
ctctcagagg ttaaactcac cagatattaa cgatgcagaa gctaccatac tcgaatctaa   8940
agagcaaaaa atcggattga ctctcaatga gagatgcacc ctagaaaagc ataaagttaa   9000
gaagcggtat gggaatgtaa agatggatat tctcaccttt gatgatgatg gactataccc   9060
caaactcaga ctatttatt acctcaccat cggtaaacct catctcaagg ctaatgacag    9120
aaaagctatt gccaaatgg gcaatgacaa taaaggcaag attctatcaa aagacttagt    9180
taataaaact tactccgctc gtgtgaaggt cttagagatt cttaaactaa ctgactttat   9240
cgacaatctt agagatgaac tcttaataac tccaataat ccagctatca ccgattttaa    9300
taatcttctg ctaagagcta agaaggattt aagagtatta ggagtcaaca tcggaaaata   9360
tccaatggcc aacattaatg ccgtacttac tctcattggt cacaaacttt ctgtaatgag   9420
agatgagttc ggaaaagaga aaaggataaa agtagatggt aaatcatacc gatgttatca   9480
acttaaaaca ttaccagatt ttaccaatga tactcttgac tactggttag aaaatgatag   9540
ccaaaaacaa gtaacagcaa cagaaaatta ctccgaaaat tttaaccctt caaatagcta   9600
caatccagac agtaagacac ttcagagggg tgcaaatttc ctatatataa ataaagaaga   9660
attgcatcca aataaattgc acctagaaat aaaagaaggt gctgaacttt ttttattcgg   9720
ggtaaaggtg attgtgaaag gaatcttgga cgggcagta actatattct ctatgggtca    9780
agaatacgat ttatccctca atgaactaga ggggatgtta acatcatgaa ctttacaaga   9840
atctttttaa agggcgatcg caccatgtta aatgatggta catttgttca gatatttgat   9900
atttaccatg accacgcatt gggagtgacc cttgacctta agacagaaaa aattatttcc   9960
gatgatgtta gggtaattac tgtcaaagac ttattgttcg atggcactta taaagggta   10020
aaatctttta tgcccgataa tgcccgataa tgcccgattg atgctacaaa atcccataat   10080
cataagcgat aatccctaa tagcttgtaa ttcttgaacc gtagcgattt tagagtattc   10140
caaaaagaag aaataaacac cgcaaaatgt cgtatttcac atatataaac caaggttttt   10200
tgccctaaaa tctttatgtt tgtagtgtga tgttgggtca aaatggtcag aaaagttgca   10260
aggttttat ggatgcttac gcgcgcgagg ggtaagcatc cccaaatagt tactttatcc     10320
tagtccatgc ccattattg ccgtcccgtt cggctttaaa aaagtgccaa aactcacaag    10380
gtgcaataaa aagttctgta cctttcgcaa ccctagataa tctttcaaca gttactttt    10440
ttcctattat ctggtacaa agtttggcta gtttctcttt tccctcttt tcaatcaagc     10500
cttcttgtat gcccaactca ttgattaatc tctctatttt taccattatt tcccgttcag   10560
gtagtttatc ccctaaatct tcatcggggg gcaatgtagg gcattctgaa ggggcttttt   10620
cttctgtctg gacattatct aatattgaag taaccaaact atcttcagtt ttttctattc   10680
ctattaattc atattcggtt actgtatccg tatcaatatc cgaataacta tctttatccg   10740
tattagctat tcggttaagt ttatccgtta actcagaaac aagactatat agcggtttta   10800
gcttttcttc tatcctgtta tctaatacgg ataagtttat acggtatca ttatccgtat    10860
tagtatcatt gggctttttt ggtagttcta cccctcata aaccgcttt attcccaatt     10920
ccaacagact gataacagta tcctttataa tgggtttttt gctgatatgg tgaacttttg   10980
cccttccat cattgcgata ctttctatct cactcatcaa cttatcgctt aagtgaatct    11040
cgtatctgtt taatcccta ctggttttat tcatatccgt ttactttatt cggttaacaa    11100
ttctattta tacgaataaa atattatcg gttaacttta tcgttaac tattttatct       11160
atacggataa cagtaacaag ttattcgtat tagttatacg ttactttta tccaaataaa    11220
attagtgcat ttaaactaaa agaatgattt tatccgagtt gatacgcattg gattaaccta  11280
aagatgttta taagctatat ctgataagta tttaagctta ttttgttatt ctgtttattg   11340
acattatcag aataaaagaa tagaaataaa ttgttgagag ataagaggtt taagtgatta   11400
tggttaagaa gttagttggt tatgtcaggg tcagtagtga atcgcaagag gataacacta   11460
gcttacagaa tcagatagag agaattgaag catattgtat ggcttttggt tatgagttgg   11520
taaaaatatt caaagaggtt gccactggta caaaagcaga tattgaaacc cgtcctattt   11580
ttaatgaagc tatagaatac ttgaacaggg ataatgctaa tggaattatt gccttgaagc   11640
tagccgaat cgcacggaat gcttagatg tattgcgttt ggttcgtgaa accttagaac    11700
cacaaaataa aatgttagtg ttactagata tcaggtaga tacttcgaca ccttcaggaa   11760
aaatgatttt aactgtaatg agtgccgttg ctgaactcga aagagacatg atctatgatc   11820
gcactcaggg gggtagaaag actaaagccc aaaagggcgg tatgcctac gggaaaccta    11880
aatttggcta taagctgaa gaaaaggaac taaagaaga ttcagcacaa caggaaacta    11940
ttaaactaat taagagacac cgtaggtcag ggaaaagcta ccagaaaata gctgattatc  12000
tcaatgccca aagtattccc actaaacaag gtaagaaatg gagttctagc gtcgtctatc   12060
gaatctgtca ggaaaaagct ggttaagtct gtttatagat atttagaatt tattgaataa   12120
aaatagtatg aacaataaat atttatggac taaccacgct cggaaacgtt taactgaacg   12180
atggaaaata aaagaatcat gggttattga taccatcgaa atcctgaaac gttcagaatt   12240
tattgttgat gagtcagggg aaaaatatca ttactataaa agaatagcta gtttaagaa    12300
tagagtgtta gaagtgataa cttctgccaa ctcaacaccc acaagaataa taacctttta   12360
ctttaaccgt aacatgagga aaaatttatg attgttactt acgataatga agttgacgca   12420
atttatttta agttaacgga aaataaaatt gatagcaccg aacctcaaac agacaggatt   12480
```

FIG. 41 (continued)

```
atcattgatt acgatgaaag taataatatt gttggcattg aggtattaga ttttaattat    12540
cttgtcaaga aaggtttaac cgttgctgat ttaccttttt ctgaagatga aagattaaca    12600
gcttctcaat attttaattt tcctgttgct atctaatcca gaagggcaa taatcccctt     12660
ctttcatcga gttagactta atatcacaaa agtcattttc attttaccgt ttcttttcca    12720
cagcgtccgt acgcccctcg ttaaatctca aaaccgacaa tttatgatgt ttataaaaag    12780
ttactcactt taataagtat ttatactcat taaagggtta ttcttttttt gtagcctgat    12840
aggttgggaa ggaatatttc agattatcag atttgttgaa tattttttcgt cagatacgca   12900
aaccttacaa acataattaa caactgaaac tattgatatg tctaggtttt agctctatca    12960
caggttggat ctg                                                       12973
```

FIG. 41 (continued)

```
ID    #1640\pABICyanol::smtB-PsmtA*2-smPDC(opt1)_dsrA-Prbc*(optRBS)-synADH(opt1)_ter
standard; circular DNA;    ; 12973 BP.

CC    This file is created by Vector NTI
CC    http://www.invitrogen.com/
CC    VNTDATE|645697411|
CC    VNTDBDATE|645697431|
CC    LSOWNER|
CC    VNTAUTHORNAME|Ulf Duehring|
FH    Key             Location/Qualifiers
FH
FT    insertion_seq   2228..2273
FT                    /vntifkey="14"
FT                    /label=dsrA
FT                    /note="dsrA terminator from E.coli"
FT    gene            2343..3353
FT                    /vntifkey="60"
FT                    /note="ADH"
FT    CDS             2343..3350
FT                    /vntifkey="4"
FT                    /label=synADH(opt1)
FT    terminator      3354..3509
FT                    /vntifkey="43"
FT                    /label=TrbcSABICyanol
FT    promoter        3546..4009
FT                    /vntifkey="30"
FT                    /label=PrbcABICyanol
FT    CDS             4011..4826
FT                    /vntifkey="4"
FT                    /label=Km**
FT                    /note="Km**"
FT    CDS             12388..12636
FT                    /vntifkey="4"
FT                    /label=ORF\6
FT                    /note="orf6"
FT    CDS             12128..12391
FT                    /vntifkey="4"
FT                    /label=ORF\5
FT                    /note="orf5"
FT    CDS             11400..12086
FT                    /vntifkey="4"
FT                    /label=ORF\4
FT                    /note="orf4 Integrase/Recombinase Similar to Site-specific
recombinase of Bacillus thuringiensis serovar israelensis ATCC 35646"
FT    CDS             complement(10310..11074)
FT                    /vntifkey="4"
FT                    /label=ORF\3
FT                    /note="orf3"
FT    CDS             9665..10050
FT                    /vntifkey="4"
FT                    /label=ORF\2
FT                    /note="orf2"
FT    rep_origin      complement(9165..9182)
FT                    /vntifkey="33"
FT                    /label=Rep_Origin_1
FT                    /note="potential rep origin; match pNostoc (Acc# 081361) nick
site (358-375); on reverse strand"
FT    misc_feature    9425..9458
FT                    /vntifkey="21"
FT                    /label=Rep\motif
FT                    /note="Rep protein active site motig EXXKYKVKXXD"
```

FIG. 43

```
FT   CDS              6644..9929
FT                    /vntifkey="4"
FT                    /label=ORF\1
FT                    /note="orf1  rep ori binding protein slr7037 homolog Similar to
hypothetical protein slr7037 of plasmid pSYSA (103 kb)  of Synechocystis sp. PCC 6803"
FT   primer_bind      complement(5432..5463)
FT                    /vntifkey="28"
FT                    /label=Bom-F
FT   primer_bind      5114..5145
FT                    /vntifkey="28"
FT                    /label=Bom-R
FT   rep_origin       complement(5069..6127)
FT                    /vntifkey="33"
FT                    /label=OriVT
FT   promoter         2274..2342
FT                    /vntifkey="30"
FT                    /label=Prbc*(optRBS)
FT                    /note="improved version of rbcL promoter from PCC6803"
FT   CDS              503..2291
FT                    /vntifkey="4"
FT                    /label=zmPDC(opt1)
FT   CDS              complement(69..392)
FT                    /vntifkey="4"
FT                    /label=smtB
FT                    /note="smtB gene from Synechococcus PCC7002"
FT   promoter         393..494
FT                    /vntifkey="30"
FT                    /label=PsmtB*2
FT                    /note="improvers version of the smtB promoter from PCC7002"
SQ   Sequence 12973 BP; 3975 A; 2324 C; 2561 G; 4113 t;
     tgagggca   aactttatga   agcagatcaa   ggctatatcc   gccaagcaac   cggcagcgc        60
     gtgattagt  gggtgtgtcc   atcctctggt   tcgtctaggt   gctccgaagc   gtcacgatag      120
     agattaagaa tgtggtgatc   cttgaggcga   taaatcacat   tccgccttc    cttgcgatag      180
     ctcactaaac gtgctgtgcg   cagggttctt   agttggtgag   agacagcga    ttcactcatt      240
     tcaacggcgg cggcgagttc   cccaccccgc   atctctccag   tggccaggc    cgaaagaata      300
     cgccagcggt tggcatcccc   caagacaccaa  aaaaattcgg   ccatccgttg   ggccttggct      360
     tggttcaaga ttttgccact   gtggtctgtc   attgttcgct   gatctaaaca   ataacctgaat      420
     aattgttcat gtgttaatct   aaaaatgtga   acaatcgttc   aactatttaa   gacaatacca      480
     aggaggtata aaccatgaat   tcttataccg   tgggtactta   tttagccgaa   cgcttagtgc      540
     aaattggttt aaaacatcat   tttgccgtgg   ctgggaacta   taatttagtg   ttattggata      600
     acttattatt aaataaaac    atggaacaag   tgtattgttg   taatgaatta   aattgtggtt      660
     tttctgctga agtttatgct   agagctaaag   gtcagctgc    tgctgttgtt   acttattctg      720
     tgggtgcttt atctgctttt   gatgctattg   gtggtgctta   tgccgaaaat   ttaccgtgaa      780
     tcttaatttc tgggtgccct   aataacatgc   atcatgccgc   tggacatgtc   ttacatcatg      840
     ccttaggtaa aaccgattat   cattatcact   tagaaatggc   caaaaatatt   actgctgctg      900
     ccgaagctat ttatactcct   gaagaagccc   ctgccaaaat   tgatcatgtg   attaaaaccg      960
     ccttccgcga aaaaaaacca   gtgtatttag   aaattgcctg   taatattgct   tctatgcctt     1020
     gtgctgctcc tgggcctgct   tctgctttat   ttaatgatga   agcctctgat   gaagctagtt     1080
     taaatgctgc cgtggagaa    aaccttaaaat ttattgccaa   tgcgataaa    gttgccgtgt     1140
     tagttggttc taaattaaga   gctgctggtg   ctgaagaacg   tgctgttaaa   tttgctgatg     1200
     cttaggtgg tgcagttgct   actatggctg   ctgccaaatc   tttttttccc   gaagaaaatc     1260
     cccattatat tggaactagt   tggggagaag   tttcttatcc   tggtgtggaa   aaaactatga     1320
     aagaagccga cgctgttatt   gctttagccc   ctgtgtttaa   tgattattct   accactggtt     1380
     ggactgatat tccgatccc   aaaaaattag   ttttagccga   acctgttct    gttgttgtta     1440
     atggtgttcg cttccctct    gtgcatttaa   aagattattt   aaccgctta    gcccaaaaag     1500
     tttctaaaaa aactggtgcc   ttagatttt   ttaaatcttt   aaatgcgggt   gaattaaaaa     1560
     aagcctcttc tgctgatct    tctgctcctt   tagttaatgc   tgaaattgcc   cgtcaagttg     1620
     aagcttatt aaccctaat    actaccgtta   ttgccgaaac   tggtgattct   tggttaatg     1680
     cccaacgcat gaaattacct   aatggtgccc   gtgttgaata   tgaaatgcaa   tggggtcata     1740
     ttggttggtc tgtacctgct   gcttttggtt   atgctgttgg   tgctcctgaa   cgtcgtaata     1800
     tttttaatggt gggtgatggt tcttttcaat   taactgccca   agaagttgcc   caaatggttc     1860
```

FIG. 43 (continued)

```
gcttaaaatt accogttatt atttttttaa taaataatta tggttatacc attgaagtga  1920
tgattcatga tgggccatat aataatatta aaaattggga ttatgcgggt ttaatggaag  1980
tgtttaatgg taatggtggt tatgattctg gtgctggtaa aggtttaaaa gccaaaactg  2040
gtggtgaatt agctgaagct attaaagttg cctagccaa tactgatggg ccaaccttaa   2100
ttgaatgttt tattggtcgc gaagattgta ccgaagaatt agttaaatgg ggtaaacgtg  2160
ttgctgctgc taattctcgc aaacccgtga ataaattatt gtaattttg gggatcaatt   2220
cgagctcagc aagtttcatc ccgacccct caggtcggg atttttttat tgtactagtt   2280
gacataagta aaggcatccc ctgcgtgata taattaccttt cagtttaagg aggtatacac 2340
atatgattaa agcctatgct gccttagaag ccatggtaa attacaaccc tttgaatatg   2400
atcctggtgc tttaggtgcc aatgaagtgg aaattgaagt gcaatattgt ggtgtgtc    2460
attctgattt atctatgatt aataatgaat gggtatttc taattatccc ttagttcctg   2520
gtcatgaagt tgttggtact gttgctgcta tgggtgaagg tgttaatcat gtggaagtgg  2580
gtgatttagt tggtttaggt tggcattctg gttattgtat gacctgtcat tcttgtttat  2640
ctggttatca taattatgt gccactgccg aatctactat tgtgggtcat tatggtggtt   2700
ttggtgatag agttcgtgct aaaggtgttt ctgtggtgaa attacccaaa ggtattgatt  2760
tagcctctgc tgggctttta ttttgtggtg gtattaccgt ttttctccc atggtggaat   2820
tatctttaaa acctaccgcc aaagttgctg ttattggtat tggtggttta ggtcatttag  2880
ccgttcaatt tttaagagcc tggggtgtg aagttactgc tttacctct tctgcccgta   2940
aacaaaccga agtttagaa ttaggtgccc atcatatttt agattctacc aatcctgaag  3000
ctattgcttc tgccgaaggt aaatttgatt atattattc taccgtgatt ttaaaattag   3060
attggaattt atatatcagt accttagccc ctcaaggtca ttttcatttt gttggtgtgg  3120
tgttagaacc cttggactta aacttattc ccttattaat gggacaacgt tctgtttctg   3180
cttctcctgt tggttctcct gctactattg ccactatgtt agattttgcc gtgggtcatg  3240
atattaaacc cgtggtggaa caattttctt ttgatcaaat taatgaagcc attgcccatt  3300
tagaatctgg taaagcccat tatcgcgtgg tgttatctca ttctaaaaat taataagatt  3360
aacttctaaa ctgaaacaaa tttgagggta ggcttcattg tctgcccttg ttttttatt   3420
taggaaaagt gaacagacta aagagtgttg gctctattgc tttgagtatg taaattaggc  3480
gttgctgaat taaggtatga ttttgaccc cttctctctt ctgcaggatc atcttgctga  3540
aaaactcgag cgctcgttcc gcaaagcggt acggagttag ttaggggcta atgggcattc  3600
tcccgtacag gaaagagtta gaagttatta attatcaaca attctccttt gcctagtgca  3660
tcgttacctt tttaattaaa acataaggaa aactaataat cgtaataatt taacctcaaa  3720
gtgtaaagaa atgtgaaatt ctgacttta taacgttaaa gagggaaaaa ttagcagttt  3780
aaaataccta gagaatagtc tggggtaagc atagagaatt agattagtta agttaatcaa  3840
attcagaaaa aataataatc gtaaatagtt aatctgggtg tatagaaaat gatcccttc   3900
atgataagat ttaaactcga aaagcaaaag ccaaaggact aacttccatt aaaagaagtt  3960
gttacatata acgctataaa gaaaatttat atattggag gataccaacc atgtctcata  4020
ttcaacgtga aactagttgt tctcgccctc gtttaaattc taatatggat gccgatttat  4080
atggttataa atgggctcgt gataatgttg gtcaatctgg tgctactatt tatcgtttat  4140
atggtaaacc tgatgctcct gaattattct tgaaacatgg taaaggttct gttgctaatg  4200
atgttactga tgaaatggtt cgtttaaact ggttgactga atttatgcct ttacctacta  4260
ttaaacattt tattgtact cccgatgatg cttggttatt aactactgct attcctggta  4320
aaactgcttt tcaagtttta gaagaatatc ctgattctgg tgaaaatatt gttgatgctt  4380
tagctgtttt tttacgtcgt ttacattcta ttcccgtttg taattgtcct tttaattctg  4440
atcgtgtttt tcgtttagct caagctcaat ctcgtatgaa taatggttta gttgatgctt  4500
ctgattttga tgatgaacgt aatggttggc ctgttgaaca agtttggaaa gaaatgcaca  4560
aatttgttacc ttttctctct gattcttctg ttattttct ttagataatt                4620
tgatctttga tgaagtaa ttgattggtt gtattgatgt tggtcgtgtt ggtattgctg  4680
atcgttatca agatttagct attttatgga attgtttagg tgaatttcct ccttctttac  4740
agaaacgttt atttcagaaa tatggtattg ataatcctga tatgcaacaag ttacaatttc  4800
atttaatgtt ggacgagttc ttttaagaat taatccatga ccaaaatccc ttaacgtgag  4860
ttttcgttcc actgagcgtc agacccgta gaaagatca aggatcttc ttgagatcct    4920
ttttttctgc gcgtaatctg ctgcttttgc aattacgtac acgtgttatt actttgttaa  4980
cgacaattgt cttaattaac tgggcctcat gggccttccg ctcactgccc gctttccagt  5040
cgggaaacct gtcgtgccag ctctgcagat gacggtgaaa acctctgaca catgcagctc  5100
ccggagacgg tcacagcttg tctgtaagcg gatgccggga gcagcaagc ccgtcaggc    5160
gcgtcagcgg gtgttggcg gtgtcgggc gcagccatga cccagtcacg tagcgatagc   5220
ggagtgtata ctggcttaac tatgcggcat cagagcagat tgtactgaga gtgcaccata  5280
tgcggtgtga aataccgcac agatgcgtaa ggagaaaata ccgcatcagg cgctcttccg  5340
cttcctcgct cactgactcg ctgcgctcgg tcgttcggct gcggcgagcg gtatcagctc  5400
```

```
actcaaaggc ggtaatacgg ttatccacag aatcagggga taacgcagga aagaacatgt    5460
gagcaaaagg ccagcaaaag gccaggaacc gtaaaaaggc cgcgttgctg gcgtttttcc    5520
ataggctccg cccccctgac gagcatcaca aaaatcgacg ctcaagtcag aggtggcgaa    5580
acccgacagg actataaaga taccaggcgt ttccccctgg aagctccctc gtgcgctctc    5640
ctgttccgac cctgccgctt accggatacc tgtccgcctt tctcccttcg ggaagcgtgg    5700
cgctttctca tagctcacgc tgtaggtatc tcagttcggt gtaggtcgtt cgctccaagc    5760
tgggctgtgt gcacgaaccc cccgttcagc ccgaccgctg cgccttatcc ggtaactatc    5820
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaaggaca gtatttggta tctgcgctct gctgaagcca gttaccttcg    6000
gaaaaagagt tggtagctct tgatccggca aacaaaccac cgctggtagc ggtggttttt    6060
ttgtttgcaa gcagcagatt acgcgcagaa aaaaggatc tcaagaagat cctttgatct    6120
tttctactgc agaagcttgt tagacaccct gtcatgtatt ttatattatt tatttcacca    6180
tacggattaa gtgaaaccta atgaaatag tacttcgga gctttaactt taatgaaggt     6240
atgttttttt atagcatcg atgtctggtt taacaatagg aaaagtagc taaaactccc      6300
atgaattaaa gaataacaa ggtgtctaac aacctgttat taagaatgtt agaaaagact    6360
taacatttgt gttgagtttt tatagacatt ggtgtctaga catacggtag ataaggttt    6420
ctcaaaaata aaataaaaa agattggact aaaaaacatt taatttagta caatttaatt    6480
agttattttt tcgtctcaaa ttttgctttg ttgagcagaa atttagataa aaaatcccc    6540
gtgatcagat tacaatgtcg ttcattgtac gatgtgtcga aaatcttta cgacactcta    6600
aactgaccac acggggaaa aagaaactg aactaataac atcatgatac tggaaaacc     6660
tagcaattct caacccctaa acaaaagaaa cttccaaaac cctgaccata taaggagtg    6720
gcaacaatca gcaatcagtc aagatttgat agcagaaaat cttgtatcgg ttgctaatgg    6780
ttttgatgta ctatttatcg gcaataaata ccgaactaac acgggtgttc tgtcacggca    6840
catattaaac tcctattctc atttagaaga tggtggttcg tatggtagaa catttgaccc    6900
atttaccaat aaagaaatgc agtgggttca atttaaaccg aatagaccaa gaaaaggttc    6960
tactggtaag gtaatcaaat atgaatcgcc aaaaggtgaa cctacaagag ttctaatgcc    7020
gtttgtgcct atgaaaatat ggcaacggat tagcgataag ttcggagtac cgattaatcc    7080
gaaaaagat actcactttt gggaatgggt aaagaataat ccatcgatac cgattgccat    7140
tacagaagga aataaaaaag ctaattgcct attatcctat ggctatctg ctattgcctt    7200
tgtaggcatt tggaacggat tagagaaaat aaatgatttc tcgaaggaaa agcagttaaa    7260
agaggatttg aaatggttgt tatccaacgg caaccgaaat attaatatca tctttgacca    7320
agaccagaaa caaaaaactg taattaatgt aaacaaagct attttcgctt tatcttctct    7380
aataagtaga aatggtcata aagttaatat tgtgcaatgg ttgcgtcaa aaggtaaagg    7440
aatagatgat tatttggtag ctttaccttt tgagaaaaga gaaaatcatt tagcaacttt    7500
aattaaaatt gcaccatcat ttaatttttg gtcaactaaa tacttattca agtgtcgtaa    7560
accagattta acgtaaatt gccgttattt gagcgatgca gtaaaagaat tacctcaaga    7620
ggatatagca ttaatagcac ctcacggcac gggtaaaact tcattagtag ctactcacgt    7680
taagatcgg agttatcacg gaaggaaaat tattcattg gtgcatctta aagtttagc     7740
caaagctaat ggcaacgcac ttggattata ttacgcaaat gaaaataata ttgaaaagca    7800
atatcttgga tttagcttat gtgtagatag ttgccgtgat aagattaacg gcattacaac    7860
tgatattatt tcaggtcaag attattgcct tttcattgat gaaattgacc aagtaattcc    7920
acacatcctt aacagtgaaa ctgaagtaag taagtataga tgcaccatca ttgacacttt    7980
ttctgaactg gtgagaaatg ctgaacaggt cattattgct gatgctgatt tatccgatgt    8040
gacgattgac ctaatagaaa acatcagagg taaaaaacta tatgtaatca agaatgaata    8100
tcagtatcag ggaatgactt taacgccgt tggttcacca ttagaaatga tggcaatgat    8160
gggcaaatcg gtgtccgaag gcagcaatt atttattaac accacatcc aaaggcaca     8220
aagtaagtac ggcacaatcg ctcttgagtc ttatatttt ggtctaaata aagaagcaaa    8280
gatattaaga atagactctg aaaccactaa aaaccctgaa catccagcct ataaaatcat    8340
tgaccaagac taaaataata tcctcaaaga ttatgattat gtcattgcct caccttgcct    8400
tcaaacaggt gtcagtatta ccttaaaagg gcattttgac cagcaattta acttttccag    8460
tggaaacatt acacctcatt gcttttaca gcaaatgtgg cggttgaggg atgcagaaat    8520
tgaaagattc tattatgtgc cgaactcatc taacctcaat ctcattggga ataagtcaag    8580
ttcaccatca gaccttctaa agagcaataa caagatggca acggcaacgg ttaaccttt     8640
gggtagaatc gactccgaat attccctaga gtatgaatcg cacggcattt ggcttgagac    8700
gtgggcaaaa ttatcagcac ggcataacag ttcaatgcgt tgttactctg aaattcttac    8760
ctatctaatt acgtctcaag ggcataaatt aaatatcaac attccctcac ctcttgcaga    8820
tattaagaag ctaaatgatg aggtaagtag taacagggaa aaggtaaaaa atgagagata    8880
ctctcagagg ttaaactcac cagatattaa cgatgcagaa gtaccatac tcgaatctaa    8940
agagcaaaaa atcggattga ctctcaatga gagatgcacc ctagaaaagc ataaagttaa    9000
gaagcggtat gggaatgtaa agatggatat tctcaccttt gatgatgatg gactataccc    9060
```

FIG. 43 (continued)

```
caaactcaga ctattttatt acctcaccat cggtaaacct catctcaagg ctaatgacag    9120
aaaagctatt gccaaaatgg gcaatgacaa taaaggcaag attctatcaa aagacttagt    9180
taataaaact tactccgctc gtgtgaaggt cttagagatt cttaaactaa ctgactttat    9240
cgacaatctt agagatgaac tcttaataac tcccaataat ccagctatca ccgattttaa    9300
taatcttctg ctaagagcta agaaggattt aagagtatta ggagtcaaca tggaaaata     9360
tccaatggcc aacattaatg ccgtacttac tctcattggt cacaaacttt ctgtaatgag    9420
agatgagttc ggaaaagaga aaaggataaa agtagatggt aaatcatacc gatgttatca    9480
acttgaaaca ttaccagatt ttaccaatga tactcttgac tactggttag aaaatgatag    9540
ccaaaaagaa gtaacagcaa cagaaaatta ctccgaaaat tttaacccct caaatagcta    9600
caatccagac agtaagacac tttcagaggg tgcaaatttc ctatatataa ataaagaaga    9660
attgcatcca aataaattgc acctagaaat aaaagaaggt gctgaacttt ttttattcgg    9720
ggtaaaggtg attgtgaaag aatcttgga cggggcagta actatattct ctatgggtca     9780
agaatacgat ttatccctca atgaactaga gggatgtta acatcatgaa ctttacaaga     9840
atcttttaa agggcgatcg caccatgtta aatgatggta catttgttca gatatttgat     9900
atttaccatg accacgcatt gggagtgacc cttgacctta agacagaaaa aattatttcc    9960
gatgatgtta gggtaattac tgtcaaagac ttattgttcg atggcactta taaagggta   10020
aaatctttta tgcccgataa tgcccgataa tgcccgattg atgctacaaa atcccataat   10080
cataagcgat aatccctaa tagcttgtaa ttcttgaacc gtagccgatt tagagtattc   10140
caaaagaag aaataaacac cgcaaatgt cgtatttcac atatataaac caaggttttt   10200
tgccctaaaa tctttatgtt tgtagtgtga tgtgggtca aaatggtcag aaaagttgca   10260
aggttttttat ggatgcttac gcgcgcgagg ggtaagcatc cccaaatagt tactttatcc   10320
tagtccatgc ccattattg ccgtccgtt cggctttaaa aaagtgccaa aactcacaag   10380
gtgcaataaa aagttctgta cctttcgcaa ccctagataa tctttcaaca gttacttttt   10440
ttcctattat ctcggtacaa agtttggcta gtttctcttt tccctctttt tcaatcaagc   10500
cttcttgtat gcccaactca ttgattaatc tctctatttt taccattatt tcccgttcag   10560
gtagtttatc ccctaaatct tcatcggggg gcaatgtagg gcattcgaa ggggctttt   10620
cttctgtctg gacattatct aatattgaag taaccaaact atcttcagtt ttttctattc   10680
ctattaattc atattcggtt actgtatccg tatcaatatc cgaataacta tctttatccg   10740
tattagctat tggttaagt ttatccgtta actcagaaac aagactatat agcggtttta   10800
gcttttcttc tatcctgtta tctaatacgg ataagtttat acggttatca ttatccgtat   10860
tagtatcatt gggctttttt ggtagttcta ccccctcata aaccgcttt attcccaatt   10920
ccaacagact gataacagta tcctttataa tgggtttttt gctgatatgg tgaacttttg   10980
ccccttccat cattgcgcta ctttctatct cactcatcaa cttatcgctt aagtgaatct   11040
cgtatctgtt taatcccta ctggttttat tcatatccgt ttactttatt cggttaacaa   11100
ttctattttta tacgaataaa atattatacg gttaacttta tacgttaac tattttatct   11160
atacggataa cagtaataag ttattcgtat tagttatacg tttacttta tccaaataaa   11220
attagtgcat tttaaactaaa agaatgattt tatccgagtt gatagcattg gattaaccta   11280
aagatgttta taagctatat ctgataagta tttaaggtta ttttgttatt ctgtttattg   11340
acattatcag aataaaagaa tagaatataa ttgttgagag ataagaggtt taagtgatta   11400
tggttaagaa gttagttggt tatgtcaggg tcagtagtga atcgcaagag gataacacta   11460
gcttacagaa tcagatagag agaattgaag catattgtat ggcttttggt tatgagttgg   11520
taaaaatatt caaagaggtt gccactggta caaaagcaga tattgaaacc cgtcctattt   11580
ttaatgaagc tatagaatac ttgaaacagg ataatgctaa tggaattatt gcttgaagc    11640
tagccgaat cgcacggaat gctttagatg tattgcgttt ggttcgtgaa acctagaac     11700
cacaaaataa aatgttagtg ttactagata ttcagtaga tactcgaca cctcaggaa     11760
aaatgatttt aactgtaatg agtgccgttg ctgaactcga agagacatg atctatgatc    11820
gcactcaggy ggggtagaaa actaaagccc aaaagggcgg gtatgcctac gggaaaccta   11860
aattggcta taagactgaa gaaaaggaac taaaagaaga ttcagcacaa caggaaacta   11940
ttaaactaat taagagacac cgtaggtcag ggaaaagcta ccagaaaata gctgattatc   12000
tcaatgccca agtattccc actaaacaag gtaagaaatg gagttctagc gtcgtctatc   12060
gaatctgtca ggaaaaagct ggttaagtct gtttatagat atttagaatt tattgaataa   12120
aaatagtatg aacaataat atttatggac taaccacgct cggaaacgtt taactgaacg   12180
atgggaaata aagaatcat gggttattga taccatcgaa aatcctgaac gttcagaatt   12240
tattgttgat gagtcagggg aaaatatca ttactataaa agaatagcta agtttaagaa   12300
tagagtgtta gaagtgataa cttctgccaa ctcaacaccc acaagaataa taccttttta   12360
ctttaaccgt aacatgagga aaatttatg attgttactt acgataatga agttgacgca   12420
atttatttta agttaacgga aataaaatt gatagcaccg aacctcaaac agacaggatt   12480
atcattgatt acgatgaaag taataatatt gttggcattg aggtattaga ttttaattat   12540
cttgtcaaga aaggtttaac cgttgctgat ttaccttttt ctgaagatga aagattaaca   12600
```

FIG. 43 (continued)

```
gcttctcaat attttaattt tcctgttgct atctaatcca gaagggcaa taatcccctt    12660
ctttcatcga gttagactta atatcacaaa agtcattttc attttaccgt ttctttccca   12720
cagcgtccgt acgccctcg ttaaatctca aaaccgacaa tttatgatgt ttataaaaag    12780
ttactcactt taataagtat ttatactcat taaagggtta ttctttttt gtagcctgat    12840
aggttgggaa ggaatatttc agattatcag atttgttgaa tatttttcgt cagatacgca   12900
aaccttacaa acataattaa caactgaaac tattgatatg tctaggtttt agctctatca   12960
caggttggat ctg                                                      12973
```

Porf0128
cctcaactacaagttcttttatatattactttaacctgagttttggataagctgaaagcattattttctcgtagtcagaaaaccttt
atagcttcttagaaataacgataaaattaccttaatccgaactgacgttaaatatattcaccoctatcaccoaaaaccctaagcc
cctacttccccttttccttcatcacctcatccccccatccctaacacttaaccttattctttattcttaaaccgaactgaggtg
aagttgcagaataccoatgggggttacagcattgtagaaaataaatattctttcattattaaggttgtttggtaaaaatatGTG
aaaaccctaataatt

FIG. 51A

Porf1486
gggaaagacatatttttatcataatggtaaattcataataatttagactttttttgcaaaaattaatctcactctcttcttttc
cctatctcccattgtttcttatatcccaatgccccaatacccaaagctcagaaaataggtattagcgaagaggtgttgatcccctc
ccctagcaaaatatactcctatatagtaaagtgagaaagtgaagaaataagatcaagttcgcaattt

FIG. 51B

Porf3164
caaatcacgagaatttatgtaggactattttgtggttgacggtggagagtatgtcgccttgaattatgaccgaagatgaagatg
tcgggaggtggaaggacggtctttaagagggtttaacatcaaagttggtcataatctctgtccctgtttgataactactatttaat
tttgagttgttttaggtacatcaaaataccaaatccttactctcccctcaatatacaacaaaaaaactttttgattcactttag
tcataaaaattagaatttatctaccgaaatattacataaatgtaatgtatatatttctgatttattccgtgtgagccatgattca
taatttataattcatasttttctaaatatgcccctacaatggatatagaatgtcattttaattataggtatcataatcgtggtagtt
actcoggaaaaactattgaatcaaattcagtctcacctgctacagatagagtagccgttattctt

FIG. 51C

Porf3293
ttgacgattgtattgacttacgccaaatggcttaccctcatagtgaatagttgataattaagaattaaaaatccgttcacgacag
aagggagtgtaagagccttcggtgcgaactctcatcttccctgaaacctgacacctgaaacctgacacctgaaacctgacacctca
tctccctaatcoctaattttaatgaaaaaatacoctgagtgggcattgaaaaaaaagaaaagttgttcgactatgaaataagaat
tctgcacttcgtgagaaaaaggaaatgaaat

FIG. 51D

Porf3621
ctatttaactaggaaaaggtaaagttaaaaggacaagggtaataattaaaaattaagaattaagaacttctaactctcattactc
attacttatttcctcctctcacccccttctcctgatcacctcttctcctcaatactcggaactcatttcccccatggtgtgacactca
aatcaaaagtctgttattgacttttcagatgaaatattactatgataacaatatcccccctatgggtatataaaaatatgagcgata
ttagttaaaaatcaaatttggatttttttttctgaaaatattttaagattaagtaaagataagtaaagaaattataagcaattttgt
taaatcatacc

FIG. 51E

Porf3635
ctcacactgaaaatattgccacaagaaatataaagatcaagcaataatcctgactaaaaaggaatacaagtcaattatcctttttcctgat
atgttatctgacttgttgtttcttagtcatgttccttccattttttatttttgttttttatcattttttattacaaaaatttcttaata
gggctaaagcatttagttagttttttagctctcaacaagttgactaatcaatataatgccctaagttaatttgccttggtttgac
ggaggatattggaaaaaagaaacttctcgttgtatttcacagggaaaagggggaaattttattaataacaaacaatagaaaataa
ttatttatttatatttattttgtgaacaaatgttcaagaattaaaagtgtaataaagaaaatttattttttttatatttatttaaaactt
agatataagcctaaaggtctgaaattattattagacaatcaattgattcagaggtaatagttttttacttaaaaatattttttcaa
aattatccctatttgggtattgaaaaataaataaattcaagtaataatatacagaataaagaaaatctaatctaaaaatttg
tgtgtgaggaattgaaa

FIG. 51F

Porf3858
TATCACCATTGTAGAAAAGCCAGAAAATCAATTAACACAAATTTCCTGTAAATTATTATGTATGATTTTC
CCCTTCTCCCCTTAAAAGGAGAAATAAAAAACTATATCCCCCAACCACCGATAAGCATTGTGAGAGAAAA
ATCATTTAGGTAGGATCAATGCTGTAACCGATAAAGATAAATAAATAATT

FIG. 51G

Porf1071
attctgtgaattgattagatttgaggttttttaagaggttgattaccttgcctcaaaaaaatcataacacactaatgctctatat
gaaagggctttagacccataggttttgagaaaaaaacttgctaactctcggacaatgtcagcataactaaagtcaattcttttcg
tacttataattgtctataatttaatatacactgttctgaaactagttttttctctacattccttagttttatctgagtaaggttg
cttgtaacttaacttcggttgggcctaaaaatatccgattaggagcaggtgtcagactttaattaattattaattattaattgctt
attgccaaccctcggcgacaccacttttttcatcagcccagataaagattgatgttttagttttgttctttttatccctaattc
aactaatacaagtaaaactaaggttgtttatcaaaaatgatggttgatgtttgggtcaattttaagatattatgaaagaaaatga
ataaaaaatgaaaaatcttt

FIG. 51H

Porf1072 ctacaggggcaagatttggcggaaatctatatgtggattctctttcaagtgaagaaggtgcagtgccgacttatctggacttatta
gaatacgatattcgaactattactactggtttgttagcaggagtgaacaattaaaaattttttcctaattgacgcataaaaaatca
atgtcaactaatagttaacaatactctctgaaaaccaaaattgtcaaccaaacataacataattttaccccaaaaacctcatttt
ataaacttaaggataaatcaatg

FIG. 51I

<ins>Porf1074</ins>
gggattagagagttcaaagttaggaatgaggtgtcaggttttaggtttcaggtttaggggagcaatgagaaagaggtttcaggttt
caggtgtcaggttgcaggtgtcaaaggtgatgaggggatgggggatgaggggggaaacaagtaagtaataagtgttcggagttttta
attcttaattcttaattttttcctttgcctcttgccttttgccttgtcttaattactaatttctaattaaaatgattgtgttttcta
gtttagtctcatggttacttgaaccttacagcatagtttt

FIG. 51J

<ins>Porf1075</ins>
ttacaaacggcgggaattattatggtagtagcgatgttagtaaccccgggtgcgatcgcatatttacttacagatcgttttgatca
aatgttaatcttatcaatagttagtagtgttctatcttgtgtttaggcacttatttaagttatcatttgatgttctacggggg
gaagtattgtcgttaatgaccataatttttatttagcgatgattttgctctaaatatggcatcatcaatcaaaataccaaa
atatattctgcttcacttgttactgatacttcaaataatcatataacctatcttcgagttaaaaataatggatattatccaact
gaggtcgagaatagagtttctttttgatagaatttttttacaccagttattcattactatcatgggata

FIG. 51K

<ins>Porf1542</ins>
taatatagtgattattataaatgcaatgtgaatcaaacctatattttaccgtacattgaccatggaacttaatttgaggtgattag
tagagggtgcgatcgccctatttgtcaaataataaagataacatttgacattgctgattgaagacataaaacacagaaaaaatcag
gtaaaaatataaagctaaagtctaaatatggtttactttgcttcgacttacaacaaaaatcatagctagaatcaccaacgcct
aatattttatttagctgaaattttgggatgaacttttgtaaaaatggggggtctaaaaatatagcaaccacgatattaaataact
gagtgattattttaatctattgggggcttattaactaaatacttgcatttttatggagggttttaatt

FIG. 51L

<ins>Porf1823</ins>
aaagattattttctacagaagcaaccctttcatcttcgaattttcaggaatttcctgcttttgtttctgaatattagcataggcg
gcttttgcccactctaaagaaggttgagactgaatttctgaggtttcagaaggagcattagattgttatcttcaacaacaggagg
ttttttgttcaatattttccttattctctttttacggcgaaaccaattaaacataatgattgtgcataaatattcgttaatatatt
gtaaccctagaaaggaatcggtttcaggtttatcccagagaatgtgaaccttttacagaaagtaaaaagtctaaaatcgtagcaac
aataaatcacagaaattgag

FIG. 51M

Porf1824
ATCTAGTAATAATCATCAAGAGTTGTTAAAACTTCACTATCAAGAATTGGTAGCAAGAGGATTACAACAT
CTGAGTTTAGATCATCGAGCAGTTATTGTTCTTCATGATTTGGAAGATTTACCACAACAGGAAATAGCGG
AAATATTATCTATTCCCCTTGGTACGGTCAAATCTCGTTTATTCAAAGCCAGAAAAAATTTGCGTCAATT
TTTAGAACTTGAAGGTATTAGCTT

FIG. 51N

Porf3126
ccaatatcttgtcatacatacttatttgcctcactattagccctatatgtctctattgtatttttctttttctcctattcctagat
cttgtaatgaatcattactctctgaaatatagctactaattttatgyttgtttgtaaaatatattaacaaatgaacaataaatcat
attttgtgttaatctaattattagacaactactgaatttatattcagatattcacagatagggaatttgatt

FIG. 51O

Porf3388
Attctattaccctccgagggtggctatctccttttatttggtggctgataaaaccctattctattaaagtagccaatgagttagtt
aatgcggcggctaaatgtcactaaaatttcatcttaggttcacatcaaagtcatatcggttgtttatagtattaagtgtcagggag
aaagataggttttcctcttagctccttcgcaacttaatccctgacttttttattttttgttcgtgtgattaatctatttgtg
tagcaattatttttatcttattttcttttcagtctagtaattaattattttatattttgtattattttagagagtttgagctg
tt

FIG. 51P

Porf0221
gaatatctcatcctcagcttctacttatacctcagcatagttaaaaatcatccttattgatggtaataaaagaacaggttttta
ttagtggagtaaccttttttaatgctcaatggttctcacttactgcttctgaagtggaagtagtacatatcatccaaaccttagct
agtggcagaattaccgaggaagaattacaacaatggttcgtaaggaaaagtaagcagatgaataattaaagcatcatttcatcctc
atttcatattctcctgtcaccatggtatggaagattaggtaaaaatgaggaaaagtttatt

FIG. 51Q

Porf0222
gcgattatcaaccacgaaaacatacaattattatcaaacctgctgagaaattatccacagaaatagatgtttctgcgaaggaaaa
tgggcttttcattgccatttaatgtatcacatggatgtggaatgtttcggactattaatgttatttcctaaaaaataatagtatt
aaagcctaaaattttataaaaaattcatgtcttttattagggtgagcattcttccttatgtctccttatttacctctttaga
ggtaactacaaacttaatcaaaaaatttagataattaattatatca

FIG. 51R

Porf0223
atacatggttggttcactgacttttaccccagtttttctctttgaacaattggcataactctgaaaaaatcagatggggcttttgtt
gaattatttgttcaatcaaagcaaaacagtgattgtctatttttcttttttttccaccactcatagataaaaatttatcccgaact
caggttatattaagttcggatgatcacttaagataattgatccgattggttaagatagagaaaattcttttttcatagtgatttca
taattgatagttacaataacgattactatttagtaaaaagattttcaaatc

FIG. 51S

Porf0316
tggtcaagttactatatgtttagaaacaacaaaaaagaagtcattataaaaataattgatacaggaattggccattaataaagaag
aacaaaaattaattttttaatcgttttttatcgaatcaatataaagcaagaaatagagagaaaggcagttgcggattaggtttagctatt
gcaaatgcgatcgcgcttaatcatggtggtagaataattttagaaagtcaagaaaatcaaggcagtattttttaccgtttatttacc
gaaaatcatttcatcctaatttcatattcttttgacagaatcaaaggtaaagataaaaagagagaaacagtc

FIG. 51T

Porf3232
catcttttacttttgactaacattcataggtatcatgacgaaaatttttagtctgttatatttgttcatgtagagagatttttaat
ttgtgattatttttatttctctctattttttcttttttgtcttgtccttcctcattttttctctacatttagtctaaactacagctct
ttaatcttcagtttctcttttcctcctcttcctcatcaaggtaatcatcccaattaatatcttcttcttgttctaatttgggttgag
attgttgtttatcaatcatatttcatactcctaaaactttcttacttatttatcagttactttttacccatttatgcaatagtgta
gaaattttttcgatcgagttaattaattttatttcaaccatatctaaataattcttgatggacattctagttaactagaaggtt
taagctaaaataattattgatattgccttcggtataactaactatatccagagaaaag

FIG. 51U

Porf3461 (petJ)
tttatatatataaactcgaataaaattatcaatataaagtcaaactatatctatcctatttaactgctattggtaagtcccttaatt
agtgttggggtgaatagattttaaaagggcaaaccccccctttatcctccctcgagagggggagggcaaaaggcaagggggcaaggg
aaaaattaagaattaagaattaaaaactccgaacacctgtagggcgcgaatagccattcgcttccctcatcccccatctccccaa
cacccaaagccctactcgttactcatttatttacatcatttatttacatcattaagaaaagtaacaaattttgacaagtagtctt
ttgacaggaaaaagcaaattctcgaagatgaaacaatagaaaaaattcaatcttacagtaacgatgaaaaaactttaggctta
att

FIG. 51V

Porf3749
ctcaagagatagttaaaaaacaaatagctttagtctatcaattaatcgaattatttttacaaacaaattttcataaaccatagaa
ctagaggaggaaagttatttatgtttaaaaatctaaaagagttttatattcccctaaaaccccccttagtaagagtgactttttcat
catttgcctgtaaattctcctctttaataagagagctagggtgtttcaaagaggattttattgctttccaattctaactaactc
aaaaacttattttatactcaataattttattaatcaagagggaaattacc

FIG. 51W

```
ID   TK443\pABICyano;PpetJABICyano1-PCCmax-PrpsLABICyano-synADHmax-PrbcABICyano-Km**-
oriVT standard; circular DNA;    ; 13804 BP.
CC   This file is created by Vector NTI
CC   http://www.invitrogen.com/
CC   VNTDATE|639135285|
CC   VNTDBDATE|639135513|
CC   LSOWNER|
CC   VNTAUTHORNAME|Irina Piven|
FH   Key             Location/Qualifiers
FH
FT   promoter        4210..4735
FT                   /vntifkey="30"
FT                   /label=PrbcABICyano
FT   CDS             4737..5552
FT                   /vntifkey="4"
FT                   /label=Km**
FT                   /note="Km**"
FT   CDS             13114..13362
FT                   /vntifkey="4"
FT                   /label=ORF\6
FT                   /note="orf6"
FT   CDS             12854..13117
FT                   /vntifkey="4"
FT                   /label=ORF\5
FT                   /note="orf5"
FT   CDS             12126..12812
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11036..11800)
FT                   /vntifkey="4"
FT                   /label=ORF\3
FT                   /note="orf3"
FT   CDS             10581..10776
FT                   /vntifkey="4"
FT                   /label=ORF\2
FT                   /note="orf2"
FT   rep_origin      complement(9891..9908)
FT                   /vntifkey="33"
FT                   /label=Rep_Origin_1\(potential)
FT                   /note="potential rep origin; match pNostoc (Acc# M81381) nick
site (353-375); on reverse strand"
FT   misc_feature    10151..10184
FT                   /vntifkey="21"
FT                   /label=Rep\motif
FT                   /note="Rep protein active site motif EXXEYKVKXXD"
FT   CDS             7378..10555
```

FIG. 54

```
FT                      /vntifkey="4"
FT                      /label=ORF\1
FT                      /note="orf1  rep ori binding protein slr7037 homolog Similar to
hypothetical protein slr7037 of plasmid pSYSA (103 kb)  of Synechocystis sp. PCC 6803"
FT   rep_origin         complement(5795..6853)
FT                      /vntifkey="33"
FT                      /label=OriVT
FT   insertion_seq      6860..99
FT                      /source="pABICyano1-6HindIIIBamHI"
FT                      /type="Custom cloned insert"
FT                      /vntifkey="14"
FT                      /label=pABICyano1-6HindIIIBamHI
FT                      /note="Unknown feature type:insert"
FT   promoter           2267..2835
FT                      /vntifkey="30"
FT                      /label=FrpsLABICyano
FT   gene               534..2243
FT                      /vntifkey="60"
FT                      /note="PDC"
FT   gene               2839..3849
FT                      /vntifkey="60"
FT                      /note="ADH"
FT   CDS                534..2240
FT                      /vntifkey="4"
FT                      /label=PDCmax
FT   CDS                2839..3846
FT                      /vntifkey="4"
FT                      /label=synADHmax
FT   terminator         3850..4005
FT                      /vntifkey="43"
FT                      /label=TrbcSABICyano1
FT   promoter           101..509
FT                      /vntifkey="30"
FT                      /label=FpetJABICyano
FT   CDS                910..933
FT                      /vntifkey="4"
FT                      /label=petJABICyano
SQ   Sequence 13604 BP; 4252 A; 2378 C; 2622 G; 4352 t;
     aatattttc gtcagatacg caaaccttac aaacataatt aacaactgaa actattgata         60
     tgtctaggtt ttagctctat cacaggttgg atctgtcgac tttatatata aactcgaata       120
     aaattatcaa tataagtca aactatatct atcctatttt aactgctatt ggtaagtccc        180
     ttaattagtg ttgggggtgaa tagattttaa aagggcaaac ccccctttac cctcctctga      240
     gaggggggag ggcaaaaggc aaggggcaag ggaaaaatta agaattaaga attaaaaact        300
     ccgaacacct gtaggggcga ataqccattc gcttccoctc atcccccat ctccccaaca        360
     ccctaagccc ctactcgtta ctcatttatt tacatcattt atttacatca ttaagaaaag       420
     taacaaattt tgacaagtag tcttttgaca ggaaaaagca aattctcgaa gatgaaaaca       480
     ataqaaaaaa attcaatctt acagtaacga tgaaaaact tttaggctta attatgaatt        540
     cttataccgt gggtacttat ttaqccgaac gcttagtgca aattggttta aaacatcatt       600
     ttgccgtggc tggggactat aatttaqtgt tattggataa cttattatta aataaaaaca       660
     tggaacaaqt gtattgttgt aatgaattaa attqtqqttt ttctqctqaa qqttatqcta       720
     qaqctaaaqq tqcaqctqct qctqttqtta cttattctgt qqqtqctttq tctqcttttq       780
     atqctattqq tqqtqcttat qccqaaaatt taccqqtqat tttaattttct qqtqccccta      840
     ataataatqa tcatqccqcq qqacatqttt tacatcatqc cttaqqtaaa accqattatc       900
```

FIG. 54 (continued)

```
attatcaatt agaaatggcc aaaaatatta ctgctgctgc cgaagctatt tatactcctg    960
aagaagcccc tgccaaaatt gatcatgtga ttaaaaccgc cttacgcgaa aaaaaaccog   1020
tgtatttaga aattgcctgt aatattgctt ctatgccttg tgctgctcct gggcctgctt   1080
ctgctttatt taatgatgaa gctctgatg aagctagttt aaatgctgcc gtggaagaaa   1140
ccttaaaatt tattgccaat cgcgataaag ttgccgtgtt agttggttct aaattaagag   1200
ctgctggtgc tgaagaagct gctgttaaat tgctgatgc tttaggtggt gcagttgcta   1260
ctatggctgc tgccaaatct ttttttcccg aagaaaatcc ccattatatt ggaactagtt   1320
ggggagaagt ttcttatcct ggtgtggaaa aaactatgaa agaagccgac gctgttattg   1380
ctttagcccc tgtgtttaat gattattcta ccactggttg gactgatatt cccgatccca   1440
aaaaattagt tttagccgaa cctcgttctg ttgttgttaa tggtgttcgc tttccctctg   1500
tgcatttaaa agattattta acccgcttag cccaaaaagt ttctaaaaaa actggtgcct   1560
tagattttt taaatctta aatgcgggtg aattaaaaaa agctgctcct gctgatcctt   1620
ctgctccttt agttaatgct gaaattgccc gtcaagttga agccttatta acccctaata   1680
ctaccgttat tgccgaaact ggtgattctt ggtttaatgc ccaacgcatg aaattaccta   1740
atggtgcccg tgttgaatat gaaatgcaat gggtcatat tgttggtct gtacctgctg   1800
cttttggtta tgctgttggt gctcctgaac gtgtaatat ttaatggtg ggtgatggtt   1860
cttttcaatt aactgcccaa gaagttgccc aaatggttcg cttaaaatta cccgttatta   1920
ttttttaat aaataattat ggttatacca ttgaagtgat gatcatgat gggccatata   1980
ataatattaa aaattgggat tatgcgggtt taatggaagt gtttaatggt aatggtggtt   2040
atgattctgg tgctggtaaa ggtttaaaag ccaaaactgg tggtgaatta gctgaagcta   2100
ttaaagttgc cttagccaat actgatggc caaccttaat tgaatgtttt attggtcgcg   2160
aagattgtac cgaagaatta gttaaatggg gtaaacgtgt tgctgctgct aattctgca   2220
aacccgtgaa taaattattg taattttgg ggatcaattc gagctcctcc gcttaaaaaa   2280
tttcattttt cgatcaaaaa agacaaatta ttactaatta gctcatggca ataaataatc   2340
agtagtaatc tgtttcaca ttttattgtt aatttcatt attgctaata tcaacctttt   2400
ctactttcgc ttaatatttt atttatgctc aatgggaaaa tctgaaataa gattgagaac   2460
agtgttacca atagaagtat taaggtta aagcatacct taaagataac atttttttt   2520
gaaagagtc aaattatttt tgaaaggctg atattttga tatttactaa tattttattt   2580
atttctttt ccttaaaat aagagctaaa tctgttttta ttatcattta tcaagctcta   2640
ttaatacctc aacttttca agaaaaata ataattttt ttccctctat tctcatgacc   2700
tttaggaaa attaatttta gaaaactat tgacaaaccc ataaaaatg agataagatt   2760
atagattgtc actggtattt tatactagag gcaaattata tttatatata caaaaatgct   2820
gtataaaaaa catctcatat gattaagcc tatgctgcct tagaagccaa tggtaaatta   2880
caaccctttg aatatgatcc tggtgcttta ggtgccaatg aagtggaaat tgaagtgcaa   2940
tattgtggtg tgtgtcattc tgatttatct atgattaata atgaatgggg tatttctaat   3000
tatcccttag ttcctggtca tgaagttgtt ggtactgttg ctgctatggg tgaaggtgtt   3060
aatcatgtgg aagtgggtga tttagttggt ttaggctggc attctggtta ttgtatgacc   3120
tgtcattctt gtttatctgg ttatcataat ttatgtgcca ctgccgaatc tactattgtg   3180
ggtcattatg gtggttttgg tgatagtt cgtgctaaag tgtttctgt ggtgaaatta   3240
cccaaggta ttgatttagc ctctgctggg cctttatttt gtggtggtat taccgttttt   3300
tctcccatgg tggaattatc tttaaaacct aaccgcaaag ttgctgttat tggtattggt   3360
ggtttaggtc atttagccgt tcaattttta agagctgggg ttgtgaagt tactgcttt   3420
acctcttctg cccgtaaaca aaccgaagtt tagaattag gtgcccatca tattagat   3480
tctaccaatc ctgaagctat tgcttctgcc gaaggtaaat ttgattatat tattctacc   3540
gtgaatttaa aattagattg gaatttatat atcagtacct tagcccctca aggtcatttt   3600
cattttgttt gtgtggtgtt agaacccttg gactaaact tatttccctt attaatggga   3660
caacgttctg tttctgcttc tctgttggt tctcctgcta ctattgccac tatgttagat   3720
tttgccgtgc gtcatgatat taaacccgtg gtggaacaat tttctttgt tcaaattaat   3780
gaagccattg cccatttaga atctggtaaa gcccattatc ggtggtgtt atctcattct   3840
aaaaattaat aagattaact tctaaactga aacaaatttg agggtaggct tcattgtctg   3900
cccttatttt ttatttagg aaagtgaac agactaaaga gtgttggctc tattgctttg   3960
agtatgtaaa ttaggcgttg ctgaattaag gtatgatttt tgaccccttc tctcttctgc   4020
agttacctag gattctggc gaaaggggga tgtgctgcaa ggcgattaag ttgggtaacg   4080
```

FIG. 54 (continued)

```
ccagggtttt ccagtcacg acgttgtaaa acgacggcca gtgagcgcga cgtaatacga   4140
ctcactatag ggcgaattgg cggaaggccg tcaaggccgc atggcgcgcc tacgtagaca   4200
attgtcgatg taattattaa ctatcttatt atagatgagg ggagaggag aaattagttc    4260
ggagagaacg ctcgagcgct cgttccgcaa acgggtacgg agttagttag gggctaatgg   4320
gcattctcc gtacaggaaa gagttagaag ttattaatta tcaacaattc tcctttgcct    4380
agtgcatcgt tacctttta attaaaacat aaggaaaact aataatcgta ataatttaac    4440
ctcaaagtgt aaagaaatgt gaaattctga ctttataac gttaaagagg gaaaaattag    4500
cagtttaaaa tacctagaga atagtctggg gtaagcatag agaattagat tagttaagtt   4560
aatcaaattc agaaaaata ataatcgtaa atagttaatc tgggtgtata gaaaatgatc    4620
ccttcatga taagatttaa actcgaaaag caaaagccaa aaaactaact tccattaaaa    4680
gaagttgtta catataacgc tataaagaaa atttatatat ttgaggata ccaaccatgt    4740
ctcatattca acgtgaaact agttgttctc gtcctcgttt aaattctaat atggatgccg   4800
atttatatgg ttataaatgg gctcgtgata atgttggtca atctggtgct actatttatc   4860
gtttatatgg taaacctgat gctcctgaat tattcttgaa acatggtaaa ggttctgttg   4920
ctaatgatgt tactgatgaa atggttcgtt taaactggtt gactgaattt atgcctttac   4980
ctactattaa acattttatt cgtactcccg atgatgctg gttattaact actgctattc    5040
ctggtaaaac tgcttttcaa gttttagaag aatatcctga ttctggtgaa aatattgttg    5100
atgttttagc tgttttttta cgtcgtttac attctattcc cgtttgtaat tgtccttta    5160
attctgatcg tgtttttcgt ttagctcaag ctcaatctcg tatgaataat ggtttagttg   5220
atgcttctga ttttgatgat gaacgtaatg gttggcctgt tgaacaagtt tggaaagaaa   5280
tgcacaaatt gttacctttt tctcctgatt ctgttgttac tcatgtgat ttttctttag    5340
ataatttgat ctttgatgaa ggtaaattga ttggttgtat tgatgttggt cgtgttggta   5400
ttgctgatcg ttatcaagat ttagctattt tatggaattg tttaggtgaa ttttctcctt   5460
ctttacagaa acgtttattt cagaaatatg gtattgataa tcctgatatg aacaagttac    5520
aatttcattt aatgttggac gagttcttt aagaattaat tcatgaccaa aatcccttaa     5580
cgtgagtttt cgttccactg agcgtcagac cccgtagaaa agatcaaagg atcttcttga   5640
gatccttttt ttctgcgcgt aatctgctgc tatttaaatt acgtacangt gttattactt    5700
tgttaacgac aattgtctta attactgggg ctcatgggc cttccgtca ctgcccgctt      5760
tccagtcggg aaacctgtcg tgccagctct gcagatgacg gtgaaaacct ctgacacatg    5820
cagctcccgg agacggtcac agcttgtctg taagcggatg ccgggagcag acaagcccgt    5880
cagggcgcgt cagcgggtgt tggcgggtgt cggggcgcag ccatgaccca gtcacgtagc    5940
gatagcggag tgtatactgg cttaactatg cggcatcaga gcagattgta ctgagagtgc    6000
accatatgcg gtgtgaaata ccgcacagat gcgtaaggag aaaataccgc atcaggcgct    6060
cttccgcttc ctcgctcact gactcgctgc gctcggtcgt tcggctgcgg cgagcggtat    6120
cagctcactc aaaggcggta atacggttat ccacagaatc agggataac gcaggaaaga    6180
acatgtgagc aaaaggccag caaaaggcca ggaaccgtaa aaaggccgcg ttgctggcgt    6240
ttttccatag gctccgcccc ctgacgagc atcacaaaaa tcgacgctca agtcagaggt    6300
ggcgaaaccc gacaggacta taaagatacc aggcgtttcc ccctggaagc tccctcgtgc    6360
gctctcctgt tccgaccctg ccgcttaccg gatacctgtc cgcctttctc ccttcgggaa   6420
gcgtggcgct ttctcatagc tcacgctgta ggtatctcag ttcggtgtag gtcgttcgct   6480
ccaagctggg ctgtgtgcac gaacccccg ttcagcccga ccgctgcgcc ttatccggta     6540
actatcgtct tgagtccaac ccggtaagac acgacttatc gccactggca gcagccactg   6600
gtaacaggat tagcagagcg aggtatgtag gcggtgctac agagttcttg aagtggtgg    6660
ctaactacgg ctacactaga aggacagtat ttggtatctg cgctctgctg aagccagtta   6720
ccttcggaaa aagagttggt agctcttgat ccggcaaaca aaccaccgct ggtagcggtg   6780
gtttttttgt ttgcaagcag cagattacgc gcagaaaaaa aggatctcaa gaagatcctt    6840
tgatctttc tactgcagaa gcttgttaga cacctgtca tgtattttat attatttatt    6900
tcaccatacg gattaagtga aacctaatga aaatagtact ttggagctt taactttaat   6960
gaaggtatgt ttttatag acatcgatgt ctggtttaac aataggaaaa agtagctaaa     7020
actccctga attaaagaaa taacaggtg tctaacaacc tgttattaag aatgttagaa    7080
aagacttaac atttgtgttg agttttata gacattggtg tctagacata cggtagataa    7140
```

FIG. 54 (continued)

```
ggtttgctca aaaataaaat aaaaaaagat tggactaaaa aacatttaat ttagtacaat      7200
ttaattagtt attttttcgt ctcaaatttt gctttgttga gcagaaattt agataaaaaa      7260
atccccgtga tcagattaca atgtcgttca ttgtacgatg tgtcgaaaaa tcttacgac       7320
actctaaact gaccacacgg gggaaaaaga aaactgaact aataacatca tgatactcgg      7380
aaaacctagc aattctcaac ccctaaacaa aagaaacttc caaaacctg accatataaa       7440
ggagtggcaa caatcagcaa tcagtcaaga tttgatagca gaaaatcttg tatcggttgc      7500
taatggtttt gatgtactat ttatcggcaa taaataccga actaacacgg gtgttctgtc      7560
acggcacata ttaaactcct attctcattt agaagatggt ggttcgtatg gtagaacatt      7620
tgaccattt  accaataaag aaatgcagtg ggttcaattt aaaccgaata gaccaagaaa      7680
aggttctact ggtaaggtaa tcaaatatga atcgccaaaa ggtgaaccta caagagttct      7740
aatgccgttt gtgcctatga aaatatggca acggattagc gataagttcg gagtaccgat      7800
taatccgaaa aaagatactc acttttggga atgggtaaag aataatccat cgataccgat      7860
tgccattaca gaaggaaata aaaagctaa  ttgcctatta tcctatggct atcctgctat      7920
tgccttgta  ggcatttgga acggattaga gaaataaat  gatttctcga aggaaaagca      7980
gttaaaaagg gattgaaat  ggttgttatc caacggcaac cgaaatatta atatcatctt      8040
tgaccaagac cagaaacaaa aactgtaat  taatgtaaac aaagctattt tcgctttatc      8100
ttctctaata agtagaaatg gtcataaagt taatattgtg caatggttgc cgtcaaaggg      8160
taaaggaata gatgattatt tggtagcttt accttttgag aaaagagaaa atcatttaga      8220
caacttaatt aaaattgcac catcatttaa ttttggtca  actaaatact tattcaagtg      8280
tcgtaaacca gattaaaccg taaattgccg ttatttgagc gatgcagtaa aagaattacc      8340
tcaagggat  atagcattaa tagcacctca cggcacggt  aaaacttcat tagtagctac      8400
tcacgttaag aatcggagtt atcacggaag gaaaactatt tcattggtgc atcttgaaag      8460
tttagccaaa gctaatggca acgcacttgg attatattac cgaaccgaaa ataatattga      8520
aaagcaatat cttggattta gcttatgtgt agatagttgc cgtgataaga ttaacggcat      8580
tacaactgat attatttcag gtcaagatta ttgccttttc attgatgaaa ttgaccaagt      8640
aattccacac atccttaaca gtgaaactga agtaagtaag tatagatgca ccatcattga      8700
cacttttct  gaactggtga gaaatgctga acaggtcatt attgctgatg ctgattatc       8760
cgatgtgacg attgacctaa tagaaaacat cagaggtaaa aaactatatg taatcaagaa      8820
tgaatatcag tatcagggaa tgacttttaa cgccgttggt tcaccattag aaatgatggc      8880
aatgatggga aaatcggtgt cagaaggcaa gaaattattt attaacacca catcccaaaa      8940
ggcaaaaagt aagtacggca aatcgctct  tgagtcttat attttggtc  taaataaaga      9000
agcaaagata ttaagaatag actctgaaac cactaaaaac cctgaacatc cagcctataa      9060
aatcattgac caagacttaa ataatatcct caaagattat gattatgtca ttgcctcacc      9120
ttgccttcaa acaggtgtca gtattaccct aaaagggcat tttgaccagc aatttaactt      9180
ttccagtgga aacattacac ctcattgctt tttacagcaa atgtgcggt  tgagggatgc      9240
agaaattgaa agattctatt atgtgccgaa ctcatctaac ctcaatctca ttgggaataa      9300
gtcaagttca ccatcagacc ttctaaagag caataacaag atggcaacgg caacggttaa      9360
ccttttgggt agaatcgact ccgaatattc cctagagtat gaatcgcacg gcatttggct      9420
tgaacgtgg  gcaaagatta cagcacggca taacagttca atgcgttgtt actctgaaat      9480
tcttacctat ctaattacgt ctcaagggca taaattaaat atcaacattc cctcacctct      9540
tgcagatatt aagaagctaa atgatgaggt aagtagtcac cgggaaaagg taaaaatga       9600
gagatactct cagaggttaa actcaccaga tattaacgat gcagaagcta ccatactcga      9660
atctaaagag caaaaaatcg gattgactct caatgagaga tgcaccctag aaaagcataa      9720
agttaagaag cggtatggga atgtaaagat ggatattctc acctttgatg atgatggact      9780
ataccccaaa ctcagactat tttattaact cacccatcgt aaacctcatc tcaaggctaa      9840
tgacagaaaa gctattgcca aaatgggcaa tgacaataaa ggcaagattc tatcaaaaga      9900
cttagttaat aaaacttact ccgctcgtgt gaaggtctta gagattctta actaactga       9960
ctttatcgac aatcttagag atgaactctt aataactccc aataatccag ctatcaccga      10020
ttttaataat cttctgctaa gagctaagaa ggatttaaga gtattaggag tcaacatcgg      10080
aaaatatcca atggccaaca ttaatgccgt acttactctc attggtcaca actttctgt       10140
aatgagagat gagttcggaa aagagaaaag gataaaagta gatggtaaat catacccgatg     10200
ttatcaactt gaaaacattac cagattttac caatgatact cttgactact ggttagaaaa      10260
tgatagccaa aaagaagtaa cagcaacaga aaattactcc gaaaattta  accttcaaa       10320
```

FIG. 54 (continued)

```
tagctacaat ccagacagta agacactttc agagggtgca aatttcctat atataaataa    10380
agaagaattg catccaaata aattgcacct agaaataaaa gaaggtgctg aactttttt    10440
attcggggta aaggtgattg tgaaaggaat cttggacggg gcagtaacta tattctctat    10500
gggtcaagaa tacgatttat ccctcaatga actagagggg atgttaacat catgaacttt    10560
acaagaatct ttttaaaggg cgatcgcacc atgttaaatg atggtacatt tgttcagata    10620
tttgatattt accatgacca cgcattggga gtgaccttg accttaagac agaaaaaatt    10680
attccgatg atgttagggt aattactgtc aaagacttat tgttcgatgg cacttataaa    10740
gggggtaaaat cttttatgcc cgataatgcc cgataatgcc cgattgatgc tacaaaatcc    10800
cataatcata agcgataatc ccctaatagc ttgtaattct tgaaccgtag cgattttaga    10860
gtattccaaa aagaagaaat aaacacccgca aaatgtcgta tttcacatat ataaccaag    10920
gttttttgcc ctaaaatctt tatgtttgta gtgtgatgtt gggtcaaaat ggtcagaaaa    10980
gttgcaaggt tttatggat gcttacgcgc gcgagggta agcatcccca aatagttact    11040
ttatcctagt ccatgccat ttattgccgt cccgttcggc tttaaaaag tgccaaaact    11100
cacaaggtgc aataaaaagt tctgtacctt tcgaaccct agataatctt tcaacagtta    11160
ctttttttcc tattatctcg gtacaaagtt tggctagttt ctctttccc tcttttcaa    11220
tcaagccttc ttgtatgccc aactcattga ttaatctctc tattttacc attattccc    11280
gttcaggtag tttatcccct aaatcttcat cggggggcaa tgtagggcat tctgaagggg    11340
cttttttcttc tgtctggaca ttatctaaata ttgaagtaac caaactatct tcagttttttt   11400
ctattcctat taattcatat tcggttactg tatccgtatc aatatccgaa taactatctt    11460
tatccgtatt agctattcgg ttaagtttat ccgttaactc agaaacaaga ctatatagcg    11520
gttttagctt ttcttctatc ctgttatcta ataccggataa gtttatacgg ttatcattat    11580
ccgtattagt atcattgggc tttttttgta gttctaccccc ctcataaacc gcttttattc    11640
ccaattccaa cagactgata acagtatcct ttataatggg ttttttgctg atatggtgaa    11700
ctttgcccc ttccatcatt gcgatacttt ctatctcact catcaactta tcgttaagt    11760
gaatctcgta tctgtttaat cccttactgg tttattcat atccgtttac tttattcggt    11820
taacaattct attttatacg aataaaatat tatacggtta actttatacg tttaactatt    11880
ttatctatac ggataacagt aataagttat tcgtattagt tatacgttta cttttatcca    11940
aataaaatta gtgcatttaa actaaaagaa tgatttatc ggagttgata gcattggatt    12000
aacctaaaga tgtttataag ctatatctga taagtattta aggttatttt gttattctgt    12060
ttattgacat tatccgaata aaagaataga atataattgt tgagagataa gaggtttaag    12120
tgattatggt taagaagtta gttggttatg tcagggtcag tagtgaatcg caagaggata    12180
acactagctt acagaatcag atagagagaa ttgaagcata ttgtatggct tttggttatg    12240
agttggtaaa aatattcaaa gaggttgcca ctggtacaaa agcagatatt gaaaccgtc    12300
ctatttttaa tgaagctata gaatacttga acaggataa tgctaatgga attattgcct    12360
tgaagctaga ccgaatcgca cggaatgctt tagatgtatt gcgtttggtt cgtgaaacct    12420
tagaaccaca aaataaaatg ttagtgttac tagatattca ggtagatact tcgacaccttt    12480
caggaaaaat gatttaact gtaatgagtg ccgttgctga actcgaaaga gacatgatct    12540
atgatcgcac tcagggggt agaaagacta aagcccaaaa gggcgggtat gcctacggga    12600
aacctaaatt tggctataag actgaagaaa aggaactaaa agaagattca gcaacaggg    12660
aaactattaa actaattaag agacaccgta ggtcagggaa aagctaccag aaaatagctg    12720
attatctcaa tgccaaagt attccccta aacaaggtaa gaaatggagt tctagcgtcg    12780
tctatcgaat ctgtcaggaa aagctggtt aagtctgttt atagatattt agaatttatt    12840
gaataaaat agtatgaaca ataaatattt atggactaac cacgctcgga aacgtttaac    12900
tgaacgatgg gaaataaaag aatcatgggt tattgatacc atcgaaaatc ctgaacgttc    12960
agaatttatt gttgatgagt caggggaaa atatcattac tataaagaa tagctaagtt    13020
taagaataga gtgttagaag tgataacttc tgccaactca acacccacaa gaataataac    13080
cttttacttt aaccgtaaca tgaggaaaaa tttatgattg ttacttacga taatgaagtt    13140
gacgcaattt attttaagtt aacggaaaat aaaattgata gcaccgaacc tcaaacagac    13200
aggattatca ttgattacga tgaaagtaat aatattgttg gcattgaggt attagatttt    13260
aattatcttg tcaagaaagg tttaaccgtt gctgatttac ctttttctga agatgaaaga    13320
ttaacagctt ctcaatattt taattttcct gttgctatct aatccagaag gggcaataat    13380
ccccttcttt catcgagtta gacttaatat cacaaaagtc atttcattt taccgtttct    13440
ttccacagc gtccgtacgc ccctcgttaa atctcaaaac cgacaattta tgatgtttat    13500
```

FIG. 54 (continued)

```
aaaaagttac tcactttaat aagtatttat actcattaaa gggttattct tttttgtag      13560
cctgataggt tgggaaggaa tatttcagat tatcagattt gttg                       13604
//
```

FIG. 54 (continued)

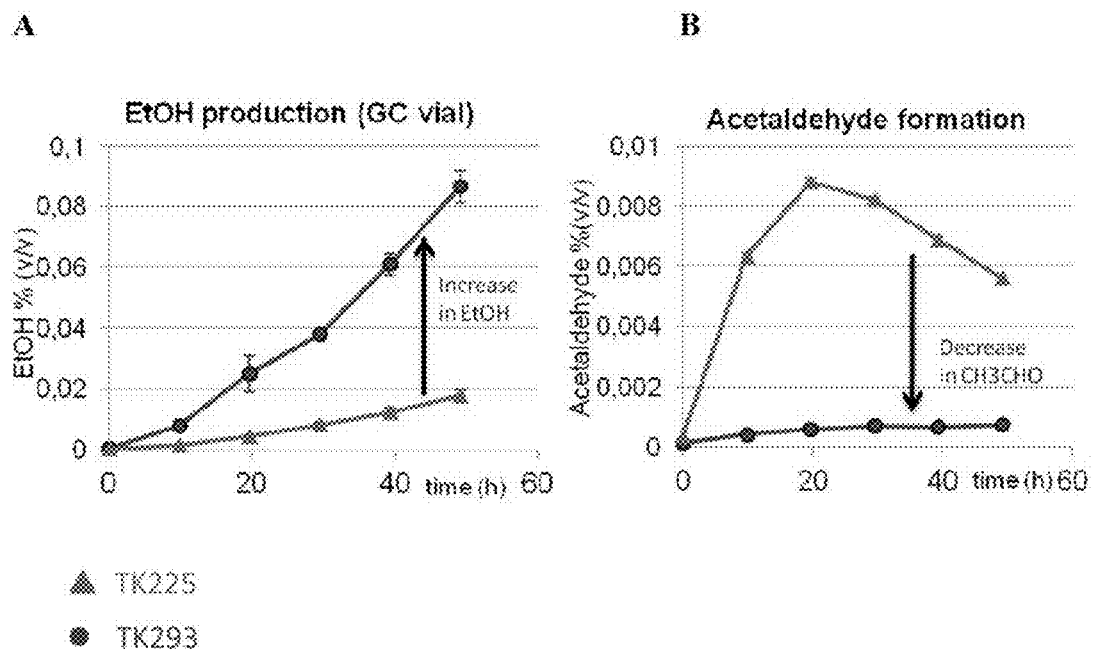
FIG. 56 A and 56B

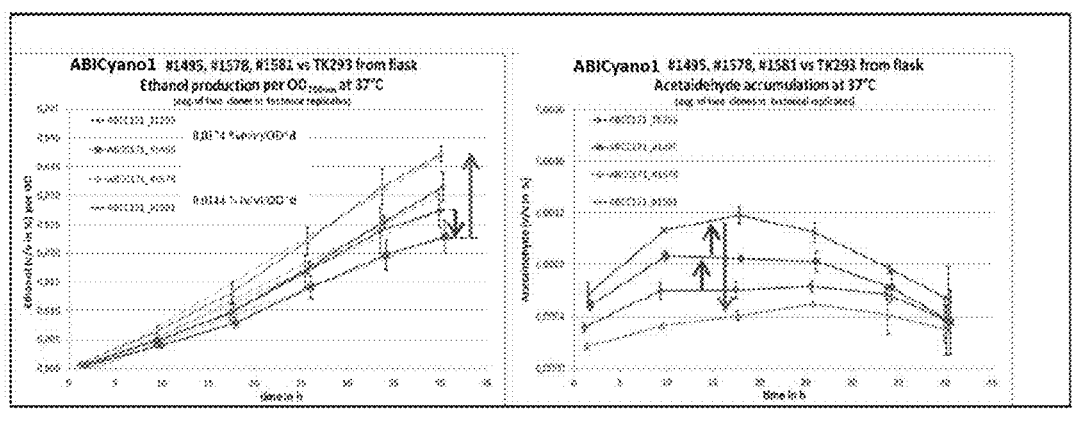
FIG. 59 A and 59B

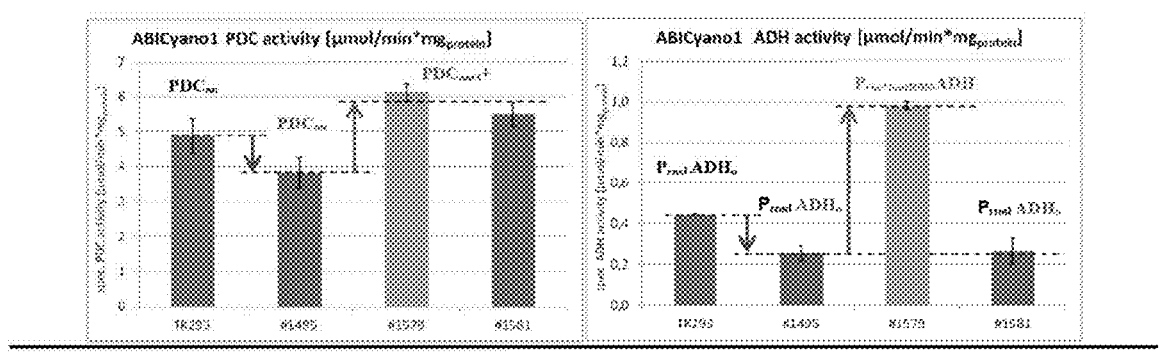
FIG. 60 A and 60 B

<18_IrtA gene promoter;DNA;Cyanobacterium ABICyano1>

TAGAGTATGATAAAATGACAAGGAAAGGATTATTTTCTCTTGTTTAAATTCTCAAGATTCTTATGCTTATT
TATTTTATGTAAGTGTCTCTTTTCCTTGAAATAGAAAGAAAAAAGTGGCTAATTTTGAGAAAAGCTAACA
ACGCTTTGGTTAACTAAAAATCAAAAGTGAGATTACTGATCGCTTAAGAAATGGAGTATTGATT

FIG. 61 A

<19_mrgA gene promoter;DNA;Cyanobacterium ABICyano1>

AGAGTTATATTTACATAGTGTGTGCGAGTAAGGGCAACTTTTGTAGGTAGATGAATAAACCTCAAATTAC
TCATCTTAAAAGACGATATTTTAATCTATTCTTCTGTAATAAAATACTTCTTTCGATAGAGATATTTAATA
CTTTTGAGAGATGAAAATAATTTCAATAATTGTCATGATAGAGAGTAAGTGCAAATAAGAAAAAATTGAT
TT

FIG. 61 B

<20_nblA gene promoter;DNA;Cyanobacterium ABICyano1>

GCAGTTAGATAAATAAGTAATGAGCGGGAGAAATAGGGGCAAATGGCCATTCGCCCCTACAGGGAGGTG
GCAGGTGTTAGGGTGTTTAGGGGATGAGGTGATGAGGGTAGAGGGAGATAAGGTGTCGGGTTTCAGAT
TTCAGGTTTTAGAAGAAAGTAACGAGTAATTATCAACTATTCACTATTCACTATTGCCTGTTGCCCTTCTC
TCCTTGAAATATAAAAAAATGTAAAAATATCATTAAGAAAAGTAACAAAATAAACAGAAAGGTTGACAAA
GTTGACGCTTTAATATCCGTATGTTAGCTTTATAACAACGAAATCAACGGAGGAGTGAAA

FIG. 61 C

<21_ggpS (glucosylglycerol-phosphate synthase) gene promoter;DNA;Cyanobacterium ABICyano1>

CTTGAAAAAGTTGAGGTATTAATAGAGCTTGATAAATGATAATAAAAACAGATTTAGCTCTTATTTTAAG
GGAAAAAGAAATAAATAAAATATTAGTAAATATCAAAAATATCAGCCTTTCAAAAATAATTTGACTCTTTT
CAAAAAAAAATGTTATCTTTAAGGTATGCTTTAAACCTTAAATACTTCTATTGGTAACACTGTTCTCAATC
TTATTTCAGATTTTCCCATTGAGCATAAATAAAATATTAAGCAGAAGTAGAAAAGGTTGATATTAGCAAT
AATAAAAATTAACAATAAAATGTGAAAACAGATTACTACTGATTATTTATTGCCATGAGCTAATTAGTAAT
AATTTGTCTTTTTTGATCGAAAAATGAAATTTTTAAGCGGAGGAACTGAAAATT

FIG. 61 D

<22_petJ gene promoter;DNA;Cyanobacterium ABICyano1>

TATTTATATATAAACTCGAATAAAATTATCAATATAAAGTCAAACTATATCTATCCTATTTTAACTGCTATT
GGTAAGTCCCTTAATTAGTGTTGGGGTGAATAGATTTTAAAAGGGCAAACCCCCCTTTATCCTCCCTCGA
GAGGGGGGAGGGCAAAAGGCAAGGGGCAAGGGAAAAATTAAGAATTAAGAATTAAAAACTCCGAACAC
CTGTAGGGGCGAATAGCCATTCGCTTCCCCTCATCCCCCCATCTCCCCAACACCCTAAGCCCCTACTCGTT
ACTCATTTATTTACATCATTTATTTACATCATTAAGAAAAGTAACAAATTTTGACAAGTAGTCTTTTGACA
GGAAAAAGCAAATTCTCGAAGATGAAAACAATAGAAAAAAATTCAATCTTACAGTAACG

FIG. 61 E

<23_ppsA promoter;DNA;Cyanobacterium ABICyano1>

GTGATATTTGGTTTATTCTATATTTTCCTTAAGTAAAAATTCAGTCATGAGGGAAACTTTTGTTAAAATTT
GCTTTAAATTAATAGGAAGATCATTAAGAAAATCTTAAAAAGATTGAGTTTTAGATCGAAATTATTGAA
GAAAAATTAACAGGGGTTCTGCTCAAAATTTTATTAAATTACTCTACTGTAGTAAAGGAGAAATTTTATT

FIG. 61 F

<24_rnpA gene promoter;DNA;Cyanobacterium ABICyano1>

GAATAGTTGATAATTACTCGTTACTCATTACTCACTTAAACCTGCCACCTGATACCTGCCACCTCTCCCCC
CATCACCTCATCCCCTCAACATTCCGAACCCCTTGACACTTTGAACTAAAATTGTATTAAAGTGCAAATCT
GGACGGGGTTAACCAGTGTGACTTATAATAGTAAACGCTGTTTTTATAATAAATAAGCTAAATATTTAA
AAACTATGAGTAAATATACACTAAATGGTACTAGACGTAAGCAGAAAAGAACCTCCGGTTTCCGCGCCCG
TATGAGAACCAAAAATGGTAGAAAAGTAATTCAAGCTCGTCGTAATAAGGGTAGAAAAAGATTAGCAGT
ATAAAATTACTGTTAAATAAGGAAGCTAAGTTTAGCATTTTAAGTTTGATATTACTAATCATTAAATTTAC
TGTGAAATATAGGTGGGACTACCATCAAAGCATCGACTGAAACGGCGTTTAAATTTCCAATCTGTTTATC
AACAGGGTATTCGCCGCTCTAGTCGTTATTTATTGTCCGAGGGTTACGG

FIG. 61 G

<25_pstS gene promoter;DNA;Cyanobacterium ABICyano1>

ATAACCAATGGGACTTGAATTTTAGATCCATTTATTTAATTCTATTTTTGTTACATTTCTTTATATTAATCA
GAATTATGTTACTTTGTTTTGTTTTATGTCGTTACCTTATTGAAGAAAGAGTGGATGAGAAGGTAAATGA
CGGGGCATAAATATCGATTCGTTGTCAGAATAAGCTGTTTTATTCACTTAACTGGTTGTTTGCCAATTTCT
CCCTAATTCCCATAACTTGTATAACTAAATTTAATAATCAATTTTAGTAAATTAAGAATAGGTTAAAAGTA
GTATTTAGAATTAAGTTAACTTTAATAAATTTCCTGTATTTTTTATAGAAAAAGTATAAAATAAAAACA
TATCAAAAAGTTTGAAATGACAAT

FIG. 61 H

<69_ cpcBA promoter;DNA;Cynobacterium ABICyano1>

TGAGAAAAAGTGTAAACAAATATTAAGAAAAAGATCAGAAAAATTTAACAACACGTAATAAAAAAATGCG
TCACTACGGGTTATAAATTTACATGAAAGGTTAAAACACTTTTCTGAGACGATTTTGATAAAAAAGTTGTC
AAAAAATTAAGTTTCTTTACAAATGCTTAACAAAAACTTGGTTTTAAGCACAAAATAAGAGAGACTAATTT
GCAGAAGTTTTACAAGGAAATCTTGAAGAAAAGATCTAAGTAAAACGACTCTGTTTAACCAAAATTTAA
CAAATTTAACAAAACAAACTAAATCTATTAGGAGATTAACTAAGC

FIG. 61 I

SEQUENCE LISTING

```
<160> NUMBER OF SEQ ID NOS: 88

<210> SEQ ID NO 1
<211> LENGTH: 6828
<212> TYPE: DNA
<213> ORGANISM: Cyanobacterium sp. ABICyano1

<400> SEQUENCE: 1 aatattttc  gtcagatacg  caaaccttac  aaacataatt  aacaactgaa  actattgata     60
tgtctaggtt  ttagctctat  cacaggttgt  tagacaccct  gtcatgtatt  ttatattatt    120
tatttcacca  tacggattaa  gtgaaaccta  atgaaaatag  tactttcgga  gctttaactt    180
taatgaaggt  atgtttttt   atagacatcg  atgtctggtt  taacaatagg  aaaaagtagc    240
taaaactccc  atgaattaaa  gaaataacaa  ggtgtctaac  aacctgttat  taagaatgtt    300
agaaaagact  taacatttgt  gttgagtttt  tatagacatt  ggtgtctaga  catacggtag    360
ataaggtttg  ctcaaaaata  aaataaaaaa  agattggact  aaaaaacatt  taatttagta    420
caatttaatt  agttatttt   tcgtctcaaa  ttttgctttg  ttgagcagaa  atttagataa    480
aaaaatcccc  gtgatcagat  tacaatgtcg  ttcattgtac  gatgtgtcga  aaaatcttta    540
cgacactcta  aactgaccac  acgggggaaa  aagaaaactg  aactaataac  atcatgatac    600
tcggaaaacc  tagcaattct  caacccctaa  acaaaagaaa  cttccaaaac  cctgaccata    660
taaaggagtg  gcaacaatca  gcaatcagtc  aagatttgat  agcagaaaat  cttgtatcgg    720
ttgctaatgg  ttttgatgta  ctatttatcg  gcaataaata  ccgaactaac  acgggtgttc    780
tgtcacggca  catattaaac  tcctattctc  atttagaaga  tggtggttcg  tatggtagaa    840
catttgaccc  atttaccaat  aaagaaatgc  agtgggttca  atttaaaccg  aatagaccaa    900
gaaaaggttc  tactggtaag  gtaatcaaat  atgaatcgcc  aaaaggtgaa  cctacaagag    960
ttctaatgcc  gtttgtgcct  atgaaaatat  ggcaacggat  tagcgataag  ttcggagtac   1020
cgattaatcc  gaaaaaagat  actcactttt  gggaatgggt  aaagaataat  ccatcgatac   1080
cgattgccat  tacagaagga  aataaaaaag  ctaattgcct  attatcctat  ggctatcctg   1140
```

-continued

```
ctattgcctt tgtaggcatt tggaacggat tagagaaaat aaatgatttc tcgaaggaaa    1200
agcagttaaa agaggatttg aaatggttgt tatccaacgg caaccgaaat attaatatca    1260
tctttgacca agaccagaaa caaaaaactg taattaatgt aaacaaagct attttcgctt    1320
tatcttctct aataagtaga aatggtcata aagttaatat tgtgcaatgg ttgccgtcaa    1380
aaggtaaagg aatagatgat tatttggtag ctttaccttt tgagaaaaga gaaaatcatt    1440
tagacaactt aattaaaatt gcaccatcat ttaattttttg gtcaactaaa tacttattca    1500
agtgtcgtaa accagattta accgtaaatt gccgttattt gagcgatgca gtaaaagaat    1560
tacctcaaga ggatatagca ttaatagcac ctcacggcac gggtaaaact tcattagtag    1620
ctactcacgt taagaatcgg agttatcacg gaaggaaaac tatttcattg gtgcatcttg    1680
aaagtttagc caaagctaat ggcaacgcac ttgattata ttaccgaacc gaaaataata    1740
ttgaaaagca atatcttgga tttagcttat gtgtagatag ttgccgtgat aagattaacg    1800
gcattacaac tgatattatt tcaggtcaag attattgcct tttcattgat gaaattgacc    1860
aagtaattcc acacatcctt aacagtgaaa ctgaagtaag taagtataga tgcaccatca    1920
ttgacacttt ttctgaactg gtgagaaatg ctgaacaggt cattattgct gatgctgatt    1980
tatccgatgt gacgattgac ctaatagaaa acatcagagg taaaaaacta tatgtaatca    2040
agaatgaata tcagtatcag ggaatgactt ttaacgccgt tggttcacca ttagaaatga    2100
tggcaatgat gggaaaatcg gtgtcagaag gcaagaaatt atttattaac accacatccc    2160
aaaaggcaaa aagtaagtac ggcacaatcg ctcttgagtc ttatattttt ggtctaaata    2220
aagaagcaaa gatattaaga atagactctg aaaccactaa aaaccctgaa catccagcct    2280
ataaaatcat tgaccaagac ttaaataata tcctcaaaga ttatgattat gtcattgcct    2340
caccttgcct tcaaacaggt gtcagtatta ccttaaaagg gcattttgac cagcaattta    2400
acttttccag tggaaacatt acacctcatt gcttttttaca gcaaatgtgg cggttgaggg    2460
atgcagaaat tgaaagattc tattatgtgc cgaactcatc taacctcaat ctcattggga    2520
ataagtcaag ttcaccatca gaccttctaa agagcaataa caagatggca acggcaacgg    2580 ttaaccttttt gggtagaatc gactccgaat attccctaga gtatgaatcg cacggcattt    2640
ggcttgagac gtgggcaaaa ttatcagcac ggcataacag ttcaatgcgt tgttactctg    2700
aaattcttac ctatctaatt acgtctcaag ggcataaatt aaatatcaac attccctcac    2760
ctcttgcaga tattaagaag ctaaatgatg aggtaagtag taacagggaa aaggtaaaaa    2820
atgagagata ctctcagagg ttaaactcac cagatattaa cgatgcagaa gctaccatac    2880
tcgaatctaa agagcaaaaa atcggattga ctctcaatga gagatgcacc ctagaaaagc    2940
ataaagttaa gaagcggtat gggaatgtaa agatggatat tctcaccttt gatgatgatg    3000
gactataccc caaactcaga ctattttatt acctcaccat cggtaaacct catctcaagg    3060
ctaatgacag aaaagctatt gccaaaatgg gcaatgacaa taaaggcaag attctatcaa    3120
aagacttagt taataaaact tactccgctc gtgtgaaggt cttagagatt cttaaactaa    3180
ctgactttat cgacaatctt agagatgaac tcttaataac tcccaataat ccagctatca    3240 ccgatttttaa taatcttctg ctaagagcta agaaggattt aagagtatta ggagtcaaca    3300
tcggaaaata tccaatggcc aacattaatg ccgtacttac tctcattggt cacaaacttt    3360
ctgtaatgag agatgagttc ggaaaagaga aaaggataaa agtagatggt aaatcatacc    3420
gatgttatca acttgaaaca ttaccagatt ttaccaatga tactcttgac tactggttag    3480
aaaatgatag ccaaaaagaa gtaacagcaa cagaaaatta ctccgaaaat tttaacccctt    3540
```

```
caaatagcta caatccagac agtaagacac tttcagaggg tgcaaatttc ctatatataa    3600
ataaagaaga attgcatcca aataaattgc acctagaaat aaaagaaggt gctgaacttt    3660
ttttattcgg ggtaaaggtg attgtgaaag gaatcttgga cggggcagta actatattct    3720
ctatgggtca agaatacgat ttatccctca atgaactaga ggggatgtta acatcatgaa    3780
ctttacaaga atcttttta agggcgatcg caccatgtta aatgatggta catttgttca    3840
gatatttgat atttaccatg accacgcatt gggagtgacc cttgacctta agacagaaaa    3900
aattatttcc gatgatgtta gggtaattac tgtcaaagac ttattgttcg atggcactta    3960
taaaggggta aaatctttta tgcccgataa tgcccgataa tgcccgattg atgctacaaa    4020
atcccataat cataagcgat aatcccctaa tagcttgtaa ttcttgaacc gtagcgattt    4080
tagagtattc caaaagaag aaataaacac cgcaaaatgt cgtatttcac atatataaac    4140
caaggttttt tgccctaaaa tctttatgtt tgtagtgtga tgttgggtca aaatggtcag    4200
aaaagttgca aggtttttat ggatgcttac gcgcgcgagg ggtaagcatc cccaaatagt    4260
tactttatcc tagtccatgc ccatttattg ccgtcccgtt cggctttaaa aaagtgccaa    4320
aactcacaag gtgcaataaa aagttctgta cctttcgcaa ccctagataa tctttcaaca    4380
gttacttttt ttcctattat ctcggtacaa agtttggcta gtttctcttt tccctctttt    4440
tcaatcaagc cttcttgtat gcccaactca ttgattaatc tctctatttt taccattatt    4500
tcccgttcag gtagtttatc ccctaaatct tcatcggggg gcaatgtagg gcattctgaa    4560
ggggcttttt cttctgtctg gacattatct aatattgaag taaccaaaact atcttcagtt    4620
ttttctattc ctattaattc atattcggtt actgtatccg tatcaatatc cgaataacta    4680
tctttatccg tattagctat tcggttaagt ttatccgtta actcagaaac aagactatat    4740
agcggtttta gcttttcttc tatcctgtta tctaatacgg ataagtttat acggttatca    4800
ttatccgtat tagtatcatt gggctttttt ggtagttcta cccccctcata aaccgctttt    4860
attcccaatt ccaacagact gataacagta tcctttataa tgggtttttt gctgatatgg    4920
tgaacttttg ccccttccat cattgcgata ctttctatct cactcatcaa cttatcgctt    4980
aagtgaatct cgtatctgtt taatccctta ctggttttat tcatatccgt ttactttatt    5040
cggttaacaa ttctatttta tacgaataaa atattatacg gttaacttta tacgtttaac    5100
tattttatct atacggataa cagtaataag ttattcgtat tagttatacg tttacttttta    5160
tccaataaaa attagtgcat ttaaactaaa agaatgattt tatcggagtt gatagcattg    5220
gattaaccta aagatgttta taagctatat ctgataagta tttaaggtta ttttgttatt    5280
ctgtttattg acattatcag aataaaagaa tagaatataa ttgttgagag ataagaggtt    5340
taagtgatta tggttaagaa gttagttggt tatgtcaggg tcagtagtga atcgcaagag    5400
gataacacta gcttacagaa tcagatagag agaattgaag catattgtat ggcttttggt    5460
tatgagttgg taaaaatatt caagagggtt gccactggta caaaagcaga tattgaaacc    5520
cgtcctattt ttaatgaagc tatagaatac ttgaaacagg ataatgctaa tggaattatt    5580
gccttgaagc tagaccgaat cgcacggaat gctttagatg tattgcgttt ggttcgtgaa    5640
accttagaac cacaaaataa aatgttagtg ttactagata ttcaggtaga tacttcgaca    5700
ccttcaggaa aaatgatttt aactgtaatg agtgccgttg ctgaactcga aagagacatg    5760
atctatgatc gcactcaggg gggtagaaag actaaagccc aaaagggcgg gtatgcctac    5820
gggaaaccta aatttggcta taagactgaa gaaaaggaac taaagaaga ttcagcacaa    5880
```

```
caggaaacta ttaaactaat taagagacac cgtaggtcag ggaaaagcta ccagaaaata    5940
gctgattatc tcaatgccca agtattccc actaaacaag gtaagaaatg gagttctagc    6000
gtcgtctatc gaatctgtca ggaaaaagct ggttaagtct gtttatagat atttagaatt    6060
tattgaataa aaatagtatg aacaataaat atttatggac taaccacgct cggaaacgtt    6120
taactgaacg atgggaaata aagaatcat gggttattga taccatcgaa atcctgaac    6180 gttcagaatt tattgttgat gagtcagggg aaaaatatca ttactataaa gaatagcta    6240 agtttaagaa tagagtgtta gaagtgataa cttctgccaa ctcaacaccc acaagaataa    6300
taacctttta ctttaaccgt aacatgagga aaaatttatg attgttactt acgataatga    6360
agttgacgca atttatttta agttaacgga aaataaaatt gatagcaccg aacctcaaac    6420
agacaggatt atcattgatt acgatgaaag taataatatt gttggcattg aggtattaga    6480
ttttaattat cttgtcaaga aaggtttaac cgttgctgat ttacctttt ctgaagatga    6540 aagattaaca gcttctcaat attttaattt tcctgttgct atctaatcca gaaggggcaa    6600 taatccccctt ctttcatcga gttagactta atatcacaaa agtcattttc attttaccgt    6660
ttcttttcca cagcgtccgt acgcccctcg ttaaatctca aaaccgacaa tttatgatgt    6720
ttataaaaag ttactcactt taataagtat ttatactcat taaagggtta ttctttttt    6780 gtagcctgat aggttgggaa ggaatatttc agattatcag atttgttg              6828
```

<210> SEQ ID NO 2
<211> LENGTH: 1061
<212> TYPE: PRT
<213> ORGANISM: Cyanobacterium sp. ABICyano1

<400> SEQUENCE: 2

```
Met Ile Leu Gly Lys Pro Ser Asn Ser Gln Pro Leu Asn Lys Arg Asn
1               5                   10                  15

Phe Gln Asn Pro Asp His Ile Lys Glu Trp Gln Gln Ser Ala Ile Ser
            20                  25                  30

Gln Asp Leu Ile Ala Glu Asn Leu Val Ser Val Ala Asn Gly Phe Asp
        35                  40                  45

Val Leu Phe Ile Gly Asn Lys Tyr Arg Thr Asn Thr Gly Val Leu Ser
    50                  55                  60

Arg His Ile Leu Asn Ser Tyr Ser His Leu Glu Asp Gly Gly Ser Tyr
65                  70                  75                  80

Gly Arg Thr Phe Asp Pro Phe Thr Asn Lys Glu Met Gln Trp Val Gln
                85                  90                  95

Phe Lys Pro Asn Arg Pro Arg Lys Gly Ser Thr Gly Lys Val Ile Lys
            100                 105                 110

Tyr Glu Ser Pro Lys Gly Glu Pro Thr Arg Val Leu Met Pro Phe Val
        115                 120                 125

Pro Met Lys Ile Trp Gln Arg Ile Ser Asp Lys Phe Gly Val Pro Ile
    130                 135                 140

Asn Pro Lys Lys Asp Thr His Phe Trp Glu Trp Val Lys Asn Asn Pro
145                 150                 155                 160

Ser Ile Pro Ile Ala Ile Thr Glu Gly Asn Lys Lys Ala Asn Cys Leu
                165                 170                 175

Leu Ser Tyr Gly Tyr Pro Ala Ile Ala Phe Val Gly Ile Trp Asn Gly
            180                 185                 190

Leu Glu Lys Ile Asn Asp Phe Ser Lys Glu Lys Gln Leu Lys Glu Asp
        195                 200                 205
```

```
Leu Lys Trp Leu Leu Ser Asn Gly Asn Arg Asn Ile Asn Ile Ile Phe
    210                 215                 220
Asp Gln Asp Gln Lys Gln Lys Thr Val Ile Asn Val Asn Lys Ala Ile
225                 230                 235                 240
Phe Ala Leu Ser Ser Leu Ile Ser Arg Asn Gly His Lys Val Asn Ile
                245                 250                 255
Val Gln Trp Leu Pro Ser Lys Gly Lys Gly Ile Asp Asp Tyr Leu Val
            260                 265                 270
Ala Leu Pro Phe Glu Lys Arg Glu Asn His Leu Asp Asn Leu Ile Lys
        275                 280                 285
Ile Ala Pro Ser Phe Asn Phe Trp Ser Thr Lys Tyr Leu Phe Lys Cys
    290                 295                 300
Arg Lys Pro Asp Leu Thr Val Asn Cys Arg Tyr Leu Ser Asp Ala Val
305                 310                 315                 320
Lys Glu Leu Pro Gln Glu Asp Ile Ala Leu Ile Ala Pro His Gly Thr
                325                 330                 335
Gly Lys Thr Ser Leu Val Ala Thr His Val Lys Asn Arg Ser Tyr His
            340                 345                 350
Gly Arg Lys Thr Ile Ser Leu Val His Leu Glu Ser Leu Ala Lys Ala
        355                 360                 365
Asn Gly Asn Ala Leu Gly Leu Tyr Tyr Arg Thr Glu Asn Asn Ile Glu
    370                 375                 380
Lys Gln Tyr Leu Gly Phe Ser Leu Cys Val Asp Ser Cys Arg Asp Lys
385                 390                 395                 400
Ile Asn Gly Ile Thr Thr Asp Ile Ile Ser Gly Gln Asp Tyr Cys Leu
                405                 410                 415
Phe Ile Asp Glu Ile Asp Gln Val Ile Pro His Ile Leu Asn Ser Glu
            420                 425                 430
Thr Glu Val Ser Lys Tyr Arg Cys Thr Ile Ile Asp Thr Phe Ser Glu
        435                 440                 445
Leu Val Arg Asn Ala Glu Gln Val Ile Ile Ala Asp Ala Asp Leu Ser
    450                 455                 460
Asp Val Thr Ile Asp Leu Ile Glu Asn Ile Arg Gly Lys Lys Leu Tyr
465                 470                 475                 480
Val Ile Lys Asn Glu Tyr Gln Tyr Gln Gly Met Thr Phe Asn Ala Val
                485                 490                 495
Gly Ser Pro Leu Glu Met Met Ala Met Met Gly Lys Ser Val Ser Glu
            500                 505                 510
Gly Lys Lys Leu Phe Ile Asn Thr Thr Ser Gln Lys Ala Lys Ser Lys
        515                 520                 525
Tyr Gly Thr Ile Ala Leu Glu Ser Tyr Ile Phe Gly Leu Asn Lys Glu
    530                 535                 540
Ala Lys Ile Leu Arg Ile Asp Ser Glu Thr Thr Lys Asn Pro Glu His
545                 550                 555                 560
Pro Ala Tyr Lys Ile Ile Asp Gln Asp Leu Asn Asn Ile Leu Lys Asp
                565                 570                 575
Tyr Asp Tyr Val Ile Ala Ser Pro Cys Leu Gln Thr Gly Val Ser Ile
            580                 585                 590
Thr Leu Lys Gly His Phe Asp Gln Gln Phe Asn Phe Ser Gly Asn
        595                 600                 605
Ile Thr Pro His Cys Phe Leu Gln Gln Met Trp Arg Leu Arg Asp Ala
    610                 615                 620
Glu Ile Glu Arg Phe Tyr Tyr Val Pro Asn Ser Ser Asn Leu Asn Leu
```

-continued

```
            625                 630                 635                 640
Ile Gly Asn Lys Ser Ser Pro Ser Asp Leu Leu Lys Ser Asn Asn
                645                 650                 655

Lys Met Ala Thr Ala Thr Val Asn Leu Leu Gly Arg Ile Asp Ser Glu
                660                 665                 670

Tyr Ser Leu Glu Tyr Glu Ser His Gly Ile Trp Leu Glu Thr Trp Ala
                675                 680                 685

Lys Leu Ser Ala Arg His Asn Ser Ser Met Arg Cys Tyr Ser Glu Ile
                690                 695                 700

Leu Thr Tyr Leu Ile Thr Ser Gln Gly His Lys Leu Asn Ile Asn Ile
            705                 710                 715                 720

Pro Ser Pro Leu Ala Asp Ile Lys Lys Leu Asn Asp Glu Val Ser Ser
                                725                 730                 735

Asn Arg Glu Lys Val Lys Asn Glu Arg Tyr Ser Gln Arg Leu Asn Ser
                740                 745                 750

Pro Asp Ile Asn Asp Ala Glu Ala Thr Ile Leu Glu Ser Lys Glu Gln
                755                 760                 765

Lys Ile Gly Leu Thr Leu Asn Glu Arg Cys Thr Leu Glu Lys His Lys
            770                 775                 780

Val Lys Lys Arg Tyr Gly Asn Val Lys Met Asp Ile Leu Thr Phe Asp
785                 790                 795                 800

Asp Asp Gly Leu Tyr Pro Lys Leu Arg Leu Phe Tyr Tyr Leu Thr Ile
                805                 810                 815

Gly Lys Pro His Leu Lys Ala Asn Asp Arg Lys Ala Ile Ala Lys Met
                820                 825                 830

Gly Asn Asp Asn Lys Gly Lys Ile Leu Ser Lys Asp Leu Val Asn Lys
            835                 840                 845

Thr Tyr Ser Ala Arg Val Lys Val Leu Glu Ile Leu Lys Leu Thr Asp
            850                 855                 860

Phe Ile Asp Asn Leu Arg Asp Glu Leu Leu Ile Thr Pro Asn Asn Pro
865                 870                 875                 880

Ala Ile Thr Asp Phe Asn Asn Leu Leu Leu Arg Ala Lys Lys Asp Leu
                885                 890                 895

Arg Val Leu Gly Val Asn Ile Gly Lys Tyr Pro Met Ala Asn Ile Asn
                900                 905                 910

Ala Val Leu Thr Leu Ile Gly His Lys Leu Ser Val Met Arg Asp Glu
            915                 920                 925

Phe Gly Lys Glu Lys Arg Ile Lys Val Asp Gly Lys Ser Tyr Arg Cys
            930                 935                 940

Tyr Gln Leu Glu Thr Leu Pro Asp Phe Thr Asn Asp Thr Leu Asp Tyr
945                 950                 955                 960

Trp Leu Glu Asn Asp Ser Gln Lys Glu Val Thr Ala Thr Glu Asn Tyr
                965                 970                 975

Ser Glu Asn Phe Asn Pro Ser Asn Ser Tyr Asn Pro Asp Ser Lys Thr
                980                 985                 990

Leu Ser Glu Gly Ala Asn Phe Leu Tyr Ile Asn Lys Glu Glu Leu His
            995                 1000                1005

Pro Asn Lys Leu His Leu Glu Ile Lys Glu Gly Ala Glu Leu Phe
            1010                1015                1020

Leu Phe Gly Val Lys Val Ile Val Lys Gly Ile Leu Asp Gly Ala
            1025                1030                1035

Val Thr Ile Phe Ser Met Gly Gln Glu Tyr Asp Leu Ser Leu Asn
            1040                1045                1050
```

```
Glu Leu Glu Gly Met Leu Thr Ser
    1055              1060

<210> SEQ ID NO 3
<211> LENGTH: 228
<212> TYPE: PRT
<213> ORGANISM: Cyanobacterium sp. ABICyano1

<400> SEQUENCE: 3

Met Val Lys Lys Leu Val Gly Tyr Val Arg Val Ser Glu Ser Gln
1               5                   10                  15

Glu Asp Asn Thr Ser Leu Gln Asn Gln Ile Glu Arg Ile Glu Ala Tyr
            20                  25                  30

Cys Met Ala Phe Gly Tyr Glu Leu Val Lys Ile Phe Lys Glu Val Ala
        35                  40                  45

Thr Gly Thr Lys Ala Asp Ile Glu Thr Arg Pro Ile Phe Asn Glu Ala
    50                  55                  60

Ile Glu Tyr Leu Lys Gln Asp Asn Ala Asn Gly Ile Ile Ala Leu Lys
65                  70                  75                  80

Leu Asp Arg Ile Ala Arg Asn Ala Leu Asp Val Leu Arg Leu Val Arg
                85                  90                  95

Glu Thr Leu Glu Pro Gln Asn Lys Met Leu Val Leu Asp Ile Gln
            100                 105                 110

Val Asp Thr Ser Thr Pro Ser Gly Lys Met Ile Leu Thr Val Met Ser
        115                 120                 125

Ala Val Ala Glu Leu Glu Arg Asp Met Ile Tyr Asp Arg Thr Gln Gly
    130                 135                 140

Gly Arg Lys Thr Lys Ala Gln Lys Gly Gly Tyr Ala Tyr Gly Lys Pro
145                 150                 155                 160

Lys Phe Gly Tyr Lys Thr Glu Lys Glu Leu Lys Glu Asp Ser Ala
                165                 170                 175

Gln Gln Glu Thr Ile Lys Leu Ile Lys Arg His Arg Arg Ser Gly Lys
            180                 185                 190

Ser Tyr Gln Lys Ile Ala Asp Tyr Leu Asn Ala Gln Ser Ile Pro Thr
        195                 200                 205

Lys Gln Gly Lys Lys Trp Ser Ser Ser Val Val Tyr Arg Ile Cys Gln
    210                 215                 220

Glu Lys Ala Gly
225

<210> SEQ ID NO 4
<211> LENGTH: 61
<212> TYPE: PRT
<213> ORGANISM: Cyanobacterium sp. ABICyano1

<400> SEQUENCE: 4

Met Leu Asn Asp Gly Thr Phe Val Gln Ile Phe Asp Ile Tyr His Asp
1               5                   10                  15

His Ala Leu Gly Val Thr Leu Asp Leu Lys Thr Glu Lys Ile Ile Ser
            20                  25                  30

Asp Asp Val Arg Val Ile Thr Val Lys Asp Leu Leu Phe Asp Gly Thr
        35                  40                  45

Tyr Lys Gly Val Lys Ser Phe Met Pro Asp Asn Ala Arg
    50                  55                  60

<210> SEQ ID NO 5
```

```
<211> LENGTH: 254
<212> TYPE: PRT
<213> ORGANISM: Cyanobacterium sp. ABICyano1

<400> SEQUENCE: 5

Met Asn Lys Thr Ser Lys Gly Leu Asn Arg Tyr Glu Ile His Leu Ser
1               5                   10                  15

Asp Lys Leu Met Ser Glu Ile Glu Ser Ile Ala Met Met Glu Gly Ala
            20                  25                  30

Lys Val His His Ile Ser Lys Lys Pro Ile Ile Lys Asp Thr Val Ile
        35                  40                  45

Ser Leu Leu Glu Leu Gly Ile Lys Ala Val Tyr Glu Gly Val Glu Leu
    50                  55                  60

Pro Lys Lys Pro Asn Asp Thr Asn Thr Asp Asn Asp Asn Arg Ile Asn
65                  70                  75                  80

Leu Ser Val Leu Asp Asn Arg Ile Glu Glu Lys Leu Lys Pro Leu Tyr
                85                  90                  95

Ser Leu Val Ser Glu Leu Thr Asp Lys Leu Asn Arg Ile Ala Asn Thr
            100                 105                 110

Asp Lys Asp Ser Tyr Ser Asp Ile Asp Thr Asp Thr Val Thr Glu Tyr
        115                 120                 125

Glu Leu Ile Gly Ile Glu Lys Thr Glu Asp Ser Leu Val Thr Ser Ile
    130                 135                 140

Leu Asp Asn Val Gln Thr Glu Glu Lys Ala Pro Ser Glu Cys Pro Thr
145                 150                 155                 160

Leu Pro Pro Asp Glu Asp Leu Gly Asp Lys Leu Pro Glu Arg Glu Ile
                165                 170                 175

Met Val Lys Ile Glu Arg Leu Ile Asn Glu Leu Gly Ile Gln Glu Gly
            180                 185                 190

Leu Ile Glu Lys Glu Gly Lys Glu Lys Leu Ala Lys Leu Cys Thr Glu
        195                 200                 205

Ile Ile Gly Lys Lys Val Thr Val Glu Arg Leu Ser Arg Val Ala Lys
    210                 215                 220

Gly Thr Glu Leu Phe Ile Ala Pro Cys Glu Phe Trp His Phe Phe Lys
225                 230                 235                 240

Ala Glu Arg Asp Gly Asn Lys Trp Ala Trp Thr Arg Ile Lys
                245                 250

<210> SEQ ID NO 6
<211> LENGTH: 87
<212> TYPE: PRT
<213> ORGANISM: Cyanobacterium sp. ABICyano1

<400> SEQUENCE: 6

Met Asn Asn Lys Tyr Leu Trp Thr Asn His Ala Arg Lys Arg Leu Thr
1               5                   10                  15

Glu Arg Trp Glu Ile Lys Glu Ser Trp Val Ile Asp Thr Ile Glu Asn
            20                  25                  30

Pro Glu Arg Ser Glu Phe Ile Val Asp Glu Ser Gly Glu Lys Tyr His
        35                  40                  45

Tyr Tyr Lys Arg Ile Ala Lys Phe Lys Asn Arg Val Leu Glu Val Ile
    50                  55                  60

Thr Ser Ala Asn Ser Thr Pro Thr Arg Ile Ile Thr Phe Tyr Phe Asn
65                  70                  75                  80

Arg Asn Met Arg Lys Asn Leu
                85
```

<210> SEQ ID NO 7
<211> LENGTH: 82
<212> TYPE: PRT
<213> ORGANISM: Cyanobacterium sp. ABICyano1

<400> SEQUENCE: 7

```
Met Ile Val Thr Tyr Asp Asn Glu Val Asp Ala Ile Tyr Phe Lys Leu
1               5                   10                  15

Thr Glu Asn Lys Ile Asp Ser Thr Glu Pro Gln Thr Asp Arg Ile Ile
            20                  25                  30

Ile Asp Tyr Asp Glu Ser Asn Asn Ile Val Gly Ile Glu Val Leu Asp
        35                  40                  45

Phe Asn Tyr Leu Val Lys Lys Gly Leu Thr Val Ala Asp Leu Pro Phe
    50                  55                  60

Ser Glu Asp Glu Arg Leu Thr Ala Ser Gln Tyr Phe Asn Phe Pro Val
65                  70                  75                  80

Ala Ile
```

<210> SEQ ID NO 8
<211> LENGTH: 16301
<212> TYPE: DNA
<213> ORGANISM: Artificial Sequence
<220> FEATURE:
<223> OTHER INFORMATION: pRL528 helper plasmid

<400> SEQUENCE: 8

```
aagtcacggt actctccgga ggcctttttc atatccggcg ggcctgacac ttccggatgc      60
agcacacgaa acagaagtc accggaacac gccattctga aaaactgtc actaatctgt      120
tttattccgc aaacagaaaa ccaccggata accggggtat aggaagtata aaccacccttt    180
ttgggtatag aagtataaaa ccacctttt gctcctcatc cgaagtatct tacctgaaat     240
tccctcactc gtttaccgct caagccccaa ttttaactgc cggtccagcc taaaccgctc    300
taataaggtt cgatttggcg gtaaaatctc tagcctgata gctcgagatc tagatatcga    360
tgaattcgag ctcggtaccc tattcaatat ttaacttgat tactgtagaa gtataacaaa    420
gtataatcag gttctaactg ttgtcaatta gtctataaaa aatagggttc aaatcttaag    480
tgatagcga tagtgctttg tcctgataga atcttaagtt acctctttgt tacaagaaaa    540
atataaaatg acttcatttg agcttgagag tccaatagaa ataaagactg acccgactga    600
tcttgatcaa gagagtgatt cctttgtaca agaaatttct cgattcaata aagcacttga    660
gcaacgtttt agagataaga tgcgattgca tgaaagttta agtcgaaaaa tagttagttt    720
tcaagctaat aagtcaaaac ctcagtatcg ctggtttaaa tataaagaag ctttttcagt    780
tgatttggta aatcagttaa tattcgagta cgagaaaaaa tcatttgaga ggattcttga    840
ccccttcgca ggagcaggaa caatgctatt tgcctgtagt gatgccggta ttcaagcaga    900
tggtatagaa gtgttaccta ttggtcaaga gattattgaa gtaaggaaaa taatccagcg    960
acaattccgt cgagaagatt ttttgagatt gattgaatgg tacaaacaaa aaccttggaa   1020
tcagcataat aatagaaaat atcttaatcg tttaagaatt actgacggag cttatcctcc   1080
tgaaacagaa gcatcaatag agagatttttt attttctata gaaaaagaga atattcttgt   1140
gaaacaagtt ctccgttttg ctctattgtg tattcttgaa tctatcagct atacccgtaa   1200
agatggacag tatctacgtt gggataaaag agcatttagg aaaagtggat cagataaatt   1260
tgataaaggt aaaattctgg atttcgatga agcaattact gagcaaataa aattaattttt   1320
```

```
gaatgattcc tttgacttaa taagtaatac attattttgt tatgggactc aaagaagtgg    1380
aattaattta tttaatgctt catgtcttaa aattctgcct gaatttgagc aagattttta    1440
cgactgtatc attacctctc caccctattg taatcgttat gactatacac gtacatacgc    1500
tctagaatta gctctattag gtgtgggaga aagagatata gtacaactta ggcaagatat    1560
gctgagttgt actgttgaaa acaaagaaaa gtctcttatt cacaattggc aggaagcatt    1620
acgcatactt gataaacaag aattgttaca agtatcttg cgctttcttg agcgagagct     1680
tgaaagaaaa aaacttaata ataacggtat tcctcgtatg ataaaaggat atttctatga    1740
aatggcttgc gttattatag aatgctttag agttttaaaa aatggctcac ctttatttat    1800
ggtaaatgat aatgttcgct atgcaggtat tgatatttcg gttgatttaa ttctttctaa    1860
tattgcagaa gaaattggtt ttaatgtgga gaaaattctt gtcttaccta ctggcaaagg    1920
taacagtagc caacaaatgg ggacacatgg aagaaagaca cttcgcaaat gtgtgtatgt    1980
ttggagaaaa ccctagtgcc atatcaatat catattcaaa gcaatgatga tcttgtgact    2040
ccatatcaag aagtccgagc aggatttgtt gctttagctt tagaaagaaa tcgaaaagca    2100
acaccatttg ttgagcaggc aagagcatta aagatccgag taagccaaat tgaaaggggg    2160
gatcctctag aagctttaat gcggtagttt atcacagtta aattgctaac gcagtcaggc    2220
accgtgtatg aaatctaaca atgcgctcat cgtcatcctc ggcaccgtca ccctggatgc    2280
tgtaggcata ggcttggtta tgccggtact gccgggcctc ttgcgggata tcgtccattc    2340
cgacagcatc gccagtcact atggcgtgct gctagcgcta tatgcgttga tgcaatttct    2400
atgcgcaccc gttctcggag cactgtccga ccgctttggc cgccgcccag tcctgctcgc    2460
ttcgctactt ggagccacta tcgactacgc gatcatggcg accacacccg tcctgtggat    2520
cttctcaacg aagaagaag aatcatcgct gaggtgaaaa ataaatactc aacggttact    2580
ggcggggatt tagcagataa atataaaggc ttagatgagt tggtatcacc gaaacatagc    2640
cgatttaagg attactgtgc gtactttgtt aatataatcc ctcgtaaacc tatcagatat    2700
aacagcccct ttactccttc aataaaggt agtggtactc tgtgtccttc gaaccctaac    2760
attagaatca ttgatggtgc gagtttctat gagcttgtca ctggcagacc agatgctctg    2820
caagaactcc atagtgctct ccctcacgca attgagtata ttttgagcga acgtcttggg    2880
cagcaaggtt tttccatccc tgataaagat agttttatta gtatttggg ctctgcttac     2940
ggctgataac catgatcaat gtttgacaaa gcacatgtaa acccatacag tagtaaccat    3000
gactaatgtt ggcatggtta ctaaatatgt taaggaaga gttttcactt tcagaagttg     3060
cagacatttt gggcgtttca aagaaactt taaggcgttg ggatactgct ggaaaattag     3120
tttctcaaag aaatgacgaa aacaactatc gatttttataa aaaagagcaa cttaaaaatt   3180
ttgaacaagc tcagttttta tttaaaagcc agtggcctga tgagactaaa ataagcaata    3240
atgtttatac tgtattagag ttatttgctg gcgcaggggg gatggcttta ggtttagaaa    3300
aagccggttt aaaatctgtt ttactaaatg aaattgactc ccatgcttgt aagacgttac    3360
gaaaaaatag gcctgaatgg aatgtggttg aaggtgatgt gagccaagta gacttcaccc    3420
cttataggaa taccgttgat gtgctggctg gtggcttttcc ttgccaggca ttctcttatg   3480
caggcaaaaa acttggtttt gaagatacac ggggcaccct tttctttgaa ttcgcccgag    3540
ccgctaaaga aatcaatccg aaagttcttt tagcagagaa tgttcgaggg ttgctaaatc    3600
atgatgctgg acgaacttta gaaacaataa aaaatattat cacagacttg ggctacactt    3660
```

```
tatttgagcc aagagtgctt aaggctattt tctacaaagt gccgcaaaaa cgcgagcgtt    3720
tgatcattgt agctgtaaga aatgatcttg ctgatggcat cgattatgag tggccttctt    3780
cttacaataa aatattaacc cttaaagatg cattaaaaaa gggagagctg tatgatagcg    3840
acgtgccaga atctgaagga caaaaatatc ccaaaagaaa agcagagatc ctaagtatgg    3900
ttcctcccgg tggctactgg agagatcttc ctgaagatat tcaaaaagaa tacatgctca    3960
agagttttta cttaggtggg ggcaaaactg gtatggctcg tcgtttgtca tgggatgaac    4020
caagcctaac attaacatgc gccccagcac agaaacaaac agagcgttgc cacccagaag    4080
aaacaagacc attaactgtg cgtgagtatg caagaataca gaccttcccc gatgaatggg    4140
tatttgaagg cccaatgtca gcgaaatata agcaaatagg aaacgctgtt cctgttaatc    4200
tgtcatttgc tgttggcaaa tctgtggtac atctttttaga taagataaat aaaagataga    4260
ccctgtaaat aattctgtgt aattgctgcc atattaaagg tgatcgctca ggcggtcacc    4320
gaactcgata taaagcgac tcatcgccag ccgccagctc tggattggca tattccattt    4380
ttttgatgca tccttgatcg ccagagaaat gaccttccgc agcgagtcgt cagtcgggaa    4440
cactttacgc ttcttaatgg ccgcacggat cacgctgttc agcgattcga tagcgttcgt    4500
ggtgtagatg gccttgcgga tatcgggcga atagccgaag aacgtgttga tattttccca    4560
gtgcgcacgc cagcttttgc tgatttgcgg gtatttatcg tcccagacat tcggaactg    4620
ctccggtgcc actagcgccg cctcttctgt tggcgcctga tacaccgttt ttaacccgcc    4680
agtgacggct ttgtagtcct tccacgatac gtatttcagg ctgttgcgca ccatatgaat    4740
gatgcacaac tggatgtgcg tctacggata cacgctgttt atcgcatccg gaaagccttt    4800
cagaccgtcc atgcaggcaa taaggatatc ctgaagcccc cgattcttaa gctctgtcag    4860
ccccccagc cagaacttcg cccccttcgtt tccggccagc cacatgccca gcaactcttt    4920
ctggcctcca gtattaatac cgagtgcaag gaacaccgct tgttaatta cggtgccacc    4980
ttgacgaact ttcaccacga tacagtcaag gtaaacaatg gatacagtg catccagagg    5040
tcgattttgc cattctgcaa cctgctcttt gaccgcatca gtgactttac atatcagcgt    5100
gggtgacaca tctgcgtcgt acatctcttt gaaggtggcg acaatttcgc gggtagtcat    5160
atctttggcg tagagggata aaatctggct gtccatctgc gtaatgcgcg tctggtgctt    5220
cttaatcaac tgcggttcga aggtgttttc acggtcacgc gacgtgttca gttcgatcct    5280
ctacgccgga cgcatcgtgg ccggcatcac cggcgccaca ggtgcggttg ctggcgccta    5340
tatcgccgac atcaccgatg gggaagatcg ggctcgccac ttcgggctca tgagcgcttg    5400
tttcggcgtg ggtatggtgg caggcccgt ggccggggga ctgttgggcg ccatctcctt    5460
gcatgcacca ttccttgcgg cggcggtgct caacggcctc aacctactac tgggctgctt    5520
cctaatgcag gagtcgcata agggagagcg tcgactctag agtcgacctg cagcaatggc    5580
aacaacgttg cgcaaactat taactggcga actacttact ctagcttccc ggcaacaatt    5640
aatagactgg atggaggcgg ataaagttgc aggaccactt ctgcgctcgg cccttccggc    5700
tggctggttt attgctgata atctggagc cggtgagcgt ggatctcgcg gtatcattgc    5760
agcactgggg ccagatggta agccctcccg tatcgtagtt atctacacga cggggagtca    5820
ggcaactatg gatgaacgaa atagacagat cgctgagata ggtgcctcac tgattaagca    5880
ttggtaactg tcagaccaag tttactcata tactttag attgatttaa aacttcattt    5940
ttaatttaaa aggatctagg tgaagatcct ttttgataat ctcatgacca aaatccctta    6000
acgtgagttt tcgttccact gagcgtcaga cccgtacat cacgaatata gtttgcttga    6060
```

```
catcctgaca agaataatat tgtaattaga aaaattatta ttttcatatt tctttccaac    6120
aaaagtaaaa atacttatgc atttaaaata ctacctacat aatttacctg aatcacttat    6180
accatggatt cttattttaa tatttaacga caatgataac actcctttgt tatttatatt    6240
tatatcatca atacatgtat tgctatatcc atactctaaa ttaaccatat ctagatatat    6300
caaagaaaat acaaagttaa aaaaagaacc ctggtactta tgcaagttat ctgcattgtt    6360
ttatttatta atggcaatcc cagtaggatt gccaagtttc atatattaca ctctaaagag    6420
aaattaaatc cctaacaact cattaagttt gctcaactca tcatccccta tgtaagaaga    6480
aacaataccT gtgacaattg caatccccca gaaaccaaga ggcacaccaa caataaaact    6540
aaacattaat gccacaattt ttgccacacc tacatcgacc gcacttttct ccagcgtgac    6600
aaacaaaggt cgccagttac cagtttctat tgcatttttA aaatcagaac caacatcata    6660
tagaaaagat actcgactgg tgattttaag cgactttgat atcttcgtta aattcttaga    6720
taactcatca taattaacag actctaacgc attaaaaata gcatcccgat caaccttact    6780
gaatttctta tccagtacat tcttatactt tcaaatgct gccagagctt catcaacacc    6840
ttgaattttc tttcctttag acttttccgc taaatcctga gcaattttTg cgtatttttc    6900
tccatattgt tcggttatat attgataaaa tccaaccata gtttcaacag catcttttat    6960
ctggctcttt tcaagagcat cctgagcttc ttttaatttc tgctctgcct ctttaacctc    7020
agcggcctta ccatccctga cactaacagc attcttaatt tcattttcaa ctgcggagta    7080
ctcagcctgc ttagcttcaa gctgacgctg tagtttttTc tgaacgtcac gccatcccgg    7140
aaatccggag accttcacgt caacactctt ctgagcgttt tcaagctctc ctgcaactct    7200
ggaaacagta gcttgcttac tctgtacatc actttcagcc ttcgccagtt cagctttcgc    7260
ctcagctaaa cgcttctctg cttccgccac cgcctgtttc tcttcattaa gagtttcatg    7320
ttcagcgacc tctgcatttt cacgagcctt tcttcagct tccttctgtt tattcacatc    7380
accaatttta ctttgcaatg tattttTata agaattaagt ttgctaatat ctgcatcaag    7440
ctgatttgat ttttttTgca actcatcaac atccctctca agatcagtga taccatgata    7500
agaatgatgc ttgaatactt ttttcatctc ctcgattttc ttctgttttt cactaatctg    7560
tgtagcaatt ttattcttct gcttttgttt ttcattaatt acattactca ccaccttcga    7620
actcttatcc atatcactga cctgagcatt cgttggtgca gtattaactg aagcagtgtt    7680
attgttgtta tttcctgagc tttctgcaaa aagtgatggc atatcactaa ttaaagaatt    7740
aagaactctg gagacccctc caaatggatt atcaaccaga gttgaattct cttctgtcat    7800
aacaatacca ttcatcaccg gaaggccatc attattaatg acaacatcac cccacggagt    7860
cagatatgac tcaccggttt tcatcacagt tgatgtagaa ccagatgaat tgaatttcc    7920 ctgaccacca ttattaccat gcccagagcc accacccag tgaacccac tattactatt    7980 attatttcca ccttgctgat tcagattcgc ccctgttccc cccatagact caccagcagt    8040
tggtccatat ccacttagtt ctttagccat aaattcctct ttgataatta aaacaataaa    8100
ttaaaaacaa tatactgtac atataaccac tggttttatg tacagtaaaa acctactact    8160
cagcattgtc catgtcaaga gcatggattt tcattttgc aataaggatc acactatggg    8220
gaggcaggca ttgagaacgt cgaaacagaa caccggagca aatcaggatg agatataaaa    8280
ctgttggatc atgaaaaaac ggagaacgat gtgagcaaat caccccgcca taaactgaac    8340
aaaacagaca aacgacttct cgacaccctt gttgctgccg gatatgagca tgacaaagcc    8400
```

-continued

```
cgtgacctca tccagaaaca ggtttacacg ctgacactgg ctgatcagcg tcatgtggtc    8460
agtgaaatca gtaatggtgt gaatcccacc caggcttact cggcggtata ccaggcaaga    8520
cgcattcgcc tcgcccgtaa atatctgaac ggtaaaaagg ttatggaaga aaccggggaa    8580
aatacgcccc catcagcgta aggatttctt ttgccgctcc agagactcca gtttttacg     8640 caaatcctct cttttttggg catctctggt gccagccagc tctgctctca actcatcgat    8700
ctgaagttgt atcttcagtc tattactgaa cattttctgt ctggcattaa catccgcaac    8760
aatgccgttt tttgtcttct cggccttttg ttgaaaaaca ttgctgtccg catgactggc    8820
aaccgaagca gaaagaacac taaaaagcag gactggcaca catttttca cgggattatt      8880 cctgactcat tgaccatcaa atcacattgg gagtaaaccg acgtatgata agagatactc    8940
ttcggagata taactccctg agtatcaaga ttaaaaacgc aaggagatgt ttatgagatc    9000
tgccgctgcc aggctgcttc tgatacctct gataacagca caatagctc ttacaggatg     9060 cacaccaaag accagcctgg aacgacatac ccggcattat gtttatgctt cagatgatgg    9120
atttgatcct aacttctaca cccagaaagc agacaccata cgtatgatgc tcccgttctt    9180
tcagcagttc cgggatatgg ggatgaaaga caaagcagcc ggagtatcag cagaaacggc    9240
acagcaacgt gtaaaagaat tccactcaga aaaattttt cactcactcc ggagcacaac     9300
agcctttgct ggcagaaaat acacaaacag cgatatgcct tcgccgaaaa aaatgaaact    9360
aatggcagac accatttctg cggtttatct cgatggatac gagggcagac agtaagggat    9420
ttaccataat cccttaattg tacgcaccgc tgaaatgcgt tcagcgcgat cacggctgct    9480
gacaggtaaa aatggcaaca aaccacccga aaagctgccg cgatcgcacc tgataaattt    9540
taaccgtatg catagctatt cagccatgtg aataacgctg gttttgcctg cgtaaacctc    9600 atgcactgt ttttttcca tcttttcagt tgatgacata cgcagacatc gcgggatgag       9660
gctgaggaat gagcgcgatc tggcaaagag gcaaaacaca gcaacaaaaa cgacacgcca    9720
gaatcgcgcc cggatgcgtt tttaacgcgt tccggtacca tctggcaacc tcccggaaca    9780
actcaccgtc acatacctat tgacgggcca cgccataccc gtgcttcccg ttcctgctct    9840
tcatgccagg accgcgcacg ctcccgttcc aggcgtgcct gcctttcctg ttcatcccct    9900
atctgctgtt cgtgataaat aaccgactca agtggtccac ctgcccggct aatctctgca    9960
cctgctgact caagtcgtcg cactgttccc tcagttgccc gttctcctgt cgtgtcagct   10020
cgaacatatg ctgcaaatcc gtgaaggcgc tctcccagtc tttcagccgc tgcatatagt   10080
cctgctgcaa ttgctctaag gcgttcagta agtgcatttc cagctctgtc atactcactt   10140
actccctgac cagtcttact gcgttcttct tctccaccgt ccagttgttt tccccttca    10200 ccccggacgg caacactaga aatttcccgt tcctgccctc gtgatacgtc acaccccatg   10260
ttttttcccg gagtttcgcc agcgtctctt cctggtccct gatagccagg atgttcgccg   10320
caatccggct ttcctgccac tgaatcagcc cccatgacg ccagaaaaat cccgcccgtg     10380
acgcagagcg ccgtcagcga cgggtacagt atccgccctt tgaccagctt ccagagcagc   10440
tcttcctgcc gccgggccag ttcgttctct gtggcgctga actgcgcgtt cacggcactg   10500
ttcagcgtct ccagttgttc tttcaccgct gctgtgtgtg cgctgatagc gtctctgatt   10560
ttctgcccgt ttaagttcag ttccctgtct acagacgctt cgagcttcct gaactcgctg   10620
ttcagcatgt tctctgtaga dacggcacgc tctttcagtt tcttctcgaa gtctgtcccc   10680
atttgtaaaa gattgctcat acagcgcccc tttcagcctg agattacgcc cacccctccgg  10740 gtcggcgata ctgatactgc tcctggttgt cctcacaacc tcaaaacctg ccgctgtaag   10800
```

```
cgcctcagtg acatcctgac gcgttttag cgctccggca tggtaaagag cctccagtcc   10860
cctcgtaatc gcttctgcgg cctcctgttt cgctttcggc agattattcg gggtgacaag   10920
tgtccgcctg ttctccggtg cgttcgggtc gtgcagcccg taatggtgat tcaccagtgt   10980
ctgccaggca ttgattcgcg gacggtccgc tcggtcgtaa tagggctgga gccgttttcc   11040
gctcgccagc tccatattcg ggatgacaaa attcagctca agacgcccct tgtcctggtg   11100
ctccacccac aggatgctgt actgattttt ttcaagaccg ggcatcagta cccgctcaaa   11160
gctctccatc accctttcac gctctcccgg tggcagggtc tgctctgcaa aagacagaac   11220
ccccgaggtg tattttttcg caaacggcgt ggcatcgatg agttcccgca cctcttcggg   11280
agcaccccgc agaactctcg cccttcccg gttacgctcc cggcccagca ggtaatcaac   11340
cggaccactg ccaccgcctt tcccctggc atgaaactta actatcatcc cgttctccct   11400
gtttacggac ctcatccctc agctcactca gttcacgtcc gatggccatc agtgcagcca   11460
ccacatgaac ccggtcatgc cccgaccact gtccgctgtt tatcttccgg gctatctgat   11520
tcaggttatt gccgaccgaa gcgaactggc gcaacagcgg cggtgccagt gtcggaagac   11580
ctgacgtttt cgatggcggt gccccaggc agaccttacg catccatgac gcaagttgtt   11640
ttccctcaca acgtgccagc agccgcgcat gttcctcatc cgtgacccgt atcgtgagca   11700
tcctttcgcg tttcaccggt atcattaaaa acctccgaca gactcccac acatggagaa   11760 acagaactgt gactaaacag gaaaaaaccg cccttaacat ggcccgcttc atcagaagcc   11820
agacgctgac cctgctggaa aaactgaatg aactggacgc cgacgaccag gctgacatct   11880
gcgaagcgct tcacgatcac gctgacgagc tttaccgcag ctgcctcgca cgcttcgggg   11940
ataacggtga aaacctctga cacatgcagc tcccggagac ggtcacagct ggcctgtgag   12000
cggatgccgg gagcagacaa gcccgtcagg gcgcgtcagc gggttttagc gggtgtcggg   12060
gcgcagccat gacccagtca cgtagcgata gcggagtgta tactggctta atcatttggc   12120
atcagtgagg attgtatgaa aagtgcacca tgccgggtgt gaaatgccgc acagatgcgt   12180
aaggagaaaa tgctcgtcca ggcgcttttc cgcttcctcg ctcactgact cgctccgctc   12240
ggtcgttcgg ctgcggcgag cggtatcagc tcactcaaag acggtaatgc ggttatccac   12300
agaatcaggg gataacacca aaagaaacat gtgagcaaaa acaagaacc cggaaaaggc   12360 cacgcagctg gcgtttttcc ataggctccg ccccccttga cgagcatcac aaaaaaccga   12420
cgctcaagtc agaggtggcg aaacccgaca ggacttaaag ataccaggcg tttccccctg   12480
gtggctccct cgtgcgctct cctgttccga ccctgccgct taccggatac ctgtccgcct   12540 ttctccctt gggaagcgtg gcgctttctc atagctcacg ctgttggtat ctcagttcgg   12600
tgtaggtcgt tcgctccaag ctgggctgtg tgcacgaacc ccccgttcag cccgaccgct   12660
gcgccttatc cggtaactat cgtcttgagt ccaacccggt aagacacgac ttaacgccac   12720
tggcagcagc cattggtaac tggatagtgg atttagatac gcagaactct tgaagttgaa   12780
gccttatagc ggctacactg gaaggacagc atttggtatc tgtgctccac taaagccagt   12840
tacccggtta agcagtcccc aactgactta accttcgact aaaccgcctc cccaggcggt   12900 ttttcgttt acaggcagca gattacgcgc agaaaaaaag gatctcaaga agatcctttg   12960
atcttttcta ctgaaccgcg atccccgtca gttcagaaga cgaagatggt gcaacggttc   13020
ctccttgtac aggggtctga cgctcagtgg aacgaaaact cacgttaagc aacgttttct   13080
acctctgacg cctcttttaa tggtctcaga tgtcctttgg tcaccagttc tgccagcgtg   13140
```

```
aaggaataat ggccgagcat attgatatgt ccgtggcaaa gcggggagag gcgtgcgata    13200
tcttcatcat tcagtgtttc accttgcgcc cggagatgat ccagggctgc ctgcatatac    13260
atagtgttcc ataacacgac ggcgttagtg accagcccca gtgcgcccag ttgatcttcc    13320
tgaccgtcgg tatatcgttt tcttatctca ccttttgac cgtgacagat ggctctggca     13380
acggcatggc ggctttctcc ccgattaagc tgggtcagaa tgcgccggcg gtaatcttca    13440
tcatcaatat aattaagcag atacagcgtt ttgttgatgc gccccacttc aatgattgcc    13500
tgagtcagtc cggaaggacg ttcactttc agcaatgaac ggaccagcac tgaagcctgt     13560
actttgccca gtttcaggga gccagcggtc cggatcattt cgtcccactg aaggactatt    13620
tttcggggat ctgattgccc tctggcaata tcattcagca cgccatagtt ggcatcatgg    13680
cccattcgcc agaaaaccga agcaccggca tcagccaggc gtggagaaaa ctggtatccc    13740
agcagccaga aaaggccaaa gacaagttcg ctggtacctg ctgtatcggt cataatttcg    13800
gttggattca gcccggtctc ctgttccaga aggccttcca gcacaaagat agagtccctc    13860
agcgtccccg gtataacgat gccatgaaag ccggaatact gatcggacac aaagttgtac    13920
caggtgatcc ctctgttatt accaaagtat ttgcggttcg gtccggcatt gattgttctg    13980 actgcgtaa caaagcgcat tccatctgca gtccgcctca gcaatatcgg gatagagcgc     14040
agggtcagga aatccttgga tatcgttcag gtagcccacg ccgcgcttga gcgcatagcg    14100 ctgggttcc ggttggaagc tgtcgattga aacacggtgc atctgatcgg acagggcgtc     14160
taagagcggc gcaatacgtc tgatctcatc ggccggcgat acaggcctcg cgtccggatg    14220
gctggcggcc ggtccgacat ccacgacgtc tgatccgact cgcagcattt cgatcgccgc    14280
ggtgacagcg ccggcggggt ctagccgccg gctctcatcg aagaaggagt cctcggtgag    14340
attcagaatg ccgaacaccg tcaccatggc gtcggcctcc gcagcgactt ccacgatggg    14400
gatcgggcga gcaaaaggc agcaattatg agccccatac ctacaaagcc ccacgcatca     14460
agcttttgcc catgaagcaa ccaggcaatg gctgtaatta tgacgacgcc gagtcccgac    14520
cagactgcat aagcaacacc gacagggatg gatttcagaa ccagagaaca tgtcattgta    14580
ctggaaggcg cattacaact gcggctgggg gatgagtggc acaccgtttc tgccggggaa    14640
tccctgcgct tccatgcgga tatcccgcac gcttacgcca atcccggtaa ggccattgtg    14700
acactgcata atctgatcca ttatccgcgc ccggcggaca aataaaaaag cagggtataa    14760
taaatatacc ccgctttgac ttaacggatc gtcttacttt atttgtaaaa taaaaccaaa    14820
ataaatatgt gttcagctta acttattata tatcatcctt ataccaaccg ggatgatatg    14880
tttatactga acagaaaagc atgccattca gaatactatc ttctgttata tatggcggtt    14940
tatttattgt ttaattacac acactcaggc atatcactat gctatcgtga tgttttcact    15000
ggtgttgtta ctactgcctt tacggcattt tggtgttgtt caaaatgact gtcgcagcag    15060
tctttctggt gtcttaaaata ctattattat aactgcatct ggtgttgtta atattattgt    15120
tactgcttac tttattatta ttgctgtcag tctttgctgt ttctttttta ttaagggtat    15180
taccaaactg cggggcatt atcgtacagt gatcctgaac cagtctgaaa cgaaattaca     15240
gattacggtt aaaatataaa aaaaagccac cattcctgcc ggatacgtg gcttaaatac     15300 agaattaatt aatttatttc agtatgttat cacacatcag ctgaagtgta ttaataaacc    15360
gtgctgcatg aaagccatca cagactgcat gatgaacctg tacagaaaca ggtaataata    15420
cgcggtcacc ttcctgctga aactttgcca tcgtaaaaac cggggcaaaa taatcatcat    15480
ttccggtgat gttcaggtta aatccgtcaa aactcaccca cggtaatgat gatatattca    15540
```

```
ggtgattctc cggtaaattt ccctgcggaa acaatctggt atcatgctga tattctgccg    15600
ttaccgcatt ataacctgcc ataaactcac tgagatccgg aaaataacgg caggacagtg    15660
cagagaatgt ttcggtttct ttatgaaaga cagtaaagac cgggtctgac tggtcccagt    15720
aaataagttc attgtctttc agtgccatcc ggaactccgg aaactgatta acagcccggg    15780
agatcaggta aatcatcagc ggataaaact tataacctgt ctccgccagt gcggtacgca    15840
aagcggtaat atcgagtttg gtggtcaggc tgaatccgca tttaatctgc tgacgataaa    15900
gggcaaagtg ttccctgcga ttccaggtat tcaggtcaat ccgggtaaaa ttcatggtta    15960
ttccttctga ttaatagtga aaatattaa taatcagaag gcagtctggt tgtctcaatg    16020
ggtaacattc cgtcctccgt aagctgtttg gtattcagta ataatccct atacgggctt    16080 aatctgtatt aagcccggct ttatttattc cggccaatca tccgcaaaca catagcggat    16140
cagttctgcg gattcacggg gcggtgctct cagcacatcc gccattaaat caatctccat    16200
ctgacaggtt tgcagcttgt cttccgccgg tacatacgga tcatccgtca ggaaactatc    16260
gccgtattta tccatcgacc cctgtatttg tgccgaaaat a                        16301

<210> SEQ ID NO 9
<211> LENGTH: 12968
<212> TYPE: DNA
<213> ORGANISM: Artificial Sequence
<220> FEATURE:
<223> OTHER INFORMATION: TK225¶ABICyano1-6.8_PnirAABICyano1-PDCmax-
      synADHmax-PrbcABICyano1-Km**-oriVT

<400> SEQUENCE: 9 aatattttc gtcagatacg caaaccttac aaacataatt aacaactgaa actattgata      60
tgtctaggtt ttagctctat cacaggttgg atctgtcgac aattaataac ttcttcctgt    120
acgggcgaat ggccatttgc tcctaactaa ctccgtactg ctttgcggaa cgagcgtagc    180
gaactctccg aattactaag ccttcatccc tgatagatgc aaaaaacgaa ttaaaattat    240
gtgtaaaaag aaaatgtgtc tttatttagt agtcaaagtt acaaaatatt aagaatcaaa    300
ttaataatgt attgggcagt taagtatata agtcttaaa tatttatttg tattcaatat    360
attaaccgag gacaaattat gaattcttat accgtgggta cttatttagc cgaacgctta    420
gtgcaaattg gtttaaaaca tcattttgcc gtggctgggg actataattt agtgttattg    480
gataacttat tattaaataa aaacatggaa caagtgtatt gttgtaatga attaaattgt    540
ggtttttctg ctgaaggtta tgctagagct aaaggtgcag ctgctgctgt tgttacttat    600
tctgtgggtg ctttatctgc ttttgatgct attggtggtg cttatgccga aaatttaccc    660
gtgattttaa tttctggtgc ccctaataat aatgatcatg ccgctggaca tgttttacat    720
catgccttag gtaaaaccga ttatcattat caattagaaa tggccaaaaa tattactgct    780
gctgccgaag ctatttatac tcctgaagaa gcccctgcca aaattgatca tgtgattaaa    840
accgccttac gcgaaaaaaa acccgtgtat ttagaaattg cctgtaatat tgcttctatg    900
ccttgtgctg ctcctgggcc tgcttctgct ttatttaatg atgaagcctc tgatgaagct    960
agtttaaatg ctgccgtgga agaaacctta aaatttattg ccaatcgcga taagttgcc   1020 gtgttagttg gttctaaatt aagagctgct ggtgctgaag aagctgctgt taaatttgct   1080
gatgctttag gtgtgcagt tgctactatg gctgctgcca atctttttt tcccgaagaa   1140 aatccccatt atattggaac tagttgggga gaagtttctt atcctggtgt ggaaaaaact   1200
atgaaagaag ccgacgctgt tattgcttta gccccctgtgt ttaatgatta ttctaccact   1260
```

```
ggttggactg atattcccga tcccaaaaaa ttagttttag ccgaacctcg ttctgttgtt    1320
gttaatggtg ttcgctttcc ctctgtgcat ttaaaagatt atttaacccg cttagcccaa    1380
aaagtttcta aaaaaactgg tgccttagat ttttttaaat ctttaaatgc gggtgaatta    1440
aaaaaagctg ctcctgctga tccttctgct cctttagtta atgctgaaat tgcccgtcaa    1500
gttgaagcct tattacccc  taatactacc gttattgccg aaactggtga ttcttggttt    1560
aatgcccaac gcatgaaatt acctaatggt gcccgtgttg aatatgaaat gcaatggggt    1620
catattggtt ggtctgtacc tgctgctttt ggttatgctg ttggtgctcc tgaacgtcgt    1680 aatatttaa  tggtgggtga tggttctttt caattaactg cccaagaagt tgcccaaatg    1740
gttcgcttaa aattacccgt tattattttt ttaataaata attatggtta taccattgaa    1800
gtgatgattc atgatgggcc atataataat attaaaaatt gggattatgc gggtttaatg    1860
gaagtgttta atggtaatgg tggttatgat tctggtgctg gtaaaggttt aaaagccaaa    1920
actggtggtg aattagctga agctattaaa gttgccttag ccaatactga tgggccaacc    1980
ttaattgaat gttttattgg tcgcgaagat tgtaccgaag aattagttaa atgggtaaa     2040 cgtgttgctg ctgctaattc tcgcaaaccc gtgaataaat tattgtaatt tttggggatc    2100
aattcgagct cggtacccaa actagtatgt agggtgaggt tatagctagc gcttttaatt    2160
aatccgcgga tttgtattca atatattaac cgaggacaac atatgattaa agcctatgct    2220
gccttagaag ccaatggtaa attacaaccc tttgaatatg atcctggtgc tttaggtgcc    2280
aatgaagtgg aaattgaagt gcaatattgt ggtgtgtgtc attctgattt atctatgatt    2340
aataatgaat ggggtatttc taattatccc ttagttcctg gtcatgaagt tgttggtact    2400
gttgctgcta gggtgaagg  tgttaatcat gtggaagtgg gtgatttagt tggtttaggt    2460
tggcattctg gttattgtat gacctgtcat tcttgtttat ctggttatca taatttatgt    2520
gccactgccg aatctactat tgtgggtcat atggtggtt  ttggtgatag agttcgtgct    2580
aaaggtgttt ctgtggtgaa attacccaaa ggtattgatt tagcctctgc tgggccttta    2640
ttttgtggtg gtattaccgt ttttctccc  atggtggaat tatctttaaa acctaccgcc    2700
aaagttgctg ttattggtat tggtggttta ggtcatttag ccgttcaatt tttaagagcc    2760
tggggttgtg aagttactgc ttttacctct tctgcccgta acaaaccga  agttttagaa    2820 ttaggtgccc atcatatttt agattctacc aatcctgaag ctattgcttc tgccgaaggt    2880
aaatttgatt atattatttc taccgtgaat ttaaaattag attggaattt atatatcagt    2940 acccttagccc ctcaaggtca ttttcatttt gttggtgtgg tgttagaacc cttggactta    3000
aacttatttc ccttattaat gggacaacgt tctgtttctg cttctcctgt tggttctcct    3060
gctactattg ccactatgtt agattttgcc gtgcgtcatg atattaaacc cgtggtggaa    3120
caatttctct ttgatcaaat taatgaagcc attgcccatt agaatctgg  taaagcccat    3180 tatcgcgtgg tgttatctca ttctaaaaat taataagatt aacttctaaa ctgaaacaaa    3240
tttgagggta ggcttcattg tctgccctta tttttttatt taggaaaagt gaacagacta    3300
aagagtgttg gctctattgc tttgagtatg taaattaggc gttgctgaat taaggtatga    3360
tttttgaccc cttctctctt ctgcagttac ctaggatttc tggcgaaagg gggatgtgct    3420
gcaaggcgat taagttgggt aacgccaggg ttttcccagt cacgacgttg taaaacgacg    3480
gccagtgagc gcgacgtaat acgactcact ataggcgaa  ttggcggaag gccgtcaagg    3540
ccgcatggcg cgcctacgta gacaattgtc gatgtaatta ttaactatct tattatagat    3600
```

```
gaggggagag ggagaaatta gttcggagag aacgctcgag cgctcgttcc gcaaagcggt    3660
acggagttag ttaggggcta atgggcattc tcccgtacag gaaagagtta gaagttatta    3720
attatcaaca attctccttt gcctagtgca tcgttacctt tttaattaaa acataaggaa    3780
aactaataat cgtaataatt taacctcaaa gtgtaaagaa atgtgaaatt ctgactttta    3840
taacgttaaa gagggaaaaa ttagcagttt aaaatcccta gagaatagtc tggggtaagc    3900
atagagaatt agattagtta agttaatcaa attcagaaaa aataataatc gtaaatagtt    3960
aatctgggtg tatagaaaat gatccccttc atgataagat ttaaactcga aaagcaaaag    4020
ccaaaaaact aacttccatt aaaagaagtt gttacatata acgctataaa gaaaatttat    4080
atatttggag gataccaacc atgtctcata ttcaacgtga aactagttgt tctcgtcctc    4140
gtttaaattc taatatggat gccgatttat atggttataa atgggctcgt gataatgttg    4200
gtcaatctgg tgctactatt tatcgtttat atggtaaacc tgatgctcct gaattattct    4260
tgaaacatgg taaaggttct gttgctaatg atgttactga tgaaatggtt cgtttaaact    4320
ggttgactga atttatgcct ttacctacta ttaaacattt tattcgtact cccgatgatg    4380
cttggttatt aactactgct attcctggta aaactgcttt tcaagttta gaagaatatc    4440 ctgattctgg tgaaaatatt gttgatgctt agctgttt tttacgtcgt ttacattcta    4500
ttcccgtttg taattgtcct tttaattctg atcgtgtttt tcgtttagct caagctcaat    4560
ctcgtatgaa taatggttta gttgatgctt ctgattttga tgatgaacgt aatggttggc    4620
ctgttgaaca gtttggaaa gaaatgcaca aattgttacc tttttctcct gattctgttg    4680
ttactcatgg tgattttct ttagataatt tgatctttga tgaaggtaaa ttgattggtt    4740
gtattgatgt tggtcgtgtt ggtattgctg atcgttatca agatttagct attttatgga    4800
attgtttagg tgaattttct ccttctttac agaaacgttt atttcagaaa tatggtattg    4860
ataatcctga tatgaacaag ttacaatttc atttaatgtt ggacgagttc ttttaagaat    4920
taattcatga ccaaaatccc ttaacgtgag tttcgttcc actgagcgtc agacccgta    4980 gaaaagatca aggatcttc ttgagatcct tttttctgc gcgtaatctg ctgctattta    5040
aattacgtac acgtgttatt actttgttaa cgacaattgt cttaattaac tgggcctcat    5100
gggccttccg ctcactgccc gctttccagt cgggaaacct gtcgtgccag ctctgcagat    5160
gacggtgaaa acctctgaca catgcagctc ccggagacgg tcacagcttg tctgtaagcg    5220
gatgccggga gcagacaagc ccgtcagggc gcgtcagcgg gtgttggcgg gtgtcggggc    5280
gcagccatga cccagtcacg tagcgatagc ggagtgtata ctggcttaac tatgcggcat    5340
cagagcagat tgtactgaga gtgcaccata tgcggtgtga ataccgcac agatgcgtaa    5400 ggagaaaata ccgcatcagg cgctcttccg cttcctcgct cactgactcg ctgcgctcgg    5460
tcgttcggct gcggcgagcg gtatcagctc actcaaaggc ggtaatacgg ttatccacag    5520
aatcagggga taacgcagga aagaacatgt gagcaaaagg ccagcaaaag gccaggaacc    5580
gtaaaaaggc cgcgttgctg gcgtttttcc ataggctccg cccccctgac gagcatcaca    5640
aaaatcgacg ctcaagtcag aggtggcgaa acccgacagg actataaaga taccaggcgt    5700
ttccccctgg aagctccctc gtgcgctctc ctgttccgac cctgccgctt accggatacc    5760
tgtccgcctt tctcccttcg ggaagcgtgg cgctttctca tagctcacgc tgtaggtatc    5820
tcagttcggt gtaggtcgtt cgctccaagc tgggctgtgt gcacgaaccc cccgttcagc    5880
ccgaccgctg cgccttatcc ggtaactatc gtcttgagtc aacccggta agacacgact    5940 tatcgccact ggcagcagcc actggtaaca ggattagcag agcgaggtat gtaggcggtg    6000
```

```
ctacagagtt cttgaagtgg tggcctaact acggctacac tagaaggaca gtatttggta    6060
tctgcgctct gctgaagcca gttaccttcg gaaaaagagt tggtagctct tgatccggca    6120
aacaaaccac cgctggtagc ggtggttttt ttgtttgcaa gcagcagatt acgcgcagaa    6180
aaaaaggatc tcaagaagat cctttgatct tttctactgc agaagcttgt tagacaccct    6240
gtcatgtatt ttatattatt tatttcacca tacggattaa gtgaaaccta atgaaaatag    6300
tactttcgga gctttaactt taatgaaggt atgtttttt atagacatcg atgtctggtt    6360
taacaatagg aaaagtagc taaaactccc atgaattaaa gaaataacaa ggtgtctaac    6420
aacctgttat taagaatgtt agaaaagact taacatttgt gttgagtttt tatagacatt    6480
ggtgtctaga catacggtag ataaggtttg ctcaaaaata aaataaaaaa agattggact    6540
aaaaaacatt taatttagta caatttaatt agttattttt tcgtctcaaa ttttgctttg    6600
ttgagcagaa atttagataa aaaaatcccc gtgatcagat tacaatgtcg ttcattgtac    6660
gatgtgtcga aaatcttta cgacactcta aactgaccac acgggggaaa aagaaaactg    6720
aactaataac atcatgatac tcggaaaacc tagcaattct caacccctaa acaaaagaaa    6780
cttccaaaac cctgaccata taaggagtg gcaacaatca gcaatcagtc aagatttgat    6840
agcagaaaat cttgtatcgg ttgctaatgg ttttgatgta ctatttatcg gcaataaata    6900
ccgaactaac acgggtgttc tgtcacggca catattaaac tcctattctc atttagaaga    6960
tggtggttcg tatggtagaa catttgaccc atttaccaat aaagaaatgc agtgggttca    7020
atttaaaccg aatagaccaa gaaaaggttc tactggtaag gtaatcaaat atgaatcgcc    7080
aaaaggtgaa cctacaagag ttctaatgcc gtttgtgcct atgaaaatat ggcaacggat    7140
tagcgataag ttcggagtac cgattaatcc gaaaaaagat actcactttt gggaatgggt    7200
aaagaataat ccatcgatac cgattgccat tacagaagga aataaaaaag ctaattgcct    7260
attatcctat ggctatcctg ctattgcctt tgtaggcatt tggaacggat tagagaaaat    7320
aaatgatttc tcgaaggaaa agcagttaaa agaggatttg aaatggttgt tatccaacgg    7380
caaccgaaat attaatatca tctttgacca agaccagaaa caaaaaactg taattaatgt    7440
aaacaaagct attttcgctt tatcttctct aataagtaga aatggtcata agttaatat    7500 tgtgcaatgg ttgccgtcaa aaggtaaagg aatagatgat tatttggtag cttaccttt    7560 tgagaaaaga gaaaatcatt tagacaactt aattaaaatt gcaccatcat ttaattttg    7620 gtcaactaaa tacttattca agtgtcgtaa accagattta accgtaaatt gccgttattt    7680
gagcgatgca gtaaaagaat tacctcaaga ggatatagca ttaatagcac ctcacggcac    7740
gggtaaaact tcattagtag ctactcacgt taagaatcgg agttatcacg aaggaaaac    7800 tatttcattg gtgcatcttg aaagtttagc caaagctaat gcaacgcac ttggattata    7860 ttaccgaacc gaaataata ttgaaaagca atatcttgga tttagcttat gtgtagatag    7920
ttgccgtgat aagattaacg gcattacaac tgatattatt tcaggtcaag attattgcct    7980
tttcattgat gaaattgacc aagtaattcc acacatcctt aacagtgaaa ctgaagtaag    8040
taagtataga tgcaccatca ttgacacttt ttctgaactg gtgagaaatg ctgaacaggt    8100
cattattgct gatgctgatt tatccgatgt gacgattgac ctaatagaaa acatcagagg    8160
taaaaaacta tatgtaatca agaatgaata tcagtatcag ggaatgactt ttaacgccgt    8220
tggttcacca ttagaaatga tggcaatgat gggaaaatcg gtgtcagaag gcaagaaatt    8280
atttattaac accacatccc aaaaggcaaa aagtaagtac ggcacaatcg ctcttgagtc    8340
```

```
ttatatttttt ggtctaaata aagaagcaaa gatattaaga atagactctg aaaccactaa    8400
aaaccctgaa catccagcct ataaaatcat tgaccaagac ttaaataata tcctcaaaga    8460
ttatgattat gtcattgcct caccttgcct tcaaacaggt gtcagtatta ccttaaaagg    8520
gcattttgac cagcaattta acttttccag tggaaacatt acacctcatt gcttttttaca   8580
gcaaatgtgg cggttgaggg atgcagaaat tgaaagattc tattatgtgc cgaactcatc    8640
taacctcaat ctcattggga ataagtcaag ttcaccatca gaccttctaa agagcaataa    8700
caagatggca acggcaacgg ttaacctttt gggtagaatc gactccgaat attccctaga    8760
gtatgaatcg cacggcattt ggcttgagac gtgggcaaaa ttatcagcac ggcataacag    8820
ttcaatgcgt tgttactctg aaattcttac ctatctaatt acgtctcaag gcataaaatt    8880
aaatatcaac attccctcac ctcttgcaga tattaagaag ctaaatgatg aggtaagtag    8940
taacagggaa aaggtaaaaa atgagagata ctctcagagg ttaaactcac cagatattaa    9000
cgatgcagaa gctaccatac tcgaatctaa agagcaaaaa atcggattga ctctcaatga    9060
gagatgcacc ctagaaaagc ataaagttaa gaagcggtat gggaatgtaa agatggatat    9120
tctcaccttt gatgatgatg gactataccc caaactcaga ctattttatt acctcaccat    9180
cggtaaacct catctcaagg ctaatgacag aaaagctatt gccaaaatgg gcaatgacaa    9240
taaaggcaag attctatcaa aagacttagt taataaaact tactccgctc gtgtgaaggt    9300
cttagagatt cttaaactaa ctgactttat cgacaatctt agagatgaac tcttaataac    9360
tcccaataat ccagctatca ccgattttaa taatcttctg ctaagagcta agaaggattt    9420
aagagtatta ggagtcaaca tcggaaaata tccaatggcc aacattaatg ccgtacttac    9480
tctcattggt cacaaacttt ctgtaatgag agatgagttc ggaaaagaga aaggataaa    9540
agtagatggt aaatcatacc gatgttatca acttgaaaca ttaccagatt ttaccaatga    9600
tactcttgac tactggttag aaaatgatag ccaaaaagaa gtaacagcaa cagaaaatta    9660
ctccgaaaat tttaaccctt caaatagcta caatccagac agtaagacac tttcagaggg    9720
tgcaaatttc ctatatataa ataaagaaga attgcatcca aataaattgc acctagaaat    9780
aaaagaaggt gctgaacttt ttttattcgg ggtaaaggtg attgtgaaag gaatcttgga    9840
cggggcagta actatattct ctatgggtca agaatacgat ttatccctca atgaactaga    9900
ggggatgtta acatcatgaa ctttacaaga atcttttaa agggcgatcg caccatgtta    9960
aatgatggta catttgttca gatatttgat atttaccatg accacgcatt gggagtgacc    10020
cttgaccta agacagaaaa aattatttcc gatgatgtta gggtaattac tgtcaaagac    10080
ttattgttcg atggcactta taaggggta aaatcttta tgcccgataa tgcccgataa    10140
tgcccgattg atgctacaaa atcccataat cataagcgat aatccctaa tagcttgtaa     10200
ttcttgaacc gtagcgattt tagagtattc caaaaagaag aaataaacac cgcaaaatgt    10260
cgtatttcac atatataaac caaggttttt tgccctaaaa tctttatgtt tgtagtgtga    10320
tgttgggtca aaatggtcag aaaagttgca aggttttat ggatgcttac gcgcgcgagg     10380
ggtaagcatc cccaaatagt tactttatcc tagtccatgc ccatttattg ccgtcccgtt    10440
cggctttaaa aaagtgccaa aactcacaag gtgcaataaa aagttctgta cctttcgcaa    10500
ccctagataa tctttcaaca gttacttttt ttcctattat ctcggtacaa agtttggcta    10560
gtttctcttt tccctctttt tcaatcaagc cttcttgtat gcccaactca ttgattaatc    10620
tctctatttt taccattatt tcccgttcag gtagtttatc ccctaaatct tcatcgggg    10680
gcaatgtagg gcattctgaa ggggcttttt cttctgtctg gacattatct aatattgaag    10740
```

```
taaccaaact atcttcagtt ttttctattc ctattaattc atattcggtt actgtatccg    10800
tatcaatatc cgaataacta tctttatccg tattagctat tcggttaagt ttatccgtta    10860
actcagaaac aagactatat agcggtttta gcttttcttc tatcctgtta tctaatacgg    10920
ataagtttat acggttatca ttatccgtat tagtatcatt gggcttttt ggtagttcta    10980 cccctcata aaccgctttt attcccaatt ccaacagact gataacagta tcctttataa    11040 tgggttttt gctgatatgg tgaacttttg ccccttccat cattgcgata ctttctatct    11100
cactcatcaa cttatcgctt aagtgaatct cgtatctgtt taatcccta ctggttttat    11160 tcatatccgt ttactttatt cggttaacaa ttctatttta tacgaataaa atattatacg    11220
gttaacttta tacgtttaac tattttatct atacggataa cagtaataag ttattcgtat    11280
tagttatacg tttactttta tccaaataaa attagtgcat ttaaactaaa agaatgattt    11340
tatcggagtt gatagcattg gattaaccta aagatgttta taagctatat ctgataagta    11400
tttaaggtta ttttgttatt ctgtttattg acattatcag aataaaagaa tagaatataa    11460
ttgttgagag ataagaggtt taagtgatta tggttaagaa gttagttggt tatgtcaggg    11520
tcagtagtga atcgcaagag gataacacta gcttacagaa tcagatagag agaattgaag    11580
catattgtat ggcttttggt tatgagttgg taaaaatatt caaagaggtt gccactggta    11640
caaaagcaga tattgaaacc cgtcctattt ttaatgaagc tatagaatac ttgaaacagg    11700
ataatgctaa tggaattatt gccttgaagc tagaccgaat cgcacggaat gctttagatg    11760
tattgcgttt ggttcgtgaa accttagaac cacaaaataa aatgttagtg ttactagata    11820
ttcaggtaga tacttcgaca ccttcaggaa aaatgatttt aactgtaatg agtgccgttg    11880
ctgaactcga aagagacatg atctatgatc gcactcaggg gggtagaaag actaaagccc    11940
aaaagggcgg gtatgcctac gggaaaccta aatttggcta taagactgaa gaaaaggaac    12000
taaaagaaga ttcagcacaa caggaaacta ttaaactaat taagagacac cgtaggtcag    12060
ggaaaagcta ccagaaaata gctgattatc tcaatgccca aagtattccc actaaacaag    12120
gtaagaaatg gagttctagc gtcgtctatc gaatctgtca ggaaaaagct ggttaagtct    12180
gtttatagat atttagaatt tattgaataa aaatagtatg aacaataaat atttatggac    12240
taaccacgct cggaaacgtt taactgaacg atgggaaata aagaatcat gggttattga    12300 taccatcgaa aatcctgaac gttcagaatt tattgttgat gagtcagggg aaaaatatca    12360
ttactataaa agaatagcta agtttaagaa tagagtgtta gaagtgataa cttctgccaa    12420
ctcaacaccc acaagaataa taaccttta ctttaaccgt aacatgagga aaaatttatg    12480
attgttactt acgataatga agttgacgca atttatttta agttaacgga aaataaaatt    12540
gatagcaccg aacctcaaac agacaggatt atcattgatt acgatgaaag taataatatt    12600
gttggcattg aggtattaga ttttaattat cttgtcaaga aaggtttaac cgttgctgat    12660
ttaccttttt ctgaagatga aagattaaca gcttctcaat attttaattt tcctgttgct    12720
atctaatcca gaaggggcaa taatcccctt ctttcatcga gttagactta atatcacaaa    12780
agtcattttc attttaccgt ttcttttcca cagcgtccgt acgcccctcg ttaaatctca    12840
aaaccgacaa tttatgatgt ttataaaaag ttactcactt taataagtat ttatactcat    12900
taaagggtta ttcttttttt gtagcctgat aggttgggaa ggaatatttc agattatcag    12960
atttgttg                                                              12968
```

<210> SEQ ID NO 10

<211> LENGTH: 13449
<212> TYPE: DNA
<213> ORGANISM: Artificial Sequence
<220> FEATURE:
<223> OTHER INFORMATION: TK293¶ABICyano1-6.8_PnirAABICyano1-PDCmax-PrpsLABICyano1-synADHmax-PrbcABICyano1-Km**-oriVT

<400> SEQUENCE: 10

```
aatattttc gtcagatacg caaaccttac aaacataatt aacaactgaa actattgata    60
tgtctaggtt ttagctctat cacaggttgg atctgtcgac aattaataac ttcttcctgt   120
acgggcgaat ggccatttgc tcctaactaa ctccgtactg ctttgcggaa cgagcgtagc   180
gaactctccg aattactaag ccttcatccc tgatagatgc aaaaaacgaa ttaaaattat   240
gtgtaaaaag aaaatgtgtc tttatttagt agtcaaagtt acaaaatatt aagaatcaaa   300
ttaataatgt attgggcagt taagtatata agtctttaaa tatttatttg tattcaatat   360
attaaccgag gacaaattat gaattcttat accgtgggta cttatttagc cgaacgctta   420
gtgcaaattg gtttaaaaca tcattttgcc gtggctgggg actataattt agtgttattg   480
gataacttat tattaaataa aaacatggaa caagtgtatt gttgtaatga attaaattgt   540
ggttttctg ctgaaggtta tgctagagct aaaggtgcag ctgctgctgt tgttacttat   600
tctgtgggtg ctttatctgc ttttgatgct attggtggtg cttatgccga aaatttaccc   660
gtgattttaa tttctggtgc ccctaataat aatgatcatg ccgctggaca tgttttacat   720
catgccttag gtaaaaccga ttatcattat caattagaaa tggccaaaaa tattactgct   780
gctgccgaag ctatttatac tcctgaagaa gcccctgcca aaattgatca tgtgattaaa   840
accgccttac gcgaaaaaaa acccgtgtat ttagaaattg cctgtaatat tgcttctatg   900
ccttgtgctg ctcctgggcc tgcttctgct ttatttaatg atgaagcctc tgatgaagct   960
agtttaaatg ctgccgtgga agaaacctta aaatttattg ccaatcgcga taaagttgcc  1020
gtgttagttg ttctaaatt aagagctgct ggtgctgaag aagctgctgt taaatttgct  1080
gatgctttag gtggtgcagt tgctactatg gctgctgcca atctttttt tcccgaagaa  1140
aatccccatt atattggaac tagttgggga gaagtttctt atcctggtgt ggaaaaaact  1200
atgaaagaag ccgacgctgt tattgcttta gcccctgtgt ttaatgatta ttctaccact  1260
ggttggactg atattcccga tcccaaaaaa ttagttttag ccgaacctcg ttctgttgtt  1320
gttaatggtg ttcgctttcc ctctgtgcat ttaaagatt atttaacccg cttagcccaa  1380
aaagtttcta aaaaaactgg tgccttagat tttttaaat ctttaaatgc gggtgaatta  1440
aaaaagctc tcctgctga tccttctgct cctttagtta atgctgaaat tgcccgtcaa  1500
gttgaagcct tattaacccc taatactacc gttattgccg aaactggtga ttcttggttt  1560
aatgcccaac gcatgaaatt acctaatggt gcccgtgttg aatatgaaat gcaatggggt  1620
catattggtt ggtctgtacc tgctgctttt ggttatgctg ttggtgctcc tgaacgtcgt  1680
aatatttta tggtgggtga tggttctttt caattaactg cccaagaagt tgcccaaatg  1740
gttcgcttaa aattacccgt tattattttt ttaataaata attatggtta taccattgaa  1800
gtgatgattc atgatgggcc atataataat attaaaaatt gggattatgc gggtttaatg  1860
gaagtgttta tggtaatgg tggttatgat tctggtgctg gtaaaggttt aaaagccaaa  1920
actggtggtg aattagctga agctattaaa gttgccttag ccaatactga tgggccaacc  1980
ttaattgaat gttttattgg tcgcgaagat tgtaccgaag aattagttaa atggggtaaa  2040
cgtgttgctg ctgctaattc tcgcaaaccc gtgaataaat tattgtaatt tttggggatc  2100
```

```
aattcgagct cctccgctta aaaaatttca tttttcgatc aaaaaagaca aattattact    2160
aattagctca tggcaataaa taatcagtag taatctgttt tcacatttta ttgttaattt    2220
ttattattgc taatatcaac cttttctact tctgcttaat attttattta tgctcaatgg    2280
gaaaatctga aataagattg agaacagtgt taccaataga agtatttaag gtttaaagca    2340
taccttaaag ataacatttt tttttgaaaa gagtcaaatt attttttgaaa ggctgatatt    2400 tttgatattt actaatattt tatttatttc ttttccctt aaaataagag ctaaatctgt    2460
ttttattatc atttatcaag ctctattaat acctcaactt tttcaagaaa aataataat    2520 aatttttccc tctattctca tgacctttta ggaaaattaa ttttagaaaa actattgaca    2580
aacccataaa aaatgagata agattataga ttgtcactgg tattttatac tagaggcaaa    2640
ttatatttat atatacaaaa atgctgtata aaaacatct catatgatta aagcctatgc    2700
tgccttagaa gccaatggta aattacaacc ctttgaatat gatcctggtg ctttaggtgc    2760
caatgaagtg gaaattgaag tgcaatattg tggtgtgtgt cattctgatt tatctatgat    2820
taataatgaa tggggtattt ctaattatcc cttagttcct ggtcatgaag ttgttggtac    2880
tgttgctgct atgggtgaag gtgttaatca tgtggaagtg ggtgatttag ttggtttagg    2940
ttggcattct ggttattgta tgacctgtca ttcttgttta tctggttatc ataatttatg    3000
tgccactgcc gaatctacta ttgtgggtca ttatggtggt tttggtgata gagttcgtgc    3060
taaaggtgtt tctgtggtga aattacccaa aggtattgat ttagcctctg ctgggccttt    3120
attttgtggt ggtattaccg ttttttctcc catggtggaa ttatctttaa aacctaccgc    3180
caaagttgct gttattggta ttggtggttt aggtcattta gccgttcaat ttttaagagc    3240
ctggggttgt gaagttactg cttttacctc ttctgcccgt aaacaaaccg aagttttaga    3300
attaggtgcc catcatattt tagattctac caatcctgaa gctattgctt ctgccgaagg    3360
taaatttgat tatattattt ctaccgtgaa tttaaaatta gattggaatt tatatatcag    3420
taccttagcc cctcaaggtc attttcattt tgttggtgtg gtgttagaac ccttggactt    3480
aaacttattt cccttattaa tgggacaacg ttctgttcct gcttctcctg ttggttctcc    3540
tgctactatt gccactatgt tagattttgc cgtgcgtcat gatattaaac ccgtggtgga    3600
acaattttct tttgatcaaa ttaatgaagc cattgcccat ttagaatctg gtaaagccca    3660
ttatcgcgtg gtgttatctc attctaaaaa ttaataagat taacttctaa actgaaacaa    3720
atttgagggt aggcttcatt gtctgccctt attttttat ttaggaaaag tgaacagact    3780 aaaagagtgtt ggctctattg ctttgagtat gtaaattagg cgttgctgaa ttaaggtatg    3840 attttttgacc ccttctctct tctgcagtta cctaggattt ctggcgaaag ggggatgtgc    3900
tgcaaggcga ttaagttggg taacgccagg gttttcccag tcacgacgtt gtaaaacgac    3960
ggccagtgag cgcgacgtaa tacgactcac tatagggcga attggcggaa ggccgtcaag    4020
gccgcatggc gcgcctacgt agacaattgt cgatgtaatt attaactatc ttattataga    4080
tgagggagag gggagaaatt agttcggaga gaacgctcga gcgctcgttc cgcaaagcgg    4140
tacggagtta gttaggggct aatgggcatt ctcccgtaca ggaaagagtt agaagttatt    4200
aattatcaac aattctcctt tgcctagtgc atcgttacct ttttaattaa aacataagga    4260
aaactaataa tcgtaataat ttaacctcaa agtgtaaaga aatgtgaaat tctgactttt    4320
ataacgttaa agagggaaaa attagcagtt taaaatacct agagaatagt ctggggtaag    4380
catagagaat tagattagtt aagttaatca aattcagaaa aaataataat cgtaaatagt    4440
taatctgggt gtatagaaaa tgatcccctt catgataaga tttaaactcg aaaagcaaaa    4500
```

```
gccaaaaaac taacttccat taaaagaagt tgttacatat aacgctataa agaaaattta    4560
tatatttgga ggataccaac catgtctcat attcaacgtg aaactagttg ttctcgtcct    4620
cgtttaaatt ctaatatgga tgccgattta tatggttata aatgggctcg tgataatgtt    4680
ggtcaatctg gtgctactat ttatcgttta tatggtaaac ctgatgctcc tgaattattc    4740
ttgaaacatg gtaaaggttc tgttgctaat gatgttactg atgaaatggt tcgtttaaac    4800
tggttgactg aatttatgcc tttacctact attaaacatt ttattcgtac tcccgatgat    4860
gcttggttat taactactgc tattcctggt aaaactgctt ttcaagtttt agaagaatat    4920
cctgattctg gtgaaaatat tgttgatgct ttagctgttt ttttacgtcg tttacattct    4980
attcccgttt gtaattgtcc ttttaattct gatcgtgttt ttcgtttagc tcaagctcaa    5040
tctcgtatga ataatggttt agttgatgct tctgattttg atgatgaacg taatggttgg    5100
cctgttgaac aagtttggaa agaaatgcac aaattgttac cttttttctcc tgattctgtt    5160
gttactcatg gtgattttc tttagataat ttgatctttg atgaaggtaa attgattggg    5220
tgtattgatg ttggtcgtgt tggtattgct gatcgttatc aagatttagc tattttatgg    5280
aattgtttag gtgaattttc tccttcttta cagaaacgtt tatttcagaa atatggtatt    5340
gataatcctg atatgaacaa gttacaattt catttaatgt tggacgagtt ctttaagaa    5400
ttaattcatg accaaaatcc cttaacgtga gttttcgttc cactgagcgt cagaccccgt    5460
agaaaagatc aaaggatctt cttgagatcc ttttttctg cgcgtaatct gctgctattt    5520
aaattacgta cacgtgttat tactttgtta acgacaattg tcttaattaa ctgggcctca    5580
tgggccttcc gctcactgcc cgctttccag tcgggaaacc tgtcgtgcca gctctgcaga    5640
tgacggtgaa aacctctgac acatgcagct cccggagacg tcacagctt gtctgtaagc    5700
ggatgccggg agcagacaag cccgtcaggg cgcgtcagcg ggtgttggcg ggtgtcgggg    5760
cgcagccatg acccagtcac gtagcgatag cggagtgtat actggcttaa ctatgcggca    5820
tcagagcaga ttgtactgag agtgcaccat atgcggtgtg aaataccgca cagatgcgta    5880
aggagaaaat accgcatcag gcgctcttcc gcttcctcgc tcactgactc gctgcgctcg    5940
gtcgttcggc tgcggcgagc ggtatcagct cactcaaagg cggtaatacg gttatccaca    6000
gaatcagggg ataacgcagg aaagaacatg tgagcaaaag gccagcaaaa ggccaggaac    6060
cgtaaaaagg ccgcgttgct ggcgtttttc cataggctcc gccccctga cgagcatcac    6120
aaaaatcgac gctcaagtca gaggtggcga aacccgacag gactataaag ataccaggcg    6180
tttccccctg gaagctccct cgtgcgctct cctgttccga ccctgccgct taccggatac    6240
ctgtccgcct ttctcccttc gggaagcgtg gcgctttctc atagctcacg ctgtaggtat    6300
ctcagttcgg tgtaggtcgt tcgctccaag ctgggctgtg tgcacgaacc cccgttcag    6360
cccgaccgct gcgccttatc cggtaactat cgtcttgagt ccaacccggt aagacacgac    6420
ttatcgccac tggcagcagc cactggtaac aggattagca gagcgaggta tgtaggcggt    6480
gctacagagt tcttgaagtg gtggcctaac tacggctaca ctagaaggac agtatttggt    6540
atctgcgctc tgctgaagcc agttaccttc ggaaaaagag ttggtagctc ttgatccggc    6600
aaacaaacca ccgctggtag cggtggtttt tttgttgca agcagcagat tacgcgcaga    6660
aaaaaaggat ctcaagaaga tcctttgatc ttttctactg cagaagcttg ttagacaccc    6720
tgtcatgtat tttatattat ttatttcacc atacggatta agtgaaacct aatgaaaata    6780
gtactttcgg agctttaact ttaatgaagg tatgtttttt tatagacatc gatgtctggt    6840
```

```
ttaacaatag gaaaaagtag ctaaaactcc catgaattaa agaaataaca aggtgtctaa    6900
caacctgtta ttaagaatgt tagaaaagac ttaacatttg tgttgagttt ttatagacat    6960
tggtgtctag acatacggta gataaggttt gctcaaaaat aaaataaaaa aagattggac    7020
taaaaaacat ttaatttagt acaatttaat tagttatttt ttcgtctcaa attttgcttt    7080
gttgagcaga aatttagata aaaaaatccc cgtgatcaga ttacaatgtc gttcattgta    7140
cgatgtgtcg aaaaatcttt acgacactct aaactgacca cacgggggaa aaagaaaact    7200
gaactaataa catcatgata ctcggaaaac ctagcaattc tcaacccta aacaaaagaa     7260
acttccaaaa ccctgaccat ataaggagt ggcaacaatc agcaatcagt caagatttga     7320
tagcagaaaa tcttgtatcg gttgctaatg gttttgatgt actatttatc ggcaataaat    7380
accgaactaa cacgggtgtt ctgtcacggc acatattaaa ctcctattct catttagaag    7440
atggtggttc gtatggtaga acatttgacc catttaccaa taagaaatg cagtgggttc      7500
aatttaaacc gaatagacca agaaaaggtt ctactggtaa ggtaatcaaa tatgaatcgc    7560
caaaaggtga acctacaaga gttctaatgc cgtttgtgcc tatgaaaata tggcaacgga    7620
ttagcgataa gttcggagta ccgattaatc cgaaaaaaga tactcacttt tgggaatggg    7680
taaagaataa tccatcgata ccgattgcca ttacagaagg aaataaaaaa gctaattgcc    7740
tattatccta tggctatcct gctattgcct ttgtaggcat ttggaacgga ttagagaaaa    7800
taaatgattt ctcgaaggaa aagcagttaa aagaggattt gaaatggttg ttatccaacg    7860
gcaaccgaaa tattaatatc atcttgacc aagaccagaa acaaaaaact gtaattaatg       7920
taaacaaagc tattttcgct ttatcttctc taataagtag aaatggtcat aaagttaata    7980
ttgtgcaatg gttgccgtca aaaggtaaag gaatagatga ttatttggta gctttaccctt    8040
ttgagaaaag agaaaatcat ttagacaact taattaaaat tgcaccatca tttaattttt    8100
ggtcaactaa atacttattc aagtgtcgta accagatt aaccgtaaat tgccgttatt      8160
tgagcgatgc agtaaaagaa ttacctcaag aggatatagc attaatagca cctcacggca    8220
cgggtaaaac ttcattagta gctactcacg ttaagaatcg gagttatcac ggaaggaaaa    8280
ctatttcatt ggtgcatctt gaaagtttag ccaaagctaa tggcaacgca cttggattat    8340
attaccgaac cgaaaataat attgaaaagc aatatcttgg atttagctta tgtgtagata    8400
gttgccgtga taagattaac ggcattacaa ctgatattat ttcaggtcaa gattattgcc    8460
ttttcattga tgaaattgac caagtaattc cacacatcct taacagtgaa actgaagtaa    8520
gtaagtatag atgcaccatc attgacactt tttctgaact ggtgagaaat gctgaacagg    8580
tcattattgc tgatgctgat ttatccgatg tgacgattga cctaatagaa aacatcagag    8640
gtaaaaaact atatgtaatc aagaatgaat atcagtatca gggaatgact tttaacgccg    8700
ttggttcacc attagaaatg atggcaatga tgggaaaatc ggtgtcagaa ggcaagaaat    8760
tatttattaa caccacatcc caaaaggcaa aagtaagta cggcacaatc gctcttgagt      8820
cttatatttt tggtctaaat aaagaagcaa agatattaag aatagactct gaaaccacta    8880
aaaccctga acatccagcc tataaaatca ttgaccaaga cttaaataat atcctcaaag      8940
attatgatta tgtcattgcc tcaccttgcc ttcaaacagg tgtcagtatt accttaaaag    9000
ggcattttga ccagcaattt aacttttcca gtggaaacat tacacctcat tgcttttac     9060
agcaaatgtg gcggttgagg gatgcagaaa ttgaaagatt ctattatgtg ccgaactcat    9120
ctaacctcaa tctcattggg aataagtcaa gttcaccatc agaccttcta aagagcaata    9180
acaagatggc aacggcaacg gttaaccttt tgggtagaat cgactccgaa tattccctag    9240
```

```
agtatgaatc gcacggcatt tggcttgaga cgtgggcaaa attatcagca cggcataaca    9300
gttcaatgcg ttgttactct gaaattctta cctatctaat tacgtctcaa gggcataaat    9360
taaatatcaa cattccctca cctcttgcag atattaagaa gctaaatgat gaggtaagta    9420
gtaacaggga aaaggtaaaa aatgagagat actctcagag gttaaactca ccagatatta    9480
acgatgcaga agctaccata ctcgaatcta aagagcaaaa aatcggattg actctcaatg    9540
agagatgcac cctagaaaag cataaagtta agaagcggta tgggaatgta aagatggata    9600
ttctcacctt tgatgatgat ggactatacc ccaaactcag actatttat tacctcacca     9660 tcggtaaacc tcatctcaag gctaatgaca gaaaagctat tgccaaaatg ggcaatgaca    9720
ataaaggcaa gattctatca aaagacttag ttaataaaac ttactccgct cgtgtgaagg    9780
tcttagagat tcttaaacta actgacttta tcgacaatct tagagatgaa ctcttaataa    9840
ctcccaataa tccagctatc accgatttta ataatcttct gctaagagct aagaaggatt    9900
taagagtatt aggagtcaac atcggaaaat atccaatggc caacattaat gccgtactta    9960
ctctcattgg tcacaaactt tctgtaatga gagatgagtt cggaaaagag aaaaggataa    10020
aagtagatgc taaatcatac cgatgttatc aacttgaaac attaccagat tttaccaatg    10080
atactcttga ctactggtta gaaaatgata gccaaaaaga agtaacagca acagaaaatt    10140
actccgaaaa ttttaacccct tcaaatagct acaatccaga cagtaagaca ctttcagagg    10200
gtgcaaattt cctatatata aataaagaag aattgcatcc aaataaattg cacctagaaa    10260
taaaagaagg tgctgaactt tttttattcg gggtaaaggt gattgtgaaa ggaatcttgg    10320
acggggcagt aactatattc tctatgggtc aagaatacga tttatccctc aatgaactag    10380
aggggatgtt aacatcatga actttacaag aatcttttta aagggcgatc gcaccatgtt    10440
aaatgatggt acatttgttc agatatttga tatttaccat gaccacgcat tgggagtgac    10500
ccttgacctt aagacagaaa aaattattc cgatgatgtt agggtaatta ctgtcaaaga    10560
cttattgttc gatggcactt ataaaggggt aaaatctttt atgcccgata atgcccgata    10620
atgcccgatt gatgctacaa aatcccataa tcataagcga taatccccta atagcttgta    10680
attcttgaac cgtagcgatt ttagagtatt ccaaaaagaa gaaataaaca ccgcaaaatg    10740
tcgtatttca catatataaa ccaaggtttt ttgccctaaa atctttatgt ttgtagtgtg    10800
atgttgggtc aaaatggtca gaaaagttgc aaggttttta tggatgctta cgcgcgcgag    10860
gggtaagcat ccccaaatag ttactttatc ctagtccatg cccatttatt gccgtcccgt    10920
tcggctttaa aaaagtgcca aaactcacaa ggtgcaataa aaagtctgt accttttcgca     10980 accctagata atctttcaac agttactttt tttcctatta tctcggtaca agtttggct     11040 agtttctctt ttccctcttt ttcaatcaag ccttcttgta tgcccaactc attgattaat    11100
ctctctattt ttaccattat ttcccgttca ggtagtttat cccctaaatc ttcatcgggg    11160
ggcaatgtag ggcattctga aggggctttt tcttctgtct ggacattatc taatattgaa    11220
gtaaccaaac tatcttcagt ttttctatt cctattaatt catattcggt tactgtatcc     11280
gtatcaatat ccgaataact atctttatcc gtattagcta ttcggttaag tttatccgtt    11340
aactcagaaa caagactata tagcggtttt agcttttctt ctatcctgtt atctaatacg    11400
gataagttta tacggttatc attatccgta ttagtatcat tgggcttttt tggtagttct    11460 acccccctcat aaaccgcttt tattcccaat tccaacagac tgataacagt atcctttata    11520
atgggttttt tgctgatatg gtgaactttt gccccttcca tcattgcgat actttctatc    11580
```

```
tcactcatca acttatcgct taagtgaatc tcgtatctgt ttaatccctt actggtttta   11640
ttcatatccg tttactttat tcggttaaca attctatttt atacgaataa aatattatac   11700
ggttaacttt atacgtttaa ctattttatc tatacggata acagtaataa gttattcgta   11760
ttagttatac gtttactttt atccaaataa aattagtgca tttaaactaa aagaatgatt   11820
ttatcggagt tgatagcatt ggattaacct aaagatgttt ataagctata tctgataagt   11880
atttaaggtt attttgttat tctgtttatt gacattatca gaataaaaga atagaatata   11940
attgttgaga gataagaggt ttaagtgatt atggttaaga agttagttgg ttatgtcagg   12000
gtcagtagtg aatcgcaaga ggataacact agcttacaga atcagataga gagaattgaa   12060
gcatattgta tggcttttgg ttatgagttg gtaaaaatat tcaaagaggt tgccactggt   12120
acaaaagcag atattgaaac ccgtcctatt tttaatgaag ctatagaata cttgaaacag   12180
gataatgcta atggaattat tgccttgaag ctagaccgaa tcgcacggaa tgctttagat   12240
gtattgcgtt tggttcgtga aaccttagaa ccacaaaata aaatgttagt gttactagat   12300
attcaggtag atacttcgac accttcagga aaaatgattt taactgtaat gagtgccgtt   12360
gctgaactcg aaagagacat gatctatgat cgcactcagg ggggtagaaa gactaaagcc   12420
caaaagggcg ggtatgccta cgggaaacct aaatttggct ataagactga agaaaaggaa   12480
ctaaagaaag attcagcaca acaggaaact attaaactaa ttaagagaca ccgtaggtca   12540
gggaaaagct accagaaaat agctgattat ctcaatgccc aaagtattcc cactaaacaa   12600
ggtaagaaat ggagttctag cgtcgtctat cgaatctgtc aggaaaaagc tggttaagtc   12660
tgtttataga tatttagaat ttattgaata aaaatagtat gaacaataaa tatttatgga   12720
ctaaccacgc tcggaaacgt ttaactgaac gatgggaaat aaaagaatca tgggttattg   12780
ataccatcga aaatcctgaa cgttcagaat ttattgttga tgagtcaggg gaaaaatatc   12840
attactataa aagaatagct aagtttaaga atagagtgtt agaagtgata acttctgcca   12900
actcaacacc cacaagaata ataacctttt acttttaaccg taacatgagg aaaaatttat   12960
gattgttact tacgataatg aagttgacgc aatttatttt aagttaacgg aaaataaaat   13020
tgatagcacc gaacctcaaa cagacaggat tatcattgat tacgatgaaa gtaataatat   13080
tgttggcatt gaggtattag attttaatta tcttgtcaag aaaggtttaa ccgttgctga   13140
tttacctttt tctgaagatg aaagattaac agcttctcaa tattttaatt ttcctgttgc   13200
tatctaatcc agaaggggca ataatcccct tctttcatcg agttagactt aatatcacaa   13260
aagtcatttt catttttaccg tttctttttcc acagcgtccg tacgcccctc gttaaatctc   13320
aaaaccgaca atttatgatg tttataaaaa gttactcact ttaataagta tttatactca   13380
ttaaagggtt attcttttt tgtagcctga taggttggga aggaatattt cagattatca   13440
gatttgttg                                                           13449
```

<210> SEQ ID NO 11
<211> LENGTH: 13033
<212> TYPE: DNA
<213> ORGANISM: Artificial Sequence
<220> FEATURE:
<223> OTHER INFORMATION: TK295¶ABICyano1-6.8_PnirAABICyano1-PDCmax-
      PpsbAABICyano1-synADHmax-PrbcABICyano1-Km**-oriVT

<400> SEQUENCE: 11

```
aatatttttc gtcagatacg caaaccttac aaacataatt aacaactgaa actattgata     60
tgtctaggtt ttagctctat cacaggttgg atctgtcgac aattaataac ttcttcctgt    120
```

```
acgggcgaat ggccatttgc tcctaactaa ctccgtactg ctttgcggaa cgagcgtagc    180
gaactctccg aattactaag ccttcatccc tgatagatgc aaaaaacgaa ttaaaattat    240
gtgtaaaaag aaaatgtgtc tttatttagt agtcaaagtt acaaatatt aagaatcaaa     300 ttaataatgt attgggcagt taagtatata agtctttaaa tatttatttg tattcaatat    360
attaaccgag gacaaattat gaattcttat accgtgggta cttatttagc cgaacgctta    420
gtgcaaattg gtttaaaaca tcattttgcc gtggctgggg actataattt agtgttattg    480
gataacttat tattaaataa aaacatggaa caagtgtatt gttgtaatga attaaattgt    540
ggtttttctg ctgaaggtta tgctagagct aaaggtgcag ctgctgctgt tgttacttat    600
tctgtgggtg ctttatctgc ttttgatgct attggtggtg cttatgccga aaatttaccc    660
gtgattttaa tttctggtgc ccctaataat aatgatcatg ccgctggaca tgttttacat    720
catgccttag gtaaaaccga ttatcattat caattagaaa tggccaaaaa tattactgct    780
gctgccgaag ctatttatac tcctgaagaa gcccctgcca aaattgatca tgtgattaaa    840
accgccttac gcgaaaaaaa acccgtgtat ttagaaattg cctgtaatat tgcttctatg    900
ccttgtgctg ctcctgggcc tgcttctgct ttatttaatg atgaagcctc tgatgaagct    960
agtttaaatg ctgccgtgga agaaacctta aaatttattg ccaatcgcga taagttgcc    1020 gtgttagttg gttctaaatt aagagctgct ggtgctgaag aagctgctgt taaatttgct    1080
gatgctttag gtggtgcagt tgctactatg gctgctgcca atctttttt tcccgaagaa    1140 aatccccatt atattggaac tagttgggga gaagtttctt atcctggtgt ggaaaaaact    1200 atgaagaag ccgacgctgt tattgcttta gcccctgtgt ttaatgatta ttctaccact    1260
ggttggactg atattcccga tcccaaaaaa ttagttttag ccgaacctcg ttctgttgtt    1320
gttaatggtg ttcgctttcc ctctgtgcat ttaaaagatt attaacccg cttagcccaa    1380 aaagtttcta aaaaaactgg tgccttagat ttttttaaat ctttaaatgc gggtgaatta    1440 aaaaagctg ctcctgctga tccttctgct cctttagtta atgctgaaat tgcccgtcaa    1500
gttgaagcct tattaacccc taatactacc gttattgccg aaactggtga ttcttggttt    1560
aatgcccaac gcatgaaatt acctaatggt gcccgtgttg aatatgaaat gcaatggggt    1620
catattggtt ggtctgtacc tgctgctttt ggttatgctg ttggtgctcc tgaacgtcgt    1680
aatattttaa tggtggggtga tggttctttt caattaactg cccaagaagt tgcccaaatg    1740
gttcgcttaa aattacccgt tattattttt ttaataaata attatggtta taccattgaa    1800
gtgatgattc atgatgggcc atataataat attaaaaatt gggattatgc gggtttaatg    1860
gaagtgttta atggtaatgg tggttatgat tctggtgctg gtaaaggttt aaaagccaaa    1920
actggtggtg aattagctga agctattaaa gttgccttag ccaatactga tgggccaacc    1980
ttaattgaat gttttattgg tcgcgaagat tgtaccgaag aattagttaa atggggtaaa    2040
cgtgttgctg ctgctaattc tcgcaaaccc gtgaataaat tattgtaatt tttggggatc    2100
aattcgagct cgccttacta taaacaaaag ttatctgaga ataactata actattctga    2160 aaatatttga caaaacttta caattttgtt atattagtaa gtgaggtgag caaatcaccc    2220
aaaatatata agtacctcga aaaattcata actgaaatca taagcatatg attaaagcct    2280
atgctgcctt agaagccaat ggtaaattac aacccttttga atatgatcct ggtgctttag    2340
gtgccaatga agtggaaatt gaagtgcaat attgtggtgt gtgtcattct gatttatcta    2400
tgattaataa tgaatggggt attttctaatt atcccttagt tcctggtcat gaagttgttg    2460
gtactgttgc tgctatgggt gaaggtgtta atcatgtgga agtgggtgat ttagttggtt    2520
```

```
taggttggca ttctggttat tgtatgacct gtcattcttg tttatctggt tatcataatt    2580
tatgtgccac tgccgaatct actattgtgg gtcattatgg tggttttggt gatagagttc    2640
gtgctaaagg tgtttctgtg gtgaaattac ccaaaggtat tgatttagcc tctgctgggc    2700
ctttattttg tggtggtatt accgtttttt ctcccatggt ggaattatct ttaaaaccta    2760
ccgccaaagt tgctgttatt ggtattggtg gtttaggtca tttagccgtt caattttttaa   2820 gagcctgggg ttgtgaagtt actgctttta cctcttctgc ccgtaaacaa accgaagttt    2880
tagaattagg tgcccatcat atttttagatt ctaccaatcc tgaagctatt gcttctgccg   2940
aaggtaaatt tgattatatt atttctaccg tgaatttaaa attagattgg aatttatata    3000
tcagtacctt agcccctcaa ggtcattttc attttgttgg tgtggtgtta gaacccttgg    3060
acttaaactt atttccctta ttaatgggac aacgttctgt ttctgcttct cctgttggtt    3120
ctcctgctac tattgccact atgttagatt ttgccgtgcg tcatgatatt aaacccgtgg    3180
tggaacaatt ttcttttgat caaattaatg aagccattgc ccatttagaa tctggtaaag    3240
cccattatcg cgtggtgtta tctcattcta aaaattaata agattaactt ctaaactgaa    3300
acaaatttga gggtaggctt cattgtctgc ccttattttt ttatttagga aaagtgaaca    3360
gactaaagag tgttggctct attgctttga gtatgtaaat taggcgttgc tgaattaagg    3420
tatgattttt gacccttcct ctcttctgca gttacctagg atttctggcg aaagggggat    3480
gtgctgcaag gcgattaagt tgggtaacgc cagggttttc ccagtcacga cgttgtaaaa    3540
cgacggccag tgagcgcgac gtaatacgac tcactatagg gcgaattggc ggaaggccgt    3600
caaggccgca tggcgcgcct acgtagacaa ttgtcgatgt aattattaac tatcttatta    3660
tagatgaggg gagagggaga aattagttcg gagagaacgc tcgagcgctc gttccgcaaa    3720
gcggtacgga gttagttagg ggctaatggg cattctcccg tacaggaaag agttagaagt    3780
tattaattat caacaattct cctttgccta gtgcatcgtt acctttttaa ttaaaacata    3840
aggaaaacta ataatcgtaa taatttaacc tcaaagtgta aagaaatgtg aaattctgac    3900
ttttataacg ttaaagaggg aaaaattagc agtttaaaat acctagagaa tagtctgggg    3960
taagcataga gaattagatt agttaagtta atcaaattca gaaaaaataa taatcgtaaa    4020
tagttaatct gggtgtatag aaaatgatcc ccttcatgat aagatttaaa ctcgaaaagc    4080
aaaagccaaa aaactaactt ccattaaaag aagttgttac atataacgct ataagaaaa    4140 tttatatatt tggaggatac caaccatgtc tcatattcaa cgtgaaacta gttgttctcg    4200
tcctcgttta aattctaata tggatgccga tttatatggt tataaatggg ctcgtgataa    4260
tgttggtcaa tctggtgcta ctatttatcg tttatatggt aaacctgatg ctcctgaatt    4320
attcttgaaa catggtaaag gttctgttgc taatgatgtt actgatgaaa tggttcgttt    4380
aaactggttg actgaattta tgcctttacc tactattaaa catttttattc gtactcccga    4440 tgatgcttgg ttattaacta ctgctattcc tggtaaaact gcttttcaag ttttagaaga    4500
atatcctgat tctggtgaaa atattgttga tgctttagct gttttttttac gtcgtttaca    4560 ttctattccc gtttgtaatt gtccttttaa ttctgatcgt gttttttcgtt tagctcaagc    4620 tcaatctcgt atgaataatg gttagttgat gcttctgat tttgatgatg aacgtaatgg    4680
ttggcctgtt gaacaagttt ggaaagaaat gcacaaattg ttaccttttt ctcctgattc    4740
tgttgttact catggtgatt tttctttaga taatttgatc tttgatgaag gtaaattgat    4800
tggttgtatt gatgttggtc gtgttggtat tgctgatcgt tatcaagatt tagctatttt    4860
```

```
atggaattgt taggtgaat tttctccttc tttacagaaa cgtttatttc agaaatatgg    4920
tattgataat cctgatatga acaagttaca atttcattta atgttggacg agttcttta    4980 agaattaatt catgaccaaa atcccttaac gtgagttttc gttccactga gcgtcagacc    5040
ccgtagaaaa gatcaaagga tcttcttgag atccttttt tctgcgcgta atctgctgct    5100
atttaaatta cgtacacgtg ttattacttt gttaacgaca attgtcttaa ttaactgggc    5160
ctcatgggcc ttccgctcac tgcccgcttt ccagtcggga aacctgtcgt gccagctctg    5220
cagatgacgg tgaaaacctc tgacacatgc agctcccgga gacggtcaca gcttgtctgt    5280
aagcggatgc cgggagcaga caagcccgtc agggcgcgtc agcgggtgtt ggcgggtgtc    5340
ggggcgcagc catgacccag tcacgtagcg atagcggagt gtatactggc ttaactatgc    5400
ggcatcagag cagattgtac tgagagtgca ccatatgcgg tgtgaaatac cgcacagatg    5460
cgtaaggaga aaataccgca tcaggcgctc ttccgcttcc tcgctcactg actcgctgcg    5520
ctcggtcgtt cggctgcggc gagcggtatc agctcactca aaggcggtaa tacggttatc    5580
cacagaatca ggggataacg caggaaagaa catgtgagca aaaggccagc aaaaggccag    5640
gaaccgtaaa aaggccgcgt tgctggcgtt tttccatagg ctccgccccc ctgacgagca    5700
tcacaaaaat cgacgctcaa gtcagaggtg gcgaaacccg acaggactat aaagatacca    5760
ggcgtttccc cctggaagct ccctcgtgcg ctctcctgtt ccgaccctgc cgcttaccgg    5820
atacctgtcc gcctttctcc cttcgggaag cgtggcgctt tctcatagct cacgctgtag    5880
gtatctcagt tcggtgtagg tcgttcgctc caagctgggc tgtgtgcacg aaccccccgt    5940
tcagcccgac cgctgcgcct tatccggtaa ctatcgtctt gagtccaacc cggtaagaca    6000
cgacttatcg ccactggcag cagccactgg taacaggatt agcagagcga ggtatgtagg    6060
cggtgctaca gagttcttga agtggtggcc taactacggc tacactagaa ggacagtatt    6120
tggtatctgc gctctgctga agccagttac cttcggaaaa agagttggta gctcttgatc    6180
cggcaaacaa accaccgctg gtagcggtgg tttttttgtt tgcaagcagc agattacgcg    6240
cagaaaaaaa ggatctcaag aagatccttt gatcttttct actgcagaag cttgttagac    6300
accctgtcat gtatttata ttatttattt caccatacgg attaagtgaa acctaatgaa    6360
aatagtactt tcggagcttt aactttaatg aaggtatgtt tttttataga catcgatgtc    6420
tggtttaaca ataggaaaaa gtagctaaaa ctcccatgaa ttaaagaaat aacaaggtgt    6480
ctaacaacct gttattaaga atgttagaaa agacttaaca tttgtgttga gtttttatag    6540
acattggtgt ctagacatac ggtagataag gtttgctcaa aaataaaata aaaaagatt    6600 ggactaaaaa acatttaatt tagtacaatt taattagtta ttttttcgtc tcaaattttg    6660
ctttgttgag cagaaattta gataaaaaaa tccccgtgat cagattacaa tgtcgttcat    6720
tgtacgatgt gtcgaaaaat ctttacgaca ctctaaactg accacacggg ggaaaaagaa    6780
aactgaacta ataacatcat gatactcgga aaacctagca attctcaacc cctaaacaaa    6840
agaaacttcc aaaaccctga ccatataaag gagtggcaac aatcagcaat cagtcaagat    6900
ttgatagcag aaaatcttgt atcggttgct aatggttttg atgtactatt tatcggcaat    6960
aaataccgaa ctaacacggg tgttctgtca cggcacatat taaactccta ttctcattta    7020
gaagatggtg gttcgtatgg tagaacattt gacccattta ccaataaaga aatgcagtgg    7080 gttcaatttta aaccgaatag accaagaaaa ggttctactg gtaaggtaat caaatatgaa    7140
tcgccaaaag gtgaacctac aagagttcta atgccgtttg tgcctatgaa aatatggcaa    7200
cggattagcg ataagttcgg agtaccgatt aatccgaaaa aagatactca cttttgggaa    7260
```

```
tgggtaaaga ataatccatc gataccgatt gccattacag aaggaaataa aaaagctaat    7320
tgcctattat cctatggcta tcctgctatt gcctttgtag gcatttggaa cggattagag    7380
aaaataaatg atttctcgaa ggaaaagcag ttaaagagg atttgaaatg gttgttatcc     7440
aacggcaacc gaaatattaa tatcatcttt gaccaagacc agaaacaaaa aactgtaatt    7500
aatgtaaaca aagctatttt cgctttatct tctctaataa gtagaaatgg tcataaagtt    7560
aatattgtgc aatggttgcc gtcaaaaggt aaggaatag atgattattt ggtagcttta     7620 cctttgaga aagagaaaa tcatttagac aacttaatta aaattgcacc atcatttaat      7680
ttttggtcaa ctaaatactt attcaagtgt cgtaaaccag atttaaccgt aaattgccgt    7740
tatttgagcg atgcagtaaa agaattacct caagaggata tagcattaat agcacctcac    7800
ggcacgggta aaacttcatt agtagctact cacgttaaga atcggagtta tcacggaagg    7860
aaaactattt cattggtgca tcttgaaagt ttagccaaag ctaatggcaa cgcacttgga    7920
ttatattacc gaaccgaaaa taatattgaa aagcaatatc ttggatttag cttatgtgta    7980
gatagttgcc gtgataagat taacggcatt acaactgata ttatttcagg tcaagattat    8040
tgccttttca ttgatgaaat tgaccaagta attccacaca tccttaacag tgaaactgaa    8100
gtaagtaagt atagatgcac catcattgac acttttctg aactggtgag aaatgctgaa     8160
caggtcatta ttgctgatgc tgatttatcc gatgtgacga ttgacctaat agaaaacatc    8220
agaggtaaaa aactatatgt aatcaagaat gaatatcagt atcagggaat gacttttaac    8280
gccgttggtt caccattaga aatgatgca atgatgggaa atcggtgtc agaaggcaag      8340 aaattattta ttaacaccac atcccaaaag gcaaaagta agtacggcac aatcgctctt     8400
gagtcttata tttttggtct aaataaagaa gcaaagatat taagaataga ctctgaaacc    8460
actaaaaacc ctgaacatcc agcctataaa atcattgacc aagacttaaa taatatcctc    8520
aaagattatg attatgtcat tgcctcacct tgccttcaaa caggtgtcag tattaccta    8580 aaagggcatt ttgaccagca atttaacttt tccagtggaa acattacacc tcattgcttt   8640
ttacagcaaa tgtggcggtt gagggatgca gaaattgaaa gattctatta tgtgccgaac    8700
tcatctaacc tcaatctcat tgggaataag tcaagttcac catcagacct tctaaagagc    8760
aataacaaga tggcaacggc aacggttaac ctttttgggta gaatcgactc cgaatattcc    8820
ctagagtatg aatcgcacgg catttggctt gagacgtggg caaaattatc agcacggcat    8880
aacagttcaa tgcgttgtta ctctgaaatt cttacctatc taattacgtc tcaagggcat    8940
aaattaaata tcaacattcc ctcacctctt gcagatatta agaagctaaa tgatgaggta    9000
agtagtaaca gggaaaaggt aaaaaatgag agatactctc agaggttaaa ctcaccagat    9060
attaacgatg cagaagctac catactcgaa tctaaagagc aaaaaatcgg attgactctc    9120
aatgagagat gcaccctaga aaagcataaa gttaagaagc ggtatgggaa tgtaaagatg    9180
gatattctca cctttgatga tgatggacta taccccaaac tcagactatt ttattacctc    9240
accatcggta aacctcatct caaggctaat gacagaaaag ctattgccaa atgggcaat    9300 gacaataaag gcaagattct atcaaaagac ttagttaata aaacttactc cgctcgtgtg    9360
aaggtcttag agattcttaa actaactgac tttatcgaca atcttagaga tgaactctta    9420
ataactccca ataatccagc tatcaccgat tttaataatc ttctgctaag agctaagaag    9480
gatttaagag tattaggagt caacatcgga aaatatccaa tggccaacat taatgccgta    9540
cttactctca ttggtcacaa actttctgta atgagagatg agttcggaaa agagaaaagg    9600
```

```
ataaaagtag atggtaaatc ataccgatgt tatcaacttg aaacattacc agattttacc   9660
aatgatactc ttgactactg gttagaaaat gatagccaaa aagaagtaac agcaacagaa   9720
aattactccg aaaattttaa cccttcaaat agctacaatc cagacagtaa gacactttca   9780
gagggtgcaa atttcctata tataaataaa gaagaattgc atccaaataa attgcaccta   9840
gaaataaaag aaggtgctga acttttttta ttcggggtaa aggtgattgt gaaaggaatc   9900
ttggacgggg cagtaactat attctctatg ggtcaagaat acgatttatc cctcaatgaa   9960
ctagagggga tgttaacatc atgaacttta caagaatctt tttaaagggc gatcgcacca  10020
tgttaaatga tggtacattt gttcagatat ttgatattta ccatgaccac gcattgggag  10080
tgacccttga ccttaagaca gaaaaaatta tttccgatga tgttagggta attactgtca  10140
aagacttatt gttcgatggc acttataaag gggtaaaatc ttttatgccc gataatgccc  10200
gataatgccc gattgatgct acaaaatccc ataatcataa gcgataatcc cctaatagct  10260
tgtaattctt gaaccgtagc gattttagag tattccaaaa agaagaaata aacaccgcaa  10320
aatgtcgtat ttcacatata taaaccaagg tttttttgccc taaaatcttt atgtttgtag  10380
tgtgatgttg ggtcaaaatg gtcagaaaag ttgcaaggtt tttatggatg cttacgcgcg  10440
cgaggggtaa gcatcccaa atagttactt tatcctagtc catgcccatt tattgccgtc  10500
ccgttcggct ttaaaaaagt gccaaaactc acaaggtgca ataaaaagtt ctgtaccttt  10560
cgcaacccta gataatcttt caacagttac ttttttttcct attatctcgg tacaaagttt  10620
ggctagtttc tcttttcccct cttttttcaat caagccttct tgtatgccca actcattgat  10680
taatctctct atttttacca ttatttcccg ttcaggtagt ttatccccta aatcttcatc  10740 gggggggcaat gtagggcatt ctgaaggggc tttttcttct gtctggacat tatctaatat  10800
tgaagtaacc aaactatctt cagttttttc tattcctatt aattcatatt cggttactgt  10860
atccgtatca atatccgaat aactatcttt atccgtatta gctattcggt taagtttatc  10920
cgttaactca gaaacaagac tatatagcgg ttttagcttt tcttctatcc tgttatctaa  10980
tacggataag tttatacggt tatcattatc cgtattagta tcattgggct ttttttggtag  11040 ttctaccccc tcataaaccg ctttttattcc caattccaac agactgataa cagtatcctt  11100
tataatgggt tttttgctga tatggtgaac ttttgccccct tccatcattg cgatactttc  11160
tatctcactc atcaacttat cgcttaagtg aatctcgtat ctgtttaatc ccttactggt  11220
tttattcata tccgtttact ttattcggtt aacaattcta ttttatacga ataaaatatt  11280
atacggttaa cttatacgt ttaactattt tatctatacg gataacagta ataagttatt  11340
cgtattagtt atacgtttac ttttatccaa ataaaattag tgcatttaaa ctaaaagaat  11400
gattttatcg gagttgatag cattggatta acctaaagat gtttataagc tatatctgat  11460
aagtatttaa ggttattttg ttattctgtt tattgacatt atcagaataa agaatagaa   11520 tataattgtt gagagataag aggtttaagt gattatggtt aagaagttag ttggttatgt  11580
cagggtcagt agtgaatcgc aagaggataa cactagctta cagaatcaga tagagagaat  11640
tgaagcatat tgtatggctt ttggttatga gttggtaaaa atattcaaag aggttgccac  11700
tggtacaaaa gcagatattg aaacccgtcc tatttttaat gaagctatag aatacttgaa  11760
acaggataat gctaatggaa ttattgcctt gaagctagac cgaatcgcac ggaatgcttt  11820
agatgtattg cgtttggttc gtgaaacctt agaaccacaa aataaaatgt tagtgttact  11880
agatattcag gtagatactt cgacaccttc aggaaaaatg atttttaactg taatgagtgc  11940 cgttgctgaa ctcgaaagag acatgatcta tgatcgcact caggggggta gaaagactaa  12000
```

```
agcccaaaag ggcgggtatg cctacgggaa acctaaattt ggctataaga ctgaagaaaa    12060
ggaactaaaa gaagattcag cacaacagga aactattaaa ctaattaaga gacaccgtag    12120
gtcagggaaa agctaccaga aaatagctga ttatctcaat gcccaaagta ttcccactaa    12180
acaaggtaag aaatggagtt ctagcgtcgt ctatcgaatc tgtcaggaaa agctggtta     12240 agtctgttta tagatattta gaatttattg aataaaaata gtatgaacaa taaatattta    12300
tggactaacc acgctcggaa acgtttaact gaacgatggg aaataaaaga atcatggggtt   12360 attgatacca tcgaaaatcc tgaacgttca gaatttattg ttgatgagtc aggggaaaaa    12420
tatcattact ataaaagaat agctaagttt aagaatagag tgttagaagt gataacttct    12480
gccaactcaa cacccacaag aataataacc ttttacttta accgtaacat gaggaaaaat    12540
ttatgattgt tacttacgat aatgaagttg acgcaattta ttttaagtta acggaaaata    12600
aaattgatag caccgaacct caaacagaca ggattatcat tgattacgat gaaagtaata    12660
atattgttgg cattgaggta ttagatttta attatcttgt caagaaaggt ttaaccgttg    12720
ctgatttacc ttttctgaa  gatgaaagat taacagcttc tcaatatttt aattttcctg    12780
ttgctatcta atccagaagg ggcaataatc cccttctttc atcgagttag acttaatatc    12840
acaaaagtca ttttcatttt accgtttctt ttccacagcg tccgtacgcc cctcgttaaa    12900
tctcaaaacc gacaatttat gatgtttata aaaagttact cactttaata agtatttata    12960
ctcattaaag ggttattctt ttttttgtagc ctgataggtt gggaaggaat atttcagatt   13020
atcagatttg ttg                                                      13033

<210> SEQ ID NO 12
<211> LENGTH: 13081
<212> TYPE: DNA
<213> ORGANISM: Artificial Sequence
<220> FEATURE:
<223> OTHER INFORMATION: TK229¶ABICyano1-6.8_PpetEABICyano1-PDCmax-
      synADHmax-PrbcABICyano1-Km**-oriVT

<400> SEQUENCE: 12 aatattttc  gtcagatacg caaaccttac aaacataatt aacaactgaa actattgata    60
tgtctaggtt ttagctctat cacaggttgg atctgtcgac gagaagggga acagggaaaa    120
gtatttataa ttgatacaaa ctgtggttca acttatttta aagacatttt tctccattta    180
atgattattt cggggaaaat tttgaggatt tttgattctt aaattgacga tattttgtca    240
ctaacacaac gtgagcggta aatttatata tagacctaaa acctttacta taagtgttat    300
atatttaaat cgctaagtat atagttaaag tgtagccaat aattaacttt taacaagtga    360
ttaccgttaa gtcccttaat ttatcactac aagctaaaac aaattttca  attagatatg    420 acattaggtc aaagttcata gtatgatagt aaaaaataaa atttgacgat ctgtaaaaat    480
aaaaaaacac aatgaattct tataccgtgg gtacttattt agccgaacgc ttagtgcaaa    540
ttggtttaaa acatcatttt gccgtggctg gggactataa tttagtgtta ttggataact    600
tattattaaa taaaaacatg gaacaagtgt attgttgtaa tgaattaaat tgtggttttt    660
ctgctgaagg ttatgctaga gctaaaggtg cagctgctgc tgttgttact tattctgtgg    720
gtgctttatc tgcttttgat gctattggtg gtgcttatgc cgaaaattta cccgtgattt    780
taatttctgg tgcccctaat aataatgatc atgccgctgg acatgtttta catcatgcct    840
taggtaaaac cgattatcat tatcaattag aaatggccaa aaatattact gctgctgccg    900 aagctatttta tactcctgaa gaagcccctg ccaaaattga tcatgtgatt aaaaccgcct    960
```

```
tacgcgaaaa aaaacccgtg tatttagaaa ttgcctgtaa tattgcttct atgccttgtg    1020
ctgctcctgg gcctgcttct gctttattta atgatgaagc ctctgatgaa gctagtttaa    1080
atgctgccgt ggaagaaacc ttaaaattta ttgccaatcg cgataaagtt gccgtgttag    1140
ttggttctaa attaagagct gctggtgctg aagaagctgc tgttaaattt gctgatgctt    1200
taggtggtgc agttgctact atggctgctg ccaaatcttt ttttcccgaa gaaaatcccc    1260
attatattgg aactagttgg ggagaagttt cttatcctgg tgtggaaaaa actatgaaag    1320
aagccgacgc tgttattgct ttagcccctg tgtttaatga ttattctacc actggttgga    1380
ctgatattcc cgatcccaaa aaattagttt tagccgaacc tcgttctgtt gttgttaatg    1440
gtgttcgctt tccctctgtg catttaaaag attatttaac ccgcttagcc caaaagtttt    1500
ctaaaaaaac tggtgcctta gattttttta aatctttaaa tgcgggtgaa ttaaaaaaag    1560
ctgctcctgc tgatccttct gctcctttag ttaatgctga aattgcccgt caagttgaag    1620
ccttattaac ccctaatact accgttattg ccgaaactgg tgattcttgg tttaatgccc    1680
aacgcatgaa attacctaat ggtgcccgtg ttgaatatga aatgcaatgg ggtcatattg    1740
gttggtctgt acctgctgct tttggttatg ctgttggtgc tcctgaacgt cgtaatattt    1800
taatggtggg tgatggttct tttcaattaa ctgcccaaga agttgcccaa atggttcgct    1860
taaaattacc cgttattatt ttttttaataa ataattatgg ttataccatt gaagtgatga    1920
ttcatgatgg gccatataat aatattaaaa attgggatta tgcgggttta atggaagtgt    1980
ttaatggtaa tggtggttat gattctggtg ctggtaaagg tttaaaagcc aaaactggtg    2040
gtgaattagc tgaagctatt aaagttgcct tagccaatac tgatgggcca accttaattg    2100
aatgttttat tggtcgcgaa gattgtaccg aagaattagt taaatggggt aaacgtgttg    2160
ctgctgctaa ttctcgcaaa cccgtgaata aattattgta attttttgggg atcaattcga    2220 gctcggtacc caaactagta tgtagggtga ggttatagct agcgctttta attaatccgc    2280
ggatttgtat tcaatatatt aaccgaggac aacatatgat taaagcctat gctgccttag    2340
aagccaatgg taaattacaa ccctttgaat atgatcctgg tgctttaggt gccaatgaag    2400
tggaaattga agtgcaatat tgtggtgtgt gtcattctga tttatctatg attaataatg    2460
aatggggtat ttctaattat cccttagttc ctggtcatga agttgttggt actgttgctg    2520
ctatgggtga aggtgttaat catgtggaag tgggtgattt agttggttta ggttggcatt    2580
ctggttattg tatgacctgt cattcttgtt tatctggtta tcataattta tgtgccactg    2640
ccgaatctac tattgtgggt cattatggtg gttttggtga tagagttcgt gctaaaggtg    2700
tttctgtggt gaaattaccc aaaggtattg atttagcctc tgctgggcct ttattttgtg    2760
gtggtattac cgttttttct cccatggtgg aattatcttt aaaacctacc gccaaagttg    2820
ctgttattgg tattggtggt ttaggtcatt tagccgttca attttttaaga gcctggggtt    2880 gtgaagttac tgcttttacc tcttctgccc gtaaacaaac cgaagtttta gaattaggtg    2940
cccatcatat tttagattct accaatcctg aagctattgc ttctgccgaa ggtaaatttg    3000
attatattat ttctaccgtg aatttaaaat tagattggaa tttatatatc agtaccttag    3060
cccctcaagg tcattttcat tttgttggtg tggtgttaga acccttggac ttaaacttat    3120
ttcccttatt aatgggacaa cgttctgttt ctgcttctcc tgttggttct cctgctacta    3180
ttgccactat gttagatttt gccgtgcgtc atgatattaa acccgtggtg gaacaatttt    3240
cttttgatca aattaatgaa gccattgccc atttagaatc tggtaaagcc cattatcgcg    3300
```

```
tggtgttatc tcattctaaa aattaataag attaacttct aaactgaaac aaatttgagg    3360
gtaggcttca ttgtctgccc ttattttttt atttaggaaa agtgaacaga ctaaagagtg    3420
ttggctctat tgctttgagt atgtaaatta ggcgttgctg aattaaggta tgattttga    3480
cccctctct cttctgcagt tacctaggat ttctggcgaa aggggatgt gctgcaaggc    3540
gattaagttg ggtaacgcca gggttttccc agtcacgacg ttgtaaaacg acggccagtg    3600
agcgcgacgt aatacgactc actatagggc gaattggcgg aaggccgtca aggccgcatg    3660
gcgcgcctac gtagacaatt gtcgatgtaa ttattaacta tcttattata gatgagggga    3720
gagggagaaa ttagttcgga gagaacgctc gagcgctcgt tccgcaaagc ggtacggagt    3780
tagttagggg ctaatgggca ttctcccgta caggaaagag ttagaagtta ttaattatca    3840
acaattctcc tttgcctagt gcatcgttac ctttttaatt aaaacataag gaaaactaat    3900
aatcgtaata atttaacctc aaagtgtaaa gaaatgtgaa attctgactt ttataacgtt    3960
aaagagggaa aaattagcag tttaaaatac ctagagaata gtctggggta agcatagaga    4020
attagattag ttaagttaat caaattcaga aaaaataata atcgtaaata gttaatctgg    4080
gtgtatagaa aatgatcccc ttcatgataa gatttaaact cgaaaagcaa agccaaaaaa    4140
actaacttcc attaaaagaa gttgttacat ataacgctat aaagaaaatt tatatatttg    4200
gaggatacca accatgtctc atattcaacg tgaaactagt tgttctcgtc ctcgtttaaa    4260
ttctaatatg gatgccgatt tatatggtta taaatgggct cgtgataatg ttggtcaatc    4320
tggtgctact atttatcgtt tatatggtaa acctgatgct cctgaattat tcttgaaaca    4380
tggtaaaggt tctgttgcta atgatgttac tgatgaaatg gttcgtttaa actggttgac    4440
tgaatttatg ccttacccta ctattaaaca ttttattcgt actcccgatg atgcttggtt    4500
attaactact gctattcctg gtaaaactgc ttttcaagtt ttagaagaat atcctgattc    4560
tggtgaaaat attgttgatg ctttagctgt ttttttacgt cgtttacatt ctattcccgt    4620
ttgtaattgt ccttttaatt ctgatcgtgt ttttcgttta gctcaagctc aatctcgtat    4680
gaataatggt ttagttgatg cttctgattt tgatgatgaa cgtaatggtt ggcctgttga    4740
acaagtttgg aaagaaatgc acaaattgtt accttttctct cctgattctg ttgttactca    4800
tggtgatttt tctttagata atttgatctt tgatgaaggt aaattgattg gttgtattga    4860
tgttggtcgt gttggtattg ctgatcgtta tcaagattta gctattttat ggaattgttt    4920
aggtgaattt tctccttctt tacagaaacg tttatttcag aaatatggta ttgataatcc    4980
tgatatgaac aagttacaat ttcatttaat gttggacgag ttcttttaag aattaattca    5040
tgaccaaaat cccttaacgt gagttttcgt tccactgagc gtcagacccc gtagaaaaga    5100
tcaaaggatc ttcttgagat cctttttttc tgcgcgtaat ctgctgctat ttaaattacg    5160
tacacgtgtt attactttgt taacgacaat tgtcttaatt aactgggcct catgggcctt    5220
ccgctcactg cccgctttcc agtcgggaaa cctgtcgtgc cagctctgca gatgacggtg    5280
aaaacctctg acacatgcag ctcccggaga cggtcacagc ttgtctgtaa gcggatgccg    5340
ggagcagaca agcccgtcag ggcgcgtcag cgggtgttgg cgggtgtcgg ggcgcagcca    5400
tgacccagtc acgtagcgat agcggagtgt atactggctt aactatgcgg catcagagca    5460
gattgtactg agagtgcacc atatgcggtg tgaaataccg cacagatgcg taaggagaaa    5520
ataccgcatc aggcgctctt ccgcttcctc gctcactgac tcgctgcgct cggtcgttcg    5580
gctgcggcga gcggtatcag ctcactcaaa ggcggtaata cggttatcca cagaatcagg    5640
ggataacgca ggaaagaaca tgtgagcaaa aggccagcaa aaggccagga accgtaaaaa    5700
```

```
ggccgcgttg ctggcgtttt tccataggct ccgccccct gacgagcatc acaaaaatcg    5760
acgctcaagt cagaggtggc gaaacccgac aggactataa agataccagg cgtttccccc    5820
tggaagctcc ctcgtgcgct ctcctgttcc gaccctgccg cttaccggat acctgtccgc    5880
ctttctccct cgggaagcg tggcgctttc tcatagctca cgctgtaggt atctcagttc    5940
ggtgtaggtc gttcgctcca agctgggctg tgtgcacgaa ccccccgttc agcccgaccg    6000
ctgcgcctta tccggtaact atcgtcttga gtccaacccg gtaagacacg acttatcgcc    6060
actggcagca gccactggta acaggattag cagagcgagg tatgtaggcg gtgctacaga    6120
gttcttgaag tggtggccta actacggcta cactagaagg acagtatttg gtatctgcgc    6180
tctgctgaag ccagttacct tcggaaaaag agttggtagc tcttgatccg gcaaacaaac    6240
caccgctggt agcggtggtt ttttttgtttg caagcagcag attacgcgca gaaaaaaagg    6300
atctcaagaa gatcctttga tcttttctac tgcagaagct tgttagacac cctgtcatgt    6360
attttatatt atttatttca ccatacggat taagtgaaac ctaatgaaaa tagtactttc    6420
ggagctttaa ctttaatgaa ggtatgtttt tttatagaca tcgatgtctg gtttaacaat    6480
aggaaaaagt agctaaaact cccatgaatt aaagaaataa caaggtgtct aacaacctgt    6540
tattaagaat gttagaaaag acttaacatt tgtgttgagt ttttatagac attggtgtct    6600
agacatacgg tagataaggt ttgctcaaaa ataaaataaa aaagattgg actaaaaaac    6660 atttaattta gtacaattta attagttatt ttttcgtctc aaattttgct tgttgagca    6720 gaaatttaga taaaaaaatc cccgtgatca gattacaatg tcgttcattg tacgatgtgt    6780
cgaaaaatct ttacgacact ctaaactgac cacacggggg aaaagaaaa ctgaactaat    6840 aacatcatga tactcggaaa acctagcaat tctcaaccc taaacaaaag aaacttccaa    6900
aaccctgacc atataaagga gtggcaacaa tcagcaatca gtcaagattt gatagcagaa    6960
aatcttgtat cggttgctaa tggttttgat gtactattta tcggcaataa ataccgaact    7020
aacacgggtg ttctgtcacg gcacatatta aactcctatt ctcatttaga agatggtggt    7080
tcgtatggta gaacatttga cccatttacc aataaagaaa tgcagtgggt tcaatttaaa    7140
ccgaatagac caagaaaagg ttctactggt aaggtaatca aatatgaatc gccaaaaggt    7200
gaacctacaa gagttctaat gccgtttgtg cctatgaaaa tatggcaacg gattagcgat    7260
aagttcggag taccgattaa tccgaaaaaa gatactcact tttgggaatg ggtaaagaat    7320
aatccatcga taccgattgc cattacagaa ggaaataaaa aagctaattg cctattatcc    7380
tatggctatc ctgctattgc ctttgtaggc atttggaacg gattagagaa ataaatgat    7440 ttctcgaagg aaaagcagtt aaaagaggat ttgaaatggt tgttatccaa cggcaaccga    7500
aatattaata tcatctttga ccaagaccag aaacaaaaaa ctgtaattaa tgtaaacaaa    7560 gctatttcg ctttatcttc tctaataagt agaaatggtc ataaagttaa tattgtgcaa    7620
tggttgccgt caaaaggtaa aggaatagat gattatttgg tagctttacc ttttgagaaa    7680
agagaaaatc atttagacaa cttaattaaa attgcaccat catttaattt ttggtcaact    7740
aaatacttat tcaagtgtcg taaaccagat ttaaccgtaa attgccgtta tttgagcgat    7800
gcagtaaaag aattacctca agaggatata gcattaatag cacctcacgg cacgggtaaa    7860
acttcattag tagctactca cgttaagaat cggagttatc acggaaggaa aactatttca    7920
ttggtgcatc ttgaaagttt agccaaagct aatggcaacg cacttggatt atattaccga    7980
accgaaaata atattgaaaa gcaatatctt ggatttagct tatgtgtaga tagttgccgt    8040
```

-continued

```
gataagatta acggcattac aactgatatt atttcaggtc aagattattg ccttttcatt    8100
gatgaaattg accaagtaat tccacacatc cttaacagtg aaactgaagt aagtaagtat    8160
agatgcacca tcattgacac tttttctgaa ctggtgagaa atgctgaaca ggtcattatt    8220
gctgatgctg atttatccga tgtgacgatt gacctaatag aaaacatcag aggtaaaaaa    8280
ctatatgtaa tcaagaatga atatcagtat cagggaatga cttttaacgc cgttggttca    8340
ccattagaaa tgatggcaat gatgggaaaa tcggtgtcag aaggcaagaa attatttatt    8400
aacaccacat cccaaaaggc aaaaagtaag tacggcacaa tcgctcttga gtcttatatt    8460
tttggtctaa ataagaagc aaagatatta agaatagact ctgaaaccac taaaaaccct    8520
gaacatccag cctataaaat cattgaccaa gacttaaata atatcctcaa agattatgat    8580
tatgtcattg cctcaccttg ccttcaaaca ggtgtcagta ttaccttaaa agggcatttt    8640
gaccagcaat ttaactttc cagtggaaac attacacctc attgcttttt acagcaaatg    8700
tggcggttga gggatgcaga aattgaaaga ttctattatg tgccgaactc atctaacctc    8760
aatctcattg ggaataagtc aagttcacca tcagaccttc taaagagcaa taacaagatg    8820
gcaacggcaa cggttaacct ttgggtaga atcgactccg aatattccct agagtatgaa    8880
tcgcacggca tttggcttga gacgtgggca aaattatcag cacggcataa cagttcaatg    8940
cgttgttact ctgaaattct tacctatcta attacgtctc aagggcataa attaaatatc    9000
aacattccct cacctcttgc agatattaag aagctaaatg atgaggtaag tagtaacagg    9060
gaaaaggtaa aaaatgagag atactctcag aggttaaact caccagatat taacgatgca    9120
gaagctacca tactcgaatc taaagagcaa aaaatcggat tgactctcaa tgagagatgc    9180
accctagaaa agcataaagt taagaagcgg tatgggaatg taaagatgga tattctcacc    9240
tttgatgatg atggactata ccccaaactc agactatttt attacctcac catcggtaaa    9300
cctcatctca aggctaatga cagaaaagct attgccaaaa tgggcaatga caataaaggc    9360
aagattctat caaaagactt agttaataaa acttactccg ctcgtgtgaa ggtcttagag    9420
attcttaaac taactgactt tatcgacaat cttagagatg aactcttaat aactcccaat    9480
aatccagcta tcaccgattt taataatctt ctgctaagag ctaagaagga tttaagagta    9540
ttaggagtca acatcggaaa atatccaatg gccaacatta atgccgtact tactctcatt    9600
ggtcacaaac tttctgtaat gagagatgag ttcggaaaag agaaaggat aaaagtagat    9660 ggtaaatcat accgatgtta tcaacttgaa acattaccag attttaccaa tgatactctt    9720
gactactggt tagaaaatga tagccaaaaa gaagtaacag caacagaaaa ttactccgaa    9780 aatttaacc cttcaaatag ctacaatcca gacagtaaga cactttcaga gggtgcaaat    9840
ttcctatata taaataaaga agaattgcat ccaaataaat tgcacctaga aataaaagaa    9900
ggtgctgaac ttttttttatt cggggtaaag gtgattgtga aaggaatctt ggacggggca    9960
gtaactatat tctctatggg tcaagaatac gatttatccc tcaatgaact agaggggatg    10020
ttaacatcat gaactttaca agaatctttt taaagggcga tcgcaccatg ttaaatgatg    10080
gtacatttgt tcagatattt gatatttacc atgaccacgc attgggagtg acccttgacc    10140
ttaagacaga aaaattatt tccgatgatg ttagggtaat tactgtcaaa gacttattgt    10200
tcgatggcac ttataaaggg gtaaaatctt ttatgcccga taatgcccga taatgcccga    10260
ttgatgctac aaaatcccat aatcataagc gataatcccc taatagcttg taattcttga    10320
accgtagcga tttagagta ttccaaaaag aagaaataaa caccgcaaaa tgtcgtattt    10380
cacatatata aaccaaggtt ttttgcccta aaatctttat gtttgtagtg tgatgttggg    10440
```

```
tcaaaatggt cagaaaagtt gcaaggtttt tatggatgct tacgcgcgcg aggggtaagc   10500
atccccaaat agttacttta tcctagtcca tgcccattta ttgccgtccc gttcggcttt   10560
aaaaaagtgc caaaactcac aaggtgcaat aaaaagttct gtacctttcg caaccctaga   10620
taatctttca acagttactt ttttttcctat tatctcggta caaagtttgg ctagtttctc   10680
ttttccctct ttttcaatca agccttcttg tatgcccaac tcattgatta atctctctat   10740
ttttaccatt atttcccgtt caggtagttt atccctaaa tcttcatcgg ggggcaatgt    10800
agggcattct gaaggggctt tttcttctgt ctggacatta tctaatattg aagtaaccaa   10860
actatcttca gtttttttcta ttcctattaa ttcatattcg gttactgtat ccgtatcaat  10920
atccgaataa ctatctttat ccgtattagc tattcggtta agtttatccg ttaactcaga   10980
aacaagacta tatagcggtt ttagcttttc ttctatcctg ttatctaata cggataagtt   11040
tatacggtta tcattatccg tattagtatc attgggcttt tttggtagtt ctaccccctc   11100
ataaaccgct tttattccca attccaacag actgataaca gtatccttta taatgggttt   11160
tttgctgata tggtgaactt tgcccctttc catcattgcg atactttcta tctcactcat   11220
caacttatcg cttaagtgaa tctcgtatct gtttaatccc ttactggttt tattcatatc   11280
cgtttacttt attcggttaa caattctatt ttatacgaat aaaatattat acggttaact   11340
ttatacgttt aactatttta tctatacgga taacagtaat aagttattcg tattagttat   11400
acgtttactt ttatccaaat aaaattagtg catttaaact aaaagaatga ttttatcgga   11460
gttgatagca ttggattaac ctaaagatgt ttataagcta tatctgataa gtatttaagg   11520
ttattttgtt attctgttta ttgacattat cagaataaaa gaatagaata taattgttga   11580
gagataagag gtttaagtga ttatggttaa gaagttagtt ggttatgtca gggtcagtag   11640
tgaatcgcaa gaggataaca ctagcttaca gaatcagata gagagaattg aagcatattg   11700
tatggctttt ggttatgagt tggtaaaaat attcaaagag gttgccactg gtacaaaagc   11760
agatattgaa acccgtccta tttttaatga agctatagaa tacttgaaac aggataatgc   11820
taatggaatt attgccttga agctagaccg aatcgcacgg aatgctttag atgtattgcg   11880
tttggttcgt gaaaccttag aaccacaaaa taaaatgtta gtgttactag atattcaggt   11940
agatacttcg acaccttcag gaaaaatgat tttaactgta atgagtgccg ttgctgaact   12000
cgaaagagac atgatctatg atcgcactca gggggggtaga aagactaaag cccaaaaggg   12060
cgggtatgcc tacgggaaac ctaaatttgg ctataagact gaagaaaagg aactaaaaga   12120
agattcagca caacaggaaa ctattaaact aattaagaga caccgtaggt cagggaaaag   12180
ctaccagaaa atagctgatt atctcaatgc ccaaagtatt cccactaaac aaggtaagaa   12240
atggagttct agcgtcgtct atcgaatctg tcaggaaaaa gctggttaag tctgttata    12300 gatatttaga atttattgaa taaaaatagt atgaacaata aatatttatg gactaaccac   12360
gctcggaaac gttaactga acgatgggaa ataaagaat catgggttat tgataccatc    12420
gaaaatcctg aacgttcaga atttattgtt gatgagtcag gggaaaaata tcattactat   12480
aaaagaatag ctaagtttaa gaatagagtg ttagaagtga taacttctgc caactcaaca   12540
cccacaagaa taataaccttt ttactttaac cgtaacatga ggaaaaattt atgattgtta  12600
cttacgataa tgaagttgac gcaatttatt ttaagttaac ggaaaataaa attgatagca   12660 ccgaaccctca aacagacagg attatcattg attacgatga aagtaataat attgttggca   12720
ttgaggtatt agatttttaat tatcttgtca agaaaggttt aaccgttgct gatttacctt  12780
```

```
tttctgaaga tgaaagatta acagcttctc aatatttttaa ttttcctgtt gctatctaat    12840
ccagaagggg caataatccc cttctttcat cgagttagac ttaatatcac aaaagtcatt    12900
ttcattttac cgtttctttt ccacagcgtc cgtacgcccc tcgttaaatc tcaaaaccga    12960
caatttatga tgtttataaa aagttactca ctttaataag tatttatact cattaaaggg    13020
ttattctttt tttgtagcct gataggttgg gaaggaatat ttcagattat cagatttgtt    13080
g                                                                    13081
```

<210> SEQ ID NO 13
<211> LENGTH: 13562
<212> TYPE: DNA
<213> ORGANISM: Artificial Sequence
<220> FEATURE:
<223> OTHER INFORMATION: TK368¶ABICyano1-6.8_PpetEABICyano1-PDCmax-
      PrpsLABICyano1-synADHmax-PrbcABICyano1-Km**-oriVT

<400> SEQUENCE: 13

```
aatatttttc gtcagatacg caaaccttac aaacataatt aacaactgaa actattgata      60
tgtctaggtt ttagctctat cacaggttgg atctgtcgac gagaagggga acagggaaaa     120
gtatttataa ttgatacaaa ctgtggttca acttatttta aagacatttt tctccattta     180
atgattattt cggggaaaat tttgaggatt tttgattctt aaattgacga tattttgtca     240
ctaacacaac gtgagcggta aatttatata tagacctaaa accttactaa tagtgttat      300
atatttaaat cgctaagtat atagttaaag tgtagccaat aattaacttt taacaagtga     360
ttaccgttaa gtcccttaat ttatcactac aagctaaaac aaatttttca attagatatg     420
acattaggtc aaagttcata gtatgatagt aaaaaataaa atttgacgat ctgtaaaaat     480
aaaaaaacac aatgaattct tataccgtgg gtacttattt agccgaacgc ttagtgcaaa     540
ttggtttaaa acatcatttt gccgtggctg gggactataa tttagtgtta ttggataact     600
tattattaaa taaaaacatg gaacaagtgt attgttgtaa tgaattaaat tgtggttttt     660
ctgctgaagg ttatgctaga gctaaaggtg cagctgctgc tgttgttact tattctgtgg     720
gtgctttatc tgcttttgat gctattggtg gtgcttatgc cgaaaattta cccgtgattt     780
taatttctgg tgcccctaat aataatgatc atgccgctgg acatgtttta catcatgcct     840
taggtaaaac cgattatcat tatcaattag aaatggccaa aaatattact gctgctgccg     900
aagctattta tactcctgaa gaagcccctg ccaaaattga tcatgtgatt aaaaccgcct     960
tacgcgaaaa aaaacccgtg tatttagaaa ttgcctgtaa tattgcttct atgccttgtg    1020
ctgctcctgg gcctgcttct gctttatta atgatgaagc ctctgatgaa gctagtttaa    1080
atgctgccgt ggaagaaacc ttaaaattta ttgccaatcg cgataaagtt gccgtgttag    1140
ttggttctaa attaagagct gctggtgctg aagaagctgc tgttaaattt gctgatgctt    1200
taggtggtgc agttgctact atggctgctg ccaaatcttt ttttcccgaa gaaaatcccc    1260
attatattgg aactagttgg ggagaagttt cttatcctgg tgtggaaaaa actatgaaag    1320
aagccgacgc tgttattgct ttagccctg tgtttaatga ttattctacc actggttgga    1380
ctgatattcc cgatcccaaa aaattagttt tagccgaacc tcgttctgtt gttgttaatg    1440
gtgttcgctt tccctctgtg catttaaaag attatttaac ccgcttagcc caaaaagttt    1500
ctaaaaaaac tggtgcctta gattttttta atctttaaa tgcgggtgaa ttaaaaaaag    1560
ctgctcctgc tgatccttct gctcctttag ttaatgctga aattgcccgt caagttgaag    1620
ccttattaac ccctaatact accgttattg ccgaaactgg tgattcttgg tttaatgccc    1680
```

```
aacgcatgaa attacctaat ggtgcccgtg ttgaatatga aatgcaatgg ggtcatattg    1740
gttggtctgt acctgctgct tttggttatg ctgttggtgc tcctgaacgt cgtaatattt    1800
taatggtggg tgatggttct tttcaattaa ctgcccaaga agttgcccaa atggttcgct    1860
taaaattacc cgttattatt tttttaataa ataattatgg ttataccatt gaagtgatga    1920
ttcatgatgg gccatataat aatattaaaa attgggatta tgcgggttta atggaagtgt    1980
ttaatggtaa tggtggttat gattctggtg ctggtaaagg tttaaaagcc aaaactggtg    2040
gtgaattagc tgaagctatt aaagttgcct tagccaatac tgatgggcca accttaattg    2100
aatgttttat tggtcgcgaa gattgtaccg aagaattagt taaatggggt aaacgtgttg    2160
ctgctgctaa ttctcgcaaa cccgtgaata aattattgta attttttgggg atcaattcga    2220 gctcctccgc ttaaaaaatt tcattttttcg atcaaaaaag acaaattatt actaattagc    2280
tcatggcaat aaataatcag tagtaatctg ttttcacatt ttattgttaa ttttttattat    2340 tgctaatatc aaccttttct acttctgctt aatattttat ttatgctcaa tgggaaaatc    2400
tgaaataaga ttgagaacag tgttaccaat agaagtattt aaggtttaaa gcataccttta    2460 aagataacat ttttttttga aaagagtcaa attattttttg aaaggctgat attttttgata    2520 tttactaata ttttattttat ttcttttttcc cttaaaataa gagctaaatc tgttttttatt    2580 atcatttatc aagctctatt aatacctcaa ctttttcaag aaaaaataat ataattttt    2640 ccctctattc tcatgacctt ttaggaaaat taattttaga aaaactattg acaaacccat    2700
aaaaaatgag ataagattat agattgtcac tggtattttta tactagaggc aaattatatt    2760
tatatataca aaaatgctgt ataaaaaaca tctcatatga ttaaagccta tgctgcctta    2820
gaagccaatg gtaaattaca acccttttgaa tatgatcctg gtgctttagg tgccaatgaa    2880
gtggaaattg aagtgcaata ttgtggtgtg tgtcattctg atttatctat gattaataat    2940
gaatggggta tttctaatta tcccttagtt cctggtcatg aagttgttgg tactgttgct    3000
gctatgggtg aaggtgttaa tcatgtggaa gtgggtgatt tagttggttt aggttggcat    3060
tctggttatt gtatgacctg tcattcttgt ttatctggtt atcataattt atgtgccact    3120
gccgaatcta ctattgtggg tcattatggt ggttttggtg atagagttcg tgctaaaggt    3180
gtttctgtgg tgaaattacc caaaggtatt gatttagcct ctgctgggcc tttatttttgt    3240 ggtggtatta ccgttttttc tcccatggtg gaattatctt taaaacctac cgccaaagtt    3300
gctgttattg gtattggtgg tttaggtcat ttagccgttc aattttttaag agcctggggt    3360 tgtgaagtta ctgctttttac ctcttctgcc cgtaaacaaa ccgaagtttt agaattaggt    3420
gcccatcata ttttagattc taccaatcct gaagctattg cttctgccga aggtaaattt    3480
gattatatta tttctaccgt gaatttaaaa ttagattgga atttatatat cagtaccttta    3540 gcccctcaag gtcatttttca ttttgttggt gtggtgttag aacccttgga cttaaactta    3600
tttcccttat taatgggaca acgttctgtt tctgcttctc ctgttggttc tcctgctact    3660
attgccacta tgttagattt tgccgtgcgt catgatatta acccgtggt ggaacaattt    3720 tcttttgatc aaattaatga agccattgcc catttagaat ctggtaaagc ccattatcgc    3780
gtggtgttat ctcattctaa aaattaataa gattaacttc taaactgaaa caaatttgag    3840
ggtaggcttc attgtctgcc cttatttttt tatttaggaa aagtgaacag actaaagagt    3900
gttggctcta ttgctttgag tatgtaaatt aggcgttgct gaattaaggt atgatttttg    3960 acccccttctc tcttctgcag ttacctagga tttctggcga aagggggatg tgctgcaagg    4020
cgattaagtt gggtaacgcc agggttttcc cagtcacgac gttgtaaaac gacggccagt    4080
```

```
gagcgcgacg taatacgact cactataggg cgaattggcg gaaggccgtc aaggccgcat   4140
ggcgcgccta cgtagacaat tgtcgatgta attattaact atcttattat agatgagggg   4200
agagggagaa attagttcgg agagaacgct cgagcgctcg ttccgcaaag cggtacggag   4260
ttagttaggg gctaatgggc attctcccgt acaggaaaga gttagaagtt attaattatc   4320
aacaattctc ctttgcctag tgcatcgtta cctttttaat taaaacataa ggaaaactaa   4380
taatcgtaat aatttaacct caaagtgtaa agaaatgtga aattctgact tttataacgt   4440
taaagaggga aaaattagca gtttaaaata cctagagaat agtctggggt aagcatagag   4500
aattagatta gttaagttaa tcaaattcag aaaaaataat aatcgtaaat agttaatctg   4560
ggtgtataga aaatgatccc cttcatgata agatttaaac tcgaaaagca aaagccaaaa   4620
aactaacttc cattaaaaga agttgttaca tataacgcta taaagaaaat ttatatattt   4680
ggaggatacc aaccatgtct catattcaac gtgaaactag ttgttctcgt cctcgtttaa   4740
attctaatat ggatgccgat ttatatggtt ataaatgggc tcgtgataat gttggtcaat   4800
ctggtgctac tatttatcgt ttatatggta aacctgatgc tcctgaatta ttcttgaaac   4860
atggtaaagg ttctgttgct aatgatgtta ctgatgaaat ggttcgttta aactggttga   4920
ctgaatttat gcctttacct actattaaac attttattcg tactcccgat gatgcttggt   4980
tattaactac tgctattcct ggtaaaactg cttttcaagt tttagaagaa tatcctgatt   5040
ctggtgaaaa tattgttgat gctttagctg ttttttttacg tcgtttacat tctattcccg   5100
tttgtaattg tccttttaat tctgatcgtg ttttttcgttt agctcaagct caatctcgta   5160
tgaataatgg tttagttgat gcttctgatt ttgatgatga acgtaatggt tggcctgttg   5220
aacaagtttg gaaagaaatg cacaaattgt tacctttttc tcctgattct gttgttactc   5280
atggtgattt ttcttttagat aatttgatct ttgatgaagg taaattgatt ggttgtattg   5340
atgttggtcg tgttggtatt gctgatcgtt atcaagattt agctattta tggaattgtt   5400 taggtgaatt ttctccttct ttacagaaac gtttatttca gaaatatggt attgataatc   5460
ctgatatgaa caagttacaa tttcatttaa tgttggacga gttctttttaa gaattaattc   5520 atgaccaaaa tcccttaacg tgagttttcg ttccactgag cgtcagaccc cgtagaaaag   5580
atcaaaggat cttcttgaga tcctttttttt ctgcgcgtaa tctgctgcta tttaaattac   5640
gtacacgtgt tattactttg ttaacgacaa ttgtcttaat taactgggcc tcatgggcct   5700
tccgctcact gcccgctttc cagtcgggaa acctgtcgtg ccagctctgc agatgacggt   5760 gaaacctct gacacatgca gctcccggag acggtcacag cttgtctgta agcggatgcc   5820
gggagcagac aagcccgtca gggcgcgtca gcgggtgttg gcgggtgtcg ggcgcagcc   5880 atgacccagt cacgtagcga tagcggagtg tatactggct taactatgcg gcatcagagc   5940
agattgtact gagagtgcac catatgcggt gtgaaatacc gcacagatgc gtaaggagaa   6000
aataccgcat caggcgctct tccgcttcct cgctcactga ctcgctgcgc tcggtcgttc   6060
ggctgcggcg agcggtatca gctcactcaa aggcggtaat acggttatcc acagaatcag   6120
gggataacgc aggaaagaac atgtgagcaa aaggccagca aaaggccagg aaccgtaaaa   6180
aggccgcgtt gctggcgttt ttccataggc tccgcccccc tgacgagcat cacaaaaatc   6240
gacgctcaag tcagaggtgg cgaaacccga caggactata agataccagg cgtttcccc   6300 ctggaagctc cctcgtgcgc tctcctgttc cgaccctgcc gcttaccgga tacctgtccg   6360
cctttctccc ttcgggaagc gtggcgcttt ctcatagctc acgctgtagg tatctcagtt   6420
```

```
cggtgtaggt cgttcgctcc aagctgggct gtgtgcacga accccccgtt cagcccgacc      6480
gctgcgcctt atccggtaac tatcgtcttg agtccaaccc ggtaagacac gacttatcgc      6540
cactggcagc agccactggt aacaggatta gcagagcgag gtatgtaggc ggtgctacag      6600
agttcttgaa gtggtggcct aactacggct acactagaag gacagtattt ggtatctgcg      6660
ctctgctgaa gccagttacc ttcggaaaaa gagttggtag ctcttgatcc ggcaaacaaa      6720
ccaccgctgg tagcggtggt ttttttgttt gcaagcagca gattacgcgc agaaaaaaag      6780
gatctcaaga agatcctttg atcttttcta ctgcagaagc ttgttagaca ccctgtcatg      6840
tattttatat tatttatttc accatacgga ttaagtgaaa cctaatgaaa atagtacttt      6900
cggagcttta actttaatga aggtatgttt ttttatagac atcgatgtct ggtttaacaa      6960
taggaaaaag tagctaaaac tcccatgaat taaagaaata acaaggtgtc taacaacctg      7020
ttattaagaa tgttagaaaa gacttaacat ttgtgttgag tttttataga cattggtgtc      7080
tagacatacg gtagataagg tttgctcaaa aataaaataa aaaagattg gactaaaaaa      7140 catttaattt agtacaattt aattagttat ttttcgtct caaattttgc tttgttgagc      7200
agaaatttag ataaaaaaat ccccgtgatc agattacaat gtcgttcatt gtacgatgtg      7260
tcgaaaaatc tttacgacac tctaaactga ccacacgggg gaaaagaaa actgaactaa      7320 taacatcatg atactcggaa aacctagcaa ttctcaaccc ctaaacaaaa gaaacttcca      7380
aaaccctgac catataaagg agtggcaaca atcagcaatc agtcaagatt tgatagcaga      7440
aaatcttgta tcggttgcta atggttttga tgtactattt atcggcaata aataccgaac      7500
taacacgggt gttctgtcac ggcacatatt aaactcctat tctcatttag aagatggtgg      7560
ttcgtatggt agaacatttg acccatttac caataaagaa atgcagtggg ttcaatttaa      7620
accgaataga ccaagaaaag gttctactgg taaggtaatc aaatatgaat cgccaaaagg      7680
tgaacctaca agagttctaa tgccgtttgt gcctatgaaa atatggcaac ggattagcga      7740
taagttcgga gtaccgatta atccgaaaaa agatactcac ttttgggaat gggtaaagaa      7800
taatccatcg ataccgattg ccattacaga aggaaataaa aaagctaatt gcctattatc      7860
ctatggctat cctgctattg cctttgtagg catttggaac ggattagaga aaataaatga      7920
tttctcgaag gaaaagcagt taaaagagga tttgaaatgg ttgttatcca acggcaaccg      7980
aaatattaat atcatctttg accaagacca gaaacaaaaa actgtaatta atgtaaacaa      8040
agctattttc gctttatctt ctctaataag tagaaatggt cataaagtta atattgtgca      8100
atggttgccg tcaaaggta aaggaataga tgattatttg gtagctttac cttttgagaa      8160
aagagaaaat catttagaca acttaattaa aattgcacca tcatttaatt tttggtcaac      8220
taaatactta ttcaagtgtc gtaaaccaga tttaaccgta aattgccgtt atttgagcga      8280
tgcagtaaaa gaattacctc aagaggatat agcattaata gcacctcacg gcacgggtaa      8340
aacttcatta gtagctactc acgttaagaa tcggagttat cacggaagga aaactatttc      8400
attggtgcat cttgaaagtt tagccaaagc taatggcaac gcacttggat tatattaccg      8460
aaccgaaaat aatattgaaa agcaatatct tggatttagc ttatgtgtag atagttgccg      8520
tgataagatt aacggcatta caactgatat tatttcaggt caagattatt gccttttcat      8580
tgatgaaatt gaccaagtaa ttccacacat ccttaacagt gaaactgaag taagtaagta      8640
tagatgcacc atcattgaca cttttttctga actggtgaga aatgctgaac aggtcattat      8700
tgctgatgct gatttatccg atgtgacgat tgacctaata gaaaacatca gaggtaaaaa      8760
actatatgta atcaagaatg aatatcagta tcagggaatg acttttaacg ccgttggttc      8820
```

```
accattagaa atgatggcaa tgatgggaaa atcggtgtca gaaggcaaga aattatttat   8880
taacaccaca tcccaaaagg caaaaagtaa gtacggcaca atcgctcttg agtcttatat   8940
ttttggtcta aataaagaag caaagatatt aagaatagac tctgaaacca ctaaaaaccc   9000
tgaacatcca gcctataaaa tcattgacca agacttaaat aatatcctca aagattatga   9060
ttatgtcatt gcctcacctt gccttcaaac aggtgtcagt attaccttaa aagggcattt   9120
tgaccagcaa tttaactttt ccagtggaaa cattacacct cattgctttt tacagcaaat   9180
gtggcggttg agggatgcag aaattgaaag attctattat gtgccgaact catctaacct   9240
caatctcatt gggaataagt caagttcacc atcagacctt ctaaagagca ataacaagat   9300
ggcaacggca acggttaacc ttttgggtag aatcgactcc gaatattccc tagagtatga   9360
atcgcacggc atttggcttg agacgtgggc aaaattatca gcacggcata acagttcaat   9420
gcgttgttac tctgaaattc ttacctatct aattacgtct caagggcata aattaaatat   9480
caacattccc tcacctcttg cagatattaa gaagctaaat gatgaggtaa gtagtaacag   9540
ggaaaaggta aaaatgaga gatactctca gaggttaaac tcaccagata ttaacgatgc   9600
agaagctacc atactcgaat ctaaagagca aaaaatcgga ttgactctca atgagagatg   9660
caccctagaa aagcataaag ttaagaagcg gtatgggaat gtaaagatgg atattctcac   9720
ctttgatgat gatggactat accccaaact cagactattt tattacctca ccatcggtaa   9780
acctcatctc aaggctaatg acagaaaagc tattgccaaa atgggcaatg acaataaagg   9840
caagattcta tcaaaagact tagttaataa aacttactcc gctcgtgtga aggtcttaga   9900
gattcttaaa ctaactgact ttatcgacaa tcttagagat gaactcttaa taactcccaa   9960
taatccagct atcaccgatt ttaataatct tctgctaaga gctaagaagg atttaagagt  10020
attaggagtc aacatcggaa aatatccaat ggccaacatt aatgccgtac ttactctcat  10080
tggtcacaaa ctttctgtaa tgagagatga gttcggaaaa gagaaaagga taaaagtaga  10140
tggtaaatca taccgatgtt atcaacttga acattacca gattttacca atgatactct  10200
tgactactgg ttagaaaatg atagccaaaa agaagtaaca gcaacagaaa attactccga  10260
aaattttaac ccttcaaata gctacaatcc agacagtaag acactttcag agggtgcaaa  10320
tttcctatat ataaataaag aagaattgca tccaaataaa ttgcacctag aaataaaaga  10380
aggtgctgaa cttttttttat tcggggtaaa ggtgattgtg aaaggaatct ggacggggc  10440 agtaactata ttctctatgg gtcaagaata cgatttatcc ctcaatgaac tagaggggat  10500
gttaacatca tgaactttac aagaatcttt ttaagggcg atcgcaccat gttaaatgat  10560
ggtacatttg ttcagatatt tgatatttac catgaccacg cattgggagt gacccttgac  10620
cttaagacag aaaaaattat ttccgatgat gttagggtaa ttactgtcaa agacttattg  10680
ttcgatggca cttataaagg ggtaaaatct tttatgcccg ataatgcccg ataatgcccg  10740
attgatgcta caaaatccca taatcataag cgataatccc ctaatagctt gtaattcttg  10800
aaccgtagcg attttagagt attccaaaaa gaagaaataa acaccgcaaa atgtcgtatt  10860
tcacatatat aaaccaaggt ttttttgccct aaaatcttta tgtttgtagt gtgatgttgg  10920
gtcaaaatgg tcagaaaagt tgcaaggttt ttatggatgc ttacgcgcgc gaggggtaag  10980
catccccaaa tagttacttt atcctagtcc atgcccattt attgccgtcc cgttcggctt  11040 taaaaagtg ccaaaactca caaggtgcaa taaaaagttc tgtacctttc gcaaccctag  11100
ataatctttc aacagttact ttttttccta ttatctcggt acaaagtttg gctagtttct  11160
```

```
cttttccctc tttttcaatc aagccttctt gtatgcccaa ctcattgatt aatctctcta   11220
tttttaccat tatttcccgt tcaggtagtt tatcccctaa atcttcatcg ggggcaatg    11280 tagggcattc tgaaggggct ttttcttctg tctggacatt atctaatatt gaagtaacca   11340
aactatcttc agttttttct attcctatta attcatattc ggttactgta tccgtatcaa   11400
tatccgaata actatcttta tccgtattag ctattcggtt aagtttatcc gttaactcag   11460
aaacaagact atatagcggt tttagctttt cttctatcct gttatctaat acggataagt   11520
ttatacggtt atcattatcc gtattagtat cattgggctt ttttggtagt tctacccct   11580 cataaaccgc ttttattccc aattccaaca gactgataac agtatccttt ataatgggtt   11640
ttttgctgat atggtgaact tttgccccctt ccatcattgc gatactttct atctcactca  11700
tcaacttatc gcttaagtga atctcgtatc tgtttaatcc cttactggtt ttattcatat   11760
ccgtttactt tattcggtta acaattctat tttatacgaa taaatatta tacggttaac    11820 tttatacgtt taactatttt atctatacgg ataacagtaa taagttattc gtattagtta   11880
tacgtttact tttatccaaa taaaattagt gcatttaaac taaaagaatg attttatcgg   11940
agttgatagc attggattaa cctaaagatg tttataagct atatctgata agtatttaag   12000
gttattttgt tattctgttt attgacatta tcagaataaa agaatagaat ataattgttg   12060
agagataaga ggtttaagtg attatggtta agaagttagt tggttatgtc agggtcagta   12120
gtgaatcgca agaggataac actagcttac agaatcagat agagagaatt gaagcatatt   12180
gtatggcttt tggttatgag ttggtaaaaa tattcaaaga ggttgccact ggtacaaaag   12240
cagatattga aacccgtcct atttttaatg aagctataga atacttgaaa caggataatg   12300
ctaatggaat tattgccttg aagctagacc gaatcgcacg gaatgcttta gatgtattgc   12360
gtttggttcg tgaaaccttta gaaccacaaa ataaaatgtt agtgttacta gatattcagg   12420
tagatacttc gacaccttca ggaaaaatga ttttaactgt aatgagtgcc gttgctgaac   12480
tcgaaagaga catgatctat gatcgcactc aggggggtag aaagactaaa gcccaaaagg   12540
gcgggtatgc ctacgggaaa cctaaatttg gctataagac tgaagaaaag gaactaaaag   12600
aagattcagc acaacaggaa actattaaac taattaagag acaccgtagg tcagggaaaa   12660
gctaccagaa aatagctgat tatctcaatg cccaaagtat tcccactaaa caaggtaaga   12720
aatggagttc tagcgtcgtc tatcgaatct gtcaggaaaa agctggttaa gtctgtttat   12780
agatatttag aatttattga ataaaaatag tatgaacaat aaatatttat ggactaacca   12840
cgctcggaaa cgtttaactg aacgatggga aataaaagaa tcatgggtta ttgataccat   12900
cgaaaatcct gaacgttcag aatttattgt tgatgagtca ggggaaaaat atcattacta   12960
taaaagaata gctaagttta agaatagagt gttagaagtg ataacttctg ccaactcaac   13020
acccacaaga ataataacct tttactttaa ccgtaacatg aggaaaaatt tatgattgtt   13080
acttacgata atgaagttga cgcaatttat tttaagttaa cggaaaataa aattgatagc   13140
accgaacctc aaacagacag gattatcatt gattacgatg aaagtaataa tattgttggc   13200
attgaggtat tagattttaa ttatcttgtc aagaaaggtt taaccgttgc tgatttacct   13260
ttttctgaag atgaaagatt aacagcttct caatatttta attttcctgt tgctatctaa   13320
tccagaaggg gcaataatcc ccttctttca tcgagttaga cttaatatca caaaagtcat   13380
tttcatttta ccgtttcttt tccacagcgt ccgtacgccc ctcgttaaat ctcaaaaccg   13440
acaatttatg atgtttataa aaagttactc actttaataa gtatttatac tcattaaagg   13500
gttattcttt ttttgtagcc tgataggttg ggaaggaata tttcagatta tcagatttgt   13560
```

<210> SEQ ID NO 14
<211> LENGTH: 13119
<212> TYPE: DNA
<213> ORGANISM: Artificial Sequence
<220> FEATURE:
<223> OTHER INFORMATION: #1495¶ABICyano1-6.8::PnirAABICyano1-zmPDCABICyano1(opt3)-PrpsLABICyano1-ADHABICyani1(opt3)_ter-PrbcABICyano1-Km**

<400> SEQUENCE: 14

```
tcgacaatta taacttctt cctgtacggg cgaatggcca tttgctccta actaactccg      60
tactgctttg cggaacgagc gtagcgaact ctccgaatta ctaagccttc atccctgata    120
gatgcaaaaa acgaattaaa attatgtgta aaagaaaat gtgtctttat ttagtagtca     180
aagttacaaa atattaagaa tcaaattaat aatgtattgg gcagttaagt atataagtct    240
ttaaatattt atttgtattc aatatattaa ccgaggacaa attatgaatt cttacactgt    300
tggaacctat ttagcagaac gtttagttca aattggtctc aaacaccatt ttgcagtagc    360
tggtgattat aatttagttt tattggataa cttattgtta aataagaata tggaacaagt    420
gtattgttgt aatgaattaa actgtggttt ttctgctgag ggatatgctc gtgcaaaagg    480
tgctgccgca gcagttgtta cttattctgt tggagcatta agtgcttttg acgctattgg    540
aggtgcttat gcagaaaatt tacctgtaat cttaatctct ggtgcaccca ataacaacga    600
tcacgctgct ggtcatgtat tgcatcatgc tttaggtaaa accgattatc attaccaatt    660
agaaatggca aaaatatta ccgctgccgc agaagctatt tatactcccg aagaagcacc     720
tgctaagatc gatcacgtaa ttaaaaccgc tctccgtgag aaaaaacccg tatatttaga    780
aatcgcttgc aatatcgctt ctatgccttg tgcagctcct ggacctgcta gtgctttatt    840
taacgatgaa gcatctgatg aggctagttt aaatgccgct gttgaagaaa ctttgaaatt    900
tattgctaat cgtgataaag tagctgtttt agttggttct aaaactccgtg ccgctggtgc    960
agaagaagcg gctgtaaaat cgcagatgc cttaggaggt gctgttgcca caatggcagc   1020
cgctaaaagt ttttccccg aagaaaatcc tcattacatt ggtacttctt ggggtgaggt   1080
atcttaccct ggtgtagaaa aaccatgaa ggaagctgat gcagtaattg cattagctcc    1140
tgttttcaat gattactcta ccactggttg gactgatatt ccagacccca aaaaattagt    1200
tttagcagaa cctcgctctg tagttgtgaa tggtgttaga tttcccagtg tacatctcaa    1260
agattattta actcgtttag ctcaaaaagt gagtaaaaag actggcgcac tgatttctt    1320
taaatcttta aatgctggtg aattaaagaa agcagctcct gctgatccca gtgctccttt    1380
agtgaatgcc gaaatcgcaa gacaagttga agccttgtta actcctaaca ctaccgttat    1440
tgccgagact ggtgatagtt ggttcaatgc tcaacgcatg aaattaccca atggtgctcg    1500
tgttgagtat gaaatgcaat ggggtcacat tggatggtct gttcctgctg catttggata    1560
tgcagttgga gcacctgagc gtagaaacat tttaatggta ggtgatggtt cttttccaact   1620
cactgctcaa gaagttgcac aaatggtacg tttaaaattg cctgttatta tctttctcat    1680
taacaactat ggttacacca ttgaagttat gattcatgat ggtccttata ataacattaa    1740
gaattgggat tacgcaggtt taatggaggt atttaacggt aatggtggat cgacagtgg    1800
agcaggtaaa ggattaaaag ctaaacagg aggtgagtta gctgaagcaa ttaaagtagc    1860
tttagccaat acagatggtc ctaccttaat cgaatgtttc attggacgtg aagattgtac    1920
```

```
tgaagagtta gttaaatggg gaaagcgtgt tgccgctgca aattctcgta aacctgtaaa    1980
caaactcttg tagttaggat ccgagctcct ccgcttaaaa aatttcattt ttcgatcaaa    2040
aaagacaaat tattactaat tagctcatgg caataaataa tcagtagtaa tctgttttca    2100
cattttattg ttaattttta ttattgctaa tatcaacctt ttctacttct gcttaatatt    2160
ttatttatgc tcaatgggaa aatctgaaat aagattgaga acagtgttac caatagaagt    2220
atttaaggtt taaagcatac cttaaagata acatttttttt ttgaaaagag tcaaattatt    2280
tttgaaaggc tgatattttt gatatttact aatatttttat ttatttcttt ttcccttaaa    2340
ataagagcta aatctgtttt tattatcatt tatcaagctc tattaatacc tcaacttttt    2400
caagaaaaaa taataataat ttttccctct attctcatga ccttttagga aaattaattt    2460
tagaaaaact attgacaaac ccataaaaaa tgagataaga ttatagattg tcactggtat    2520
tttatactag aggcaaatta tatttatata tacaaaaatg ctgtataaaa aacatctcat    2580
atgattaagg cttatgctgc attagaagct aatggtaaat tacaaccttt tgaatacgat    2640
cccggtgctt taggtgcaaa tgaagtagaa attgaggttc agtattgtgg tgtatgtcat    2700
tctgatttat ctatgattaa caacgaatgg ggaatttcca attatcccctt agttcctgga    2760 cacgaagttg ttggtactgt agcagctatg ggagaaggag ttaatcatgt tgaagtaggt    2820
gacttagtag gtttgggatg gcattctggt tactgtatga cctgtcatag ttgttatctct    2880 ggttatcaca acttatgtgc aactgctgaa agtaccattg ttggtcatta cggtggttt    2940 ggtgatagag taagagctaa aggagttagt gttgttaaat taccaaaagg tatcgactta    3000
gcaagtgcag gtcctctctt ttgtgggggt attactgttt ttagtcctat ggttgaatta    3060
agtttaaagc caactgcaaa agtagccgtc attggtattg gaggattggg acacttagct    3120
gttcaatttc tccgtgcatg gggatgtgaa gttactgcct ttacttctag tgctcgtaaa    3180
caaaccgagg tattagaatt aggagcacac catatcttag attccaccaa ccctgaagct    3240
atcgctagtg cagagggaaa aattcgattat attattagta ctgttaattt gaaattagat    3300
tggaacctct acatctctac tttagctccc caaggtcatt ttcactttgt tggagttgta    3360
ttagaacccc tcgatttaaa cttattccct ttattaatgg acaacgttc tgttagtgca    3420 tctcctgttg gatctcccgc tactattgct accatgttag atttttgcagt acgtcacgat    3480 attaaacctg tagtagaaca attctctttc gatcaaatca acgaagctat tgctcattta    3540
gaaagtggta aggctcatta ccgtgttgtt ttatctcact ctaaaaacta actagatctc    3600
tgcagagaat ataaaaagcc agattattaa tccggctttt ttattattta aatactgtgc    3660
acgatcctgc aggatcatct tgctgaaaaa ctcgagcgct cgttccgcaa agcggtacgg    3720
agttagttag gggctaatgg gcattctccc gtacaggaaa gagttagaag ttattaatta    3780
tcaacaattc tcctttgcct agtgcatcgt tacctttta attaaaacat aaggaaaact    3840
aataatcgta ataatttaac ctcaaagtgt aaagaaatgt gaaattctga cttttataac    3900
gttaaagagg gaaaaattag cagtttaaaa tacctagaga atagtctggg gtaagcatag    3960
agaattagat tagttaagtt aatcaaattc agaaaaaata ataatcgtaa atagttaatc    4020
tgggtgtata gaaaatgatc cccttcatga taagatttaa actcgaaaag caaaagccaa    4080
aaaactaact tccattaaaa gaagttgtta catataacgc tataaagaaa atttatatat    4140
ttggaggata ccaaccatgt ctcatattca acgtgaaact agttgttctc gccctcgttt    4200
aaattctaat atggatgccg atttatatgg ttataaatgg gctcgtgata atgttggtca    4260
atctggtgct actatttatc gtttatatgg taaacctgat gctcctgaat tattcttgaa    4320
```

```
acatggtaaa ggttctgttg ctaatgatgt tactgatgaa atggttcgtt taaactggtt    4380
gactgaattt atgcctttac ctactattaa acatttatt cgtactcccg atgatgcttg    4440
gttattaact actgctattc ctggtaaaac tgcttttcaa gttttagaag aatatcctga    4500
ttctggtgaa aatattgttg atgctttagc tgttttttta cgtcgtttac attctattcc    4560
cgtttgtaat tgtcctttta attctgatcg tgttttcgt ttagctcaag ctcaatctcg    4620
tatgaataat ggtttagttg atgcttctga ttttgatgat gaacgtaatg gttggcctgt    4680
tgaacaagtt tggaaagaaa tgcacaaatt gttacctttt tctcctgatt ctgttgttac    4740
tcatggtgat ttttctttag ataatttgat ctttgatgaa ggtaaattga ttggttgtat    4800
tgatgttggt cgtgttggta ttgctgatcg ttatcaagat ttagctattt tatggaattg    4860
tttaggtgaa ttttctcctt ctttacagaa acgtttattt cagaaatatg gtattgataa    4920
tcctgatatg aacaagttac aatttcattt aatgttggac gagttctttt aagaattaat    4980
tcatgaccaa aatcccttaa cgtgagtttt cgttccactg agcgtcagac cccgtagaaa    5040
agatcaaagg atcttcttga tccttttttt ttctgcgcgt aatctgctgc tatttaaatt    5100
acgtacacgt gttattactt tgttaacgac aattgtctta attactggg cctcatgggc    5160 cttccgctca ctgcccgctt tccagtcggg aaacctgtcg tgccagctct gcagatgacg    5220
gtgaaaacct ctgacacatg cagctcccgg agacggtcac agcttgtctg taagcggatg    5280
ccgggagcag acaagcccgt cagggcgcgt cagcgggtgt tggcgggtgt cggggcgcag    5340
ccatgaccca gtcacgtagc gatagcggag tgtatactgg cttaactatg cggcatcaga    5400
gcagattgta ctgagagtgc accatatgcg gtgtgaaata ccgcacagat gcgtaaggag    5460
aaaataccgc atcaggcgct cttccgcttc ctcgctcact gactcgctgc gctcggtcgt    5520
tcggctgcgg cgagcggtat cagctcactc aaaggcggta atacggttat ccacagaatc    5580
aggggataac gcaggaaaga acatgtgagc aaaaggccag caaaaggcca ggaaccgtaa    5640
aaaggccgcg ttgctggcgt ttttccatag gctccgcccc cctgacgagc atcacaaaaa    5700
tcgacgctca agtcagaggt ggcgaaaccc gacaggacta taaagatacc aggcgtttcc    5760
ccctggaagc tccctcgtgc gctctcctgt tccgaccctg ccgcttaccg gatacctgtc    5820
cgcctttctc ccttcgggaa gcgtggcgct ttctcatagc tcacgctgta ggtatctcag    5880
ttcggtgtag gtcgttcgct ccaagctggg ctgtgtgcac gaaccccccg ttcagcccga    5940
ccgctgcgcc ttatccggta actatcgtct tgagtccaac ccggtaagac acgacttatc    6000
gccactggca gcagccactg gtaacaggat tagcagagcg aggtatgtag gcggtgctac    6060
agagttcttg aagtggtggc ctaactacgg ctacactaga aggacagtat ttggtatctg    6120
cgctctgctg aagccagtta ccttcggaaa aagagttggt agctcttgat ccggcaaaca    6180
aaccaccgct ggtagcggtg gtttttttgt ttgcaagcag cagattacgc gcagaaaaaa    6240
aggatctcaa gaagatcctt tgatctttc tactgcagaa gcttgttaga cccctgtca    6300 tgtattttat attatttatt tcaccatacg gattaagtga aacctaatga aaatagtact    6360
ttcggagctt taactttaat gaaggtatgt ttttttatag acatcgatgt ctggtttaac    6420
aataggaaaa agtagctaaa actcccatga attaaagaaa taacaaggtg tctaacaacc    6480
tgttattaag aatgttagaa aagacttaac atttgtgttg agttttata gacattggtg    6540 tctagacata cggtagataa ggtttgctca aaaataaaat aaaaaagat tggactaaaa    6600 aacatttaat ttagtacaat ttaattagtt atttttttcgt ctcaaatttt gctttgttga    6660
```

```
gcagaaattt agataaaaaa atccccgtga tcagattaca atgtcgttca ttgtacgatg    6720
tgtcgaaaaa tctttacgac actctaaact gaccacacgg gggaaaaaga aaactgaact    6780
aataacatca tgatactcgg aaaacctagc aattctcaac ccctaaacaa agaaacttc     6840 caaaaccctg accatataaa ggagtggcaa caatcagcaa tcagtcaaga tttgatagca    6900
gaaaatcttg tatcggttgc taatggtttt gatgtactat ttatcggcaa taaataccga    6960
actaacacgg gtgttctgtc acggcacata ttaaactcct attctcattt agaagatggt    7020
ggttcgtatg gtagaacatt tgacccattt accaataaag aaatgcagtg ggttcaattt    7080
aaaccgaata gaccaagaaa aggttctact ggtaaggtaa tcaaatatga atcgccaaaa    7140
ggtgaaccta caagagttct aatgccgttt gtgcctatga aaatatggca acggattagc    7200
gataagttcg gagtaccgat taatccgaaa aaagatactc acttttggga atgggtaaag    7260
aataatccat cgataccgat tgccattaca gaaggaaata aaaaagctaa ttgcctatta    7320
tcctatggct atcctgctat tgcctttgta ggcatttgga acggattaga gaaaataaat    7380
gatttctcga aggaaaagca gttaaaagag gatttgaaat ggttgttatc caacggcaac    7440
cgaaatatta atatcatctt tgaccaagac cagaaacaaa aaactgtaat taatgtaaac    7500
aaagctattt tcgctttatc ttctctaata agtagaaatg gtcataaagt taatattgtg    7560
caatggttgc cgtcaaaagg taaggaata gatgattatt tggtagcttt acctttgag    7620 aaaagagaaa atcatttaga caacttaatt aaaattgcac catcatttaa tttttggtca    7680
actaaatact tattcaagtg tcgtaaacca gatttaaccg taaattgccg ttatttgagc    7740
gatgcagtaa aagaattacc tcaagaggat atagcattaa tagcacctca cggcacgggt    7800
aaaacttcat tagtagctac tcacgttaag aatcggagtt atcacggaag gaaaactatt    7860
tcattggtgc atcttgaaag tttagccaaa gctaatggca acgcacttgg attatattac    7920
cgaaccgaaa ataatattga aaagcaatat cttggattta gcttatgtgt agatagttgc    7980
cgtgataaga ttaacggcat tacaactgat attatttcag gtcaagatta ttgccttttc    8040
attgatgaaa ttgaccaagt aattccacac atccttaaca gtgaaactga agtaagtaag    8100
tatagatgca ccatcattga cactttttct gaactggtga gaaatgctga acaggtcatt    8160
attgctgatg ctgatttatc cgatgtgacg attgacctaa tagaaaacat cagaggtaaa    8220
aaactatatg taatcaagaa tgaatatcag tatcagggaa tgactttaa cgccgttggt    8280 tcaccattag aaatgatggc aatgatggga aaatcggtgt cagaaggcaa gaaattattt    8340
attaacacca catcccaaaa ggcaaaaagt aagtacggca caatcgctct tgagtcttat    8400 attttggtc taaataaaga agcaaagata ttaagaatag actctgaaac cactaaaaac    8460
cctgaacatc cagcctataa aatcattgac caagacttaa ataatatcct caaagattat    8520
gattatgtca ttgcctcacc ttgccttcaa acaggtgtca gtattacctt aaaagggcat    8580
tttgaccagc aatttaactt ttccagtgga acattacac ctcattgctt tttacagcaa    8640
atgtggcggt tgagggatgc agaaattgaa agattctatt atgtgccgaa tcatctcaac    8700
ctcaatctca ttgggaataa gtcaagttca ccatcagacc ttctaaagag caataacaag    8760
atggcaacgg caacgttaa ccttttgggt agaatcgact ccgaatattc cctagagtat    8820
gaatcgcacg gcatttggct tgagacgtgg gcaaaattat cagcacggca taacagttca    8880
atgcgttgtt actctgaaat tcttaccat ctaattacgt ctcaagggca taaattaat     8940 atcaacattc cctcacctct tgcagatatt aagaagctaa atgatgaggt aagtagtaac    9000
agggaaaagg taaaaaatga gagatactct cagaggttaa actcaccaga tattaacgat    9060
```

```
gcagaagcta ccatactcga atctaaagag caaaaaatcg gattgactct caatgagaga   9120
tgcaccctag aaaagcataa agttaagaag cggtatggga atgtaaagat ggatattctc   9180
acctttgatg atgatggact atacccaaa ctcagactat tttattacct caccatcggt    9240
aaacctcatc tcaaggctaa tgacagaaaa gctattgcca aaatgggcaa tgacaataaa   9300
ggcaagattc tatcaaaaga cttagttaat aaaacttact ccgctcgtgt gaaggtctta   9360
gagattctta aactaactga ctttatcgac aatcttagag atgaactctt aataactccc   9420
aataatccag ctatcaccga ttttaataat cttctgctaa gagctaagaa ggatttaaga   9480
gtattaggag tcaacatcgg aaaatatcca atggccaaca ttaatgccgt acttactctc   9540
attggtcaca aactttctgt aatgagagat gagttcggaa aagagaaaag gataaaagta   9600
gatggtaaat cataccgatg ttatcaactt gaaacattac cagattttac caatgatact   9660
cttgactact ggttagaaaa tgatagccaa aaagaagtaa cagcaacaga aaattactcc   9720
gaaaatttta acccttcaaa tagctacaat ccagacagta agacactttc agagggtgca   9780
aatttcctat atataaataa agaagaattg catccaaata aattgcacct agaaataaaa   9840
gaaggtgctg aactttttttt attcggggta aaggtgattg tgaaaggaat cttggacggg   9900
gcagtaacta tattctctat gggtcaagaa tacgatttat ccctcaatga actagagggg   9960
atgttaacat catgaacttt acaagaatct ttttaaaggg cgatcgcacc atgttaaatg  10020
atggtacatt tgttcagata tttgatattt accatgacca cgcattggga gtgacccttg  10080
accttaagac agaaaaaatt atttccgatg atgttagggt aattactgtc aaagacttat  10140
tgttcgatgg cacttataaa ggggtaaaat ctttatgcc cgataatgcc cgataatgcc   10200
cgattgatgc tacaaaatcc cataatcata agcgataatc ccctaatagc ttgtaattct   10260
tgaaccgtag cgatttttaga gtattccaaa aagaagaaat aaacaccgca aaatgtcgta  10320
tttcacatat ataaaccaag gttttttgcc ctaaaatctt tatgtttgta gtgtgatgtt   10380
gggtcaaaat ggtcagaaaa gttgcaaggt ttttatggat gcttacgcgc gcgagggta   10440 agcatcccca aatagttact ttatcctagt ccatgcccat ttattgccgt cccgttcggc   10500
tttaaaaaag tgccaaaact cacaaggtgc aataaaaagt tctgtacctt tcgcaaccct   10560
agataatctt tcaacagtta cttttttttcc tattatctcg gtacaaagtt tggctagttt   10620
ctcttttccc tctttttcaa tcaagccttc ttgtatgccc aactcattga ttaatctctc   10680
tatttttacc attatttccc gttcaggtag tttatcccct aaatcttcat cgggggggcaa  10740 tgtagggcat tctgaagggg cttttttcttc tgtctggaca ttatctaata ttgaagtaac   10800
caaactatct tcagttttttt ctattcctat taattcatat tcggttactg tatccgtatc   10860
aatatccgaa taactatctt tatccgtatt agctattcgg ttaagtttat ccgttaactc   10920
agaaacaaga ctatatagcg gttttagctt ttcttctatc ctgttatcta atacggataa   10980
gtttatacgg ttatcattat ccgtattagt atcattgggc tttttttggta gttctacccc  11040 ctcataaacc gcttttattc ccaattccaa cagactgata acagtatcct ttataatggg   11100
ttttttgctg atatggtgaa cttttgcccc ttccatcatt gcgatacttt ctatctcact   11160
catcaactta tcgcttaagt gaatctcgta tctgtttaat cccttactgg ttttattcat   11220
atccgtttac tttattcggt taacaattct attttatacg aataaaatat tatacggtta   11280
actttatacg tttaactatt ttatctatac ggataacagt aataagttat tcgtattagt   11340 tatacgtttta cttttatcca aataaaatta gtgcatttaa actaaaagaa tgattttatc   11400
```

```
ggagttgata gcattggatt aacctaaaga tgtttataag ctatatctga taagtattta    11460
aggttatttt gttattctgt ttattgacat tatcagaata aaagaataga atataattgt    11520
tgagagataa gaggtttaag tgattatggt taagaagtta gttggttatg tcagggtcag    11580
tagtgaatcg caagaggata acactagctt acagaatcag atagagaaa ttgaagcata     11640 ttgtatggct tttggttatg agttggtaaa aatattcaaa gaggttgcca ctggtacaaa    11700
agcagatatt gaaacccgtc ctatttttaa tgaagctata gaatacttga acaggataa     11760 tgctaatgga attattgcct tgaagctaga ccgaatcgca cggaatgctt tagatgtatt    11820
gcgtttggtt cgtgaaacct tagaaccaca aaataaaatg ttagtgttac tagatattca    11880
ggtagatact tcgacacctt caggaaaaat gattttaact gtaatgagtg ccgttgctga    11940
actcgaaaga gacatgatct atgatcgcac tcagggggt agaaagacta aagcccaaaa     12000
gggcgggtat gcctacggga aacctaaatt tggctataag actgaagaaa aggaactaaa    12060
agaagattca gcacaacagg aaactattaa actaattaag agacaccgta ggtcagggaa    12120
aagctaccag aaaatagctg attatctcaa tgcccaaagt attcccacta acaaggtaa     12180 gaaatggagt tctagcgtcg tctatcgaat ctgtcaggaa aaagctggtt aagtctgttt    12240
atagatattt agaatttatt gaataaaaat agtatgaaca ataaatattt atggactaac    12300
cacgctcgga aacgtttaac tgaacgatgg gaaataaaag aatcatgggt tattgatacc    12360
atcgaaaatc ctgaacgttc agaatttatt gttgatgagt caggggaaaa atatcattac    12420 tataaagaa tagctaagtt taagaataga gtgttagaag tgataacttc tgccaactca     12480
acacccacaa gaataataac cttttacttt aaccgtaaca tgaggaaaaa tttatgattg    12540
ttacttacga taatgaagtt gacgcaattt attttaagtt aacggaaaat aaaattgata    12600
gcaccgaacc tcaaacagac aggattatca ttgattacga tgaaagtaat aatattgttg    12660
gcattgaggt attagatttt aattatcttg tcaagaaagg tttaaccgtt gctgatttac    12720 cttttctga agatgaaaga ttaacagctt ctcaatattt taattttcct gttgctatct     12780
aatccagaag gggcaataat ccccttcttt catcgagtta gacttaatat cacaaaagtc    12840
atttcatttt taccgtttct tttccacagc gtccgtacgc ccctcgttaa atctcaaaac    12900
cgacaattta tgatgtttat aaaaagttac tcactttaat aagtatttat actcattaaa    12960
gggttattct tttttttgtag cctgataggt tgggaaggaa tatttcagat tatcagatttt   13020 gttgaatatt tttcgtcaga tacgcaaacc ttacaaacat aattaacaac tgaaactatt    13080
gatatgtcta ggttttagct ctatcacagg ttggatctg                           13119
```

<210> SEQ ID NO 15
<211> LENGTH: 12648
<212> TYPE: DNA
<213> ORGANISM: Artificial Sequence
<220> FEATURE:
<223> OTHER INFORMATION: #1578¶ABICyano1-6.8::PnirAABICyano1-
      zmPDCABICyano1(opt3)-dsrA-Prbc*(optRBS)-synADHøop-PrbcABICyano1-
      Km**

<400> SEQUENCE: 15

```
cagcaagttt catcccgacc ccctcagggt cggattttt ttattgtact agttgacata       60
agtaaaggca tccctgcgt gatataatta ccttcagttt aaggaggtat acacatatga      120
ttaaagccta cgctgccctg gaagccaacg gaaaactcca acccttgaa tacgaccccg     180 gtgccctggg tgctaatgag gtggagattg aggtgcagta ttgtggggtg tgccacagtg    240
atttgtccat gattaataac gaatggggca tttccaatta ccccctagtg ccgggtcatg    300
```

```
aggtggtggg tactgtggcc gccatgggcg aagggg tgaa ccatgttgag gtggggatt      360
tagtggggct gggttggcat tcgggctact gcatgacctg ccatagttgt ttatctggct      420
accacaacct ttgtgccacg gcggaatcga ccattgtggg ccactacggt ggctttggcg      480
atcgggttcg ggccaaggga gtcagcgtgg tgaaattacc taaaggcatt gacctagcca      540
gtgccgggcc ccttttctgt ggaggaatta ccgttttcag tcctatggtg gaactgagtt      600
taaagcccac tgcaaaagtg gcagtgatcg gcattggggg cttgggccat ttagcggtgc      660
aatttctccg ggcctggggc tgtgaagtga ctgcctttac ctccagtgcc aggaagcaaa      720
cggaagtgtt ggaattgggc gctcaccaca tactagattc caccaatcca gaggcgatcg      780
ccagtgcgga aggcaaattt gactatatta tctccactgt gaacctgaag cttgactgga      840
acttatacat cagcacccctg cgcgccccagg gacatttcca ctttgttggg gtggtgttgg      900
agcctttgga tctaaatctt tttccccttt tgatgggaca acgctccgtt tctgcctccc      960
cagtgggtag tcccgccacc attgccacca tgttggactt tgctgtgcgc catgacatta     1020
aacccgtggt ggaacaattt agctttgatc agatcaacga ggcgatcgcc catctagaaa     1080
gcggcaaagc ccattatcgg gtagtgctca gccatagtaa aaattagctc tgcaaaggtt     1140
gcttctgggt ccgtggaacg ctcggttgcc gccgggcgtt ttttattcct gcaggatcat     1200
cttgctgaaa aactcgagcg ctcgttccgc aaagcggtac ggagttagtt aggggctaat     1260
gggcattctc ccgtacagga aagagttaga agttattaat tatcaacaat tctcctttgc     1320
ctagtgcatc gttaccttt taattaaaac ataaggaaaa ctaataatcg taataattta     1380
acctcaaagt gtaaagaaat gtgaaattct gactttata acgttaaaga gggaaaaatt     1440
agcagtttaa ataccctaga gaatagtctg gggtaagcat agagaattag attagttaag     1500
ttaatcaaat tcagaaaaaa taataatcgt aaatagttaa tctgggtgta tagaaaatga     1560
tccccttcat gataagattt aaactcgaaa agcaaaagcc aaaaaactaa cttccattaa     1620
aagaagttgt tacatataac gctataaaga aaatttatat atttggagga taccaaccat     1680
gtctcatatt caacgtgaaa ctagttgttc tcgccctcgt ttaaattcta atatggatgc     1740
cgatttatat ggttataaat gggctcgtga taatgttggt caatctggtg ctactattta     1800
tcgtttatat ggtaaacctg atgctcctga attattcttg aaacatggta aaggttctgt     1860
tgctaatgat gttactgatg aaatggttcg tttaaactgg ttgactgaat ttatgccttt     1920
acctactatt aaacatttta ttcgtactcc cgatgatgct tggttattaa ctactgctat     1980
tcctggtaaa actgcttttc aagttttaga agaaatatcct gattctggtg aaaatatggt     2040
tgatgcttta gctgtttttt tacgtcgttt acattctatt cccgtttgta attgtccttt     2100
taattctgat cgtgtttttc gtttagctca agctcaatct cgtatgaata atggtttagt     2160
tgatgcttct gattttgatg atgaacgtaa tggttggcct gttgaacaag tttggaaaga     2220
aatgcacaaa ttgttacctt tttctcctga ttctgttgtt actcatgtg attttttcttt     2280
agataaattg atctttgatg aaggtaaatt gattggttgt attgatgttg gtcgtgttgg     2340
tattgctgat cgttatcaag atttagctat tttatggaat tgtttaggtg aattttctcc     2400
ttctttacag aaacgttat ttcagaaata tggtattgat aatcctgata tgaacaagtt     2460
acaatttcat ttaatgttgg acgagttctt ttaagaatta attcatgacc aaaatcccctt     2520
aacgtgagtt ttcgttccac tgagcgtcag acccgtaga aaagatcaaa ggatcttctt     2580
gagatccttt ttttctgcgc gtaatctgct gctatttaaa ttacgtacac gtgttattac     2640
```

```
tttgttaacg acaattgtct taattaactg ggcctcatgg gccttccgct cactgcccgc    2700
tttccagtcg ggaaacctgt cgtgccagct ctgcagatga cggtgaaaac ctctgacaca    2760
tgcagctccc ggagacggtc acagcttgtc tgtaagcgga tgccgggagc agacaagccc    2820
gtcagggcgc gtcagcgggt gttggcgggt gtcgggcgc agccatgacc cagtcacgta    2880
gcgatagcgg agtgtatact ggcttaacta tgcggcatca gagcagattg tactgagagt    2940
gcaccatatg cggtgtgaaa taccgcacag atgcgtaagg agaaaatacc gcatcaggcg    3000
ctcttccgct tcctcgctca ctgactcgct gcgctcggtc gttcggctgc ggcgagcggt    3060
atcagctcac tcaaaggcgg taatacggtt atccacagaa tcaggggata acgcaggaaa    3120
gaacatgtga gcaaaaggcc agcaaaaggc caggaaccgt aaaaaggccg cgttgctggc    3180
gttttccat aggctccgcc cccctgacga gcatcacaaa aatcgacgct caagtcagag    3240
gtggcgaaac ccgacaggac tataaagata ccaggcgttt ccccctggaa gctccctcgt    3300
gcgctctcct gttccgaccc tgccgcttac cggatacctg tccgcctttc tcccttcggg    3360
aagcgtggcg ctttctcata gctcacgctg taggtatctc agttcggtgt aggtcgttcg    3420
ctccaagctg ggctgtgtgc acgaaccccc cgttcagccc gaccgctgcg ccttatccgg    3480
taactatcgt cttgagtcca acccggtaag acacgactta tcgccactgg cagcagccac    3540
tggtaacagg attagcagag cgaggtatgt aggcggtgct acagagttct tgaagtggtg    3600
gcctaactac ggctacacta aggacagt atttggtatc tgcgctctgc tgaagccagt    3660
taccttcgga aaaagagttg gtagctcttg atccggcaaa caaaccaccg ctggtagcgg    3720
tggttttttt gtttgcaagc agcagattac gcgcagaaaa aaggatctc aagaagatcc    3780
tttgatcttt tctactgcag aagcttgtta cacccctgt catgtatttt atattattta    3840
tttcaccata cggattaagt gaaacctaat gaaaatagta ctttcggagc tttaacttta    3900
atgaaggtat gttttttat agacatcgat gtctggttta caataggaa aagtagcta    3960
aaactcccat gaattaaaga aataacaagg tgtctaacaa cctgttatta agaatgttag    4020
aaaagactta acatttgtgt tgagtttta tagacattgg tgtctagaca tacggtagat    4080
aaggtttgct caaaaataaa ataaaaaaag attggactaa aaaacattta atttagtaca    4140
atttaattag ttattttttc gtctcaaatt ttgctttgtt gagcagaaat ttagataaaa    4200
aaatccccgt gatcagatta caatgtcgtt cattgtacga tgtgtcgaaa atctttacg    4260
acactctaaa ctgaccacac gggggaaaaa gaaaactgaa ctaataacat catgatactc    4320
ggaaaaccta gcaattctca accccctaaac aaaagaaact tccaaaaccc tgaccatata    4380
aaggagtggc aacaatcagc aatcagtcaa gatttgatag cagaaaatct tgtatcggtt    4440
gctaatggtt ttgatgtact atttatcggc aataaatacc gaactaacac gggtgttctg    4500
tcacggcaca tattaaactc ctattctcat ttagaagatg gtggttcgta tggtagaaca    4560
tttgacccat ttaccaataa agaaatgcag tgggttcaat ttaaaccgaa tagaccaaga    4620
aaaggttcta ctggtaaggt aatcaaatat gaatcgccaa aggtgaacc tacaagagtt    4680
ctaatgccgt ttgtgcctat gaaaatatgg caacggatta gcgataagtt cggagtaccg    4740
attaatccga aaaagatac tcactttggg gaatgggtaa agaataatcc atcgataccg    4800
attgccatta cagaaggaaa taaaaagct aattgcctat tatcctatgg ctatcctgct    4860
attgcctttg taggcatttg gaacggatta gagaaaataa atgatttctc gaaggaaaag    4920
cagttaaaaag aggatttgaa atggttgtta tccaacggca accgaaatat taatatcatc    4980
tttgaccaag accagaaaca aaaaactgta attaatgtaa acaaagctat tttcgcttta    5040
```

```
tcttctctaa taagtagaaa tggtcataaa gttaatattg tgcaatggtt gccgtcaaaa    5100
ggtaaaggaa tagatgatta tttggtagct ttacctttg agaaaagaga aaatcattta     5160
gacaacttaa ttaaaattgc accatcattt aattttggt caactaaata cttattcaag     5220
tgtcgtaaac cagatttaac cgtaaattgc cgttatttga gcgatgcagt aaaagaatta    5280
cctcaagagg atatagcatt aatagcacct cacggcacgg gtaaaacttc attagtagct    5340
actcacgtta agaatcggag ttatcacgga aggaaaacta tttcattggt gcatcttgaa    5400
agtttagcca aagctaatgg caacgcactt ggattatatt accgaaccga aataatatt     5460 gaaaagcaat atcttggatt tagcttatgt gtagatagtt gccgtgataa gattaacggc    5520
attacaactg atattatttc aggtcaagat tattgccttt tcattgatga aattgaccaa    5580
gtaattccac acatccttaa cagtgaaact gaagtaagta agtatagatg caccatcatt    5640 gacactttt ctgaactggt gagaaatgct gaacaggtca ttattgctga tgctgattta     5700
tccgatgtga cgattgacct aatagaaaac atcagaggta aaaaactata tgtaatcaag    5760
aatgaatatc agtatcaggg aatgactttt aacgccgttg gttccaccat agaaatgatg    5820
gcaatgatgg gaaaatcggt gtcagaaggc aagaaattat ttattaacac cacatcccaa    5880
aaggcaaaaa gtaagtacgg cacaatcgct cttgagtctt atatttttgg tctaaataaa    5940
gaagcaaaga tattaagaat agactctgaa accactaaaa accctgaaca tccagcctat    6000
aaaatcattg accaagactt aaataatatc ctcaaagatt atgattatgt cattgcctca    6060
ccttgccttc aaacaggtgt cagtattacc ttaaaagggc attttgacca gcaatttaac    6120
ttttccagtg gaaacattac acctcattgc tttttacagc aaatgtggcg gttgagggat    6180
gcagaaattg aaagattcta ttatgtgccg aactcatcta acctcaatct cattgggaat    6240
aagtcaagtt caccatcaga ccttctaaag agcaataaca agatggcaac ggcaacggtt    6300
aaccttttgg gtagaatcga ctccgaatat tccctagagt atgaatcgca cggcatttgg    6360
cttgagacgt gggcaaaatt atcagcacgg cataacagtt caatgcgttg ttactctgaa    6420
attcttacct atctaattac gtctcaaggg cataaattaa atatcaacat tcccctcacct    6480 cttgcagata ttaagaagct aaatgatgag gtaagtagta acagggaaaa ggtaaaaaat    6540
gagagatact ctcagaggtt aaactcacca gatattaacg atgcagaagc taccatactc    6600
gaatctaaag agcaaaaaat cggattgact ctcaatgaga gatgcaccct agaaaagcat    6660
aaagttaaga agcggtatgg gaatgtaaag atggatattc tcacctttga tgatgatgga    6720 ctataccca aactcagact attttattac ctcaccatcg gtaaacctca tctcaaggct     6780
aatgacagaa aagctattgc caaaatgggc aatgacaata aggcaagat tctatcaaaa     6840 gacttagtta ataaaactta ctccgctcgt gtgaaggtct tagagattct taaactaact    6900
gactttatcg acaatcttag agatgaactc ttaataactc ccaataatcc agctatcacc    6960
gattttaata atcttctgct aagagctaag aaggatttaa gagtattagg agtcaacatc    7020
ggaaaatatc caatggccaa cattaatgcc gtacttactc tcattggtca caaactttct    7080
gtaatgagag atgagttcgg aaaagagaaa aggataaaag tagatggtaa atcataccga    7140
tgttatcaac ttgaaacatt accagatttt accaatgata ctcttgacta ctggttagaa    7200
aatgatagcc aaaaagaagt aacagcaaca gaaaattact ccgaaaattt taacccttca    7260
aatagctaca atccagacag taagacactt tcagagggtg caatttcct atatataat      7320 aaagaagaat tgcatccaaa taattgcac ctagaaataa aagaaggtgc tgaacttttt     7380
```

```
ttattcgggg taaaggtgat tgtgaaagga atcttggacg gggcagtaac tatattctct    7440
atgggtcaag aatacgattt atccctcaat gaactagagg ggatgttaac atcatgaact    7500
ttacaagaat cttttaaag gcgatcgca ccatgttaaa tgatggtaca tttgttcaga      7560
tatttgatat ttaccatgac cacgcattgg gagtgaccct tgaccttaag acagaaaaaa    7620
ttatttccga tgatgttagg gtaattactg tcaaagactt attgttcgat ggcacttata    7680
aaggggtaaa atcttttatg cccgataatg cccgataatg cccgattgat gctacaaaat    7740
cccataatca taagcgataa tcccctaata gcttgtaatt cttgaaccgt agcgatttta    7800
gagtattcca aaaagaagaa ataaacaccg caaaatgtcg tatttcacat atataaacca    7860
aggttttttg ccctaaaatc tttatgtttg tagtgtgatg ttgggtcaaa atggtcagaa    7920
aagttgcaag gttttatgg atgcttacgc gcgcgagggg taagcatccc caaatagtta    7980
ctttatccta gtccatgccc atttattgcc gtcccgttcg gctttaaaaa agtgccaaaa    8040
ctcacaaggt gcaataaaaa gttctgtacc tttcgcaacc ctagataatc tttcaacagt    8100 tactttttt cctattatct cggtacaaag tttggctagt ttctcttttc cctcttttc     8160 aatcaagcct tcttgtatgc ccaactcatt gattaatctc tctattttta ccattatttc    8220
ccgttcaggt agtttatccc ctaaatcttc atcgggggc aatgtagggc attctgaagg     8280 ggcttttct tctgtctgga cattatctaa tattgaagta accaaactat cttcagtttt     8340
ttctattcct attaattcat attcggttac tgtatccgta tcaatatccg aataactatc    8400
tttatccgta ttagctattc ggttaagttt atccgttaac tcagaaacaa gactatatag    8460
cggttttagc ttttcttcta tcctgttatc taatacggat aagttatac ggttatcatt     8520 atccgtatta gtatcattgg gcttttttgg tagttctacc ccctcataaa ccgcttttat    8580
tcccaattcc aacagactga taacagtatc ctttataatg ggttttttgc tgatatggtg    8640
aacttttgcc ccttccatca ttgcgatact ttctatctca ctcatcaact tatcgcttaa    8700
gtgaatctcg tatctgttta atcccttact ggttttattc atatccgttt acttattcg     8760 gttaacaatt ctattttata cgaataaaat attatacggt taactttata cgtttaacta    8820
ttttatctat acggataaca gtaataagtt attcgtatta gttatacgtt tacttttatc    8880
caaataaaat tagtgcattt aaactaaaag aatgatttta tcggagttga tagcattgga    8940
ttaacctaaa gatgtttata agctatatct gataagtatt taaggttatt ttgttattct    9000
gtttattgac attatcagaa taaagaata gaatataatt gttgagagat aagaggttta     9060
agtgattatg gttaagaagt tagttggtta tgtcagggtc agtagtgaat cgcaagagga    9120
taacactagc ttacagaatc agatagagag aattgaagca tattgtatgg cttttggtta    9180
tgagttggta aaaatattca aagaggttgc cactggtaca aaagcagata ttgaaacccg    9240
tcctattttt aatgaagcta tagaatactt gaaacaggat aatgctaatg gaattattgc    9300
cttgaagcta gaccgaatcg cacggaatgc tttagatgta ttgcgtttgg ttcgtgaaac    9360
cttagaacca caaaataaaa tgttagtgtt actagatatt caggtagata cttcgacacc    9420
ttcaggaaaa atgatttaa ctgtaatgag tgccgttgct gaactcgaaa gagacatgat    9480
ctatgatcgc actcaggggg gtagaaagac taaagcccaa aagggcgggt atgcctacgg    9540
gaaacctaaa tttggctata agactgaaga aaaggaacta aaagaagatt cagcacaaca    9600
ggaaactatt aaactaatta agagacaccg taggtcaggg aaaagctacc agaaaatagc    9660
tgattatctc aatgcccaaa gtattcccac taaacaaggt aagaaatgga gttctagcgt    9720
cgtctatcga atctgtcagg aaaaagctgg ttaagtctgt ttatagatat ttagaattta    9780
```

```
ttgaataaaa atagtatgaa caataaatat ttatggacta accacgctcg gaaacgttta    9840
actgaacgat gggaaataaa agaatcatgg gttattgata ccatcgaaaa tcctgaacgt    9900
tcagaattta ttgttgatga gtcagggaaa aaatatcatt actataaaag aatagctaag    9960
tttaagaata gagtgttaga agtgataact tctgccaact caacacccac aagaataata   10020
acctttact ttaaccgtaa catgaggaaa aatttatgat tgttacttac gataatgaag    10080
ttgacgcaat ttatttaag ttaacggaaa ataaaattga tagcaccgaa cctcaaacag    10140
acaggattat cattgattac gatgaaagta ataatattgt tggcattgag gtattagatt   10200
ttaattatct tgtcaagaaa ggtttaaccg ttgctgattt accttttct gaagatgaaa    10260
gattaacagc ttctcaatat tttaattttc ctgttgctat ctaatccaga aggggcaata   10320
atccccttct ttcatcgagt tagacttaat atcacaaaag tcattttcat tttaccgttt   10380
cttttccaca gcgtccgtac gcccctcgtt aaatctcaaa accgacaatt tatgatgttt   10440
ataaaaagtt actcacttta ataagtattt atactcatta aagggttatt cttttttgt    10500
agcctgatag gttgggaagg aatatttcag attatcagat ttgttgaata ttttcgtca    10560
gatacgcaaa ccttacaaac ataattaaca actgaaacta ttgatatgtc taggttttag   10620
ctctatcaca ggttggatct gtcgacaatt aataacttct tcctgtacgg gcgaatggcc   10680
atttgctcct aactaactcc gtactgcttt gcggaacgag cgtagcgaac tctccgaatt   10740
actaagcctt catccctgat agatgcaaaa aacgaattaa aattatgtgt aaaagaaaa    10800
tgtgtcttta tttagtagtc aaagttcaa aatattaaga atcaaattaa taatgtattg    10860
ggcagttaag tatataagtc tttaaatatt tatttgtatt caatatatta accgaggaca   10920
aattatgaat tcttacactg ttggaaccta tttagcagaa cgtttagttc aaattggtct   10980
caaacaccat tttgcagtag ctggtgatta taatttagtt ttattggata acttattgtt   11040
aaataagaat atggaacaag tgtattgttg taatgaatta aactgtggtt tttctgctga   11100
gggatatgct cgtgcaaaag gtgctgccgc agcagttgtt acttattctg ttggagcatt   11160
aagtgctttt gacgctattg gaggtgctta tgcagaaaat ttacctgtaa tcttaatctc   11220
tggtgcaccc aataacaacg atcacgctgc tggtcatgta ttgcatcatg ctttaggtaa   11280
aaccgattat cattaccaat tagaaatggc aaaaaatatt accgctgccg cagaagctat   11340
ttatactccc gaagaagcac ctgctaagat cgatcacgta attaaaaccg ctctccgtga   11400
gaaaaaccc gtatatttag aaatcgcttg caatatcgct tctatgcctt gtgcagctcc   11460
tggacctgct agtgctttat ttaacgatga agcatctgat gaggctagtt taaatgccgc   11520
tgttgaagaa actttgaaat ttattgctaa tcgtgataaa gtagctgttt tagttggttc   11580
taaactccgt gccgctggtg cagaagaagc ggctgtaaaa ttcgcagatg ccttaggagg   11640
tgctgttgcc acaatggcag ccgctaaaag ttttttcccc gaagaaaatc ctcattacat   11700
tggtacttct tgggggtgagg tatcttaccc tggtgtagaa aaaaccatga aggaagctga   11760
tgcagtaatt gcattagctc ctgttttcaa tgattactct accactggtt ggactgatat   11820
tccagacccc aaaaaattag ttttagcaga acctcgctct gtagttgtga atggtgttag   11880
atttcccagt gtacatctca aagattattt aactcgttta gctcaaaaag tgagtaaaaa   11940
gactggcgca ctcgatttct ttaaatcttt aaatgctggt gaattaaaga aagcagctcc   12000
tgctgatccc agtgctccct tagtgaatgc cgaaatcgca agacaagttg aagccttgtt   12060
aactcctaac actaccgtta ttgccgagac tggtgatagt tggttcaatg ctcaacgcat   12120
```

-continued

```
gaaattaccc aatggtgctc gtgttgagta tgaaatgcaa tggggtcaca ttggatggtc      12180
tgttcctgct gcatttggat atgcagttgg agcacctgag cgtagaaaca ttttaatggt      12240
aggtgatggt tctttccaac tcactgctca agaagttgca caaatggtac gtttaaaatt      12300
gcctgttatt atctttctca ttaacaacta tggttacacc attgaagtta tgattcatga      12360
tggtccttat aataacatta agaattggga ttacgcaggt ttaatggagg tatttaacgg      12420
taatggtgga tacgcagtg gagcaggtaa aggattaaaa gctaaaacag gaggtgagtt       12480
agctgaagca attaaagtag ctttagccaa tacagatggt cctaccttaa tcgaatgttt      12540
cattggacgt gaagattgta ctgaagagtt agttaaatgg ggaaagcgtg ttgccgctgc      12600
aaattctcgt aaacctgtaa acaaactctt gtagttagga tccgagct                  12648
```

<210> SEQ ID NO 16
<211> LENGTH: 13165
<212> TYPE: DNA
<213> ORGANISM: Artificial Sequence
<220> FEATURE:
<223> OTHER INFORMATION: #1581¶ABICyano1-6.8::PnirAABICyano1-
zmPDCABICyano1(opt3)-dsrA-PrpsLABICyano1-ADHABICyano1(opt3)_ter-
PrbcABICyano1-Km**

<400> SEQUENCE: 16

```
gatccagcaa gtttcatccc gaccccctca gggtcgggat ttttttattg tgagctcctc        60
cgcttaaaaa atttcatttt tcgatcaaaa aagacaaatt attactaatt agctcatggc       120
aataaataat cagtagtaat ctgttttcac atttttattgt taattttat tattgctaat       180 atcaaccttt tctacttctg cttaatattt tatttatgct caatgggaaa atctgaaata       240
agattgagaa cagtgttacc aatagaagta tttaaggttt aaagcatacc ttaaagataa       300
catttttttt tgaaaagagt caaattattt ttgaaaggct gatattttg atatttacta       360 atattttatt tatttctttt tcccttaaaa taagagctaa atctgttttt attatcatt        420 atcaagctct attaatacct caactttttc aagaaaaaat aataataatt tttccctcta       480
ttctcatgac cttttaggaa aattaatttt agaaaaacta ttgacaaacc cataaaaaat       540
gagataagat tatagattgt cactggtatt ttatactaga ggcaaattat atttatatat       600
acaaaaatgc tgtataaaaa acatctcata tgattaaggc ttatgctgca ttagaagcta       660
atggtaaatt acaaccttt gaatacgatc ccggtgcttt aggtgcaaat gaagtagaaa        720
ttgaggttca gtattgtggt gtatgtcatt ctgatttatc tatgattaac aacgaatggg       780
gaatttccaa ttatccctta gttcctggac acgaagttgt tggtactgta gcagctatgg       840
gagaaggagt taatcatgtt gaagtaggtg acttagtagg tttgggatgg cattctggtt       900
actgtatgac ctgtcatagt tgtttatctg gttatcacaa cttatgtgca actgctgaaa       960
gtaccattgt tggtcattac ggtggttttg tgatagagt aagagctaaa ggagttagtg       1020
ttgttaaatt accaaaaggt atcgactag caagtgcagg tcctctctt tgtggggta        1080 ttactgtttt tagtcctatg gttgaattaa gtttaaagcc aactgcaaaa gtagccgtca      1140
ttggtattgg aggattggga cacttagctg ttcaatttct ccgtgcatgg ggatgtgaag      1200
ttactgcctt tacttctagt gctcgtaaac aaaccgaggt attagaatta ggagcacacc      1260
atatcttaga ttccaccaac cctgaagcta tcgctagtgc agagggaaaa ttcgattata      1320
ttattagtac tgttaatttg aaattagatt ggaacctcta catctctact ttagctcccc      1380
aaggtcattt tcactttgtt ggagttgtat tagaacccct cgatttaaac ttattcccctt     1440 tattaatggg acaacgttct gttagtgcat ctcctgttgg atctcccgct actattgcta      1500
```

```
ccatgttaga ttttgcagta cgtcacgata ttaaacctgt agtagaacaa ttctctttcg    1560
atcaaatcaa cgaagctatt gctcatttag aaagtggtaa ggctcattac cgtgttgttt    1620
tatctcactc taaaaactaa ctagatctct gcagagaata taaaaagcca gattattaat    1680 ccggctttt  tattatttaa atactgtgca cgatcctgca ggatcatctt gctgaaaaac    1740
tcgagcgctc gttccgcaaa gcggtacgga gttagttagg ggctaatggg cattctcccg    1800
tacaggaaag agttagaagt tattaattat caacaattct cctttgccta gtgcatcgtt    1860
acctttttaa ttaaaacata aggaaaacta ataatcgtaa taatttaacc tcaaagtgta    1920
aagaaatgtg aaattctgac ttttataacg ttaaagaggg aaaaattagc agtttaaaat    1980
acctagagaa tagtctgggg taagcataga gaattagatt agttaagtta atcaaattca    2040
gaaaaaataa taatcgtaaa tagttaatct gggtgtatag aaaatgatcc ccttcatgat    2100
aagatttaaa ctcgaaaagc aaaagccaaa aaactaactt ccattaaaag aagttgttac    2160
atataacgct ataagaaaaa tttatatatt tggaggatac caaccatgtc tcatattcaa    2220
cgtgaaacta gttgttctcg ccctcgttta aattctaata tggatgccga tttatatggt    2280
tataaatggg ctcgtgataa tgttggtcaa tctggtgcta ctatttatcg tttatatggt    2340
aaacctgatg ctcctgaatt attcttgaaa catggtaaag gttctgttgc taatgatgtt    2400
actgatgaaa tggttcgttt aaactggttg actgaattta tgcctttacc tactattaaa    2460
cattttattc gtactcccga tgatgcttgg ttattaacta ctgctattcc tggtaaaact    2520
gcttttcaag tttttagaaga atatcctgat tctggtgaaa atattgttga tgctttagct    2580
gtttttttac gtcgtttaca ttctattccc gtttgtaatt gtccttttaa ttctgatcgt    2640
gtttttcgtt tagctcaagc tcaatctcgt atgaataatg gtttagttga tgcttctgat    2700
tttgatgatg aacgtaatgg ttggcctgtt gaacaagttt ggaaagaaat gcacaaattg    2760 ttacctttt  ctcctgattc tgttgttact catggtgatt tttctttaga taatttgatc    2820
tttgatgaag gtaaattgat tggttgtatt gatgttggtc gtgttggtat tgctgatcgt    2880
tatcaagatt tagctatttt atggaattgt ttaggtgaat tttctccttc tttacagaaa    2940
cgtttatttc agaaatatgg tattgataat cctgatatga acaagttaca atttcattta    3000
atgttggacg agttcttta  agaattaatt catgaccaaa atcccttaac gtgagttttc    3060
gttccactga gcgtcagacc ccgtagaaaa gatcaaagga tcttcttgag atccttttt     3120 tctgcgcgta atctgctgct atttaaatta cgtacacgtg ttattacttt gttaacgaca    3180
attgtcttaa ttaactgggc ctcatgggcc ttccgctcac tgcccgcttt ccagtcggga    3240
aacctgtcgt gccagctctg cagatgacgg tgaaaacctc tgacacatgc agctcccgga    3300
gacggtcaca gcttgtctgt aagcggatgc cgggagcaga caagcccgtc agggcgcgtc    3360
agcgggtgtt ggcgggtgtc ggggcgcagc catgacccag tcacgtagcg atagcggagt    3420
gtatactggc ttaactatgc ggcatcagag cagattgtac tgagagtgca ccatatgcgg    3480
tgtgaaatac cgcacagatg cgtaaggaga aaataccgca tcaggcgctc ttccgcttcc    3540
tcgctcactg actcgctgcg ctcggtcgtt cggctgcggc gagcggtatc agctcactca    3600
aaggcggtaa tacggttatc cacagaatca ggggataacg caggaaagaa catgtgagca    3660
aaaggccagc aaaaggccag gaaccgtaaa aaggccgcgt tgctggcgtt tttccatagg    3720
ctccgccccc ctgacgagca tcacaaaaat cgacgctcaa gtcagaggtg gcgaaacccg    3780
acaggactat aaagatacca ggcgtttccc cctggaagct ccctcgtgcg ctctcctgtt    3840
```

```
ccgaccctgc cgcttaccgg atacctgtcc gcctttctcc cttcgggaag cgtggcgctt    3900
tctcatagct cacgctgtag gtatctcagt tcggtgtagg tcgttcgctc caagctgggc    3960
tgtgtgcacg aaccccccgt tcagcccgac cgctgcgcct tatccggtaa ctatcgtctt    4020
gagtccaacc cggtaagaca cgacttatcg ccactggcag cagccactgg taacaggatt    4080
agcagagcga ggtatgtagg cggtgctaca gagttcttga agtggtggcc taactacggc    4140
tacactagaa ggacagtatt tggtatctgc gctctgctga agccagttac cttcggaaaa    4200
agagttggta gctcttgatc cggcaaacaa accaccgctg gtagcggtgg ttttttttgtt    4260
tgcaagcagc agattacgcg cagaaaaaaa ggatctcaag aagatccttt gatcttttct    4320
actgcagaag cttgttagac accctgtcat gtatttttata ttatttattt caccatacgg    4380
attaagtgaa acctaatgaa aatagtactt tcggagcttt aactttaatg aaggtatgtt    4440
tttttataga catcgatgtc tggtttaaca ataggaaaaa gtagctaaaa ctcccatgaa    4500
ttaaagaaat aacaaggtgt ctaacaacct gttattaaga atgttagaaa agacttaaca    4560
tttgtgttga gttttttatag acattggtgt ctagacatac ggtagataag gtttgctcaa    4620
aaataaaata aaaaagatt ggactaaaaa acatttaatt tagtacaatt taattagtta    4680
ttttttcgtc tcaaatttg ctttgttgag cagaaattta gataaaaaaa tccccgtgat    4740
cagattacaa tgtcgttcat tgtacgatgt gtcgaaaaat ctttacgaca ctctaaactg    4800
accacacggg ggaaaagaa aactgaacta ataacatcat gatactcgga aaacctagca    4860
attctcaacc cctaaacaaa agaaacttcc aaaaccctga ccatataaag gagtggcaac    4920
aatcagcaat cagtcaagat ttgatagcag aaaatcttgt atcggttgct aatggttttg    4980
atgtactatt tatcggcaat aaataccgaa ctaacacggg tgttctgtca cggcacatat    5040
taaactccta ttctcattta gaagatggtg gttcgtatgg tagaacattt gacccattta    5100
ccaataaaga aatgcagtgg gttcaattta aaccgaatag accaagaaaa ggttctactg    5160
gtaaggtaat caaatatgaa tcgccaaaag gtgaacctac aagagttcta atgccgtttg    5220
tgcctatgaa aatatggcaa cggattagcg ataagttcgg agtaccgatt aatccgaaaa    5280
aagatactca cttttgggaa tgggtaaaga ataatccatc gataccgatt gccattacag    5340
aaggaaataa aaaagctaat tgcctattat cctatggcta tcctgctatt gcctttgtag    5400
gcatttggaa cggattagag aaaataaatg atttctcgaa ggaaaagcag ttaaaagagg    5460
atttgaaatg gttgttatcc aacggcaacc gaaatattaa tatcatcttt gaccaagacc    5520
agaaacaaaa aactgtaatt aatgtaaaca aagctatttt cgctttatct tctctaataa    5580
gtagaaatgg tcataaagtt aatattgtgc aatggttgcc gtcaaaaggt aaaggaatag    5640
atgattattt ggtagcttta cctttttgaga aaagagaaaa tcatttagac aacttaatta    5700
aaattgcacc atcatttaat ttttggtcaa ctaaatactt attcaagtgt cgtaaaccag    5760
atttaaccgt aaattgccgt tatttgagcg atgcagtaaa agaattaccct caagaggata    5820
tagcattaat agcacctcac ggcacgggta aaacttcatt agtagctact cacgttaaga    5880
atcggagtta tcacggaagg aaaactattt cattggtgca tcttgaaagt ttagccaaag    5940
ctaatggcaa cgcacttgga ttatattacc gaaccgaaaa taatattgaa aagcaatatc    6000
ttggatttag cttatgtgta gatagttgcc gtgataagat taacggcatt acaactgata    6060
ttatttcagg tcaagattat tgccttttca ttgatgaaat tgaccaagta attccacaca    6120
tccttaacag tgaaactgaa gtaagtaagt atagatgcac catcattgac acttttctg    6180
aactggtgag aaatgctgaa caggtcatta ttgctgatgc tgatttatcc gatgtgacga    6240
```

```
ttgacctaat agaaaacatc agaggtaaaa aactatatgt aatcaagaat gaatatcagt    6300
atcagggaat gacttttaac gccgttggtt caccattaga aatgatggca atgatgggaa    6360
aatcggtgtc agaaggcaag aaattattta ttaacaccac atcccaaaag gcaaaaagta    6420
agtacggcac aatcgctctt gagtcttata tttttggtct aaataaagaa gcaaagatat    6480
taagaataga ctctgaaacc actaaaaacc ctgaacatcc agcctataaa atcattgacc    6540
aagacttaaa taatatcctc aaagattatg attatgtcat tgcctcacct tgccttcaaa    6600
caggtgtcag tattacctta aaagggcatt ttgaccagca atttaacttt tccagtggaa    6660
acattacacc tcattgcttt ttacagcaaa tgtggcggtt gagggatgca gaaattgaaa    6720
gattctatta tgtgccgaac tcatctaacc tcaatctcat tgggaataag tcaagttcac    6780
catcagacct tctaaagagc aataacaaga tggcaacggc aacggttaac cttttgggta    6840
gaatcgactc cgaatattcc ctagagtatg aatcgcacgg catttggctt gagacgtggg    6900
caaaattatc agcacggcat aacagttcaa tgcgttgtta ctctgaaatt cttacctatc    6960
taattacgtc tcaagggcat aaattaaata tcaacattcc ctcacctctt gcagatatta    7020
agaagctaaa tgatgaggta agtagtaaca gggaaaaggt aaaaaatgag agatactctc    7080
agaggttaaa ctcaccagat attaacgatg cagaagctac catactcgaa tctaaagagc    7140
aaaaaatcgg attgactctc aatgagagat gcaccctaga aaagcataaa gttaagaagc    7200
ggtatgggaa tgtaaagatg gatattctca cctttgatga tgatggacta taccccaaac    7260
tcagactatt ttattacctc accatcggta aacctcatct caaggctaat gacagaaaag    7320
ctattgccaa aatgggcaat gacaataaag gcaagattct atcaaaagac ttagttaata    7380
aaacttactc cgctcgtgtg aaggtcttag agattcttaa actaactgac tttatcgaca    7440
atcttagaga tgaactctta ataactccca ataatccagc tatcaccgat tttaataatc    7500
ttctgctaag agctaagaag gatttaagag tattaggagt caacatcgga aaatatccaa    7560
tggccaacat taatgccgta cttactctca ttggtcacaa actttctgta atgagagatg    7620
agttcggaaa agagaaaagg ataaaagtag atggtaaatc ataccgatgt tatcaacttg    7680
aaacattacc agatttttacc aatgatactc ttgactactg gttagaaaat gatagccaaa    7740
aagaagtaac agcaacagaa aattactccg aaaattttaa cccttcaaat agctacaatc    7800
cagacagtaa gacactttca gagggtgcaa atttcctata tataaataaa gaagaattgc    7860
atccaaataa attgcaccta gaaataaaag aaggtgctga acttttttta ttcggggtaa    7920
aggtgattgt gaaaggaatc ttggacgggg cagtaactat attctctatg ggtcaagaat    7980
acgatttatc cctcaatgaa ctagagggga tgttaacatc atgaacttta caagaatctt    8040 tttaagggc gatcgcacca tgttaaatga tggtacattt gttcagatat ttgatattta    8100
ccatgaccac gcattgggag tgacccttga ccttaagaca gaaaaaatta tttccgatga    8160
tgttagggta attactgtca aagacttatt gttcgatggc acttataaag gggtaaaatc    8220
ttttatgccc gataatgccc gataatgccc gattgatgct acaaaatccc ataatcataa    8280
gcgataatcc cctaatagct tgtaattctt gaaccgtagc gattttagag tattccaaaa    8340
agaagaaata aacaccgcaa aatgtcgtat ttcacatata taaaccaagg ttttttgccc    8400
taaaatcttt atgtttgtag tgtgatgttg ggtcaaaatg gtcagaaaag ttgcaaggtt    8460
tttatggatg cttacgcgcg cgaggggtaa gcatccccaa atagttactt tatcctagtc    8520
catgcccatt tattgccgtc ccgttcggct ttaaaaaagt gccaaaactc acaaggtgca    8580
```

```
ataaaaagtt ctgtaccttt cgcaacccta gataatcttt caacagttac ttttttttcct    8640 attatctcgg tacaaagttt ggctagtttc tcttttccct cttttcaat caagccttct      8700 tgtatgccca actcattgat taatctctct attttttacca ttatttcccg ttcaggtagt    8760
ttatccccta aatcttcatc gggggcaat gtagggcatt ctgaagggc ttttttcttct    8820 gtctggacat tatctaatat tgaagtaacc aaactatctt cagttttttc tattcctatt    8880
aattcatatt cggttactgt atccgtatca atatccgaat aactatcttt atccgtatta    8940
gctattcggt taagtttatc cgttaactca gaaacaagac tatatagcgg ttttagcttt    9000
tcttctatcc tgttatctaa tacggataag tttatacggt tatcattatc cgtattagta    9060
tcattgggct tttttggtag ttctacccc tcataaaccg cttttattcc caattccaac     9120
agactgataa cagtatcctt tataatgggt ttttgctga tatggtgaac ttttgccct     9180 tccatcattg cgatactttc tatctcactc atcaacttat cgcttaagtg aatctcgtat    9240
ctgtttaatc ccttactggt tttattcata tccgtttact ttattcggtt aacaattcta    9300
ttttatacga ataaaatatt atacggttaa ctttatacgt ttaactatt tatctatacg    9360 gataacagta ataagttatt cgtattagtt atacgtttac tttttatccaa ataaaattag    9420 tgcatttaaa ctaaaagaat gattttatcg gagttgatag cattggatta acctaaagat    9480
gtttataagc tatatctgat aagtatttaa ggttattttg ttattctgtt tattgacatt    9540
atcagaataa aagaatagaa tataattgtt gagagataag aggtttaagt gattatggtt    9600
aagaagttag ttggttatgt cagggtcagt agtgaatcgc aagaggataa cactagctta    9660
cagaatcaga tagagagaat tgaagcatat tgtatggctt ttggttatga gttggtaaaa    9720
atattcaaag aggttgccac tggtacaaaa gcagatattg aaacccgtcc tatttttaat    9780
gaagctatag aatacttgaa acaggataat gctaatggaa ttattgcctt gaagctagac    9840
cgaatcgcac ggaatgcttt agatgtattg cgtttggttc gtgaaacctt agaaccacaa    9900
aataaaatgt tagtgttact agatattcag gtagatactt cgacaccttc aggaaaaatg    9960
attttaactg taatgagtgc cgttgctgaa ctcgaaagag acatgatcta tgatcgcact    10020
caggggggta gaaagactaa agcccaaaag ggcgggtatg cctacgggaa acctaaatt    10080 ggctataaga ctgaagaaaa ggaactaaaa gaagattcag cacaacagga aactattaaa    10140
ctaattaaga gacaccgtag gtcagggaaa agctaccaga aaatagctga ttatctcaat    10200
gcccaaagta ttcccactaa acaaggtaag aaatggagtt ctagcgtcgt ctatcgaatc    10260
tgtcaggaaa aagctggtta agtctgttta tagatattta gaatttattg aataaaaata    10320
gtatgaacaa taaatattta tggactaacc acgctcggaa acgtttaact gaacgatggg    10380
aaataaaaga atcatgggtt attgatacca tcgaaaatcc tgaacgttca gaatttattg    10440
ttgatgagtc aggggaaaaa tatcattact ataaaagaat agctaagttt aagaatagag    10500
tgttagaagt gataacttct gccaactcaa cacccacaag aataataacc ttttacttta    10560
accgtaacat gaggaaaaat ttatgattgt tacttacgat aatgaagttg acgcaattta    10620
ttttaagtta acggaaaata aaattgatag caccgaacct caaacagaca ggattatcat    10680
tgattacgat gaaagtaata atattgttgg cattgaggta ttagatttta attatcttgt    10740
caagaaaggt ttaaccgttg ctgatttacc ttttttctgaa gatgaaagat taacagcttc    10800
tcaatatttt aattttcctg ttgctatcta atccagaagg ggcaataatc cccttctttc    10860
atcgagttag acttaatatc acaaaagtca ttttcatttt accgtttctt ttccacagcg    10920
tccgtacgcc cctcgttaaa tctcaaaacc gacaatttat gatgtttata aaaagttact    10980
```

```
cactttaata agtatttata ctcattaaag ggttattctt tttttgtagc ctgataggtt    11040
gggaaggaat atttcagatt atcagatttg ttgaatattt ttcgtcagat acgcaaacct    11100
tacaaacata attaacaact gaaactattg atatgtctag gttttagctc tatcacaggt    11160
tggatctgtc gacaattaat aacttcttcc tgtacgggcg aatggccatt tgctcctaac    11220
taactccgta ctgctttgcg gaacgagcgt agcgaactct ccgaattact aagccttcat    11280
ccctgataga tgcaaaaaac gaattaaaat tatgtgtaaa aagaaaatgt gtctttattt    11340
agtagtcaaa gttacaaaat attaagaatc aaattaataa tgtattgggc agttaagtat    11400
ataagtcttt aaatatttat ttgtattcaa tatattaacc gaggacaaat tatgaattct    11460
tacactgttg gaacctattt agcagaacgt ttagttcaaa ttggtctcaa acaccatttt    11520
gcagtagctg gtgattataa tttagtttta ttggataact tattgttaaa taagaatatg    11580
gaacaagtgt attgttgtaa tgaattaaac tgtggttttt ctgctgaggg atatgctcgt    11640
gcaaaaggtg ctgccgcagc agttgttact tattctgttg gagcattaag tgcttttgac    11700
gctattggag gtgcttatgc agaaaattta cctgtaatct taatctctgg tgcacccaat    11760
aacaacgatc acgctgctgg tcatgtattg catcatgctt taggtaaaac cgattatcat    11820
taccaattag aaatggcaaa aaatattacc gctgccgcag aagctattta ctcccgaa     11880 gaagcacctg ctaagatcga tcacgtaatt aaaaccgctc tccgtgagaa aaacccgta    11940 tatttagaaa tcgcttgcaa tatcgcttct atgccttgtg cagctcctgg acctgctagt    12000
gctttattta acgatgaagc atctgatgag gctagtttaa atgccgctgt tgaagaaact    12060
ttgaaattta ttgctaatcg tgataaagta gctgttttag ttggttctaa actccgtgcc    12120
gctggtgcag aagaagcggc tgtaaaattc gcagatgcct taggaggtgc tgttgccaca    12180
atggcagccg ctaaaagttt ttttccccgaa gaaaatcctc attacattgg tacttcttgg    12240
ggtgaggtat cttaccctgg tgtagaaaaa accatgaagg aagctgatgc agtaattgca    12300
ttagctcctg ttttcaatga ttactctacc actggttgga ctgatattcc agaccccaaa    12360
aaattagttt tagcagaacc tcgctctgta gttgtgaatg tgttagatt tcccagtgta    12420 catctcaaag attatttaac tcgtttagct caaaaagtga gtaaaagac tggcgcactc    12480 gatttctttta aatctttaaa tgctggtgaa ttaaagaaag cagctcctgc tgatcccagt    12540
gctcctttag tgaatgccga aatcgcaaga caagttgaag ccttgttaac tcctaacact    12600
accgttattg ccgagactgg tgatagttgg ttcaatgctc aacgcatgaa attacccaat    12660
ggtgctcgtg ttgagtatga aatgcaatgg ggtcacattg gatggtctgt tcctgctgca    12720
tttggatatg cagttggagc acctgagcgt agaaacattt taatggtagg tgatggttct    12780
ttccaactca ctgctcaaga agttgcacaa atggtacgtt taaaattgcc tgttattatc    12840
tttctcatta acaactatgg ttacaccatt gaagttatga ttcatgatgg tccttataat    12900
aacattaaga attgggatta cgcaggttta atggaggtat ttaacggtaa tggtggatac    12960
gacagtggag caggtaaagg attaaaagct aaaacaggag gtgagttagc tgaagcaatt    13020
aaagtagctt tagccaatac agatggtcct accttaatcg aatgtttcat tggacgtgaa    13080
gattgtactg aagagttagt taaatgggga agcgtgttg ccgctgcaaa ttctcgtaaa    13140
cctgtaaaca aactcttgta gttag                                          13165
```

<210> SEQ ID NO 17
<211> LENGTH: 12762
<212> TYPE: DNA

<213> ORGANISM: Artificial Sequence
<220> FEATURE:
<223> OTHER INFORMATION: #1606[\]pABICyano1::PnirA-zmPDC(opt1)_dsrA-Prbc*(optRBS)-synADH(opt1)_ter

<400> SEQUENCE: 17

```
tcgacaatta ataacttctt cctgtacggg cgaatggcca tttgctccta actaactccg    60
tactgctttg cggaacgagc gtagcgaact ctccgaatta ctaagccttc atccctgata   120
gatgcaaaaa acgaattaaa attatgtgta aaagaaaat gtgtctttat ttagtagtca    180
aagttacaaa atattaagaa tcaaattaat aatgtattgg gcagttaagt ataaagtct    240
ttaaatattt atttgtattc aatatattaa ccgaggacaa attatgaatt cttataccgt   300
gggtacttat ttagccgaac gcttagtgca aattggttta aaacatcatt ttgccgtggc   360
tggggactat aatttagtgt tattggataa cttattatta aataaaaaca tggaacaagt   420
gtattgttgt aatgaattaa attgtggttt ttctgctgaa ggttatgcta gagctaaagg   480
tgcagctgct gctgttgtta cttattctgt gggtgcttta tctgcttttg atgctattgg   540
tggtgcttat gccgaaaatt tacccgtgat tttaatttct ggtgccccta ataataatga   600
tcatgccgct ggacatgttt tacatcatgc cttaggtaaa accgattatc attatcaatt   660
agaaatggcc aaaaatatta ctgctgctgc cgaagctatt tatactcctg aagaagcccc   720
tgccaaaatt gatcatgtga ttaaaaccgc cttacgcgaa aaaaaacccg tgtatttaga   780
aattgcctgt aatattgctt ctatgccttg tgctgctcct gggcctgctt ctgctttatt   840
taatgatgaa gcctctgatg aagctagttt aaatgctgcc gtggaagaaa ccttaaaatt   900
tattgccaat cgcgataaag ttgccgtgtt agttggttct aaattaagag ctgctggtgc   960
tgaagaagct gctgttaaat tgctgatgc tttaggtggt gcagttgcta ctatggctgc  1020
tgccaaatct tttttttcccg aagaaaatcc ccattatatt ggaactagtt ggggagaagt  1080
ttcttatcct ggtgtggaaa aaactatgaa agaagccgac gctgttattg ctttagcccc  1140
tgtgtttaat gattattcta ccactggttg gactgatatt cccgatccca aaaaattagt  1200
tttagccgaa cctcgttctg ttgttgttaa tggtgttcgc tttccctctg tgcatttaaa  1260
agattattta acccgcttag cccaaaaagt ttctaaaaaa actggtgcct tagatttttt  1320
taaatcttta aatgcgggtg aattaaaaaa agctgctcct gctgatcctt ctgctcctt  1380
agttaatgct gaaattgccc gtcaagttga agccttatta ccccctaata ctaccgttat  1440
tgccgaaact ggtgattctt ggtttaatgc ccaacgcatg aaattaccta atggtgcccg  1500
tgttgaatat gaaatgcaat ggggtcatat tggttggtct gtacctgctg cttttggtta  1560
tgctgttggt gctcctgaac gtcgtaatat tttaatggtg ggtgatggtt cttttcaatt  1620
aactgcccaa gaagttgccc aaatggttcg cttaaaatta cccgttatta ttttttttaat  1680
aaataattat ggttataccg ttgaagtgat gattcatgat gggccatata ataatattaa  1740
aaattgggat tatgcgggtt taatggaagt gtttaatggt aatggtggtt atgattctgg  1800
tgctggtaaa ggtttaaaag ccaaaactgg tggtgaatta gctgaagcta ttaaagttgc  1860
cttagccaat actgatgggc caaccttaat tgaatgtttt attggtcgcg aagattgtac  1920
cgaagaatta gttaaatggg gtaaacgtgt tgctgctgct aattctcgca aacccgtgaa  1980
taaattattg taattttggg ggatcaattc gagctcagca gtttcatcc cgaccccctc  2040
agggtcggga ttttttttatt gtactagttg acataagtaa aggcatcccc tgcgtgatat  2100
aattaccttc agtttaagga ggtatacaca tatgattaaa gcctatgctg ccttagaagc  2160
```

```
caatggtaaa ttacaaccct tgaatatga tcctggtgct ttaggtgcca atgaagtgga      2220
aattgaagtg caatattgtg gtgtgtgtca ttctgattta tctatgatta ataatgaatg      2280
gggtatttct aattatccct tagttcctgg tcatgaagtt gttggtactg ttgctgctat      2340
gggtgaaggt gttaatcatg tggaagtggg tgatttagtt ggtttaggtt ggcattctgg      2400
ttattgtatg acctgtcatt cttgtttatc tggttatcat aatttatgtg ccactgccga      2460
atctactatt gtgggtcatt atggtggttt tggtgataga gttcgtgcta aaggtgtttc      2520
tgtggtgaaa ttacccaaag gtattgattt agcctctgct gggcctttat tttgtggtgg      2580
tattaccgtt ttttctccca tggtggaatt atctttaaaa cctaccgcca aagttgctgt      2640
tattggtatt ggtggtttag gtcatttagc cgttcaattt ttaagagcct ggggttgtga      2700
agttactgct tttacctctt ctgcccgtaa acaaaccgaa gttttagaat taggtgccca      2760
tcatatttta gattctacca atcctgaagc tattgcttct gccgaaggta aatttgatta      2820
tattatttct accgtgaatt taaaattaga ttggaattta tatatcagta ccttagcccc      2880
tcaaggtcat tttcattttg ttggtgtggt gttagaaccc ttggacttaa acttatttcc      2940
cttattaatg ggacaacgtt ctgtttctgc ttctcctgtt ggttctcctg ctactattgc      3000
cactatgtta gattttgccg tgcgtcatga tattaaaccc gtggtggaac aattttctttt      3060 tgatcaaatt aatgaagcca ttgcccattt agaatctggt aaagcccatt atcgcgtggt      3120
gttatctcat tctaaaaatt aataagatta acttctaaac tgaaacaaat ttgagggtag      3180
gcttcattgt ctgcccttat tttttttattt aggaaaagtg aacagactaa agagtgttgg      3240
ctctattgct ttgagtatgt aaattaggcg ttgctgaatt aaggtatgat ttttgacccc      3300
ttctctcttc tgcaggatca tcttgctgaa aaactcgagc gctcgttccg caaagcggta      3360
cggagttagt taggggctaa tgggcattct cccgtacagg aaagagttag aagttattaa      3420
ttatcaacaa ttctcctttg cctagtgcat cgttaccttt ttaattaaaa cataaggaaa      3480
actaataatc gtaataattt aacctcaaag tgtaaagaaa tgtgaaattc tgactttat       3540 aacgttaaag agggaaaaat tagcagttta aaataccttag agaatagtct ggggtaagca      3600
tagagaatta gattagttaa gttaatcaaa ttcagaaaaa ataataatcg taaatagtta      3660
atctgggtgt atagaaaatg atccccttca tgataagatt taaactcgaa aagcaaaagc      3720
caaaaaacta acttccatta aaagaagttg ttacatataa cgctataaag aaaatttata      3780
tatttggagg ataccaacca tgtctcatat tcaacgtgaa actagttgtt ctcgccctcg      3840
tttaaattct aatatggatg ccgatttata tggtttataaa tgggctcgtg ataatgttgg      3900
tcaatctggt gctactattt atcgtttata tggtaaacct gatgctcctg aattattctt      3960
gaaacatggt aaaggttctg ttgctaatga tgttactgat gaaatggttc gtttaaactg      4020
gttgactgaa tttatgcctt tacctactat taaacatttt attcgtactc ccgatgatgc      4080
ttggttatta actactgcta ttcctggtaa aactgctttt caagttttag aagaatatcc      4140
tgattctggt gaaaatattg ttgatgcttt agctgttttt ttacgtcgtt tacattctat      4200
tcccgtttgt aattgtcctt ttaattctga tcgtgttttt cgtttagctc aagctcaatc      4260
tcgtatgaat aatggtttag ttgatgcttc tgattttgat gatgaacgta atggttggcc      4320
tgttgaacaa gtttggaaag aaatgcacaa attgttacct ttttctcctg attctgttgt      4380
tactcatggt gatttttctt tagataattt gatcttgat gaaggtaaat tgattggttg      4440
tattgatgtt ggtcgtgttg gtattgctga tcgttatcaa gatttagcta ttttatggaa      4500
ttgtttaggt gaattttctc cttctttaca gaaacgttta tttcagaaat atggtattga      4560
```

```
taatcctgat atgaacaagt tacaatttca tttaatgttg gacgagttct tttaagaatt    4620
aattcatgac caaaatccct taacgtgagt tttcgttcca ctgagcgtca gaccccgtag    4680
aaaagatcaa aggatcttct tgagatcctt ttttctgcg cgtaatctgc tgctatttaa    4740
attacgtaca cgtgttatta ctttgttaac gacaattgtc ttaattaact gggcctcatg    4800
ggccttccgc tcactgcccg ctttccagtc gggaaacctg tcgtgccagc tctgcagatg    4860
acggtgaaaa cctctgacac atgcagctcc cggagacggt cacagcttgt ctgtaagcgg    4920
atgccgggag cagacaagcc cgtcagggcg cgtcagcggg tgttggcggg tgtcggggcg    4980
cagccatgac ccagtcacgt agcgatagcg gagtgtatac tggcttaact atgcggcatc    5040
agagcagatt gtactgagag tgcaccatat gcggtgtgaa ataccgcaca gatgcgtaag    5100
gagaaaatac cgcatcaggc gctcttccgc ttcctcgctc actgactcgc tgcgctcggt    5160
cgttcggctg cggcgagcgg tatcagctca ctcaaaggcg gtaatacggt tatccacaga    5220 atcagggga taacgcagga a agaacatgtg agcaaaaggc cagcaaaagg ccaggaaccg    5280
taaaaaggcc gcgttgctgg cgttttttcca taggctccgc cccctgacg agcatcacaa    5340 aaatcgacgc tcaagtcaga ggtggcgaaa cccgacagga ctataaagat accaggcgtt    5400
tccccctgga agctccctcg tgcgctctcc tgttccgacc ctgccgctta ccggatacct    5460
gtccgccttt ctcccttcgg gaagcgtggc gctttctcat agctcacgct gtaggtatct    5520
cagttcggtg taggtcgttc gctccaagct gggctgtgtg cacgaacccc ccgttcagcc    5580
cgaccgctgc gccttatccg gtaactatcg tcttgagtcc aacccggtaa gacacgactt    5640
atcgccactg gcagcagcca ctggtaacag gattagcaga gcgaggtatg taggcggtgc    5700
tacagagttc ttgaagtggt ggcctaacta cggctacact agaaggacag tatttggtat    5760
ctgcgctctg ctgaagccag ttaccttcgg aaaaagagtt ggtagctctt gatccggcaa    5820
acaaaccacc gctggtagcg gtggtttttt tgtttgcaag cagcagatta cgcgcagaaa    5880
aaaaggatct caagaagatc ctttgatctt ttctactgca gaagcttgtt agacaccctg    5940
tcatgtattt tatattattt atttcaccat acggattaag tgaaacctaa tgaaaatagt    6000
actttcggag ctttaacttt aatgaaggta tgttttttta tagacatcga tgtctggttt    6060
aacaatagga aaaagtagct aaaactccca tgaattaaag aaataacaag gtgtctaaca    6120
acctgttatt aagaatgtta gaaaagactt aacatttgtg ttgagttttt atagacattg    6180
gtgtctagac atacggtaga taaggtttgc tcaaaataa aataaaaaaa gattggacta    6240
aaaaacattt aatttagtac aatttaatta gttatttttt cgtctcaaat tttgctttgt    6300
tgagcagaaa tttagataaa aaaatccccg tgatcagatt acaatgtcgt tcattgtacg    6360
atgtgtcgaa aaatctttac gacactctaa actgaccaca cggggaaaa agaaaactga    6420 actaataaca tcatgatact cggaaaacct agcaattctc aaccccctaaa caaaagaaac    6480 ttccaaaacc ctgaccatat aaaggagtgg caacaatcag caatcagtca agatttgata    6540
gcagaaaatc ttgtatcggt tgctaatggt tttgatgtac tatttatcgg caataaatac    6600
cgaactaaca cgggtgttct gtcacggcac atattaaact cctattctca tttagaagat    6660
ggtggttcgt atggtagaac atttgaccca tttaccaata aagaaatgca gtgggttcaa    6720
tttaaaccga atagaccaag aaaaggttct actggtaagg taatcaaata tgaatcgcca    6780
aaaggtgaac ctacaagagt tctaatgccg tttgtgccta tgaaaatatg gcaacggatt    6840
agcgataagt tcggagtacc gattaatccg aaaaaagata ctcactttg ggaatgggta    6900
```

```
aagaataatc catcgatacc gattgccatt acagaaggaa ataaaaaagc taattgccta    6960
ttatcctatg gctatcctgc tattgccttt gtaggcattt ggaacggatt agagaaaata    7020
aatgatttct cgaaggaaaa gcagttaaaa gaggatttga atggttgtt atccaacggc     7080
aaccgaaata ttaatatcat ctttgaccaa gaccagaaac aaaaaactgt aattaatgta    7140
aacaaagcta ttttcgcttt atcttctcta ataagtagaa atggtcataa agttaatatt    7200
gtgcaatggt tgccgtcaaa aggtaaagga atagatgatt atttggtagc tttacctttt    7260
gagaaaagag aaaatcattt agacaactta attaaaattg caccatcatt taatttttgg    7320
tcaactaaat acttattcaa gtgtcgtaaa ccagatttaa ccgtaaattg ccgttatttg    7380
agcgatgcag taaagaatt acctcaagag gatatagcat taatagcacc tcacggcacg    7440
ggtaaaactt cattagtagc tactcacgtt aagaatcgga gttatcacgg aaggaaaact    7500
atttcattgg tgcatcttga aagtttagcc aaagctaatg gcaacgcact tggattatat    7560
taccgaaccg aaaataatat tgaaaagcaa tatcttggat ttagcttatg tgtagatagt    7620
tgccgtgata agattaacgg cattacaact gatattattt caggtcaaga ttattgcctt    7680
ttcattgatg aaattgacca agtaattcca cacatcctta acagtgaaac tgaagtaagt    7740
aagtatagat gcaccatcat tgacactttt tctgaactgg tgagaaatgc tgaacaggtc    7800
attattgctg atgctgattt atccgatgtg acgattgacc taatagaaaa catcagaggt    7860
aaaaaactat atgtaatcaa gaatgaatat cagtatcagg gaatgacttt taacgccgtt    7920
ggttcaccat tagaaatgat ggcaatgatg ggaaaatcgg tgtcagaagg caagaaatta    7980
tttattaaca ccacatccca aaaggcaaaa agtaagtacg gcacaatcgc tcttgagtct    8040
tatatttttg gtctaaataa agaagcaaag atattaagaa tagactctga aaccactaaa    8100
aaccctgaac atccagccta taaatcatt gaccaagact taaataatat cctcaaagat    8160
tatgattatg tcattgcctc accttgcctt caaacaggtg tcagtattac cttaaaaggg    8220
cattttgacc agcaatttaa cttttccagt ggaaacatta cacctcattg cttttttacag   8280
caaatgtggc ggttgaggga tgcagaaatt gaaagattct attatgtgcc gaactcatct    8340
aacctcaatc tcattgggaa taagtcaagt tcaccatcag accttctaaa gagcaataac    8400
aagatggcaa cggcaacggt taaccttttg ggtagaatcg actccgaata ttccctagag    8460
tatgaatcgc acggcatttg gcttgagacg tgggcaaaat tatcagcacg gcataacagt    8520
tcaatgcgtt gttactctga aattcttacc tatctaatta cgtctcaagg gcataaatta    8580
aatatcaaca ttccctcacc tcttgcagat attaagaagc taaatgatga ggtaagtagt    8640
aacagggaaa aggtaaaaaa tgagagatac tctcagaggt taaactcacc agatattaac    8700
gatgcagaag ctaccatact cgaatctaaa gagcaaaaaa tcggattgac tctcaatgag    8760
agatgcaccc tagaaaagca taaagttaag aagcggtatg ggaatgtaaa gatggatatt    8820
ctcacctttg atgatgatgg actataccc aaactcagac tatttttatta cctcaccatc     8880
ggtaaacctc atctcaaggc taatgacaga aaagctattg ccaaaatggg caatgacaat    8940
aaaggcaaga ttctatcaaa agacttagtt aataaaactt actccgctcg tgtgaaggtc    9000
ttagagattc ttaaactaac tgactttatc gacaatctta gagatgaact cttaataact    9060
cccaataatc cagctatcac cgattttaat aatcttctgc taagagctaa gaaggattta    9120
agagtattag gagtcaacat cggaaaatat ccaatggcca acattaatgc cgtacttact    9180
ctcattggtc acaaactttc tgtaatgaga gatgagttcg gaaaagagaa aaggataaaa    9240
gtagatggta aatcataccg atgttatcaa cttgaaacat taccagattt taccaatgat    9300
```

```
actcttgact actggttaga aaatgatagc caaaaagaag taacagcaac agaaaattac    9360
tccgaaaatt ttaacccttc aaatagctac aatccagaca gtaagacact ttcagagggt    9420
gcaaatttcc tatatataaa taaagaagaa ttgcatccaa ataaattgca cctagaaata    9480
aaagaaggtg ctgaactttt tttattcggg gtaaaggtga ttgtgaaagg aatcttggac    9540
ggggcagtaa ctatattctc tatgggtcaa gaatacgatt tatccctcaa tgaactagag    9600
gggatgttaa catcatgaac tttacaagaa tcttttttaaa gggcgatcgc accatgttaa   9660
atgatggtac atttgttcag atatttgata tttaccatga ccacgcattg ggagtgaccc    9720
ttgaccttaa gacagaaaaa attatttccg atgatgttag ggtaattact gtcaaagact    9780
tattgttcga tggcacttat aaaggggtaa aatctttat gcccgataat gcccgataat    9840
gcccgattga tgctacaaaa tcccataatc ataagcgata atcccctaat agcttgtaat    9900
tcttgaaccg tagcgatttt agagtattcc aaaaagaaga aataaacacc gcaaaatgtc    9960
gtatttcaca tatataaacc aaggttttt gccctaaaat ctttatgttt gtagtgtgat    10020
gttgggtcaa aatggtcaga aaagttgcaa ggttttatg gatgcttacg cgcgcgaggg    10080
gtaagcatcc ccaaatagtt actttatcct agtccatgcc catttattgc cgtcccgttc    10140
ggctttaaaa aagtgccaaa actcacaagg tgcaataaaa agttctgtac ctttcgcaac    10200
cctagataat ctttcaacag ttacttttt tcctattatc tcggtacaaa gtttggctag    10260
tttctctttt ccctcttttt caatcaagcc ttcttgtatg cccaactcat tgattaatct    10320
ctctatttt accattattt cccgttcagg tagtttatcc cctaaatctt catcgggggg    10380
caatgtaggg cattctgaag gggcttttc ttctgtctgg acattatcta atattgaagt    10440
aaccaaacta tcttcagttt tttctattcc tattaattca tattcggtta ctgtatccgt    10500
atcaatatcc gaataactat ctttatccgt attagctatt cggttaagtt tatccgttaa    10560
ctcagaaaca agactatata gcggttttag ctttctcttt atcctgttat ctaatacgga    10620
taagtttata cggttatcat tatccgtatt agtatcattg ggcttttttg gtagttctac    10680
ccctcataa accgctttta ttcccaattc aacagactg ataacagtat ccttataat     10740
gggtttttg ctgatatggt gaacttttgc cccttccatc attgcgatac tttctatctc   10800
actcatcaac ttatcgctta agtgaatctc gtatctgttt aatcccttac tggttttatt   10860
catatccgtt tactttattc ggttaacaat tctattttat acgaataaaa tattatacgg   10920
ttaactttat acgtttaact attttatcta tacggataac agtaataagt tattcgtatt   10980
agttatacgt ttactttat ccaaataaaa ttagtgcatt taaactaaaa gaatgatttt    11040
atcggagttg atagcattgg attaacctaa agatgtttat aagctatatc tgataagtat   11100
ttaaggttat tttgttattc tgtttattga cattatcaga ataaagaat agaatataat   11160
tgttgagaga taagaggttt aagtgattat ggttaagaag ttagttggtt atgtcagggt   11220
cagtagtgaa tcgcaagagg ataacactag cttacagaat cagatagaga gaattgaagc   11280
atattgtatg gcttttggtt atgagttggt aaaaatattc aaagaggttg ccactggtac   11340
aaaagcagat attgaaaccc gtcctatttt taatgaagct atagaatact tgaaacagga   11400
taatgctaat ggaattattg ccttgaagct agaccgaatc gcacggaatg ctttagatgt   11460
attgcgtttg gttcgtgaaa ccttagaacc acaaaataaa atgttagtgt tactagatat   11520
tcaggtagat acttcgacac cttcaggaaa aatgattttta actgtaatga gtgccgttgc   11580
tgaactcgaa agagacatga tctatgatcg cactcagggg ggtagaaaga ctaaagccca   11640
```

```
aaagggcggg tatgcctacg ggaaacctaa atttggctat aagactgaag aaaaggaact    11700
aaaagaagat tcagcacaac aggaaactat taaactaatt aagagacacc gtaggtcagg    11760
gaaaagctac cagaaaatag ctgattatct caatgcccaa agtattccca ctaaacaagg    11820
taagaaatgg agttctagcg tcgtctatcg aatctgtcag gaaaaagctg gttaagtctg    11880
tttatagata tttagaatttt attgaataaa aatagtatga acaataaata tttatggact    11940
aaccacgctc ggaaacgttt aactgaacga tgggaaataa aagaatcatg ggttattgat    12000
accatcgaaa atcctgaacg ttcagaattt attgttgatg agtcagggga aaaatatcat    12060
tactataaaa gaatagctaa gtttaagaat agagtgttag aagtgataac ttctgccaac    12120
tcaacaccca caagaataat aaccttttac tttaaccgta acatgaggaa aaatttatga    12180
ttgttactta cgataatgaa gttgacgcaa tttattttaa gttaacggaa aataaaattg    12240
atagcaccga acctcaaaca gacaggatta tcattgatta cgatgaaagt aataatattg    12300
ttggcattga ggtattagat tttaattatc ttgtcaagaa aggtttaacc gttgctgatt    12360
tacctttttc tgaagatgaa agattaacag cttctcaata ttttaatttt cctgttgcta    12420
tctaatccag aaggggcaat aatcccctc tttcatcgag ttagacttaa tatcacaaaa    12480
gtcattttca ttttaccgtt tcttttccac agcgtccgta cgcccctcgt taaatctcaa    12540
aaccgacaat ttatgatgtt tataaaaagt tactcacttt aataagtatt tatactcatt    12600
aaagggttat tctttttttg tagcctgata ggttgggaag gaatatttca gattatcaga    12660
tttgttgaat attttttcgtc agatacgcaa accttacaaa cataattaac aactgaaact    12720
attgatatgt ctaggtttta gctctatcac aggttggatc tg                      12762
```

<210> SEQ ID NO 18
<211> LENGTH: 13354
<212> TYPE: DNA
<213> ORGANISM: Artificial Sequence
<220> FEATURE:
<223> OTHER INFORMATION: TK471[\]mpABICyano1::pilT-
PrbcLABICyano1_Km**pilC-sacB-oriVT

<400> SEQUENCE: 18

```
aatattttttc gtcagatacg caaaccttac aaacataatt aacaactgaa actattgata     60
tgtctaggtt ttagctctat cacaggttgg atctgtcgac gatccttttt aacccatcac    120
atatacctgc cgttcactat tatttagtga aatgagatat tatgatattt tctgaattgt    180
gattaaaaag gcaactttat gcccatgcaa cagaaactat aaaaaataca gagaatgaaa    240
agaaacagat agatttttta gttcttttagg cccgtagtct gcaaatcctt ttatgatttt    300
ctatcaaaca aaagaggaaa atagaccagt tgcaatccaa acgagagtct aatagaatga    360
ggtcgaaaag taaatcgcgc gggtttgtta ctgataaagc aggcaagacc taaaatgtgt    420
aaagggcaaa gtgtatactt tggcgtcacc ccttacatat tttaggtctt ttttttattgt   480 gcgtaactaa cttgccatct tcaaacagga gggctggaag aagcagaccg ctaacacagt    540
acataaaaaa ggagacatga acgatgaaca tcaaaaagtt tgcaaaacaa gcaacagtat    600
taacctttac taccgcactg ctggcaggag gcgcaactca agcgtttgcg aaagaaacga    660
accaaaagcc atataaggaa acatacgca tttcccatat tacacgccat gatatgctgc    720
aaatccctga acagcaaaaa aatgaaaaat atcaagttcc tgaattcgat tcgtccacaa    780
ttaaaaatat ctcttctgca aaaggcctgg aggtttggga cagctggcca ttacaaaacg    840
ctgacggcac tgtcgcaaac tatcacggct accacatcgt ctttgcatta gccggagatc    900
```

```
ctaaaaatgc ggatgacaca tcgatttaca tgttctatca aaaagtcggc gaaacttcta    960
ttgacagctg gaaaaacgct ggccgcgtct ttaaagacag cgacaaattc gatgcaaatg   1020
attctatcct aaaagaccaa acacaagaat ggtcaggttc agccacattt acatctgacg   1080
gaaaaatccg tttattctac actgatttct ccggtaaaca ttacggcaaa caaacactga   1140
caactgcaca agttaacgta tcagcatcag acagctcttt gaacatcaac ggtgtagagg   1200
attataaatc aatctttgac ggtgacggaa aaacgtatca aaatgtacag cagttcatcg   1260
atgaaggcaa ctacagctca ggcgacaacc atacgctgag agatcctcac tacgtagaag   1320
ataaaggcca caaatactta gtatttgaag caaacactgg aactgaagat ggctaccaag   1380
gcgaagaatc tttatttaac aaagcatact atggcaaaag cacatcattc ttccgtcaag   1440
aaagtcaaaa acttctgcaa agcgataaaa acgcacggc tgagttagca acggcgctc   1500
tcggtatgat tgagctaaac gatgattaca cactgaaaaa agtgatgaaa ccgctgattg   1560
catctaacac agtaacagat gaaattgaac gcgcgaacgt ctttaaaatg aacggcaaat   1620
ggtacctgtt cactgactcc cgcggatcaa aaatgacgat tgacggcatt acgtctaacg   1680
atatttacat gcttggttat gtttctaatt ctttaactgg cccatacaag ccgctgaaca   1740
aaactggcct tgtgttaaaa atggatcttg atcctaacga tgtaaccttt acttactcac   1800
acttcgctgt acctcaagcg aaaggaaaca atgtcgtgat tacaagctat atgacaaaca   1860
gaggattcta cgcagacaaa caatcaacgt ttgcgccaag cttcctgctg aacatcaaag   1920
gcaagaaaac atctgttgtc aaagacagca tccttgaaca aggacaatta acagttaaca   1980
aataaaaacg caaagaaaa tgccgatatc ctattggcat tttctttat ttcttatcaa    2040
cataaaggtg aatcccatat gaactatgga tcggcgcagc atgctcccgg ccgccatcac   2100
tagtgctcga tgacgctggt taatgcctta actgcttgtt ctacttcatc ttcataaaaa   2160
tctgcaactt tcatcatcat tgcatctaat tcccccgttt cttcaccaat catcatcatt   2220
tgaattgcca tagagggaaa aacctttctt tccgagatcg caacacttaa catacctcct   2280
tctaaaatag aatcttttgc ggcgccaatg gcattagaaa ttactttatt agggatagtc   2340
tcttgagata tttctaaaca ttgtaagata ggcacaccag aacgggttaa agtaccaaaa   2400
atacgacaaa aacgagcaac agcacttttt tcatttaagt ccccaaaaat gggagcttta   2460
agtgcgatcg tatctatttg taaacgtcca gcaggagttt tataatattg acggaaggca   2520
aaaacaaccc caataatcac acccacggga ataattgctt tccagctacg caaaaaatca   2580
ctaagagtaa cctaaaattg agtcaaagcc ggcaattctg cacccaattg gtcgaaaata   2640
ccagcaaata caggaatcaa gaaaatggtc atacccaaaa aagcaatgac cgcaaaaata   2700
ccaacagtga caggataagc cattgctgat ttaatttggt tttgcaaacg agcaacatct   2760
tcgagaagtt tagcaagacg attcatgact tcgtctaaaa ccccccctgt ttctcccgct   2820
tctaccatac tcacatatag cctatcaaaa cagtcgggat gctttgccat tgcttcagat   2880
aaattaaccc cctgttgaac atcctctcca atagtagtta gagccttctt aaatttagga   2940
tttcctgatt gctctgccaa tactgacaaa gagcggccgc atttaaatag cagcagatta   3000
cgcgcagaaa aaaggatct caagaagatc ctttgatctt ttctacgggg tctgacgctc   3060
agtggaacga aaactcacgt taagggattt tggtcatgaa ttaattctta aaagaactcg   3120
tccaacatta aatgaaattg taacttgttc atatcaggat tatcaatacc atatttctga   3180
aataaacgtt tctgtaaaga aggagaaaat tcacctaaac aattccataa aatagctaaa   3240
tcttgataac gatcagcaat accaacacga ccaacatcaa tacaaccaat caatttacct   3300
```

```
tcatcaaaga tcaaattatc taaagaaaaa tcaccatgag taacaacaga atcaggagaa    3360
aaaggtaaca atttgtgcat ttctttccaa acttgttcaa caggccaacc attacgttca    3420
tcatcaaaat cagaagcatc aactaaacca ttattcatac gagattgagc ttgagctaaa    3480
cgaaaaacac gatcagaatt aaaaggacaa ttacaaacgg gaatagaatg taaacgacgt    3540
aaaaaaacag ctaaagcatc aacaatattt tcaccagaat caggatattc ttctaaaact    3600
tgaaaagcag ttttaccagg aatagcagta gttaataacc aagcatcatc gggagtacga    3660
ataaaatgtt taatagtagg taaaggcata aattcagtca accagtttaa acgaaccatt    3720
tcatcagtaa catcattagc aacagaacct ttaccatgtt tcaagaataa ttcaggagca    3780
tcaggtttac catataaacg ataaatagta gcaccagatt gaccaacatt atcacgagcc    3840
catttataac catataaatc ggcatccata ttagaattta aacgaggacg agaacaacta    3900
gtttcacgtt gaatatgaga catggttggt atcctccaaa tatataaatt ttctttatag    3960
cgttatatgt aacaacttct tttaatggaa gttagttttt tggcttttgc ttttcgagtt    4020
taaatcttat catgaagggg atcatttcct atacacccag attaactatt tacgattatt    4080
attttttctg aatttgatta acttaactaa tctaattctc tatgcttacc ccagactatt    4140
ctctaggtat tttaaactgc taattttttcc ctctttaacg ttataaagt cagaatttca    4200 catttcttta cactttgagg ttaaattatt acgattatta gttttcctta tgttttaatt    4260 aaaaggtaa cgatgcacta ggcaaaggag aattgttgat aattaataac ttctaactct    4320
ttcctgtacg ggagaatgcc cattagcccc taactaactc cgtaccgctt tgcggaacga    4380
gcgctcgagc gttctctccg aactaatttc tccctctccc ctcatctata ataagatagt    4440
taataattac atcgacaatt gtctacgtag gcgcgccatg cggccttgac ggccttccgc    4500
caattcgccc tatagtgagt cgtattacgt cgcgctcact ggccgtcgtt ttacaacgtc    4560
gtgactggga aaaccctggc gttacccaac ttaatcgcct tgcagcacat cccccttttcg   4620 ccagctgcgc cggatccctg caggtcgacg atcgcaggtg tcacaatcat gatttcttga    4680
gccattgccc taccaaattc gcccggtttg ggattttttct ttttagccaa agtttgagca   4740
aatactgcca ataaagagtt agataacatt gctctaattt gggcttgttc tgccgaagga    4800
aatacatcaa taatacgatc aattgttccc gccgcagagc tagtatgtaa agtaccaaag    4860
acaaggtgtc cagtttccgc cgccgtaatc gccaaagaaa tggttctaa gtcgcgcatc     4920 tcacccacta gaataatatc tggatcttcc cttaacgccg ctttttaaggc attggcaaaa   4980 cttttagtat cttctccttt ttgacgttgg tgaaatagac tgttaatatt gggaaaaaca    5040
tactcgatcg gatcttctac tgttaagatg tgttctgcac gagtgcggtt aattaagtcc    5100
aacattgccg ctaaagtagt agttttttcca gaacctgtct gccctgtcac taaaatcata   5160 ccctagggc gttcggacat ctccttgaca atatctggta agcctaattg atcaaaattg     5220
ggaattttgg aagataaagc ccttaaacaa gcggcataac aaccccttc cttataaaca    5280 tttacacgaa atcgagccaa gccttttacc ccgtaggaac agtctaactc ccattcttgc    5340
tctaatgttt tacgttgagt attattgagc atactaaaaa ttaattttttg gcactcttga   5400 gcattaaggg gttcatctcc aatgcaaaat tacgtacacg tgttattact ttgttaacga    5460
caattgtctt aattaactgg cctcatgggc cttccgctca ctgcccgctt tccagtcggg    5520
aaacctgtcg tgccagctct gcagatgacg gtgaaaacct ctgacacatg cagctcccgg    5580
agacggtcac agcttgtctg taagcggatg ccggagcag acaagcccgt cagggcgcgt    5640
```

```
cagcgggtgt tggcgggtgt cggggcgcag ccatgaccca gtcacgtagc gatagcggag    5700
tgtatactgg cttaactatg cggcatcaga gcagattgta ctgagagtgc accatatgcg    5760
gtgtgaaata ccgcacagat gcgtaaggag aaaataccgc atcaggcgct cttccgcttc    5820
ctcgctcact gactcgctgc gctcggtcgt tcggctgcgg cgagcggtat cagctcactc    5880
aaaggcggta atacggttat ccacagaatc aggggataac gcaggaaaga acatgtgagc    5940
aaaaggccag caaaaggcca ggaaccgtaa aaaggccgcg ttgctggcgt ttttccatag    6000
gctccgcccc cctgacgagc atcacaaaaa tcgacgctca agtcagaggt ggcgaaaccc    6060
gacaggacta taaagatacc aggcgtttcc ccctggaagc tccctcgtgc gctctcctgt    6120
tccgaccctg ccgcttaccg gatacctgtc cgcctttctc ccttcgggaa gcgtggcgct    6180
ttctcaatgc tcacgctgta ggtatctcag ttcggtgtag gtcgttcgct ccaagctggg    6240
ctgtgtgcac gaaccccccg ttcagcccga ccgctgcgcc ttatccggta actatcgtct    6300
tgagtccaac ccggtaagac acgacttatc gccactggca gcagccactg gtaacaggat    6360
tagcagagcg aggtatgtag gcggtgctac agagttcttg aagtggtggc ctaactacgg    6420
ctacactaga aggacagtat ttggtatctg cgctctgctg aagccagtta ccttcggaaa    6480
aagagttggt agctcttgat ccggcaaaca accaccgct ggtagcggtg ttttttttgt    6540
ttgcaagcag cagattacgc gcagaaaaaa aggatctcaa gaagatcctt tgatcttttc    6600
tactgcagaa gcttgttaga cccctgtca tgtatttat attatttatt tcaccatacg    6660
gattaagtga aacctaatga aaatagtact ttcggagctt taactttaat gaaggtatgt    6720 tttttttatag acatcgatgt ctggtttaac aataggaaaa agtagctaaa actcccatga    6780
attaaagaaa taacaaggtg tctaacaacc tgttattaag aatgttagaa aagacttaac    6840
atttgtgttg agtttttata gacattggtg tctagacata cggtagataa ggtttgctca    6900
aaaataaaat aaaaaagat tggactaaaa aacatttaat ttagtacaat ttaattagtt    6960 atttttttcgt ctcaaattt gctttgttga gcagaaattt agataaaaaa atccccgtga    7020
tcagattaca atgtcgttca ttgtacgatg tgtcgaaaaa tctttacgac actctaaact    7080
gaccacacgg gggaaaaaga aaactgaact aataacatca tgatactcgg aaaacctagc    7140
aattctcaac ccctaaacaa aagaaacttc caaaaccctg accatataaa ggagtggcaa    7200
caatcagcaa tcagtcaaga tttgatagca gaaaatcttg tatcggttgc taatggtttt    7260
gatgtactat ttatcggcaa taaataccga actaacacgg gtgttctgtc acggcacata    7320
ttaaactcct attctcattt agaagatggt ggttcgtatg gtagaacatt tgacccattt    7380
accaataaag aaatgcagtg ggttcaattt aaaccgaata gaccaagaaa aggttctact    7440
ggtaaggtaa tcaaatatga atcgccaaaa ggtgaaccta caagagttct aatgccgttt    7500
gtgcctatga aaatatggca acggattagc gataagttcg gagtaccgat taatccgaaa    7560
aaagatactc acttttggga atgggtaaag aataatccat cgataccgat tgccattaca    7620
gaaggaaata aaaagctaa ttgcctatta tcctatggct atcctgctat tgcctttgta    7680
ggcatttgga acggattaga gaaaataaat gatttctcga aggaaaagca gttaaaagag    7740
gatttgaaat ggttgttatc caacggcaac cgaaatatta atatcatctt tgaccaagac    7800
cagaaacaaa aaactgtaat taatgtaaac aaagctattt tcgctttatc ttctctaata    7860
agtgaaaatg gtcataaagt taatattgtg caatggttgc cgtcaaaagg taaggaata    7920 gatgattatt tggtagcttt accttttgag aaaaagagaaa atcatttaga caacttaatt    7980
aaaattgcac catcatttaa ttttttggtca actaaatact tattcaagtg tcgtaaacca    8040
```

```
gatttaaccg taaattgccg ttatttgagc gatgcagtaa aagaattacc tcaagaggat    8100
atagcattaa tagcacctca cggcacgggt aaaacttcat tagtagctac tcacgttaag    8160
aatcggagtt atcacggaag gaaaactatt tcattggtgc atcttgaaag tttagccaaa    8220
gctaatggca acgcacttgg attatattac cgaaccgaaa ataatattga aaagcaatat    8280
cttggattta gcttatgtgt agatagttgc cgtgataaga ttaacggcat tacaactgat    8340
attatttcag gtcaagatta ttgccttttc attgatgaaa ttgaccaagt aattccacac    8400
atccttaaca gtgaaactga agtaagtaag tatagatgca ccatcattga cacttttttct   8460
gaactggtga gaaatgctga acaggtcatt attgctgatg ctgatttatc cgatgtgacg    8520
attgacctaa tagaaaacat cagaggtaaa aaactatatg taatcaagaa tgaatatcag    8580
tatcagggaa tgacttttaa cgccgttggt tcaccattag aaatgatggc aatgatggga    8640
aaatcggtgt cagaaggcaa gaaattattt attaacacca catcccaaaa ggcaaaaagt    8700
aagtacggca caatcgctct tgagtcttat atttttggtc taaataaaga agcaaagata    8760
ttaagaatag actctgaaac cactaaaaac cctgaacatc cagcctataa aatcattgac    8820
caagacttaa ataatatcct caaagattat gattatgtca ttgcctcacc ttgccttcaa    8880
acaggtgtca gtattacctt aaaagggcat tttgaccagc aatttaactt ttccagtgga    8940
aacattacac ctcattgctt tttacagcaa atgtggcggt tgagggatgc agaaattgaa    9000
agattctatt atgtgccgaa ctcatctaac ctcaatctca ttgggaataa gtcaagttca    9060
ccatcagacc ttctaaagag caataacaag atggcaacgg caacggttaa ccttttgggt    9120
agaatcgact ccgaatattc cctagagtat gaatcgcacg gcatttggct tgagacgtgg    9180
gcaaaattat cagcacggca taacagttca atgcgttgtt actctgaaat tcttacctat    9240
ctaattacgt ctcaagggca taaattaaat atcaacattc cctcacctct tgcagatatt    9300
aagaagctaa atgatgaggt aagtagtaac agggaaaagg taaaaaatga gagatactct    9360
cagaggttaa actcaccaga tattaacgat gcagaagcta ccatactcga atctaaagag    9420
caaaaaatcg gattgactct caatgagaga tgcaccctag aaaagcataa agttaagaag    9480
cggtatggga atgtaaagat ggatattctc acctttgatg atgatggact ataccccaaa    9540
ctcagactat tttattacct caccatcggt aaacctcatc tcaaggctaa tgacagaaaa    9600
gctattgcca aaatgggcaa tgacaataaa ggcaagattc tatcaaaaga cttagttaat    9660
aaaacttact ccgctcgtgt gaaggtctta gagattctta aactaactga ctttatcgac    9720
aatcttagag atgaactctt aataactccc aataatccag ctatcaccga ttttaataat    9780
cttctgctaa gagctaagaa ggatttaaga gtattaggag tcaacatcgg aaaatatcca    9840
atggccaaca ttaatgccgt acttactctc attggtcaca aactttctgt aatgagagat    9900
gagttcggaa aagagaaaag gataaaagta gatggtaaat cataccgatg ttatcaactt    9960
gaaacattac cagattttac caatgatact cttgactact ggttagaaaa tgatagccaa   10020
aaagaagtaa cagcaacaga aaattactcc gaaaatttta acccttcaaa tagctacaat   10080
ccagacagta agacactttc agagggtgca aatttcctat atataaataa agaagaattg   10140
catccaaata aattgcacct agaaataaaa gaaggtgctg aacttttttt attcggggta   10200
aaggtgattg tgaaaggaat cttggacggg gcagtaacta tattctctat gggtcaagaa   10260
tacgatttat ccctcaatga actagagggg atgttaacat catgaacttt acaagaatct   10320
ttttaaaggg cgatcgcacc atgttaaatg atggtacatt tgttcagata tttgatattt   10380
```

```
accatgacca cgcattggga gtgacccttg accttaagac agaaaaaatt atttccgatg   10440
atgttagggt aattactgtc aaagacttat tgttcgatgg cacttataaa ggggtaaaat   10500
cttttatgcc cgataatgcc cgataatgcc cgattgatgc tacaaaatcc cataatcata   10560
agcgataatc ccctaatagc ttgtaattct tgaaccgtag cgattttaga gtattccaaa   10620
aagaagaaat aaacaccgca aaatgtcgta tttcacatat ataaaccaag gttttttgcc   10680
ctaaaatctt tatgtttgta gtgtgatgtt gggtcaaaat ggtcagaaaa gttgcaaggt   10740
ttttatggat gcttacgcgc gcgaggggta agcatcccca aatagttact ttatcctagt   10800
ccatgcccat ttattgccgt cccgttcggc tttaaaaaag tgccaaaact cacaaggtgc   10860
aataaaaagt tctgtacctt tcgcaaccct agataatctt tcaacagtta cttttttcc   10920
tattatctcg gtacaaagtt tggctagttt ctcttttccc tcttttcaa tcaagccttc   10980
ttgtatgccc aactcattga ttaatctctc tattttacc attatttccc gttcaggtag   11040
tttatcccct aaatcttcat cgggggcaa tgtagggcat tctgaagggg cttttcttc    11100
tgtctggaca ttatctaata ttgaagtaac caaactatct tcagttttt ctattcctat    11160
taattcatat tcggttactg tatccgtatc aatatccgaa taactatctt tatccgtatt   11220
agctattcgg ttaagtttat ccgttaactc agaaacaaga ctatatagcg ttttagctt    11280
ttcttctatc ctgttatcta atacggataa gtttatacgg ttatcattat ccgtattagt   11340
atcattgggc ttttttggta gttctacccc ctcataaacc gcttttattc ccaattccaa   11400
cagactgata acagtatcct ttataatggg ttttttgctg atatggtgaa cttttgcccc   11460
ttccatcatt gcgatacttt ctatctcact catcaactta tcgcttaagt gaatctcgta   11520
tctgtttaat cccttactgg ttttattcat atccgtttac tttattcggt taacaattct   11580
attttatacg aataaaatat tatacggtta actttatacg tttaactatt ttatctatac   11640
ggataacagt aataagttat tcgtattagt tatacgttta cttttatcca aataaaatta   11700
gtgcatttaa actaaaagaa tgattttatc ggagttgata gcattggatt aacctaaaga   11760
tgtttataag ctatatctga taagtattta aggttatttt gttattctgt ttattgacat   11820
tatcagaata aaagaataga atataattgt tgagagataa gaggtttaag tgattatggt   11880
taagaagtta gttggttatg tcagggtcag tagtgaatcg caagaggata acactagctt   11940
acagaatcag atagagagaa ttgaagcata ttgtatggct tttggttatg agttggtaaa   12000
aatattcaaa gaggttgcca ctggtacaaa agcagatatt gaaacccgtc ctattttta a   12060
tgaagctata gaatacttga aacaggataa tgctaatgga attattgcct gaagctaga    12120
ccgaatcgca cggaatgctt tagatgtatt gcgtttggtt cgtgaaacct tagaaccaca   12180
aaataaaatg ttagtgttac tagatattca ggtagatact tcgacacctt caggaaaaat   12240
gattttaact gtaatgagtg ccgttgctga actcgaaaga gacatgatct atgatcgcac   12300
tcaggggggt agaaagacta aagcccaaaa gggcgggtat gcctacggga aacctaaatt   12360
tggctataag actgaagaaa aggaactaaa agaagattca gcacaacagg aaactattaa   12420
actaattaag agacaccgta ggtcagggaa aagctaccag aaaatagctg attatctcaa   12480
tgcccaaagt attcccacta aacaaggtaa gaaatggagt tctagcgtcg tctatcgaat   12540
ctgtcaggaa aaagctggtt aagtctgttt atagatattt agaatttatt gaataaaaat   12600
agtatgaaca ataaatattt atggactaac cacgctcgga aacgtttaac tgaacgatgg   12660
gaaataaaag aatcatggt tattgatacc atcgaaaatc ctgaacgttc agaatttatt    12720
gttgatgagt cagggaaaa atatcattac tataaaagaa tagctaagtt taagaataga   12780
```

```
gtgttagaag tgataacttc tgccaactca acacccacaa gaataataac cttttacttt    12840
aaccgtaaca tgaggaaaaa tttatgattg ttacttacga taatgaagtt gacgcaattt    12900
attttaagtt aacggaaaat aaaattgata gcaccgaacc tcaaacagac aggattatca    12960
ttgattacga tgaaagtaat aatattgttg gcattgaggt attagatttt aattatcttg    13020
tcaagaaagg tttaaccgtt gctgatttac cttttcctga agatgaaaga ttaacagctt    13080
ctcaatattt taattttcct gttgctatct aatccagaag gggcaataat ccccttcttt    13140
catcgagtta gacttaatat cacaaaagtc attttcattt taccgtttct tttccacagc    13200
gtccgtacgc ccctcgttaa atctcaaaac cgacaattta tgatgtttat aaaaagttac    13260
tcactttaat aagtatttat actcattaaa gggttattct tttttttgtag cctgataggt    13320 tgggaaggaa tatttcagat tatcagattt gttg                                13354

<210> SEQ ID NO 19
<211> LENGTH: 12763
<212> TYPE: DNA
<213> ORGANISM: Artificial Sequence
<220> FEATURE:
<223> OTHER INFORMATION: #1629[\]pABICyano1::PnirA(opt2)-
      zmPDC(opt1)_dsrA-Prbc*(optRBS)-synADH(opt1)_ter

<400> SEQUENCE: 19
tcgacaatta ataacttctt cctgtacggg cgaatggcca tttgctccta actaactccg      60
tactgctttg cggaacgagc gtagcgaact ctccgaatta ctaagccttc atccctgata     120
gatgcaaaaa acgaattaaa attatgtgta aaagaaaat gtgtctttat ttagtagtca     180
aagttacaaa atattaagaa tcaaattaat aatgtattgg gcagttaagt atataagtct     240
ttaaatattt atttgtattc aatatattaa ggaggatcag ccttatgaat tcttataccg     300
tgggtactta tttagccgaa cgcttagtgc aaattggttt aaaacatcat tttgccgtgg     360
ctggggacta aatttagtg ttattggata acttattatt aaataaaaac atggaacaag     420
tgtattgttg taatgaatta aattgtggtt tttctgctga aggttatgct agagctaaag     480
gtgcagctgc tgctgttgtt acttattctg tgggtgcttt atctgctttt gatgctattg     540
gtggtgctta tgccgaaaat ttacccgtga ttttaatttc tggtgcccct aataataatg     600
atcatgccgc tggacatgtt ttacatcatg ccttaggtaa aaccgattat cattatcaat     660
tagaaatggc caaaaatatt actgctgctg ccgaagctat ttatactcct gaagaagccc     720
ctgccaaaat tgatcatgtg attaaaaccg ccttacgcga aaaaaaaccc gtgtatttag     780
aaattgcctg taatattgct tctatgcctt gtgctgctcc tgggcctgct tctgctttat     840
ttaatgatga agcctctgat gaagctagtt taaatgctgc cgtggaagaa accttaaaat     900
ttattgccaa tcgcgataaa gttgccgtgt tagttggttc taaattaaga gctgctggtg     960
ctgaagaagc tgctgttaaa tttgctgatg ctttaggtgg tgcagttgct actatggctg    1020
ctgccaaatc tttttttccc gaagaaaatc ccattatat tggaactagt tggggagaag    1080
tttcttatcc tggtgtggaa aaaactatga agaagccga cgctgttatt gctttagccc    1140
ctgtgtttaa tgattattct accactggtt ggactgatat tcccgatccc aaaaaattag    1200
ttttagccga acctcgttct gttgttgtta atggtgttcg ctttccctct gtgcatttaa    1260
aagattattt aacccgctta gcccaaaaag tttctaaaaa aactggtgcc ttagattttt    1320
ttaaatcttt aaatgcgggt gaattaaaaa agctgctcc tgctgatcct tctgctcctt    1380
tagttaatgc tgaaattgcc cgtcaagttg aagccttatt aaccctaat actaccgtta    1440
```

```
ttgccgaaac tggtgattct tggtttaatg cccaacgcat gaaattacct aatggtgccc    1500
gtgttgaata tgaaatgcaa tggggtcata ttggttggtc tgtacctgct gcttttggtt    1560
atgctgttgg tgctcctgaa cgtcgtaata ttttaatggt gggtgatggt tcttttcaat    1620
taactgccca agaagttgcc caaatggttc gcttaaaatt acccgttatt attttttaa     1680 taaataatta tggttatacc attgaagtga tgattcatga tgggccatat aataatatta    1740
aaaattggga ttatgcgggt ttaatggaag tgtttaatgg taatggtggt tatgattctg    1800
gtgctggtaa aggtttaaaa gccaaaactg gtggtgaatt agctgaagct attaaagttg    1860
ccttagccaa tactgatggg ccaaccttaa ttgaatgttt tattggtcgc gaagattgta    1920
ccgaagaatt agttaaatgg ggtaaacgtg ttgctgctgc taattctcgc aaacccgtga    1980
ataaattatt gtaattttg gggatcaatt cgagctcagc aagtttcatc ccgaccccct     2040
cagggtcggg atttttttat tgtactagtt gacataagta aaggcatccc ctgcgtgata    2100
taattacctt cagtttaagg aggtatacac atatgattaa agcctatgct gccttagaag    2160
ccaatggtaa attacaaccc tttgaatatg atcctggtgc tttaggtgcc aatgaagtgg    2220
aaattgaagt gcaatattgt ggtgtgtgtc attctgattt atctatgatt aataatgaat    2280
ggggtatttc taattatccc ttagttcctg gtcatgaagt tgttggtact gttgctgcta    2340
tgggtgaagg tgttaatcat gtggaagtgg gtgatttagt tggtttaggt tggcattctg    2400
gttattgtat gacctgtcat tcttgtttat ctggttatca taatttatgt gccactgccg    2460
aatctactat tgtgggtcat tatggtggtt ttggtgatag agttcgtgct aaaggtgttt    2520
ctgtggtgaa attacccaaa ggtattgatt tagcctctgc tgggccttta ttttgtggtg    2580
gtattaccgt tttttctccc atggtggaat tatctttaaa acctaccgcc aaagttgctg    2640
ttattggtat tggtggttta ggtcatttag ccgttcaatt tttaagagcc tggggttgtg    2700
aagttactgc ttttacctct tctgcccgta acaaaccga agttttagaa ttaggtgccc    2760
atcatatttt agattctacc aatcctgaag ctattgcttc tgccgaaggt aaatttgatt    2820
atattatttc taccgtgaat ttaaaattag attggaattt atatatcagt accttagccc    2880
ctcaaggtca ttttcatttt gttggtgtgg tgttagaacc cttggactta aacttatttc    2940
ccttattaat gggacaacgt tctgtttctg cttctcctgt tggttctcct gctactattg    3000
ccactatgtt agattttgcc gtgcgtcatg atattaaacc cgtggtggaa caattttctt    3060
ttgatcaaat taatgaagcc attgcccatt tagaatctgg taaagcccat tatcgcgtgg    3120
tgttatctca ttctaaaaat aataagatt aacttctaaa ctgaaacaaa tttgagggta    3180
ggcttcattg tctgccctta tttttttatt taggaaaagt gaacagacta aagagtgttg    3240
gctctattgc tttgagtatg taaattaggc gttgctgaat taaggtatga tttttgaccc    3300
cttctctctt ctgcaggatc atcttgctga aaaactcgag cgctcgttcc gcaaagcggt    3360
acggagttag ttaggggcta atgggcattc tcccgtacag gaaagagtta gaagttatta    3420
attatcaaca attctccttt gcctagtgca tcgttacctt tttaattaaa acataaggaa    3480
aactaataat cgtaataatt taacctcaaa gtgtaaagaa atgtgaaatt ctgacttta    3540 taacgttaaa gagggaaaaa ttagcagttt aaaataccta gagaatagtc tggggtaagc    3600
atagagaatt agattagtta agttaatcaa attcagaaaa aataataatc gtaaatagtt    3660
aatctgggtg tatagaaaat gatccccttc atgataagat ttaaactcga aaagcaaaag    3720
ccaaaaaact aacttccatt aaaagaagtt gttacatata acgctataaa gaaaatttat    3780
```

```
atatttggag gataccaacc atgtctcata ttcaacgtga aactagttgt tctcgccctc    3840
gtttaaattc taatatggat gccgatttat atggttataa atgggctcgt gataatgttg    3900
gtcaatctgg tgctactatt tatcgtttat atggtaaacc tgatgctcct gaattattct    3960
tgaaacatgg taaaggttct gttgctaatg atgttactga tgaaatggtt cgtttaaact    4020
ggttgactga atttatgcct ttacctacta ttaaacattt tattcgtact cccgatgatg    4080
cttggttatt aactactgct attcctggta aaactgcttt tcaagtttta gaagaatatc    4140
ctgattctgg tgaaaatatt gttgatgctt tagctgtttt tttacgtcgt ttacattcta    4200
ttcccgtttg taattgtcct tttaattctg atcgtgtttt tcgtttagct caagctcaat    4260
ctcgtatgaa taatggttta gttgatgctt ctgattttga tgatgaacgt aatggttggc    4320
ctgttgaaca agtttggaaa gaaatgcaca aattgttacc tttttctcct gattctgttg    4380
ttactcatgg tgattttttct ttagataatt tgatctttga tgaaggtaaa ttgattggtt    4440
gtattgatgt tggtcgtgtt ggtattgctg atcgttatca agatttagct attttatgga    4500
attgtttagg tgaattttct ccttcttttac agaaacgttt atttcagaaa tatggtattg    4560
ataatcctga tatgaacaag ttacaatttc atttaatgtt ggacgagttc ttttaagaat    4620
taattcatga ccaaaatccc ttaacgtgag ttttcgttcc actgagcgtc agaccccgta    4680
gaaaagatca aaggatcttc ttgagatcct ttttttctgc gcgtaatctg ctgctattta    4740
aattacgtac acgtgttatt actttgttaa cgacaattgt cttaattaac tgggcctcat    4800
gggccttccg ctcactgccc gctttccagt cgggaaacct gtcgtgccag ctctgcagat    4860
gacggtgaaa acctctgaca catgcagctc ccggagacgg tcacagcttg tctgtaagcg    4920
gatgccggga gcagacaagc ccgtcagggc gcgtcagcgg gtgttggcgg gtgtcggggc    4980
gcagccatga cccagtcacg tagcgatagc ggagtgtata ctggcttaac tatgcggcat    5040
cagagcagat tgtactgaga gtgcaccata tgcggtgtga ataccgcac agatgcgtaa    5100
ggagaaaata ccgcatcagg cgctcttccg cttcctcgct cactgactcg ctgcgctcgg    5160
tcgttcggct gcggcgagcg gtatcagctc actcaaaggc ggtaatacgg ttatccacag    5220
aatcagggga taacgcagga aagaacatgt gagcaaaagg ccagcaaaag gccaggaacc    5280
gtaaaaaggc cgcgttgctg gcgtttttcc ataggctccg ccccctgac gagcatcaca    5340
aaaatcgacg ctcaagtcag aggtggcgaa acccgacagg actataaaga taccaggcgt    5400
ttccccctgg aagctccctc gtgcgctctc ctgttccgac cctgccgctt accggatacc    5460
tgtccgcctt tctcccttcg ggaagcgtgg cgctttctca tagctcacgc tgtaggtatc    5520
tcagttcggt gtaggtcgtt cgctccaagc tgggctgtgt gcacgaaccc cccgttcagc    5580
ccgaccgctg cgccttatcc ggtaactatc gtcttgagtc aacccggta agacacgact    5640
tatcgccact ggcagcagcc actggtaaca ggattagcag agcgaggtat gtaggcggtg    5700
ctacagagtt cttgaagtgg tggcctaact acgctacac tagaaggaca gtatttggta    5760
tctgcgctct gctgaagcca gttaccttcg gaaaaagagt tggtagctct tgatccggca    5820
aacaaaccac cgctggtagc ggtggttttt tgtttgcaa gcagcagatt acgcgcagaa    5880
aaaaaggatc tcaagaagat cctttgatct tttctactgc agaagcttgt tagacaccct    5940
gtcatgtatt ttatattatt tatttcacca tacggattaa gtgaaaccta atgaaaatag    6000
tactttcgga gctttaactt taatgaaggt atgttttttt atagcatcg atgtctggtt    6060
taacaatagg aaaagtagc taaaactccc atgaattaaa gaaataacaa ggtgtctaac    6120
aacctgttat taagaatgtt agaaaagact taacatttgt gttgagtttt tatagacatt    6180
```

```
ggtgtctaga catacggtag ataaggtttg ctcaaaaata aaataaaaaa agattggact    6240
aaaaaacatt taatttagta caatttaatt agttatttttt tcgtctcaaa ttttgctttg    6300
ttgagcagaa atttagataa aaaaatcccc gtgatcagat tacaatgtcg ttcattgtac    6360
gatgtgtcga aaaatcttta cgacactcta aactgaccac acggggaaa aagaaaactg    6420 aactaataac atcatgatac tcggaaaacc tagcaattct caaccccctaa acaaaagaaa    6480 cttccaaaac cctgaccata taaggagtg caacaatca gcaatcagtc aagatttgat    6540
agcagaaaat cttgtatcgg ttgctaatgg ttttgatgta ctatttatcg gcaataaata    6600
ccgaactaac acgggtgttc tgtcacggca catattaaac tcctattctc atttagaaga    6660
tggtggttcg tatggtagaa catttgaccc atttaccaat aaagaaatgc agtgggttca    6720
atttaaaccg aatagaccaa gaaaaggttc tactggtaag gtaatcaaat atgaatcgcc    6780
aaaaggtgaa cctacaagag ttctaatgcc gttgtgcct atgaaaatat ggcaacggat    6840
tagcgataag ttcggagtac cgattaatcc gaaaaaagat actcactttt gggaatgggt    6900
aaagaataat ccatcgatac cgattgccat tacagaagga aataaaaaag ctaattgcct    6960
attatcctat ggctatcctg ctattgcctt tgtaggcatt tggaacggat tagagaaaat    7020
aaatgatttc tcgaaggaaa agcagttaaa agaggatttg aaatggttgt tatccaacgg    7080
caaccgaaat attaatatca tcttttgacca agaccagaaa caaaaaactg taattaatgt    7140
aaacaaagct atttcgctt tatcttctct aataagtaga aatggtcata agttaatat    7200 tgtgcaatgg ttgccgtcaa aaggtaaagg aatagatgat tatttggtag ctttaccttt    7260
tgagaaaaga gaaaatcatt tagacaactt aattaaaatt gcaccatcat ttaatttttg    7320
gtcaactaaa tacttattca agtgtcgtaa accagattta accgtaaatt gccgttattt    7380
gagcgatgca gtaaaagaat taccctcaaga ggatatagca ttaatagcac ctcacggcac    7440
gggtaaaact tcattagtag ctactcacgt taagaatcgg agttatcacg gaaggaaaac    7500
tatttcattg gtgcatcttg aaagtttagc caaagctaat ggcaacgcac ttggattata    7560
ttaccgaacc gaaaataata ttgaaaagca atatcttgga tttagcttat gtgtagatag    7620
ttgccgtgat aagattaacg gcattacaac tgatattatt tcaggtcaag attattgcct    7680
tttcattgat gaaattgacc aagtaattcc acacatcctt aacagtgaaa ctgaagtaag    7740
taagtataga tgcaccatca ttgacacttt ttctgaactg gtgagaaatg ctgaacaggt    7800
cattattgct gatgctgatt tatccgatgt gacgattgac ctaatagaaa acatcagagg    7860
taaaaaacta tatgtaatca agaatgaata tcagtatcag ggaatgactt ttaacgcgt    7920 tggttcacca ttagaaatga tggcaatgat gggaaaatcg gtgtcagaag gcaagaaatt    7980
atttattaac accacatccc aaaaggcaaa agtaagtac ggcacaatcg ctcttgagtc    8040 ttatatttt ggtctaaata aagaagcaaa gatattaaga atagactctg aaaccactaa    8100
aaaccctgaa catccagcct ataaaatcat tgaccaagac ttaaataata tcctcaaaga    8160
ttatgattat gtcattgcct caccttgcct tcaaacaggt gtcagtatta ccttaaaagg    8220
gcattttgac cagcaatttta acttttccag tggaaacatt acacctcatt gcttttaca    8280 gcaaatgtgg cggttgaggg atgcagaaat tgaaagattc tattatgtgc cgaactcatc    8340
taacctcaat ctcattggga ataagtcaag ttcaccatca gaccttctaa agagcaataa    8400
caagatggca acggcaacgg ttaaccttt gggtagaatc gactccgaat attccctaga    8460
gtatgaatcg cacggcattt ggcttgagac gtgggcaaaa ttatcagcac ggcataacag    8520
```

```
ttcaatgcgt tgttactctg aaattcttac ctatctaatt acgtctcaag ggcataaatt    8580
aaatatcaac attccctcac ctcttgcaga tattaagaag ctaaatgatg aggtaagtag    8640
taacagggaa aaggtaaaaa atgagagata ctctcagagg ttaaactcac cagatattaa    8700
cgatgcagaa gctaccatac tcgaatctaa agagcaaaaa atcggattga ctctcaatga    8760
gagatgcacc ctagaaaagc ataaagttaa gaagcggtat gggaatgtaa agatggatat    8820
tctcaccttt gatgatgatg gactataccc caaactcaga ctattttatt acctcaccat    8880
cggtaaacct catctcaagg ctaatgacag aaaagctatt gccaaaatgg gcaatgacaa    8940
taaaggcaag attctatcaa aagacttagt taataaaact tactccgctc gtgtgaaggt    9000
cttagagatt cttaaactaa ctgactttat cgacaatctt agagatgaac tcttaataac    9060
tcccaataat ccagctatca ccgattttaa taatcttctg ctaagagcta agaaggattt    9120
aagagtatta ggagtcaaca tcggaaaata tccaatggcc aacattaatg ccgtacttac    9180
tctcattggt cacaaacttt ctgtaatgag agatgagttc ggaaaagaga aaaggataaa    9240
agtagatggt aaatcatacc gatgttatca acttgaaaca ttaccagatt ttaccaatga    9300
tactcttgac tactggttag aaaatgatag ccaaaaagaa gtaacagcaa cagaaaatta    9360
ctccgaaaat tttaaccctt caaatagcta caatccagac agtaagacac tttcagaggg    9420
tgcaaatttc ctatatataa ataaagaaga attgcatcca aataaattgc acctagaaat    9480
aaaagaaggt gctgaacttt ttttattcgg ggtaaaggtg attgtgaaag gaatcttgga    9540
cggggcagta actatattct ctatgggtca agaatacgat ttatccctca atgaactaga    9600
ggggatgtta acatcatgaa ctttacaaga atcttttttaa agggcgatcg caccatgtta    9660
aatgatggta catttgttca gatatttgat atttaccatg accacgcatt gggagtgacc    9720
cttgacctta agacagaaaa aattatttcc gatgatgtta gggtaattac tgtcaaagac    9780
ttattgttcg atggcactta taaggggta aaatctttta tgcccgataa tgcccgataa    9840
tgcccgattg atgctacaaa atcccataat cataagcgat aatcccctaa tagcttgtaa    9900
ttcttgaacc gtagcgattt tagagtattc caaaagaag aaataaacac cgcaaaatgt    9960
cgtatttcac atatataaac caaggttttt tgccctaaaa tctttatgtt tgtagtgtga   10020
tgttgggtca aaatggtcag aaaagttgca aggtttttat ggatgcttac gcgcgcgagg   10080
ggtaagcatc cccaaatagt tactttatcc tagtccatgc ccatttattg ccgtcccgtt   10140
cggctttaaa aaagtgccaa aactcacaag gtgcaataaa aagttctgta cctttcgcaa   10200
ccctagataa tcttttcaaca gttacttttt ttcctattat ctcggtacaa agtttggcta   10260
gtttctcttt tccctctttt tcaatcaagc cttcttgtat gcccaactca ttgattaatc   10320
tctctatttt taccattatt tcccgttcag gtagtttatc ccctaaatct tcatcggggg   10380
gcaatgtagg gcattctgaa ggggcttttt cttctgtctg acattatct aatattgaag   10440
taaccaaact atcttcagtt ttttctattc ctattaattc atattcggtt actgtatccg   10500
tatcaatatc cgaataacta tctttatccg tattagctat tcggttaagt ttatccgtta   10560
actcagaaac aagactatat agcggtttta gcttttcttc tatcctgtta tctaatacgg   10620
ataagtttat acggtatca ttatccgtat tagtatcatt gggcttttt ggtagttcta   10680
ccccctcata aaccgctttt attcccaatt ccaacagact gataacagta tcctttataa   10740
tgggttttttt gctgatatgg tgaacttttg ccccttccat cattgcgata ctttctatct   10800
cactcatcaa cttatcgctt aagtgaatct cgtatctgtt taatccctta ctggttttat   10860
tcatatccgt ttactttatt cggttaacaa ttctatttta tacgaataaa atattatacg   10920
```

| gttaacttta tacgtttaac tattttatct atacggataa cagtaataag ttattcgtat | 10980 |
| tagttatacg tttactttta tccaaataaa attagtgcat ttaaactaaa agaatgattt | 11040 |
| tatcggagtt gatagcattg gattaaccta aagatgttta taagctatat ctgataagta | 11100 |
| tttaaggtta ttttgttatt ctgtttattg acattatcag aataaaagaa tagaatataa | 11160 |
| ttgttgagag ataagaggtt taagtgatta tggttaagaa gttagttggt tatgtcaggg | 11220 |
| tcagtagtga atcgcaagag gataacacta gcttacagaa tcagatagag agaattgaag | 11280 |
| catattgtat ggcttttggt tatgagttgg taaaaatatt caagagggtt gccactggta | 11340 |
| caaaagcaga tattgaaacc cgtcctattt ttaatgaagc tatagaatac ttgaaacagg | 11400 |
| ataatgctaa tggaattatt gccttgaagc tagaccgaat cgcacggaat gctttagatg | 11460 |
| tattgcgttt ggttcgtgaa acctagaac cacaaaataa aatgttagtg ttactagata | 11520 |
| ttcaggtaga tacttcgaca ccttcaggaa aaatgatttt aactgtaatg agtgccgttg | 11580 |
| ctgaactcga aagagacatg atctatgatc gcactcaggg gggtagaaag actaaagccc | 11640 |
| aaaagggcgg gtatgcctac gggaaaccta aatttggcta taagactgaa gaaaaggaac | 11700 |
| taaaagaaga ttcagcacaa caggaaacta ttaaactaat taagagacac cgtaggtcag | 11760 |
| ggaaaagcta ccagaaaata gctgattatc tcaatgccca aagtattccc actaaacaag | 11820 |
| gtaagaaatg gagttctagc gtcgtctatc gaatctgtca ggaaaaagct ggttaagtct | 11880 |
| gtttatagat atttagaatt tattgaataa aaatagtatg aacaataaat atttatggac | 11940 |
| taaccacgct cggaaacgtt taactgaacg atgggaaata aaagaatcat gggttattga | 12000 |
| taccatcgaa aatcctgaac gttcagaatt tattgttgat gagtcagggg aaaaatatca | 12060 |
| ttactataaa agaatagcta agtttaagaa tagagtgtta gaagtgataa cttctgccaa | 12120 |
| ctcaacaccc acaagaataa taacctttta cttaaccgt aacatgagga aaaatttatg | 12180 |
| attgttactt acgataatga agttgacgca atttatttta agttaacgga aaataaaatt | 12240 |
| gatagcaccg aacctcaaac agacaggatt atcattgatt acgatgaaag taataatatt | 12300 |
| gttggcattg aggtattaga ttttaattat cttgtcaaga aaggtttaac cgttgctgat | 12360 |
| ttacctttt ctgaagatga aagattaaca gcttctcaat attttaattt tcctgttgct | 12420 |
| atctaatcca gaagggggcaa taatcccctt cttcatcga gttagactta atatcacaaa | 12480 |
| agtcattttc attttaccgt ttcttttcca cagcgtccgt acgcccctcg ttaaatctca | 12540 |
| aaaccgacaa tttatgatgt ttataaaaag ttactcactt taataagtat ttatactcat | 12600 |
| taaagggtta ttcttttttt gtagcctgat aggttgggaa ggaatatttc agattatcag | 12660 |
| atttgttgaa tattttcgt cagatacgca aaccttacaa acataattaa caactgaaac | 12720 |
| tattgatatg tctaggtttt agctctatca caggttggat ctg | 12763 |

<210> SEQ ID NO 20
<211> LENGTH: 12762
<212> TYPE: DNA
<213> ORGANISM: Artificial Sequence
<220> FEATURE:
<223> OTHER INFORMATION: #1636[\]pABICyano1::PnirA(opt3)-
      zmPDC(opt1)_dsrA-Prbc*(optRBS)-synADH(opt1)_ter

<400> SEQUENCE: 20

| tcgacaatta taacttctt cctgtacggg cgaatggcca tttgctccta actaactccg | 60 |
| tactgctttg cggaacgagc gtagcgaact ctccgaatta ctaagccttc atccctgata | 120 |
| gatgcaaaaa acgcattaaa attatgcgta aaaagcatat ttgtctttat ttagtaatca | 180 |

```
aagttacaaa ttattaagaa tcaaattaat aatatattgg gcagttaagt atataagtct      240
ttaaatattt atttgtattc aatatattaa ccgaggacaa attatgaatt cttataccgt      300
gggtacttat ttagccgaac gcttagtgca aattggttta aacatcatt ttgccgtggc       360 tggggactat aatttagtgt tattggataa cttattatta aataaaaaca tggaacaagt      420
gtattgttgt aatgaattaa attgtggttt ttctgctgaa ggttatgcta gagctaaagg      480
tgcagctgct gctgttgtta cttattctgt gggtgcttta tctgcttttg atgctattgg      540
tggtgcttat gccgaaaatt tacccgtgat tttaatttct ggtgccccta ataataatga      600
tcatgccgct ggacatgttt tacatcatgc cttaggtaaa accgattatc attatcaatt      660
agaaatggcc aaaaatatta ctgctgctgc cgaagctatt tatactcctg aagaagcccc      720
tgccaaaatt gatcatgtga ttaaaaccgc cttacgcgaa aaaaaaccccg tgtatttaga     780 aattgcctgt aatattgctt ctatgccttg tgctgctcct gggcctgctt ctgctttatt      840
taatgatgaa gcctctgatg aagctagttt aaatgctgcc gtggaagaaa ccttaaaatt      900
tattgccaat cgcgataaag ttgccgtgtt agttggttct aaattaagag ctgctggtgc      960
tgaagaagct gctgttaaat ttgctgatgc tttaggtggt gcagttgcta ctatggctgc     1020
tgccaaatct ttttttcccg aagaaaatcc ccattatatt ggaactagtt ggggagaagt     1080
ttcttatcct ggtgtggaaa aaactatgaa agaagccgac gctgttattg ctttagcccc     1140
tgtgtttaat gattattcta ccactggttg gactgatatt cccgatccca aaaaattagt     1200
tttagccgaa cctcgttctg ttgttgttaa tggtgttcgc tttccctctg tgcatttaaa     1260
agattattta acccgcttag cccaaaaagt ttctaaaaaa actggtgcct tagatttttt     1320
taaatcttta aatgcgggtg aattaaaaaa agctgctcct gctgatcctt ctgctccttt     1380
agttaatgct gaaattgccc gtcaagttga agccttatta accctaata ctaccgttat      1440 tgccgaaact ggtgattctt ggtttaatgc ccaacgcatg aaattaccta atggtgcccg     1500
tgttgaatat gaaatgcaat ggggtcatat tggttggtct gtacctgctg cttttggtta     1560
tgctgttggt gctcctgaac gtcgtaatat tttaatggtg ggtgatggtt cttttcaatt     1620
aactgcccaa gaagttgccc aaatggttcg cttaaaatta cccgttatta tttttttaat     1680
aaataattat ggttataccaa ttgaagtgat gattcatgat gggccatata ataatattaa     1740
aaattgggat tatgcgggtt taatggaagt gtttaatggt aatggtggtt atgattctgg     1800
tgctggtaaa ggtttaaaag ccaaaactgg tgtgaatta gctgaagcta ttaaagttgc      1860
cttagccaat actgatgggc caaccttaat tgaatgtttt attggtcgcg aagattgtac      1920
cgaagaatta gttaaatggg gtaaacgtgt tgctgctgct aattctcgca aacccgtgaa     1980
taaattattg taattttggg ggatcaattc gagctcagca agtttcatcc cgacccctc      2040 agggtcggga ttttttttatt gtactagttg acataagtaa aggcatcccc tgcgtgatat     2100
aattaccttc agtttaagga ggtatacaca tatgattaaa gcctatgctg ccttagaagc      2160
caatggtaaa ttacaaccct tgaatatga tcctggtgct ttaggtgcca atgaagtgga      2220
aattgaagtg caatattgtg gtgtgtgtca ttctgattta tctatgatta ataatgaatg     2280
gggtatttct aattatccct tagttcctgg tcatgaagtt gttggtactg ttgctgctat     2340
gggtgaaggt gttaatcatg tggaagtggg tgatttagtt ggtttaggtt ggcattctgg     2400
ttattgtatg acctgtcatt cttgtttatc tggttatcat aatttatgtg ccactgccga     2460
atctactatt gtgggtcatt atggtggttt tggtgataga gttcgtgcta aaggtgtttc     2520
```

```
tgtggtgaaa ttacccaaag gtattgattt agcctctgct gggcctttat tttgtggtgg    2580
tattaccgtt ttttctccca tggtggaatt atctttaaaa cctaccgcca aagttgctgt    2640
tattggtatt ggtggtttag gtcatttagc cgttcaattt ttaagagcct ggggttgtga    2700
agttactgct tttacctctt ctgcccgtaa acaaaccgaa gttttagaat taggtgccca    2760
tcatatttta gattctacca atcctgaagc tattgcttct gccgaaggta aatttgatta    2820
tattatttct accgtgaatt taaaattaga ttggaattta tatatcagta ccttagcccc    2880
tcaaggtcat tttcattttg ttggtgtggt gttagaaccc ttggacttaa acttatttcc    2940
cttattaatg ggacaacgtt ctgtttctgc ttctcctgtt ggttctcctg ctactattgc    3000
cactatgtta gattttgccg tgcgtcatga tattaaaccc gtggtggaac aatttttcttt   3060 tgatcaaatt aatgaagcca ttgcccattt agaatctggt aaagcccatt atcgcgtggt    3120
gttatctcat tctaaaaatt aataagatta acttctaaac tgaaacaaat ttgagggtag    3180
gcttcattgt ctgcccttat tttttttattt aggaaaagtg aacagactaa agagtgttgg   3240
ctctattgct ttgagtatgt aaattaggcg ttgctgaatt aaggtatgat ttttgacccc    3300
ttctctcttc tgcaggatca tcttgctgaa aaactcgagc gctcgttccg caaagcggta    3360
cggagttagt taggggctaa tgggcattct cccgtacagg aaagagttag aagttattaa    3420
ttatcaacaa ttctccttt cctagtgcat cgttacctt ttaattaaaa cataaggaaa    3480
actaataatc gtaataattt aacctcaaag tgtaaagaaa tgtgaaattc tgactttat    3540 aacgttaaag agggaaaaat tagcagttta aaatacctag agaatagtct ggggtaagca    3600
tagagaatta gattagttaa gttaatcaaa ttcagaaaaa ataataatcg taaatagtta    3660
atctgggtgt atagaaaatg atccccttca tgataagatt taaactcgaa aagcaaaagc    3720
caaaaaacta acttccatta aaagaagttg ttacatataa cgctataaag aaaatttata    3780
tatttggagg ataccaacca tgtctcatat tcaacgtgaa actagttgtt ctcgccctcg    3840
tttaaattct aatatggatg ccgatttata tggttataaa tgggctcgtg ataatgttgg    3900
tcaatctggt gctactattt atcgtttata tggtaaacct gatgctcctg aattattctt    3960
gaaacatggt aaaggttctg ttgctaatga tgttactgat gaaatggttc gtttaaactg    4020
gttgactgaa tttatgcctt tacctactat taaacatttt attcgtactc ccgatgatgc    4080
ttggttatta actactgcta ttcctggtaa aactgctttt caagttttag aagaatatcc    4140
tgattctggt gaaaatattg ttgatgcttt agctgtttttt ttacgtcgtt tacattctat   4200 tcccgttgt aattgtccctt ttaattctga tcgtgttttt cgtttagctc aagctcaatc    4260
tcgtatgaat aatggtttag ttgatgcttc tgattttgat gatgaacgta atggttggcc    4320
tgttgaacaa gtttggaaag aaatgcacaa attgttacct ttttctcctg attctgttgt    4380
tactcatggt gattttttctt tagataattt gatctttgat gaaggtaaat tgattggttg    4440
tattgatgtt ggtcgtgttg gtattgctga tcgttatcaa gatttagcta ttttatggaa    4500
ttgtttaggt gaattttctc cttctttaca gaaacgttta tttcagaaat atggtattga    4560
taatcctgat atgaacaagt tacaatttca tttaatgttg gacgagttct tttaagaatt    4620
aattcatgac caaaatccct taacgtgagt tttcgttcca ctgagcgtca gaccccgtag    4680
aaaagatcaa aggatcttct tgagatcctt ttttctgcg cgtaatctgc tgctatttaa    4740
attacgtaca cgtgttatta ctttgttaac gacaattgtc ttaattaact gggcctcatg    4800
ggccttccgc tcactgcccg ctttccagtc gggaaacctg tcgtgccagc tctgcagatg    4860
acggtgaaaa cctctgacac atgcagctcc cggagacggt cacagcttgt ctgtaagcgg    4920
```

```
atgccggag cagacaagcc cgtcagggcg cgtcagcggg tgttggcggg tgtcggggcg     4980
cagccatgac ccagtcacgt agcgatagcg gagtgtatac tggcttaact atgcggcatc     5040
agagcagatt gtactgagag tgcaccatat gcggtgtgaa ataccgcaca gatgcgtaag     5100
gagaaaatac cgcatcaggc gctcttccgc ttcctcgctc actgactcgc tgcgctcggt     5160
cgttcggctg cggcgagcgg tatcagctca ctcaaaggcg gtaatacggt tatccacaga     5220
atcaggggat aacgcaggaa agaacatgtg agcaaaaggc cagcaaaagg ccaggaaccg     5280
taaaaaggcc gcgttgctgg cgttttccca taggctccgc cccctgacg agcatcacaa      5340 aaatcgacgc tcaagtcaga ggtggcgaaa cccgacagga ctataaagat accaggcgtt     5400 tcccctgga agctccctcg tgcgctctcc tgttccgacc ctgccgctta ccggatacct      5460
gtccgccttt ctcccttcgg gaagcgtggc gctttctcat agctcacgct gtaggtatct     5520
cagttcggtg taggtcgttc gctccaagct gggctgtgtg cacgaacccc ccgttcagcc     5580
cgaccgctgc gccttatccg gtaactatcg tcttgagtcc aacccggtaa gacacgactt     5640
atcgccactg gcagcagcca ctggtaacag gattagcaga gcgaggtatg taggcggtgc     5700
tacagagttc ttgaagtggt ggcctaacta cggctacact agaaggacag tatttggtat     5760
ctgcgctctg ctgaagccag ttaccttcgg aaaaagagtt ggtagctctt gatccggcaa     5820
acaaaccacc gctggtagcg gtggtttttt tgtttgcaag cagcagatta cgcgcagaaa     5880
aaaaggatct caagaagatc ctttgatctt ttctactgca gaagcttgtt agacaccctg     5940
tcatgtattt tatattattt atttcaccat acggattaag tgaaacctaa tgaaaatagt     6000
actttcggag ctttaacttt aatgaaggta tgttttttta tagacatcga tgtctggttt     6060
aacaatagga aaagtagct aaaactccca tgaattaaag aaataacaag gtgtctaaca      6120
acctgttatt aagaatgtta gaaaagactt aacatttgtg ttgagttttt atagacattg     6180
gtgtctagac atacggtaga taaggtttgc tcaaaaataa aataaaaaaa gattggacta     6240
aaaaacattt aatttagtac aatttaatta gttatttttt cgtctcaaat tttgctttgt     6300
tgagcagaaa tttagataaa aaaatccccg tgatcagatt acaatgtcgt tcattgtacg     6360
atgtgtcgaa aaatctttac gacactctaa actgaccaca cggggaaaa agaaaactga      6420 actaataaca tcatgatact cggaaaacct agcaattctc aaccctaaa caaaagaaac      6480 ttccaaaacc ctgaccatat aaaggagtgg caacaatcag caatcagtca agatttgata     6540
gcagaaaatc ttgtatcggt tgctaatggt tttgatgtac tatttatcgg caataaatac     6600
cgaactaaca cgggtgttct gtcacggcac atattaaact cctattctca tttagaagat     6660
ggtggttcgt atggtagaac atttgaccca tttaccaata agaaatgca gtgggttcaa      6720 tttaaaccga atagaccaag aaaaggttct actggtaagg taatcaaata tgaatcgcca     6780 aaggtgaac ctacaagagt tctaatgccg tttgtgccta tgaaaatatg caacggatt       6840 agcgataagt tcgagtacc gattaatccg aaaaaagata ctcacttttg ggaatgggta     6900
aagaataatc catcgatacc gattgccatt acagaaggaa ataaaaaagc taattgccta    6960
ttatcctatg gctatcctgc tattgccttt gtaggcattt ggaacggatt agagaaaata    7020
aatgatttct cgaaggaaaa gcagttaaaa gaggatttga atggttgtt atccaacggc      7080 aaccgaaata ttaatatcat ctttgaccaa gaccagaaac aaaaaactgt aattaatgta     7140
aacaaagcta ttttcgcttt atcttctcta ataagtagaa atggtcataa agttaatatt     7200
gtgcaatggt tgccgtcaaa aggtaaagga atagatgatt atttggtagc tttacctttt    7260
```

```
gagaaaagag aaaatcattt agacaactta attaaaattg caccatcatt taattttttgg    7320
tcaactaaat acttattcaa gtgtcgtaaa ccagatttaa ccgtaaattg ccgttatttg    7380
agcgatgcag taaaagaatt acctcaagag gatatagcat taatagcacc tcacggcacg    7440
ggtaaaactt cattagtagc tactcacgtt aagaatcgga gttatcacgg aaggaaaact    7500
atttcattgg tgcatcttga aagtttagcc aaagctaatg gcaacgcact tggattatat    7560
taccgaaccg aaaataatat tgaaaagcaa tatcttggat ttagcttatg tgtagatagt    7620
tgccgtgata agattaacgg cattacaact gatattattt caggtcaaga ttattgcctt    7680
ttcattgatg aaattgacca agtaattcca cacatcctta acagtgaaac tgaagtaagt    7740
aagtatagat gcaccatcat tgacactttt tctgaactgg tgagaaatgc tgaacaggtc    7800
attattgctg atgctgattt atccgatgtg acgattgacc taatagaaaa catcagaggt    7860
aaaaaactat atgtaatcaa gaatgaatat cagtatcagg gaatgacttt taacgccgtt    7920
ggttcaccat tagaaatgat ggcaatgatg ggaaaatcgg tgtcagaagg caagaaatta    7980
tttattaaca ccacatccca aaaggcaaaa agtaagtacg gcacaatcgc tcttgagtct    8040
tatatttttg gtctaaataa agaagcaaag atattaagaa tagactctga aaccactaaa    8100
aaccctgaac atccagccta taaatcatt gaccaagact taaataatat cctcaaagat    8160
tatgattatg tcattgcctc accttgcctt caaacaggtg tcagtattac cttaaagggg    8220
cattttgacc agcaatttaa cttttccagt ggaaacatta cacctcattg ctttttacag    8280
caaatgtggc ggttgaggga tgcagaaatt gaaagattct attatgtgcc gaactcatct    8340
aacctcaatc tcattgggaa taagtcaagt tcaccatcag accttctaaa gagcaataac    8400
aagatggcaa cggcaacggt taaccttttg ggtagaatcg actccgaata ttccctagag    8460
tatgaatcgc acggcatttg gcttgagacg tgggcaaaat tatcagcacg gcataacagt    8520
tcaatgcgtt gttactctga aattcttacc tatctaatta cgtctcaagg gcataaatta    8580
aatatcaaca ttccctcacc tcttgcagat attaagaagc taaatgatga ggtaagtagt    8640
aacagggaaa aggtaaaaaa tgagagatac tctcagaggt taaactcacc agatattaac    8700
gatgcagaag ctaccatact cgaatctaaa gagcaaaaaa tcggattgac tctcaatgag    8760
agatgcaccc tagaaaagca taaagttaag aagcggtatg ggaatgtaaa gatggatatt    8820
ctcacctttg atgatgatgg actataccc aaactcagac tatttttatta cctcaccatc    8880
ggtaaacctc atctcaaggc taatgacaga aaagctattg ccaaaatggg caatgacaat    8940
aaaggcaaga ttctatcaaa agacttagtt aataaaactt actccgctcg tgtgaaggtc    9000
ttagagattc ttaaactaac tgactttatc gacaatctta gagatgaact cttaataact    9060
cccaataatc cagctatcac cgattttaat aatcttctgc taagagctaa gaaggattta    9120
agagtattag gagtcaacat cggaaaatat ccaatggcca acattaatgc cgtacttact    9180
ctcattggtc acaaactttc tgtaatgaga tgagttcg gaaaagagaa aaggataaaa    9240
gtagatggta atcataccg atgttatcaa cttgaaacat taccagattt taccaatgat    9300
actcttgact actggttaga aaatgatagc caaaagaag taacagcaac agaaaattac    9360
tccgaaaatt ttaaccccttc aaatagctac aatccagaca gtaagacact ttcagagggt    9420
gcaaatttcc tatatataaa taaagaagaa ttgcatccaa ataaattgca cctagaaata    9480
aaagaaggtg ctgaactttt tttattcggg gtaaaggtga ttgtgaaagg aatcttggac    9540
ggggcagtaa ctatattctc tatgggtcaa gaatacgatt tatccctcaa tgaactagag    9600
gggatgttaa catcatgaac tttacaagaa tcttttaaa gggcgatcgc accatgttaa    9660
```

```
atgatggtac atttgttcag atatttgata tttaccatga ccacgcattg ggagtgaccc    9720
ttgaccttaa gacagaaaaa attatttccg atgatgttag ggtaattact gtcaaagact    9780
tattgttcga tggcacttat aaaggggtaa aatcttttat gcccgataat gcccgataat    9840
gcccgattga tgctacaaaa tcccataatc ataagcgata atcccctaat agcttgtaat    9900
tcttgaaccg tagcgatttt agagtattcc aaaagaaga aataaacacc gcaaaatgtc    9960
gtatttcaca tatataaacc aaggtttttt gccctaaaat ctttatgttt gtagtgtgat   10020
gttgggtcaa aatggtcaga aaagttgcaa ggttttttatg gatgcttacg cgcgcgaggg   10080
gtaagcatcc ccaaatagtt actttatcct agtccatgcc catttattgc cgtcccgttc   10140
ggctttaaaa aagtgccaaa actcacaagg tgcaataaaa agttctgtac ctttcgcaac   10200
cctagataat ctttcaacag ttactttttt tcctattatc tcggtacaaa gtttggctag   10260
tttctctttt ccctcttttt caatcaagcc ttcttgtatg cccaactcat tgattaatct   10320
ctctatttt accattattt cccgttcagg tagtttatcc cctaaatctt catcgggggg   10380
caatgtaggg cattctgaag gggcttttc ttctgtctgg acattatcta atattgaagt   10440
aaccaaacta tcttcagttt tttctattcc tattaattca tattcggtta ctgtatccgt   10500
atcaatatcc gaataactat ctttatccgt attagctatt cggttaagtt tatccgttaa   10560
ctcagaaaca agactatata gcggttttag cttttcttct atcctgttat ctaatacgga   10620
taagtttata cggttatcat tatccgtatt agtatcattg ggcttttttg gtagttctac   10680
cccctcataa accgcttta ttcccaattc aacagactg ataacagtat cctttataat   10740
gggtttttg ctgatatggt gaacttttgc cccttccatc attgcgatac tttctatctc   10800
actcatcaac ttatcgctta agtgaatctc gtatctgttt aatcccttac tggttttatt   10860
catatccgtt tactttattc ggttaacaat tctattttat acgaataaaa tattatacgg   10920
ttaactttat acgtttaact attttatcta tacggataac agtaataagt tattcgtatt   10980
agttatacgt ttacttttat ccaaataaaa ttagtgcatt taaactaaaa gaatgatttt   11040
atcggagttg atagcattgg attaacctaa agatgtttat aagctatatc tgataagtat   11100
ttaaggttat tttgttattc tgtttattga cattatcaga ataaagaat agaatataat   11160
tgttgagaga taagaggttt aagtgattat ggttaagaag ttagttggtt atgtcagggt   11220
cagtagtgaa tcgcaagagg ataacactag cttacagaat cagatagaga gaattgaagc   11280
atattgtatg gcttttggtt atgagttggt aaaaatattc aaagaggttg ccactggtac   11340
aaaagcagat attgaaaccc gtcctatttt taatgaagct atagaatact gaaacagga   11400
taatgctaat ggaattattg ccttgaagct agaccgaatc gcacggaatg ctttagatgt   11460
attgcgtttg gttcgtgaaa ccttagaacc acaaataaa atgttagtgt tactagatat   11520
tcaggtagat acttcgacac cttcaggaaa aatgatttta actgtaatga gtgccgttgc   11580
tgaactcgaa agagacatga tctatgatcg cactcagggg ggtagaaaga ctaaagccca   11640
aaagggcggg tatgcctacg ggaaacctaa atttggctat aagactgaag aaaaggaact   11700
aaaagaagat tcagcacaac aggaaactat taaactaatt aagagacacc gtaggtcagg   11760
gaaaagctac cagaaaatag ctgattatct caatgcccaa agtattccca ctaaacaagg   11820
taagaaatgg agttctagcg tcgtctatcg aatctgtcag gaaaaagctg ttaagtctg   11880
tttatagata tttagaattt attgaataaa aatagtatga acaataaata tttatggact   11940
aaccacgctc ggaaacgttt aactgaacga tgggaaataa aagaatcatg ggttattgat   12000
```

```
accatcgaaa atcctgaacg ttcagaattt attgttgatg agtcagggga aaaatatcat    12060
tactataaaa gaatagctaa gtttaagaat agagtgttag aagtgataac ttctgccaac    12120
tcaacaccca caagaataat aacctttac tttaaccgta acatgaggaa aaatttatga     12180
ttgttactta cgataatgaa gttgacgcaa tttattttaa gttaacggaa ataaaaattg    12240
atagcaccga acctcaaaca gacaggatta tcattgatta cgatgaaagt aataatattg    12300
ttggcattga ggtattagat tttaattatc ttgtcaagaa aggtttaacc gttgctgatt    12360
tacctttttc tgaagatgaa agattaacag cttctcaata ttttaatttt cctgttgcta    12420
tctaatccag aaggggcaat aatccccttc tttcatcgag ttagacttaa tatcacaaaa    12480
gtcattttca ttttaccgtt tcttttccac agcgtccgta cgcccctcgt taaatctcaa    12540
aaccgacaat ttatgatgtt tataaaaagt tactcacttt aataagtatt tatactcatt    12600
aaagggttat tcttttttg tagcctgata ggttgggaag gaatatttca gattatcaga     12660
tttgttgaat atttttcgtc agatacgcaa accttacaaa cataattaac aactgaaact    12720
attgatatgt ctaggtttta gctctatcac aggttggatc tg                      12762
```

<210> SEQ ID NO 21
<211> LENGTH: 13726
<212> TYPE: DNA
<213> ORGANISM: Artificial Sequence
<220> FEATURE:
<223> OTHER INFORMATION: #1630[\]pABICyano1::corR-PcorT*1-
      zmPDC(opt1)_dsrA-Prbc*(optRBS)-synADH(opt1)_ter

<400> SEQUENCE: 21

```
tcgaccatgc gtccaaaact ttcaccatcc tttccctatc aacctttact gcactaaaga     60
caagtgagat agcagtggca atctggcttt gcaatcaatg tttccactaa agcgtttagc    120
gttactgcgg ctagaagtcc tccaccgagg ctcccctgaa tggtgatatg gggaatggga    180
ctggtcatca gtcgtcgttt tgcccccgga gcatgactaa aaccgatcgg cattccgatc    240
acaagagccg gctgaatatg ttgttgctct atcagcttac aggcagtgag taaaacagaa    300
ggggcatagc cgatcgccag cacacatcct tggggaatct gttgtaaccg ctgttgccaa    360
tggtcatggt gccaaaaagc ttgctcggct tccctaagcc ctgtgatgtg agggtcgtca    420
atcagcgttt taaccgtaca tcctaaatga gctaaccgag tttgatcaag agccgcagcc    480
acaaccggaa catcggtgac gactggacac cctgctttca gtgcatctcg tgccgaggcg    540
atcgctccct gactcaatcg aacggcgttt accaagctaa catcaccaca ggccagcact    600
aattgatgta gtaagtgaat ggtaatttca gagtaagccg ataaatccgg tagcaggtgt    660
ttgagggatt cctgaaaggc ttctggatga gttgttgtct ccgcatctag gttcgtccac    720
aactgatcga gttttcctaa cccctcctgg acatccacat caagctgttt cagttgggcc    780
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc    1020
tgctgagtat aaaggcggta gttgccctct gagcgttgaa cgggggggaag caatcccagg   1080 gtgtggtaat ggcgcaccat gcgaggcgta acgccacctc ccactgcatc tgtgagttct    1140
ttaatcgtta agtgattagt cttcatgact ttagtttact caaaaccttg acattgacac    1200
taatgttaag gtttaggctg agaaggtaaa aatcgaggat aaaaagcatg aattcttata    1260
```

```
ccgtgggtac ttatttagcc gaacgcttag tgcaaattgg tttaaaacat cattttgccg    1320
tggctgggga ctataattta gtgttattgg ataacttatt attaaataaa acatggaac    1380
aagtgtattg ttgtaatgaa ttaaattgtg gttttttctgc tgaaggttat gctagagcta   1440
aaggtgcagc tgctgctgtt gttacttatt ctgtgggtgc tttatctgct tttgatgcta   1500
ttggtggtgc ttatgccgaa aatttacccg tgattttaat ttctggtgcc cctaataata   1560
atgatcatgc cgctggacat gttttacatc atgccttagg taaaaccgat tatcattatc   1620
aattagaaat ggccaaaaat attactgctg ctgccgaagc tatttatact cctgaagaag   1680
cccctgccaa aattgatcat gtgattaaaa ccgccttacg cgaaaaaaaa cccgtgtatt   1740
tagaaattgc ctgtaatatt gcttctatgc cttgtgctgc tcctgggcct gcttctgctt   1800
tatttaatga tgaagcctct gatgaagcta gtttaaatgc tgccgtggaa gaaaccttaa   1860
aatttattgc caatcgcgat aaagttgccg tgttagttgg ttctaaatta agagctgctg   1920
gtgctgaaga agctgctgtt aaatttgctg atgcttagg tggtgcagtt gctactatgg    1980
ctgctgccaa atcttttttt cccgaagaaa atccccatta tattggaact agttggggag   2040
aagtttctta tcctggtgtg gaaaaaacta tgaaagaagc cgacgctgtt attgctttag   2100
cccctgtgtt taatgattat tctaccactg gttggactga tattcccgat cccaaaaaat   2160
tagttttagc cgaacctcgt tctgttgttg ttaatggtgt tcgctttccc tctgtgcatt   2220
taaaagatta tttaacccgc ttagcccaaa aagtttctaa aaaaactggt gccttagatt   2280
tttttaaatc tttaaatgcg ggtgaattaa aaaagctgc tcctgctgat ccttctgctc    2340
ctttagttaa tgctgaaatt gcccgtcaag ttgaagcctt attaaccccet aatactaccg   2400
ttattgccga aactggtgat tcttggttta atgcccaacg catgaaatta cctaatggtg   2460
cccgtgttga atatgaaatg caatggggtc atattggttg gtctgtacct gctgcttttg   2520
gttatgctgt tggtgctcct gaacgtcgta atattttaat ggtgggtgat ggttcttttc   2580
aattaactgc ccaagaagtt gcccaaatgg ttcgcttaaa attacccgtt attatttttt   2640
taataaataa ttatggttat accattgaag tgatgattca tgatgggcca tataataata   2700
ttaaaaattg ggattatgcg ggtttaatgg aagtgtttaa tggtaatggt ggttatgatt   2760
ctggtgctgg taaaggttta aaagccaaaa ctggtggtga attagctgaa gctattaaag   2820
ttgccttagc caatactgat gggccaacct taattgaatg ttttattggt cgcgaagatt   2880
gtaccgaaga attagttaaa tggggtaaac gtgttgctgc tgctaattct cgcaaacccg   2940
tgaataaatt attgtaattt ttggggatca attcgagctc agcaagtttc atcccgaccc   3000
cctcagggtc gggattttt tattgtacta gttgacataa gtaaaggcat cccctgcgtg    3060
atataattac cttcagttta aggaggtata cacatatgat taaagcctat gctgccttag   3120
aagccaatgg taaattacaa cccttttgaat atgatcctgg tgctttaggt gccaatgaag   3180
tggaaattga agtgcaatat tgtggtgtgt gtcattctga tttatctatg attaataatg   3240
aatggggtat ttctaattat ccccttagttc ctggtcatga agttgttggt actgttgctg   3300
ctatgggtga aggtgttaat catgtggaag tgggtgattt agttggttta ggttggcatt   3360
ctggttattg tatgacctgt cattcttgtt tatctggtta tcataattta tgtgccactg   3420
ccgaatctac tattgtgggt cattatggtg gttttggtga tagagttcgt gctaaaggtg   3480
tttctgtggt gaaattaccc aaaggtattg atttagcctc tgctgggcct ttattttgtg   3540
gtggtattac cgtttttttct cccatggtgg aattatcttt aaaacctacc gccaaagttg   3600
ctgttattgg tattggtggt ttaggtcatt tagccgttca attttttaaga gcctggggtt   3660
```

```
gtgaagttac tgcttttacc tcttctgccc gtaaacaaac cgaagtttta gaattaggtg   3720
cccatcatat tttagattct accaatcctg aagctattgc ttctgccgaa ggtaaatttg   3780
attatattat ttctaccgtg aatttaaaat tagattggaa tttatatatc agtaccttag   3840
cccctcaagg tcattttcat tttgttggtg tggtgttaga acccttggac ttaaacttat   3900
ttcccttatt aatgggacaa cgttctgttt ctgcttctcc tgttggttct cctgctacta   3960
ttgccactat gttagatttt gccgtgcgtc atgatattaa acccgtggtg gaacaatttt   4020
cttttgatca aattaatgaa gccattgccc atttagaatc tggtaaagcc cattatcgcg   4080
tggtgttatc tcattctaaa aattaataag attaacttct aaactgaaac aaatttgagg   4140
gtaggcttca ttgtctgccc ttattttttt atttaggaaa agtgaacaga ctaaagagtg   4200
ttggctctat tgctttgagt atgtaaatta ggcgttgctg aattaaggta tgattttga    4260
cccccttctct cttctgcagg atcatcttgc tgaaaaactc gagcgctcgt tccgcaaagc   4320
ggtacggagt tagttagggg ctaatgggca ttctcccgta caggaaagag ttagaagtta   4380
ttaattatca acaattctcc tttgcctagt gcatcgttac ctttttaatt aaaacataag   4440
gaaaactaat aatcgtaata atttaacctc aaagtgtaaa gaaatgtgaa attctgactt   4500
ttataacgtt aaagagggaa aaattagcag tttaaaatac ctagagaata gtctggggta   4560
agcatagaga attagattag ttaagttaat caaattcaga aaaataata atcgtaaata    4620
gttaatctgg gtgtatagaa aatgatcccc ttcatgataa gatttaaact cgaaaagcaa   4680
aagccaaaaa actaacttcc attaaaagaa gttgttacat ataacgctat aaagaaaatt   4740
tatatatttg gaggatacca accatgtctc atattcaacg tgaaactagt tgttctcgcc   4800
ctcgttaaaa ttctaatatg gatgccgatt tatatggtta taaatgggct cgtgataatg   4860
ttggtcaatc tggtgctact atttatcgtt tatatggtaa acctgatgct cctgaattat   4920
tcttgaaaca tggtaaaggt tctgttgcta atgatgttac tgatgaaatg gttcgtttaa   4980
actggttgac tgaatttatg cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt ttttttacgt cgtttacatt   5160
ctattcccgt ttgtaattgt ccttttaatt ctgatcgtgt ttttcgttta gctcaagctc   5220
aatctcgtat gaataatggt ttagttgatg cttctgattt tgatgatgaa cgtaatggtt   5280
ggcctgttga acaagtttgg aaagaaatgc acaaattgtt accttttttct cctgattctg   5340
ttgttactca tggtgatttt tctttagata atttgatctt tgatgaaggt aaattgattg   5400
gttgtattga tgttggtcgt gttggtattg ctgatcgtta tcaagattta gctattttat   5460
ggaattgttt aggtgaattt tctccttctt tacagaaacg tttatttcag aaatatggta   5520
ttgataatcc tgatatgaac aagttacaat ttcatttaat gttggacgag ttctttttaag   5580
aattaattca tgaccaaaat cccttaacgt gagttttcgt tccactgagc gtcagacccc   5640
gtagaaaaga tcaaaggatc ttcttgagat cctttttttc tgcgcgtaat ctgctgctat   5700
ttaaattacg tacacgtgtt attactttgt taacgacaat tgtcttaatt aactgggcct   5760
catgggcctt ccgctcactg cccgctttcc agtcgggaaa cctgtcgtgc cagctctgca   5820
gatgacggtg aaaacctctg acacatgcag ctcccggaga cggtcacagc ttgtctgtaa   5880
gcggatgccg ggagcagaca agcccgtcag ggcgcgtcag cgggtgttgg cgggtgtcgg   5940
ggcgcagcca tgacccagtc acgtagcgat agcggagtgt atactggctt aactatgcgg   6000
```

```
catcagagca gattgtactg agagtgcacc atatgcggtg tgaaataccg cacagatgcg    6060
taaggagaaa ataccgcatc aggcgctctt ccgcttcctc gctcactgac tcgctgcgct    6120
cggtcgttcg gctgcggcga gcggtatcag ctcactcaaa ggcggtaata cggttatcca    6180
cagaatcagg ggataacgca ggaaagaaca tgtgagcaaa aggccagcaa aaggccagga    6240
accgtaaaaa ggccgcgttg ctggcgtttt tccataggct ccgcccccct gacgagcatc    6300
acaaaaatcg acgctcaagt cagaggtggc gaaacccgac aggactataa agataccagg    6360
cgtttccccc tggaagctcc ctcgtgcgct ctcctgttcc gaccctgccg cttaccggat    6420
acctgtccgc ctttctccct tcgggaagcg tggcgctttc tcatagctca cgctgtaggt    6480
atctcagttc ggtgtaggtc gttcgctcca agctgggctg tgtgcacgaa ccccccgttc    6540
agcccgaccg ctgcgcctta tccggtaact atcgtcttga gtccaacccg gtaagacacg    6600
acttatcgcc actggcagca gccactggta acaggattag cagagcgagg tatgtaggcg    6660
gtgctacaga gttcttgaag tggtggccta actacggcta cactagaagg acagtatttg    6720
gtatctgcgc tctgctgaag ccagttacct tcggaaaaag agttggtagc tcttgatccg    6780
gcaaacaaac caccgctggt agcggtggtt tttttgtttg caagcagcag attacgcgca    6840
gaaaaaaagg atctcaagaa gatcctttga tcttttctac tgcagaagct tgttagacac    6900
cctgtcatgt attttatatt atttatttca ccatacggat taagtgaaac ctaatgaaaa    6960
tagtactttc ggagctttaa ctttaatgaa ggtatgtttt tttatagaca tcgatgtctg    7020
gtttaacaat aggaaaaagt agctaaaact cccatgaatt aaagaaataa caaggtgtct    7080
aacaacctgt tattaagaat gttagaaaag acttaacatt tgtgttgagt ttttatagac    7140
attggtgtct agacatacgg tagataaggt ttgctcaaaa ataaaataaa aaagattgg    7200 actaaaaaac atttaattta gtacaattta attagttatt ttttcgtctc aaattttgct    7260
ttgttgagca gaaatttaga taaaaaaatc cccgtgatca gattacaatg tcgttcattg    7320
tacgatgtgt cgaaaaatct ttacgacact ctaaactgac cacacggggg aaaaagaaaa    7380
ctgaactaat aacatcatga tactcggaaa acctagcaat tctcaacccc taaacaaaag    7440
aaacttccaa aaccctgacc atataaagga gtggcaacaa tcagcaatca gtcaagattt    7500
gatagcagaa aatcttgtat cggttgctaa tggttttgat gtactattta tcggcaataa    7560
ataccgaact aacacgggtg ttctgtcacg gcacatatta aactcctatt ctcatttaga    7620
agatggtggt tcgtatggta gaacatttga cccatttacc aataaagaaa tgcagtgggt    7680
tcaatttaaa ccgaatagac caagaaaagg ttctactggt aaggtaatca aatatgaatc    7740
gccaaaaggt gaacctacaa gagttctaat gccgtttgtg cctatgaaaa tatggcaacg    7800
gattagcgat aagttcggag taccgattaa tccgaaaaaa gatactcact tttgggaatg    7860
ggtaaagaat aatccatcga taccgattgc cattacagaa ggaaataaaa aagctaattg    7920
cctattatcc tatggctatc ctgctattgc ctttgtaggc atttggaacg gattagagaa    7980
aataaatgat ttctcgaagg aaaagcagtt aaaagaggat ttgaaatggt tgttatccaa    8040
cggcaaccga atattaata tcatctttga ccaagaccag aaacaaaaaa ctgtaattaa    8100
tgtaaacaaa gctattttcg ctttatcttc tctaataagt agaaatggtc ataaagttaa    8160
tattgtgcaa tggttgccgt caaaaggtaa aggaatagat gattatttgg tagctttacc    8220
ttttgagaaa agagaaaatc atttagacaa cttaattaaa attgcaccat catttaattt    8280
ttggtcaact aaatacttat tcaagtgtcg taaaccagat ttaaccgtaa attgccgtta    8340
tttgagcgat gcagtaaaag aattaccctca agaggatata gcattaatag cacctcacgg    8400
```

```
cacgggtaaa acttcattag tagctactca cgttaagaat cggagttatc acggaaggaa    8460
aactatttca ttggtgcatc ttgaaagttt agccaaagct aatggcaacg cacttggatt    8520
atattaccga accgaaaata atattgaaaa gcaatatctt ggatttagct tatgtgtaga    8580
tagttgccgt gataagatta acggcattac aactgatatt atttcaggtc aagattattg    8640
ccttttcatt gatgaaattg accaagtaat tccacacatc cttaacagtg aaactgaagt    8700
aagtaagtat agatgcacca tcattgacac tttttctgaa ctggtgagaa atgctgaaca    8760
ggtcattatt gctgatgctg atttatccga tgtgacgatt gacctaatag aaaacatcag    8820
aggtaaaaaa ctatatgtaa tcaagaatga atatcagtat cagggaatga cttttaacgc    8880
cgttggttca ccattagaaa tgatggcaat gatgggaaaa tcggtgtcag aaggcaagaa    8940
attatttatt aacaccacat cccaaaaggc aaaagtaag tacggcacaa tcgctcttga    9000
gtcttatatt tttggtctaa ataaagaagc aaagatatta agaatagact ctgaaaccac    9060
taaaaaccct gaacatccag cctataaaat cattgaccaa gacttaaata atatcctcaa    9120
agattatgat tatgtcattg cctcaccttg ccttcaaaca ggtgtcagta ttaccttaaa    9180 agggcattt gaccagcaat ttaacttttc cagtggaaac attacacctc attgcttttt    9240
acagcaaatg tggcggttga gggatgcaga aattgaaaga ttctattatg tgccgaactc    9300
atctaacctc aatctcattg ggaataagtc aagttcacca tcagaccttc taaagagcaa    9360
taacaagatg gcaacggcaa cggttaacct tttgggtaga atcgactccg aatattccct    9420
agagtatgaa tcgcacggca tttggcttga gacgtgggca aaattatcag cacggcataa    9480
cagttcaatg cgttgttact ctgaaattct tacctatcta attacgtctc aagggcataa    9540
attaaatatc aacattccct cacctcttgc agatattaag aagctaaatg atgaggtaag    9600
tagtaacagg gaaaaggtaa aaaatgagag atactctcag aggttaaact caccagatat    9660
taacgatgca gaagctacca tactcgaatc taaagagcaa aaaatcggat tgactctcaa    9720
tgagagatgc accctagaaa agcataaagt taagaagcgg tatgggaatg taaagatgga    9780
tattctcacc tttgatgatg atggactata ccccaaactc agactatttt attacctcac    9840
catcggtaaa cctcatctca aggctaatga cagaaaagct attgccaaaa tgggcaatga    9900
caataaaggc aagattctat caaaagactt agttaataaa acttactccg ctcgtgtgaa    9960
ggtcttagag attcttaaac taactgactt tatcgacaat cttagagatg aactcttaat   10020
aactcccaat aatccagcta tcaccgattt taataatctt ctgctaagag ctaagaagga   10080
tttaagagta ttaggagtca acatcggaaa atatccaatg ccaacatta atgccgtact    10140 tactctcatt ggtcacaaac tttctgtaat gagagatgag ttcggaaaag agaaaaggat   10200
aaaagtagat ggtaaatcat accgatgtta tcaacttgaa acattaccag attttaccaa   10260
tgatactctt gactactggt tagaaaatga tagccaaaaa gaagtaacag caacagaaaa   10320
ttactccgaa aattttaacc cttcaaatag ctacaatcca gacagtaaga cactttcaga   10380
gggtgcaaat ttcctatata taaataaaga agaattgcat ccaaataaat tgcacctaga   10440
aataaaagaa ggtgctgaac ttttttttatt cggggtaaag gtgattgtga aaggaatctt   10500
ggacggggca gtaactatat tctctatggg tcaagaatac gatttatccc tcaatgaact   10560 agagggatg ttaacatcat gaactttaca agaatctttt taagggcga tcgcaccatg    10620 ttaaatgatg gtacatttgt tcagatattt gatatttacc atgaccacgc attgggagtg   10680
acccttgacc ttaagacaga aaaattatt tccgatgatg ttagggtaat tactgtcaaa   10740
```

```
gacttattgt tcgatggcac ttataaaggg gtaaaatctt ttatgcccga taatgcccga   10800
taatgcccga ttgatgctac aaaatcccat aatcataagc gataatcccc taatagcttg   10860
taattcttga accgtagcga ttttagagta ttccaaaaag aagaaataaa caccgcaaaa   10920
tgtcgtattt cacatatata aaccaaggtt ttttgcccta aaatctttat gtttgtagtg   10980
tgatgttggg tcaaaatggt cagaaaagtt gcaaggtttt tatggatgct tacgcgcgcg   11040
aggggtaagc atccccaaat agttacttta tcctagtcca tgcccattta ttgccgtccc   11100
gttcggcttt aaaaaagtgc caaaactcac aaggtgcaat aaaaagttct gtacctttcg   11160
caaccctaga taatctttca acagttactt tttttcctat tatctcggta caaagtttgg   11220
ctagtttctc ttttccctct ttttcaatca agccttcttg tatgcccaac tcattgatta   11280
atctctctat ttttaccatt atttcccgtt caggtagttt atcccctaaa tcttcatcgg   11340
ggggcaatgt agggcattct gaaggggctt tttcttctgt ctggacatta tctaatattg   11400
aagtaaccaa actatcttca gttttttcta ttcctattaa ttcatattcg gttactgtat   11460
ccgtatcaat atccgaataa ctatctttat ccgtattagc tattcggtta agtttatccg   11520
ttaactcaga aacaagacta tatagcggtt ttagcttttc ttctatcctg ttatctaata   11580
cggataagtt tatacggtta tcattatccg tattagtatc attgggcttt tttggtagtt   11640 ctacccctc ataaaccgct tttattccca attccaacag actgataaca gtatccttta   11700
taatgggttt tttgctgata tggtgaactt ttgccccttc catcattgcg atactttcta   11760
tctcactcat caacttatcg cttaagtgaa tctcgtatct gtttaatccc ttactggttt   11820
tattcatatc cgtttacttt attcggttaa caattctatt ttatacgaat aaaatattat   11880
acggttaact ttatacgttt aactatttta tctatacgga taacagtaat aagttattcg   11940
tattagttat acgtttactt ttatccaaat aaaattagtg catttaaact aaaagaatga   12000
ttttatcgga gttgatagca ttggattaac ctaaagatgt ttataagcta tatctgataa   12060
gtatttaagg ttattttgtt attctgttta ttgacattat cagaataaaa gaatagaata   12120
taattgttga gagataagag gtttaagtga ttatggttaa gaagttagtt ggttatgtca   12180
gggtcagtag tgaatcgcaa gaggataaca ctagcttaca gaatcagata gagagaattg   12240
aagcatattg tatggctttt ggttatgagt tggtaaaaat attcaaagag gttgccactg   12300
gtacaaaagc agatattgaa acccgtccta tttttaatga agctatagaa tacttgaaac   12360
aggataatgc taatggaatt attgccttga agctagaccg aatcgcacgg aatgctttag   12420
atgtattgcg tttggttcgt gaaaccttag aaccacaaaa taaaatgtta gtgttactag   12480
atattcaggt agatacttcg acaccttcag gaaaaatgat tttaactgta atgagtgccg   12540
ttgctgaact cgaaagagac atgatctatg atcgcactca gggggtaga aagactaaag   12600 cccaaaaggg cgggtatgcc tacgggaaac ctaaatttgg ctataagact gaagaaaagg   12660
aactaaaaga agattcagca caacaggaaa ctattaaact aattaagaga caccgtaggt   12720
cagggaaaag ctaccagaaa atagctgatt atctcaatgc ccaaagtatt cccactaaac   12780
aaggtaagaa atggagttct agcgtcgtct atcgaatctg tcaggaaaaa gctggttaag   12840 tctgttata gatatttaga atttattgaa taaaaatagt atgaacaata atatttatg   12900 gactaaccac gctcggaaac gtttaactga acgatgggaa ataaagaat catgggttat   12960 tgataccatc gaaaatcctg aacgttcaga atttattgtt gatgagtcag gggaaaaata   13020
tcattactat aaaagaatag ctaagttaa gaatagagtg ttagaagtga taacttctgc   13080
caactcaaca cccacaagaa taataacctt ttactttaac cgtaacatga ggaaaaattt   13140
```

```
atgattgtta cttacgataa tgaagttgac gcaatttatt ttaagttaac ggaaaataaa    13200
attgatagca ccgaacctca aacagacagg attatcattg attacgatga agtaataat     13260 attgttggca ttgaggtatt agattttaat tatcttgtca agaaaggttt aaccgttgct    13320
gatttacctt tttctgaaga tgaaagatta acagcttctc aatatttaa ttttcctgtt     13380 gctatctaat ccagaagggg caataatccc cttctttcat cgagttagac ttaatatcac    13440
aaaagtcatt tcattttac cgtttctttt ccacagcgtc cgtacgcccc tcgttaaatc     13500
tcaaaaccga caatttatga tgtttataaa agttactca ctttaataag tatttatact     13560
cattaaaggg ttattctttt tttgtagcct gataggttgg gaaggaatat ttcagattat    13620
cagatttgtt gaatattttt cgtcagatac gcaaaccttaa caaacataat taacaactga   13680
aactattgat atgtctaggt tttagctcta tcacaggttg gatctg                   13726
```

<210> SEQ ID NO 22
<211> LENGTH: 13726
<212> TYPE: DNA
<213> ORGANISM: Artificial Sequence
<220> FEATURE:
<223> OTHER INFORMATION: #1631[\]pABICyano1::corR-PcorT*2-
      zmPDC(opt1)_dsrA-Prbc*(optRBS)-synADH(opt1)_ter

<400> SEQUENCE: 22

```
tcgaccatgc gtccaaaact ttaccatcc tttccctatc aacctttact gcactaaaga     60
caagtgagat agcagtggca atctggcttt gcaatcaatg tttccactaa agcgtttagc    120
gttactgcgg ctagaagtcc tccaccgagg ctcccctgaa tggtgatatg gggaatggga    180
ctggtcatca gtcgtcgttt tgccccggga gcatgactaa aaccgatcgg cattccgatc    240
acaagagccg gctgaatatg ttgttgctct atcagcttac aggcagtgag taaaacagaa    300
ggggcatagc cgatcgccag cacacatcct tggggaatct gttgtaaccg ctgttgccaa    360
tggtcatggt gccaaaaagc ttgctcggct tccctaagcc ctgtgatgtg agggtcgtca    420
atcagcgttt taaccgtaca tcctaaatga gctaaccgag tttgatcaag agccgcagcc    480
acaaccggaa catcggtgac gactggacac cctgctttca gtgcatctcg tgccgaggcg    540
atcgctccct gactcaatcg aacggcgttt accaagctaa catcaccaca ggccagcact    600
aattgatgta gtaagtgaat ggtaatttca gagtaagccg ataaatccgg tagcaggtgt    660
ttgagggatt cctgaaaggc ttctggatga gttgttgtct ccgcatctag gttcgtccac    720
aactgatcga gttttcctaa cccctcctgg acatccacat caagctgttt cagttgggcc    780
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc    1020
tgctgagtat aaaggcggta gttgccctct gagcgttgaa cggggggaag caatcccagg    1080
gtgtggtaat ggcgcaccat gcgaggcgta acgccacctc ccactgcatc tgtgagttct    1140
ttaatcgtta agtgattagt cttcatgact ttagtttact caaaaccttg acattgacac    1200
taatgttaag gtttagaatg agaaggtaaa aatccaagtt aaaaagcatg aattcttata    1260
ccgtgggtac ttatttagcc gaacgcttag tgcaaattgg tttaaaacat cattttgccg    1320
tggctgggga ctataattta gtgttattgg ataacttatt attaaataaa acatgaac    1380 aagtgtattg ttgtaatgaa ttaaattgtg gttttctgc tgaaggttat gctagagcta    1440
```

```
aaggtgcagc tgctgctgtt gttacttatt ctgtgggtgc tttatctgct tttgatgcta    1500
ttggtggtgc ttatgccgaa aatttacccg tgattttaat ttctggtgcc cctaataata    1560
atgatcatgc cgctggacat gttttacatc atgccttagg taaaaccgat tatcattatc    1620
aattagaaat ggccaaaaat attactgctg ctgccgaagc tatttatact cctgaagaag    1680
cccctgccaa aattgatcat gtgattaaaa ccgccttacg cgaaaaaaaa cccgtgtatt    1740
tagaaattgc ctgtaatatt gcttctatgc cttgtgctgc tcctgggcct gcttctgctt    1800
tatttaatga tgaagcctct gatgaagcta gtttaaatgc tgccgtggaa gaaaccttaa    1860
aatttattgc caatcgcgat aaagttgccg tgttagttgg ttctaaatta gagctgctg     1920 gtgctgaaga agctgctgtt aaatttgctg atgctttagg tggtgcagtt gctactatgg    1980
ctgctgccaa atcttttttt cccgaagaaa atccccatta tattggaact agttggggag    2040
aagtttctta tcctggtgtg gaaaaaacta tgaaagaagc cgacgctgtt attgctttag    2100
cccctgtgtt taatgattat tctaccactg gttggactga tattcccgat cccaaaaaat    2160
tagttttagc cgaacctcgt tctgttgttg ttaatggtgt tcgctttccc tctgtgcatt    2220
taaaagatta tttaacccgc ttagcccaaa aagtttctaa aaaaactggt gccttagatt    2280
tttttaaatc tttaaatgcg ggtgaattaa aaaagctgc tcctgctgat ccttctgctc     2340
ctttagttaa tgctgaaatt gcccgtcaag ttgaagcctt attacccct aatactaccg      2400 ttattgccga aactggtgat tcttggttta atgcccaacg catgaaatta cctaatggtg    2460
cccgtgttga atatgaaatg caatggggtc atattggttg gtctgtacct gctgcttttg    2520
gttatgctgt tggtgctcct gaacgtcgta atatttaat ggtgggtgat ggttcttttc     2580
aattaactgc ccaagaagtt gcccaaatgg ttcgcttaaa attacccgtt attattttt    2640 taataaataa ttatggttat accattgaag tgatgattca tgatgggcca tataataata    2700
ttaaaaattg ggattatgcg ggtttaatgg aagtgtttaa tggtaatggt ggttatgatt    2760
ctggtgctgg taaaggtta aaagccaaaa ctggtggtga attagctgaa gctattaaag    2820
ttgccttagc caatactgat gggccaacct taattgaatg ttttattggt cgcgaagatt    2880
gtaccgaaga attagttaaa tggggtaaac gtgttgctgc tgctaattct cgcaaacccg    2940
tgaataaatt attgtaattt ttggggatca attcgagctc agcaagtttc atcccgaccc    3000
cctcagggtc gggattttt tattgtacta gttgacataa gtaaaggcat cccctgcgtg     3060
atataattac cttcagttta aggaggtata cacatatgat taaagcctat gctgccttag    3120
aagccaatgg taaattacaa ccctttgaat atgatcctgg tgctttaggt gccaatgaag    3180
tggaaattga agtgcaatat tgtggtgtgt gtcattctga tttatctatg attaataatg    3240 aatgggtat ttctaattat cccttagttc ctggtcatga gttgttggt actgttgctg     3300 ctatgggtga aggtgttaat catgtggaag tgggtgattt agttggttta ggttggcatt    3360
ctggttattg tatgacctgt cattcttgtt tatctggtta tcataattta tgtgccactg    3420
ccgaatctac tattgtgggt cattatggtg gttttggtga tagttcgt gctaaggtg       3480 tttctgtggt gaaattaccc aaaggtattg atttagcctc tgctgggcct ttattttgtg    3540
gtggtattac cgtttttct cccatggtgg aattatcttt aaaacctacc gccaaagttg     3600
ctgttattgg tattggtggt ttaggtcatt tagccgttca attttaaga gcctgggtt      3660 gtgaagttac tgctttacc tcttctgccc gtaaacaaac cgaagtttta gaattaggtg     3720
cccatcatat tttagattct accaatcctg aagctattgc ttctgccgaa ggtaaatttg    3780
```

```
attatattat ttctaccgtg aatttaaaat tagattggaa tttatatatc agtaccttag   3840
cccctcaagg tcattttcat tttgttggtg tggtgttaga acccttggac ttaaacttat   3900
ttcccttatt aatgggacaa cgttctgttt ctgcttctcc tgttggttct cctgctacta   3960
ttgccactat gttagatttt gccgtgcgtc atgatattaa acccgtggtg gaacaatttt   4020
cttttgatca aattaatgaa gccattgccc atttagaatc tggtaaagcc cattatcgcg   4080
tggtgttatc tcattctaaa aattaataag attaacttct aaactgaaac aaatttgagg   4140
gtaggcttca ttgtctgccc ttattttttt atttaggaaa agtgaacaga ctaaagagtg   4200
ttggctctat tgctttgagt atgtaaatta ggcgttgctg aattaaggta tgattttga   4260
ccccttctct cttctgcagg atcatcttgc tgaaaaactc gagcgctcgt tccgcaaagc   4320
ggtacggagt tagttagggg ctaatgggca ttctcccgta caggaaagag ttagaagtta   4380
ttaattatca acaattctcc tttgcctagt gcatcgttac cttttaatt aaaacataag    4440
gaaaactaat aatcgtaata atttaacctc aaagtgtaaa gaaatgtgaa attctgactt   4500
ttataacgtt aaagagggaa aaattagcag tttaaaatac ctagagaata gtctggggta   4560
agcatagaga attagattag ttaagttaat caaattcaga aaaaataata atcgtaaata   4620
gttaatctgg gtgtatagaa aatgatcccc ttcatgataa gatttaaact cgaaaagcaa   4680
aagccaaaaa actaacttcc attaaaagaa gttgttacat ataacgctat aagaaaatt    4740
tatatatttg gaggatacca accatgtctc atattcaacg tgaaactagt tgttctcgcc   4800
ctcgttaaa ttctaatatg gatgccgatt tatatggtta taaatgggct cgtgataatg    4860
ttggtcaatc tggtgctact atttatcgtt tatatgtaa  acctgatgct cctgaattat   4920
tcttgaaaca tggtaaaggt tctgttgcta atgatgttac tgatgaaatg gttcgtttaa   4980
actggttgac tgaattatg  cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt ttttttacgt cgtttacatt   5160
ctattcccgt ttgtaattgt cctttaatt ctgatcgtgt ttttcgttta gctcaagctc     5220
aatctcgtat gaataatggt ttagttgatg cttctgatt tgatgatgaa cgtaatggtt    5280
ggcctgttga acaagtttgg aaagaaatgc acaaattgtt acctttttct cctgattctg   5340
ttgttactca tggtgatttt tctttagata atttgatctt tgatgaaggt aaattgattg   5400
gttgtattga tgttggtcgt gttggtattg ctgatcgtta tcaagattta gctatttat    5460
ggaattgttt aggtgaattt tctccttctt tacagaaacg tttatttcag aaatatggta   5520
ttgataatcc tgatatgaac aagttacaat tcatttaat gttggacgag ttcttttaag    5580
aattaattca tgaccaaaat cccttaacgt gagttttcgt tccactgagc gtcagacccc   5640
gtagaaaaga tcaaaggatc ttcttgagat ccttttttc tgcgcgtaat ctgctgctat    5700
ttaaattacg tacacgtgtt attactttgt taacgacaat tgtcttaatt aactgggcct   5760
catgggcctt ccgctcactg cccgctttcc agtcgggaaa cctgtcgtgc cagctctgca   5820
gatgacggtg aaaacctctg acacatgcag ctcccggaga cggtcacagc ttgtctgtaa   5880
gcggatgccg ggagcagaca gcccgtcag  ggcgcgtcag cgggtgttgg cgggtgtcgg   5940
ggcgcagcca tgacccagtc acgtagcgat agcggagtgt atactggctt aactatgcgg   6000
catcagagca gattgtactg agagtgcacc atatgcggtg tgaaataccg cacagatgcg   6060
taaggagaaa ataccgcatc aggcgctctt ccgcttcctc gctcactgac tcgctgcgct   6120
cggtcgttcg gctgcggcga gcggtatcag ctcactcaaa ggcggtaata cggttatcca   6180
```

```
cagaatcagg ggataacgca ggaaagaaca tgtgagcaaa aggccagcaa aaggccagga    6240
accgtaaaaa ggccgcgttg ctggcgtttt tccataggct ccgcccccct gacgagcatc    6300
acaaaaatcg acgctcaagt cagaggtggc gaaacccgac aggactataa agataccagg    6360
cgtttccccc tggaagctcc ctcgtgcgct ctcctgttcc gaccctgccg cttaccggat    6420
acctgtccgc ctttctccct tcgggaagcg tggcgctttc tcatagctca cgctgtaggt    6480
atctcagttc ggtgtaggtc gttcgctcca agctgggctg tgtgcacgaa ccccccgttc    6540
agcccgaccg ctgcgcctta tccggtaact atcgtcttga gtccaacccg gtaagacacg    6600
acttatcgcc actggcagca gccactggta acaggattag cagagcgagg tatgtaggcg    6660
gtgctacaga gttcttgaag tggtggccta actacggcta cactagaagg acagtatttg    6720
gtatctgcgc tctgctgaag ccagttacct tcggaaaaag agttggtagc tcttgatccg    6780
gcaaacaaac caccgctggt agcggtggtt tttttgtttg caagcagcag attacgcgca    6840 gaaaaaagg atctcaagaa gatcctttga tcttttctac tgcagaagct tgttagacac    6900
cctgtcatgt atttatatt atttatttca ccatacggat taagtgaaac ctaatgaaaa    6960
tagtactttc ggagctttaa ctttaatgaa ggtatgtttt tttatagaca tcgatgtctg    7020
gtttaacaat aggaaaaagt agctaaaact cccatgaatt aaagaaataa caaggtgtct    7080
aacaacctgt tattaagaat gttagaaaag acttaacatt tgtgttgagt ttttatagac    7140
attggtgtct agacatacgg tagataaggt ttgctcaaaa ataaaataaa aaagattgg    7200 actaaaaaac atttaattta gtacaattta attagttatt ttttcgtctc aaattttgct    7260
ttgttgagca gaaatttaga taaaaaaatc cccgtgatca gattacaatg tcgttcattg    7320
tacgatgtgt cgaaaaatct ttacgacact ctaaactgac cacacggggg aaaaagaaaa    7380
ctgaactaat aacatcatga tactcggaaa acctagcaat tctcaacccc taaacaaaag    7440
aaacttccaa aaccctgacc atataaagga gtggcaacaa tcagcaatca gtcaagattt    7500
gatagcagaa atcttgtat cggttgctaa tggttttgat gtactattta tcggcaataa    7560
ataccgaact aacacgggtg ttctgtcacg gcacatatta aactcctatt ctcatttaga    7620
agatggtggt tcgtatggta gaacatttga cccatttacc aataaagaaa tgcagtgggt    7680
tcaatttaaa ccgaatagac caagaaaagg ttctactggt aaggtaatca aatatgaatc    7740
gccaaaaggt gaacctacaa gagttctaat gccgtttgtg cctatgaaaa tatggcaacg    7800
gattagcgat aagttcggag taccgattaa tccgaaaaaa gatactcact tttgggaatg    7860
ggtaaagaat aatccatcga taccgattgc cattacagaa ggaaataaaa aagctaattg    7920
cctattatcc tatggctatc ctgctattgc ctttgtaggc atttggaacg gattagagaa    7980
aataaatgat ttctcgaagg aaaagcagtt aaaagaggat tgaaatggt tgttatccaa    8040 cggcaaccga atattaata tcatctttga ccaagaccag aaacaaaaaa ctgtaattaa    8100
tgtaaacaaa gctattttcg ctttatcttc tctaataagt agaaatggtc ataaagttaa    8160
tattgtgcaa tggttgccgt caaaggtaa aggaatagat gattatttgg tagctttacc    8220
ttttgagaaa agagaaaatc atttagacaa cttaattaaa attgcaccat catttaattt    8280
ttggtcaact aaatacttat tcaagtgtcg taaaccagat ttaaccgtaa attgccgtta    8340
tttgagcgat gcagtaaaag aattacctca agaggatata gcattaatag cacctcacgg    8400
cacgggtaaa acttcattag tagctactca cgttaagaat cggagttatc acggaaggaa    8460
aactatttca ttggtgcatc ttgaaagttt agccaaagct aatggcaacg cacttggatt    8520
```

```
atattaccga accgaaaata atattgaaaa gcaatatctt ggatttagct tatgtgtaga    8580
tagttgccgt gataagatta acggcattac aactgatatt atttcaggtc aagattattg    8640
ccttttcatt gatgaaattg accaagtaat tccacacatc cttaacagtg aaactgaagt    8700
aagtaagtat agatgcacca tcattgacac tttttctgaa ctggtgagaa atgctgaaca    8760
ggtcattatt gctgatgctg atttatccga tgtgacgatt gacctaatag aaaacatcag    8820
aggtaaaaaa ctatatgtaa tcaagaatga atatcagtat cagggaatga cttttaacgc    8880
cgttggttca ccattagaaa tgatggcaat gatgggaaaa tcggtgtcag aaggcaagaa    8940
attatttatt aacaccacat cccaaaaggc aaaagtaag  tacggcacaa tcgctcttga    9000
gtcttatatt tttggtctaa ataaagaagc aaagatatta agaatagact ctgaaaccac    9060
taaaaaccct gaacatccag cctataaaat cattgaccaa gacttaaata atatcctcaa    9120
agattatgat tatgtcattg cctcaccttg ccttcaaaca ggtgtcagta ttaccttaaa    9180
agggcatttt gaccagcaat ttaacttttc cagtggaaac attacacctc attgcttttt    9240
acagcaaatg tggcggttga gggatgcaga aattgaaaga ttctattatg tgccgaactc    9300
atctaacctc aatctcattg gaataagtc  aagttcacca tcagaccttc taaagagcaa    9360
taacaagatg gcaacggcaa cggttaacct tttgggtaga atcgactccg aatattccct    9420
agagtatgaa tcgcacggca tttggcttga gacgtgggca aaattatcag cacggcataa    9480
cagttcaatg cgttgttact ctgaaattct tacctatcta attcgtctc  aagggcataa    9540
attaaatatc aacattccct cacctcttgc agatattaag aagctaaatg atgaggtaag    9600
tagtaacagg gaaaaggtaa aaaatgagag atactctcag aggttaaact caccagatat    9660
taacgatgca gaagctacca tactcgaatc taaagagcaa aaaatcggat tgactctcaa    9720
tgagagatgc accctagaaa agcataaagt taagaagcgg tatgggaatg taaagatgga    9780
tattctcacc tttgatgatg atggactata ccccaaactc agactatttt attacctcac    9840
catcggtaaa cctcatctca aggctaatga cagaaaagct attgccaaaa tgggcaatga    9900
caataaaggc aagattctat caaaagactt agttaataaa acttactccg ctcgtgtgaa    9960
ggtcttagag attcttaaac taactgactt tatcgacaat cttagagatg aactcttaat   10020
aactcccaat aatccagcta tcaccgattt taataatctt ctgctaagag ctaagaagga   10080
tttaagagta ttaggagtca acatcggaaa atatccaatg gccaacatta atgccgtact   10140
tactctcatt ggtcacaaac tttctgtaat gagagatgag ttcggaaaag agaaaaggat   10200
aaaagtagat ggtaaatcat accgatgtta tcaacttgaa acattaccag attttaccaa   10260
tgatactctt gactactggt tagaaaatga tagccaaaaa gaagtaacag caacagaaaa   10320
ttactccgaa aatttttaacc cttcaaatag ctacaatcca gacagtaaga cacttttcaga  10380
gggtgcaaat ttcctatata taaataaaga agaattgcat ccaaataaat tgcacctaga   10440
aataaaagaa ggtgctgaac ttttttttatt cggggtaaag gtgattgtga aaggaatctt   10500
ggacggggca gtaactatat tctctatggg tcaagaatac gatttatccc tcaatgaact   10560
agagggatg  ttaacatcat gaactttaca agaatctttt taaagggcga tcgcaccatg   10620
ttaaatgatg gtacatttgt tcagatattt gatatttacc atgaccacgc attgggagtg   10680
accccttgacc ttaagacaga aaaattatt tccgatgatg ttagggtaat tactgtcaaa   10740
gacttattgt tcgatggcac ttataaaggg gtaaatcttt ttatgcccga taatgcccga   10800
taatgcccga ttgatgctac aaaatcccat aatcataagc gataatcccc taatagcttg   10860
taattcttga accgtagcga ttttagagta ttccaaaaag aagaaataaa caccgcaaaa   10920
```

```
tgtcgtattt cacatatata aaccaaggtt ttttgccccta aaatctttat gtttgtagtg   10980
tgatgttggg tcaaaatggt cagaaaagtt gcaaggtttt tatggatgct tacgcgcgcg   11040
aggggtaagc atccccaaat agttacttta tcctagtcca tgcccattta ttgccgtccc   11100
gttcggcttt aaaaaagtgc caaaactcac aaggtgcaat aaaaagttct gtacctttcg   11160
caaccctaga taatctttca acagttactt ttttttcctat tatctcggta caaagtttgg   11220
ctagtttctc ttttccctct ttttcaatca agccttcttg tatgcccaac tcattgatta   11280
atctctctat ttttaccatt atttcccgtt caggtagttt atcccctaaa tcttcatcgg   11340
ggggcaatgt agggcattct gaaggggctt tttcttctgt ctggacatta tctaatattg   11400
aagtaaccaa actatcttca gttttttcta ttcctattaa ttcatattcg gttactgtat   11460
ccgtatcaat atccgaataa ctatctttat ccgtattagc tattcggtta agtttatccg   11520
ttaactcaga aacaagacta tatagcggtt ttagcttttc ttctatcctg ttatctaata   11580
cggataagtt tatacggtta tcattatccg tattagtatc attgggcttt tttggtagtt   11640
ctacccccctc ataaaccgct tttattccca attccaacag actgataaca gtatccttta   11700
taatgggttt tttgctgata tggtgaactt ttgcccccttc catcattgcg atactttcta   11760
tctcactcat caacttatcg cttaagtgaa tctcgtatct gtttaatccc ttactggttt   11820
tattcatatc cgtttacttt attcggttaa caattctatt ttatacgaat aaaatattat   11880
acggttaact ttatacgttt aactatttta tctatacgga taacagtaat aagttattcg   11940
tattagttat acgtttactt ttatccaaat aaaattagtg catttaaact aaaagaatga   12000
ttttatcgga gttgatagca ttggattaac ctaaagatgt ttataagcta tatctgataa   12060
gtatttaagg ttattttgtt attctgttta ttgacattat cagaataaaa gaatagaata   12120
taattgttga gagataagag gtttaagtga ttatggttaa aagttagtt ggttatgtca   12180
gggtcagtag tgaatcgcaa gaggataaca ctagcttaca gaatcagata gagagaattg   12240
aagcatattg tatggctttt ggttatgagt tggtaaaaat attcaaagag gttgccactg   12300
gtacaaaagc agatattgaa acccgtccta tttttaatga agctatagaa tacttgaaac   12360
aggataatgc taatggaatt attgccttga agctagaccg aatcgcacgg aatgctttag   12420
atgtattgcg tttggttcgt gaaaccttag aaccacaaaa taaaatgtta gtgttactag   12480
atattccaggt agatacttcg acaccttcag gaaaaatgat tttaactgta atgagtgccg   12540
ttgctgaact cgaaagagac atgatctatg atcgcactca gggggtaga aagactaaag   12600
cccaaaaggg cgggtatgcc tacgggaaac ctaaatttgg ctataagact gaagaaaagg   12660
aactaaaaga agattcagca caacaggaaa ctattaaact aattaagaga caccgtaggt   12720
cagggaaaag ctaccagaaa atagctgatt atctcaatgc ccaaagtatt cccactaaac   12780
aaggtaagaa atggagttct agcgtcgtct atcgaatctg tcaggaaaaa gctggttaag   12840
tctgttata gatatttaga atttattgaa taaaaatagt atgaacaata atatttatg   12900
gactaaccac gctcggaaac gtttaactga acgatgggaa ataaaagaat catgggttat   12960
tgataccatc gaaaatcctg aacgttcaga atttattgtt gatgagtcag gggaaaaata   13020
tcattactat aaaagaatag ctaagtttaa gaatagagtg ttagaagtga taacttctgc   13080
caactcaaca cccacaagaa taataacctt ttacttaac cgtaacatga ggaaaaattt   13140
atgattgtta cttacgataa tgaagttgac gcaatttatt ttaagttaac ggaaaataaa   13200
attgatagca ccgaacctca aacagacagg attatcattg attacgatga aagtaataat   13260
```

```
attgttggca ttgaggtatt agattttaat tatcttgtca agaaaggttt aaccgttgct    13320
gatttacctt tttctgaaga tgaaagatta acagcttctc aatattttaa ttttcctgtt    13380
gctatctaat ccagaagggg caataatccc cttctttcat cgagttagac ttaatatcac    13440
aaaagtcatt ttcattttac cgtttctttt ccacagcgtc cgtacgcccc tcgttaaatc    13500
tcaaaaccga caatttatga tgtttataaa aagttactca ctttaataag tatttatact    13560
cattaaaggg ttattctttt tttgtagcct gataggttgg gaaggaatat ttcagattat    13620
cagatttgtt gaatattttt cgtcagatac gcaaaccttaa caaacataat aacaactga     13680 aactattgat atgtctaggt tttagctcta tcacaggttg gatctg                   13726
```

<210> SEQ ID NO 23
<211> LENGTH: 13726
<212> TYPE: DNA
<213> ORGANISM: Artificial Sequence
<220> FEATURE:
<223> OTHER INFORMATION: #1632[\]pABICyano1::corR-PcorT*3-
      zmPDCABICyano1(opt1)_dsrA-Prbc*(optRBS)-synADH(opt1)_ter

<400> SEQUENCE: 23

```
tcgaccatgc gtccaaaact ttcaccatcc tttccctatc aacctttact gcactaaaga      60
caagtgagat agcagtggca atctggcttt gcaatcaatg tttccactaa agcgtttagc     120
gttactgcgg ctagaagtcc tccaccgagg ctcccctgaa tggtgatatg gggaatggga     180
ctggtcatca gtcgtcgttt tgcccccgga gcatgactaa aaccgatcgg cattccgatc     240
acaagagccg gctgaatatg ttgttgctct atcagcttac aggcagtgag taaaacagaa     300
ggggcatagc cgatcgccag cacacatcct tggggaatct gttgtaaccg ctgttgccaa     360
tggtcatggt gccaaaaagc ttgctcggct tccctaagcc ctgtgatgtg agggtcgtca     420
atcagcgttt taaccgtaca tcctaaatga gctaaccgag tttgatcaag agccgcagcc     480
acaaccggaa catcggtgac gactggacac cctgctttca gtgcatctcg tgccgaggcg     540
atcgctccct gactcaatcg aacggcgttt accaagctaa catcaccaca ggccagcact     600
aattgatgta gtaagtgaat ggtaatttca gagtaagccg ataaatccgg tagcaggtgt     660
ttgagggatt cctgaaaggc ttctggatga gttgttgtct ccgcatctag gttcgtccac     720
aactgatcga gttttcctaa cccctcctgg acatccacat caagctgttt cagttgggcc     780
agagcttccg cttgggtaat ctggcaactc tggtcgcgtc ccagtaatcc ttctaaagca     840
gatgcggttt ggcggagtcg agtaatctgc tgaatcacag cctgatattg ctgttgcaac     900
tgcaccatta gggtgggatc aaggctctct tcagaatggc tatccagcag ttgccgaata     960
tgagacaact gaaagccctg ctgtttgagg gcaatgactc gttggagccg ttgtacgtcc    1020
tgctgagtat aaaggcggta gttgccctct gagcgttgaa cggggggaag caatcccagg    1080
gtgtggtaat ggcgcaccat gcgaggcgta acgccacctc ccactgcatc tgtgagttct    1140
ttaatcgtta agtgattagt cttcatgact ttagtttact caaaaccttg acattgacac    1200
taatgttaag gtttagaatg agaaggtaaa aatcgaggat aaaaagcatg aattcttata    1260
ccgtgggtac ttatttagcc gaacgcttag tgcaaattgg tttaaaacat cattttgccg    1320
tggctgggga ctataattta gtgttattgg ataacttatt attaaataaa acatggaac     1380 aagtgtattg ttgtaatgaa ttaaattgtg gttttctgc tgaaggttat gctagagcta    1440
aaggtgcagc tgctgctgtt gttacttatt ctgtgggtgc tttatctgct tttgatgcta    1500
ttggtggtgc ttatgccgaa aatttaccg tgattttaat ttctggtgcc cctaataata    1560
```

```
atgatcatgc cgctggacat gttttacatc atgccttagg taaaaccgat tatcattatc  1620
aattagaaat ggccaaaaat attactgctg ctgccgaagc tatttatact cctgaagaag  1680
cccctgccaa aattgatcat gtgattaaaa ccgccttacg cgaaaaaaaa cccgtgtatt  1740
tagaaattgc ctgtaatatt gcttctatgc cttgtgctgc tcctgggcct gcttctgctt  1800
tatttaatga tgaagcctct gatgaagcta gtttaaatgc tgccgtggaa gaaaccttaa  1860
aatttattgc caatcgcgat aaagttgccg tgttagttgg ttctaaatta agagctgctg  1920
gtgctgaaga agctgctgtt aaatttgctg atgctttagg tggtgcagtt gctactatgg  1980
ctgctgccaa atcttttttt cccgaagaaa atccccatta tattggaact agttggggag  2040
aagtttctta tcctggtgtg gaaaaaacta tgaaagaagc cgacgctgtt attgctttag  2100
cccctgtgtt taatgattat tctaccactg gttggactga tattcccgat cccaaaaaat  2160
tagttttagc cgaacctcgt tctgttgttg ttaatggtgt tcgctttccc tctgtgcatt  2220
taaaagatta tttaacccgc ttagcccaaa aagtttctaa aaaaactggt gccttagatt  2280
tttttaaatc tttaaatgcg ggtgaattaa aaaaagctgc tcctgctgat ccttctgctc  2340
ctttagttaa tgctgaaatt gcccgtcaag ttgaagcctt attacccct aatactaccg  2400
ttattgccga aactggtgat tcttggttta tgcccaacg catgaaatta cctaatggtg  2460
cccgtgttga atatgaaatg caatggggtc atattggttg gtctgtacct gctgcttttg  2520
gttatgctgt tggtgctcct gaacgtcgta atatttaat ggtgggtgat ggttctttc  2580
aattaactgc ccaagaagtt gcccaaatgg ttcgcttaaa attaccgtt attattttt  2640
taataaataa ttatgttat accattgaag tgatgattca tgatgggcca tataataata  2700
ttaaaaattg ggattatgcg ggtttaatgg aagtgtttaa tggtaatggt ggttatgatt  2760
ctggtgctgg taaggttta aaagccaaaa ctggtggtga attagctgaa gctattaaag  2820
ttgccttagc caatactgat gggccaacct taattgaatg ttttattggt cgcgaagatt  2880
gtaccgaaga attagttaaa tggggtaaac gtgttgctgc tgctaattct cgcaaacccg  2940
tgaataaatt attgtaattt ttggggatca attcgagctc agcaagtttc atcccgaccc  3000
cctcagggtc gggatttttt tattgtacta gttgacataa gtaaaggcat cccctgcgtg  3060
atataattac cttcagttta aggaggtata cacatatgat taaagcctat gctgccttag  3120
aagccaatgg taaattacaa ccctttgaat atgatcctgg tgctttaggt gccaatgaag  3180
tggaaattga agtgcaatat tgtggtgtgt gtcattctga tttatctatg attaataatg  3240
aatggggtat ttctaattat cccttagttc ctggtcatga agttgttggt actgttgctg  3300
ctatgggtga aggtgttaat catgtggaag tgggtgattt agttggttta ggttggcatt  3360
ctggttattg tatgacctgt cattcttgtt tatctggtta tcataattta tgtgccactg  3420
ccgaatctac tattgtgggt cattatggtg gttttggtga tagagttcgt gctaaaggtg  3480
tttctgtggt gaaattaccc aaaggtattg atttagcctc tgctgggcct ttattttgtg  3540
gtggtattac cgttttttct cccatggtgg aattatcttt aaaacctacc gccaaagttg  3600
ctgttattgg tattggtggt ttaggtcatt tagccgttca atttttaaga gcctgggtt  3660
gtgaagttac tgcttttacc tcttctgccc gtaaacaaac cgaagtttta gaattaggtg  3720
cccatcatat tttagattct accaatcctg aagctattgc ttctgccgaa ggtaaatttg  3780
attatattat ttctaccgtg aatttaaaat tagattggaa tttatatatc agtaccttag  3840
cccctcaagg tcatttttcat tttgttggtg tggtgttaga acccttggac ttaaacttat  3900
ttccttatt aatgggacaa cgttctgttt ctgcttctcc tgttggttct cctgctacta  3960
```

```
ttgccactat gttagatttt gccgtgcgtc atgatattaa acccgtggtg gaacaatttt    4020
cttttgatca aattaatgaa gccattgccc atttagaatc tggtaaagcc cattatcgcg    4080
tggtgttatc tcattctaaa aattaataag attaacttct aaactgaaac aaatttgagg    4140
gtaggcttca ttgtctgccc ttattttttt atttaggaaa agtgaacaga ctaaagagtg    4200
ttggctctat tgctttgagt atgtaaatta ggcgttgctg aattaaggta tgattttttga   4260 cccttctct cttctgcagg atcatcttgc tgaaaaactc gagcgctcgt tccgcaaagc     4320
ggtacggagt tagttagggg ctaatgggca ttctcccgta caggaaagag ttagaagtta    4380
ttaattatca acaattctcc tttgcctagt gcatcgttac cttttttaatt aaaacataag   4440 gaaaactaat aatcgtaata atttaacctc aaagtgtaaa gaaatgtgaa attctgactt    4500
ttataacgtt aaagagggaa aaattagcag tttaaaatac ctagagaata gtctggggta    4560
agcatagaga attagattag ttaagttaat caaattcaga aaaaataata atcgtaaata    4620
gttaatctgg gtgtatagaa aatgatcccc ttcatgataa gatttaaact cgaaaagcaa    4680
aagccaaaaa actaacttcc attaaaagaa gttgttacat ataacgctat aaagaaaatt    4740
tatatatttg gaggatacca accatgtctc atattcaacg tgaaactagt tgttctcgcc    4800 ctcgttttaaa ttctaatatg gatgccgatt tatatggtta taaatgggct cgtgataatg   4860
ttggtcaatc tggtgctact atttatcgtt tatatggtaa acctgatgct cctgaattat    4920
tcttgaaaca tggtaaaggt tctgttgcta atgatgttac tgatgaaatg gttcgtttaa   4980
actggttgac tgaatttatg cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt tttttttacgt cgtttacatt  5160 ctattcccgt ttgtaattgt ccttttaatt ctgatcgtgt ttttcgttta gctcaagctc   5220
aatctcgtat gaataatggt ttagttgatg cttctgattt tgatgatgaa cgtaatggtt   5280
ggcctgttga acaagtttgg aaagaaatgc acaaattgtt acctttttct cctgattctg   5340
ttgttactca tggtgatttt tctttagata atttgatctt tgatgaaggt aaattgattg   5400
gttgtattga tgttggtcgt gttggtattg ctgatcgtta tcaagattta gctatttat    5460 ggaattgttt aggtgaattt tctccttctt tacagaaacg tttatttcag aaatatggta   5520
ttgataatcc tgatatgaac aagttacaat ttcatttaat gttggacgag ttcttttaag   5580
aattaattca tgaccaaaat ccccttaacgt gagttttcgt tccactgagc gtcagacccc   5640
gtagaaaaga tcaaggatc ttcttgagat ccttttttttc tgcgcgtaat ctgctgctat    5700
ttaaattacg tacacgtgtt attactttgt taacgacaat tgtcttaatt aactgggcct    5760
catgggcctt ccgctcactg cccgctttcc agtcggaaa cctgtcgtgc cagctctgca    5820
gatgacggtg aaaacctctg acacatgcag ctcccggaga cggtcacagc ttgtctgtaa    5880
gcggatgccg ggagcagaca gcccgtcag ggcgcgtcag cgggtgttgg cgggtgtcgg    5940
ggcgcagcca tgacccagtc acgtagcgat agcggagtgt atactggctt aactatgcgg    6000
catcagagca gattgtactg agagtgcacc atatgcggtg tgaaataccg cacagatgcg    6060
taaggagaaa ataccgcatc aggcgctctt ccgcttcctc gctcactgac tcgctgcgct    6120
cggtcgttcg gctgcggcga gcggtatcag ctcactcaaa ggcggtaata cggttatcca    6180
cagaatcagg ggataacgca ggaaagaaca tgtgagcaaa aggccagcaa aaggccagga    6240
accgtaaaaa ggccgcgttg ctggcgtttt tccataggct ccgcccccct gacgagcatc    6300
```

```
acaaaaatcg acgctcaagt cagaggtggc gaaacccgac aggactataa agataccagg    6360
cgtttccccc tggaagctcc ctcgtgcgct ctcctgttcc gacccctgccg cttaccggat   6420 acctgtccgc ctttctccct cgggaagcg tggcgctttc tcatagctca cgctgtaggt    6480
atctcagttc ggtgtaggtc gttcgctcca agctgggctg tgtgcacgaa ccccccgttc   6540
agcccgaccg ctgcgcctta tccggtaact atcgtcttga gtccaacccg gtaagacacg   6600
acttatcgcc actggcagca gccactggta acaggattag cagagcgagg tatgtaggcg   6660
gtgctacaga gttcttgaag tggtggccta actacggcta cactagaagg acagtatttg   6720
gtatctgcgc tctgctgaag ccagttacct tcggaaaaag agttggtagc tcttgatccg   6780
gcaaacaaac caccgctggt agcggtggtt ttttttgtttg caagcagcag attacgcgca   6840
gaaaaaaagg atctcaagaa gatcctttga tcttttctac tgcagaagct tgttagacac   6900
cctgtcatgt attttatatt atttatttca ccatacggat taagtgaaac ctaatgaaaa   6960
tagtactttc ggagctttaa ctttaatgaa ggtatgtttt tttatagaca tcgatgtctg   7020
gtttaacaat aggaaaaagt agctaaaact cccatgaatt aaagaaataa caaggtgtct   7080
aacaacctgt tattaagaat gttagaaaag acttaacatt tgtgttgagt ttttatagac   7140
attggtgtct agacatacgg tagataaggt ttgctcaaaa ataaaataaa aaagattgg    7200 actaaaaaac atttaattta gtacaattta attagttatt ttttcgtctc aaattttgct   7260
ttgttgagca gaaatttaga taaaaaaatc cccgtgatca gattacaatg tcgttcattg   7320
tacgatgtgt cgaaaaatct ttacgacact ctaaactgac cacacggggg aaaaagaaaa   7380
ctgaactaat aacatcatga tactcggaaa acctagcaat tctcaacccc taaacaaaag   7440
aaacttccaa aaccctgacc atataaagga gtggcaacaa tcagcaatca gtcaagattt   7500
gatagcagaa atcttgtat cggttgctaa tggttttgat gtactattta tcggcaataa    7560
ataccgaact aacacgggtg ttctgtcacg gcacatatta aactcctatt ctcatttaga   7620
agatggtggt tcgtatggta gaacatttga cccatttacc aataaagaaa tgcagtgggt   7680
tcaatttaaa ccgaatagac caagaaaagg ttctactggt aaggtaatca aatatgaatc   7740
gccaaaaggt gaacctacaa gagttctaat gccgtttgtg cctatgaaaa tatggcaacg   7800
gattagcgat aagttcggag taccgattaa tccgaaaaaa gatactcact tttgggaatg   7860
ggtaaagaat aatccatcga taccgattgc cattacagaa ggaaataaaa aagctaattg   7920
cctattatcc tatggctatc ctgctattgc ctttgtaggc atttggaacg gattagagaa   7980
aataaatgat ttctcgaagg aaaagcagtt aaaagaggat tgaaatggt tgttatccaa    8040 cggcaaccga atattaata tcatctttga ccaagaccag aaacaaaaaa ctgtaattaa    8100
tgtaaacaaa gctattttcg ctttatcttc tctaataagt agaaatggtc ataaagttaa   8160
tattgtgcaa tggttgccgt caaaaggtaa aggaatagat gattatttgg tagctttacc   8220
ttttgagaaa agagaaaatc atttagacaa cttaattaaa attgcaccat catttaattt   8280
ttggtcaact aaatacttat tcaagtgtcg taaaccagat ttaaccgtaa attgccgtta   8340
tttgagcgat gcagtaaaag aattacctca agaggatata gcattaatag cacctcacgg   8400
cacgggtaaa acttcattag tagctactca cgttaagaat cggagttatc acggaaggaa   8460
aactatttca ttggtgcatc ttgaaagttt agccaaagct aatggcaacg cacttggatt   8520
atattaccga accgaaaata atattgaaaa gcaatatctt ggatttagct tatgtgtaga   8580
tagttgccgt gataagatta acggcattac aactgatatt atttcaggtc aagattattg   8640
ccttttcatt gatgaaattg accaagtaat tccacacatc cttaacagtg aaactgaagt   8700
```

```
aagtaagtat agatgcacca tcattgacac tttttctgaa ctggtgagaa atgctgaaca   8760
ggtcattatt gctgatgctg atttatccga tgtgacgatt gacctaatag aaaacatcag   8820
aggtaaaaaa ctatatgtaa tcaagaatga atatcagtat cagggaatga cttttaacgc   8880
cgttggttca ccattagaaa tgatggcaat gatgggaaaa tcggtgtcag aaggcaagaa   8940
attatttatt aacaccacat cccaaaaggc aaaagtaag tacggcacaa tcgctcttga    9000
gtcttatatt tttggtctaa ataaagaagc aaagatatta agaatagact ctgaaaccac   9060
taaaaaccct gaacatccag cctataaaat cattgaccaa gacttaaata atatcctcaa   9120
agattatgat tatgtcattg cctcaccttg ccttcaaaca ggtgtcagta ttaccttaaa   9180
agggcatttt gaccagcaat ttaacttttc cagtggaaac attacacctc attgctttt    9240
acagcaaatg tggcggttga gggatgcaga aattgaaaga ttctattatg tgccgaactc   9300
atctaacctc aatctcattg gaataagtc aagttcacca tcagaccttc taaagagcaa    9360
taacaagatg caacggcaa cggttaacct tttgggtaga atcgactccg aatattccct    9420
agagtatgaa tcgcacggca tttggcttga gacgtgggca aaattatcag cacggcataa   9480
cagttcaatg cgttgttact ctgaaattct tacctatcta attacgtctc aagggcataa   9540
attaaatatc aacattccct cacctcttgc agatattaag aagctaaatg atgaggtaag   9600
tagtaacagg gaaaaggtaa aaaatgagag atactctcag aggttaaact caccagatat   9660
taacgatgca gaagctacca tactcgaatc taaagagcaa aaaatcggat tgactctcaa   9720
tgagagatgc accctagaaa agcataaagt taagaagcgg tatgggaatg taaagatgga   9780
tattctcacc tttgatgatg atggactata ccccaaactc agactatttt attacctcac   9840
catcggtaaa cctcatctca aggctaatga cagaaaagct attgccaaaa tgggcaatga   9900
caataaaggc aagattctat caaaagactt agttaataaa acttactccg ctcgtgtgaa   9960
ggtcttagag attcttaaac taactgactt tatcgacaat cttagagatg aactcttaat  10020
aactcccaat aatccagcta tcaccgattt taataatctt ctgctaagag ctaagaagga  10080
tttaagagta ttaggagtca acatcggaaa atatccaatg ccaacatta atgccgtact    10140
tactctcatt ggtcacaaac tttctgtaat gagagatgag ttcggaaaag agaaaaggat  10200
aaaagtagat ggtaaatcat accgatgtta tcaacttgaa acattaccag attttaccaa  10260
tgatactctt gactactggt tagaaaatga tagccaaaaa gaagtaacag caacagaaaa  10320
ttactccgaa aattttaacc cttcaaatag ctacaatcca gacagtaaga cactttcaga  10380
gggtgcaaat ttcctatata taaataaaga agaattgcat ccaaataaat tgcacctaga  10440
aataaaagaa ggtgctgaac ttttttttatt cggggtaaag gtgattgtga aaggaatctt  10500
ggacggggca gtaactatat tctctatggg tcaagaatac gatttatccc tcaatgaact  10560
agagggggatg ttaacatcat gaactttaca agaatctttt taaagggcga tcgcaccatg  10620
ttaaatgatg gtacatttgt tcagatattt gatatttacc atgaccacgc attgggagtg  10680
acccttgacc ttaagacaga aaaattatt tccgatgatg ttagggtaat tactgtcaaa   10740
gacttattgt tcgatggcac ttataaaggg gtaaaatctt ttatgcccga taatgcccga  10800
taatgcccga ttgatgctac aaaatcccat aatcataagc gataatcccc taatagcttg  10860
taattcttga accgtagcga ttttagagta ttccaaaaag aagaaataaa caccgcaaaa  10920
tgtcgtattt cacatatata aaccaaggtt ttttgcccta aaatctttat gtttgtagtg  10980
tgatgttggg tcaaaatggt cagaaaagtt gcaaggtttt tatggatgct tacgcgcgcg  11040
```

```
aggggtaagc atccccaaat agttacttta tcctagtcca tgcccattta ttgccgtccc   11100
gttcggcttt aaaaaagtgc caaaactcac aaggtgcaat aaaaagttct gtaccttcg    11160
caaccctaga taatctttca acagttactt tttttcctat tatctcggta caaagtttgg   11220
ctagtttctc ttttccctct ttttcaatca agccttcttg tatgcccaac tcattgatta   11280
atctctctat ttttaccatt atttcccgtt caggtagttt atccctaaa tcttcatcgg    11340
ggggcaatgt agggcattct gaaggggctt tttcttctgt ctggacatta tctaatattg   11400
aagtaaccaa actatcttca gttttttcta ttcctattaa ttcatattcg gttactgtat   11460
ccgtatcaat atccgaataa ctatctttat ccgtattagc tattcggtta agtttatccg   11520
ttaactcaga aacaagacta tatagcggtt ttagcttttc ttctatcctg ttatctaata   11580
cggataagtt tatacggtta tcattatccg tattagtatc attgggcttt tttggtagtt   11640
ctaccccctc ataaaccgct tttattccca attccaacag actgataaca gtatccttta   11700
taatgggttt tttgctgata tggtgaactt tgcccccttc catcattgcg atactttcta   11760
tctcactcat caacttatcg cttaagtgaa tctcgtatct gtttaatccc ttactggttt   11820
tattcatatc cgtttacttt attcggttaa caattctatt ttatacgaat aaaatattat   11880
acggttaact ttatacgttt aactatttta tctatacgga taacagtaat aagttattcg   11940
tattagttat acgtttactt ttatccaaat aaaattagtg catttaaact aaaagaatga   12000
ttttatcgga gttgatagca ttggattaac ctaaagatgt ttataagcta tatctgataa   12060
gtatttaagg ttatttttgtt attctgtttta ttgacattat cagaataaaa gaatagaata  12120
taattgttga gagataagag gtttaagtga ttatggttaa gaagttagtt ggttatgtca   12180
gggtcagtag tgaatcgcaa gaggataaca ctagcttaca gaatcagata gagagaattg   12240
aagcatattg tatggctttt ggttatgagt tggtaaaaat attcaaagag gttgccactg   12300
gtacaaaagc agatattgaa acccgtccta tttttaatga agctatagaa tacttgaaac   12360
aggataatgc taatggaatt attgccttga agctagaccg aatcgcacgg aatgctttag   12420
atgtattgcg tttggttcgt gaaaccttag aaccacaaaa taaaatgtta gtgttactag   12480
atattcaggt agatacttcg acaccttcag gaaaaatgat tttaactgta atgagtgccg   12540
ttgctgaact cgaaagagac atgatctatg atcgcactca ggggggtaga aagactaaag   12600
cccaaaaggg cgggtatgcc tacgggaaac ctaaatttgg ctataagact gaagaaaagg   12660
aactaaaaga agattcagca caacaggaaa ctattaaact aattaagaga caccgtaggt   12720
cagggaaaag ctaccagaaa atagctgatt atctcaatgc ccaaagtatt cccactaaac   12780
aaggtaagaa atggagttct agcgtcgtct atcgaatctg tcaggaaaaa gctggttaag   12840
tctgttata gatatttaga atttattgaa taaaaatagt atgaacaata aatatttatg    12900
gactaaccac gctcggaaac gtttaactga acgatgggaa ataaaagaat catgggttat   12960
tgataccatc gaaaatcctg aacgttcaga atttattgtt gatgagtcag gggaaaaata   13020
tcattactat aaaagaatag ctaagtttaa gaatagagtg ttagaagtga taacttctgc   13080
caactcaaca cccacaagaa taataacctt ttactttaac cgtaacatga ggaaaaattt   13140
atgattgtta cttacgataa tgaagttgac gcaatttatt ttaagttaac ggaaaataaa   13200
attgatagca ccgaacctca aacagacagg attatcattg ttacgatga aagtaataat    13260
attgttggca ttgaggtatt agatttaat tatcttgtca agaaaggttt aaccgttgct    13320
gatttaccttt tttctgaaga tgaaagatta acagcttctc aatattttaa ttttcctgtt  13380
gctatctaat ccagaagggg caataatccc cttctttcat cgagttagac ttaatatcac   13440
```

```
aaaagtcatt tcattttac cgtttcttt ccacagcgtc cgtacgcccc tcgttaaatc    13500
tcaaaaccga caatttatga tgtttataaa aagttactca ctttaataag tatttatact    13560
cattaaaggg ttattctttt tttgtagcct gataggttgg gaaggaatat ttcagattat    13620
cagatttgtt gaatatttt cgtcagatac gcaaaccttt caaacataat taacaactga    13680
aactattgat atgtctaggt tttagctcta tcacaggttg gatctg                   13726
```

<210> SEQ ID NO 24
<211> LENGTH: 12973
<212> TYPE: DNA
<213> ORGANISM: Artificial Sequence
<220> FEATURE:
<223> OTHER INFORMATION: #1635¶ABICyano1::smtB-PsmtA-zmPDC(opt1)_dsrA-
     Prbc*(optRBS)-synADH(opt1)_ter

<400> SEQUENCE: 24

```
tcgtcagata cgcaaacctt acaaacataa ttaacaactg aaactattga tatgtctagg     60
ttttagctct atcacaggtt ggatctgtcg acgggcaaac tttatgaagc agatcaagcc    120
tatatccgcc aagcaaccgg cagccgcgtt gattagtggg tgtgtccatc ctctggttcg    180
tctaggtgct ccgaagcgtc acgatagaga ttaagaatgt ggtgatcctt gaggcgataa    240
atcacattcc gcccttcctt gcgatagctc actaaacgtg ctgtgcgcag ggttcttagt    300
tggtgagaga cagccgattc actcatttca acggcggcgg cgagttcccc cacccgcatc    360
tctccagtgg ccagggccga agaatacgc cagcggttgg catcccccaa gacaccaaaa    420
aattcggcca tccgttgggc cttggcttgg ttcaagattt tgccactgtg gtctgtcatt    480
gttcgctgat ctaaacaata cctgaataat tgttcatgtg ttaatctaaa aatgtgaaca    540
atcgttcaac tatttaagac aataccttgg aggtttaaac catgaattct tataccgtgg    600
gtacttattt agccgaacgc ttagtgcaaa ttggtttaaa acatcatttt gccgtggctg    660
gggactataa tttagtgtta ttggataact tattattaaa taaaaacatg gaacaagtgt    720
attgttgtaa tgaattaaat tgtggttttt ctgctgaagg ttatgctaga gctaaaggtg    780
cagctgctgc tgttgttact tattctgtgg gtgctttatc tgcttttgat gctattggtg    840
gtgcttatgc cgaaaattta cccgtgattt taatttctgg tgccctaat aataatgatc    900 atgccgctgg acatgtttta catcatgcct taggtaaaac cgattatcat tatcaattag    960
aaatggccaa aaatattact gctgctgccg aagctattta ctcctgaa gaagcccctg   1020 ccaaaattga tcatgtgatt aaaaccgcct acgcgaaaa aaaacccgtg tatttagaaa   1080
ttgcctgtaa tattgcttct atgccttgtg ctgctcctgg gcctgcttct gctttattta   1140
atgatgaagc ctctgatgaa gctagtttaa atgctgccgt ggaagaaacc ttaaaattta   1200
ttgccaatcg cgataaagtt gccgtgttag ttggttctaa attaagagct gctggtgctg   1260
aagaagctgc tgttaaattt gctgatgctt aggtggtgc agttgctact atggctgctg   1320
ccaaatcttt ttttcccgaa gaaaatcccc attatattgg aactagttgg ggagaagttt   1380
cttatcctgg tgtggaaaaa actatgaaag aagccgacgc tgttattgct ttagcccctg   1440
tgtttaatga ttattctacc actggttgga ctgatattcc cgatcccaaa aaattagttt   1500
tagccgaacc tcgttctgtt gttgttaatg gtgttcgctt tccctctgtg catttaaaag   1560 attattaac ccgcttagcc caaaaagttt ctaaaaaaac tggtgcctta gatttttta   1620 aatcttaaa tgcgggtgaa ttaaaaaaag ctgctcctgc tgatccttct gctccttag   1680 ttaatgctga aattgcccgt caagttgaag ccttattaac ccctaatact accgttattg   1740
```

```
ccgaaactgg tgattcttgg tttaatgccc aacgcatgaa attacctaat ggtgcccgtg    1800
ttgaatatga aatgcaatgg ggtcatattg gttggtctgt acctgctgct tttggttatg    1860
ctgttggtgc tcctgaacgt cgtaatattt taatggtggg tgatggttct tttcaattaa    1920
ctgcccaaga agttgcccaa atggttcgct taaaattacc cgttattatt tttttaataa    1980
ataattatgg ttataccatt gaagtgatga ttcatgatgg gccatataat aatattaaaa    2040
attgggatta tgcgggttta atggaagtgt taatggtaa tggtggttat gattctggtg    2100
ctggtaaagg tttaaaagcc aaaactggtg gtgaattagc tgaagctatt aaagttgcct    2160
tagccaatac tgatgggcca accttaattg aatgttttat tggtcgcgaa gattgtaccg    2220
aagaattagt taaatggggt aaacgtgttg ctgctgctaa ttctcgcaaa cccgtgaata    2280
aattattgta atttttgggg atcaattcga gctcagcaag tttcatcccg acccctcag    2340 ggtcgggatt tttttattgt actagttgac ataagtaaag gcatcccctg cgtgatataa    2400
ttaccttcag tttaaggagg tatacacata tgattaaagc ctatgctgcc ttagaagcca    2460
atggtaaatt acaacccttt gaatatgatc ctggtgcttt aggtgccaat gaagtggaaa    2520
ttgaagtgca atattgtggt gtgtgtcatt ctgatttatc tatgattaat aatgaatggg    2580
gtatttctaa ttatcccctta gttcctggtc atgaagttgt tggtactgtt gctgctatgg    2640
gtgaaggtgt taatcatgtg gaagtgggtg atttagttgg tttaggttgg cattctggtt    2700
attgtatgac ctgtcattct tgtttatctg gttatcataa tttatgtgcc actgccgaat    2760
ctactattgt gggtcattat ggtggttttg gtgatagagt tcgtgctaaa ggtgtttctg    2820
tggtgaaatt acccaaaggt attgatttag cctctgctgg gcctttattt tgtggtggta    2880
ttaccgtttt ttctcccatg gtggaattat ctttaaaacc taccgccaaa gttgctgtta    2940
ttggtattgg tggtttaggt catttagccg ttcaatttt aagagcctgg ggttgtgaag    3000
ttactgcttt tacctcttct gcccgtaaac aaaccgaagt tttagaatta ggtgcccatc    3060 atatttttaga ttctaccaat cctgaagcta ttgcttctgc cgaaggtaaa tttgattata    3120
ttatttctac cgtgaattta aaattagatt ggaatttata tatcagtacc ttagcccctc    3180
aaggtcattt tcattttgtt ggtgtggtgt tagaacccctt ggacttaaac ttatttccct    3240
tattaatggg acaacgttct gtttctgctt ctcctgttgg ttctcctgct actattgcca    3300
ctatgttaga ttttgccgtg cgtcatgata ttaaacccgt ggtggaacaa ttttcttttg    3360
atcaaattaa tgaagccatt gcccatttag aatctggtaa agcccattat cgcgtggtgt    3420
tatctcattc taaaaattaa taagattaac ttctaaactg aaacaaattt gagggtaggc    3480
ttcattgtct gcccttattt tttttattag gaaaagtgaa cagactaaag agtgttggct    3540
ctattgcttt gagtatgtaa attaggcgtt gctgaattaa ggtatgattt ttgacccctt    3600
ctctcttctg caggatcatc ttgctgaaaa actcgagcgc tcgttccgca aagcggtacg    3660
gagttagtta ggggctaatg ggcattctcc cgtacaggaa agagttagaa gttattaatt    3720
atcaacaatt ctcctttgcc tagtgcatcg ttaccttttt aattaaaaca taaggaaaac    3780
taataatcgt aataatttaa cctcaaagtg taaagaaatg tgaaattctg acttttataa    3840
cgttaaagag ggaaaaatta gcagtttaaa atacctagaa aatagtctgg ggtaagcata    3900
gagaattaga ttagttaagt taatcaaatt cagaaaaaat aataatcgta aatagttaat    3960
ctgggtgtat agaaaatgat ccccttcatg ataagattta aactcgaaaa gcaaaagcca    4020
aaaaactaac ttccattaaa agaagttgtt acatataacg ctataaagaa aatttatata    4080
```

```
tttggaggat accaaccatg tctcatattc aacgtgaaac tagttgttct cgccctcgtt    4140
taaattctaa tatggatgcc gatttatatg gttataaatg ggctcgtgat aatgttggtc    4200
aatctggtgc tactatttat cgtttatatg gtaaacctga tgctcctgaa ttattcttga    4260
aacatggtaa aggttctgtt gctaatgatg ttactgatga atggttcgt ttaaactggt     4320
tgactgaatt tatgccttta cctactatta aacattttat tcgtactccc gatgatgctt    4380
ggttattaac tactgctatt cctggtaaaa ctgcttttca agttttagaa gaatatcctg    4440
attctggtga aaatattgtt gatgctttag ctgtttttt acgtcgttta cattctattc     4500
ccgtttgtaa ttgtcctttt aattctgatc gtgtttttcg tttagctcaa gctcaatctc    4560
gtatgaataa tggtttagtt gatgcttctg attttgatga tgaacgtaat ggttggcctg    4620
ttgaacaagt ttggaaagaa atgcacaaat tgttaccttt ttctcctgat tctgttgtta    4680
ctcatggtga ttttctttta gataatttga tctttgatga aggtaaattg attggttgta    4740
ttgatgttgg tcgtgttggt attgctgatc gttatcaaga tttagctatt ttatggaatt    4800
gtttaggtga attttctcct tctttacaga aacgttatt tcagaaatat ggtattgata    4860
atcctgatat gaacaagtta caatttcatt taatgttgga cgagttcttt taagaattaa    4920
ttcatgacca aaatcccctta acgtgagttt tcgttccact gagcgtcaga ccccgtagaa    4980
aagatcaaag gatcttcttg agatcctttt tttctgcgcg taatctgctg ctatttaaat    5040
tacgtacacg tgttattact tgttaacga caattgtctt aattaactgg gcctcatggg     5100
ccttccgctc actgcccgct ttccagtcgg gaaacctgtc gtgccagctc tgcagatgac    5160
ggtgaaaacc tctgacacat gcagctcccg gagacggtca gcttgtctt gtaagcggat     5220
gccgggagca gacaagcccg tcagggcgcg tcagcgggtg ttggcgggtg tcggggcgca    5280
gccatgaccc agtcacgtag cgatagcgga gtgtatactg gcttaactat gcggcatcag    5340
agcagattgt actgagagtg caccatatgc ggtgtgaaat accgcacaga tgcgtaagga    5400
gaaaataccg catcaggcgc tcttccgctt cctcgctcac tgactcgctg cgctcggtcg    5460
ttcggctgcg gcgagcggta tcagctcact caaaggcggt aatacggtta tccacagaat    5520
caggggataa cgcaggaaag aacatgtgag caaaaggcca gcaaaaggcc aggaaccgta    5580
aaaaggccgc gttgctggcg ttttccata ggctccgccc cctgacgag catcacaaaa     5640
atcgacgctc aagtcagagg tggcgaaacc cgacaggact ataaagatac caggcgtttc    5700
cccctggaag ctccctcgtg cgctctcctg ttccgaccct gccgcttacc ggatacctgt    5760
ccgcctttct cccttcggga agcgtggcgc tttctcatag ctcacgctgt aggtatctca    5820
gttcggtgta ggtcgttcgc tccaagctgg gctgtgtgca cgaacccccc gttcagcccg    5880
accgctgcgc cttatccggt aactatcgtc ttgagtccaa cccggtaaga cacgacttat    5940
cgccactggc agcagccact ggtaacagga ttagcagagc gaggtatgta ggcggtgcta    6000
cagagttctt gaagtggtgg cctaactacg gctacactag aaggacagta tttggtatct    6060
gcgctctgct gaagccagtt accttcggaa aaagagttgg tagctcttga tccggcaaac    6120
aaaccaccgc tggtagcggt ggtttttttg tttgcaagca gcagattacg cgcagaaaaa    6180
aaggatctca agaagatcct ttgatctttt ctactgcaga gcttgttag acaccctgtc     6240
atgtatttta ttatttat ttcaccatac ggattaagtg aaacctaatg aaaatagtac       6300
tttcggagct ttaactttaa tgaaggtatg ttttttata gacatcgatg tctggtttaa    6360
caataggaaa aagtagctaa aactcccatg aattaaagaa ataacaaggt gtctaacaac    6420
ctgttattaa gaatgttaga aaagacttaa catttgtgtt gagttttat agacattggt     6480
```

```
gtctagacat acggtagata aggtttgctc aaaaataaaa taaaaaaaga ttggactaaa    6540
aaacatttaa tttagtacaa tttaattagt tattttttcg tctcaaattt tgctttgttg    6600
agcagaaatt tagataaaaa aatccccgtg atcagattac aatgtcgttc attgtacgat    6660
gtgtcgaaaa atctttacga cactctaaac tgaccacacg ggggaaaaag aaaactgaac    6720
taataacatc atgatactcg gaaaacctag caattctcaa cccctaaaca aagaaacttt    6780
ccaaaaccct gaccatataa aggagtggca acaatcagca atcagtcaag atttgatagc    6840
agaaaatctt gtatcggttg ctaatggttt tgatgtacta tttatcggca ataaataccg    6900
aactaacacg ggtgttctgt cacggcacat attaaactcc tattctcatt tagaagatgg    6960
tggttcgtat ggtagaacat ttgacccatt taccaataaa gaaatgcagt gggttcaatt    7020
taaaccgaat agaccaagaa aaggttctac tggtaaggta atcaaatatg aatcgccaaa    7080
aggtgaacct acaagagttc taatgccgtt tgtgcctatg aaaatatggc aacggattag    7140
cgataagttc ggagtaccga ttaatccgaa aaaagatact cacttttggg aatgggtaaa    7200
gaataatcca tcgataccga ttgccattac agaaggaaat aaaaaagcta attgcctatt    7260
atcctatggc tatcctgcta ttgcctttgt aggcatttgg aacggattag agaaaataaa    7320
tgatttctcg aaggaaaagc agttaaaaga ggatttgaaa tggttgttat ccaacggcaa    7380
ccgaaatatt aatatcatct ttgaccaaga ccagaaacaa aaaactgtaa ttaatgtaaa    7440
caaagctatt ttcgctttat cttctctaat aagtagaaat ggtcataaag ttaatattgt    7500
gcaatggttg ccgtcaaaag gtaaaggaat agatgattat ttggtagctt tacctttga     7560 gaaaagagaa aatcatttag acaacttaat taaaattgca ccatcattta attttggtc     7620 aactaaatac ttattcaagt gtcgtaaacc agatttaacc gtaaattgcc gttatttgag    7680
cgatgcagta aaagaattac ctcaagagga tatagcatta atagcacctc acggcacggg    7740
taaaacttca ttagtagcta ctcacgttaa gaatcggagt tatcacgaaa ggaaaactat    7800
ttcattggtg catcttgaaa gtttagccaa agctaatggc aacgcacttg gattatatta    7860
ccgaaccgaa aataatattg aaaagcaata tcttggattt agcttatgtg tagatagttg    7920
ccgtgataag attaacggca ttacaactga tattatttca ggtcaagatt attgcctttt    7980
cattgatgaa attgaccaag taattccaca catccttaac agtgaaactg aagtaagtaa    8040
gtatagatgc accatcattg acactttttc tgaactggtg agaaatgctg aacaggtcat    8100
tattgctgat gctgatttat ccgatgtgac gattgaccta atagaaaaca tcagaggtaa    8160
aaaactatat gtaatcaaga atgaatatca gtatcaggga atgacttttta cgccgttgg    8220 ttcaccatta gaaatgatgg caatgatggg aaaatcggtg tcagaaggca agaaattatt    8280
tattaacacc acatcccaaa aggcaaaaag taagtacggc acaatcgctc ttgagtctta    8340 tattttggt ctaaataaag aagcaaagat attaagaata gactctgaaa ccactaaaaa     8400
ccctgaacat ccagcctata aaatcattga ccaagactta aataatatcc tcaaagatta    8460
tgattatgtc attgcctcac cttgccttca aacaggtgtc agtattacct aaaagggca     8520 ttttgaccag caatttaact tttccagtgg aaacattaca cctcattgct ttttacagca    8580
aatgtggcgg ttgagggatg cagaaattga agattctat tatgtgccga actcatctaa     8640
cctcaatctc attgggaata agtcaagttc accatcagac cttctaaaga gcaataacaa    8700
gatggcaacg gcaacggtta accttttggg tagaatcgac tccgaatatt ccctagagta    8760
tgaatcgcac ggcatttggc ttgagacgtg ggcaaaatta tcagcacggc ataacagttc    8820
```

```
aatgcgttgt tactctgaaa ttcttaccta tctaattacg tctcaagggc ataaattaaa    8880
tatcaacatt ccctcacctc ttgcagatat taagaagcta aatgatgagg taagtagtaa    8940
cagggaaaag gtaaaaaatg agagatactc tcagaggtta aactcaccag atattaacga    9000
tgcagaagct accatactcg aatctaaaga gcaaaaaatc ggattgactc tcaatgagag    9060
atgcacccta gaaaagcata agttaagaa gcggtatggg aatgtaaaga tggatattct    9120
cacctttgat gatgatggac tatacccaa actcagacta ttttattacc tcaccatcgg    9180
taaacctcat ctcaaggcta atgacagaaa agctattgcc aaaatgggca atgacaataa    9240
aggcaagatt ctatcaaaag acttagttaa taaaacttac tccgctcgtg tgaaggtctt    9300
agagattctt aaactaactg actttatcga caatcttaga gatgaactct taataactcc    9360
caataatcca gctatcaccg attttaataa tcttctgcta agagctaaga aggatttaag    9420
agtattagga gtcaacatcg gaaaatatcc aatggccaac attaatgccg tacttactct    9480
cattggtcac aaactttctg taatgagaga tgagttcgga aaagagaaaa ggataaaagt    9540
agatggtaaa tcataccgat gttatcaact tgaaacatta ccagatttta ccaatgatac    9600
tcttgactac tggttagaaa atgatagcca aaaagaagta acagcaacag aaaattactc    9660
cgaaaatttt aacccttcaa atagctacaa tccagacagt aagacacttt cagagggtgc    9720
aaatttccta tatataaata agaagaatt gcatccaaat aaattgcacc tagaataaa     9780
agaaggtgct gaacttttt tattcggggt aaaggtgatt gtgaaaggaa tcttggacgg    9840
ggcagtaact atattctcta tgggtcaaga atacgattta tccctcaatg aactagaggg    9900
gatgttaaca tcatgaactt tacaagaatc ttttttaaagg gcgatcgcac catgttaaat    9960
gatggtacat ttgttcagat atttgatatt taccatgacc acgcattggg agtgaccctt   10020
gaccttaaga cagaaaaaat tatttccgat gatgttaggg taattactgt caaagactta   10080
ttgttcgatg gcacttataa agggtaaaa tcttttatgc ccgataatgc ccgataatgc   10140
ccgattgatg ctacaaaatc ccataatcat aagcgataat cccctaatag cttgtaattc   10200
ttgaaccgta gcgatttag agtattccaa aaagaagaaa taaacaccgc aaaatgtcgt   10260
atttcacata tataaaccaa ggttttttgc cctaaaatct ttatgtttgt agtgtgatgt   10320
tgggtcaaaa tggtcagaaa agttgcaagg ttttatgga tgcttacgcg cgcgaggggt   10380
aagcatcccc aaatagttac tttatcctag tccatgccca tttattgccg tcccgttcgg   10440
ctttaaaaaa gtgccaaaac tcacaaggtg caataaaaag ttctgtacct ttcgcaaccc   10500
tagataatct ttcaacagtt actttttttc ctattatctc ggtacaaagt ttggctagtt   10560
tctcttttcc ctcttttca atcaagcctt cttgtatgcc caactcattg attaatctct   10620
ctatttttac cattatttcc cgttcaggta gtttatcccc taaatcttca tcgggggca   10680
atgtagggca ttctgaaggg gcttttttctt ctgtctggac attatctaat attgaagtaa   10740
ccaaactatc ttcagttttt tctattccta ttaattcata ttcggttact gtatccgtat   10800
caatatccga ataactatct ttatccgtat tagctattcg gttaagttta tccgttaact   10860
cagaaacaag actatatagc ggttttagct tttcttctat cctgttatct aatacggata   10920
agttatacg gttatcatta tccgtattag tatcattggg cttttttggt agttctaccc   10980
cctcataaac cgcttttatt cccaattcca acagactgat aacagtatcc tttataatgg   11040
gttttttgct gatatggtga acttttgccc cttccatcat tgcgatactt tctatctcac   11100
tcatcaactt atcgcttaag tgaatctcgt atctgtttaa tcccttactg gttttattca   11160
tatccgttta ctttattcgg ttaacaattc tattttatac gaataaaata ttatacggtt   11220
```

```
aactttatac gtttaactat tttatctata cggataacag taataagtta ttcgtattag    11280
ttatacgttt acttttatcc aaataaaatt agtgcattta aactaaaaga atgattttat    11340
cggagttgat agcattggat taacctaaag atgtttataa gctatatctg ataagtattt    11400
aaggttattt tgttattctg tttattgaca ttatcagaat aaaagaatag aatataattg    11460
ttgagagata agaggtttaa gtgattatgg ttaagaagtt agttggttat gtcagggtca    11520
gtagtgaatc gcaagaggat aacactagct tacagaatca gatagagaga attgaagcat    11580
attgtatggc ttttggttat gagttggtaa aaatattcaa agaggttgcc actggtacaa    11640
aagcagatat tgaaacccgt cctattttta atgaagctat agaatacttg aaacaggata    11700
atgctaatgg aattattgcc ttgaagctag accgaatcgc acggaatgct ttagatgtat    11760
tgcgtttggt tcgtgaaacc ttagaaccac aaaataaaat gttagtgtta ctagatattc    11820
aggtagatac ttcgacacct tcaggaaaaa tgattttaac tgtaatgagt gccgttgctg    11880
aactcgaaag agacatgatc tatgatcgca ctcagggggg tagaaagact aaagcccaaa    11940
agggcgggta tgcctacggg aaacctaaat ttggctataa gactgaagaa aaggaactaa    12000
aagaagattc agcacaacag gaaactatta aactaattaa gagacaccgt aggtcaggga    12060
aaagctacca gaaaatagct gattatctca atgcccaaag tattcccact aaacaaggta    12120
agaaatggag ttctagcgtc gtctatcgaa tctgtcagga aaaagctggt taagtctgtt    12180
tatagatatt tagaatttat tgaataaaaa tagtatgaac aataaatatt tatggactaa    12240
ccacgctcgg aaacgtttaa ctgaacgatg ggaaataaaa gaatcatggg ttattgatac    12300
catcgaaaat cctgaacgtt cagaatttat tgttgatgag tcaggggaaa aatatcatta    12360
ctataaaaga atagctaagt ttaagaatag agtgttagaa gtgataactt ctgccaactc    12420
aacacccaca agaataataa ccttttactt taaccgtaac atgaggaaaa atttatgatt    12480
gttacttacg ataatgaagt tgacgcaatt tattttaagt taacgaaaaa taaaattgat    12540
agcaccgaac ctcaaacaga caggattatc attgattacg atgaaagtaa taatattgtt    12600
ggcattgagg tattagattt taattatctt gtcaagaaag gtttaaccgt tgctgattta    12660
ccttttttctg aagatgaaag attaacagct tctcaatatt ttaattttcc tgttgctatc    12720
taatccagaa ggggcaataa tccccttctt tcatcgagtt agacttaata tcacaaaagt    12780
cattttcatt ttaccgtttc ttttccacag cgtccgtacg cccctcgtta aatctcaaaa    12840
ccgacaattt atgatgttta taaaagtta ctcactttaa taagtattta tactcattaa    12900
agggttattc ttttttttgta gcctgatagg ttgggaagga atatttcaga ttatcagatt    12960
tgttgaatat ttt                                                       12973
```

<210> SEQ ID NO 25
<211> LENGTH: 12973
<212> TYPE: DNA
<213> ORGANISM: Artificial Sequence
<220> FEATURE:
<223> OTHER INFORMATION: #1639[\]pABICyano1::smtB-PsmtA*1-
      zmPDC(opt1)_dsrA-Prbc*(optRBS)-synADH(opt1)_ter

<400> SEQUENCE: 25

```
tcgacgggca aactttatga agcagatcaa gcctatatcc gccaagcaac cggcagccgc      60
gttgattagt gggtgtgtcc atcctctggt tcgtctaggt gctccgaagc gtcacgatag     120
agattaagaa tgtggtgatc cttgaggcga taaatcacat tccgcccttc cttgcgatag     180
ctcactaaac gtgctgtgcg cagggttctt agttggtgag agacagccga ttcactcatt     240
```

```
tcaacggcgg cggcgagttc ccccacccgc atctctccag tggccagggc cgaaagaata    300
cgccagcggt tggcatcccc caagacacca aaaaattcgg ccatccgttg ggccttggct    360
tggttcaaga ttttgccact gtggtctgtc attgttcgct gatctaaaca atacctgaat    420
aattgttcat gtgttaatct aaaaatgtga acaatcgttc aactatttaa gacaatacca    480
aggaggtgat aaccatgaat tcttataccg tgggtactta tttagccgaa cgcttagtgc    540
aaattggttt aaaacatcat tttgccgtgg ctggggacta taatttagtg ttattggata    600
acttattatt aaataaaaac atggaacaag tgtattgttg taatgaatta aattgtggtt    660
tttctgctga aggttatgct agagctaaag gtgcagctgc tgctgttgtt acttattctg    720
tgggtgcttt atctgctttt gatgctattg gtggtgctta tgccgaaaat ttacccgtga    780
ttttaatttc tggtgcccct aataaatatg atcatgccgc tggacatgtt ttacatcatg    840
ccttaggtaa aaccgattat cattatcaat tagaaatggc caaaaatatt actgctgctg    900
ccgaagctat ttatactcct gaagaagccc ctgccaaaat tgatcatgtg attaaaaccg    960
ccttacgcga aaaaaacccc gtgtatttag aaattgcctg taatattgct tctatgcctt   1020
gtgctgctcc tgggcctgct tctgctttat ttaatgatga agcctctgat gaagctagtt   1080
taaatgctgc cgtggaagaa accttaaaat ttattgccaa tcgcgataaa gttgccgtgt   1140
tagttggttc taaattaaga gctgctggtg ctgaagaagc tgctgttaaa tttgctgatg   1200
ctttaggtgg tgcagttgct actatggctg ctgccaaatc tttttttccc gaagaaaatc   1260
cccattatat tggaactagt tggggagaag tttcttatcc tggtgtggaa aaaactatga   1320
aagaagccga cgctgttatt gctttagccc ctgtgtttaa tgattattct accactggtt   1380
ggactgatat tcccgatccc aaaaaattag ttttagccga acctcgttct gttgttgtta   1440
atggtgttcg ctttccctct gtgcatttaa aagattattt aacccgctta gcccaaaaag   1500
tttctaaaaa aactggtgcc ttagattttt ttaaatcttt aaatgcgggt gaattaaaaa   1560
aagctgctcc tgctgatcct tctgctcctt tagttaatgc tgaaattgcc cgtcaagttg   1620
aagccttatt aaccccctaat actaccgtta ttgccgaaac tggtgattct tggtttaatg   1680
cccaacgcat gaaattacct aatggtgccc gtgttgaata tgaaatgcaa tggggtcata   1740
ttggttggtc tgtacctgct gcttttggtt atgctgttgg tgctcctgaa cgtcgtaata   1800
ttttaatggt gggtgatggt tcttttcaat taactgccca agaagttgcc caaatggttc   1860
gcttaaaatt acccgttatt attttttaa taaataatta tggttatacc attgaagtga   1920
tgattcatga tgggccatat aataatatta aaaattggga ttatgcgggt ttaatgaag   1980 tgtttaatgg taatggtggt tatgattctg tgctggtaa aggtttaaaa gccaaaactg   2040
gtggtgaatt agctgaagct attaaagttg ccttagccaa tactgatggg ccaaccttaa   2100
ttgaatgttt tattggtcgc gaagattgta ccgaagaatt agttaaatgg ggtaaacgtg   2160
ttgctgctgc taattctcgc aaacccgtga ataaattatt gtaatttttg gggatcaatt   2220
cgagctcagc aagtttcatc ccgaccccct cagggtcggg atttttttat tgtactagtt   2280
gacataagta aaggcatccc ctgcgtgata taattacctt cagtttaagg aggtatacac   2340
atatgattaa agcctatgct gccttagaag ccaatggtaa attacaaccc ttgaatatg   2400 atcctggtgc tttaggtgcc aatgaagtgg aaattgaagt gcaatattgt ggtgtgtgtc   2460
attctgattt atctatgatt aataatgaat ggggtatttc taattatccc ttagttcctg   2520
gtcatgaagt tgttggtact gttgctgcta tgggtgaagg tgttaatcat gtggaagtgg   2580
```

```
gtgatttagt tggtttaggt tggcattctg gttattgtat gacctgtcat tcttgtttat   2640
ctggttatca taatttatgt gccactgccg aatctactat tgtgggtcat tatggtggtt   2700
ttggtgatag agttcgtgct aaaggtgttt ctgtggtgaa attacccaaa ggtattgatt   2760
tagcctctgc tgggccttta ttttgtggtg gtattaccgt tttttctccc atggtggaat   2820
tatctttaaa acctaccgcc aaagttgctg ttattggtat tggtggttta ggtcatttag   2880
ccgttcaatt tttaagagcc tggggttgtg aagttactgc ttttacctct tctgcccgta   2940
aacaaaccga agttttagaa ttaggtgccc atcatatttt agattctacc aatcctgaag   3000
ctattgcttc tgccgaaggt aaatttgatt atattatttc taccgtgaat ttaaaattag   3060
attggaattt atatatcagt accttagccc ctcaaggtca ttttcatttt gttggtgtgg   3120
tgttagaacc cttggactta aacttatttc ccttattaat gggacaacgt tctgtttctg   3180
cttctcctgt tggttctcct gctactattg ccactatgtt agattttgcc gtgcgtcatg   3240
atattaaacc cgtggtggaa caattttctt ttgatcaaat taatgaagcc attgcccatt   3300
tagaatctgg taaagcccat tatcgcgtgg tgttatctca ttctaaaaat taataagatt   3360
aacttctaaa ctgaaacaaa tttgagggta ggcttcattg tctgcccttr tttttttatt   3420
taggaaaagt gaacagacta aagagtgttg gctctattgc tttgagtatg taaattaggc   3480
gttgctgaat taaggtatga tttttgaccc cttctctctt ctgcaggatc atcttgctga   3540
aaaactcgag cgctcgttcc gcaaagcggt acggagttag ttaggggcta atgggcattc   3600
tcccgtacag gaaagagtta gaagttatta attatcaaca attctccttt gcctagtgca   3660
tcgttacctt tttaattaaa acataaggaa aactaataat cgtaataatt taacctcaaa   3720
gtgtaaagaa atgtgaaatt ctgactttta taacgttaaa gagggaaaaa ttagcagttt   3780
aaaataccta gagaatagtc tggggtaagc atagagaatt agattagtta agttaatcaa   3840
attcagaaaa aataataatc gtaaatagtt aatctgggtg tatagaaaat gatccccttc   3900
atgataagat ttaaactcga aaagcaaaag ccaaaaaact aacttccatt aaaagaagtt   3960
gttacatata acgctataaa gaaaatttat atatttggag ataccaacc atgtctcata   4020
ttcaacgtga aactagttgt tctcgccctc gtttaaattc taatatggat gccgatttat   4080
atggttataa atgggctcgt gataatgttg gtcaatctgg tgctactatt tatcgtttat   4140
atggtaaacc tgatgctcct gaattattct tgaaacatgg taaaggttct gttgctaatg   4200
atgttactga tgaaatggtt cgtttaaact ggttgactga atttatgcct ttacctacta   4260
ttaaacattt tattcgtact cccgatgatg cttggttatt aactactgct attcctggta   4320
aaactgcttt tcaagtttta gaagaatatc ctgattctgg tgaaaatatt gttgatgctt   4380
tagctgtttt tttacgtcgt ttacattcta ttcccgtttg taattgtcct tttaattctg   4440
atcgtgtttt tcgtttagct caagctcaat ctcgtatgaa taatggttta gttgatgctt   4500
ctgattttga tgatgaacgt aatggttggc ctgttgaaca agtttggaaa gaaatgcaca   4560
aattgttacc tttttctcct gattctgttg ttactcatgg tgattttttct ttagataatt   4620
tgatctttga tgaaggtaaa ttgattggtt gtattgatgt tggtcgtgtt ggtattgctg   4680
atcgttatca agatttagct attttatgga attgttaggg tgaattttct ccttctttac   4740
agaaacgttt atttcagaaa tatggtattg ataatcctga tatgaacaag ttacaatttc   4800
atttaatgtt ggacgagttc ttttaagaat taattcatga ccaaaatccc ttaacgtgag   4860
ttttcgttcc actgagcgtc agaccccgta gaaaagatca aaggatcttc ttgagatcct   4920
ttttttctgc gcgtaatctg ctgctattta aattacgtac acgtgttatt actttgttaa   4980
```

```
cgacaattgt cttaattaac tgggcctcat gggccttccg ctcactgccc gctttccagt    5040
cgggaaacct gtcgtgccag ctctgcagat gacggtgaaa acctctgaca catgcagctc    5100
ccggagacgg tcacagcttg tctgtaagcg gatgccggga gcagacaagc ccgtcagggc    5160
gcgtcagcgt gtgttggcgg gtgtcggggc gcagccatga cccagtcacg tagcgatagc    5220
ggagtgtata ctggcttaac tatgcggcat cagagcagat tgtactgaga gtgcaccata    5280
tgcggtgtga ataccgcac agatgcgtaa ggagaaaata ccgcatcagg cgctcttccg    5340
cttcctcgct cactgactcg ctgcgctcgg tcgttcggct gcggcgagcg gtatcagctc    5400
actcaaaggc ggtaatacgg ttatccacag aatcagggga taacgcagga agaacatgt    5460 gagcaaaagg ccagcaaaag gccaggaacc gtaaaaaggc cgcgttgctg gcgttttcc    5520 ataggctccg ccccctgac gagcatcaca aaaatcgacg ctcaagtcag aggtggcgaa    5580
acccgacagg actataaaga taccaggcgt ttccccctgg aagctccctc gtgcgctctc    5640
ctgttccgac cctgccgctt accggatacc tgtccgcctt ctcccttcg ggaagcgtgg    5700 cgctttctca tagctcacgc tgtaggtatc tcagttcggt gtaggtcgtt cgctccaagc    5760
tgggctgtgt gcacgaaccc cccgttcagc ccgaccgctg cgccttatcc ggtaactatc    5820
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaaggaca gtatttggta tctgcgctct gctgaagcca gttaccttcg    6000
gaaaaagagt tggtagctct tgatccggca aacaaaccac cgctggtagc ggtggttttt    6060
ttgtttgcaa gcagcagatt acgcgcagaa aaaaggatc tcaagaagat cctttgatct    6120
tttctactgc agaagcttgt tagacaccct gtcatgtatt ttatattatt tatttcacca    6180 tacgattaa gtgaaaccta atgaaaatag tactttcgga gctttaactt taatgaaggt    6240
atgttttttt atagacatcg atgtctggtt taacaatagg aaaaagtagc taaaactccc    6300
atgaattaaa gaaataacaa ggtgtctaac aacctgttat taagaatgtt agaaaagact    6360
taacatttgt gttgagtttt tatagacatt ggtgtctaga catacggtag ataaggtttg    6420
ctcaaaaata aaataaaaaa agattggact aaaaaacatt taatttagta caatttaatt    6480
agttattttt tcgtctcaaa ttttgctttg ttgagcagaa atttagataa aaaaatcccc    6540
gtgatcagat tacaatgtcg ttcattgtac gatgtgtcga aaaatcttta cgacactcta    6600
aactgaccac acgggggaaa aagaaaactg aactaataac atcatgatac tcggaaaacc    6660
tagcaattct caaccctaa acaaaagaaa cttccaaaac cctgaccata taaggagtg    6720 gcaacaatca gcaatcagtc aagatttgat agcagaaaat cttgtatcgg ttgctaatgg    6780
ttttgatgta ctatttatcg gcaataaata ccgaactaac acgggtgttc tgtcacggca    6840
catattaaac tcctattctc atttagaaga tggtggttcg tatggtagaa catttgaccc    6900
atttaccaat aaagaaatgc agtgggttca atttaaaccg aatagaccaa gaaaaggttc    6960
tactggtaag gtaatcaaat atgaatcgcc aaaaggtgaa cctacaagag ttctaatgcc    7020
gtttgtgcct atgaaaatat ggcaacggat tagcgataag ttcggagtac cgattaatcc    7080
gaaaaaagat actcactttt gggaatgggt aagaataat ccatcgatac cgattgccat    7140
tacagaagga aataaaaaag ctaattgcct attatcctat ggctatcctg ctattgcctt    7200
tgtaggcatt tggaacggat tagagaaaat aaatgatttc tcgaaggaaa agcagttaaa    7260
agaggatttg aaatggttgt tatccaacgg caaccgaaat attaatatca tctttgacca    7320
```

```
agaccagaaa caaaaaactg taattaatgt aaacaaagct attttcgctt tatcttctct    7380
aataagtaga aatggtcata aagttaatat tgtgcaatgg ttgccgtcaa aaggtaaagg    7440
aatagatgat tatttggtag cttaccttt tgagaaaaga gaaaatcatt tagacaactt    7500
aattaaaatt gcaccatcat ttaatttttg gtcaactaaa tacttattca agtgtcgtaa    7560
accagattta accgtaaatt gccgttattt gagcgatgca gtaaagaat tacctcaaga    7620
ggatatagca ttaatagcac ctcacggcac gggtaaaact tcattagtag ctactcacgt    7680
taagaatcgg agttatcacg gaaggaaaac tatttcattg gtgcatcttg aaagtttagc    7740
caaagctaat ggcaacgcac ttggattata ttaccgaacc gaaataata ttgaaaagca    7800
atatcttgga tttagcttat gtgtagatag ttgccgtgat aagattaacg gcattacaac    7860
tgatattatt tcaggtcaag attattgcct tttcattgat gaaattgacc aagtaattcc    7920
acacatcctt aacagtgaaa ctgaagtaag taagtataga tgcaccatca ttgacacttt    7980
ttctgaactg gtgagaaatg ctgaacaggt cattattgct gatgctgatt tatccgatgt    8040
gacgattgac ctaatagaaa acatcagagg taaaaaacta tatgtaatca agaatgaata    8100
tcagtatcag ggaatgactt ttaacgccgt tggttcacca ttagaaatga tggcaatgat    8160
gggaaaatcg gtgtcagaag gcaagaaatt atttattaac accacatccc aaaaggcaaa    8220
aagtaagtac ggcacaatcg ctcttgagtc ttatattttt ggtctaaata agaagcaaa    8280
gatattaaga atagactctg aaaccactaa aaacctgaa catccagcct ataaaatcat    8340
tgaccaagac ttaaataata tcctcaaaga ttatgattat gtcattgcct caccttgcct    8400
tcaaacaggt gtcagtatta ccttaaaagg gcattttgac cagcaattta acttttccag    8460
tggaaacatt acacctcatt gcttttaca gcaaatgtgg cggttgaggg atgcagaaat    8520
tgaaagattc tattatgtgc cgaactcatc taacctcaat ctcattggga ataagtcaag    8580
ttcaccatca gaccttctaa agagcaataa caagatggca acggcaacgg ttaaccttt    8640
gggtagaatc gactccgaat attccctaga gtatgaatcg cacggcattt ggcttgagac    8700
gtgggcaaaa ttatcagcac ggcataacag ttcaatgcgt tgttactctg aaattcttac    8760
ctatctaatt acgtctcaag ggcataaatt aaatatcaac attccctcac ctcttgcaga    8820
tattaagaag ctaaatgatg aggtaagtag taacagggaa aaggtaaaaa atgagagata    8880
ctctcagagg ttaaactcac cagatattaa cgatgcagaa gctaccatac tcgaatctaa    8940
agagcaaaaa atcggattga ctctcaatga gagatgcacc ctagaaaagc ataaagttaa    9000
gaagcggtat gggaatgtaa agatggtat tctcacctt gatgatgatg gactatacc    9060
caaactcaga ctatttttatt acctcaccat cggtaaacct catctcaagg ctaatgacag    9120
aaaagctatt gccaaaatgg gcaatgcaa taaaggcaag attctatcaa aagacttagt    9180
taataaaact tactccgctc gtgtgaaggt cttagagatt cttaaactaa ctgactttat    9240
cgacaatctt agagatgaac tcttaataac tcccaataat ccagctatca ccgatttaa    9300
taatcttctg ctaagagcta agaaggattt aagagtatta ggagtcaaca tcggaaaata    9360
tccaatggcc aacattaatg ccgtacttac tctcattggt cacaaacttt ctgtaatgag    9420
agatgagttc ggaaaagaga aaaggataaa agtagatggt aaatcatacc gatgttatca    9480
acttgaaaca ttaccagatt ttaccaatga tactcttgac tactggttag aaaatgatag    9540
ccaaaaagaa gtaacagcaa cagaaaaatta ctccgaaaat tttaacccctt caaatagcta    9600
caatccagac agtaagacac tttcagaggg tgcaaatttc ctatatataa ataaagaaga    9660
attgcatcca aataaattgc acctagaaat aaaagaaggt gctgaactt ttttattcgg    9720
```

```
ggtaaaggtg attgtgaaag gaatcttgga cggggcagta actatattct ctatgggtca    9780
agaatacgat ttatccctca atgaactaga ggggatgtta acatcatgaa ctttacaaga    9840 atcttttaa agggcgatcg caccatgtta aatgatggta catttgttca gatatttgat     9900
atttaccatg accacgcatt gggagtgacc cttgacctta agacagaaaa aattatttcc    9960
gatgatgtta gggtaattac tgtcaaagac ttattgttcg atggcactta taaggggta    10020 aaatctttta tgcccgataa tgcccgataa tgcccgattg atgctacaaa atcccataat   10080
cataagcgat aatcccctaa tagcttgtaa ttcttgaacc gtagcgattt tagagtattc   10140 caaaagaag aaataaacac cgcaaaatgt cgtatttcac atatataaac caaggttttt   10200
tgccctaaaa tctttatgtt tgtagtgtga tgttgggtca aaatggtcag aaaagttgca   10260 aggttttat ggatgcttac gcgcgcgagg ggtaagcatc cccaaatagt tactttatcc    10320
tagtccatgc ccatttattg ccgtcccgtt cggctttaaa aaagtgccaa aactcacaag   10380
gtgcaataaa aagttctgta cctttcgcaa ccctagataa tctttcaaca gttacttttt   10440
ttcctattat ctcggtacaa agtttggcta gtttctcttt tccctctttt tcaatcaagc   10500
cttcttgtat gcccaactca ttgattaatc tctctatttt taccattatt tcccgttcag   10560
gtagtttatc ccctaaatct tcatcggggg gcaatgtagg gcattctgaa ggggcttttt   10620
cttctgtctg gacattatct aatattgaag taaccaaact atcttcagtt ttttctattc   10680
ctattaattc atattcggtt actgtatccg tatcaatatc cgaataacta tctttatccg   10740
tattagctat tcggttaagt ttatccgtta actcagaaac aagactatat agcggtttta   10800
gcttttcttc tatcctgtta tctaatacgg ataagtttat acggttatca ttatccgtat   10860
tagtatcatt gggcttttt ggtagttcta ccccctcata aaccgctttt attcccaatt    10920
ccaacagact gataacagta tcctttataa tgggttttt gctgatatgg tgaacttttg    10980
ccccttccat cattgcgata ctttctatct cactcatcaa cttatcgctt aagtgaatct   11040
cgtatctgtt taatcccta ctggttttat tcatatccgt ttactttatt cggttaacaa    11100
ttctatttta tacgaataaa atattatacg gttaactta tacgtttaac tattttatct    11160
atacggataa cagtaataag ttattcgtat tagttatacg tttacttta tccaaataaa    11220 attagtgcat ttaaactaaa agaatgattt tatcggagtt gatagcattg gattaaccta   11280
aagatgttta taagctatat ctgataagta tttaaggtta ttttgttatt ctgttattg    11340 acattatcag aataaaagaa tagaatataa ttgttgagag ataagaggtt taagtgatta   11400
tggttaagaa gttagttggt tatgtcaggg tcagtagtga atcgcaagag gataacacta   11460
gcttacagaa tcagatagag agaattgaag catattgtat ggcttttggt tatgagttgg   11520
taaaaatatt caaagaggtt gccactggta caaaagcaga tattgaaacc cgtcctattt   11580
ttaatgaagc tatagaatac ttgaaacagg ataatgctaa tggaattatt gccttgaagc   11640
tagaccgaat cgcacggaat gctttagatg tattgcgttt ggttcgtgaa accttagaac   11700
cacaaaataa aatgttagtg ttactagata ttcaggtaga tacttcgaca ccttcaggaa   11760
aaatgatttt aactgtaatg agtgccgttg ctgaactcga aagagacatg atctatgatc   11820
gcactcaggg gggtagaaag actaaagccc aaaagggcgg gtatgcctac gggaaaccta   11880
aatttggcta taagactgaa gaaaaggaac taaaagaaga ttcagcacaa caggaaacta   11940
ttaaactaat taagagacac cgtaggtcag ggaaaagcta ccagaaaata gctgattatc   12000
tcaatgccca aagtattccc actaaacaag gtaagaaatg gagttctagc gtcgtctatc   12060
```

| | | | | |
|---|---|---|---|---|
|gaatctgtca|ggaaaaagct|ggttaagtct|gtttatagat|atttagaatt|tattgaataa|12120|
|aaatagtatg|aacaataaat|atttatggac|taaccacgct|cggaaacgtt|taactgaacg|12180|
|atgggaaata|aaagaatcat|gggttattga|taccatcgaa|aatcctgaac|gttcagaatt|12240|
|tattgttgat|gagtcagggg|aaaaatatca|ttactataaa|agaatagcta|agtttaagaa|12300|
|tagagtgtta|gaagtgataa|cttctgccaa|ctcaacaccc|acaagaataa|taacctttta|12360|
|ctttaaccgt|aacatgagga|aaaatttatg|attgttactt|acgataatga|agttgacgca|12420|
|atttatttta|agttaacgga|aaataaaatt|gatagcaccg|aacctcaaac|agacaggatt|12480|
|atcattgatt|acgatgaaag|taataatatt|gttggcattg|aggtattaga|ttttaattat|12540|
|cttgtcaaga|aaggtttaac|cgttgctgat|ttacctttt|ctgaagatga|aagattaaca|12600|
|gcttctcaat|attttaattt|tcctgttgct|atctaatcca|gaaggggcaa|taatccccttt|12660|
|ctttcatcga|gttagactta|atatcacaaa|agtcattttc|attttaccgt|ttcttttcca|12720|
|cagcgtccgt|acgcccctcg|ttaaatctca|aaaccgacaa|tttatgatgt|ttataaaag|12780|
|ttactcactt|taataagtat|ttatactcat|taaagggtta|ttcttttttt|gtagcctgat|12840|
|aggttgggaa|ggaatatttc|agattatcag|atttgttgaa|tattttttcgt|cagatacgca|12900|
|aaccttacaa|acataattaa|caactgaaac|tattgatatg|tctaggtttt|agctctatca|12960|
|caggttggat|ctg| | | |12973|

<210> SEQ ID NO 26
<211> LENGTH: 12973
<212> TYPE: DNA
<213> ORGANISM: Artificial Sequence
<220> FEATURE:
<223> OTHER INFORMATION: #1640¶ABICyano1::smtB-PsmtA*2-
      zmPDC(opt1)_dsrA-Prbc*(optRBS)-synADH(opt1)_ter

<400> SEQUENCE: 26

| | | | | |
|---|---|---|---|---|
|tcgacgggca|aactttatga|agcagatcaa|gcctatatcc|gccaagcaac|cggcagccgc|60|
|gttgattagt|gggtgtgtcc|atcctctggt|tcgtctaggt|gctccgaagc|gtcacgatag|120|
|agattaagaa|tgtggtgatc|cttgaggcga|taaatcacat|tccgcccttc|cttgcgatag|180|
|ctcactaaac|gtgctgtgcg|cagggttctt|agttggtgag|agacagccga|ttcactcatt|240|
|tcaacggcgg|cggcgagttc|ccccacccgc|atctctccag|tggccagggc|cgaaagaata|300|
|cgccagcggt|tggcatcccc|caagacacca|aaaaattcgg|ccatccgttg|ggccttggct|360|
|tggttcaaga|ttttgccact|gtggtctgtc|attgttcgct|gatctaaaca|atacctgaat|420|
|aattgttcat|gtgttaatct|aaaaatgtga|acaatcgttc|aactatttaa|gacaatacca|480|
|aggaggtata|aaccatgaat|tcttataccg|tgggtactta|tttagccgaa|cgcttagtgc|540|
|aaattggttt|aaaacatcat|tttgccgtgg|ctggggacta|taatttagtg|ttattggata|600|
|acttattatt|aaataaaaac|atggaacaag|tgtattgttg|taatgaatta|aattgtggtt|660|
|tttctgctga|aggttatgct|agagctaaag|gtgcagctgc|tgctgttgtt|acttattctg|720|
|tgggtgcttt|atctgctttt|gatgctattg|gtggtgctta|tgccgaaaat|ttacccgtga|780|
|ttttaatttc|tggtgcccct|aataataatg|atcatgccgc|tggacatgtt|ttacatcatg|840|
|ccttaggtaa|aaccgattat|cattatcaat|tagaaatggc|caaaaatatt|actgctgctg|900|
|ccgaagctat|ttatactcct|gaagaagccc|ctgccaaaat|tgatcatgtg|attaaaaccg|960|
|ccttacgcga|aaaaaaaccc|gtgtatttag|aaattgcctg|taatattgct|tctatgcctt|1020|
|gtgctgctcc|tgggcctgct|tctgctttat|ttaatgatga|agcctctgat|gaagctagtt|1080|

```
taaatgctgc cgtggaagaa accttaaaat ttattgccaa tcgcgataaa gttgccgtgt     1140
tagttggttc taaattaaga gctgctggtg ctgaagaagc tgctgttaaa tttgctgatg     1200
ctttaggtgg tgcagttgct actatggctg ctgccaaatc tttttttccc gaagaaaatc     1260
cccattatat tggaactagt tggggagaag tttcttatcc tggtgtggaa aaaactatga     1320
aagaagccga cgctgttatt gctttagccc ctgtgtttaa tgattattct accactggtt     1380
ggactgatat tcccgatccc aaaaaattag ttttagccga acctcgttct gttgttgtta     1440
atggtgttcg ctttccctct gtgcatttaa aagattattt aacccgctta gcccaaaaag     1500
tttctaaaaa aactggtgcc ttagattttt ttaaatcttt aaatgcgggt gaattaaaaa     1560
aagctgctcc tgctgatcct tctgctcctt tagttaatgc tgaaattgcc cgtcaagttg     1620
aagccttatt aaccctaat actaccgtta ttgccgaaac tggtgattct tggtttaatg     1680
cccaacgcat gaaattacct aatggtgccc gtgttgaata tgaaatgcaa tggggtcata     1740
ttggttggtc tgtacctgct gcttttggtt atgctgttgg tgctcctgaa cgtcgtaata     1800
ttttaatggt gggtgatggt tcttttcaat taactgccca agaagttgcc caaatggttc     1860
gcttaaaatt acccgttatt attttttttaa taaataatta tggttatacc attgaagtga     1920
tgattcatga tgggccatat aataatatta aaaattggga ttatgcgggt ttaatggaag     1980
tgtttaatgg taatggtggt tatgattctg tgctggtaa aggtttaaaa gccaaaactg     2040
gtggtgaatt agctgaagct attaaagttg ccttagccaa tactgatggg ccaaccttaa     2100
ttgaatgttt tattggtcgc gaagattgta ccgaagaatt agttaaatgg ggtaaacgtg     2160
ttgctgctgc taattctcgc aaacccgtga ataaattatt gtaattttg gggatcaatt     2220 cgagctcagc aagtttcatc ccgaccccct cagggtcggg attttttttat tgtactagtt     2280 gacataagta aaggcatccc ctgcgtgata taattacctt cagtttaagg aggtatacac     2340
atatgattaa agcctatgct gccttagaag ccaatggtaa attacaaccc tttgaatatg     2400
atcctggtgc tttaggtgcc aatgaagtgg aaattgaagt gcaatattgt ggtgtgtgtc     2460
attctgattt atctatgatt aataatgaat ggggtatttc taattatccc ttagttcctg     2520
gtcatgaagt tgttggtact gttgctgcta tgggtgaagg tgttaatcat gtggaagtgg     2580
gtgatttagt tggtttaggt tggcattctg gttattgtat gacctgtcat tcttgtttat     2640
ctggttatca taatttatgt gccactgccg aatctactat tgtgggtcat tatggtggtt     2700
ttggtgatag agttcgtgct aaaggtgttt ctgtggtgaa attacccaaa ggtattgatt     2760
tagcctctgc tgggccttta ttttgtggtg gtattaccgt tttttctccc atggtggaat     2820
tatctttaaa acctaccgcc aaagttgctg ttattggtat tggtggttta ggtcatttag     2880
ccgttcaatt tttaagagcc tggggttgtg aagttactgc ttttacctct tctgcccgta     2940
aacaaaccga agttttagaa ttaggtgccc atcatatttt agattctacc aatcctgaag     3000
ctattgcttc tgccgaaggt aaatttgatt atattatttc taccgtgaat ttaaaattag     3060
attggaattt atatatcagt accttagccc ctcaaggtca ttttcatttt gttggtgtgg     3120
tgttagaacc cttggactta aacttatttc ccttattaat gggacaacgt tctgtttctg     3180
cttctcctgt tggttctcct gctactattg ccactatgtt agattttgcc gtgcgtcatg     3240
atattaaacc cgtggtggaa caattttctt ttgatcaaat taatgaagcc attgcccatt     3300
tagaatctgg taaagcccat tatcgcgtgg tgttatctca ttctaaaaat taataagatt     3360
aacttctaaa ctgaaacaaa tttgagggta ggcttcattg tctgcccctta ttttttattt     3420 taggaaaagt gaacagacta aagagtgttg gctctattgc tttgagtatg taaattaggc     3480
```

```
gttgctgaat taaggtatga tttttgaccc cttctctctt ctgcaggatc atcttgctga   3540
aaaactcgag cgctcgttcc gcaaagcggt acggagttag ttaggggcta atgggcattc   3600
tcccgtacag gaaagagtta gaagttatta attatcaaca attctccttt gcctagtgca   3660
tcgttacctt tttaattaaa acataaggaa aactaataat cgtaataatt taacctcaaa   3720
gtgtaaagaa atgtgaaatt ctgactttta taacgttaaa gagggaaaaa ttagcagttt   3780
aaaataccta gagaatagtc tggggtaagc atagagaatt agattagtta agttaatcaa   3840
attcagaaaa aataataatc gtaaatagtt aatctgggtg tatagaaaat gatcccttc    3900
atgataagat ttaaactcga aaagcaaaag ccaaaaaact aacttccatt aaaagaagtt   3960
gttacatata acgctataaa gaaaatttat atatttggag ataccaacc atgtctcata    4020
ttcaacgtga aactagttgt tctcgccctc gtttaaattc taatatggat gccgatttat   4080
atggttataa atgggctcgt gataatgttg gtcaatctgg tgctactatt tatcgtttat   4140
atggtaaacc tgatgctcct gaattattct tgaaacatgg taaaggttct gttgctaatg   4200
atgttactga tgaaatggtt cgtttaaact ggttgactga atttatgcct ttacctacta   4260
ttaaacattt tattcgtact cccgatgatg cttggttatt aactactgct attcctggta   4320
aaactgcttt tcaagtttta gaagaatatc ctgattctgg tgaaaatatt gttgatgctt   4380
tagctgtttt tttacgtcgt ttacattcta ttcccgtttg taattgtcct tttaattctg   4440
atcgtgtttt tcgtttagct caagctcaat ctcgtatgaa taatggttta gttgatgctt   4500
ctgattttga tgatgaacgt aatggttggc ctgttgaaca agtttggaaa gaaatgcaca   4560
aattgttacc ttttctcct gattctgttg ttactcatgg tgatttttct ttagataatt    4620
tgatctttga tgaaggtaaa ttgattggtt gtattgatgt tggtcgtgtt ggtattgctg   4680
atcgttatca agatttagct attttatgga attgtttagg tgaattttct ccttctttac   4740
agaaacgttt atttcagaaa tatggtattg ataatcctga tatgaacaag ttacaatttc   4800
atttaatgtt ggacgagttc ttttaagaat taattcatga ccaaaatccc ttaacgtgag   4860
ttttcgttcc actgagcgtc agacccgta gaaaagatca aaggatcttc ttgagatcct    4920
tttttctgc gcgtaatctg ctgctattta aattacgtac acgtgttatt actttgttaa    4980
cgacaattgt cttaattaac tgggcctcat gggccttccg ctcactgccc gctttccagt   5040
cgggaaacct gtcgtgccag ctctgcagat gacggtgaaa acctctgaca catgcagctc   5100
ccggagacgg tcacagcttg tctgtaagcg gatgccggga gcagacaagc ccgtcagggc   5160
gcgtcagcgg gtgttggcgg gtgtcggggc gcagccatga cccagtcacg tagcgatagc   5220
ggagtgtata ctggcttaac tatgcggcat cagagcagat tgtactgaga gtgcaccata   5280
tgcggtgtga ataccgcac agatgcgtaa ggagaaaata ccgcatcagg cgctcttccg    5340
cttcctcgct cactgactcg ctgcgctcgg tcgttcggct gcggcgagcg gtatcagctc   5400
actcaaaggc ggtaatacgg ttatccacag aatcagggga taacgcagga aagaacatgt   5460
gagcaaaagg ccagcaaaag gccaggaacc gtaaaaaggc cgcgttgctg gcgttttcc    5520
ataggctccg ccccctgac gagcatcaca aaaatcgacg ctcaagtcag aggtggcgaa    5580
acccgacagg actataaaga taccaggcgt ttccccctgg aagctccctc gtgcgctctc   5640
ctgttccgac cctgccgctt accggatacc tgtccgcctt tctcccttcg ggaagcgtgg   5700
cgctttctca tagctcacgc tgtaggtatc tcagttcggt gtaggtcgtt cgctccaagc   5760
tgggctgtgt gcacgaaccc cccgttcagc ccgaccgctg cgccttatcc ggtaactatc   5820
```

```
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaaggaca gtatttggta tctgcgctct gctgaagcca gttaccttcg    6000
gaaaaagagt tggtagctct tgatccggca aacaaccac cgctggtagc ggtggttttt    6060
ttgtttgcaa gcagcagatt acgcgcagaa aaaaggatc tcaagaagat cctttgatct    6120
tttctactgc agaagcttgt tagacaccct gtcatgtatt ttatattatt tatttcacca    6180
tacggattaa gtgaaaccta atgaaaatag tactttcgga gctttaactt taatgaaggt    6240
atgtttttt atagacatcg atgtctggtt taacaatagg aaaaagtagc taaaactccc    6300
atgaattaaa gaaataacaa ggtgtctaac aacctgttat taagaatgtt agaaaagact    6360
taacatttgt gttgagtttt tatagacatt ggtgtctaga catacggtag ataaggtttg    6420
ctcaaaaata aaataaaaaa agattggact aaaaaacatt taatttagta caatttaatt    6480
agttattttt tcgtctcaaa ttttgctttg ttgagcagaa atttagataa aaaaatcccc    6540
gtgatcagat tacaatgtcg ttcattgtac gatgtgtcga aaaatcttta cgacactcta    6600
aactgaccac acgggggaaa aagaaaactg aactaataac atcatgatac tcggaaaacc    6660
tagcaattct caacccctaa acaaaagaaa cttccaaaac cctgaccata taaggagtg     6720
gcaacaatca gcaatcagtc aagatttgat agcagaaaat cttgtatcgg ttgctaatgg    6780
ttttgatgta ctatttatcg gcaataaata ccgaactaac acgggtgttc tgtcacggca    6840
catattaaac tcctattctc atttagaaga tggtggttcg tatggtagaa catttgaccc    6900
atttaccaat aaagaaatgc agtgggttca atttaaaccg aatagaccaa gaaaaggttc    6960
tactggtaag gtaatcaaat atgaatcgcc aaaaggtgaa cctacaagag ttctaatgcc    7020
gtttgtgcct atgaaaatat ggcaacggat tagcgtaaag ttcggagtac cgattaatcc    7080
gaaaaagat actcacttt gggaatgggt aaagaataat ccatcgatac cgattgccat      7140
tacagaagga aataaaaaag ctaattgcct attatcctat ggctatcctg ctattgcctt    7200
tgtaggcatt tggaacggat tagagaaaat aaatgatttc tcgaaggaaa agcagttaaa    7260
agaggatttg aaatggttgt tatccaacgg caaccgaaat attaatatca tctttgacca    7320
agaccagaaa caaaaaactg taattaatgt aaacaaagct attttcgctt tatcttctct    7380
aataagtaga aatggtcata aagttaatat tgtgcaatgg ttgccgtcaa aaggtaaagg    7440
aatagatgat tatttggtag ctttaccttt tgagaaaaga gaaaatcatt tagacaactt    7500
aattaaaatt gcaccatcat ttaatttttg gtcaactaaa tacttattca agtgtcgtaa    7560
accagattta accgtaaatt gccgttattt gagcgatgca gtaaaagaat tacctcaaga    7620
ggatatagca ttaatagcac ctcacggcac gggtaaaact tcattagtag ctactcacgt    7680
taagaatcgg agttatcacg gaaggaaaac tatttcattg gtgcatcttg aaagtttagc    7740
caaagctaat ggcaacgcac ttggattata ttaccgaacc gaaaataata ttgaaaagca    7800
atatcttgga tttagcttat gtgtagatag ttgccgtgat aagattaacg gcattacaac    7860
tgatattatt tcaggtcaag attattgcct tttcattgat gaaattgacc aagtaattcc    7920
acacatcctt aacagtgaaa ctgaagtaag taagtataga tgcaccatca ttgacacttt    7980
ttctgaactg gtgagaaatg ctgaacaggt cattattgct gatgctgatt tatccgatgt    8040
gacgattgac ctaatagaaa acatcagagg taaaaaacta tatgtaatca agaatgaata    8100
tcagtatcag ggaatgactt ttaacgccgt tggttcacca ttagaaatga tggcaatgat    8160
gggaaaatcg gtgtcagaag gcaagaaatt atttattaac accacatccc aaaaggcaaa    8220
```

```
aagtaagtac ggcacaatcg ctcttgagtc ttatattttt ggtctaaata aagaagcaaa    8280
gatattaaga atagactctg aaaccactaa aaaccctgaa catccagcct ataaaatcat    8340
tgaccaagac ttaaataata tcctcaaaga ttatgattat gtcattgcct caccttgcct    8400
tcaaacaggt gtcagtatta ccttaaaagg catttttgac cagcaattta acttttccag    8460
tggaaacatt acacctcatt gcttttttaca gcaaatgtgg cggttgaggg atgcagaaat    8520
tgaaagattc tattatgtgc cgaactcatc taacctcaat ctcattggga ataagtcaag    8580
ttcaccatca gaccttctaa agagcaataa caagatggca acggcaacgg ttaaccttt     8640 gggtagaatc gactccgaat attccctaga gtatgaatcg cacggcattt ggcttgagac    8700
gtgggcaaaa ttatcagcac ggcataacag ttcaatgcgt tgttactctg aaattcttac    8760
ctatctaatt acgtctcaag ggcataaatt aaatatcaac attccctcac ctcttgcaga    8820
tattaagaag ctaaatgatg aggtaagtag taacagggaa aaggtaaaaa atgagagata    8880
ctctcagagg ttaaactcac cagatattaa cgatgcagaa gctaccatac tcgaatctaa    8940
agagcaaaaa atcggattga ctctcaatga gagatgcacc ctagaaaagc ataaagttaa    9000
gaagcggtat gggaatgtaa agatggatat tctcaccttt gatgatgatg gactataccc    9060
caaactcaga ctattttatt acctcaccat cggtaaacct catctcaagg ctaatgacag    9120
aaaagctatt gccaaaatgg gcaatgacaa taaaggcaag attctatcaa aagacttagt    9180
taataaaact tactccgctc gtgtgaaggt cttagagatt cttaaactaa ctgactttat    9240
cgacaatctt agagatgaac tcttaataac tcccaataat ccagctatca ccgattttaa    9300
taatcttctg ctaagagcta agaaggattt aagagtatta ggagtcaaca tcggaaaata    9360
tccaatggcc aacattaatg ccgtacttac tctcattggt cacaaacttt ctgtaatgag    9420
agatgagttc ggaaaagaga aaaggataaa agtagatggt aaatcatacc gatgttatca    9480
acttgaaaca ttaccagatt ttaccaatga tactcttgac tactggttag aaaatgatag    9540
ccaaaaagaa gtaacagcaa cagaaaatta ctccgaaaat tttaaccctt caaatagcta    9600
caatccagac agtaagacac tttcagaggg tgcaaatttc ctatatataa ataaagaaga    9660
attgcatcca aataaattgc acctagaaat aaaagaaggt gctgaacttt ttttattcgg    9720
ggtaaaggtg attgtgaaag gaatcttgga cggggcagta actatattct ctatgggtca    9780
agaatacgat ttatccctca atgaactaga ggggatgtta acatcatgaa ctttacaaga    9840 atcttttaa agggcgatcg caccatgtta aatgatggta catttgttca gatatttgat    9900
atttaccatg accacgcatt gggagtgacc cttgacctta agacagaaaa aattatttcc    9960
gatgatgtta gggtaattac tgtcaaagac ttattgttcg atggcactta taaaggggta   10020
aaatctttta tgcccgataa tgcccgataa tgcccgattg atgctacaaa atcccataat   10080
cataagcgat aatcccctaa tagcttgtaa ttcttgaacc gtagcgattt tagagtattc   10140 caaaagaag aaataaacac cgcaaaatgt cgtatttcac atatataaac caaggttttt    10200
tgccctaaaa tctttatgtt tgtagtgtga tgttgggtca aaatggtcag aaaagttgca   10260
aggtttttat ggatgcttac gcgcgcgagg ggtaagcatc cccaaatagt tactttatcc   10320
tagtccatgc ccatttattg ccgtcccgtt cggctttaaa aaagtgccaa aactcacaag   10380
gtgcaataaa aagttctgta cctttcgcaa ccctagataa tctttcaaca gttacttttt   10440
ttcctattat ctcggtacaa agtttggcta gtttctcttt tccctctttt tcaatcaagc   10500
cttcttgtat gcccaactca ttgattaatc tctctatttt taccattatt tcccgttcag   10560
```

```
gtagtttatc ccctaaatct tcatcggggg gcaatgtagg gcattctgaa ggggcttttt      10620
cttctgtctg gacattatct aatattgaag taaccaaact atcttcagtt ttttctattc      10680
ctattaattc atattcggtt actgtatccg tatcaatatc cgaataacta tctttatccg      10740
tattagctat tcggttaagt ttatccgtta actcagaaac aagactatat agcggtttta      10800
gcttttcttc tatcctgtta tctaatacgg ataagtttat acggttatca ttatccgtat      10860
tagtatcatt gggctttttt ggtagttcta cccctcata  aaccgctttt attcccaatt      10920
ccaacagact gataacagta tcctttataa tgggtttttt gctgatatgg tgaacttttg      10980 cccctttccat cattgcgata ctttctatct cactcatcaa cttatcgctt aagtgaatct     11040
cgtatctgtt taatccctta ctggttttat tcatatccgt ttactttatt cggttaacaa      11100
ttctatttta tacgaataaa atattatacg gttaacttta tacgtttaac tattttatct      11160
atacggataa cagtaataag ttattcgtat tagttatacg tttactttta tccaaataaa      11220
attagtgcat ttaaactaaa agaatgattt tatcggagtt gatagcattg gattaaccta      11280
aagatgttta taagctatat ctgataagta tttaaggtta ttttgttatt ctgtttattg      11340
acattatcag aataaaagaa tagaatataa ttgttgagag ataagaggtt taagtgatta      11400
tggttaagaa gttagttggt tatgtcaggg tcagtagtga atcgcaagag gataacacta     11460
gcttacagaa tcagatagag agaattgaag catattgtat ggcttttggt tatgagttgg      11520
taaaaatatt caagagggtt gccactggta caaaagcaga tattgaaacc cgtcctattt      11580
ttaatgaagc tatagaatac ttgaaacagg ataatgctaa tggaattatt gccttgaagc      11640
tagaccgaat cgcacggaat gctttagatg tattgcgttt ggttcgtgaa accttagaac      11700
cacaaaataa aatgttagtg ttactagata ttcaggtaga tacttcgaca ccttcaggaa      11760
aaatgatttt aactgtaatg agtgccgttg ctgaactcga aagagacatg atctatgatc      11820
gcactcaggg gggtagaaag actaaagccc aaaagggcgg gtatgcctac gggaaaccta      11880
aatttggcta taagactgaa gaaaaggaac taaaagaaga ttcagcacaa caggaaacta      11940
ttaaactaat taagagacac cgtaggtcag ggaaaagcta ccagaaaata gctgattatc      12000
tcaatgccca aagtattccc actaaacaag gtaagaaatg gagttctagc gtcgtctatc      12060
gaatctgtca ggaaaaagct ggttaagtct gtttatagat atttagaatt tattgaataa      12120
aaatagtatg aacaataaat atttatggac taaccacgct cggaaacgtt taactgaacg      12180
atgggaaata aaagaatcat gggttattga taccatcgaa atcctgaac  gttcagaatt      12240 tattgttgat gagtcagggg aaaaatatca ttactataaa agaatagcta agtttaagaa      12300
tagagtgtta gaagtgataa cttctgccaa ctcaacaccc acaagaataa taacctttta      12360
ctttaaccgt aacatgagga aaaatttatg attgttactt acgataatga agttgacgca      12420
atttatttta agttaacgga aaataaaatt gatagcaccg aacctcaaac agacaggatt      12480
atcattgatt acgatgaaag taataatatt gttggcattg aggtattaga ttttaattat      12540
cttgtcaaga aaggtttaac cgttgctgat ttacctttt  ctgaagatga aagattaaca      12600
gcttctcaat attttaattt tcctgttgct atctaatcca gaaggggcaa taatccccctt     12660 ctttcatcga gttagactta atatcacaaa agtcattttc attttaccgt ttctttttcca     12720 cagcgtccgt acgcccctcg ttaaatctca aaaccgacaa tttatgatgt ttataaaaag      12780
ttactcactt taataagtat ttatactcat taaagggtta ttcttttttt gtagcctgat      12840
aggttgggaa ggaatatttc agattatcag atttgttgaa tatttttcgt cagatacgca      12900
aaccttacaa acataattaa caactgaaac tattgatatg tctaggtttt agctctatca      12960
```

```
caggttggat ctg                                                      12973
```

<210> SEQ ID NO 27
<211> LENGTH: 359
<212> TYPE: DNA
<213> ORGANISM: Cyanobacterium sp. ABICyano1

<400> SEQUENCE: 27

```
cctcaactac aagttctttt atatattact ttaacctgag ttttggataa gctgaaagca    60
ttattttctc gtagtcagaa aaccttatag cttcttagaa ataacgataa aattaccttta   120
atccgaactg acgttaaata tattcacccc tatcacccca aaaccctaag ccccctacttc   180
cccctttccc ttcatcacct catcccccca tccctaaca cttaaccttta ttctttattc    240
ttaaaccgaa ctgaggtgaa gttgcagaat acccatgggg ggttacagca ttgtagaaaa    300
ataaatattc tttcattatt aaggttgttt ggtaaaaata tgtgaaaacc ctaataatt     359
```

<210> SEQ ID NO 28
<211> LENGTH: 239
<212> TYPE: DNA
<213> ORGANISM: Cyanobacterium sp. ABICyano1

<400> SEQUENCE: 28

```
ggggacagac atattttat cataatggta aattcataat aatttagac ttttttttgc      60
aaaaattaat ctcactctct tctttcccta tctcccattg tttcttatat cccaatgccc   120
caataccccaa agctcagaaa ataggtatta gcgaagaggt gttgatcccc tcccctagca   180
aaatatactc ctatatagta aagtgagaaa gtgaagaaat aagatcaagt tcgcaattt    239
```

<210> SEQ ID NO 29
<211> LENGTH: 496
<212> TYPE: DNA
<213> ORGANISM: Cyanobacterium sp. ABICyano1

<400> SEQUENCE: 29

```
caaatcacga gaatttatgt agggactatt ttgggttgac ggtggagagt atgtcgccct    60
tgaattatga cccgaagatg aagatgtcgg ggaggtggaa ggacggtctt taagaggttt   120
aacatcaaag ttggtcataa tctctgtccc tgtttgataa ctactattta attttgagtt   180
gttttaggta catcaaaata cccaaatcct tactctcccc tcaatataca acaaaaaaaa   240
cttttttgatt cactttagtc ataaaaatta gaatttatct accgaaatat tacataaatg   300
taatgtatat attttctgat ttattccgtg tgagccatga ttcataattt ataattcata   360
atttctaaat atgcccctac aatggatata gaatgtcatt ttaattatag gtatcataat   420
cgtggtagtt actccggaaa aaactattga atcaaattca gtctcacctg ctacagatag   480
agtagccgtt attctt                                                    496
```

<210> SEQ ID NO 30
<211> LENGTH: 290
<212> TYPE: DNA
<213> ORGANISM: Cyanobacterium sp. ABICyano1

<400> SEQUENCE: 30

```
ttgacgattg tattgactta cgccaaatgg cttaccctca tagtgaatag ttgataatta    60
agaattaaaa atcccgttca cgacagaagg gagtgtaaga gccttcggtg cgaactctca   120
tcttccctga aacctgacac ctgaaacctg acacctgaaa cctgacacct catctcccta   180
```

```
atcccctaat tttaatgaaa aaatacctg  agtgggcatt gaaaaaaaag aaaagttgtt       240
cgactatgaa ataagaattc tgcacttcgt gagaaaaaag gaaatgaaat                  290
```

<210> SEQ ID NO 31
<211> LENGTH: 355
<212> TYPE: DNA
<213> ORGANISM: Cyanobacterium sp. ABICyano1

<400> SEQUENCE: 31

```
ctatttaact aggaaaaggt aaagttaaaa ggacaagggt aaataattaa aaattaagaa        60
ttaagaactt ctaactctca ttactcatta cttatttcct cctctcaccc cttctcctga      120
tcacctcttc tcctcaatac tcggaactca tttccccatg gtgtgacact caaatcaaaa      180
gtctgttatt gactttcaga tgaaatatta ctatgataac aatatccccc ctatgggtat      240
ataaaaatat gagcgatatt agttaaaaat caaatttgga ttttttttct gaaaatattt      300
taagattaag taaagataag taaagaaatt ataagcaatt ttgttaaatc atacc           355
```

<210> SEQ ID NO 32
<211> LENGTH: 619
<212> TYPE: DNA
<213> ORGANISM: Cyanobacterium sp. ABICyano1

<400> SEQUENCE: 32

```
ctcacactga aaatattgcc acaagaaata aagatcaagc aataatcctg actaaaaagg       60
aataaagtaa ttatcctttt cctgatatgt tatctgactt gttgtttctt agtcatgttc     120
cttccatttt tattttttgtt tttatcattt ttattacaaa aatttcttaa tagggctaaa    180
gcatttagtt agttttttag ctctcaacaa gttgactaat caatataatg ccctaagtta     240
atttgccctt ggtttgacgg aggatattgg aaaaagaaa  cttctcgttg tatttcacag     300
ggaaaagggg gaaatttat  taataactaa acaatagaaa ataattattt atttatatta     360
ttttgtgaac aaatgttcaa gaattaaagt gtaataagaa aatttatttt tttatattta     420
tttaaaactt agatataagc ctaaaggtct gaaattatta ttagacaatc aattgattca     480
gaggtaatag ttttttactt aaaaatattt tttcaaaatt atccctatt  tgggtattga     540 aaaataaata aattcaagta ataatataca gaataaagga aaatctaatc ttaaaaattt     600
tgtgtgtgag gaattgaaa                                                   619
```

<210> SEQ ID NO 33
<211> LENGTH: 190
<212> TYPE: DNA
<213> ORGANISM: Cyanobacterium sp. ABICyano1

<400> SEQUENCE: 33

```
tatcaccatt gtagaaaagc cagaaaatca attaacacaa atttcctgta aattattatg       60
tatgattttc cccttctccc cttaaaagga gaaataaaaa actatatccc ccaaccaccg      120
ataagcattg tgagagaaaa atcatttagg taggatcaat gctgtaaccg ataaagataa      180
ataaataatt                                                              190
```

<210> SEQ ID NO 34
<211> LENGTH: 536
<212> TYPE: DNA
<213> ORGANISM: Cyanobacterium sp. ABICyano1

<400> SEQUENCE: 34

```
attctgtgaa ttgattagat ttgaggtttt ttaagaggtt gattaccttg cctccaaaaa       60
```

```
aatcataaca cactaatgct ctatatgaaa gggctttaga cccataggtt tttgagaaaa    120
aaacttgcta actctcggac aatgtcagca taactaaagt caattctttt cgtactttat    180
aattgtctat aatttaatat acaactgttc tgaaactagt ttttctctac attccttagt    240
tttatctgag taaggttgct tgtaacttaa cttcggttgg gcctaaaaat atccgattag    300
gagcaggtgt cagactttaa ttaattatta attattaatt gcttattgcc aaccctcggc    360
gacaccactt tttcatcagc ccagataaa gattgatgtt ttagttttgt ttcttttttat    420 cccctaattc aactaataca agtaaaacta aggttgttta tcaaaaatga tggttgatgt    480
ttgggtaaat tttaagatat tatgaaaaga aaatgaataa aaaatgaaaa atcttt        536

<210> SEQ ID NO 35
<211> LENGTH: 283
<212> TYPE: DNA
<213> ORGANISM: Cyanobacterium sp. ABICyano1

<400> SEQUENCE: 35
ctacaggggc aagatttggc ggaaatctat atgtggattc tctttcaagt gaagaaggtg     60
cagtgccgac ttatctggac ttattagaat acgatattcg cactattact aatggtttgt    120
tagcaggagt gaacaattaa aaattttttc ctaattgacg aataaaaaat caatgtcaac    180
taatagttaa caatactctc tgaaaaccaa aaattgtcaa ccaaaacata acataatttt    240
tacccaaaaa cctcatttat aaactttaag gataaaatca atg                      283

<210> SEQ ID NO 36
<211> LENGTH: 299
<212> TYPE: DNA
<213> ORGANISM: Cyanobacterium sp. ABICyano1

<400> SEQUENCE: 36
gggattagag agttcaaagt taggaatgag gtgtcaggtt ttaggtttca ggtttagggg     60
agcaatgaga aagaggtttc aggtttcagg tgtcaggttg caggtgtcac aggtgatgag    120
gggatggggg atgaggggga acaagtaagt aataagtgt tcggagtttt taattcttaa    180
ttcttaattt ttcctttgcc tcttgccttt tgccttgtct taattactaa tttctaatta    240
aaatgattgt gttttctagt ttagtctcat ggttacttga acccttacag catagttttt    299

<210> SEQ ID NO 37
<211> LENGTH: 414
<212> TYPE: DNA
<213> ORGANISM: Cyanobacterium sp. ABICyano1

<400> SEQUENCE: 37
ttacaaacgg cgggaattat tatggtagta gcgatgttag taaccccggg tgcgatcgca     60
tatttactta cagatcgttt tgatcaaatg ttaatcttat caatagttag tagtgttcta    120
tcttgtgttt taggcactta tttaagttat catttttgatg tttctacggg gggaagtatt   180
gtcgttttaa tgaccataat ttttatttta gcgatgattt ttgctcctaa atatggcatc    240
atcaatcaaa ataccaaaat atattctgct taacttgttt actgatactt caaataatca    300
tataacctat cttccgagtt aaaaataatg gatattatcc aactgaggtc gagaatagag    360 tttcttttttt gatagaattt ttttacacca gttattcatt actatcatgg gata          414

<210> SEQ ID NO 38
<211> LENGTH: 412
<212> TYPE: DNA
```

<213> ORGANISM: Cyanobacterium sp. ABICyano1

<400> SEQUENCE: 38

```
taatatagtg attattataa atgcaatgtg aatcaaacct atattttacc gtacattgac      60
catggaactt aatttgaggt gattagtaga gggtgcgatc gccctatttg tcaaataata     120
aagataacat ttgacattgc tgattgaaga cataaaacac agaaaaaatc aggtaaaaat     180
ataaagctaa agtctaaata tggtttactt ttgccttcga cttacaacaa aaaatcatag     240
ctagaatcac caacgcctaa tattttattt agctgaaatt ttgggatgaa cttttttgtaa    300
aaatcggggg tctaaaaata tagcaaccac gatattaaat aactgagtga ttatttttaat   360
ctattggggg cttattaact aaatacttgc attttatgg agggttttaa tt            412
```

<210> SEQ ID NO 39
<211> LENGTH: 364
<212> TYPE: DNA
<213> ORGANISM: Cyanobacterium sp. ABICyano1

<400> SEQUENCE: 39

```
aaagattatt ttctacagaa gcaaccettt catcttccga attttcagga atttcctgct      60
tttgtttctg aatattagca taggcggctt ttgcccactc taaagaaggt tgagactgaa     120
tttctgaggt ttcagaagga gcattagatt gtttatcttc aacaacagga ggttttttgtt    180
caatattttc cttattctct tttttacggc gaaaccaatt aaacataatg attgtgcata     240
aatattcgtt aatatattgt aaccctagaa aggaatcggt ttcaggttta tccccagaga    300
atgtgaacct ttacagaaag taaaaagtct aaaatcgtag caacaataaa tcacagaaat    360
tgag                                                                  364
```

<210> SEQ ID NO 40
<211> LENGTH: 234
<212> TYPE: DNA
<213> ORGANISM: Cyanobacterium sp. ABICyano1

<400> SEQUENCE: 40

```
atctagtaat aatcatcaag agttgttaaa acttcactat caagaattgg tagcaagagg      60
attacaacat ctgagtttag atcatcgagc agttattgtt cttcatgatt tggaagattt     120
accacaacag gaaatagcgg aaatattatc tattccccctt ggtacggtca atctcgttt    180
attcaaagcc agaaaaaatt tgcgtcaatt tttagaactt gaaggtatta gctt           234
```

<210> SEQ ID NO 41
<211> LENGTH: 246
<212> TYPE: DNA
<213> ORGANISM: Cyanobacterium sp. ABICyano1

<400> SEQUENCE: 41

```
ccaatatctt gtcatacata cttatttgcc tcactattag ccctatatgt ctctattgta      60
ttttttcttt tctcctattc ctagatcttg taatgaatca ttactctctg aaatatagct    120
actaattta tggttgtttg taaaatatat taacaaatga acaataaatc atattttgtg     180
ttaatctaat tattagacaa ctactgaatt tatattcaga tattcacaga taggagaatt    240
ttgatt                                                                246
```

<210> SEQ ID NO 42
<211> LENGTH: 346
<212> TYPE: DNA
<213> ORGANISM: Cyanobacterium sp. ABICyano1

<400> SEQUENCE: 42

```
attctattac cctccgaggg tggctatctc cttttatttg gtggctgata aaccctatt      60
ctattaaagt agccaatgag ttagttaatg cggcggctaa atgtcactaa aatttcatct    120
taggttcaca tcaaagtcat atcggttgtt tatagtatta agtgtcaggg agaaagatag    180
gttttcctct ttagctcctt cgcacccttta atccctgact ttttttattt tttgttcgt    240
gtgattaatc tatttgtgta gcaattattt ttatcttatt ttcttttcag tctagtaatt    300
aattattttt atattttgta ttatttttag agaggtttga gctgtt                   346
```

<210> SEQ ID NO 43
<211> LENGTH: 320
<212> TYPE: DNA
<213> ORGANISM: Cyanobacterium sp. ABICyano1

<400> SEQUENCE: 43

```
gaatatctca tccttagctt ctacttatac cttcagcata gttaaaaatc atccctttat    60
tgatggtaat aaaagaacag gttttattag tggagtaacc ttttaatgc tcaatggttc    120
tcactttact gcttctgaag tggaagtagt acatatcatc caaaccttag ctagtggcag    180
aattaccgag gaagaattac aacaatggtt cgtaaggaaa agtaagcaga tgaataatta    240
aagcatcatt tcatcctcat ttcatattct cctgtcacca tggtatggaa gattaggtaa    300
aaatgaggaa aaagtttatt                                                320
```

<210> SEQ ID NO 44
<211> LENGTH: 304
<212> TYPE: DNA
<213> ORGANISM: Cyanobacterium sp. ABICyano1

<400> SEQUENCE: 44

```
gcgattatca accacgaaaa catacaatta ttatcaaacc tgctgagaaa ttatccacag    60
aaatagatgt ttctgcgaag ggaaaatggg cttttcattg ccatttaatg tatcacatgg   120
atgtgggaat gtttcggact attaatgtta tttcctaaaa aataatagta ttaaagccta   180
aaatttttat aaaaaaattc atgtctttta ttagggtgag cattcttcct ttatgtctcc   240
ttattttacc tctttagagg taactacaaa cttaatcaaa aaatttagat aattaattat   300
atca                                                                 304
```

<210> SEQ ID NO 45
<211> LENGTH: 309
<212> TYPE: DNA
<213> ORGANISM: Cyanobacterium sp. ABICyano1

<400> SEQUENCE: 45

```
atacatggtt ggttcactga cttttacccc agttttctct ttgaacaatt ggcataactc    60
tgaaaaaatc agatcgggct tttgttgaat tatttgttca atcaaagcaa aaccgtgatt   120
gtctattttc tttttttttcc caccactcat agataaaaat ttatcccgaa ctcaggttat   180
attaagttcg gatgatcact taagataatt gatcagattg gttaagatag agaaaaattc   240
tttttcatag tgatttcata attgatagtt acaataacga ttattattta gtaaaagat   300
tttcaaatc                                                            309
```

<210> SEQ ID NO 46
<211> LENGTH: 330
<212> TYPE: DNA

<213> ORGANISM: Cyanobacterium sp. ABICyano1

<400> SEQUENCE: 46

```
tggtcaagtt actatatgtt tagaaacaac aaaaaaagaa gtcattataa aaataattga      60
tacaggaatt ggcattaata agaagaaca aaaattaatt tttaatcgtt tttatcgaat     120
caataaagca agaaatagag agaaaggcag ttgcggatta ggtttagcta ttgcaaatgc     180
gatcgcgctt aatcatggtg gtagaataat tttagaaagt caagaaaatc aaggcagtat     240
ttttaccgtt tatttaccga aaatcatttc atcctaattt catattcttt tgacagaatc     300
aaaggtaaag ataaaaagag agaaacagtc                                       330
```

<210> SEQ ID NO 47
<211> LENGTH: 490
<212> TYPE: DNA
<213> ORGANISM: Cyanobacterium sp. ABICyano1

<400> SEQUENCE: 47

```
catctttact tttgactaac atttcatagg tatcatgacg aaaattttttt agtctgttat      60
atttgttcat gtagagagat tttaatttgt gattatttta ttttctctct attttttcttt    120
tttgtcttgt ccttcctcat ttttctctac atttagtcta aactcagct ctttaatctc      180
cagtttctct ttcctcctct tcctcatcaa ggtaatcatc ccaattaata tcttcttctt     240
gttctaattt gggttgagat tgttgttat caatcatatt tcatactcct aaaactttct     300
tacttattta tcagttactt tttacccatt tatgcaatag tgtagaaatt ttttttcgatc     360
gagttaatta atttttattt caaccatatc taaataattc ttgatggaca ttctagttaa     420
ctagaaggtt taagctaaaa ataattattg atattgcctt cggtataact aactatatcc     480
agagaaaaag                                                             490
```

<210> SEQ ID NO 48
<211> LENGTH: 433
<212> TYPE: DNA
<213> ORGANISM: Cyanobacterium sp. ABICyano1

<400> SEQUENCE: 48

```
tttatatata aactcgaata aaattatcaa tataaagtca aactatatct atcctatttt      60
aactgctatt ggtaagtccc ttaattagtg ttggggtgaa tagattttaa aagggcaaac     120
cccccttat cctccctcga gagggggag gcaaaaggc aaggggcaag ggaaaaatta        180
agaattaaga attaaaaaact ccgaacacct gtagggcga atagccattc gcttcccctc    240
atccccccat ctccccaaca ccctaagccc ctactcgtta ctcattttatt tacatcattt    300
atttacatca ttaagaaaag taacaaattt tgacaagtag tcttttgaca ggaaaaagca     360
aattctcgaa gatgaaaaca atagaaaaaa attcaatctt acagtaacga tgaaaaaact     420
tttaggctta att                                                        433
```

<210> SEQ ID NO 49
<211> LENGTH: 306
<212> TYPE: DNA
<213> ORGANISM: Cyanobacterium sp. ABICyano1

<400> SEQUENCE: 49

```
ctcaagagat agttaaaaaa caaatagctt tagtctatca attaatcgaa ttatttttac      60
aaacaaattt tcataaaccc atagaactag aggaggaagt tatttatgtt taaaaatcta    120
aaagagtttt atattcccct aaaaccccct tagtaagagt gacttttttc atcatttgcc    180
```

```
tgtaaattct cctcttttaa taagagagct agggtgtttt aaaagaggat tttattgctt      240
tccaattcta actacttcaa aaacttattt tatactcaat aatttattaa tcaagaggaa      300
attacc                                                                306
```

<210> SEQ ID NO 50
<211> LENGTH: 13604
<212> TYPE: DNA
<213> ORGANISM: Artificial Sequence
<220> FEATURE:
<223> OTHER INFORMATION: TK441¶ABICyano:PpetJABICyano1-PDCmax-
    PrpsLABICyano-synADHmax-PrbcABICyano-Km**-oriVT

<400> SEQUENCE: 50

```
aatattttc gtcagatacg caaaccttac aaacataatt aacaactgaa actattgata       60
tgtctaggtt ttagctctat cacaggttgg atctgtcgac tttatatata aactcgaata     120
aaattatcaa tataaagtca aactatatct atcctatttt aactgctatt ggtaagtccc     180
ttaattagtg ttggggtgaa tagattttaa aagggcaaac ccccctttat cctccctcga     240 gagggggggag ggcaaaaggc aaggggcaag ggaaaaatta agaattaaga attaaaaact    300
ccgaacacct gtaggggcga atagccattc gcttcccctc atcccccat ctccccaaca      360 ccctaagccc ctactcgtta ctcatttatt tacatcattt atttacatca ttaagaaaag     420
taacaaattt tgacaagtag tcttttgaca ggaaaaagca aattctcgaa gatgaaaaca     480
atagaaaaaa attcaatctt acagtaacga tgaaaaaact tttaggctta attatgaatt     540
cttataccgt gggtacttat ttagccgaac gcttagtgca aattggttta aaacatcatt     600
ttgccgtggc tggggactat aatttagtgt tattggataa cttattatta aataaaaaca     660
tggaacaagt gtattgttgt aatgaattaa attgtggttt ttctgctgaa ggttatgcta     720
gagctaaagg tgcagctgct gctgttgtta cttattctgt gggtgcttta tctgcttttg     780
atgctattgg tggtgcttat gccgaaaatt tacccgtgat tttaatttct ggtgccccta     840
ataataatga tcatgccgct ggacatgttt tacatcatgc cttaggtaaa accgattatc     900
attatcaatt agaaatggcc aaaaatatta ctgctgctgc cgaagctatt tatactcctg     960
aagaagcccc tgccaaaatt gatcatgtga ttaaaaccgc cttacgcgaa aaaaacccg    1020 tgtatttaga aattgcctgt aatattgctt ctatgccttg tgctgctcct gggcctgctt    1080
ctgctttatt taatgatgaa gcctctgatg aagctagttt aaatgctgcc gtggaagaaa    1140
ccttaaaatt tattgccaat cgcgataaag ttgccgtgtt agttggttct aaattaagag    1200
ctgctggtgc tgaagaagct gctgttaaat ttgctgatgc tttaggtggt gcagttgcta    1260
ctatggctgc tgccaaatct tttttttccg aagaaaatcc ccattatatt ggaactagtt    1320
ggggagaagt ttcttatcct ggtgtggaaa aaactatgaa agaagccgac gctgttattg    1380
ctttagcccc tgtgtttaat gattattcta ccactggttg gactgatatt cccgatccca    1440
aaaaattagt tttagccgaa cctcgttctg ttgttgttaa tggtgttcgc tttccctctg    1500
tgcatttaaa agattatttta acccgcttag cccaaaaagt ttctaaaaaa actggtgcct    1560
tagatttttt taaatctta aatgcgggtg aattaaaaaa agctgctcct gctgatcctt    1620
ctgctccttt agttaatgct gaaattgccc gtcaagttga agccttatta accctaata     1680 ctaccgttat tgccgaaact ggtgattctt ggtttaatgc ccaacgcatg aaattaccta    1740
atggtgcccg tgttgaatat gaaatgcaat ggggtcatat tggttggtct gtacctgctg    1800
cttttggtta tgctgttggt gctcctgaac gtcgtaatat tttaatggtg ggtgatggtt    1860
```

-continued

```
cttttcaatt aactgcccaa gaagttgccc aaatggttcg cttaaaatta cccgttatta    1920 ttttttttaat aaataattat ggttatacca ttgaagtgat gattcatgat gggccatata   1980
ataatattaa aaattgggat tatgcgggtt taatggaagt gtttaatggt aatggtggtt    2040
atgattctgg tgctggtaaa ggtttaaaag ccaaaactgg tggtgaatta gctgaagcta    2100
ttaaagttgc cttagccaat actgatgggc caaccttaat tgaatgtttt attggtcgcg    2160
aagattgtac cgaagaatta gttaaatggg gtaaacgtgt tgctgctgct aattctcgca    2220
aacccgtgaa taaattattg taattttggg ggatcaattc gagctcctcc gcttaaaaaa    2280
tttcattttt cgatcaaaaa agacaaatta ttactaatta gctcatggca ataaataatc    2340
agtagtaatc tgttttcaca ttttattgtt aattttattt attgctaata tcaaccttttt   2400 ctacttctgc ttaatatttt atttatgctc aatgggaaaa tctgaaataa gattgagaac    2460
agtgttacca atagaagtat ttaaggttta aagcatacct taaagataac attttttttt    2520
gaaaagagtc aaattatttt tgaaaggctg atattttga tatttactaa tatttttattt    2580 atttcttttt cccttaaaat aagagctaaa tctgttttta ttatcattta tcaagctcta    2640 ttaataccctc aacttttttca agaaaaaata ataataattt ttccctctat tctcatgacc   2700
ttttaggaaa attaatttta gaaaaactat tgacaaaccc ataaaaatg agataagatt     2760 atagattgtc actggtattt tatactagag gcaaattata tttatatata caaaaatgct    2820
gtataaaaaa catctcatat gattaaagcc tatgctgcct tagaagccaa tggtaaatta    2880
caaccctttg aatatgatcc tggtgcttta ggtgccaatg aagtggaaat tgaagtgcaa    2940
tattgtggtg tgtgtcattc tgatttatct atgattaata atgaatgggg tatttctaat    3000
tatcccttag ttcctggtca tgaagttgtt ggtactgttg ctgctatggg tgaaggtgtt    3060
aatcatgtgg aagtgggtga tttagttggt ttaggttggc attctggtta ttgtatgacc    3120
tgtcattctt gttatctggg ttatcataat ttatgtgcca ctgccgaatc tactattgtg    3180
ggtcattatg gtggttttgg tgatagagtt cgtgctaaag gtgtttctgt ggtgaaatta    3240
cccaaaggta ttgatttagc ctctgctggg cctttatttt gtggtggtat taccgttttt    3300
tctcccatgg tggaattatc tttaaaacct accgccaaag ttgctgttat tggtattggt    3360
ggtttaggtc atttagccgt tcaatttttta agagcctggg gttgtgaagt tactgcttttt  3420 accttcttctg cccgtaaaca aaccgaagtt ttagaattag gtgccatca tattttagat    3480 tctaccaatc ctgaagctat tgcttctgcc gaaggtaaat tgattatat tatttctacc    3540 gtgaatttaa aattagattg gaattatat atcagtacct tagcccctca aggtcatttt    3600
cattttgttg gtgtggtgtt agaacccttg gacttaaact tatttcccttt attaatggga  3660 caacgttctg tttctgcttc tcctgttggt tctcctgcta ctattgccac tatgttagat    3720
tttgccgtgc gtcatgatat taaacccgtg gtggaacaat tttctttttga tcaaattaat    3780 gaagccattg cccatttaga atctggtaaa gccattatc gcgtggtgtt atctcattct    3840
aaaaattaat aagattaact tctaaactga acaaatttg agggtaggct tcattgtctg    3900
cccttatttt tttatttagg aaaagtgaac agactaaaga gtgttggctc tattgctttg   3960
agtatgtaaa ttaggcgttg ctgaattaag gtatgatttt tgacccccttc tctcttctgc   4020 agttacctag gatttctggc gaaagggga tgtgctgcaa ggcgattaag ttgggtaacg    4080
ccagggtttt cccagtcacg acgttgtaaa acgacggcca gtgagcgcga cgtaatacga    4140
ctcactatag ggcgaattgg cggaaggccg tcaaggccgc atggcgcgcc tacgtagaca    4200
```

-continued

```
attgtcgatg taattattaa ctatcttatt atagatgagg ggagagggag aaattagttc    4260
ggagagaacg ctcgagcgct cgttccgcaa agcggtacgg agttagttag gggctaatgg    4320
gcattctccc gtacaggaaa gagttagaag ttattaatta tcaacaattc tcctttgcct    4380
agtgcatcgt tacctttta attaaaacat aaggaaaact aataatcgta ataatttaac     4440
ctcaaagtgt aaagaaatgt gaaattctga cttttataac gttaaagagg gaaaaattag    4500
cagtttaaaa tacctagaga atagtctggg gtaagcatag agaattagat tagttaagtt    4560
aatcaaattc agaaaaaata ataatcgtaa atagttaatc tgggtgtata gaaaatgatc    4620
cccttcatga taagatttaa actcgaaaag caaaagccaa aaaactaact tccattaaaa    4680
gaagttgtta catataacgc tataaagaaa atttatatat ttggaggata ccaaccatgt    4740
ctcatattca acgtgaaact agttgttctc gtcctcgttt aaattctaat atggatgccg    4800
atttatatgg ttataaatgg gctcgtgata atgttggtca atctggtgct actatttatc    4860
gtttatatgg taaacctgat gctcctgaat tattcttgaa acatggtaaa ggttctgttg    4920
ctaatgatgt tactgatgaa atggttcgtt taaactggtt gactgaattt atgcctttac    4980
ctactattaa acatttatt cgtactcccg atgatgcttg ttattaact actgctattc       5040
ctggtaaaac tgcttttcaa gttttagaag aatatcctga ttctggtgaa aatattgttg    5100
atgctttagc tgttttttta cgtcgtttac attctattcc cgtttgtaat tgtccttta     5160
attctgatcg tgtttttcgt ttagctcaag ctcaatctcg tatgaataat ggtttagttg    5220
atgcttctga ttttgatgat gaacgtaatg gttggcctgt tgaacaagtt tggaaagaaa    5280
tgcacaaatt gttaccttt tctcctgatt ctgttgttac tcatggtgat ttttctttag     5340
ataatttgat ctttgatgaa ggtaaattga ttggttgtat tgatgttggt cgtgttggta    5400
ttgctgatcg ttatcaagat ttagctcttt tatggaattg tttaggtgaa ttttctcctt    5460
ctttacagaa acgtttattt cagaaatatg gtattgataa tcctgatatg aacaagttac    5520
aatttcattt aatgttggac gagttctttt aagaattaat tcatgaccaa aatcccttaa    5580
cgtgagtttt cgttccactg agcgtcagac cccgtagaaa agatcaaagg atcttcttga    5640
gatccttttt ttctgcgcgt aatctgctgc tatttaaatt acgtacacgt gttattactt    5700
tgttaacgac aattgtctta attaactggg cctcatgggc cttccgctca ctgcccgctt    5760
tccagtcggg aaacctgtcg tgccagctct gcagatgacg gtgaaaacct ctgacacatg    5820
cagctcccgg agacggtcac agcttgtctg taagcggatg ccgggagcag acaagcccgt    5880
cagggcgcgt cagcgggtgt tggcgggtgt cggggcgcag ccatgaccca gtcacgtagc    5940
gatagcggag tgtatactgg cttaactatg cggcatcaga gcagattgta ctgagagtgc    6000
accatatgcg gtgtgaaata ccgcacagat gcgtaaggag aaaataccgc atcaggcgct    6060
cttccgcttc ctcgctcact gactcgctgc gctcggtcgt tcggctgcgg cgagcggtat    6120
cagctcactc aaaggcggta atacggttat ccacagaatc aggggataac gcaggaaaga    6180
acatgtgagc aaaaggccag caaaaggcca ggaaccgtaa aaaggccgcg ttgctggcgt    6240
ttttccatag gctccgcccc cctgacgagc atcacaaaaa tcgacgctca agtcagaggt    6300
ggcgaaaccc gacaggacta taaagatacc aggcgtttcc ccctggaagc tccctcgtgc    6360
gctctcctgt tccgaccctg ccgcttaccg gatacctgtc cgcctttctc ccttcgggaa    6420
gcgtggcgct ttctcatagc tcacgctgta ggtatctcag ttcggtgtag gtcgttcgct    6480
ccaagctggg ctgtgtgcac gaaccccccg ttcagcccga ccgctgcgcc ttatccggta    6540
actatcgtct tgagtccaac ccggtaagac acgacttatc gccactggca gcagccactg    6600
```

-continued

```
gtaacaggat tagcagagcg aggtatgtag gcggtgctac agagttcttg aagtggtggc    6660
ctaactacgg ctacactaga aggacagtat ttggtatctg cgctctgctg aagccagtta    6720
ccttcggaaa aagagttggt agctcttgat ccggcaaaca aaccaccgct ggtagcggtg    6780 gttttttgt ttgcaagcag cagattacgc gcagaaaaaa aggatctcaa gaagatcctt    6840
tgatcttttc tactgcagaa gcttgttaga caccctgtca tgtatttat attatttatt    6900 tcaccatacg gattaagtga aacctaatga aaatagtact ttcggagctt taactttaat    6960
gaaggtatgt ttttttatag acatcgatgt ctggtttaac aataggaaaa agtagctaaa    7020
actcccatga attaaagaaa taacaaggtg tctaacaacc tgttattaag aatgttagaa    7080
aagacttaac atttgtgttg agttttata gacattggtg tctagacata cggtagataa     7140
ggtttgctca aaataaaat aaaaaagat tggactaaaa aacatttaat ttagtacaat      7200
ttaattagtt attttttcgt ctcaaatttt gctttgttga gcagaaattt agataaaaaa   7260
atccccgtga tcagattaca atgtcgttca ttgtacgatg tgtcgaaaaa tctttacgac    7320
actctaaact gaccacacgg gggaaaaaga aaactgaact aataacatca tgatactcgg    7380
aaaacctagc aattctcaac ccctaaacaa aagaaacttc caaaaccctg accatataaa    7440
ggagtggcaa caatcagcaa tcagtcaaga tttgatagca gaaaatcttg tatcggttgc    7500
taatggtttt gatgtactat ttatcggcaa taaataccga actaacacgg tgttctgtc    7560 acggcacata ttaaactcct attctcattt agaagatggt ggttcgtatg gtagaacatt    7620
tgacccattt accaataaag aaatgcagtg ggttcaattt aaaccgaata gaccaagaaa    7680
aggttctact ggtaaggtaa tcaaatatga atcgccaaaa ggtgaaccta caagagttct    7740
aatgccgttt gtgcctatga aaatatggca acggattagc gataagttcg gagtaccgat    7800
taatccgaaa aaagatactc acttttggga atgggtaaag aataatccat cgataccgat    7860
tgccattaca gaaggaaata aaaagctaa ttgcctatta tcctatggct atcctgctat     7920
tgcctttgta ggcatttgga acggattaga gaaataaat gatttctcga aggaaaagca    7980
gttaaaagag gatttgaaat ggttgttatc caacggcaac cgaaatatta atatcatctt    8040
tgaccaagac cagaaacaaa aaactgtaat taatgtaaac aaagctattt tcgctttatc    8100
ttctctaata agtagaaatg gtcataaagt taatattgtg caatggttgc cgtcaaaagg    8160
taaaggaata gatgattatt tggtagcttt acctttgag aaaagagaaa atcatttaga    8220
caacttaatt aaaattgcac catcatttaa tttttggtca actaaatact tattcaagtg    8280
tcgtaaacca gatttaaccg taaattgccg ttatttgagc gatgcagtaa aagaattacc    8340
tcaagaggat atagcattaa tagcacctca cggcacgggt aaaacttcat tagtagctac    8400
tcacgttaag aatcggagtt atcacggaag gaaaactatt tcattggtgc atcttgaaag    8460
tttagccaaa gctaatggca acgcacttgg attatattac cgaaccgaaa ataatattga    8520
aaagcaatat cttggattta gcttatgtgt agatagttgc cgtgataaga ttaacggcat    8580
tacaactgat attatttcag gtcaagatta ttgccttttc attgatgaaa ttgaccaagt    8640
aattccacac atccttaaca gtgaaactga agtaagtaag tatagatgca ccatcattga    8700
cactttttct gaactggtga gaaatgctga acaggtcatt attgctgatg ctgatttatc    8760
cgatgtgacg attgacctaa tagaaaacat cagaggtaaa aaactatatg taatcaagaa    8820
tgaatatcag tatcagggaa tgacttttaa cgccgttggt tcaccattag aaatgatggc    8880
aatgatggga aaatcggtgt cagaaggcaa gaaattattt attaacacca catcccaaaa    8940
```

```
ggcaaaaagt aagtacggca caatcgctct tgagtcttat attttttggtc taaataaaga   9000 agcaaagata ttaagaatag actctgaaac cactaaaaac cctgaacatc cagcctataa   9060
aatcattgac caagacttaa ataatatcct caaagattat gattatgtca ttgcctcacc   9120
ttgccttcaa acaggtgtca gtattacctt aaaagggcat tttgaccagc aatttaactt   9180
ttccagtgga aacattacac ctcattgctt tttacagcaa atgtggcggt tgagggatgc   9240
agaaattgaa agattctatt atgtgccgaa ctcatctaac ctcaatctca ttgggaataa   9300
gtcaagttca ccatcagacc ttctaaagag caataacaag atggcaacgg caacggttaa   9360
ccttttgggt agaatcgact ccgaatattc cctagagtat gaatcgcacg gcatttggct   9420
tgagacgtgg gcaaaattat cagcacggca taacagttca atgcgttgtt actctgaaat   9480
tcttacctat ctaattacgt ctcaaggca taaattaaat atcaacattc cctcacctct   9540
tgcagatatt aagaagctaa atgatgaggt aagtagtaac agggaaaagg taaaaaatga   9600
gagatactct cagaggttaa actcaccaga tattaacgat gcagaagcta ccatactcga   9660
atctaaagag caaaaaatcg gattgactct caatgagaga tgcaccctag aaaagcataa   9720
agttaagaag cggtatggga atgtaaagat ggatattctc acctttgatg atgatggact   9780 atccccaaa ctcagactat tttattacct caccatcggt aaacctcatc tcaaggctaa   9840
tgacagaaaa gctattgcca aaatgggcaa tgacaataaa ggcaagattc tatcaaaaga   9900
cttagttaat aaaacttact ccgctcgtgt gaaggtctta gagattctta aactaactga   9960
ctttatcgac aatcttagag atgaactctt aataactccc aataatccag ctatcaccga  10020
ttttaataat cttctgctaa gagctaagaa ggatttaaga gtattaggag tcaacatcgg  10080
aaaatatcca atggccaaca ttaatgccgt acttactctc attggtcaca aactttctgt  10140
aatgagagat gagttcggaa aagagaaaag gataaaagta gatggtaaat cataccgatg  10200
ttatcaactt gaaacattac cagattttac caatgatact cttgactact ggttagaaaa  10260
tgatagccaa aaagaagtaa cagcaacaga aaattactcc gaaaattta acccttcaaa  10320 tagctacaat ccagacagta agacactttc agagggtgca aatttcctat atataaataa  10380
agaagaattg catccaaata aattgcacct agaaataaaa gaaggtgctg aacttttttt  10440
attcggggta aaggtgattg tgaaaggaat cttggacggg gcagtaacta tattctctat  10500
gggtcaagaa tacgatttat ccctcaatga actagagggg atgttaacat catgaacttt  10560
acaagaatct ttttaaaggg cgatcgcacc atgttaaatg atggtacatt tgttcagata  10620
tttgatattt accatgacca cgcattggga gtgacccttg accttaagac agaaaaaatt  10680
atttccgatg atgttagggt aattactgtc aaagactat tgttcgatgg cacttataaa  10740
ggggtaaaat ctttttatgcc cgataatgcc cgataatgcc cgattgatgc tacaaaatcc  10800
cataatcata agcgataatc ccctaatagc ttgtaattct tgaaccgtag cgatttaga   10860 gtattccaaa aagaagaaat aaacaccgca aaatgtcgta tttcacatat ataaaccaag  10920
gttttttgcc ctaaaatctt tatgtttgta gtgtgatgtt gggtcaaaat ggtcagaaaa  10980
gttgcaaggt ttttatggat gcttacgcgc gcgagggta agcatcccca aatagttact  11040
ttatcctagt ccatgcccat ttattgccgt cccgttcggc tttaaaaaag tgccaaaact  11100
cacaaggtgc aataaaaagt tctgtacctt tcgcaaccct agataatctt tcaacagtta  11160 cttttttttcc tattatctcg gtacaaagtt tggctagttt ctcttttccc tcttttttcaa  11220 tcaagccttt tgtatgccc aactcattga ttaatctctc tattttttacc attatttccc  11280 gttcaggtag tttatcccct aaatcttcat cggggggcaa tgtagggcat tctgaagggg  11340
```

```
cttttcttc tgtctggaca ttatctaata ttgaagtaac caaactatct tcagtttttt   11400
ctattcctat taattcatat tcggttactg tatccgtatc aatatccgaa taactatctt   11460
tatccgtatt agctattcgg ttaagtttat ccgttaactc agaaacaaga ctatatagcg   11520
gttttagctt ttcttctatc ctgttatcta atacggataa gtttatacgg ttatcattat   11580
ccgtattagt atcattgggc ttttttggta gttctacccc ctcataaacc gcttttattc   11640
ccaattccaa cagactgata acagtatcct ttataatggg ttttttgctg atatggtgaa   11700
cttttgcccc ttccatcatt gcgatacttt ctatctcact catcaactta tcgcttaagt   11760
gaatctcgta tctgtttaat cccttactgg ttttattcat atccgtttac tttattcggt   11820
taacaattct attttatacg aataaaatat tatacggtta actttatacg tttaactatt   11880
ttatctatac ggataacagt aataagttat tcgtattagt tatacgttta cttttatcca   11940
aataaaatta gtgcatttaa actaaagaaa tgattttatc ggagttgata gcattggatt   12000
aacctaaaga tgtttataag ctatatctga taagtattta aggttatttt gttattctgt   12060
ttattgacat tatcagaata aaagaataga atataattgt tgagagataa gaggtttaag   12120
tgattatggt taagaagtta gttggttatg tcagggtcag tagtgaatcg caagaggata   12180
acactagctt acagaatcag atagagagaa ttgaagcata ttgtatggct tttggttatg   12240
agttggtaaa atattcaaa gaggttgcca ctggtacaaa agcagatatt gaaaccegtc   12300 ctattttaa tgaagctata gaatacttga aacaggataa tgctaatgga attattgcct   12360
tgaagctaga ccgaatcgca cggaatgctt tagatgtatt gcgtttggtt cgtgaaacct   12420
tagaaccaca aaataaaatg ttagtgttac tagatattca ggtagatact tcgacacctt   12480
caggaaaaat gattttaact gtaatgagtg ccgttgctga actcgaaaga gacatgatct   12540
atgatcgcac tcagggggt agaaagacta aagcccaaaa gggcgggtat gcctacggga   12600
aacctaaatt tggctataag actgaagaaa aggaactaaa agaagattca gcacaacagg   12660
aaactattaa actaattaag agacaccgta ggtcagggaa aagctaccag aaaatagctg   12720
attatctcaa tgcccaaagt attcccacta aacaaggtaa gaaatggagt tctagcgtcg   12780
tctatcgaat ctgtcaggaa aaagctggtt aagtctgttt atagatattt agaatttatt   12840
gaataaaaat agtatgaaca ataaatattt atggactaac cacgctcgga aacgtttaac   12900
tgaacgatgg gaaataaaag aatcatgggt tattgatacc atcgaaaatc ctgaacgttc   12960
agaatttatt gttgatgagt caggggaaaa atatcattac tataaaagaa tagctaagtt   13020
taagaataga gtgttagaag tgataacttc tgccaactca acacccacaa gaataataac   13080
cttttacttt aaccgtaaca tgaggaaaaa tttatgattg ttacttacga taatgaagtt   13140
gacgcaattt attttaagtt aacgaaaaat aaaattgata gcaccgaacc tcaaacagac   13200
aggattatca ttgattacga tgaaagtaat aatattgttg gcattgaggt attagatttt   13260
aattatcttg tcaagaaagg tttaaccgtt gctgatttac cttttctga agatgaaaga   13320 ttaacagctt ctcaatattt taattttcct gttgctatct aatccagaag gggcaataat   13380
ccccttcttt catcgagtta gacttaatat cacaaaagtc attttcattt taccgtttct   13440
tttccacagc gtccgtacgc ccctcgttaa atctcaaaac cgacaattta tgatgtttat   13500
aaaaagttac tcactttaat aagtattat actcattaaa gggttattct ttttttgtag   13560
cctgataggt tgggaaggaa tatttcagat tatcagattt gttg           13604
```

<210> SEQ ID NO 51

```
<211> LENGTH: 205
<212> TYPE: DNA
<213> ORGANISM: Cyanobacterium sp. ABICyano1

<400> SEQUENCE: 51
tagagtatga taaaatgaca aggaaaggat tattttctct tgtttaaatt ctcaagattc    60
ttatgcttat ttattttatg taagtgtctc ttttccttga aatagaaaga aaaaagtggc   120
taattttgag aaaagctaac aacgctttgg ttaactaaaa atcaaaagtg agattactga   180
tcgcttaaga aatggagtat tgatt                                        205

<210> SEQ ID NO 52
<211> LENGTH: 327
<212> TYPE: DNA
<213> ORGANISM: Cyanobacterium sp. ABICyano1

<400> SEQUENCE: 52
tgagaaaaag tgtaaacaaa tattaagaaa aagatcagaa aaatttaaca acacgtaata    60
aaaaaatgcg tcactacggg ttataaattt acatgaaagg ttaaaacact tttctgagac   120
gattttgata aaaagttgt caaaaaatta agtttcttta caaatgctta acaaaaactt   180
ggttttaagc acaaaataag agagactaat ttgcagaagt tttacaagga aatcttgaag   240
aaaaagatct aagtaaaacg actctgttta accaaaattt aacaaattta acaaaacaaa   300
ctaaatctat taggagatta actaagc                                      327

<210> SEQ ID NO 53
<211> LENGTH: 214
<212> TYPE: DNA
<213> ORGANISM: Cyanobacterium sp. ABICyano1

<400> SEQUENCE: 53
agagttatat ttacatagtg tgtgcgagta agggcaactt ttgtaggtag atgaataaac    60
ctcaaattac tcatcttaaa agacgatatt tttaatctat tcttctgtaa taaaatactt   120
ctttcgatag agatatttaa tacttttgag agatgaaaat aatttcaata attgtcatga   180
tagagagtaa gtgcaaataa gaaaaaattg attt                              214

<210> SEQ ID NO 54
<211> LENGTH: 338
<212> TYPE: DNA
<213> ORGANISM: Cyanobacterium sp. ABICyano1

<400> SEQUENCE: 54
gcagttagat aaataagtaa tgagcgggag aaatagggc aaatggccat tcgcccctac    60
agggaggtgg caggtgttag ggtgtttagg ggatgaggtg atgagggtag agggagataa   120
ggtgtcgggt ttcagatttc aggttttaga agaaagtaac gagtaattat caactattca   180
ctattcacta ttgcctgttg cccttctctc cttgaaatat aaaaaaatgt aaaaatatca   240
ttaagaaaag taacaaaata aacagaaagg ttgacaaagt tgacgcttta atatccgtat   300
gttagcttta taacaacgaa atcaacggag gagtgaaa                          338

<210> SEQ ID NO 55
<211> LENGTH: 408
<212> TYPE: DNA
<213> ORGANISM: Cyanobacterium sp. ABICyano1

<400> SEQUENCE: 55
cttgaaaaag ttgaggtatt aatagagctt gataaatgat aataaaaaca gatttagctc    60
```

```
ttattttaag ggaaaaagaa ataaataaaa tattagtaaa tatcaaaaat atcagccttt    120
caaaaataat ttgactcttt tcaaaaaaaa atgttatctt taaggtatgc tttaaacctt    180
aaatacttct attggtaaca ctgttctcaa tcttatttca gattttccca ttgagcataa    240
ataaaatatt aagcagaagt agaaaaggtt gatattagca ataataaaaa ttaacaataa    300
aatgtgaaaa cagattacta ctgattattt attgccatga gctaattagt aataatttgt    360
cttttttgat cgaaaatga aattttttaa gcggaggaac tgaaaatt                 408

<210> SEQ ID NO 56
<211> LENGTH: 411
<212> TYPE: DNA
<213> ORGANISM: Cyanobacterium sp. ABICyano1

<400> SEQUENCE: 56
tatttatata taaactcgaa taaaattatc aatataaagt caaactatat ctatcctatt     60
ttaactgcta ttggtaagtc ccttaattag tgttggggtg aatagatttt aaaagggcaa    120
accccccttt atcctccctc gagagggggg agggcaaaag gcaaggggca agggaaaaat    180
taagaattaa gaattaaaaa ctccgaacac ctgtaggggc gaatagccat tcgcttcccc    240 tcatccccccc atctccccaa caccctaagc ccctactcgt tactcattta tttacatcat    300
ttatttacat cattaagaaa agtaacaaat tttgacaagt agtctttga caggaaaaag    360 caaattctcg aagatgaaaa caatagaaaa aaattcaatc ttacagtaac g             411

<210> SEQ ID NO 57
<211> LENGTH: 211
<212> TYPE: DNA
<213> ORGANISM: Cyanobacterium sp. ABICyano1

<400> SEQUENCE: 57
gtgatatttg gtttattcta tattttcctt aagtaaaaat tcagtcatga gggaaacttt     60
tgttaaaatt tgctttaaat taataggaag atcattaaga aaatcttaaa aagattgagt    120
ttttagatcg aaattattga agaaaaatta acaggggttc tgctcaaaat tttattaaat    180
tactctactg tagtaaagga gaaattttat t                                   211

<210> SEQ ID NO 58
<211> LENGTH: 542
<212> TYPE: DNA
<213> ORGANISM: Cyanobacterium sp. ABICyano1

<400> SEQUENCE: 58
gaatagttga taattactcg ttactcatta ctcacttaaa cctgccacct gatacctgcc     60
acctctcccc ccatcacctc atccctcaa cattccgaac ccttgacac tttgaactaa     120 aattgtatta aagtgcaaat ctggacgggg ttaaccagtg tgacttataa tagtaaacgc    180
tgttttttat aataaataag ctaaatattt aaaaactatg agtaaatata cactaaatgg    240
tactagacgt aagcagaaaa gaacctccgg tttccgcgcc cgtatgagaa ccaaaaatgg    300
tagaaaagta attcaagctc gtcgtaataa gggtagaaaa agattagcag tataaaatta    360
ctgttaaata aggaagctaa gtttagcatt ttaagtttga tattactaat cattaaattt    420
actgtgaaat ataggtggga ctaccatcaa agcatcgact gaaacggcgt ttaaatttcc    480
aatctgttta tcaacagggt attgccgcgct ctagtcgtta ttttattgtc cgagggttac    540
gg                                                                   542
```

<210> SEQ ID NO 59
<211> LENGTH: 380
<212> TYPE: DNA
<213> ORGANISM: Cyanobacterium sp. ABICyano1

<400> SEQUENCE: 59

| | | | | | |
|---|---|---|---|---|---|
| ataaccaatg | ggacttgaat | tttagatcca | tttatttaat | tctattttg | ttacatttct | 60 |
| ttatattaat | cagaattatg | ttactttgtt | ttgttttatg | tcgttacctt | attgaagaaa | 120 |
| gagtggatga | aaggtaaat | gacggggcat | aaatatcgat | tcgttgtcag | aataagctgt | 180 |
| tttattcact | taactggttg | tttgccaatt | tctccctaat | tcccataact | tgtataacta | 240 |
| aatttaataa | tcaattttag | taaattaaga | ataggttaaa | agtagtattt | agaattaagt | 300 |
| taactttaat | aaatttcctg | tattttttta | tagaaaaaag | tataaaataa | aaacatatca | 360 |
| aaaaagtttg | aaatgacaat | | | | | 380 |

<210> SEQ ID NO 60
<211> LENGTH: 1252
<212> TYPE: DNA
<213> ORGANISM: Cyanobacterium sp. MBIC10216

<400> SEQUENCE: 60

| | | | | | |
|---|---|---|---|---|---|
| acctgcctca | aggtcgggga | caacagttgg | aaacgactgc | taataccgga | tgagccgaat | 60 |
| aggtaaaaga | tttatcgcct | tgagagggc | tcgcgtctga | ttagctagat | ggtgaggtaa | 120 |
| aggcttacca | tggcgacgat | cagtagctgg | tctgagagga | tgagcagcca | cactgggact | 180 |
| gagacacggc | ccagactcct | acgggaggca | gcagtgggga | attttccgca | atgggcgaaa | 240 |
| gcctgacgga | gcaataccgc | gtgagggagg | aaggctcttg | ggttgtaaac | ctcaaaactt | 300 |
| agggaagaaa | aaaatgacgg | tacctaatgt | aagcatcggc | taactccgtg | ccagcagccg | 360 |
| cggtaatacg | gaggatgcaa | gcgttatccg | gaatcattgg | gcgtaaagag | tccgtaggtg | 420 |
| gcacttcaag | tctgctttca | aagaccgaag | ctcaacttcg | gaaagggagt | ggaaactgaa | 480 |
| gagctagagt | atagtagggg | tagagggaat | tcctagtgta | gcggtgaaat | gcgtagagat | 540 |
| taggaagaac | accagtggcg | aaggcgctct | actgggcata | tactgacact | gagggacgaa | 600 |
| agctagggga | gcgaaaggga | ttagataccc | ctgtagtcct | agcggtaaac | gatggatact | 660 |
| aggcgtagtg | ctgtaaaagg | gactgtgccg | aagctaacgc | gttaagtatc | cgcctgggg | 720 |
| agtacgcacg | caagtgtgaa | actcaaagga | attgacgggg | acccgcacaa | gcggtggagt | 780 |
| atgtggttta | attcgatgca | acgcgaagaa | ccttaccaag | gcttgacatc | ctgcgaatct | 840 |
| tgatgaaagt | tgagagtgcc | taaggaacg | cagagacagg | tggtgcatgg | ctgtcgtcag | 900 |
| ctcgtgtcgt | gagatgttgg | gttaagtccc | gcaacgagcg | caaccctcgt | ccttagttgc | 960 |
| cagcattaag | ttggggactc | tagggagacc | gccggggaga | actcggagga | aggtggggat | 1020 |
| gacgtcaagt | cagcatgccc | cttacgtctt | gggctacaca | cgtactacaa | tggttgggac | 1080 |
| aaagggagc | gaagccgcga | ggtggagcga | atctcatcaa | acccagccac | agttcagatt | 1140 |
| gcaggctgaa | actcgcctgc | atgaaggagg | aatcgctagt | aatcgcaggt | cagcatactg | 1200 |
| cggtgaatcc | gttcccgggt | cttgtacaca | ccgcccgtca | caccatggaa | gt | 1252 |

<210> SEQ ID NO 61
<211> LENGTH: 1390
<212> TYPE: DNA
<213> ORGANISM: Cyanobacterium aponinum ETS-03

<400> SEQUENCE: 61

```
gcagctacac atgcaagtcg aacgggctct tcggagctag tggcggacgg gtgaggaacg        60
cgtgagaacc tgcctcaagg tcggggacaa cagttggaaa cgactgctaa taccggatga       120
gccgaatagg taaaagattt atcgcctaga gagggctcg cgtctgatta gctagatggt        180
gaggtaaagg cttaccatgg cgacgatcag tagctggtct gagaggatga gcagccacac       240
tgggactgag acacggccca gactcctacg ggaggcagca gtggggaatt ttccgcaatg       300
ggcgaaagcc tgacggagca ataccgcgtg agggaggaag gctcttgggt tgtaaacctc       360
aaaacttagg gaagaaaaaa atgacggtac ctaatgtaag catcggctaa ctccgtgcca       420
gcagccgcgg taatacggag gatgcaagcg ttatccggaa tcattgggcg taaagagtcc       480
gtaggtggca cttcaagtct gctttcaaag accgaagctc aacttcggaa agggagtgga       540
aactgaagag ctagagtata gtaggggta ggagggaat tcctagtgta gcggtgaaat         600
gcgtagagat taggaagaac accagtggcg aaggcgctct actgggcata tactgacact       660
gagggacgaa agctagggga gcgaaaggga ttagataccc ctgtagtcct agcggtaaac      720
gatggatact aggcgtagtg ctgttagaag gactgtgccg aagctaacgc gttaagtatc       780
ccgcctgggg agtacgcacg caagtgtgaa actcaaagga attgacgggg acccgcacaa       840
gcggtggagt atgtggttta attcgatgca acgcgaagaa ccttaccaag gcttgacatc       900
ctgcgaatct tggagaaatc tgagagtgcc taagggaacg cagagacagg tggtgcatgg       960
ctgtcgtcag ctcgtgtcgt gagatgttgg gttaagtccc gcaacgagcg caaccctcgt      1020
ccttagttgc cagcattaag ttggggactc taggagacc gccggggaga actcggagga      1080
aggtggggat gacgtcaagt cagcatgccc cttacgtctt gggctacaca cgtactacaa      1140
tggttgggac aaaggggagc gaaaccgcga ggtggagcga atctcatcaa acccagccac      1200
agttcagatt gcaggctgaa actcgcctgc atgaaggagg aatcgctagt aatcgcaggt      1260
cagcatactg cggtgaatcc gttcccgggt cttgtacaca ccgcccgtca ccatggaa        1320 gttggtcacg cccgaagtcg ttattctaac ccaagggaag agacgccaag tgggactagt      1380
gactggggtg                                                             1390
```

<210> SEQ ID NO 62
<211> LENGTH: 1474
<212> TYPE: DNA
<213> ORGANISM: Cyanobacterium sp. ABICyano2

<400> SEQUENCE: 62

```
agagtttgat cctggctcag gatgaacgct ggcggtatgc ctaacacatg caagtcgaac        60
gggctcttcg gagctagtgg cggacgggtg aggaacgcgt gagaacctgc ctcaaggtcg       120
gggacaacag ttgaaacga ctgctaatac cggatgagcc gaataggtaa aagatttatc        180
gccttgagag gggctcgcgt ctgattagct agatggtgag gtaaaggctt accatggcga       240
cgatcagtag ctggtctgag aggatgagca gccacactgg gactgagaca cggcccagac       300
tcctacggga ggcagcagtg ggaattttc gcaatgggc gaaagcctga cggagcaata       360
ccgcgtgagg aggaaggct cttgggttgt aaacctcaaa acttagggaa gaaaaaatg         420 acggtaccta atgtaagcat cggctaactc cgtgccagca gccgcggtaa tacgaggat        480 gcaagcgtta tccggaatca ttgggcgtaa agagtccgta ggtggcactt caagtctgct       540
ttcaaagacc gaagctcaac ttcggaaagg gagtggaaac tgaagagcta gagtatagta      600
ggggtagagg gaattcctag tgtagcggtg aaatgcgtag agattaggaa gaacaccagt      660
```

```
ggcgaaggcg ctctactggg catatactga cactgaggga cgaaagctag gggagcgaaa      720
gggattagat acccctgtag tcctagcggt aaacgatgga tactaggcgt agtgctgtaa      780
aagggactgt gccgaagcta acgcgttaag tatcccgcct ggggagtacg cacgcaagtg      840
tgaaactcaa aggaattgac ggggacccgc acaagcggtg gagtatgtgg tttaattcga      900
tgcaacgcga agaaccttac caaggcttga catcctgcga atcttgatga agttgagag       960
tgcctaaggg aacgcagaga caggtggtgc atggctgtcg tcagctcgtg tcgtgagatg     1020
ttgggttaag tcccgcaacg agcgcaaccc tcgtccttag ttgccagcat taagttgggg     1080
actctaggga accgccggg gagaactcgg aggaaggtgg ggatgacgtc aagtcagcat      1140
gccccttacg tcttgggcta cacacgtact acaatggttg gacaaaggg gagcgaagcc      1200
gcgaggtgga gcgaatctca tcaaacccag ccacagttca gattgcaggc tgaaactcgc     1260
ctgcatgaag gaggaatcgc tagtaatcgc aggtcagcat actgcggtga atccgttccc     1320
gggtcttgta cacaccgccc gtcacaccat ggaagttggt cacgcccgaa gtcgttattc     1380
taacccaagt ggaaggagac gccgaaggtg ggactagtga ctgggtgaa gtcgtaacaa      1440
ggtagccgta ccggaaggtg tggctggatc acct                                 1474

<210> SEQ ID NO 63
<211> LENGTH: 1474
<212> TYPE: DNA
<213> ORGANISM: Cyanobacterium sp. ABICyano1

<400> SEQUENCE: 63
agagtttgat cctggctcag gatgaacgct ggcggtatgc ctaacacatg caagtcgaac       60
ggtctcttcg gagatagtgg cggacgggtg aggaacgcgt gagaacctgc ctcaaggtcg      120
gggacaacag ttgaaaacga ctgctaatac cggatgagcc gaataggtaa agatttatc      180
gcctagagag gggctcgcgt ctgattagct agatggtgag gtaaaggctt accatggcga      240
cgatcagtag ctggtctgag aggatgagca gccacactgg gactgagaca cggcccagac      300
tcctacggga ggcagcagtg gggaatttc gcaatgggc gaaagcctga cggagcaata      360
ccgcgtgagg gaggaaggct cttgggttgt aaacctcaaa acttagggaa gaaaaaatg      420
acggtaccta atgtaagcat cggctaactc cgtgccagca gccgcggtaa tacggaggat      480
gcaagcgtta tccggaatca ttgggcgtaa agagtccgta ggtggcactt caagtctgct      540
ttcaaagacc gaagctcaac ttcggaaagg gagtggaaac tgaagagcta gagtatagta      600
ggggtagagg gaattcctag tgtagcggtg aaatgcgtag agattaggaa gaacaccagt     660
ggcgaaggcg ctctactggg catatactga cactgaggga cgaaagctag gggagcgaaa     720
gggattagat accctgtag tcctagcggt aaacgatgga tactaggcgt agtgctgtta     780
gaaggactgt gccgaagcta acgcgttaag tatcccgcct ggggagtacg cacgcaagtg     840
tgaaactcaa aggaattgac ggggacccgc acaagcggtg gagtatgtgg tttaattcga     900
tgcaacgcga agaaccttac caaggcttga catcctgcga atcttggaga atctgagag      960
tgcctaaggg aacgcagaga caggtggtgc atggctgtcg tcagctcgtg tcgtgagatg    1020
ttgggttaag tcccgcaacg agcgcaaccc tcgtccttag ttgccagcat taagttgggg    1080
actctaggga accgccggg gagaactcgg aggaaggtgg ggatgacgtc aagtcagcat     1140
gccccttacg tcttgggcta cacacgtact acaatggttg gacaaaggg gagcgaaacc     1200
gcgaggtgga gcgaatctca tcaaacccag ccacagttca gattgcaggc tgaaactcgc    1260
ctgcatgaag gaggaatcgc tagtaatcgc aggtcagcat actgcggtga atccgttccc    1320
```

-continued

```
gggtcttgta cacaccgccc gtcacaccat ggaagttggt cacgcccgaa gtcgttattc    1380
taacccaagt ggaaggagac gccgaaggtg ggactagtga ctggggtgaa gtcgtaacaa    1440
ggtagccgta ccggaaggtg tggctggatc acct                                1474
```

<210> SEQ ID NO 64
<211> LENGTH: 1460
<212> TYPE: DNA
<213> ORGANISM: Cyanobacterium sp. LLi5

<400> SEQUENCE: 64

```
gatgaacgct ggcggtatgc ttaacacatg caagtcgaac gggcacttcg gtgatagtgg      60
cgcacgggtg aggaacacgt gagaatctgc ctcaaagtcg gggacaacag ttggaaacga    120
ctgctaatac cggatgagcc gcaaggtaaa agatttatcg ctttgagagg agctcgcgtc    180
tgattagcta gatggtgagg taaaggctta ccatggcgac gatcagtagc tggtctgaga    240
ggatgagcag ccacactggg actgagacac ggcccagact cctacgggag gcagcagtgg    300
ggaattttcc gcaatgggcg aaagcctgac ggagcaatac cgcgtgaggg aggaaggctc    360
ttgggttgta aacctcaaaa cttagggaag aagcaagtga cggtacctaa tataagcatc    420
ggctaactcc gtgccagcag ccgcggtaat acggaggatg caagcgttat ccggaatcat    480
tgggcgtaaa gcgtccgtag gtggcatttc aagtctgctg tcaaagaccg aagctcaact    540
tcgggccggc ggtggaaact gaaaagctag agtgaagtag gggtagaggg aattcctagt    600
gtagcggtga atgcgtagag attaggaaga acaccagtg gcgaaggcgc tctactggac    660
ttaaactgac actgagggac gaaagctaag ggagcgaaag ggattagata cccctgtagt    720
cttagcggta aacgatggat actaggtgtt gtctgtatcg acccggacag tgccgaagca    780
aacgcgttaa gtatcccgcc tggggagtac gcacgcaagt gtgaaactca aaggaattga    840
cggggacccg cacaagcggt ggagtatgtg gtttaattcg atgcaacgcg aagaaccttaa    900 ccaaggcttg acatcctgtg aatctcgatg aaagttgaga gtgccttagg gaacacagag    960
acaggtggtg catggctgtc gtcagctcgt gtcgtgagat gttgggttaa gtcccgcaac   1020
gagcgcaacc ctcgtcctta gttgccagca ttaagttggg gactctaggg agactgccgg   1080
ggagaactcg gaggaaggtg gggatgacgt caagtcagca tgccccttac gtcttgggct   1140
acacacgtac tacaatggta gggacaaagg gaggcgaaac tgcgaagtgg agcgaatcct   1200
gtcaaaccct gccccagttc agattgtagg ctgaaactcg cctacatgaa ggaggaatcg   1260
ctagtaatcg caggtcagca tactgcggtg aatccgttcc cgggtcttgt acacaccgcc   1320
cgtcacacca tggaagttgg taacatccga agtcgttact ccaacccgca aggggggagg   1380
atgccgaagg tgggactagt gactggggtg aagtcgtaac aaggtagccg taccggaagg   1440
tgtggctgga tcacctcctt                                               1460
```

<210> SEQ ID NO 65
<211> LENGTH: 1476
<212> TYPE: DNA
<213> ORGANISM: Cyanobacterium stanieri PCC 7202

<400> SEQUENCE: 65

```
agagtttgat cctggctcag gatgaacgct ggcggtatgc ctaacacatg caagtcgaac     60
ggtcacttcg gtgatagtgg cggacgggtg agtaacacgt gagaatctgc ccttaggtcg   120
gggacaacag ttggaaacga ctgctaatac cggatgagct gaaaagtaaa agatttatcg   180
```

| | |
|---|---|
| cctagggaag agctcgcggc tgattagcta gttggtgatg taaaggatca ccaaggcaac | 240 |
| gatcagtagc tggtctgaga ggatgagcag ccacactggg actgagacac ggcccagact | 300 |
| cctacgggag gcagcagtgg ggaattttcc gcaatgggcg aaagcctgac ggagcaatac | 360 |
| cgcgtgaggg aggaaggctc ttgggttgta aacctcaaaa ctcagggaag aagaaagtga | 420 |
| cggtacctga tataagcatc ggctaactcc gtgccagcag ccgcggtaat acggaggatg | 480 |
| caagcgttat ccggaatcat tgggcgtaaa gcgtccgtag gtggcatttc aagtctgcat | 540 |
| tcaaagaccg aggctcaacc tcgggcaggg tgtggaaact gaaaagctag agtacaggag | 600 |
| gggtagaggg aattcctagt gtagcggtga aatgcgtaga gattaggaag aacaccagtg | 660 |
| gcgaaggcgc tctactggac atgtactgac actgagggac gaaagctagg gtagcgaaag | 720 |
| ggattagata cccctgtagt cttagctgta aacgatggat actaagtgta gcgggtataa | 780 |
| actccggctg tgctgaagcg aacgcgttaa gtatcccgcc tggggagtac gcacgcaagt | 840 |
| gtgaaactca aaggaattga cggggacccg cacaagcggt ggagtatgtg gtttaattcg | 900 |
| atgcaacgcg aagaaccttac caagacttg acatccgatg aatcttttg aaagaagaga | 960 |
| gtgccttagg gaacatcgtg acaggtggtg catggctgtc gtcagctcgt gtcgtgagat | 1020 |
| gttgggttaa gtcccgcaac gagcgcaacc ctcgtcctta gttgccagca ttaagttggg | 1080 |
| gactctaggg agaccgccgg ggagaactcg aggaaggtg gggatgacgt caagtcagca | 1140 |
| tgcccccttac gtcttgggct acacacgtac tacaatggtt gggacaaagg gatgcgagac | 1200 |
| cgcaaggtgg agcgaaaccc atcaaaccca gccccagttc agatcgtcgg ctgaaactcg | 1260 |
| ccgacgtgaa ggaggaatcg ctagtaatcg caggtcagca tactgcggtg aatccgttcc | 1320 |
| cgggtcttgt acacaccgcc cgtcacacca tggaagttgg taacatccga agtcgttact | 1380 |
| ccaaccattt atggaggagg acgccgaagg tgggactagt gactggggtg aagtcgtaac | 1440 |
| aaggtagccg taccggaagg tgtggctgga tcacct | 1476 |

<210> SEQ ID NO 66
<211> LENGTH: 292
<212> TYPE: DNA
<213> ORGANISM: Cyanobacterium sp. ABICyano1

<400> SEQUENCE: 66

| | |
|---|---|
| gtcgacaatt aataacttct tcctgtacgg gcgaatggcc atttgctcct aactaactcc | 60 |
| gtactgcttt gcggaacgag cgtagcgaac tctccgaatt actaagcctt catccctgat | 120 |
| agatgcaaaa aacgaattaa aattatgtgt aaaaagaaaa tgtgtcttta tttagtagtc | 180 |
| aaagttacaa aatattaaga atcaaattaa taatgtattg ggcagttaag tatataagtc | 240 |
| tttaaatatt tatttgtatt caatatatta accgaggaca aattatgaat tc | 292 |

<210> SEQ ID NO 67
<211> LENGTH: 293
<212> TYPE: DNA
<213> ORGANISM: Artificial Sequence
<220> FEATURE:
<223> OTHER INFORMATION: Promoter nirA*2

<400> SEQUENCE: 67

| | |
|---|---|
| gtcgacaatt aataacttct tcctgtacgg gcgaatggcc atttgctcct aactaactcc | 60 |
| gtactgcttt gcggaacgag cgtagcgaac tctccgaatt actaagcctt catccctgat | 120 |
| agatgcaaaa aacgaattaa aattatgtgt aaaaagaaaa tgtgtcttta tttagtagtc | 180 |
| aaagttacaa aatattaaga atcaaattaa taatgtattg ggcagttaag tatataagtc | 240 |

```
tttaaatatt tatttgtatt caatatatta aggaggatca gccttatgaa ttc        293
```

<210> SEQ ID NO 68
<211> LENGTH: 196
<212> TYPE: DNA
<213> ORGANISM: Artificial Sequence
<220> FEATURE:
<223> OTHER INFORMATION: Promoter nirA*3

<400> SEQUENCE: 68

```
gtcgactaag ccttcatccc tgatagatgc aaaaaacgca ttaaaattat gcgtaaaaag   60
catatgtgtc tttatttagt aatcaaagtt acaaattatt aagaatcaaa ttaataatat  120
attgggcagt taagtatata agtctttaaa tatttatttg tattcaatat attaaccgag  180
gacaaattat gaattc                                                  196
```

<210> SEQ ID NO 69
<211> LENGTH: 197
<212> TYPE: DNA
<213> ORGANISM: Artificial Sequence
<220> FEATURE:
<223> OTHER INFORMATION: Promoter nirA*4

<400> SEQUENCE: 69

```
gtcgactaag ccttcatccc tgatagatgc aaaaaacgca ttaaaattat gcgtaaaaag   60
catatgtgtc tttatttagt aatcaaagtt acaaattatt aagaatcaaa ttaataatat  120
attgggcagt taagtatata agtctttaaa tatttatttg tattcaatat attaaggagg  180
atcagcctta tgaattc                                                 197
```

<210> SEQ ID NO 70
<211> LENGTH: 93
<212> TYPE: DNA
<213> ORGANISM: Synechocystis PCC6803

<400> SEQUENCE: 70

```
tcatgacttt agtttactca aaaccttgac attgacacta atgttaaggt ttaggctgag   60
aaggtaaaaa tccaagttaa aaagcatgaa ttc                               93
```

<210> SEQ ID NO 71
<211> LENGTH: 93
<212> TYPE: DNA
<213> ORGANISM: Artificial Sequence
<220> FEATURE:
<223> OTHER INFORMATION: promoter corT*1

<400> SEQUENCE: 71

```
tcatgacttt agtttactca aaaccttgac attgacacta atgttaaggt ttaggctgag   60
aaggtaaaaa tcgaggataa aaagcatgaa ttc                               93
```

<210> SEQ ID NO 72
<211> LENGTH: 93
<212> TYPE: DNA
<213> ORGANISM: Artificial Sequence
<220> FEATURE:
<223> OTHER INFORMATION: Promoter corT*2

<400> SEQUENCE: 72

```
tcatgacttt agtttactca aaaccttgac attgacacta atgttaaggt ttagaatgag   60
aaggtaaaaa tccaagttaa aaagcatgaa ttc                               93
```

<210> SEQ ID NO 73
<211> LENGTH: 93
<212> TYPE: DNA
<213> ORGANISM: Artificial Sequence
<220> FEATURE:
<223> OTHER INFORMATION: Promoter corT*3

<400> SEQUENCE: 73
tcatgacttt agtttactca aaaccttgac attgacacta atgttaaggt ttagaatgag    60
aaggtaaaaa tcgaggataa aaagcatgaa ttc                                 93

<210> SEQ ID NO 74
<211> LENGTH: 93
<212> TYPE: DNA
<213> ORGANISM: Artificial Sequence
<220> FEATURE:
<223> OTHER INFORMATION: Promoter corT*4

<400> SEQUENCE: 74
tcatgacttt agtttactca aaaccttgac attgacacta atgttaaggt ttagaatgag    60
aaggtaaaaa aggaggtgat caagcatgaa ttc                                 93

<210> SEQ ID NO 75
<211> LENGTH: 101
<212> TYPE: DNA
<213> ORGANISM: Synechococcus PCC7002

<400> SEQUENCE: 75
atctaaacaa tacctgaata attgttcatg tgttaatcta aaaatgtgaa caatcgttca    60
actatttaag acaatacctt ggaggtttaa accatgaatt c                       101

<210> SEQ ID NO 76
<211> LENGTH: 101
<212> TYPE: DNA
<213> ORGANISM: Artificial Sequence
<220> FEATURE:
<223> OTHER INFORMATION: Promoter smtA*1

<400> SEQUENCE: 76
atctaaacaa tacctgaata attgttcatg tgttaatcta aaaatgtgaa caatcgttca    60
actatttaag acaataccaa ggaggtgata accatgaatt c                       101

<210> SEQ ID NO 77
<211> LENGTH: 101
<212> TYPE: DNA
<213> ORGANISM: Artificial Sequence
<220> FEATURE:
<223> OTHER INFORMATION: Promoter smtA*2

<400> SEQUENCE: 77
atctaaacaa tacctgaata attgttcatg tgttaatcta aaaatgtgaa caatcgttca    60
actatttaag acaataccaa ggaggtataa accatgaatt c                       101

<210> SEQ ID NO 78
<211> LENGTH: 281
<212> TYPE: DNA
<213> ORGANISM: Artificial Sequence
<220> FEATURE:
<223> OTHER INFORMATION: Generalized sequence of nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t

<400> SEQUENCE: 78
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnatgc     120
aaaaaacgaa tnnnnnnnat gtgtaaaaag aaannnnnnn nnnnnnnngt agtcaaagtt     180
acnnnnnnnn nnnnnnnnnn nnnntaatgt nnnnnnnnnn nnnnnnnnnn nnnnnnnnnn     240
nnnnnnnnnn nnnnnnnnnn nnnnnccgag gacaaannat g                         281

<210> SEQ ID NO 79
<211> LENGTH: 282
<212> TYPE: DNA
<213> ORGANISM: Artificial Sequence
<220> FEATURE:
<223> OTHER INFORMATION: Generalized sequence for nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (278)..(279)
<223> OTHER INFORMATION: n is a, c, g, or t

<400> SEQUENCE: 79
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnatgc     120
aaaaaacgaa tnnnnnnnat gtgtaaaaag aaannnnnnn nnnnnnnngt agtcaaagtt     180
acnnnnnnnn nnnnnnnnnn nnnntaatgt nnnnnnnnnn nnnnnnnnnn nnnnnnnnnn     240
nnnnnnnnnn nnnnnnnnnn nnnnnggagg atcagccnna tg                        282

<210> SEQ ID NO 80

```
<211> LENGTH: 281
<212> TYPE: DNA
<213> ORGANISM: Artificial Sequence
<220> FEATURE:
<223> OTHER INFORMATION: Variation on a generalized nirA promoter with
      changes to the operator region and the TATA box
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t

<400> SEQUENCE: 80
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnatgc     120
aaaaaacgca tnnnnnnnat gcgtaaaaag catnnnnnnn nnnnnnnngt aatcaaagtt     180
acnnnnnnnn nnnnnnnnnn nnnntaatat nnnnnnnnnn nnnnnnnnnn nnnnnnnnnn     240
nnnnnnnnnn nnnnnnnnnn nnnnnccgag gacaaannat g                        281

<210> SEQ ID NO 81
<211> LENGTH: 280
<212> TYPE: DNA
<213> ORGANISM: Artificial Sequence
<220> FEATURE:
<223> OTHER INFORMATION: Variation of generalized nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (276)..(277)
<223> OTHER INFORMATION: n is a, c, g, or t

<400> SEQUENCE: 81
nnnnnnnnnn nnnnnnnnnn nnnnnnnnnn nnnnnnnnnn nnnnnnnnnn nnnnnnnnnn      60
```

-continued

```
nnnnnnnnnn nnnnnnnnnn nnnnnnnnnn nnnnnnnnnn nnnnnnnnnn nnnnnatgc      120 aaaaaacgca tnnnnnnnat gcgtaaaaag catnnnnnnn nnnnnnnngt aatcaaagtt      180
acnnnnnnnn nnnnnnnnnn nnnntaatat nnnnnnnnnn nnnnnnnnnn nnnnnnnnnn      240
nnnnnnnnnn nnnnnnnnnn nnnnnggagt cagccnnatg                            280
```

<210> SEQ ID NO 82
<211> LENGTH: 87
<212> TYPE: DNA
<213> ORGANISM: Artificial Sequence
<220> FEATURE:
<223> OTHER INFORMATION: Generalized sequence of promoter corT
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 82

```
catnnnnnnn gtttactcaa aaccttgaca ttgacactaa tgttaaggtt taggctnnnn      60
nnnnnnnnnn ncaagttaaa aagcatg                                          87
```

<210> SEQ ID NO 83
<211> LENGTH: 87
<212> TYPE: DNA
<213> ORGANISM: Artificial Sequence
<220> FEATURE:
<223> OTHER INFORMATION: A generalized corT promoter sequence with
      changes to the ribosomal binding site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 83

```
catnnnnnnn gtttactcaa aaccttgaca ttgacactaa tgttaaggtt taggctnnnn      60
nnnnnnnnnn ngaggataaa aagcatg                                          87
```

<210> SEQ ID NO 84
<211> LENGTH: 87
<212> TYPE: DNA
<213> ORGANISM: Artificial Sequence
<220> FEATURE:
<223> OTHER INFORMATION: Generalized sequence of corT promoter having
      changes in the TATA box
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 84

```
catnnnnnnn gtttactcaa aaccttgaca ttgacactaa tgttaaggtt tagaatnnnn      60
nnnnnnnnnn ncaagttaaa aagcatg                                          87
```

<210> SEQ ID NO 85
<211> LENGTH: 87

```
<212> TYPE: DNA
<213> ORGANISM: Artificial Sequence
<220> FEATURE:
<223> OTHER INFORMATION: A generalized corT promoter sequence with
      changes to the ribosomal binding site and the TATA box
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 85
catnnnnnnn gtttactcaa aaccttgaca ttgacactaa tgttaaggtt tagaatnnnn    60
nnnnnnnnnn ngaggataaa aagcatg                                       87

<210> SEQ ID NO 86
<211> LENGTH: 96
<212> TYPE: DNA
<213> ORGANISM: Artificial Sequence
<220> FEATURE:
<223> OTHER INFORMATION: A generalized smtA promoter sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(80)
<223> OTHER INFORMATION: n is a, c, g, or t
<220> FEATURE:
<221> NAME/KEY: misc_feature
<222> LOCATION: (87)..(93)
<223> OTHER INFORMATION: n is a, c, g, or t

<400> SEQUENCE: 86
nnnnnnnnaa tacctgaata attgttcatg tgttnnnnta aaaatgtgaa caatcgttca    60
actatttann nnnnnnnnnn ggaggtnnnn nnnatg                              96

<210> SEQ ID NO 87
<211> LENGTH: 96
<212> TYPE: DNA
<213> ORGANISM: Artificial Sequence
<220> FEATURE:
<223> OTHER INFORMATION: A generalized sequence for smtA promoter having
      changes in the ribosomal binding site
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(78)
<223> OTHER INFORMATION: n is a, c, g, or t
<220> FEATURE:
<221> NAME/KEY: misc_feature
<222> LOCATION: (90)..(93)
<223> OTHER INFORMATION: n is a, c, g, or t

<400> SEQUENCE: 87
nnnnnnnnaa tacctgaata attgttcatg tgttnnnnta aaaatgtgaa caatcgttca    60
```

```
actatttann nnnnnnnnaa ggaggtgatn nnnatg                              96

<210> SEQ ID NO 88
<211> LENGTH: 96
<212> TYPE: DNA
<213> ORGANISM: Artificial Sequence
<220> FEATURE:
<223> OTHER INFORMATION: A generalized sequence of smtA promoter having
      changes to the ribosomal binding site
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(78)
<223> OTHER INFORMATION: n is a, c, g, or t
<220> FEATURE:
<221> NAME/KEY: misc_feature
<222> LOCATION: (89)..(93)
<223> OTHER INFORMATION: n is a, c, g, or t

<400> SEQUENCE: 88
nnnnnnnnaa tacctgaata attgttcatg tgttnnnnta aaaatgtgaa caatcgttca    60
actatttann nnnnnnnnaa ggaggtatnn nnnatg                              96
```

CYANOBACTERIUM SP. HOST CELL AND VECTOR FOR PRODUCTION OF CHEMICAL COMPOUNDS IN CYANOBACTERIAL CULTURES

CROSS-REFERENCE TO RELATED APPLICATION

This application is a divisional application of U.S. application Ser. No. 14/041,122 filed on Sep. 30, 2013, issued as U.S. Pat. No. 8,846,369 on Sep. 30, 2014, which claims priority to U.S. Provisional Application No. 61/741,000 filed on Dec. 21, 2012, both of which are incorporated herein by reference.

STATEMENT REGARDING FEDERALLY SPONSORED RESEARCH

This invention was made in part with United States government support under the Department of Energy grant number DE-EE0002867. The government has certain rights associated with this invention.

REFERENCE TO SEQUENCE LISTING

This application contains a sequence listing submitted by EFS-Web, thereby satisfying the requirements of 37 C.F.R. §1.821-1.825.

FIELD OF THE INVENTION

The present invention relates to the genetic enhancement of Cyanobacteria to produce compounds of interest. In particular, the genus *Cyanobacterium* includes hardy organisms that can be useful for genetic engineering.

BACKGROUND OF THE INVENTION

Cyanobacteria are small, prokaryotic, generally aquatic organisms that can be genetically manipulated to be capable of utilizing light and $CO_2$ to produce compounds of interest, such as biofuels, industrial chemicals, pharmaceuticals, nutrients, carotenoids, food supplements, etc. Because cyanobacterial cells are capable of fixing carbon dioxide as a carbon source for autotrophic growth, they do not require the costly input of organic carbon as a starting material. Further, the $CO_2$ that is utilized by the cyanobacterial culture can be derived from any source, such as a waste byproduct of industrial production. In this way, Cyanobacteria can be used to recycle $CO_2$ to desired products, such as biofuel.

Various cyanobacterial species have been genetically enhanced to produce compounds of interest. The transformation of the cyanobacterial genus *Synechococcus* with genes that encode enzymes that can produce ethanol for biofuel production has been described (U.S. Pat. Nos. 6,699,696 and 6,306,639, both to Woods et al,). The transformation of the cyanobacterial genus *Synechocystis* has been described, for example, in PCT/EP2009/000892 and in PCT/EP2009/060526.

The cyanobacteria as a whole are a very divergent group of organisms. Due to this diversity, it is often difficult to find a method to effectively and efficiently transform a given host cyanobacterial species. Further, it is also often difficult for the inserted DNA vehicle to replicate adequately once it is present in the host cyanobacterial cell.

Certain strains of cyanobacteria can be naturally and relatively easily transformed. Other cyanobacterial strains can be transformed, for example, by the use of conjugation or electroporation. Some cyanobacterial strains are difficult to transform by any known means. For many of these types of difficult to transform strains, specific methods of preparing the cells for transformation, as well as specific methods of allowing entry of the foreign DNA into the cells, need to be designed.

The transfer of foreign genes into cyanobacteria often involves the construction of vectors having a backbone from a broad-host range bacterial plasmid, such as RSF1010. The RSF1010-based vector has been widely used as a conjugation vector for transforming bacteria, including cyanobacteria (Mermet-Bouvier et al. (1993) "Transfer and replication of RSF1010-derived plasmids in several cyanobacteria of the genera *Synechocystis* and *Synechococcus*" Current Microbiology 27:323-327). This plasmid has an *E. coli* origin of replication, but does not have a cyanobacterial origin of replication.

Several endogenous plasmids from *Synechococcus* sp. PCC7002 have been utilized as a backbone plasmid to prepare vectors for heterologous gene expression (Xu et al., Photosynthesis Research Protocols 684:273-293 (2011). Other vectors for transformation of cyanobacteria include the pDUI-based vectors, The pDUI origin of replication is best suited for filamentous cyanobacteria, however. Attempts to transform certain species of cyanobacteria, such as *Cyanobacterium* sp. ABICyanol, with either RSF1010 or pDUI-based shuttle vectors were previously unsuccessful.

The cyanobacterial genus *Cyanobacterium* was first established in 1983 (see Rippka et al. (2001), Bergey's Manual of Systematic Bacteriology, Vol. 1, p, 497-498). In general, the genus differs from the genus *Synechococcus* by differences in DNA base composition and by differences in sensitivity to cyanophages (Moro, et al., 2007, Algological Studies, 123:1-15). Members of the *Cyanobacterium* genus are often found in thermal mats.

The species *Cyanobacterium* ABICyanol is a coccoid, unicellular cell somewhat similar to *Synechococcus* when viewed under the microscope. Cells of *Cyanobacterium* ABI-Cyanol appear to have a substantial layer of mucilaginous sheath covering each individual cell. This mucilage can participate in the formation of cellular aggregates or "clumps". The species differs from other species in the *Cyanobacterium* genus, as well as from other cyanobacteria such as *Synechococcus* and *Synechocystis*, by differences in the carotenoid and chlorophyll composition. The species also appears to differ from other cyanobacteria, such as the above two species, by differences in its 16S rDNA and its internal transcribed spacer rDNA (ITS) composition.

What is needed in the art is a new cyanobacterial strain that grows relatively quickly, is tolerant to various environmental stresses, and can successfully harbor foreign genes for the production of compounds of interest, such as biofuels.

SUMMARY

An object of this invention is a new cyanobacterial strain, *Cyanobacterium* sp. ABICyanol , that is capable of tolerating exposure to elevated temperatures and is capable of being transformed.

A further object of this invention is a new cyanobacterial strain, *Cyanobacterium* sp. ABICyanol, that is capable of tolerating exposure to elevated oxygen concentrations and is capable of being transformed.

A further object of this invention is a new cyanobacterial strain, *Cyanobacterium* sp. ABICyanol, that is capable of tolerating exposure to ethanol and is capable of being transformed.

A further object of this invention is a new cyanobacterial strain, *Cyanobacterium* sp. ABICyanol, that is capable of tolerating exposure to elevated salinity and is capable of being transformed.

A further object of this invention is a new cyanobacterial strain, *Cyanobacterium* sp. ABICyanol, that is capable of being transformed and exhibits native biocidal properties with respect to potential contaminants.

A genetically enhanced *Cyanobacterium* sp. host cell of the present invention comprises at least one recombinant gene, wherein said recombinant gene encodes one protein selected from a group consisting of a protein that is involved in a biosynthetic pathway for the production of a chemical compound or a marker protein.

A method of the present invention for producing a chemical compound comprises the method steps of culturing the genetically enhanced *Cyanobacterium* sp. host cells in a culture medium, the host cells thereby producing the chemical compound, and retrieving the chemical compound from either one of: the host cells, the medium or the headspace above the medium.

A plasmid vector of the present invention suitable for transformation of *Cyanobacterium* sp. ABICyanol comprises a recombinant gene, wherein said recombinant gene encodes at least one protein selected from a group consisting of a protein that is involved in a biosynthetic pathway for the production of a chemical compound or a marker protein and an origin of replication suitable for replication in the *Cyanobacterium* ABICyanol.

An isolated nucleic acid sequence of the present invention has at least 95% identity to the sequence of the 6.8 kb plasmid shown in FIG. 4A.

An isolated *Cyanobacterium* sp. ABICyanol of the present invention has the deposition number ATCC No. PTA-13311.

A method of the present invention for introducing a recombinant nucleic acid sequence into a cyanobacterial cell with an extracellular polymeric layer (EPS) comprises the method steps of subjecting the cyanobacterial cell to compounds increasing the permeability of the extracellular polymeric layer (EPS) and cell wall, respectively of the cyanobacterial cell, and introducing said recombinant nucleic acid sequence into the cyanobacterial cell.

BRIEF DESCRIPTION OF THE DRAWINGS

FIG. 2 is a panel of graphs comparing the growth of *Synechococcus* PCC7002 (panel B) and *Cyanobacterium* ABICyanol (panel A) under simulated high daylight temperatures that often occur in outdoor photobioreactor environments, particularly in hotter climates. The graph shows that *Cyanobacterium* ABICyanol grows well even when daytime temperatures get up to about 45° C. to 50° C. for about 2 hours. Growth was measured by chlorophyll content (diamonds; μg/ml) and absorbance at $OD_{750}$ (squares).

FIG. 7 is the nucleotide sequence (SEQ ID NO: 8) of this helper plasmid.

Figure 44:
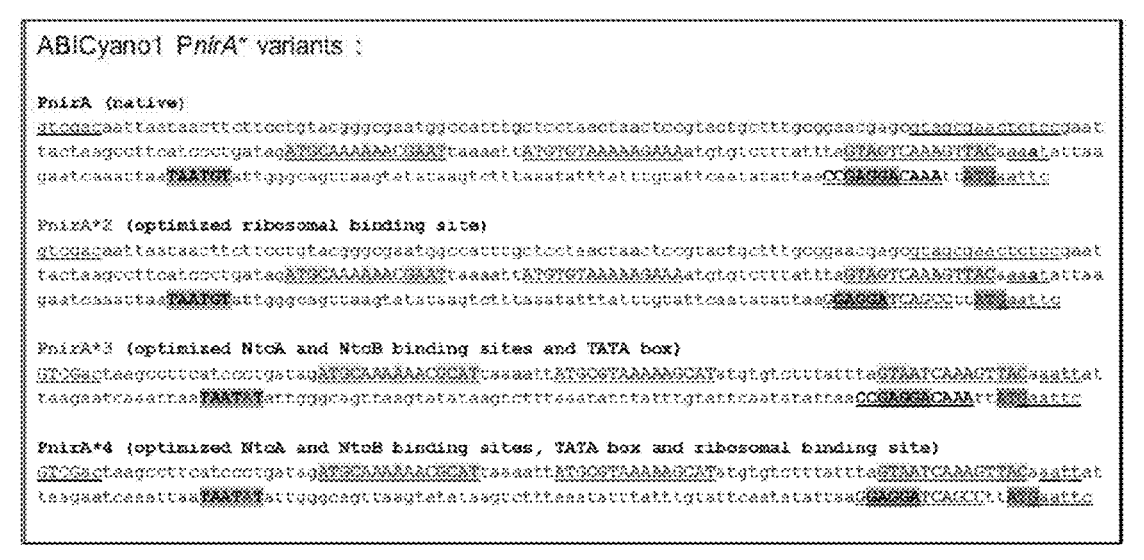

FIG. 44 shows a sequence comparison between the native promoter nirA (SEQ ID NO: 66) from ABICyanol and different variants of the promoter harboring nucleotide changes in the ribosomal binding site (PnirA*2 SEQ ID NO: 67), the binding sites for the regulators NtcA and NtcB (PnirA*3 SEQ ID NO: 68), and the TATA box (PrirA*4 SEQ ID NO: 69). These promoters are included in the plasmids #1606, #1629 and #1636.

Figure 45:
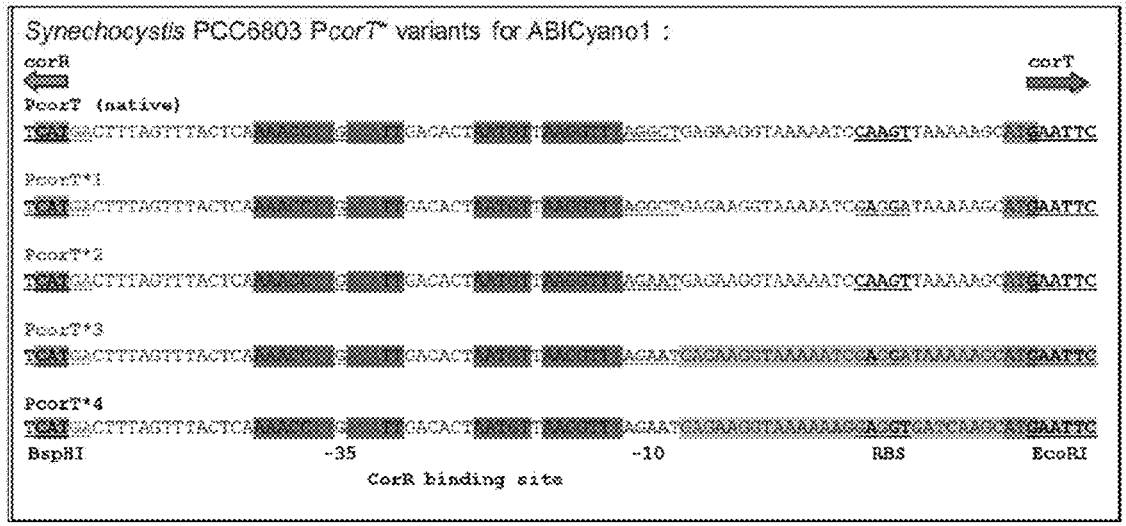

A nucleotide sequence comparison between different corT promoters including the native promoter from *Synechocystis* PCC6803 (SEQ ID NO: 70) and variants containing nucleotide changes in the TATA box, ribosomal binding site and the binding sites for the regulator corR including promoter corT*1 (SEQ ID NO: 71), promoter corT*2 (SEQ ID NO: 72), promoter corT*3 (SEQ ID NO: 73), and promoter corT*4 (SEQ ID NO: 74) is shown in FIG. 45. These promoters are included in the above described plasmids #1630, #1631 and #1632.

Figure 46:
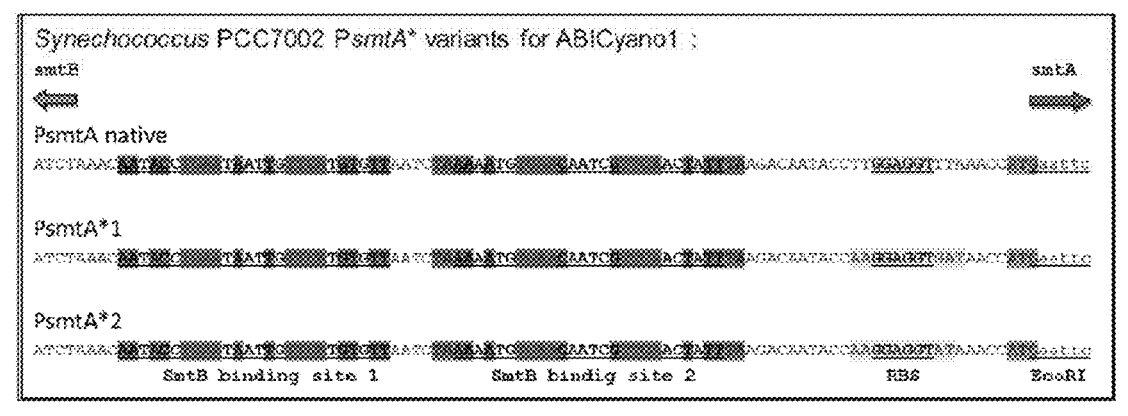

FIG. 46 presents a sequence comparison between the native smtA promoter from *Synechococcus* PCC7002 (SEQ ID NO: 75) and two different variants of the promoter harboring mutations in the ribosomal binding site, smtA*1 (SEQ ID NO: 76) and smtA*2 (SEQ ID NO: 77). These promoters are included in the above described plasmids #1635, #1639 and #1640.

Figure 47:
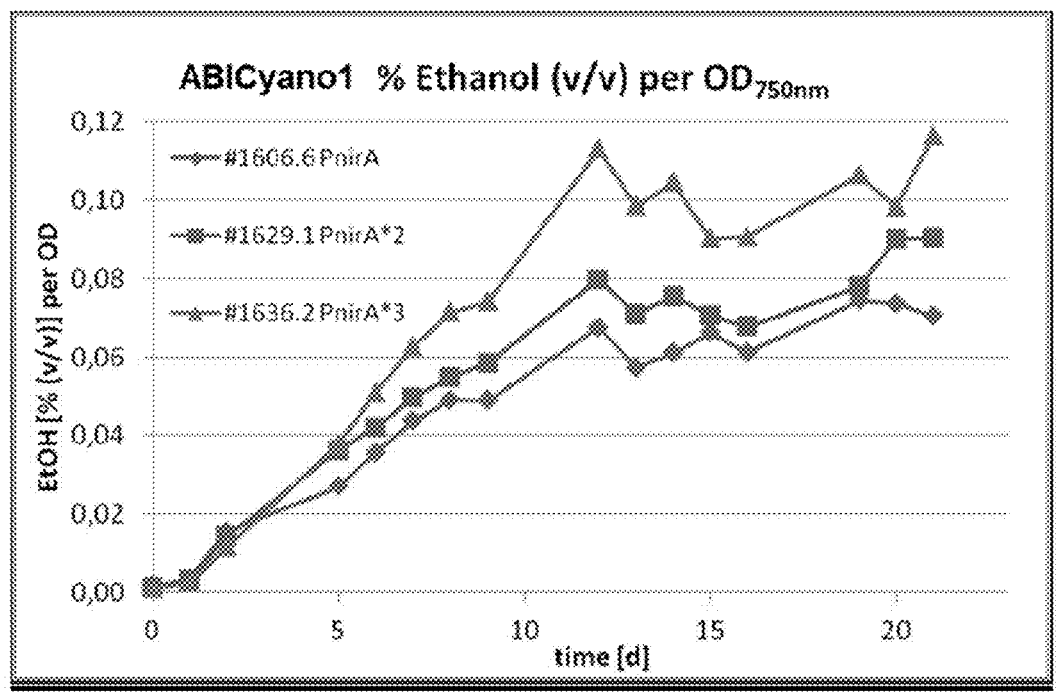

FIG. 47 shows the ethanol production normalized to the growth ($OD_{750nm}$) determined by the CG vial method for ABICyanol strains transformed with the plasmids #1606, plasmid #1629 and plasmid #1636 for a period of time of at least 20 days.

Figure 48A:
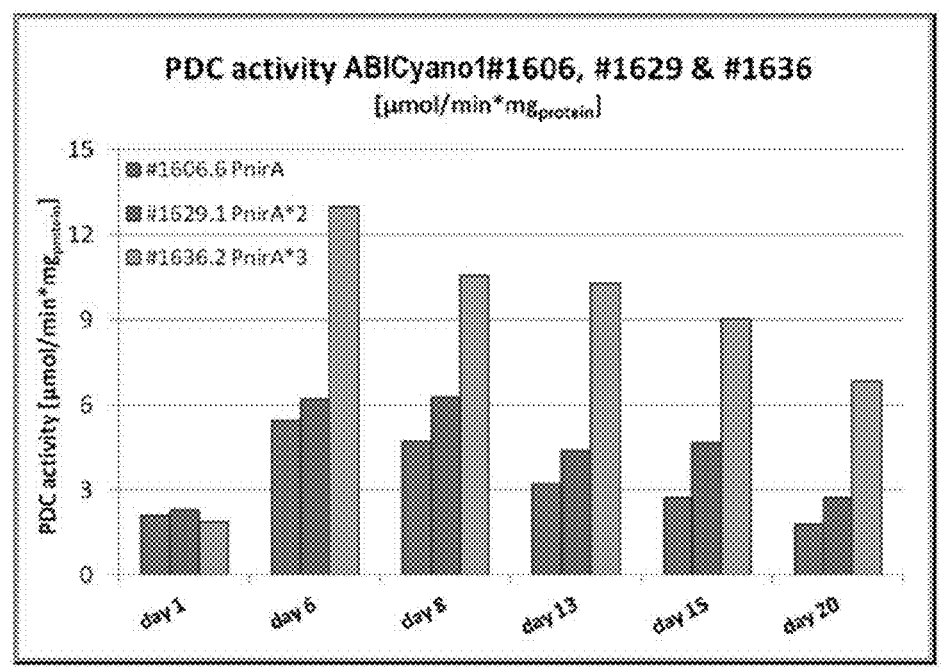
Figure 48B:
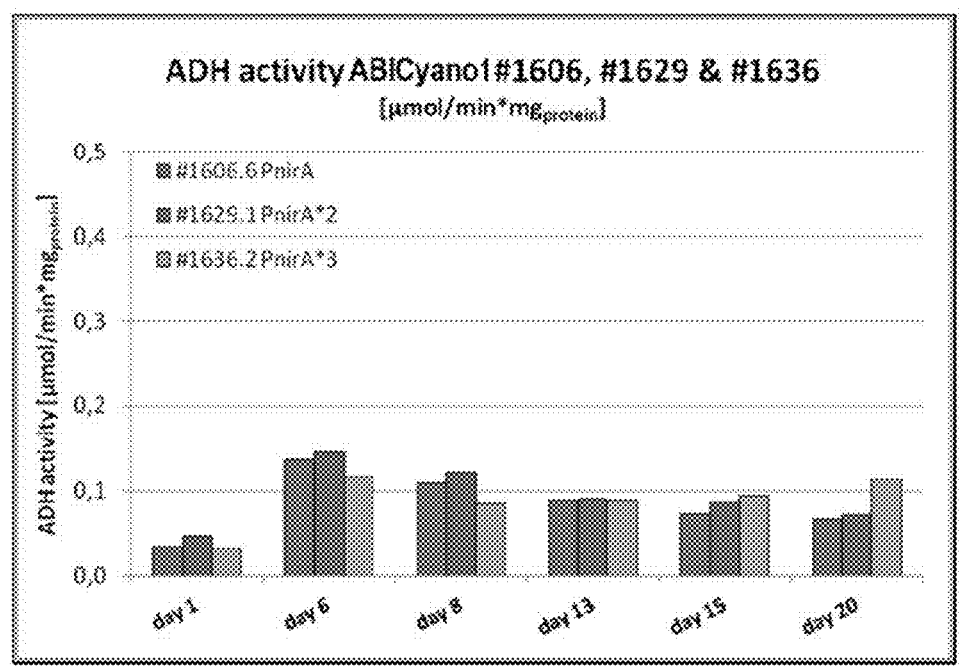

FIGS. 48A and 48B show the specific activity of PDC enzyme and ADH enzyme during the course of the above mentioned cultivation.

Figure 49:
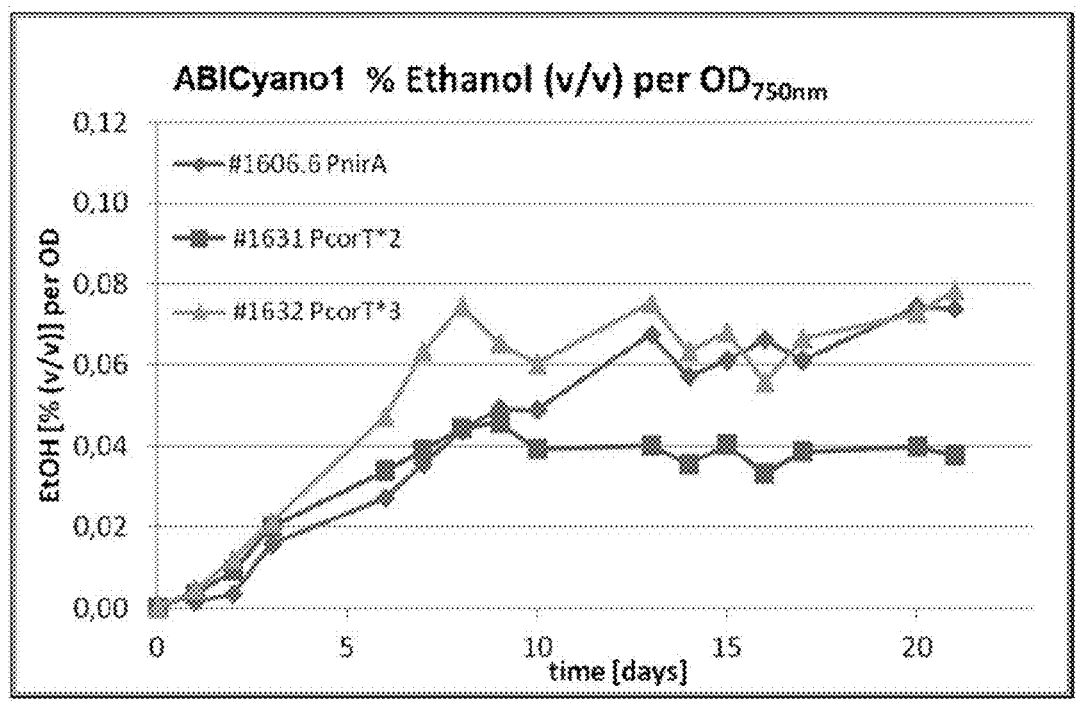

FIG. 49 shows the ethanol production normalized to the growth ($OD_{750nm}$) determined by the GC vial method for ABICyanol strains transformed with the plasmids #1606, plasmid #1631 and plasmid #1632 for a period of time of at least 20 days.

Figure 50A:
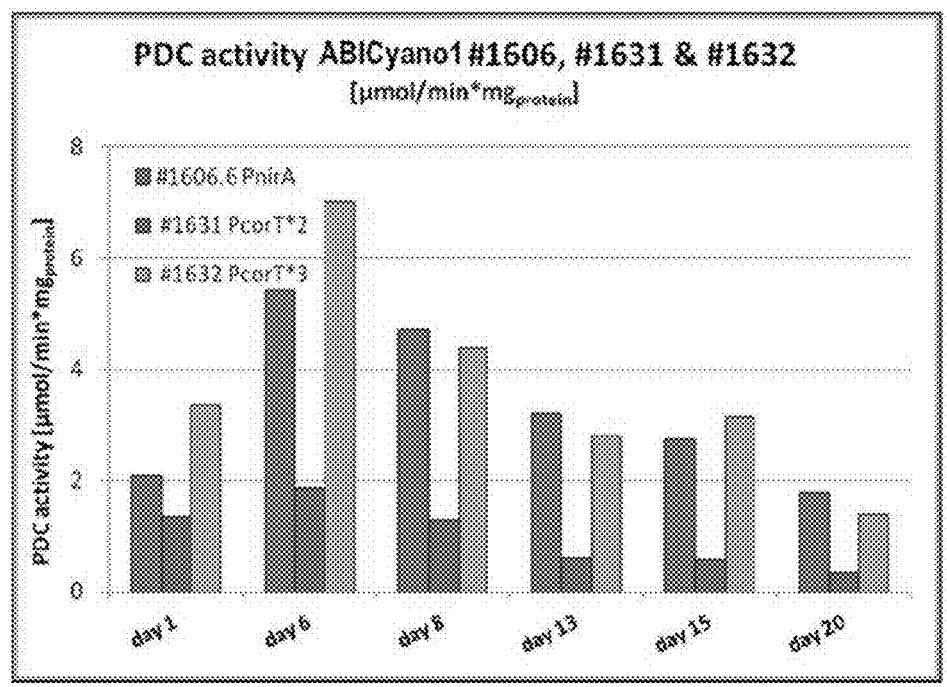
Figure 50B:
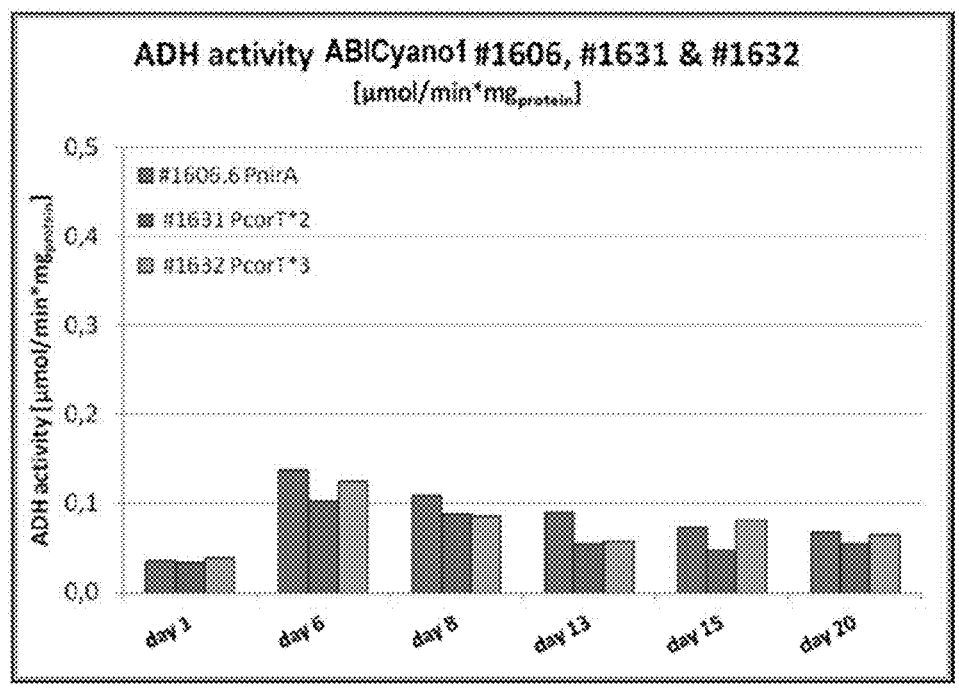
Figure 50C:
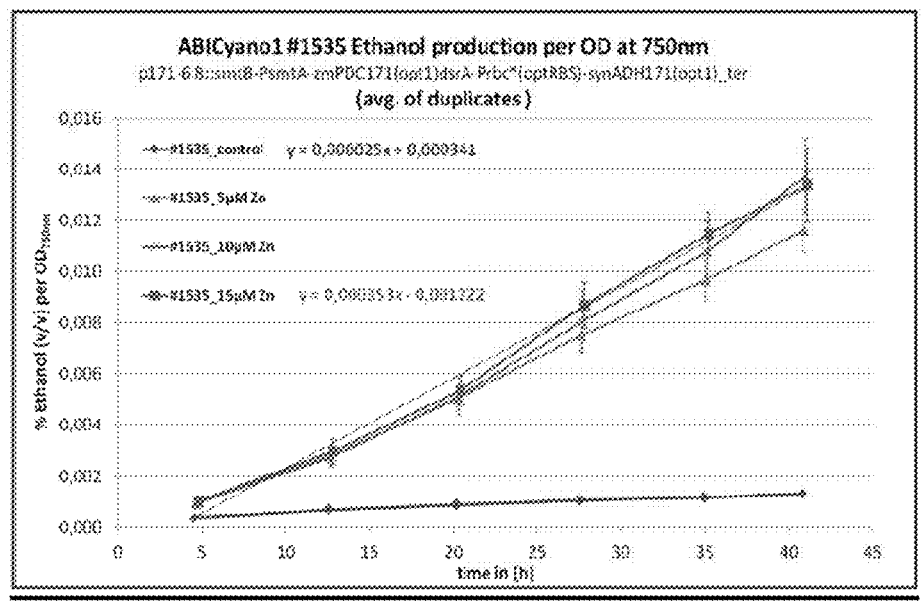
Figure 50D:
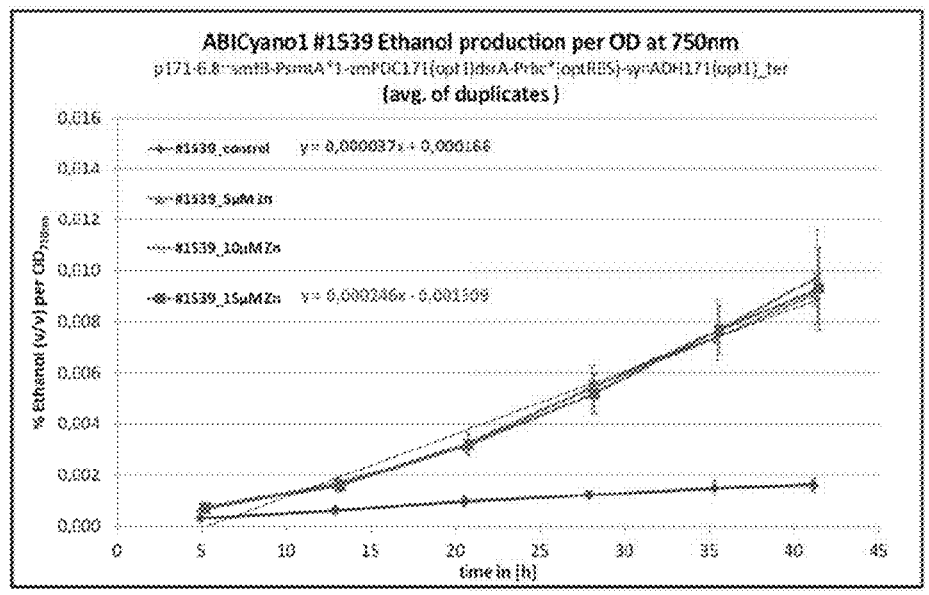
Figure 50E:
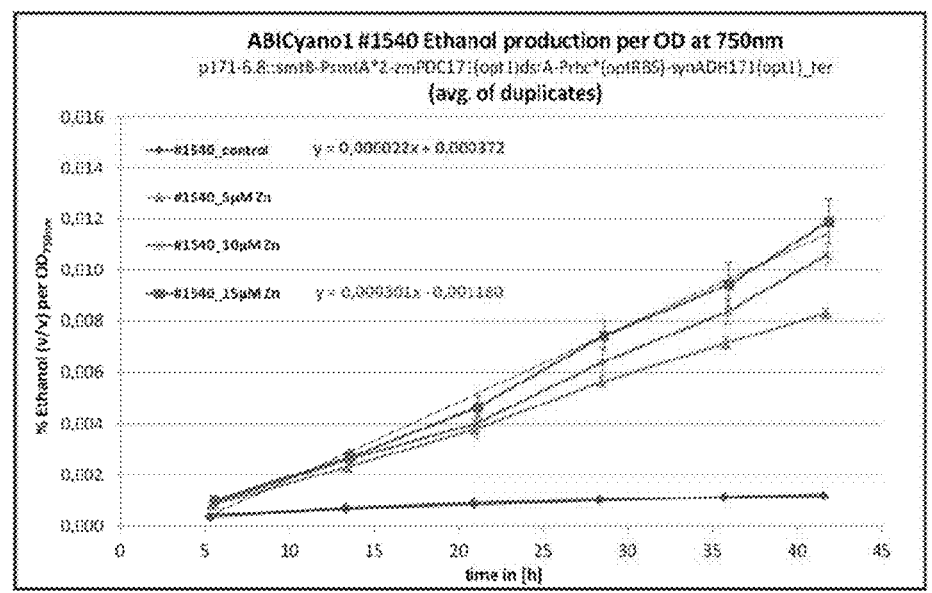

FIG. 50A and 50B show the specific activity of PDC enzyme and ADH enzyme during the course of the above mentioned cultivation. FIGS. 50C to 50E show the ethanol production rates of the ABICyanol strains transformed with the plasmids #1535, #1539 and #1540, respectively, including the native PsmtA promoter from *Synechococcus*

PCC7002 as well as modified versions of PsmtA. It can clearly be seen that all promoters are repressed in the absence of Zn2+ and can be induced upon addition of Zn2+.

FIGS. 51A to 51W (SEQ ID NOs: 27-49, respectively) denote the nucleic acid sequences of various putative metal inducible promoters found in ABICyanol.

Figure 52A:
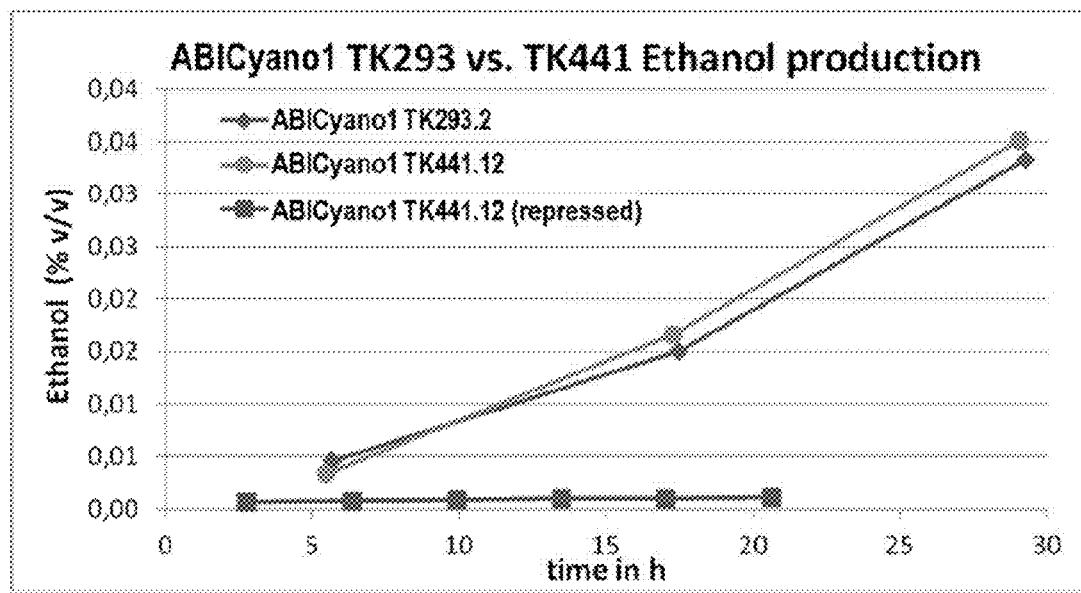
Figure 52B:
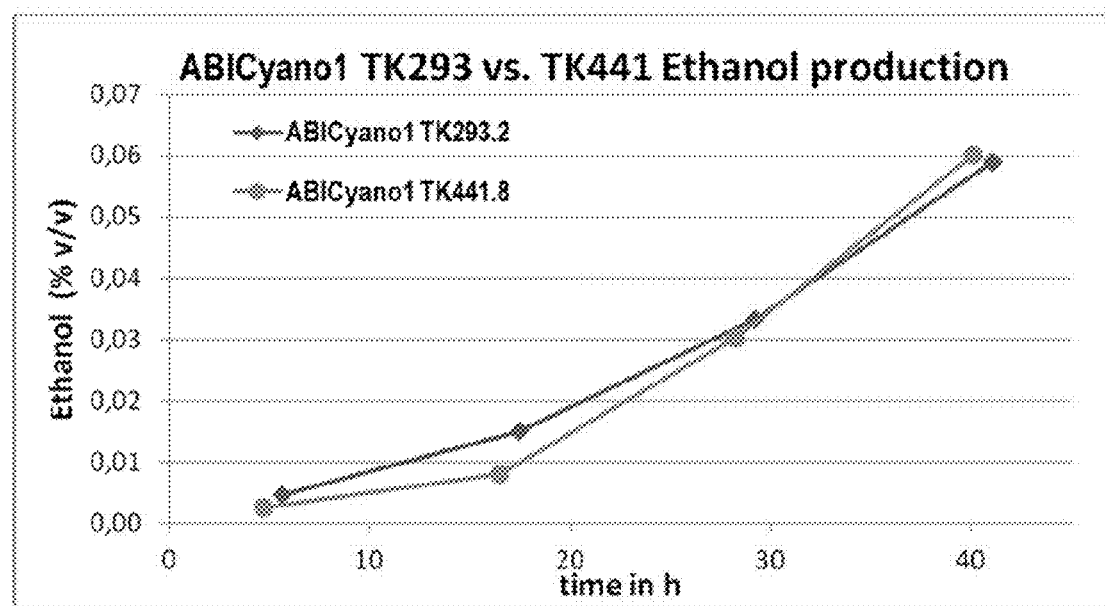

FIG. 52A to 52B depict a graph showing the ethanol production determined by the GC vial method of a new ABICyanol strain with PpetJ from ABICyanol as promoter.

Figure 53:
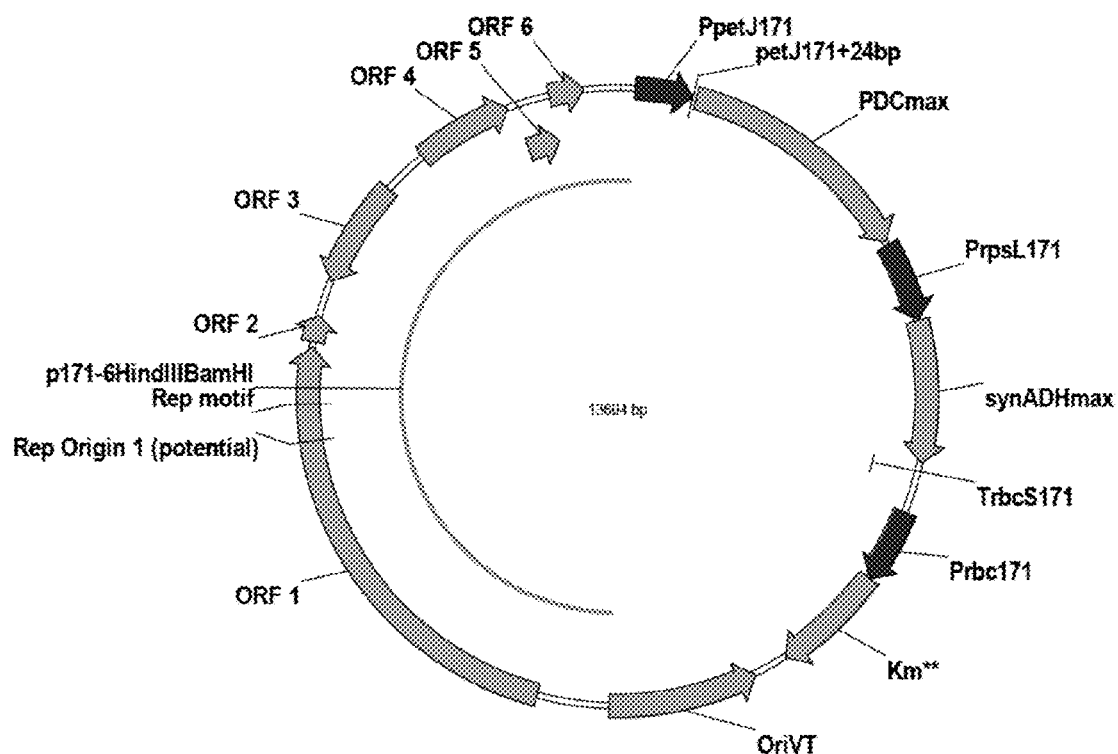

The plasmid map of plasmid TK441 is shown in FIG. 53 and its nucleic acid sequence is depicted in FIG. 54 (SEQ ID NO: 50).

Figure 55:
Figure 57C:
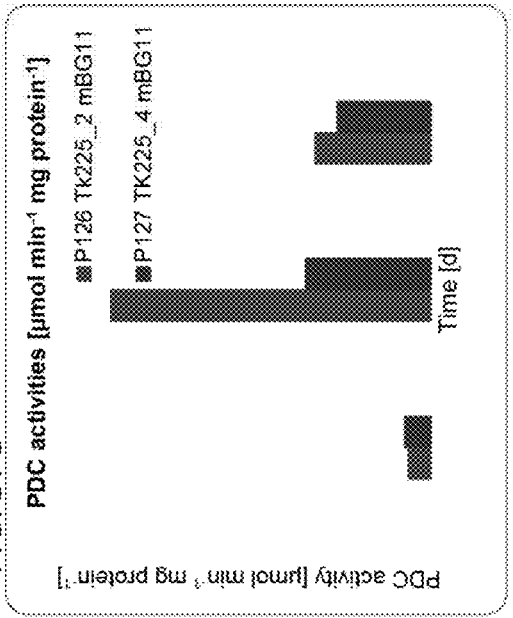
Figure 57D:
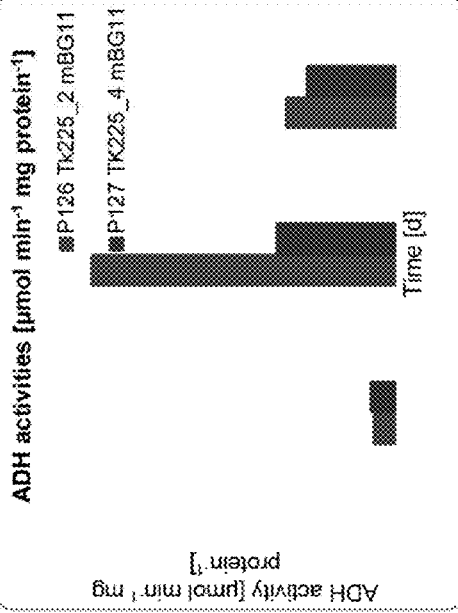
Figure 57A:
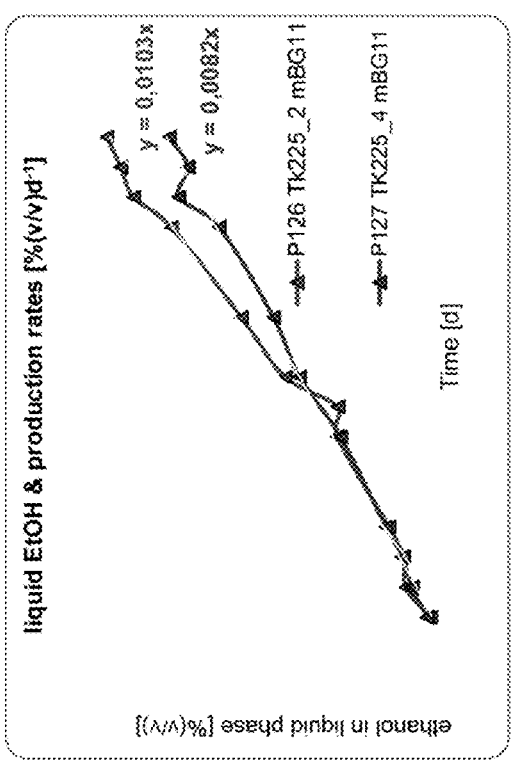
Figure 57B:
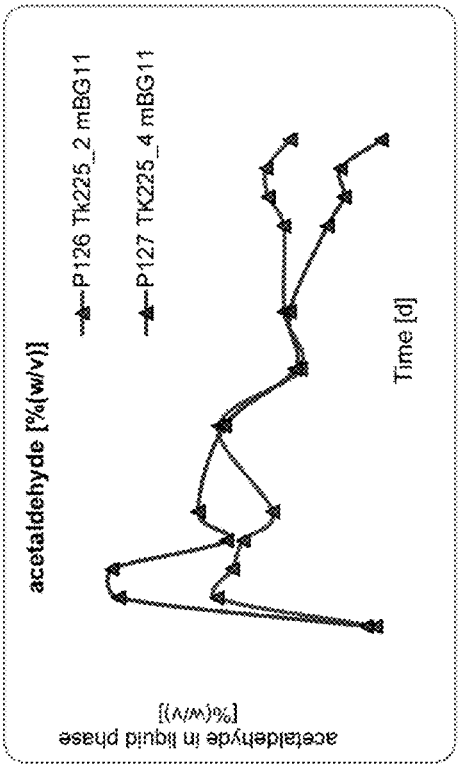

FIG. 55 is a photograph of a gel separation showing how methylation of a plasmid only containing antibiotic resistance genes may at least partially protect it from digestion by a crude extract of ABICyanol. A plasmid including AvaI and AcyI (BsaHI) restriction sites, was incubated with ABICyanol crude extract, either with or without methylation to protect the plasmid (first plasmid: AvaI: 2x, AcyI: 2x). Lane 1: plasmid without crude extract, lane 2: methylated plasmid without crude extract, lane 3: plasmid with crude extract (digestion), lane 4: methylated plasmid with crude extract. The plasmid was fully protected from digestion by the methylation procedure.

FIG. 56A and 56B are line graphs showing the production of ethanol and acetaldehyde determined by the GC vial method from *Cyanobacterium* ABICyanol harboring the ethanologenic plasmids TK293 and TK225.

FIG. 57A to 57D show the results of a 15 day cultivation of *Cyanobacterium* ABICyanol harboring the ethanologenic plasmid TK225, including the ethanol production rate, acetaldehyde accumulation and enzyme activities. Panel A: ethanol production (% ethanol per volume per day); Panel B: Acetaldehyde (% w/v) Panel C: PDC enzyme activity over time; Panel D: ADH enzyme activity over time.

Figure 58A:
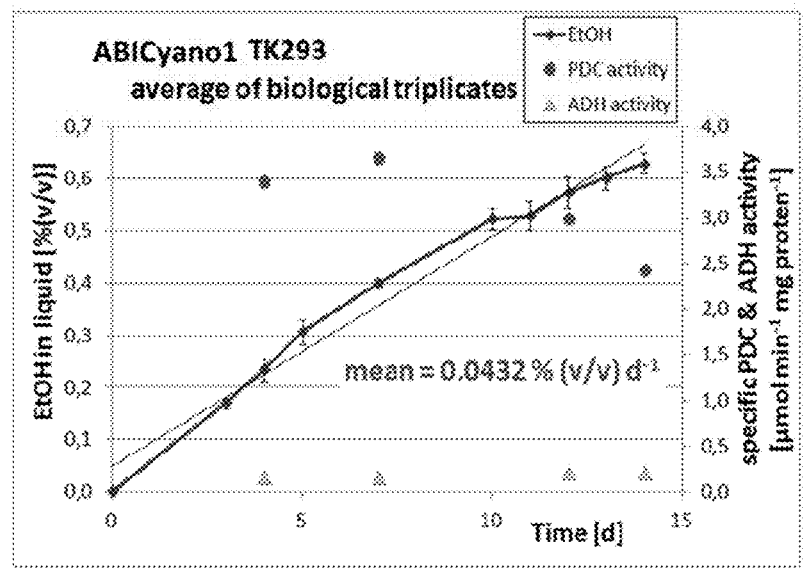
Figure 58B:
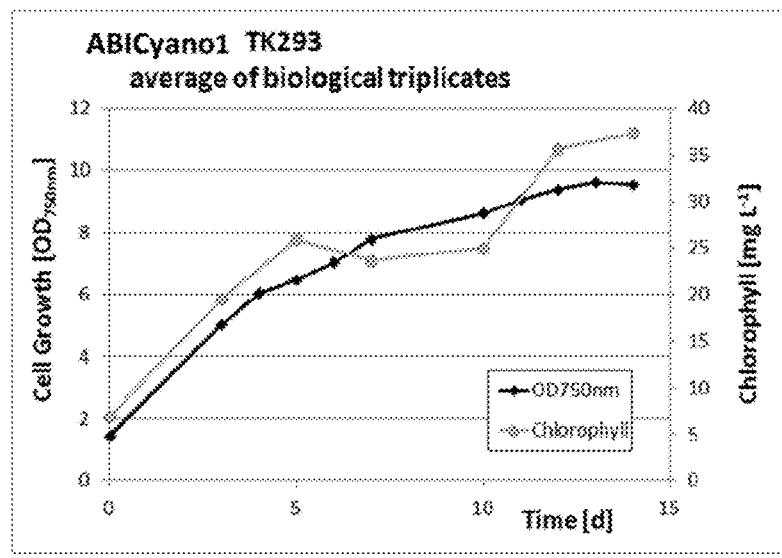
Figure 58C:
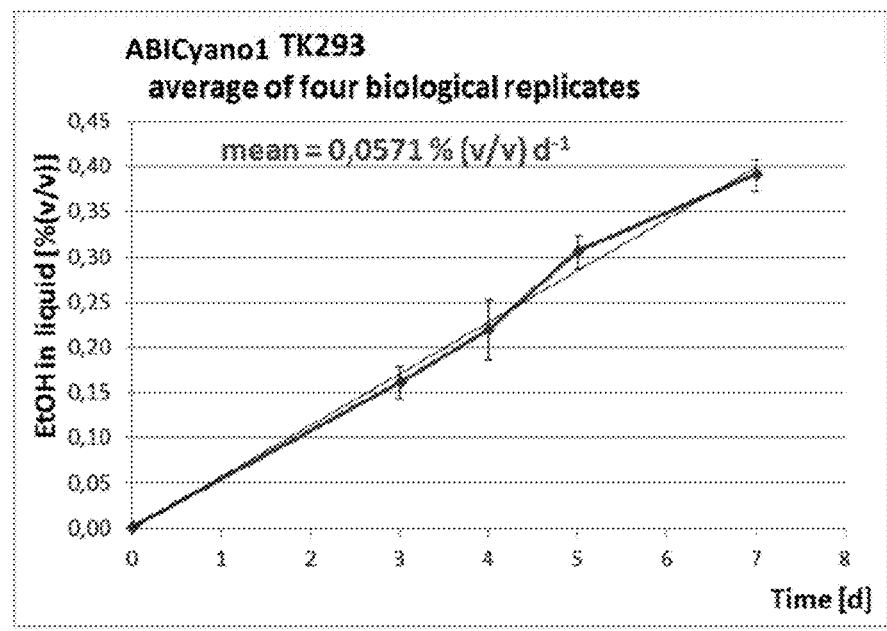

FIG. 58A to 58C show the results of a 14 day cultivation of *Cyanobacterium* ABICyanol harboring the ethanologenic plasmid TK293, including the ethanol production rate, the cell growth and the maximum ethanol production rate for 7 days.

FIG. 59A and 59B show the ethanol production rates and the acetaldehyde accumulation determined by the GC vial method for *Cyanobacterium* ABICyanol harboring the different ethanologenic plasmids TK293, #1495, #1578 and #1581, cultured for 40 hours.

FIG. 60A and 60B depict the PDC enzyme and ADH enzyme activity of the culturing experiments already presented in the FIG. 59A and 59B.

FIGS. 61A-61I depict nucleotide sequences of exemplary promoters from ABICyanol, including cpcB from *Cyanobacterium* ABICyanol (see FIG. 61I (SEQ ID NO: 52)), mrgA gene promoter (214 bp) from *Cyanobacterium* ABICyanol (see FIG. 61B (SEQ ID NO: 53)), nblA gene promoter (338 bp) from *Cyanobacterium* ABICyanol (see FIG. 61C (SEQ ID NO: 54)), ggpS (glucosylglycerol-phospate synthase) gene promoter (408 bp) from *Cyanobacterium* ABICyanol (see FIG. 61D (SEQ ID NO: 55)), petJ gene promoter (411 bp) from *Cyanobacterium* ABICyanol (see FIG. 61E (SEQ ID NO: 56)), ppsA (phosphoenolpyruvate synthase gene) promoter (211 bp) from *Cyanobacterium* ABICyanol (see FIG. 61F ((SEQ ID NO: 57)), rnpA (Ribonuclease P) gene promoter (542 bp) from *Cyanobacterium* ABICyanol (see FIG. 61G (SEQ ID NO: 58)), the pstS gene promoter (380 bp) from *Cyanobacterium* ABICyanol (see FIG. 61H (SEQ ID NO: 59)), and the IrtA gene promoter (see FIG. 61A (SEQ ID NO: 51)).

DETAILED DESCRIPTION

One strain of *Cyanobacterium* sp., named *Cyanobacterium* sp. ABICyanol, has been isolated and examined for its hardiness in various environmental conditions that would be likely to be present in a large-scale algae culture system, such as temperature extremes, oxygen level extremes, extremes in light levels, pH variation, as well as the presence of contaminants. Further, an endogenous plasmid (p6.8) derived from this strain can be modified, either in vivo or in vitro, to be a useful plasmid vector capable of carrying production genes of interest in a wide range of host cyanobacterial cells (either *Cyanobacterium*, or other cyanobacterial genera such as *Synechocystis* and *Synechococcus*).

Figure 1:
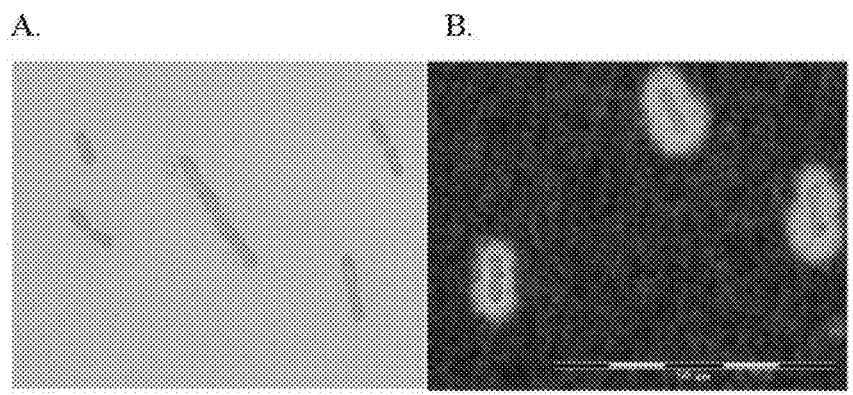
FIG. 1 is a panel of microscopic images that demonstrate the presence of the extracellular polymer (EPS) layer that is present in a sheath surrounding the *Cyanobacterium* ABICyanol cell. Panel A: unstained cells. Panel B: the cells are stained with scribtol black, which cannot penetrate the EPS layer. The thick EPS layer can be seen. Bar=50 μm.

The cyanobacterial genus *Cyanobacterium* includes several species. As mentioned above, a new isolate of this genus, *Cyanobacterium* ABICyanol, has been found. The new isolate is hardy, grows quickly, is high temperature tolerant, and can tolerate a range of salinities. The new strain can also tolerate high temperatures, in comparison to other cyanobacterial species. This new strain has been analyzed by DNA sequencing, and appears to be a member of the species *Cyanobacterium*, which has been found in thermal mats in Italy (Moro, et al., 2007, Algological Studies, 123:1-15). The new isolate appears to be sheathed with copious amounts of mucilaginous extracellular material, as shown in FIG. 1B. This material may help the cell survive in adverse environmental conditions.

Although this new *Cyanobacterium* isolate has shown a hard and fast growing phenotype, it has been very difficult to transform the cells with foreign DNA. The mucilaginous sheath may play a role in the transformation difficulties, as may the presence of certain restriction enzyme systems in the host cell. Nevertheless, it has recently been found to be transformable when using certain plasmids, certain cell pretreatments, and growth conditions, An embodiment of the invention thus relates to the transformation of this species with heterologous DNA.

General Explanations and Definitions:

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture Biotechnology And Applied Phycology (2003) Richmond, A.; (ed.), Blackwell Publishing; and "The cyanobacteria,, molecular Biology, Genomics and Evolution", Edited by Antonia Herrero and Enrique Flores, Caister Academic Press, Norfolk, UK, 2008.

It is well known to as person of ordinary skill in the art that large plasmids can be produced using techniques such as the ones described in the U.S. Pat. No. 6,472,184 B1 titled "method for producing nucleic acid polymers" and U.S. Pat. No. 5,750,380 titled "DNA polymerase mediated synthesis of double stranded nucleic acid molecules", which are hereby incorporated in their entirety.

Denominations of genes are in the following presented in a three letter lower case name followed by a capitalized letter if more than one related gene exists, for example nirA. The respective protein encoded by that gene is denominated by the same name with the first letter capitalized, such as NirA.

Denominations for promoter sequences, which control the transcription of a certain gene in their natural environment are given by a capitalized letter "P" followed by the gene name according to the above described nomenclature, for example "PnirA" for the promoter controlling the transcription of the nirA gene.

Denominations for enzyme names can be given in a two or three letter code indicating the origin of the enzyme, followed by the above mentioned three letter code for the enzyme itself, such as SynAdh ($Zn^{2+}$ dependent Alcohol dehydrogenase from *Synechocystis* PCC6803), ZmPdc (pyruvate decarboxylase from *Zymomonas mobilis*).

All publications and patent applications mentioned in this specification are herein incorporated by reference to the same extent as if each individual publication or patent application was specifically and individually indicated to be incorporated by reference.

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

The term "Cyanobacteria" refers to a member from the group of photoautotrophic prokaryotic microorganisms which can utilize solar energy and fix carbon dioxide. Cyanobacteria are also referred to as blue-green algae.

The term "terminator" refers to a nucleic acid sequence, which is able to terminate the transcription of a mRNA. The terminators can exert their function in various was including, but not limited to forming a hairpin structure in the mRNA transcript, which disrupts the mRNA-DNA RNA polymerase complex during transcription or via forming a recognition site for a transcription termination factor. Non-limiting examples are dsrA from *E. coli*, the oop terminator or the rho terminator.

The term "*Cyanobacterium* sp." refers to a cyanobacterial member of the genus *Cyanobacterium*, which was among other characterized by Rippka et Cohen-Bazire, 1983. Ann. Microbiol. (Inst. Pasteur) 134B: 32.

The terms "host cell" and "recombinant host cell" are intended to include a cell suitable for metabolic manipulation, e.g., which can incorporate heterologous polynucleotide sequences, e.g., which can be transformed. The term is intended to include progeny of the cell originally transformed, In particular embodiments, the cell is a prokaryotic cell, e.g., a cyanobacterial cell. The term recombinant host cell is intended to include a cell that has already been selected or engineered to have certain desirable properties and suitable for further enhancement using the compositions and methods of the invention. The term "shuttle vector" refers to vector, such as a plasmid, which can propagate in different host species. For example a shuttle vector can be propagated in different cyanobacterial species such as *Cyanobacterium* sp., *Synechococcus* sp., and *Synechocystis* sp. because the cyanobacterial origin of replication of the vector allows for a separate replication in different species. Alternatively or in addition a shuttle vector also can contain an origin of replication for different families of bacteria such as *Enterobacteriaceae* and for cyanobacterial genera, so that cloning/genetic enhancements can be easily done in *E. coli* and the recombinant plasmid can be expressed/maintained in cyanobacterial hosts. In the latter case, the shuttle vector is either a broad host range vector whose origin of replication is recognized by *E. coli* and cyanobacteria, or a plasmid, which contains at least two different origins of replication for the species The term "genome" refers to the chromosomal genome as well as to extrachromosomal plasmids which are normally present in the wild type cyanobacterium without having performed recombinant DNA technology. For example, cyanobacteria such as *Synechococcus* PCC7002 can include at least up to 6 extrachromosomal plasmids in their wild type form.

"Competent to express" refers to a host cell that provides a sufficient cellular environment for expression of endogenous and/or exogenous polynucleotides.

As used herein, the term "genetically enhanced" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

As used herein, the term "recombinant" refers to nucleic acid sequences and in particular to genes, which are changed by laboratory methods thereby creating combinations of nucleic acid sequences in a host cell which are not found in the respective wild type host cell. This term can apply nucleic acid sequences which are both endogenous as well as heterologous with respect to the host cell.

The terms "Polynucleotide" and "nucleic acid" also refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be recombinantly introduced into the host cell.

The term "homology" refers to the percentage of identity between two polynucleotide or two polypeptide moieties. The correspondence between the sequence from one moiety to another can be determined by techniques known to the art.

For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, "substantially similar" refers to nucleic acid fragments wherein changes in one or more nucleotide bases results in substitution of one or more amino acids, but do not affect the functional properties of the protein encoded by the DNA sequence.

The term "substantially similar" also refers to modifications of the nucleic acid fragments of the instant invention such as deletion or insertion alone or more nucleotide bases that do not substantially affect the functional properties of the resulting transcript.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994 Nucleic Acid Research 22: 4673-4, 680), A nucleotide sequence or an amino acid sequence can also be used as a so-called "query sequence" to perform a search against public nucleic acid or protein sequence databases in order, for example, to identify further unknown homologous sequences, which can also be used in embodiments of this invention. Such searches can be performed using the algorithm of Karlin and Altschul (1999 Proceedings of the National Academy of Sciences U.S.A. 87: 2,264 to 2,268), modified as in Karlin and Altschul (1993 Proceedings of the National Academy of Sciences U.S.A. 90: 5,873 to 5,877). Such an algorithm is incorporated in the NBLAST and XBLAST programs of Altschul et al. (1999 Journal of Molecular Biology 215: 403 to 410). Where gaps exist between two sequences, gapped BLAST can be utilized as described in Altschul et al. (1997 Nucleic Acid Research, 25: 3,389 to 3,402).

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacteria." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides).

The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58: 123-137 (2002). Additionally, transformation methods and selectable markers for use in bacteria are well known (see. e.g., Sambrook et al, supra).

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non- equivalent crossover events. Equivalent crossing over occurs between two equivalent sequences or chromosome regions, whereas non-equivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at an of a large number of genomic locations.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along With the host genome. Moreover, certain vectors are capable of directing the expression of genes to which they are operatively linked. Such vectors are referred to herein as "recombinant expression vectors" (or simply "expression vectors").

The term "promoter" is intended to include a polynucleotide segment that can transcriptionally control a gene of interest, e.g., a pyruvate decarboxylase gene that it does or does not transcriptionally control in nature. In one embodiment, the transcriptional control of a promoter results in an increase in expression of the gene of interest. In an embodiment, a promoter is placed 5' to the gene-of-interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.) will induce the promoter leading to the transcription of the gene.

The phrase "operably linked" means that the nucleotide sequence of the nucleic. acid molecule or gene of interest is linked to the regulatory sequence(s) in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence.

The term "endogenous gene" refers to a native gene in its natural location in the genome of an organism. A "foreign" gene or "heterologous" gene refers to it gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "fragment" refers to a nucleotide sequence of reduced length relative to the reference nucleic acid and comprising, over the common portion, a nucleotide sequence substantially identical to the reference nucleic acid. Such a nucleic acid fragment. according, to the invention may be, where appropriate, included in a larger polynucleotide of which it is a constituent. Such fragments comprise, or alternatively consist of, oligonucleotides ranging in length from at least about 6 to about 1500 or more consecutive nucleotides of a polynucleotide according to the invention.

The term "open reading frame" abbreviated as "ORF," refers to a length of nucleic acid sequence, either DNA, cDNA or RNA, that comprises a translation start signal or initiation codon, such as an ATG or AUG, and a termination codon and can be potentially translated into to polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The terms "restriction endonuclease" and "restriction enzyme" refer to an enzyme that binds and cuts within a specific nucleotide sequence within double stranded DNA.

The term "expression" as used herein, refers to the transcription and stable accumulation mRNA derived from a nucleic acid or polynucleotide. Expression may also refer to translation of mRNA into a protein or polypeptide.

An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term "codon" refers to a triplet of nucleotides coding for a single amino acid.

The term "codon-anticodon recognition" refers to the interaction between a codon on an mRNA molecule and the corresponding anticodon on a tRNA molecule.

The term "codon bias" refers to the fact that different organisms use different codon frequencies.

The term "codon improvement" refers to the modification of at least some of the codons present in a heterologous gene sequence from a triplet code that is not generally used in the host organism to a triplet code that is more common in the particular host organism. This can result in a higher expression level of the gene of interest.

The term "reporter gene" means a nucleic acid encoding an identifying factor that can be identified based upon the reporter gene's effect, in order to determine or confirm that a cell or organism contains the nucleic acid of interest, and/or to measure gene expression induction or transcription. Examples of reporter genes known and used in the art include but are not limited to luciferase (Luc), green fluorescent protein (GFP), chloramphenicol acetyltransferase (CAT), β-galactosidase (LacZ), β-glucuronidase (GUS), and the like. Selectable marker genes may also be considered reporter genes.

The term "selectable marker" means an identifying factor, usually an antibiotic or chemical resistance gene, that is able to be selected for based upon the marker gene's effect, such as resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the an include: genes providing resistance to ampicillin, streptomycin, gentamycin, spectinomycin, kanamycin, hygromycin, and the like.

A "polypeptide" is a polymeric compound comprised of covalently linked amino acid residues. A "protein" is a polypeptide that performs a structural or functional role in a living cell.

A "heterologous protein" refers to a protein not naturally produced in the cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids).

The term "fragment" of a polypeptide refers to a polypeptide whose amino acid sequence is shorter than that of the reference polypeptide. Such fragments of a polypeptide according to the invention may have a length of at least about 2 to about 300 or more amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification, The skilled artisan can produce variants having single or multiple amino acid substitutions, deletions, additions, or replacements.

As used herein, the phrase "increased activity" refers to any genetic modification resulting in increased levels of enzyme function in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme, which increases the half-life of the protein, leading to the presence of more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Biomedical Engineering Handbook (2000) Bronzino, J. D., Springer, ISBN 354066808X).

The terms "pyruvate decarboxylase" and "PDC" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide. The terms "Alcohol dehydrogenase" and "ADH" refer to an enzyme that facilitates the interconversion between alcohols and aldehydes or ketones. An "adh gene" refers to the gene encoding an enzyme that facilitates the interconversion between alcohols and aldehydes or ketones, "pdc/adh" refers to the pdc and adh genes collectively. A "pdc/adh cassette" refers to a nucleic acid sequence encoding a PDC enzyme and an ADH enzyme.

The term "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

The term "polymerase chain reaction," also termed "PCR," refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

Database entry numbers given in the following are from the NCBI database (National Center for Biotechnology Information) or from the CyanoBase, the genome database for cyanobacteria (Yazukazu et al. "CyanoBase, the genome database for *Synechocystis* sp. Strain PCC6803: status for the year 2000", Nucleic Acid Research, 2000, Vol. 18, page 72).

The EC numbers cited throughout this patent application are enzyme commission numbers which is a numerical classification scheme for enzymes based on the chemical reactions which are catalyzed by the enzymes.

DESCRIPTION OF EMBODIMENTS OF THE INVENTION

One species of *Cyanobacterium* sp., has been found to be particularly hardy under extreme conditions that often occur in production-scale algal cultures. The cells are heat tolerant, and appear to be more tolerant to many other environmental stress conditions than are more commonly used cyanobacterial species. After several unsuccessful attempts, the inventors were able to transform these cells with desired recombinant genes, so that they can be used to harbor recombinant biosynthetic pathway genes to produce various chemical compounds of interest.

A deposit of the Algenol Biofuels Inc. proprietary strain of *Cyanobacterium* sp., strain ABICyanol, disclosed above and recited in the appended claims has been made with the American Type Culture Collection (ATCC), 10801 University Boulevard, Manassas, Va. 20110. The date of receipt of the deposit was Nov. 9, 2012, as confirmed by ATCC on Nov. 14, 2012. The ATCC Accession Number is ATCC No, PTA-13311. The deposit includes 25 2-ml vials, each containing about 1.5 ml of cryopreserved cyanobacterial cells at a concentration of about $2.39 \times 10^7$ cells per mL. All restrictions will be removed upon granting of a patent, and the deposit is intended to meet all of the requirements of 37 C.F.R. §§1.801-1.809. The deposit will be maintained in the depository for a period of thirty years, or five years after the last request, or for the enforceable life of the patent, whichever is longer, and will be replaced as necessary during that period.

The 16S rDNA of *Cyanobacterium* sp. ABICyanol show a high sequence identity of around 99% to the 16S rDNA sequences of different cyanobacterial species of the genus *Cyanobacterium*, including *Cyanobacterium* IHB-410, *Cyanobacterium* aponinum ETS-03, and *Cyanobacterium* sp. MBIC10216. The 16S ribosomal RNA (rRNA) gene sequences (16S rDNA) of ABICyanol was predicted from the genome sequence with RNAmmer program (Lagesen K, et al. (2007) RNAmmer: consistent and rapid annotation of ribosomal RNA genes. *Nucleic Acids Research* 35(9):3100-3108.). These sequences were then used as a query to search against the NCBI database and 16S rDNA sequences from 4 species belonging to the genus *Cyanobacterium* were retrieved as the top BLAST (Altschul SF, et al. (1997) Gapped BLAST and PSI-BLAST: a new generation of protein database search programs. *Nucl. Acids. Res.* 25(17):3389-3402) hits. Comparison of 16S rDNA shows that ABICyanol (SEQ ID NO. 63) and ABICyano2 (SEQ ID NO. 62) are 99% identical to *Cyanobacterium* spp. A sequence comparison of the 16S rDNA sequences of some cyanobacterial species is shown in FIG. 5B. In this sequence comparison "Cyano10216" denotes the 16S rDNA sequence of *Cyanobacterium* sp. MBIC10216 (SEQ ID NO. 60) (available at the NCBI with the accession number AB058249.1), "Cyano-ETS-03" denotes the 16S rDNA of *Cyanobacterium* aponinum ETS-03 (SEQ ID NO. 61) (available at the NCBI with the accession number AM238427.1), the denomination "CyanoLLi5" is for *Cyanobacterium* sp. LLi5 (SEQ ID NO. 64) (available at the NCBI with the accession number DQ786164.1) and "Cyano7202" stands for *Cyanobacterium* stanieri PCC7202, (SEQ ID NO. 65) which is available at the NCBI with the accession number AM258981.1.

*Cyanobacterium* sp. ABICyanol was examined for its hardiness in various environmental conditions that would be likely to be present in a large-scale algae culture system, such as temperature extremes, oxygen level extremes, extremes in light levels, pH variation, and the presence of contaminants, as described in Examples 7 to 9. In particular, *Cyanobacterium* for example *Cyanobacterium* ABICyanol was shown to withstand at least 1% (v/v) ethanol in the medium, for example marine medium, which can for example have a salinity of between 30 to 38, in particular 35 psu (practical salinity units). This culturing was done for at least 6 weeks, preferably at least 12 weeks, most preferred at least 16 weeks. The test for ethanol tolerance was as done by adding 1% ethanol to the medium of *Cyanobacterium* ABICyanol. Cyanobacterial cultures were examined, for example under the microscope after a predetermined period of time, for example 6, 12 or 16 weeks and cyanobacterial cultures were deemed to have passed the ethanol tolerance test if at least or more than 50% of the cyanobacterial cells were found to be intact. ,i.e. viable according to microscopic analysis meaning that the cell morphology did not change significantly, the cells were still green, and the cells were not lysed.

Another test for temperature tolerance was conducted wherein *Cyanobacterium* sp., for example *Cyanobacterium* ABICyanol was cultured in a medium, for example a marine medium under conditions of light illumination and omitting light illumination (day/night cycle) at maximum temperatures between 45 to 55° C. for a certain period of time, for example 1 to 2 hours during illumination. Cyanobacterial cells were deemed to have passed the test, if the cultures were still growing after having been subjected to 7 days of day night/cycles as described above. Growth could be detected for example by an increase in the chlorophyll content of the cyanobacterial cultures. *Cyanobacterium* sp., for example *Cyanobacterium* ABICyanol was found to withstand at 48° C., preferably 50° C. most preferred at least 53 to 55° C. for at least 2 hours per day over a time period of at least 7 days.

In addition, an oxygen tolerance test was carried out, which showed that *Cyanobacterium* sp., for example *Cyanobacterium* ABICyanol can tolerate purging with 60% (v/v) to 80% oxygen (resulting in oxygen levels of up to 1000 µmol/L in the culture during the day) when cultured at temperatures between 28° C. to 37° C. and when being illuminated with a light intensity of between 200 µE m$^{-2}$ s$^{-1}$ to 400 µE m$^{-2}$ s$^{-1}$ in a medium such as marine medium.

*Cyanobacterium* sp., in particular *Cyanobacterium* ABICyanol was also shown to tolerate a wide range of pH values and can be cultured at a pH between 5.5 to 10, preferably at a pH between 6 to 7.5, most preferred at neutral or slightly alkaline pH of pH 7.5.

In addition, it could be shown that contaminating strains in *Cyanobacterium* ABICyanol cultures do not grow to such a high density as in other cultures of known cyanobacterial strains. For comparison ~10$^5$-10$^6$ cfu/mL of contaminating strains were found in *Cyanobacterium* ABICyanol cultures and ~10$^9$-10$^{15}$ cfu/mL of contaminating strains in *Synechococcus* sp. PCC7002 cultures.

Subject matter of one embodiment of the invention are *Cyanobacterium* host cells, for example *Cyanobacterium* ABICyanol host cells, which can withstand at least one of the following culturing conditions:
  1% (v/v) ethanol in the medium for at least 6, 12 or 16 weeks,
  48° C., preferably 50° C. most preferred at least 53 to 55° C. for at least 2 hours per day over a time period of at least 7 days, and
  Purging with 60% (v/v) to 80% oxygen (, resulting in oxygen concentrations of up to 1000 µmol/L in the culture during the day).

Preferably the *Cyanobacterium* sp., in particular *Cyanobacterium* ABICyanol host cells can tolerate at least two or all of the above mentioned culturing conditions.

The hardiness, tolerance to a wide range of growth temperatures, and tolerance to environmental conditions in general, make *Cyanobacterium*, in particular *Cyanobacterium* ABICyanol a good choice for genetic enhancements to produce chemical compounds of interest on an industrial scale.

Subject matter of another embodiment of the invention are therefore genetically enhanced *Cyanobacterium* sp. host cells, in particular *Cyanobacterium* ABICyanol host cells, including at least one recombinant gene encoding at least one protein selected from a group consisting of a protein that is involved in a biosynthetic pathway for the production of a chemical compound or a marker protein. Owing to the recombinant gene, the genetically enhanced *Cyanobacterium* host cells can be used for the production of various chemical compounds of interest by culturing the host cells under harsh conditions of high temperature, high oxygen levels and in the case of the chemical compound being ethanol, under high levels of ethanol in the medium. The marker protein or reporter protein, which for example can be a fluorescent protein such as a red or green fluorescent protein or a marker gene conferring resistance to a biocide such as an antibiotic can be used in order to successfully select for and maintain cultures of the *Cyanobacterium* sp. host cells in the presence of other bacterial contaminating strains.

In a further embodiment of the invention, the recombinant gene is present on an extrachromosomal plasmid. This extrachromosomal plasmid can replicate independently from the chromosomes of the *Cyanobacterium* sp. host cells and can for example be present in a high number of copies in these cells so that the chemical compound can be produced in a high yield.

Apart from this recombinant gene, the genetically enhanced *Cyanobacterium* sp. or *Cyanobacterium* ABICyanol host cells can include further genetic enhancements such as partial deletions of endogenous genes of *Cyanobacterium* or further recombinant genes, which can increase the overall yield of the chemical compound being produced by the host cells. For example, if the chemical compound to be produced is ethanol, the genetic enhancements can relate to either knock out enhancements of endogenous genes coding for enzymes converting pyruvate or acetyl-CoA into a reserve or storage compound or the genetic enhancements can relate to the overexpression of enzymes of the glycolysis pathway, Calvin-cycle, intermediate steps of metabolism, amino acid metabolism, the fermentation pathway and the citric acid cycle in order to increase the production of ethanol by the *Cyanobacterium* host cells. These genetic enhancements are described in the PCT patent application WO 2009/098089 A2 starting from page 70 and following, which is hereby incorporated for this purpose. In addition, genetic enhancements further increasing the production of the chemical compound of interest can be done for example genetic enhancement of the enzymes of the carbon fixation and the subsequent carbohydrate metabolism (esp. pathways which compete with the EtOH production pathway) further genetic enhancements increasing the production of the chemical compound of interest include but are not limited to, components of the photosystems (antennas and pigment modification), components of the photosynthetic and respiratory electron transport systems and manipulations of local and global regulatory factors incl. 2-component system, sigma factors, small regulating RNAs and antisense RNAs. Further embodiments of the invention are therefore also directed to *Cyanobacterium* sp. host cells, in particular *Cyanobacterium* ABICyanol host cells, which in comparison to the wild type *Cyanobacterium* contain knock out mutations of endogenous genes, as long as these knock out mutations do not affect at least one of the above mentioned advantageous properties of *Cyanobacterium* with regard to culturing, which are as follows:
Tolerance to:
  1% (v/v) ethanol in the medium for at least 6, 12 or 16 weeks,
  48° C., preferably 50° C. most preferred at least 53 to 55° C. for at least 2 hours per day over a time period of at least 7 days, and
  Purging with 60% (v/v) to 80% oxygen (, resulting in oxygen concentrations of up to 1000 µmol/L in the culture during the day).

Further, an endogenous plasmid derived from this strain can be modified, either in vivo or in vitro, to be a useful plasmid vector capable of carrying production genes of interest in a wide range of host cyanobacterial cells (either *Cyano-*

*bacterium* sp., or other cyanobacterial genera such as *Synechocystis* and *Synechococcus*).

Cyanobacteria can be genetically enhanced to add enzymatic pathways of interest as shown herein in order to produce compounds of interest. The recombinant DNA sequences encoding the genes can be amplified by polymerase chain reaction (PCR) using specific primers. The amplified PCR fragments can then be digested with the appropriate restriction enzymes and cloned into either a self-replicating plasmid or an integrative plasmid. An antibiotic resistance cassette for selection of positive clones can be present on the appropriate plasmid.

In an embodiment, the recombinant nucleic acids of interest can be amplified from nucleic, acid samples using known amplification techniques. PCR can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, and for nucleic acid sequencing.

To use isolated sequences in the above techniques, recombinant DNA vectors suitable for transformation of cyanobacteria can be prepared. Techniques for transformation are well known and described in the technical and scientific literature. For example, a DNA sequence encoding one or more of the genes described herein can be combined with transcriptional and other regulatory sequences which will direct the transcription of the sequence from the gene in the transformed cyanobacteria.

In an embodiment, the recombinant genes of interest are inserted into the cyanobacterial chromosome. When the cell is polyploid, the gene insertions can be present in all of the copies of the chromosome, or in some of the copies of the chromosome.

In another embodiment, the inserted recombinant genes are present on an extrachromosomal plasmid. The extrachromosomal plasmid can be derived from an outside source, such as, for example, RSF10-based plasmid vectors, or it can be derived from an endogenous plasmid from the cyanobacterial cell or from another species of cyanobacteria.

In an embodiment, the inserted genes are present on an extrachromosomal plasmid, wherein the plasmid has multiple copies per cell. The plasmid can be present, for example, at about 1, 3, 5, 8, 10, 15, 20, 30, 40, 50, 60, 70, 80, 90, or more copies per host cyanobacterial cell. In an embodiment, the plasmids are fully segregated.

In another embodiment, the inserted genes are present on one cassette driven by one promoter. In another embodiment, the inserted genes are present on separate plasmids, or on different cassettes.

In yet another embodiment, the inserted genes are modified for optimal expression by modifying the nucleic acid sequence to accommodate the cyanobacterial cell's protein translation system. Modifying the nucleic acid sequences in this manner can result in an increased expression of the genes.
Vector suitable for transformation of *Cyanobacterium* ABICyanol and its use as a Novel Shuttle Vector System for Transformation and Expression in Cyanobacteria In an embodiment, a novel vector system based on the endogenous vector from *Cyanobacterium* ABICyanol has been developed. The modified vector can be used to transform cyanobacteria from a broad range of genera, including *Cyanobacterium* ABICyanol itself. The new vector or extrachromosomal plasmid comprises the following minimal features:

a recombinant gene, wherein said recombinant gene encodes at least one protein selected from a group consisting of a protein that is involved in a biosynthetic pathway for the production of a chemical compound or a marker protein and an origin of replication suitable for replication in the *Cyanobacterium* ABICyanol.

One gene coding for a replication initiation factor binding to said origin of replication can either be present on the new vector itself or can be present in the chromosomes or other extrachromosomal plasmids of *Cyanobacterium* ABICyanol. The origin of replication suitable for replication in ABICyanol and the gene coding for the replication initiation factor binding to that origin of replication ensure that the vector can be replicated in *Cyanobacterium* ABICyanol.

The nucleotide sequence of this origin of replication of this plasmid vector can have at least 80%, 90%, preferably 95% identity or can be identical to the nucleotides 3375 to 3408 of the sequence of the endogenous 6.8 kb plasmid shown in FIG. 4A. This putative origin of replication was found on the endogenous 6.8 kb plasmid identified and isolated from *Cyanobacterium* ABICyanol.

The sequence of the gene coding for the replication initiation factor has at least 80%, 90%, preferably 95% identity or is identical to nucleotides 594 to 3779 of the sequence of the endogenous 6.8 kb plasmid shown in FIG. 4A. Furthermore the gene coding for the replication initiation factor codes for a protein having at least 80%, 90%, preferably 95% sequence identity or is identical to the protein coded by nucleotides 594 to 3779 of the sequence of the endogenous 6.8 kb plasmid. This putative initiation replication factor is believed to bind to the putative origin of replication thereby ensuring the replication of this plasmid in *Cyanobacterium* ABICyanol.

The plasmid vector further can comprise a sequence having at least 95% identity to the sequence of the endogenous 6.8 kb plasmid shown in FIG. 4A. In a further variant of the invention, the backbone of the new vector is an endogenous plasmid originally isolated from *Cyanobacterium* strain ABICyanol.

The ABICyanol endogenous plasmid, shown in FIG. 4A was captured by in vitro transposition reaction with EZ-Tn5 R6Kγ Ori/Kan-2 transposition kit from the company Epicentre®, following the manufacturer's protocol. The cyanobacterial plasmid was rescued in surrogate *E. coli* host cells. The sequence and size of the captured plasmid was confirmed and validated by PCR, as well as by comparison with available genome sequence data. A replication protein (ORF1) was predicted to be present on the plasmid, as well as a recombinase protein (ORF4) and an origin of replication suitable for replication in *Cyanobacterium* ABICyanol. The amino acid sequences of the putative proteins coded by ORF1, ORF2, ORF3, ORF4, ORF5 and ORF6 are depicted in FIG. 4B, 4C, 4D, 4E, 4F and 4G. respectively.

In an embodiment, gene delivery vehicles that are developed, using: this plasmid (or a substantial portion of the plasmid) as a backbone may be able to be efficiently transformed to a wide range of cyanobacteria. Such vectors may also be able to efficiently produce heterologous proteins and other compounds of interest in cyanobacterial cultures.

In an embodiment of the invention, this ABICyanol-based plasmid sequence can be used to carry recombinant, for example heterologous genes of interest in a cyanobacterial host cell. This plasmid sequence was chosen to be the backbone for the construction of new modified vectors that can be utilized as a gene delivery vehicle to transform various cyanobacterial host cells.

Figure 3:
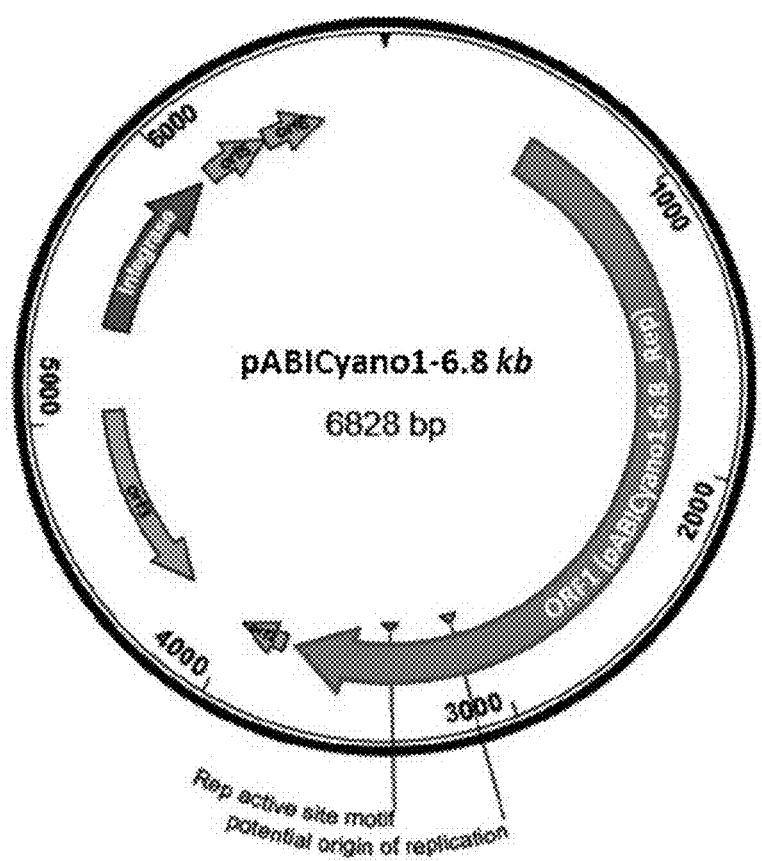
FIG. 3 is a plasmid map of the 6828 bp endogenous plasmid that was identified in the *Cyanobacterium* ABICyanol cell. The DNA sequence (SEQ ID NO: 1) is shown in FIG. 4A including the annotation of the genes and promoters done with the program vector NTI. The location of 5 putative open reading frames is shown, including the Replication Binding Protein (SEQ ID NO: 2) (ORF1 whose amino acid sequence is depicted in FIG. 4B) (CDS=complementary DNA sequence from nucleotides 594 to 3779 of the DNA sequence), which is similar to the hypothetical protein slr7037 of plasmid pSYSA (103 kb) of *Synechocystis* sp. PCC6803 and a recombinase whose amino acid sequence is depicted in FIG. 4E (SEQ ID NO: 3) (ORF4) (CDS=complementary DNA sequence from nucleotides 5350 to 6036 of the DNA sequence), which is similar to a site-specific recombinase of *Bacillus thuringiensis* serovar israelensis ATCC 35646. ORF2 whose amino acid sequence is depicted in FIG. 4C (SEQ ID NO: 4) runs from nucleotides 3815 to 4000, ORF3 whose amino acid sequence is depicted in FIG. 4D (SEQ ID NO: 5) from nucleotides 4260 to 5024 in antisense direction. ORF5 whose amino acid sequence is depicted in FIG. 4F (SEQ ID NO: 6) from nucleotides 6078 to 6341 and ORF6 whose amino acid sequence is depicted in FIG. 4G (SEQ. ID NO: 7) from nucleotides 6338 to 6586 the DNA sequence.

In an embodiment, the above-described vector was used as a starting point for producing the modified vector of the invention. FIG. 3 shows a generalized plasmid map based on the endogenous 6.8 kb plasmid from *Cyanobacterium* ABICyanol.

In an embodiment, starting with the backbone of the 6.8 plasmid from ABICyanol, modifications as described herein can be performed individually or together to increase transformation efficiency, increase the replication rate within the cell, and to increase the production of a desired product from the cyanobacterial cell. Suitable modifications include, for example, insertion of selection markers (such as antibiotic resistance genes), recombinant genes or cassettes for the production of a desired compound, and other modifications to increase the expression or stability of the plasmid in the cyanobacterial cell.

In another embodiment of the invention, codon improvement of the inserted at least one recombinant gene, to allow for improved expression in the cyanobacterial host cell, can also be performed by adapting the codon usage of the at least one recombinant gene to the codon usage of *Cyanobacterium* sp., in particular *Cyanobacterium* ABICyanol. In particular, the G and/or C wobble bases in the codons for the amino acids in the at least one recombinant gene can be replaced by A and/or T, because the GC content of the genome of *Cyanobacterium* ABICyanol is rather low (36%). For example in variants of the recombinant genes, which are only marginally codon improved, between 1% to 10%, preferably only 2% to 6% of the codons have been changed. In highly codon improved variants of the recombinant genes at least 25%, preferably at least 50% to 65% or even at least 70% of the codons have been changed. In a further embodiment of the invention, recombinant genes can be used, which are not codon improved, such as SynAdh (see for example the extrachromosomal plasmid #1578).

In some embodiments, the plasmid construct preparation is performed in *E. coli* to allow for ease of genetic manipulation. In order to be propagated in *E. coli*, an origin of replication suitable for *Enterobacteriaceae*, in particular *E. coli*, is incorporated into the plasmid vector. Once the construct is prepared and changed in *E. coli*, the plasmid can then be transferred to the cyanobacterial cell, where it can replicate as an independent plasmid. Methods of genetic engineering of plasmids using *E. coli* are generally known in the art. Alternatively the plasmid vector can also be synthesized via solid phase synthesis so that an origin of replication for *Enterobacteriaceae* does not need to be present in the plasmid vector.

Figure 8:
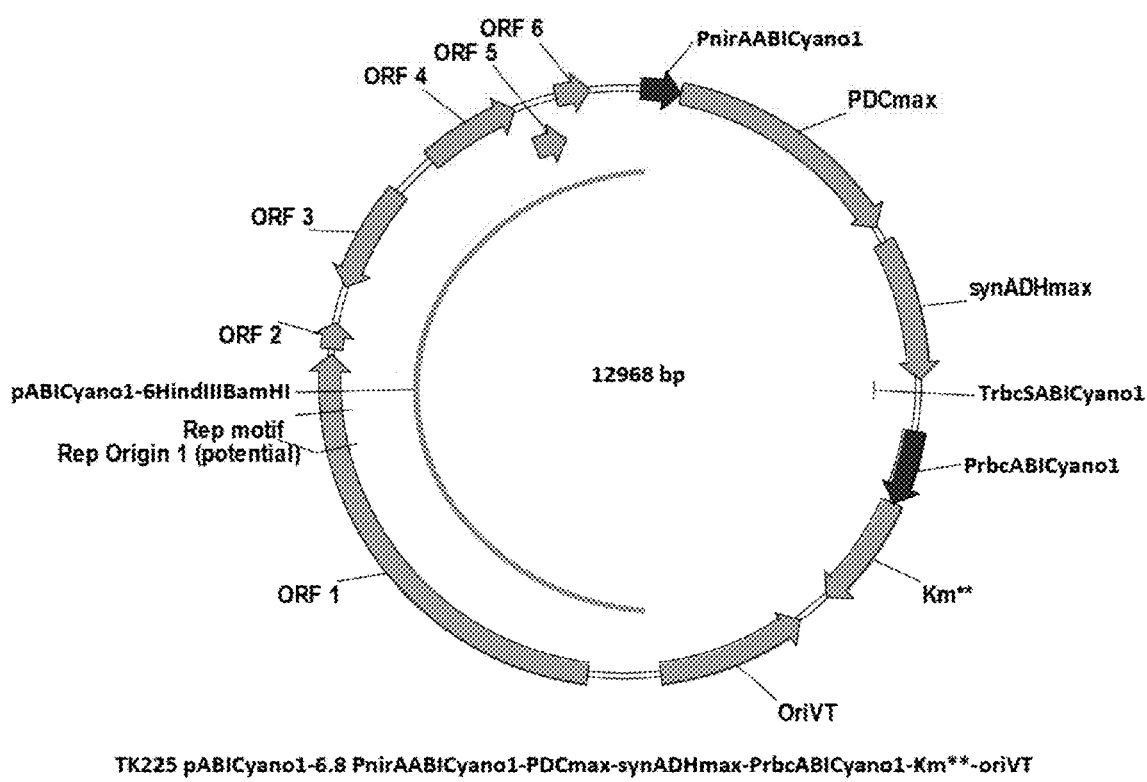
FIG. 8 is a map of the plasmid construct TK225. Its nucleotide sequence (SEQ ID NO: 9) is shown in FIG. 9. PrbcL from *Cyanobacterium* ABICyanol runs from nucleotides 3574 to 4099, the codon improved kanamycin resistance cassette Km** is located from nucleotides 4101 to 4916, the origin of replication and transfer oriVT is located from nucleotides 5159 to 6217 in antisense direction, PnirA runs from nucleotides 96 to 378, the codon improved variant of SynAdh denoted "SynADH max" is located from nucleotides 2203 to 3210, the codon improved variant from Pyruvate decarboxylase "PDC" runs from nucleotides 379 to 2085.
Figure 10:
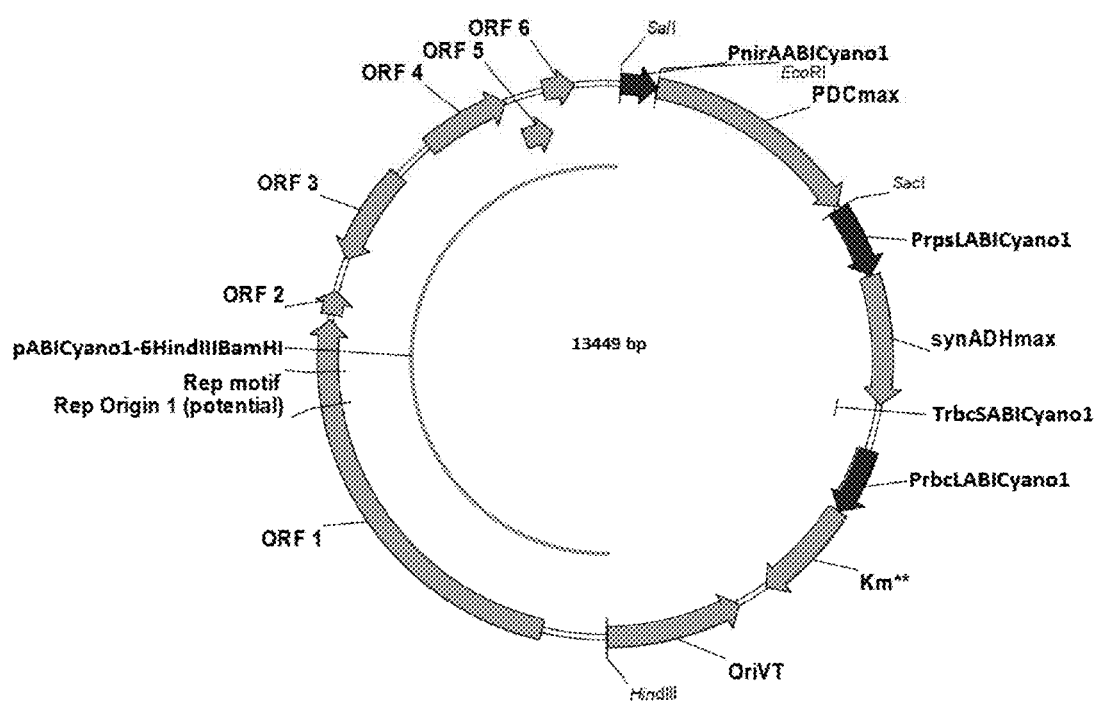
FIG. 10 is a map of the plasmid construct TK293. Its nucleotide sequence (SEQ ID NO: 10) is depicted in FIG. 11 including the annotation of the genes and promoters done with the program vector NTI.
Figure 12:
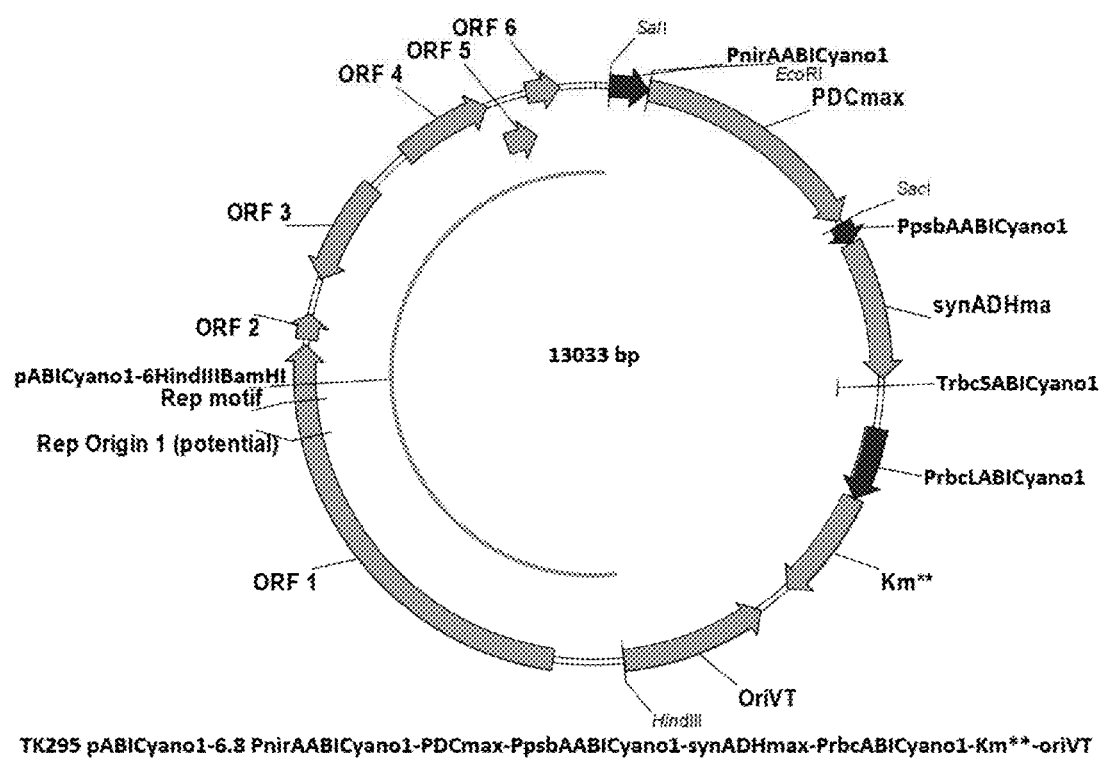
FIG. 12 is a map of the plasmid construct TK295. Its nucleotide sequence (SEQ ID NO: 11) is depicted in FIG. 13 including the annotation of the genes and promoters done with the program vector NTI.
Figure 14:
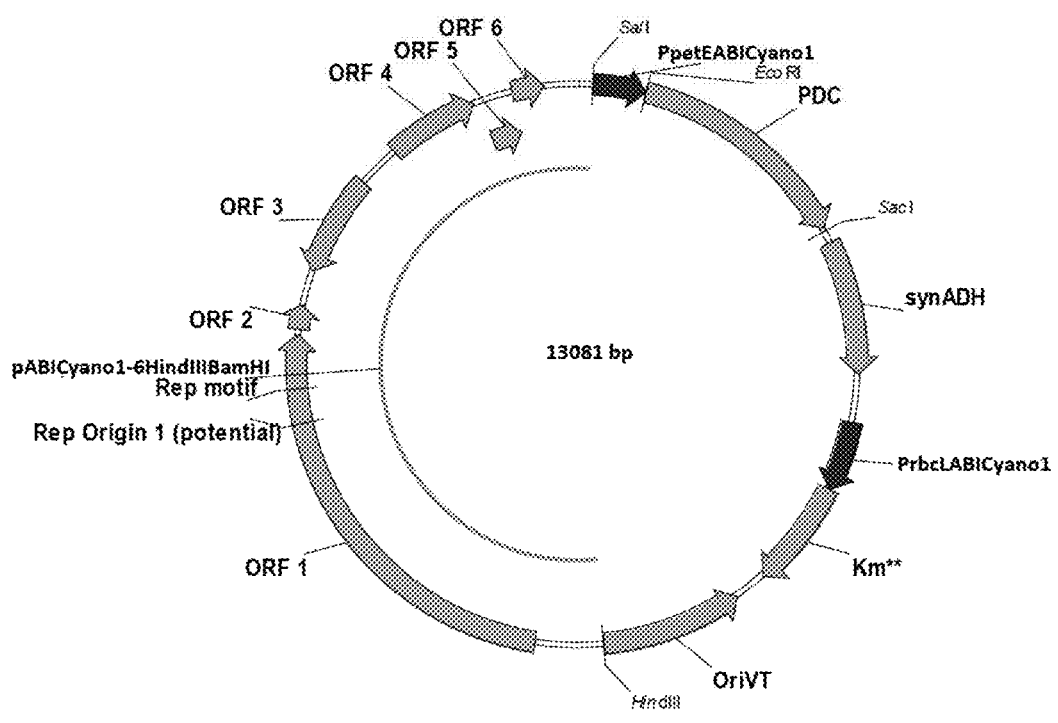
FIG. 14 is a map of the plasmid construct TK229. Its nucleotide sequence (SEQ ID NO: 12) is depicted in FIG. 15 including the annotation of the genes and promoters done with the program vector NTI.
Figure 16:
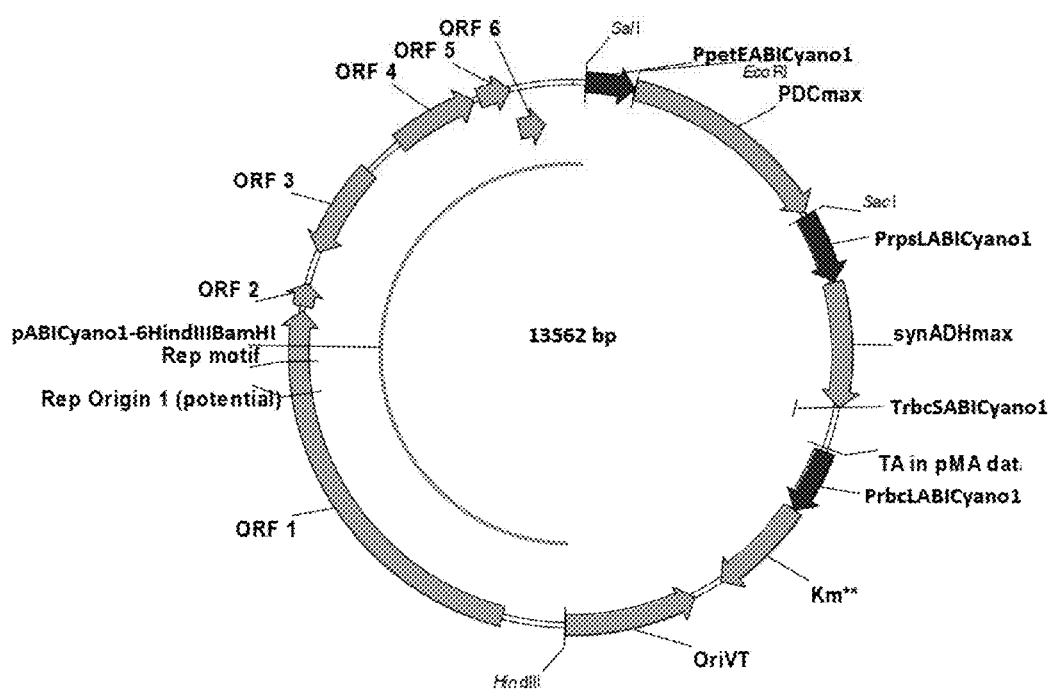
FIG. 16 is a map of the plasmid construct TK368. Its nucleotide sequence (SEQ ID NO: 13) is depicted in FIG. 17 including the annotation of the genes and promoters done with the program vector NTI.
Figure 18:
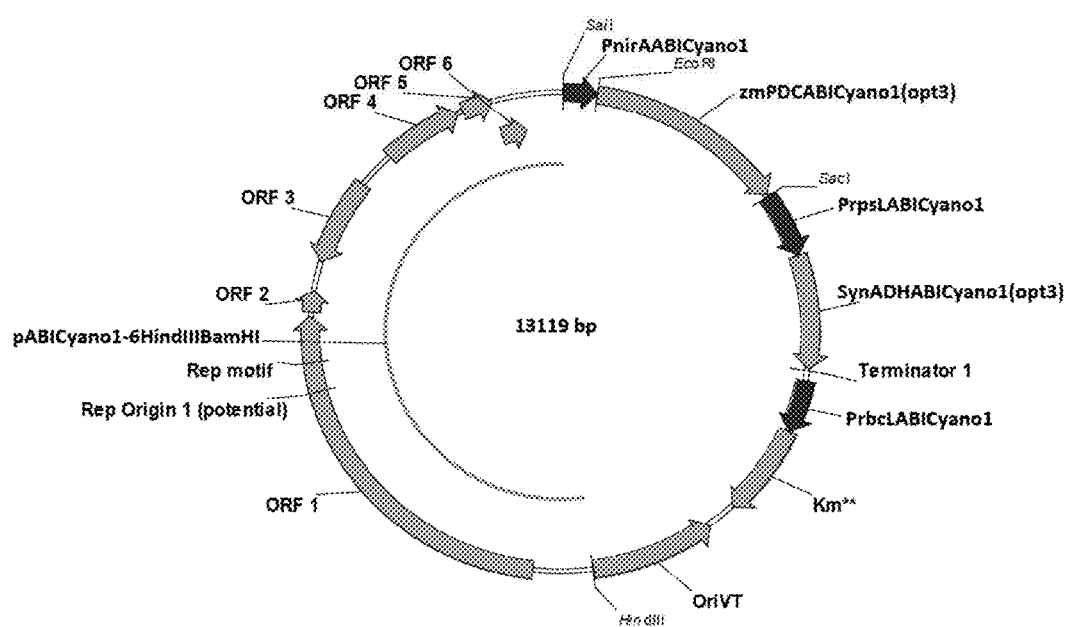
FIG. 18 is a map of the plasmid construct #1495. Its nucleotide sequence (SEQ ID NO: 14) is depicted in FIG. 19 including the annotation of the genes and promoters done with the program vector NTI.
Figure 20:
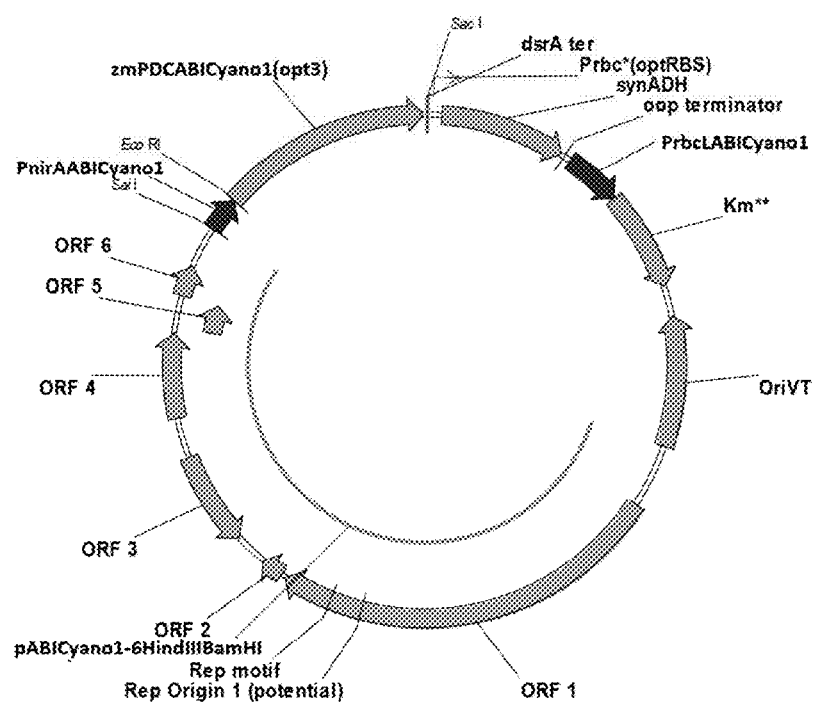
FIG. 20 is a map of the plasmid construct #1578. Its nucleotide sequence (SEQ ID NO: 15) is depicted in FIG. 21 including the annotation of the genes and promoters done with the program vector NTI.
Figure 22:
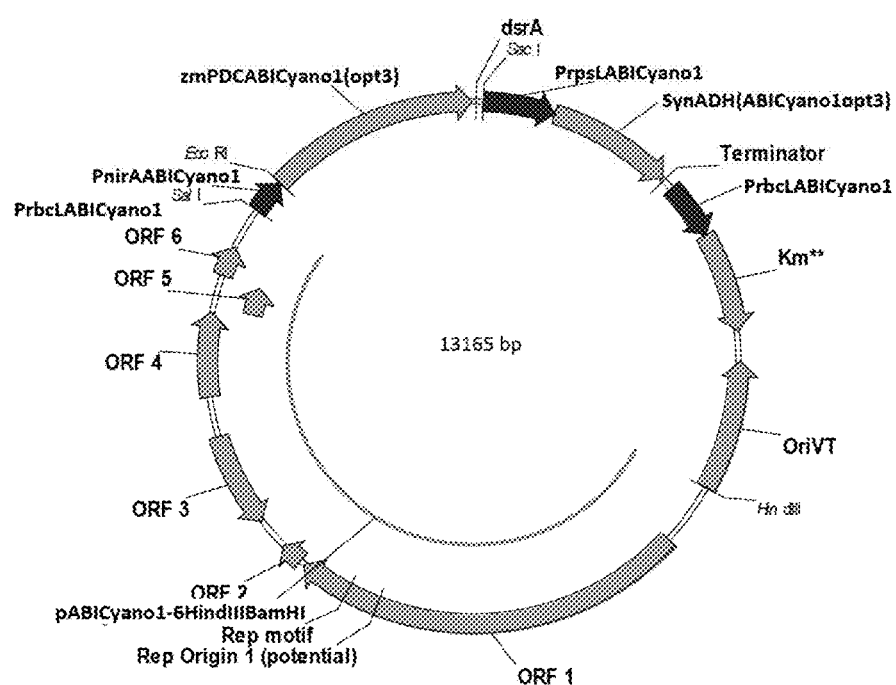
FIG. 22 is a map of the plasmid construct #1581. Its nucleotide sequence (SEQ ID NO: 16) is depicted in FIG. 23 including the annotation of the genes and promoters done with the program vector NTI.
Figure 24:
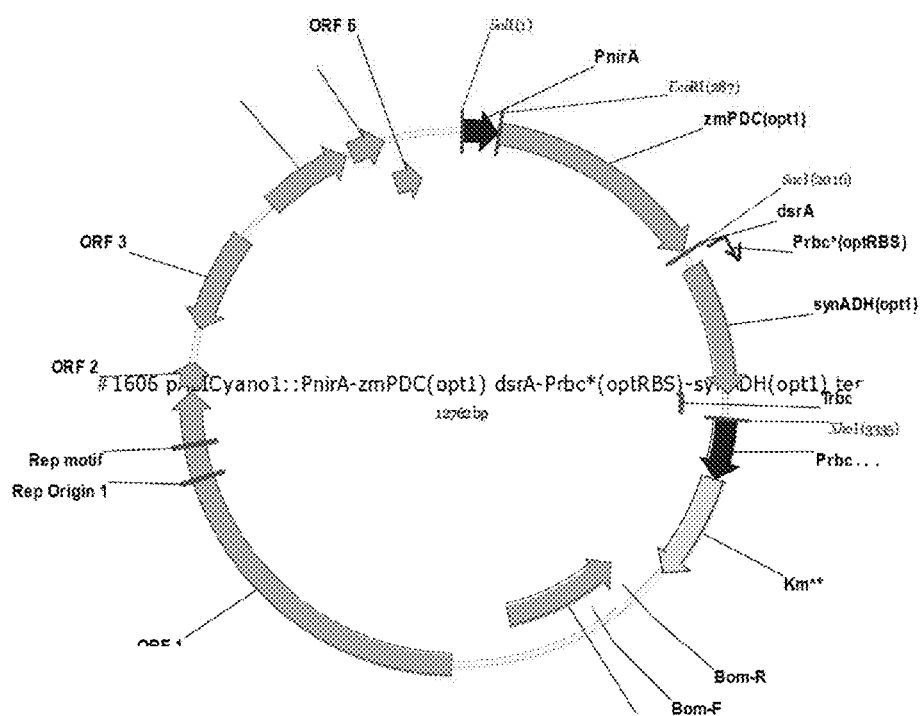
FIG. 24 is a map of the plasmid construct #1606. Its nucleotide sequence (SEQ ID NO: 17) is depicted in FIG. 25 including the annotation of the genes and promoters done with the program vector NTI.

In an embodiment, the ABICyanol 6.8 kb endogenous plasmid (FIG. 3) was used as a backbone for the initial plasmid vector for transformation of *Cyanobacterium* sp. Since this is the endogenous vector from the species, it may be more stable when transformed to the cell than plasmids derived from completely different organisms. In an embodiment, the entire endogenous plasmid is inserted into the vector. Extrachromosomal plasmids containing the entire nucleic acid sequence of the 6.8 kb endogenous plasmid are for example shown in FIGS. 8, 10 or 12. In another embodiment, a sequence of about 50%,70%, 75%, 80% 85%, 90%, 95%, 98%, 99%, or 99.5% of the entire endogenous plasmid sequence is inserted into the vector, the extrachromosomal plasmid.

In an embodiment, the modified vector of the invention is designed to have several modular units that can be easily swapped out using specific restriction enzymes. Promoters, genes of interest, selectable markers, and other desired sequences can be moved in and out of the vector as desired. This modular design makes genetic experiments faster and more efficient.

The new vector according to certain embodiments of the invention can replicate in both cyanobacteria and in *E. coli*. The vector contains a replication unit that can function in a broad range of cyanobacterial genera. The vector also contains a replicon for propagation in *E. coli* for ease of cloning and genetic manipulation using *E. coli*.

In an embodiment, a plasmid shuttle vector is provided which is characterized by being replicable in both *Escherichia coli* and in a cyanobacterial species. The plasmid comprises a promoter capable of functioning in cyanobacteria and *E. coli* and a DNA sequence encoding a sequence capable of functioning as a selective marker for both *Escherichia coli* and cyanobacteria. Alternatively, the shuttle vector includes two different promoter systems, one functioning in cyanobacteria and the other one functional in *E. coli*. The plasmid shuttle vector enables the efficient transformation of cyanobacteria and the expression of recombinant genes of interest.

According to a further embodiment of the invention, the plasmid vector also contains an origin of transfer (oriT) which is suitable for conjugation. In particular, the plasmid vector can contain a combined origin of replication and an origin of transfer (oriVT), which enables replication in *Enterobacteriaceae*, in particular *E. coli* and which also enables conjugation with for example an *E. coli* donor strain and *Cyanobacterium* sp., in particular *Cyanobacterium* ABICyanol as a recipient strain. Such an plasmid vector can be used for triparental mating wherein a conjugative plasmid present in one bacterial strain assists the transfer of a mobilizable plasmid, the plasmid vector of the present invention present in a second bacterial strain into a third recipient bacterial strain, which can be *Cyanobacterium* ABICyanol.

Also disclosed is a recombinant vector in which a gene of interest, the recombinant gene is operably linked to the shuttle vector, and cyanobacterial cells transformed with the recombinant shuttle vector. The shuttle vector is relatively small in size, relatively stable in a cyanobacterial host cell, and can replicate in a variety cyanobacterial species. This new vector is useful for expressing a variety of heterologous genes in cyanobacteria.

In an embodiment, the shuttle vector efficiently expresses a codon-optimized antibiotic resistance gene for selection of transformants, such as codon improved kanamycin or gentamycin resistance genes. The shuttle vector was constructed based on a modular basis, so that all of the key elements (replication ori, AbR gene and reporter gene) are exchangeable via unique restriction sites, providing versatile cloning options and facilitating the delivery of genes of interest to the target organisms.

Other antibiotic resistance genes can be used if desired. For example, genes conferring, resistance to ampicillin, chloramphenicol, spectinomycin or other antibiotics can be inserted into the vector, under the control of a suitable promoter. In some embodiments, the vector contains more than one antibiotic resistance gene.

The vector of the invention has been modified by several factors so that it is capable of efficient replication in multiple types of cyanobacterial species. It has also been organized so that various sequences can be easily replaced with other desired sequences as needed. Thus, a construct having a different gene (or genes) of interest, a different antibiotic, a different promoter, etc. can be made with relative ease. The modified vector allows for rapid testing of various heterologous constructs in a cyanobacterial cell.

Any suitable promoter can be used to regulate the expression of the genes present in the vector. Exemplary promoter types include, for example, constitutive promoters, inducible promoters, endogenous promoters, heterologous promoters, and the like.

In an embodiment, the modular design of the modified plasmid vector allows complex sequence manipulation in cyanobacteria.

Transformation of *Cyanobacterium* sp., in Particular *Cyanobacterium* ABICyanol Cells A method for producing a genetically enhanced *Cyanobacterium* sp. host cell as described above generally comprises introducing a recombinant nucleic acid sequence including any of the recombinant genes, which were already disclosed above, into the cyanobacterial host cell. In particular, the at least one recombinant gene can be introduced into the host cells via an extrachromosomal plasmid, which can separately replicate in the host cell or the at least one recombinant gene can be introduced into the genome of the host cell, for example via homologous recombination.

In a further embodiment of the method of the invention, the method of producing a genetically enhanced *Cyanobacterium* sp. host cell comprises the method steps of:
  A) Subjecting the host cell to compounds increasing the permeability of the extracellular polymer layer (EPS) and cell wall, respectively of the host cell, and
  B) Introducing said recombinant nucleic acid sequence into the host cell.

The inventors found out that in order to introduce the at least one recombinant gene into the *Cyanobacterium* host cell, the permeability of the extracellular polymer layer (EPS) has to be increased beforehand so that the recombinant nucleic acid sequence can pass the EPS and reach the interior of the cyanobacterial cell.

The recombinant nucleic acid sequence can be provided as part of an extrachromosomal plasmid containing cyanobacterial nucleic acid sequences in order to increase the likelihood of success for the transformation.

The method further comprises a variant, wherein during method step A) an extrachromosomal plasmid derived from an endogenous plasmid of said host cell is provided. This endogenous plasmid can for example be an extrachromosomal plasmid derived from the 6.8 kb endogenous plasmid of *Cyanobacterium* sp. ABICyanol.

Another method of the current invention further comprises protecting said recombinant nucleic acid sequence, in particular the plasmid, against endogenous restriction endonucleases of the host cell by, for example methylating at least a part of said recombinant nucleic acid sequence or modifying and/or eliminating the recognition sequences of the endogenous restriction endonucleases. By changing the nucleic acid sequence of potential recognition sites of restriction endonucleases, a digest of the recombinant nucleic acid sequence can be avoided. It was discovered that endogenous restriction endonucleases of *Cyanobacterium* ABICyanol can cut the extrachromosomal plasmid, thereby preventing a genetic transformation of this host cell. In particular, methyltransferases, for example AvaI and AcyI can be used to protect the extrachromosomal plasmid. This plasmid can either be incubated with the methylatransferases in vitro or a helper plasmid can be present during the transformation of *Cyanobacterium* ABICyanol in a helper *E. coli* strain in order to methylate the extrachromosomal plasmids in vivo before conjugation takes place. In addition recognition sequences for the restriction enzymes can be modified or even be deleted.

The above described method can include a further embodiment, wherein in method step A) compounds selected from a group consisting of: N-acetylcysteine, lysozyme, and β-galactosidase and combinations thereof, are used in order to increase the permeability of the EPS layer. Preferably a combination of N-acetylcysteine and lysozyme is used.

In method step B) the host cell can preferably be first subjected to N-Acetylcysteine followed by a treatment of lysozyme. The inventors found out that such a pre-treatment drastically increased the number of transformants.

The host cell can be subjected to N-acetylcysteine for 0.5 to 3 days, preferably to 1 to 2 days and can further be treated with lysozyme for 3 min. to 1 hour, preferably for 10 to 30 min, most preferred for 10 to 15 min.

The N-acetylcysteine treatment can be carried out at a temperature of 12 to 37° C., preferably 16° C., and the lysozyme treatment can be conducted in a temperature range from 20° C. to 37° C., preferably at a temperature from 20° C. to 30° C.

During method step B) the concentration of N-acetylcysteine can be kept between 0.05 mg/ml and 1 mg/ml and the concentration of lysozyme can be between 10 to 60 µg/ml.

The transformation of the plasmid vector to the host *Cyanobacterium* sp., in particular *Cyanobacterium* ABICyanol cell can utilize any of several methods, such as natural transformation, conjugation (bi- or tri-parental mating), biolistic methods, electroporation, or other methods. In an embodiment, the transformation method is conjugation, as described in Example 19. Electroporation methods can also be used. In addition, the vector can be modified to allow for integration into the cyanobacterial chromosome by adding an appropriate DNA sequence homologous to the target region of the host genome, or through in vivo transposition by introducing the mosaic ends (ME) to the vector. Once the plasmid is established in the host cell, it can be present, for example, at a range of from 1 to many copies per cell.

Exemplary methods suitable for transformation of Cyanobacteria, include, as nonlimiting examples, natural DNA uptake (Chung, et al, (1998) FEMS Microbiol. Lett. 164: 353-361; Frigaard, et al. (2004) Methods Mol. Biol. 274: 325-40; Zang, et al. (2007) J. Microbiol. 45: 241-245), conjugation, transduction, glass bead transformation (Kindle, et al. (1989) J. Cell Biol. 109: 2589-601; Feng, et al. (2009) Mol. Biol. Rep. 36: 1433-9; U.S. Pat. No. 5,661,017), silicon carbide whisker transformation (Dunahay, et al. (1997) Methods Mol. Biol. (1997) 62: 503-9), biolistics (Dawson, et al. (1997) Curr. Microbiol. 35: 356-62, Hallmann, et al. (1997) Proc. Natl. Acad. USA 94: 7469-7474; Jakobiak, et al. (2004) Protist 155: 381-93; Tan, et al. (2005) J. Microbiol. 43: 361-365; Steinbrenner, et al. (2006) Appl Environ. Microbiol. 72: 7477-7484; Kroth (2007) Methods Mol. Biol. 390: 257-267; U.S. Pat. No. 5,661,017) electroporation (Kjaerulff, et at. (1994) Photosynth. Res. 41: 277-283; Iwai, et al. (2004) Plant Cell Physiol. 45: 171-5; Ravindran, et al. (2006) J. Microbiol. Methods 66: 174-6; Sun, et al. (2006) Gene 377: 140-149; Wang, et al, (2007) Appl. Microbiol. Biotechnol. 76: 651-657; Chaurasia, et al, (2008) J. Microbiol. Methods 73: 133-141; Ludwig, et al. (2008) Appl. Microbiol. Biotechnol. 78: 729-35), laser-mediated transformation, or incubation with DNA in the presence of or after pre-treatment with any of poly(amidoamine) dendrimers (Pasupathy, et al. (2008) Biotechnol. J. 3: 1078-82), polyethylene glycol (Ohnuma, et al. (2008) Plant Cell Physiol. 49: 117-120), cationic lipids (Muradawa, et al. (2008) J. Biosci. Bioeng. 105: 77-80), dextran, calcium phosphate, or calcium chloride (Mendez-Alvarez, et al. (1994) J. Bacteriol. 176: 7395-7397), optionally after treatment of the cells with cell wall-degrading enzymes (Perrone, et al. (1998) Mol. Biol. Cell 9: 3351-3365). Biolistic methods (see, for example, Ramesh, et al. (2004) Methods Mol. Biol. 274: 355-307; Doestch, et al. (2001) Curr. Genet. 39: 49-60; all incorporated herein by reference in their entireties).

The above described pre-treatment for the transformation of *Cyanobacterium* ABICyanol can also be used for introducing recombinant nucleic acid sequences such as plasmids into other cyanobacterial cells harboring an extracellular polymer layer (EPS), which are different from *Cyanobacterium* ABICyanol. Non-limiting examples for cyanobacteria with an EPS include several Nostoc and Anabaena strains, such as *Nostoc commune*, and *Anabanena cylindrica* and several *Cyanothece* sp. strains, such as *Cyanothece* PCC9224, *Cyanothece* CA 3, *Cyanothece* CE 4. *Cyanothece* ET 5, *Cyanothece* ET 2. and *Cyanothece capsulata* ATCC 43193. Further non-limiting examples of cyanobacteria with an EPS are *Aphanocapsa, Anacystis, Chroococcus Gloeothece, Microcystis Synechocystis Lyngbya Microcoleus Oscillatoria Phormidium Spirulina Anabaena Cyanospira Nostoc Scytonema Tolypothrix Chlorogloeopsis Fischerella Mastigocladus* (see for example: "Exopolysaccharide-producing cyanobacteria and their possible exploitation: A review" Roberto De Philippis et al., *Journal of Applied Phycology* 13: 293-299, 2001, and "Exocellular polysaccharides from cyanobacteria and their possible applications" Roberto De Philippis et al., FEMS Microbiology Reviews 22 (1998) 151-175).

Transformation to Other Cyanobacterial Species using the Plasmid Vectors of the Invention In an embodiment of the invention, the modified vector based on the endogenous 6.8 kb plasmid from *Cyanobacterium* ABICyanol is transformed to a *Cyanobacterium* ABICyanol host cell. In another embodiment, a vector including the endogenous 6.8 kb plasmid from *Cyanobacterium* ABICyanol is transformed to another species in the *Cyanobacterium* genus. In yet another embodiment, the endogenous 6.8 kb plasmid from *Cyanobacterium* ABICyanol is transformed to another species of cyanobacteria, such as, for example, *Synechocystis* or *Synechococcus*, as described in Example 36.

The novel *Cyanobacterium* ABICyanol-based vector of the invention is capable of transforming and replicating in several different types of cyanobacteria. Exemplary cyanobacterial genera that can be transformed with the nucleic acids described herein include, but are not limited to, *Synechocystis, Synechococcus, Acaryochloris, Anabaena, ThermoSynechococcus, Chamaesiphon, Chroococcus, Cyanobacterium, Cyanobium, Dactylococcopsis, Gloeobacter, Gloeocapsa, Gloeothece, Microsystis, Prochlorococcus, Prochloron, Chroococcidiopsis, Cyanocystis, Dermocarpella, Myxosarcina, Pleurocapsa, Stanieria, Xenococcus, Arthrospira, Borzia, Crinalium, Geitlerinema, Halospirulina, Leptolyngbya, Limnothrix, Lyngbya, Microcoleus, Cyanodictyon, Aphanocapsa, Oscillatoria, Planktothrix, Prochlorothrix, Pseudanabaena, Spirulina, Starria, Symploca, Trichodesmium, Tychonema, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema, Tolypthrix, Cyanothece, Phormidium, Adrianema*, and the like.

Promoters

Any desired promoter can be used to regulate the expression of the genes for the production of a desired compound in *Cyanobacterium* ABICyanol. Exemplary promoter types include but are not limited to, for example, constitutive promoters, inducible promoters (e.g., by nutrient starvation, heat shock, mechanical stress, environmental stress, metal concentration, light exposure, etc.), endogenous promoters, heterologous promoters, and the like.

In an embodiment, the inserted genes are placed under the transcriptional control of promoters selected from a group consisting of rbcLS, ntcA, nblA, isiA, petJ, petE, PcorT, PsmtA, PziaA, sigB, IrtA (see FIG. 61A (SEQ ID NO: 51)), htpG, hspA, clpB1, hliB, ggpS, psbA2, psaA, nirA, PnarB, PnrtA and crhC. The inserted genes can be regulated by one promoter, or they can be regulated by individual promoters. The promoters can be constitutive or inducible. The promoter sequences can be derived, for example, from the host cell, from another organism, or can be synthetically derived.

Exemplary promoters for expression in Cyanobacteria include but are not limited to PpetJ, PpsbD, PnblA, PrpoA, PisiB, PrbcLS, PntcA, PnblA, PisiA, PpetJ, PpetE, PcorT, PsmtA, PziaA, PsigB, PlrtA, PhtpG, PhspA, PclpB1, PhliB, PggpS, PpsbA2, PpsaA, PnirA, PnarB, PnrtA, PcrhC, and further metal ion inducible promoters and the like. Examples of constitutive promoters that can be used include but are not limited to PrbcL, PrnpA, PrpsL, PrpoA, PpsaA, PpsbA2, PpsbD, PcpcB.

The promoters hspA, clpBl, and hliB can be induced by heat shock (raising the growth temperature of the host cell culture from 300° C. to 400° C.), cold shock (reducing the growth temperature of the cell culture from 300° C. to 20° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium and the promoters psaA and psbA2 can be induced by low light or high light conditions. The promoter htpG can be induced by osmotic stress and heat shock. The promoter crhC can be induced by cold shock. An increase in copper concentration can be used in order to induce the promoter petE, whereas the promoter petJ is induced by decreasing the copper concentration. Additional details of these promoters can be found, for example, in PCT/EP2009/060526, which is incorporated by reference herein in its entirety.

In certain other preferred embodiments, truncated or partially truncated versions of these promoters including only a small portion of the native promoters upstream of the transcription start point, such as the region ranging from −35 to the transcription start can often be used. Furthermore, introducing nucleotide changes into the promoter sequence, e.g. into the TATA box, the operator sequence and/or the ribosomal binding site (RBS) can be used to tailor or improve the promoter strength and/or its induction conditions, e.g. the concentration of inductor required for induction. For example the inducible promoter can be PnirA from *Cyanobacterium* ABICyanol, which is repressed by ammonium and induced by nitrite. This promoter may harbor nucleotide changes in either one of the ribosomal binding site,
the TATA box,
the operator
the 5'-UTR (untranslated region).

In particular, PnirA can have the following generalized nucleotide sequence (SEQ ID NO: 78):

5' $(N)_{116}$ATGCAAAAAACGAAT$(N)_{7}$ATGTGTAAAAAGAAA$(N)_{15}$GTA GTCAAAGTTAC$(N)_{22}$TAATGT$(N)_{55}$CCGAGGACAAA$(N)_{2}$ATG-3' wherein each of the nucleotides N is independently selected from a group consisting of: A, T, C and G and wherein the two ATGs in the 5'-region of the promoter are the start for NtcB binding sites
the capital letter GTA is the start for the NtcA binding site,
the capital letter CCG denotes the start of the RBS, and
the 3'-ATG is the start codon for the first recombinant gene transcriptionally controlled by this promoter.

Another generalized DNA sequence of the nirA promoter includes nucleotide changes in the ribosomal binding site leading to the following general DNA sequence (SEQ ID NO: 79):

5'(N)₁₁₆ATGCAAAAAACGAAT(N)₇ATGTGTAAAAAGAAA(N)₁₅GTA
GTCAAAGTTAC(N)₂₂TAATGT(N)₅₅GGAGGATCAGCC(N)₂ATG-3' wherein the capitalized underlined nucleotides denote nucleotide changes in comparison to the native promoter.

In another embodiment the modified nirA promoter can include changes in the operator region (binding site for NtcB and NtcA) and the TATA box leading to the following general nucleotide sequence (SEQ ID NO: 80):

5'(N)₁₁₆ATGCAAAAAACGCAT(N)₇ATGCGTAAAAAGCAT(N)₁₅GTA
ATCAAAGTTAC(N)₂₂TAATAT(N)₅₅CCGAGGACAAA(N)₂ATG-3' wherein the capitalized underlined nucleotides denote nucleotide changes in comparison to the native promoter.

Another variant of PnirA combines the above changes thereby having the following DNA sequence (SEQ ID NO: 81):

5'(N)₁₁₆ATGCAAAAAACGCAT(N)₇ATGCGTAAAAAGCAT(N)₁₅GTA
ATCAAAGTTAC(N)₂₂TAATAT(N)₅₅GGAGGATCAGCC(N)₂ATG-3'

Another embodiment of the invention provides the $Co^{2+}$-inducible promoter corT, which has the general nucleotide sequence (SEQ ID NO: 82) of:

CAT(N)₇GTTTACTCAAAACCTTGACATTGACACTAATGTTAAGGTT
TAGGCT(N)₁₅CAAGTTAAAAAGCATG, wherein each of the nucleotides N is independently selected from a group consisting of: A, T, C and G and wherein the 5'-CAT is the start codon of corR (antisense orientation) the 3'-ATG is the start codon for the first recombinant gene transcriptionally controlled by this promoter.

A modified variant of PcorT includes changes in the RBS having the following nucleotide sequence (SEQ ID NO: 83):

CAT(N)₇GTTTACTCAAAACCTTGACATTGACACTAATGTTAAGGTTT
AGGCT(N)₁₅GAGGATAAAAAGCATG, wherein the capitalized underlined nucleotides denote nucleotide changes in comparison to the native promoter.

Yet another variant of PcorT includes changes in the TATA box having the general DNA sequence (SEQ ID NO: 84) of:

CAT(N)₇GTTTACTCAAAACCTTGACATTGACTAATGTTAAGGTTT
AGAAT(N)₁₅CAAGTTAAAAAGCATG wherein the capitalized underlined nucleotides denote nucleotide changes in comparison to the native promoter.

A third modified corT promoter combines the above mentioned two modifications having the following DNA sequence (SEQ ID NO: 85):

CAT(N)₇GTTTACTCAAAACCTTGACATTGACACTAATGTTAAGGTT
TAGAAT(N)₁₅GAGGATAAAAACCATG

Furthermore the Zn2+-inducible promoter smtA from *Synechococcus* PCC7002 can be used having the following general nucleotide sequence (SEQ ID NO: 86):

(N)₈AATACCTGAATAATTGTTCATGTGTT(N)₄TAAAAATGTGAACA
ATCGTTCAACTATTTA(N)₁₂GGAGGT(N)₇ATG

Changes in the ribosomal binding site can lead to the following generalized nucleotide sequences of PsmtA (SEQ ID NO: 87):

(N)₈AATACCTGAATAATTGTTCATGTGTT(N)₄TAAAAATGTGAAC
AATCGTTCAACTATTTA(N)₁₀AAGGAGGTGAT(N)₄ATG,
or (N)₈AATACCTGAATAATTGTTCATGTGTT(N)₄TAAAAATGTGAAC
AATCGTTCAACTATTTA(N)₁₀AAGGAGGTAT(N)₅ATG wherein the capitalized underlined nucleotides denote nucleotide changes in comparison to the native promoter.

In an embodiment of the invention, the recombinant genes to be inserted into the shuttle vector can have an inducible promoter or a constitutive promoter. The promoter can be upstream of one gene to regulate that gene, or the promoter can be upstream of several genes, so that one promoter regulates the expression of more than one gene. Alternatively, in some embodiments, each inserted gene can be regulated by a separate promoter. In an embodiment, the promoter can be derived from the cyanobacterial host cell, or can be obtained from another cyanobacterial species, or can be obtained from another organism.

Exemplary promoters include, but are not limited to the psbA2 promoter from Synechocystis PCC6803, cpcBA promoter from *Synechocystis* PCC6803, cpcB from *Cyanobacterium* ABICyanol (see FIG. 61I (SEQ ID NO: 52)), nirA gene promoter (278 bp) from *Cyanobacterium* ABICyanol, lrtA (light-repressed protein, ribosomal subunit interface protein) gene promoter from *Cyanobacterium* ABICyanol, mrgA gene promoter (214 bp) from *Cyanobacterium* ABICyanol (see FIG. 61B (SEQ ID NO: 53)), nblA gene promoter (338 bp) from *Cyanobacterium* ABICyanol (see FIG. 61C (SEQ ID NO: 54)), ggpS (glucosylglycerol-phosphate synthase) gene promoter (408 bp) from *Cyanobacterium* ABICyanol (see FIG. 61D (SEQ ID NO: 55)), petJ gene promoter (411 bp) from *Cyanobacterium* ABICyanol (see FIG. 61E (SEQ ID NO: 56)), ppsA (phosphoenolpyruvate synthase gene) promoter (211 bp) from *Cyanobacterium* ABICyanol (see FIG. 61F (SEQ ID NO: 57)), rnpA (Ribonuclease P) gene promoter (542 bp) from *Cyanobacterium* ABICyanol (see FIG. 61G (SEQ ID NO: 58)), the pstS gene promoter (380 bp) from *Cyanobacterium* ABICyanol (see FIG. 61H (SEQ ID NO: 59)), and the like.

Examples of other suitable promoters include, for instance, the PrpsL promoter, The PnblA7120 promoter from Nostoc sp. PCC7120, The PrbcL6803 promoter from *Synechocystis* sp. PCC6803 and the PsmtA1535 promoter from *Synechococcus* sp. PCC7002.

Many types of inducible promoters can be used. Exemplary inducible promoters include but are not limited to PpetJ, PnirA, PnblA, and PisiB, further metal-inducible promoters e.g. PsmtA, PziaA, PcorT, PnrsB, and the like. Differentially expressed promoters like PlrtA, PmrgA, PpstS, as well as synthetic promoters can also be used.

The promoters hspA, clpB1, and hliB, for example, can be induced by heat shock (raising the growth temperature of the host cell culture from 30° C. to 40° C.), cold shock (reducing the growth temperature of the cell culture from 30° C. to 20° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium.

The promoters PpsaA and PpsbA2 can be induced by low light or high light conditions. The promoter htpG can be induced by osmotic stress and heat shock. The promoter PcrhC can be induced by cold shock.

The promoter petE can be induced by an increase in copper concentration. Alternatively, the promoter petJ can be induced by decreasing the copper concentration.

Furthermore the promoter controlling the transcription of the at least one recombinant gene can be a cyanobacterial promoter. The promoter can be endogenous to the genetically enhanced $Cyanobacterium$ sp. or can be a promoter, which was modified in order to increase its efficiency. The promoter can also be a heterologous promoter from a different cyanobacterial or bacterial species. For example the promoter and transcription regulator gene combinations of ziaR-PziaA from $Synechocystis$ sp. PCC6803, smtB-PsmtA from $Synechoccocus$ sp. PCC7002, corR-PcorT from $Synechocystis$ sp. PCC6803, nrsRS-PnrsB from $Synechocystis$ sp. PCC6803, and aztR-PaztA from $Anabaena$ ($Nostoc$) sp. strain PCC7120 can be used to control the transcription of the at least one recombinant gene in $Cyanobacterium$ sp. in particular in $Cyanobacterium$ ABICyanol. The promoter/regulator pair aztR-PaztA can be activated by adding $Zn^{2+}$. In $Synechococcus$ PCC7002 smtB-PsmtA is induced by $Zn^{2+}$ and corR-PcorT by adding $Co^{2+}$. The regulator/promoter combination nrsRS-PnrsB can be induced by the addition of $Ni^{2+}$. The combination of ziaR-PziaA with the ziaA promoter and the ziaR repressor can be induced by the addition of $Zn^{2+}$.

Another possibility is to use the promoter PsmtA which is endogenous to $Synechococcus$ PCC7942 and $Synechococcus$ PCC7002. The gene smtA (SYNPCC7002_A2563) which is transcriptionally controlled by this promoter codes for a met-allothionein (YP_001735795.1) involved in resistance to inter alia zinc. A repressor protein (YP_001735796.1) binds to the PsmtA in the uninduced state which is encoded by the gene smtB (SYNPCC7002_A2564).

In $Anabaena$ PCC7120 the gene aztA (alr7622) codes for a $Zn^{2+}$, Cd2+ and Pb2+ transporting ATPase (NP_478269.1) which is transcriptionally controlled by the promoter PaztA. The promoter is blocked in the uninduced state by a repressor protein (NP_478268.1) coded by the gene aztR (all7621).

In $Synechocystis$ PCC6803 the gene corT (slr0797) can be found coding for a cobalt transporting ATPase (NP_442633.1). This gene is transcriptionally controlled by the promoter PcorT, which is transcriptionally controlled by a regulator protein (NP_442632.1) coded by the gene corR (sll0794), which binds to the corT promoter. The promoter PcorT is one example for a cobalt inducible promoter, whereas the other already mentioned promoters PziaA. PsmtA, and PsmtA are examples for zinc inducible promoters.

It is also possible to improve the tightness and the level of expression of the protein involved in the biosynthetic pathway for the production of a chemical compound or the marker protein if mutations are introduced in the TATA-box, the operator sequence and/or the ribosomal binding site of the promoter controlling the recombinant gene so that the promoter can have at least 90% sequence identity to an endogenous promoter of the genetically enhanced $Cyanobacterium$ sp. or to another cyanobacterial promoter.

The promoter also can be another inducible promoter selected from a group consisting of PnirA for example from $Cyanobacterium$ sp. ABICyanol, PnrtA, and PnarB. The promoter is repressed by ammonium and induced by nitrite.

The promoter can furthermore be a constitutive promoter selected from a group consisting of: PrpsL, Prbc, PcpcB and PpetE which for example all can be endogenous promoters of $Cyanobacterium$ sp. ABICyanol.

In the case that more than one recombinant gene is present, the for example first and second recombinant gene can be controlled by one promoter thereby forming, a transcriptional operon. Alternatively the first and second recombinant genes can be controlled by different first and second promoters. In the case that the first recombinant gene codes for a protein catalyzing a reaction not present in the wild-type $Cyanobacterium$ sp. directing the carbon flux away from the metabolic, pathways of the wild-type $cyanobacterium$ sp. such as Pyruvate decarboxylase enzyme, this gene can be controlled by an inducible promoter such as PnirA from $Cyanobacterium$ sp. ABICyanol. Such a configuration ensures that this gene is only turned on upon induction if a sufficiently high culture density of $Cyanobacterium$ sp. is reached. In the case that the second recombinant gene codes for a protein catalyzing a chemical reaction present in the wild-type $Cyanobacterium$ sp., such as alcohol dehydrogenase, this gene can be under the control of either an inducible or a constitutive promoter, because it does not disturb the carbon flux to the same extend as the protein coded by the first recombinant gene. The second recombinant gene then may be under the control of constitutive promoters such as PrbcL, PpetE, or PrpsL all from $Cyanobacterium$ sp. ABICyanol.

The chosen promoter elements can be combined with any of the genes encoding any of the enzymes of the invention by using standard molecular cloning techniques. Further description and characterization of constitutive or inducible promoters that can be useful in combination with the genes inserted onto the shuttle vector of the invention can include, for example: Samartzidou et al., "Transcriptional and Post-transcriptional Control of mRNA from lrtA, a Light-repressed Transcript in $Synechococcus$ sp. PCC7002," Plant Physiol. 117:225-234 (1998); Duran et al., "The Efficient Functioning of Photosynthesis and Respiration in $Synechocystis$ sp. PCC6803 Strictly Requires the Presence of either Cytochrome c6 or Plastocyanin," Journal of Biological Chemistry 279:7229-7233 (2004); Singh et al., "The Heat Shock Response in the $Cyanobacterium\ Synechocystis$ sp. Strain PCC6803 and Regulation of Gene Expression by HrcA and SigB," Arch Microbiol. 186:273-286 (2006); Imamura et al., "Antagonistic Dark/light-induced SigB/SigD, Group 2 Sigma Factors, Expression Through Redox Potential and their Roles in $Cyanobacteria$," FEBS Lett. 554:357-362 (2003); Imamura et al., "Growth Phase-dependent Activation of Nitrogen-related Genes by a Control Network of Group 1 and Group 2 Sigma Factors in a $Cyanobacterium$," Jour. Biol. Chem. 281:2668-2675 (2006); Agrawal et al., "Light-dependent and Rhythmic psbA Transcripts in Homologous/heterologous Cyanobacterial Cells," Biochem. Biophys. Res. Commun. 255:47-53 (1999); Mohamed et al., "Influence of Light on Accumulation of Photosynthesis-specific Transcripts in the $Cyanobacterium\ Synechocystis$ 6803," Plant Mol. Biol. 13:693-700 (1989); Muramatsu et al., "Characterization of High-light-responsive Promoters of the psaAB Genes in $Synechocystis$ sp. PCC6803," Plant Cell Physiol. 47:878-890 (2006); Marin et al., "Gene Expression Profiling Reflects Physiological Processes in Salt Acclimation of *Synechocystis* sp. strain PCC6803," Plant Physiol. 136:3290-3300 (2004). Marin et al., "Salt-dependent Expression of Glucosylglycerol-phosphate Synthase, Involved in Osmolyte Synthesis in the *Cyanobacterium Synechocystis* sp. Strain PCC6803," Jour. Bacteriol. 184:2870-2877 (2002). Qi et al., "Application of the *Synechococcus* nirA Promoter to Establish an Inducible Expression System for Engineering the *Synechocystis* Tocopherol Pathway," Appl. Environ. Microbiol. 71:5678-5684 (2005); Maeda et al., "cis-acting Sequences Required for NtcB-dependent, Nitrite-responsive Positive Regulation of the Nitrate Assimilation Operon in the *Cyanobacterium Synechococcus* sp. Strain PCC7942," Jour. Bacteriol. 180:4080-4088 (1998); and Herranen at al., "Regulation of Photosystem I Reaction Center Genes in *Synechocystis* sp. Strain PCC6803 During Light Acclimation," Plant Cell Physiol. 46:1484-1493 (2005; Buikema et al., "Expression of the Anabaena hetR gene from a Copper-regulated Promoter Leads to Heterocyst Differentiation under Repressing Conditions," Proc. Natl. Acad. Sci. U S A. 98:2729-2734 (2001), Mary et al., "Effects of High Light on Transcripts of Stress-associated Genes for the Cyanobacteria *Synechocystis* sp. PCC6803 and *Prochlorococcus* MED4 and MIT9313," Microbiology 150:1271-1281 (2004); He et al., "The High Light-inducible Polypeptides in *Synechocystis* PCC6803. Expression and Function in High Light," Jour. Biol. Chem. 276:306-314 (2001); Fang et al., "Expression of the Heat Shock Gene hsp16.6 and Promoter Analysis in the *Cyanobacterium, Synechocystis* sp. PCC6803," Curr Microbiol. 49:192-198 (2004); Kappell et al., "The Response Regulator RpaB Binds the High Light Regulatory 1 Sequence Upstream of the High-light-inducible hliB Gene from the *Cyanobacterium Synechocystis* PCC6803," Arch. Microbiol. 187:337-342 (2007).

Codon Improvement or the Inserted Sequences

At least some of the nucleic acid sequences to be expressed in the cyanobacterial cell can be codon optimized for optimal expression in the target cyanobacterial strain. The underlying rationale is that the codon usage frequency of highly expressed genes is generally correlated to the host cognate tRNA abundance. (Bulmer, Nature 325:728-730; 1987). In an embodiment, the codon optimization is based on the *cyanobacterium* ABICyanol (as well as its close relative species) codon usage frequency (host codon bias), in order to achieve desirable heterologous gene expression (Sharp et al., Nucleic Acids Res. 15:1281-1295).

The codon optimization can be performed with the assistance of publicly available software, such as Gene Designer (DNA 2.o). Additional modifications to minimize unwanted restriction sites, internal Shine-Dalgarno sequences, and other sequences such as internal termination sequences and repeat sequences can also be performed. These general codon-optimization methods have been shown to result in up to approximately 1000 fold higher expression of heterologous genes in target organisms (Welch et al., PLoS One 4, e7002;2009 and Welch et al., Journal of the Royal Society; Interface 6 (Suppl 4), S467-S476; 2009).

Accordingly, in an embodiment of the invention, the nucleic acid sequences of the inserted genes are modified so that they will have improved expression in cyanobacteria. For example, the selectable marker gene that confers spectinomycin resistance was codon optimized for higher expression in cyanobacteria. Additionally, the selectable marker gene that confers kanamycin resistance was codon optimized for higher expression in cyanobacteria. The gene that encodes the GFP marker was also codon optimized for higher expression in cyanobacteria using this method.

Further, the gene that encodes ADH was codon optimized for higher expression in cyanobacteria. The gene that encodes PDC was codon optimized for higher expression in cyanobacteria.

Restriction Systems in *Cyanobacterium*

Restriction systems are important barriers for the introduction of DNA in cyanobacteria. Foreign DNA is restricted and degraded by restriction enzymes and other non-specific nucleases during its entry into a cell, An understanding of the restriction systems is therefore critical in developing new transformation systems and protocols, especially in uncharacterized bacteria.

In a cyanobacterial cell. systems occur in pairs comprising a restriction enzyme and a specific DNA methyltransferase. Specific methylation of the restriction enzyme recognition sequence protects DNA in the cell from degradation by the corresponding restriction enzyme. In natural systems, this is one mechanism of protecting the cell from foreign invasion.

Different cyanobacterial cells have different restriction systems. Knowledge of the specific system that is naturally present in a cell can assist in making necessary modifications to foreign plasmid DNA to make the transformation process proceed more readily. For example, knowing which restriction systems exist in a given host cell can allow one to protect foreign plasmid DNA prior to entry into the cell by treating it with either a specific methylase, or a general methylase, that allows for protection of the DNA from degradation by the host cell's restriction enzyme(s). This type of DNA methylation can provide an effective protection against restriction barriers during the transformation or conjugation process. The selection of suitable DNA methyltransferases relies on the thorough understanding of the restriction enzyme repertoire of the organism. Since restriction enzymes and DNA methyltransferases occur in pairs, identification of the restriction enzymes implies the existence and specificity of the corresponding DNA methyltransferases.

As described in Examples 13 and 14, *Cyanobacterium* ABICyanol was found to have an endogenous restriction enzyme system. This was initially observed using sequence analysis, which predicted the presence of AvaI and HgiDI (AcyI) in ABICyanol. Subsequent detection of restriction activity in ABICyanol crude extracts confirmed this finding. Because of this finding, the appropriate methylating agent can be added to protect foreign genes from being degraded soon after entry into the cell, as described in Example 18 and demonstrated in FIG. 26. In an embodiment, this is performed in vivo during conjugation using a "helper plasmid" having genes encoding specific methylases that are capable of protecting the identified restriction sites from degradation. Another possibility would be to first incubate the nucleic acid constructs to be transferred to ABICyanol with the methylases and then introduced these methylated nucleic, acid constructs into ABICyanol.

Selecting for Successful Transformation

The presence of a foreign gene encoding antibiotic resistance can be selected, for example, by placing the putative transformed cells into an amount of the corresponding antibiotic, and picking the cells that survive. The selected cells are then scaled-up in the appropriate culture medium, to allow for further testing.

Production of Compounds of Interest in Cyanobacteria

The 6.8 endogenous plasmid vector from *Cyanobacterium* sp. ABICyanol cell can be genetically enhanced to carry genes of interest into a new host *Cyanobacterium* sp. ABICyanol cell. In an embodiment, the added genes are part of a biochemical pathway to produce a chemical compound of interest in the cyanobacterial host cell. One, two, three, four, five, six, or seven or more recombinant genes can be added to the vector. In an embodiment, the compound of interest is a biofuel. In another embodiment, the compound of interest is ethanol.

The introduction of the first as well as, if necessary, second recombinant gene or even further recombinant genes, directs the metabolic flux of the genetically enhanced *Cyanobacterium* sp. towards the production of the chemical compound. During the course of the synthesis of the chemical compound, $CO_2$ is consumed and oxygen and carbon based compounds, like sugars are produced. Owing to the at least one recombinant gene the carbon based compounds are further converted into the chemical compound of interest.

In particular, the chemical compound can be a biofuel or an organic compound which, for example, can he selected from the group of: alkanols, alkanes, polyhydroxyalkanoates, e.g. PHB, fatty acids, fatty acid esters, carboxylic acids, such as amino acids, hydrogen, terpenes and terpenoids, peptides, polyketides, alkaloids, lactams, such as pyrrolidone, alkenes and ethers, such as THF and combinations thereof.

In a further variant of the genetically enhanced *Cyanobacterium* of the invention, the chemical compound is selected from various alkanols, such as ethanol, propanol or butanol, alkanes and alkenes, such as ethylene or propylene, biopolymers such as polyhdyroxyalkanoates like polyhydroxybutyrate, fatty acids, fatty acid esters, carboxylic acids such a amino acids, terpenes and terpenoids. Furthermore, the valuable chemical compound can be selected from peptides, polyketides, alkaloids, lactams and ethers such as tetrahydrofuran or any combinations of the above-mentioned chemical compounds.

Depending on the valuable chemical compound to be produced, the respective recombinant genes encoding the proteins for the production of these chemical compounds have to be introduced into the *Cyanobacterium* sp. For example, if the first chemical compound is ethanol, the recombinant genes encoding enzymes for ethanol production can be Pdcenzyme (pyruvate decarboxylase) catalyzing the reaction from pyruvate to acetaldehyde, Adh enzyme (alcohol dehydrogenase), catalyzing the reaction from acetaldehyde to ethanol, or a AdhE enzyme (alcohol dehydrogenase E) which directly converts acetyl-coenzyme A to ethanol. The Adh enzyme can, for example, be a $Zn^{2+}$-dependent alcohol dehydrogenase such as AdhI from *Zymomonas mobilis* (ZmAdh) or the Adh enzyme from *Synechocystis* PCC6803(SynAdh). Alternatively or in addition, the enzyme can also be an iron-dependent alcohol dehydrogenase (e.g. AdhII from *Zymomonas mobilis*), The $Zn^{2+}$-dependent alcohol dehydrogenase can, for example, be an alcohol dehydrogenase enzyme having at least 60%, 70%, preferably 80% and most preferred 90% or even more than 90% sequence identity to the amino acid sequence of Zn2+ dependent *Synechocystis* Adh. Experiments have shown that in particular *Synechocystis* alcohol dehydrogenase SynAdh (slr1192) is able to ensure a high ethanol production in genetically enhanced cyanobacteria due to the fact that the forward reaction, the reduction of acetaldehyde to ethanol is much more preferred for *Synechocystis* alcohol dehydrogenase enzyme than the unwanted back reaction from ethanol to acetaldehyde. For these reasons the use of a SynAdh encoding recombinant gene for production of ethanol as a first chemical compound is preferred.

The AdhE is an iron-dependent, bifunctional enzyme containing a CoA-depending aldehyde dehydrogenase and an alcohol dehydrogenase activity. One characteristic of iron-dependent alcohol dehydrogenases (e.g. AdhE and AdhII) is the sensitivity to oxygen. In the case of the AdhE from *E. coli* a mutant was described that shows in contrast to the wild type also Adh activity under aerobic conditions. The site of the mutation was determined in the coding region at the codon position 568. The G to A nucleotide transition in this codon results in an amino acid exchange from glutamate to lysine (E568K). The E568K derivate of the *E. coli* AdhE is active both aerobically and anaerobically. [Holland-Staley, et al., Aerobic activity of *Escherichia coli* alcohol dehydrogenase is determined by a single amino acid, J Bacteriol. 2000 Nov; 182(21):6049-54].

AdhE enzymes directly converting acetyl coenzyme A to ethanol can preferably be from a thermophilic source thereby conferring an enhanced degree of stability. The AdhE can be from *Thermosynechococcus elongatus* BP-1 or also can be a non-thermophilic AdhE enzyme from *E. coli*.

The pyruvate decarboxylase can for example be from *Zymomonas mobilis*, Zymobacter palmae or the yeast *Saccharomyces cerevisiae*. Regarding the nucleic acid sequences, protein sequences and properties of these above mentioned ethanologenic enzymes, reference is made to the PCT patent application WO 2009/098089 A2, which is hereby incorporated for this purpose.

Two other alcohols which are relatively widespread are propanol and butanol. Similar to ethanol, they can be produced by fermentation processes. The following enzymes are involved in isopropanol fermentation and can be encoded first and/or second recombinant genes: acetyl-CoA acetyltransferase (EC: 2.3.1.9), acetyl-CoA:acetoacetyl-CoA transferase (EC: 2.8.3.8), acetoacetate decarboxylase (EC: 4.1.1.4) and isopropanol dehydrogenase (EC: 1.1.1.80).

The following enzymes are involved in isobutanol fermentation: acetolactate synthase (EC: 2.2.1.6), acetolactate reductoisomerase (EC: 1.1.1.86), 2,3-dihydroxy-3-methylbutanoate dehydratase (EC: 4.2.1.9), α-ketoisovalerate decarboxylase (EC: 4.1.1.74), and alcohol dehydrogenase (EC: 1.1.1.1).

In the case that ethylene is to be produced as a chemical compound, the at least one recombinant gene encodes an enzyme for ethylene formation, in particular the ethylene-forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene-forming enzyme is synthesized by the enzyme 1-aminocyclopropane-1-carboxylic acid synthase (EC 4.4.1.14) from the amino acid methionine.

If the chemical compound is an isoprenoid such as isoprene, the at least one recombinant gene encodes an enzyme such as isoprene synthase. Isoprene synthase (EC 4.2.3.27) catalyzes the chemical reaction from dimethylallyl diphosphate to isoprene and diphosphate.

Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl pyrophosphate synthase (EC 2.5.1.1), which catalyzes the reaction of dimethylallylpyrophosphate and isopentenyl pyrophosphate yielding farnesyl pyrophosphate, Another example is geranylgeranyl pyrophosphate synthase (EC 2.5.1.29), which catalyzes the reaction between transfarnesyl diphosphate and isopentenyl diphosphate yielding diphosphate and geranylgeranyl diphosphate.

In the case that the chemical compound is hydrogen, the first and/or second recombinant genes can for example code for hydrogenase an enzyme catalyzing the following reaction:

$12H^+ + 12X_{reduced} \rightarrow 6\ H_2 + 12X_{oxidized}$, wherein X is an electron carrier such as ferredoxin.

Further examples of valuable chemical compounds are the so-called non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities of high pharmacological relevance. Hybrids of non-ribosomal peptides and polyketides also exist, exhibiting both a peptide and a polyketide part. Recombinant genes for the production of non-ribosomal peptides as the first chemical compounds are for example gene clusters encoding for non-ribosomal peptide synthetases (NRPS). NRPS are characteristic modular multidomain enzyme complexes encoded by modular non-ribosomal peptide synthetase gene clusters, Examples for non-ribosomal peptide synthetases are actinomycin synthetase and gramicidin synthetase.

In general there are two distinct groups of polyketides (PK), the reduced polyketides of type I, the so-called macrolides and the aromatic polyketides of type II. Type I polyketides are synthesized by modular polyketide synthases (PKS), which are characteristic modular multidomain enzyme complexes encoded by modular PKS gene clusters. Examples for recombinant genes for the production of type I polyketides are the rapamycin synthase gene cluster and the oleandomycin synthase gene cluster. One example for a recombinant gene for type II polyketides is the actinorhodin polyketide synthase gene cluster.

Examples for recombinant genes for the production of hybrids of polyketides and non-ribosomal peptides are the microcystin synthetase gene cluster, microginin synthetase gene cluster, and myxothiazole synthetase gene cluster.

Further examples of valuable chemical compounds are the alkaloids. Alkaloids are a compound group which is synthesized by plants. Alkaloids have highly complex chemical structures and pronounced pharmacological activities. Examples for biosynthetic enzymes for alkaloids which can be encoded by recombinant genes for the production of the chemical compound are strictosidine synthase, which catalyzes the stereoselective Pictet-Spengler reaction of tryptamine and secologanin to form 3a(S)-strictosidine. The primary importance of strictosidine is not only its precursor role for the biosynthetic pathway of ajmaline but also because it initiates all pathways leading to the entire monoterpene indol alkaloid family. Another example of an enzyme encoded by a first recombinant gene is strictosidine glucosidase from the ajmaline biosynthetic pathway. This enzyme is able to activate strictosidine by deglycosylation thus generating an aglycon. This aglycon of strictosidine is the precursor for more than 2,000 monoterpenoid indol alkaloids.

Further examples of enzymes encoded by at least one recombinant gene are:
  (RS)-3'-hydroxy-N-methylcoclaurine 4'-O-methyl-transferase (4'OMT) central to the biosynthesis of most tetrahydrobenzyl-isoquinolin-derived alkaloids;
  Berberine bridge enzyme (BBE) specific to the sanguinarine pathway;
  (R,S)-reticuline 7-O-methyltransferase (7OMT) specific to laudanosine formation;
  Salutaridinol 7-O-acetyltransferase (SalAT) and codeinone reductase that lead to morphine.

Vitamins, as further examples of chemical compounds, are organic compounds that are essential nutrients for certain organisms and act mainly as cofactors in enzymatic reactions but can also have further importance, e.g. as antioxidants in case of vitamin C. Vitamin C can be synthesized via the L-Ascorbic acid (L-AA) biosynthetic pathway from D-glucose in plants. The following enzymes are involved in vitamin C synthesis and can be encoded by first and/or second recombinant genes:

Hexokinase, Glucose-6-phosphate isomerase, Mannose-6-phosphate isomerase, Phosphomannomutase, Mannose-1-phosphate guanylyltransferase, GDP-mannose-3,5-epimerase, GDP-L-galactose phosphorylase, L-Galactose 1-phosphate phosphatase, L-galactose dehydrogenase, L-galactono-1,4-lactone dehydrogenase.

Lactams are cyclic amides whereas the prefixes indicate how many carbon atoms (apart from the carbonyl moiety) are present in the ring: β-lactam (2 carbon atoms outside the carbonyl, 4 ring atoms in total), γ-lactam (3 and 5). δ-lactam (4 and 6). One example for a γ-lactam is Pyrrolidone, a colorless liquid which is used in industrial settings as a high-boiling, non-corrosive, polar solvent for a wide variety of applications. It is also an intermediate in the manufacture of polymers such as polyvinylpyrrolidone and polypyrrolidone.

Ethers are a class of organic compounds that contain an ether group—an oxygen atom connected to two alkyl or aryl groups—of general formula R—O—R. A well-known example is tetrahydrofuran (THF), a colorless, water-miscible organic liquid. This heterocyclic compound is one of the most polar ethers with a wide liquid range, it is a useful solvent. Its main use, however, is as a precursor to polymers.

One example for the natural occurring ethers are the divinyl ether oxylipins. The main enzymes involved in their biosynthesis are the lipoxygenase and especially the divinyl ether synthase.

Alkanes (also known as saturated hydrocarbons) are chemical compounds that consist only of the elements carbon (C) and hydrogen (H) (i.e., hydrocarbons), wherein these atoms are linked together exclusively by single bonds (i.e., they are saturated compounds). Each carbon atom must have 4 bonds (either C—H or C—C bonds), and each hydrogen atom must be joined to a carbon atom (H—C bonds). The simplest possible alkane is methane, CH4. There is no limit to the number of carbon atoms that can be linked together. Alkanes, observed throughout nature, are produced directly from fatty acid metabolites. A two-gene pathway widespread in cyanobacteria is responsible for alkane biosynthesis and can be included in the first recombinant genes. An acyl-ACP reductase (EC: 1.3.1.9) converts a fatty acyl-ACP into a fatty aldehyde that is subsequently converted into an alkanealkene by an aldehyde decarbonylase (EC: 4.1.99.5.), Biopolymers such as polyhydroxyalkanoates or PHAs are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB) but many other polymers of this class are produced by a variety of organisms: these include poly-4-hydroxybutyrate (P4HB), polyhydroxyvalerate (PHV), polyhydroxyhexanoate (PHH), polyhydroxyoctanoate (PHO) and their copolymers. The main enzymes involved in PHA synthesis are as follows: For P3HB synthesis two molecules of acetyl-CoA were condensed by a β-ketothiolase (EC: 2.3.1.9) to synthesize acetoacetyl-CoA, which is converted to (R)-3-hydroxybutyryl-CoA (3HBCoA)

by NADPH-dependent acetoacetyl-CoA reductase (EC: 1.1.1.36). The 3HBCoA is subsequently polymerized by poly (3-hydroxyalkanoate) synthase (EC: 2.3.1.–) and converted, to (P3HB).

About 100,000 metric tons of the natural fatty acids are consumed in the preparation of various fatty acid esters. The simple esters with lower chain alcohols (methyl-, ethyl-, n-propyl-, isopropyl- and butyl esters) are used as emollients in cosmetics and other personal care products and as lubricants. Esters of fatty acids with more complex alcohols, such as sorbitol, ethylene glycol, diethylene glycol and polyethylene glycol are consumed in foods, personal care, paper. water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMEs, usually obtained from vegetable oils by transesterification with methanol. The esterification of the ethanol with the acyl moieties of coenzyme A thioesters of fatty acids can be realized enzymatically by an unspecific long-chain-alcohol O-fatty-acyltransferase (EC 2.3.1.75) from Acinetobacter baylyi strain ADP1.

*Cyanobacterium* host cells according to certain embodiments of the invention can comprise a whole sequence of recombinant genes coding for proteins for the production of the chemical compound in the case that a cascade, for example of different enzymes, is necessary to produce the chemical compound.

In particular, the first protein encoded by the first recombinant gene can produce a first intermediate which is further converted by the second protein encoded by the second recombinant gene into another second intermediate, which then in turn is further converted by a third protein encoded by a third recombinant gene into a third intermediate, so that a sequence of consecutive recombinant biocatalysts, which provide intermediates for the next recombinant enzyme for the production of the chemical compound can be introduced into the *Cyanobacterium* host cells.

According to a further preferred embodiment of the invention, the compound can be alkanols, particularly ethanol. In the case of ethanol production as a chemical compound, the at least one recombinant gene preferably encodes a pyruvate decarboxylase as a first protein, which catalyzes the chemical reaction leading from pyruvate to acetaldehyde. According to a further embodiment of the invention, the *Cyanobacterium* of the invention further comprise at least a second recombinant gene encoding a second protein for the production of the chemical compound.

In the case that the chemical compound of interest is ethanol, the second recombinant gene preferably encodes alcohol dehydrogenase, which is able to convert the acetaldehyde provided by the pyruvate decarboxylase, the first protein, into the final chemical compound, ethanol.

The alcohol dehydrogenases can be $Zn^{2+}$ or iron dependent alcohol dehydrogenases, for example AdhI, AdhII from *Zymomonas mobilis*, SynAdh from *Synechocystis* PCC6803 or even AdhE, which is able to directly convert acetyl coenzyme A into ethanol. Especially with regard to AdhE only one biocatalyst can be sufficient in order to produce the first chemical compound ethanol.

In an embodiment, a Pdc protein and an Adh protein are produced, which in turn produce ethanol in the cell, as shown herein in Examples 20 and 21. In an embodiment, genes that are involved in a biosynthetic pathway are inserted.

The plasmid vector of the invention can be used to carry a gene or genes involved in other biosynthetic pathways to produce a compound of interest in the *Cyanobacterium* sp. ABICyanol cell. Exemplary compounds include but are not limited to organic carbon compounds, alcohols, fatty acids, oils, carotenoids, proteins, enzymes, biofuels, nutraceuticals, pharmaceuticals, and the like. Additional information on the compounds that can be produced from cyanobacteria can be found, for example, in PCT/EP2009/000892, filed Feb. 9, 2009, and in PCT/EP2009/060526, filed Aug. 13, 2009, both of which are incorporated by reference herein in their entirety. Genes involved in the biosynthetic pathway for the production of other compounds can be inserted into the vector.

In an embodiment, the compounds of interest that are produced from the recombinant *Cyanobacterium* sp. ABICyanol can be removed intermittently as desired from the growing culture as the culture grows, or the compounds can be separated at the end of a batch growth period. The cultures can be grown indoors, or can be grown outdoors in enclosed containers such as plastic bioreactors, or in another suitable type of container.

In an embodiment of the invention, genes that encode enzymes involved in the production of ethanol can be inserted into the vector. The genes can be codon optimized for optimal expression in *Cyanobacterium* sp. ABICyanol, and can utilize any suitable promoter and regulatory sequences.

In an embodiment, the enzyme involved in the biosynthetic pathway for ethanol production is a pyruvate decarboxylase (Pdc). Pyruvate decarboxylase converts pyruvate to acetaldehyde. In a further embodiment, the enzyme involved in the biosynthetic pathway for ethanol production is an alcohol dehydrogenase (Adh). Alcohol dehydrogenase converts acetaldehyde to ethanol.

In another embodiment, the Adh and/or Pdc genes are originally derived from *Zymomonas mobilis*, *Zymobacter palmae*, or another cyanobacteria such as *Synechocystis* sp. PCC6803, *Synechococcus* sp. PCC7002, and the like. in an embodiment, the gene encoding the Pdc enzyme is from *Zymomonas* or *Zymobacter*, while the gene encoding Adh is from *Synechocystis* sp PCC6803.

Production of a Chemical Compound of Interest: Demonstration using Ethanol Production The chemical compound of interest that is produced can he chosen from a number of compounds, wherein a biosynthetic pathway for the production of the compound in known. In an embodiment, the inserted genes are derived from the genes present in a biochemical pathway in a prokaryote or a eukaryote. In an embodiment, the pathway genes are derived from a prokaryote such as *E. coli*. In another embodiment, the pathway genes are derived from a eukaryotic cell, such as yeast. The genes can be derived from one organism, or can be derived from multiple organisms. Some of the genes can be derived, for example, from a cyanobacterial cell.

In an embodiment, the vector can harbor genes for ethanol production. For example, a gene encoding a PDC enzyme, along with a gene encoding an ADH enzyme can be inserted into the vector. Each of the genes can be regulated by a separate promoter, or one upstream promoter can regulate several or all of the inserted genes. The transformed cells are cultured, and ethanol can then be produced.

The ethanol that is produced can be quantitated by several methods. In one method, gas chromatography is used, following methods derived from blood alcohol quantitation methods, as described in Example 35. In another method, ethanol is measured by a commercially available ethanol determination kit.

Cyanobacterial Growth Medium

A number of known recipes for cyanobacterial growth medium can be used. In an embodiment. BG11 medium, shown below in Tables 1 and 2, is used for growing *Cyanobacterium* sp. ABICyanol. In an embodiment, the cyanobacterial strain is a fresh water strain, and the general medium recipe below (BG-11) is used). In another embodiment of the invention, the culture grows best in a marine (salt water) medium, by adding an amount of salt to the BG11 medium.

TABLE 1

Composition of BG-11 medium

| Compound | Amount (per liter) | Final Concentration |
|---|---|---|
| NaNO$_3$ | 1.5 g | 17.6 mM |
| K$_2$HPO$_4$ | 0.04 g | 0.23 mM |
| MgSO$_4$•7H$_2$O | 0.075 g | 0.3 mM |
| CaCl$_2$•2H$_2$O | 0.036 g | 0.24 mM |
| Citric acid | 0.006 g | 0.031 mM |
| Ferric ammonium citrate | 0.006 g | — |
| EDTA (disodium salt) | 0.001 g | 0.0030 mM |
| NaCO$_3$ | 0.02 g | 0.19 mM |
| Trace metal mix A5 | 1.0 ml | — |

TABLE 2

Trace Metal Composition of BG-11 medium

| Trace Metal mix A5 | Amount | Final Concentration in Working Medium |
|---|---|---|
| H$_3$BO$_3$ | 2.86 g | 46.26 μM |
| MnCl$_2$•4H$_2$O | 1.81 g | 9.15 μM |
| ZnSO$_4$•7H$_2$O | 0.222 g | 0.772 μM |
| NaMoO$_4$•2H$_2$O | 0.39 g | 1.61 μM |
| CuSO$_4$•5H$_2$O | 0.079 g | 0.32 μM |
| Co(NO$_3$)$_2$•6H$_2$O | 49.4 mg | 0.170 μM |
| Distilled water | 1.0 L | — |

Distilled water or seawater (35 practical salinity units=psu; see Unesco (1981a). The Practical Salinity Scale 1978 and the International Equation of State of Seawater 1980. Tech. Pap. Mar. Sci., 36: 25 pp.) is added to the final volume of 1.0 L.

In an embodiment, the cells are grown autotrophically, and the only carbon source is $CO_2$. In another embodiment, the cells are grown mixotrophically, for example with the addition of a carbon source such as glycerol.

The cultures can be grown indoors or outdoors. The light cycle can be set as desired, for example: continuous light, or 16 hours on and 8 hours off, or 14 hours on and 10 hours off, or 12 hours on and 2 hours off.

The cultures can be axenic, or the cultures can also contain other contaminating species.

In an embodiment, the cyanobacteria are grown in enclosed bioreactors in quantities of at least about 100 liters, 500 liters, 1,000 liters, 2,000 liters, 5,000 liters, or more. In an embodiment, the cyanobacterial cell cultures are grown in disposable, flexible, tubular photobioreactors made of a clear plastic material.

In another embodiment, the cultures are grown indoors, with continuous light, in a sterile environment. in another embodiment, the cultures are grown outdoors in an open pond type of photobioreactor.

The present invention is further described, by the following non-limiting examples. However, it will be appreciated that those skilled in the art, on consideration of this disclosure, may make modifications and improvements within the spirit and scope of the present invention.

EXAMPLES

Example 1

Bacterial Strains, Growth Conditions, and Selection of Transformants

*Escherichia coli* (*E. coli*) strains HB101 (Promega), XL10-Gold (Stratagene), α-select (Bioline) were grown in Luria-Bertani (LB) medium at 37° C. Ampicillin (50 μg/ml), kanamycin (50 μg/ml), and chloramphenicol (34 μg/ml) were used when appropriate. Cultures were continuously shaken overnight at 200 rpm and at 100 rpm, respectively, when used for conjugation. ABICyanol was cultured at 28° C.-37° C. in liquid BG11 fresh water medium on a reciprocal shaker at 150 rpm under continuous illumination of approximately 30-40 μmol photons*m$^{-2}$*sec$^{-1}$ Unless otherwise noted, the *Cyanobacterium* sp. ABICyanol transformants were selected on solid BG11 medium containing 10-20 μg/ml kanamycin and were maintained on BG11 plates containing 40 μg/ml kanamycin. For growth in liquid freshwater BG11 medium, 30-40 μg/ml of kanamycin was applied.

Example 2

DNA Isolation

Plasmid DNA from *E. coli* strains was isolated using a GeneJetTM Plasmid Miniprep Kit (Fermentas) according to the manufacture's protocol. For plasmid isolation from putative ABICyanol transformants, total DNA was prepared according to Saha et al. (2005), World Jour. Microbiol Biotechnol 21:877-881. Briefly, 25 ml of *Cyanobacterium* sp. ABICyanol culture was harvested, washed with TE buffer and frozen at −80° C. for 30 minutes. The cyanobacterial cells were then lysed by a lysozyme treatment at 37° C. for 60 minutes. The suspension was then incubated with 10% (v/v) SDS and proteinase K until the suspension became clear. The DNA was extracted using phenol and chloroform/isoamylalcohol (24:1 v/v) and then precipitated with isopropanol.

Example 3

Plasmid Rescue

For plasmid rescue from putative *Cyanobacterium* ABICyanol transformants, total DNA was isolated and transformed in both α-select and XL10-Gold. *E. coli* colonies were selected for kanamycin resistance; DNA was isolated from single colonies and analyzed by PCR and restriction analysis, respectively, for the presence of the correct plasmid. In particular, the endogenous plasmid of ABICyanol was captured with the EZ-Tn5™ (R6Kγori/KAN-2) Tnp Transposome™ kit (Epicentre, Madison, Wis.) by following the protocol provided by the manufacture. The rescued clones were amplified in TransforMax™ EC100D™ pir-116 electro-competent *E. coli* host cells (Epicentre, Madison, Wis.). Plasmid DNA was prepared with Qiagen plasmid Maxi kit (Qiagen Inc., Valencis, Calif.). Approximately 8 to 16 rescued clones were selected for sequencing via the conventional Sanger sequencing protocol. Protein-coding genes from each of the plasmids were predicted with the gene finder Glimmer (Delcher AL, Bratke KA, Powers EC, & Salzberg SL (2007) identifying bacterial genes and endosyntbiont DNA with Glimmer. *Bioinformatics* 23(6):673-679) version 3.02, followed by BLAST against the NCBI NR database.

Example 4

Preparation of Cyanobacterial Culture Medium

BG-11 stock solution was purchased from Sigma Aldrich (Sigma Aldrich, St. Louis, Mo.). Stock solutions of the antibiotics spectinomycin (100 mg/ml) and kanamycin (50 mg/ml) were purchased from Teknova (Teknova, Hollister, Calif.). Stock solution of the antibiotic gentamycin (10 mg/ml) was purchased from MP Biomedicals (MP Biomedicals, Solon, Ohio). Marine BG-11 (mBG-11) was prepared by dissolving 35 g Crystal Sea Marinemix (Marine Enterprises International, Inc., Md.) in 1 L water and supplementing with BG-11 stock solution. Vitamin B12 (Sigma Aldrich) was supplemented to mBG-11 to achieve a final concentration of 1 µg/L, as needed.

Example 5

Isolation and Initial Characterization of *Cyanobacterium* ABICyanol Strain

*Cyanobacterium* ABICyanol is a unicellular *cyanobacterium* which has been found to be very hardy and tolerant to many common environmental stresses, such as high light intensity, and high temperature. This strain also tolerates a wide range of salinities.

Figure 5A:
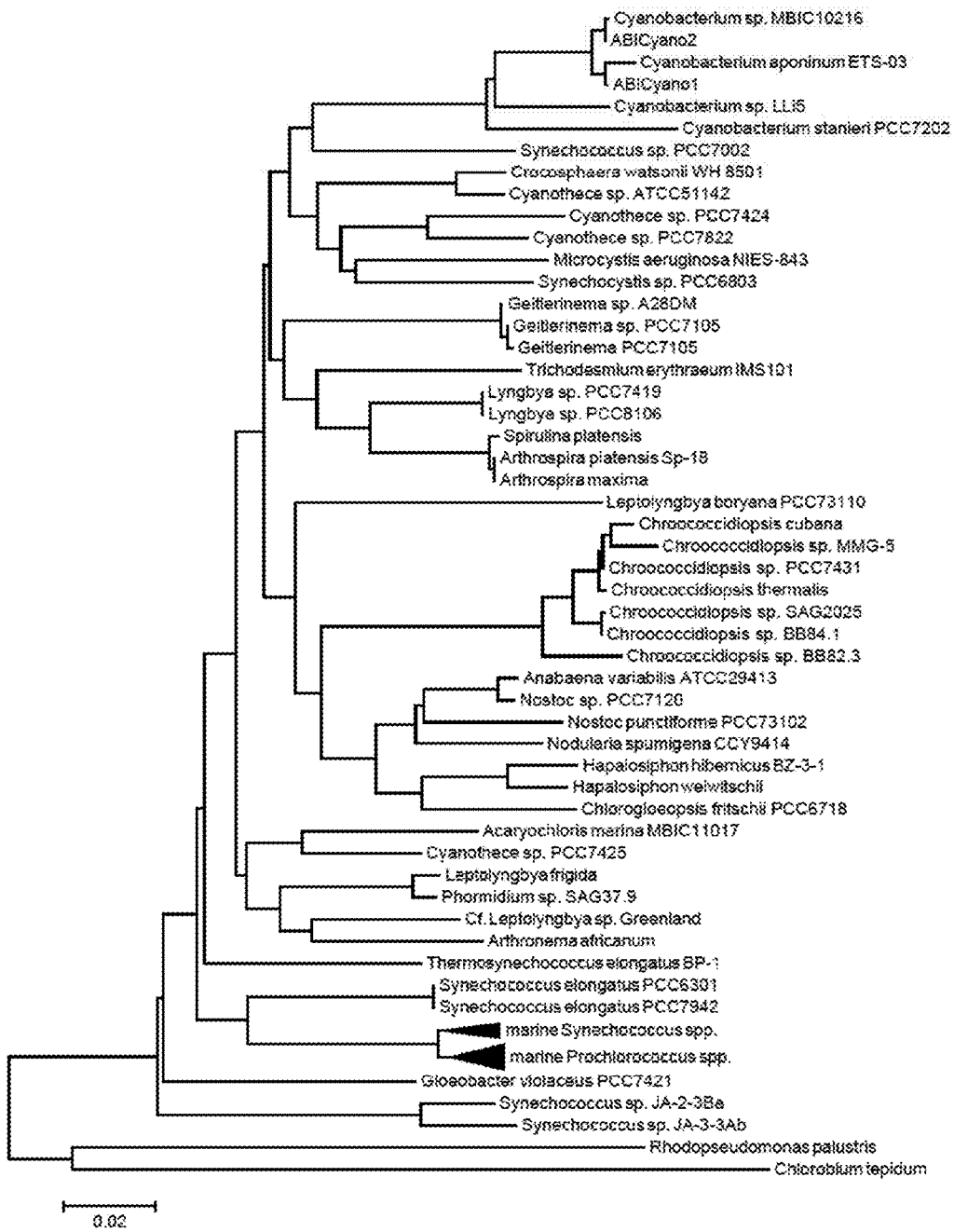
FIG. 5A is a phylogenetic tree showing the relationship between the new *Cyanobacterium* isolate (ABICyanol) and other cyanobacterial species. The tree was built with the 16S rRNA gene sequences with the Neighbor-Joining method using the Tamura-Nei nucleotide substitution model assuming uniform heterogeneity among sites. The scale bar indicates number of substitutions per site. A sequence comparison of 16S rDNA of ABICyanol (SEQ ID NO: 63) with 16S rDNA from *Cyanobacterium* spp. *Cyanobacterium* sp. MBIC10216, *Cyanobacterium* aponinum ETS-03, ABICyano2, *Cyanobacterium* sp. LLi5, and *Cyanobacterium* stanieri PCC7202 (SEQ ID NOs: 60-62 and 64-65, respectively) which shows that ABICyanol is 99% identical to *Cyanobacterium* spp. is presented in FIG. 5B.
Figure 6:
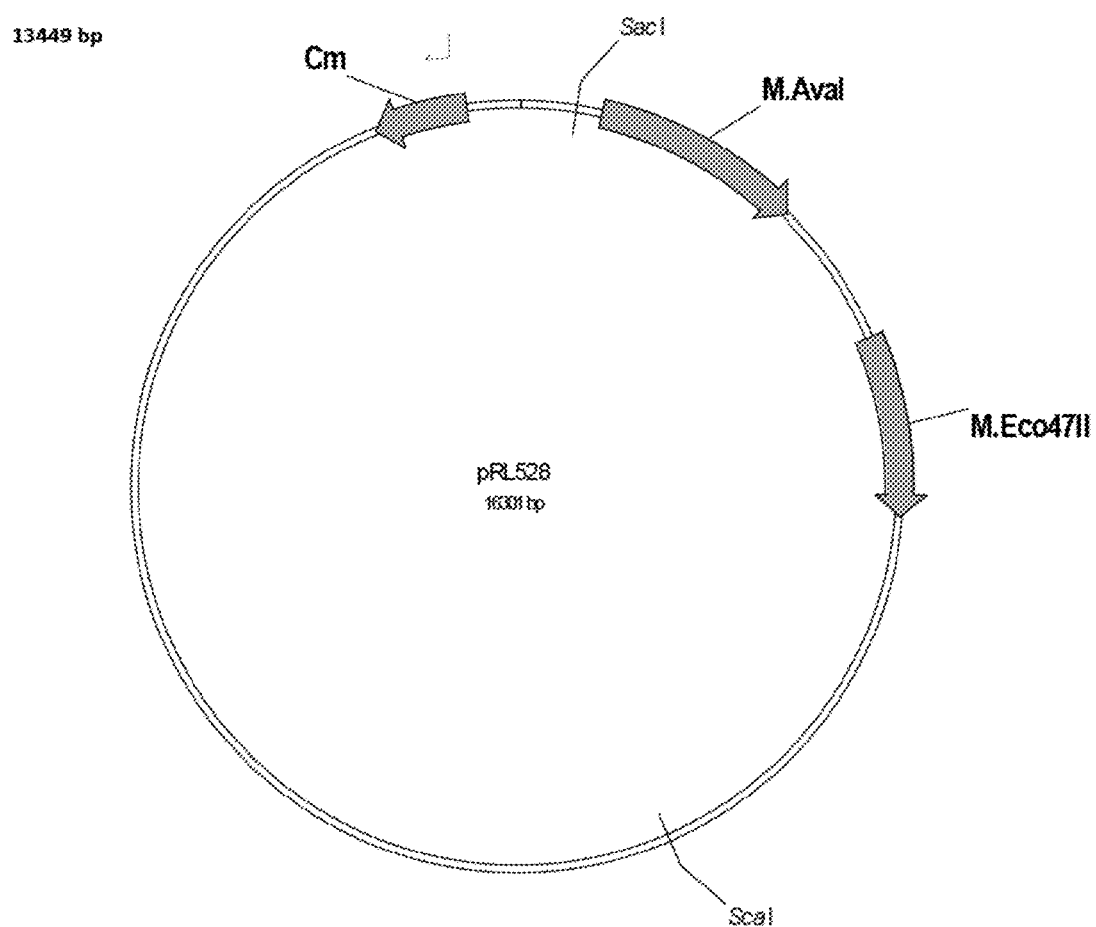
FIG. 6 is a plasmid map of pRL528, a helper plasmid for conjugal transfer, as described in Elhai and Wolk, 1988. The indicated genes are M. AvaI coding for the methyltransferase protecting against the restriction endonuclease AvaI and the respective gene coding for M. AvaII. The latter is not required for transformation of ABICyanol, as it lacks any endonuclease activity of AvaII.

A phylogenetic tree showing, the relationship between the new *Cyanobacterium* isolate (ABICyanol) and other cyanobacterial species is shown in FIG. 5A. This tree utilized the 16S rRNA gene sequences with the Neighbor-joining method using the Tamura-Nei nucleotide substitution model assuming uniform heterogeneity among sites. The scale bar indicates number of substitutions per site. In particular, the 16S ribosomal RNA (rRNA) gene sequences (16S rDNA) of ABI-Cyanol was predicted from the genome sequence with RNAmmer program (Lagesen K, el al. (2007) RNAmmer: consistent and rapid annotation of ribosomal RNA genes. *Nucleic Acids Research* 35(9):3100-3108). These sequences were then used as a query to search against the NCBI database and 16S rDNA sequences from 4 species belonging to the genus *Cyanobacterium* were retrieved as the top BLAST hits (Altschul SF, et al. (1997) Gapped BLAST and PSI-BLAST: a new generation of protein database search programs. *Nucl. Acids. Res*. 25(17):3389-3402). Comparison of 16S rDNA shows that ABICyanol is 99% identical to *Cyanobacterium* spp. (See FIG. 5B), The phylogenetic tree constructed with 16S rDNA from known cyanobacteria reveals that ABICyanol is clustered together with *Cyanobacterium* spp. in monophyletic clade, with ABICyanol and *Cyanobacterium aponinum* ETS-03 in a single sub-clade, and *Cyanobacterium* sp. MBIC10216 in another Example 6

Characterization of the *Cyanobacterium* ABICyanol Strain: Ethanol Tolerance

The new *Cyanobacterium* ABICyanol strain was tested to determine its tolerance to the presence of ethanol in the culture medium, in comparison to two publicly available strains, *Synechocystis* PCC6803 and *Synechococcus* PCC7002. The cells were cultured in 100 mL Erlenmeyer flasks with 50 mL culture volume in marine BG11 media [35 psu]. The cultures were spiked with 1% (v/v) ethanol. The cultures were examined weekly for cell viability and remaining ethanol concentration. At each of the weekly samplings, the ethanol level was replenished as needed in order to maintain the 1% (v/v) ethanol concentration. The cells were also examined using a microscope (light microscope, phase contrast, auto-fluorescence). If more than 50% of cells were intact the test was continued. Cyanobacterial cells were deemed to be intact if cell morphology did not change significantly upon addition of ethanol, the cells were still green, and cells were not lysed after addition of ethanol. The table below shows the number of weeks that each of the strains remained at least 50% viable in the cultures spiked with 1% ethanol. Growth for at least 8 weeks is considered to be a positive screening result. The below data therefore show that *Cyanobacterium*, in particular *Cyanobacterium* sp. ABICyanol (ATCC No. PTA-13311) can withstand at least 1% ethanol in the medium for at least eight weeks, preferably at least 12 weeks, most preferred at least 16 weeks.

TABLE

| Cyanobacterial Strain | 1% EtOH tolerance test [weeks] |
| --- | --- |
| *Synechocystis* sp. PCC 6803 | 3 |
| *Synechococcus* sp. PCC 7002 | 13 |
| *Cyanobacterium* sp. ABICyano1 | >16 |

Example 7

Characterization of the New *Cyanobacterium* ABICyanol Strain: Cell Survival at High Temperatures The new *Cyanobacterium* ABICyanol wild type strain was tested to determine its ability to grow at various temperatures. The initial starting cultures (50 mL in Erlenmeyer) were grown under standard growth conditions (continuous 28° C. and light). The cultures were diluted to a chlorophyll content of ~5 µg/mL. The temperature changes during the assay were made without any prior temperature adaptation of the cultures. All tests were performed in marine media in day night cycle (14/10 h) for temperature (test depending) and light intensity (40 µmol*m2*sec-1/darkness). The temperature tolerance tests were performed with increasing temperature profiles: maximum peak of 2 h at 45° C., 48° C., 50° C., 53° C., 55° C. and a day/night difference of 18° C. Each temperature profile (45° C., 48° C., 50° C., 53° C. and 55° C.) was run for 7 days. Cultures were sampled on days 0, 2, 5 and 7 with determination of $OD_{750}$ (if possible) and chlorophyll. If a strain was grown under one temperature profile, the culture was diluted to same starting chlorophyll content and directly tested in the next higher temperature profile. An increase in chlorophyll content was used as the growth indicator. *Cyanobacterium* ABICyanol can therefore tolerate culturing conditions of at least 48° C., preferably 50° C., most preferred at least 53 to 55° C. for at least two hours over a period of time of at least 7 days.

TABLE X

| | Thermotolerance Test | | | | |
|---|---|---|---|---|---|
| Genera, strain # | 2 hours 45° C. for 1 week | 2 hours 48° C. for 1 week | 2 hours 50° C. for 1 week | 2 hours 53° C. for 1 week | 2 hours 55° C. for 1 week |
| Synechocystis sp. PCC 6803 | pos. | pos. | neg. | | |
| Synechococcus sp. PCC 7002 | pos. | pos. | pos. | neg. | |
| Cyanobacterium sp. ABICyano1 | pos. | pos. | pos. | pos. | pos. |

Example 8

Characterization of the New *Cyanobacterium* ABICyanol Strain: Tolerance Large Temperature Changes in 0.51 Photobioreactors The growth of the new *Cyanobacterium* ABICyanol wild type strain was then compared with the publicly available strain *Synechococcus* PCC7002 to further elucidate its ability to grow in a photobioreactor environment while under extreme temperature fluxuations. Cultivation ABICyanol was performed in 0.5 L round photobioreactor glass vessels (Schott) with implemented ports for sampling, in and out-gas tubings, and pH as well as oxygen sensors. These glass vessels are in the following called photobioreactors (PBR). Mixing is assured via magnetic stir bar (cross magnet). pH is controlled via $CO_2$ inflow. The oxygen and pH sensors are connected to an oxygen and pH measurement box (Crison Instruments, SA), and the gas flow is controlled by mass flow controller system (Vögtlin Instruments). All parameters (oxygen, temperature, gas flow, pH) are controlled and monitored using a computer software programmed by HTK Hamburg. The system temperatures of the PBRs were set to be comparable to the temperature profiles used in the temperature tolerance test in the above example, with maximum temperatures of 45° C., 50° C. and 55° C. compared to the standard PBR growth temperature of 37° C. Each temperature profile experimental culture was run for 7 days. Culture sampling was performed 3 times per week: $OD_{750}$, chlorophyll and protein content were measured. At the beginning and at the end of each week, the dry weight was determined. If a strain passed a given temperature profile, the culture was diluted to the same starting condition (chlorophyll content ~10 µg/mL) and the next higher temperature profile was tested.

The resulting graphs (FIG. 2) show that the new wild type strain *Cyanobacterium* ABICyanol is able to grow well at high temperatures, as compared to other species, such as *Synechococcus* PCC7002.

Example 9

Characterization of the Oxygen Tolerance of *Cyanobacterium* ABICyanol

Cells of *Cyanobacterium* ABICyanol including a recombinant pdc gene under the transcriptional control of PnirA and a further recombinant synadh gene under the control of PrpsL were grown in mBG11 medium (PrpsL is the promoter of the 30S ribosomal protein S12). Cells were diluted to a starting OD of approximately $OD_{750}=1$. Cells were cultivated in 500 mL photobioreactors (PBR, round vessels with 9.5 cm diameter). PBRs were illuminated with day/night cycle of 12 h/12 h from two sides with fluorescent tubes. The light intensity was approximately 400 µE m$^{-2}$ s$^{-1}$ from each side. Temperature followed the day/night cycle with 37° C. during the illumination phase and 28° C. during the night. Cultures were constantly mixed with a magnetic stirrer with 450 rpm. $CO_2$ was supplied pH-regulated (on/off modus); pH was maintained at 7.3±0.05 by computer-controlled supply of $CO_2$ (as 5% (v/v) $CO_2$ in air) into the medium. Growth medium was mBG11. 3 PBRs were run in parallel, the pBRs were purged with three different oxygen/nitrogen mixtures with a flow rate of 100 mL*min$^{-1}$ during the illumination period. During the night phase gas was not supplied to the PBR. The mixtures of oxygen and nitrogen (here given in % oxygen (v/v)) were obtained with computer controlled mass flow meters. The actual oxygen concentration in the medium was measured online with an optical oxygen sensors and a multi-channel fiber optic oxygen transmitter (OXY-4 mini, PreSens). In contrast to Clark-type oxygen electrodes this setup allows the measurement of very high oxygen concentrations.

At different time points samples were taken and analyzed for (i) ethanol and acetaldehyde in the medium, (ii) $A_{750}$, (iii) chlorophyll and (iv) total protein. Chlorophyll and total protein were measured as in Tandeau De Marsac, N. and Houmard, J. in: Methods in Enzymology. Vol. 169, 318-328. L. Packer, ed., Academic Press, 1988. in order to characterize the energy metabolism of the cells the oxygen production rates in the light and the oxygen consumption rate in the dark were also measured. A Clark-type electrode (Rank brothers, diameter 1 cm) was used. Cells were diluted with mBG11 to 5 to 10 µg chlorophyll/mL, $NaHCO_3$ was added to 5 mM. Temperature was adjusted to 37° C. Illumination was with a slide projector H50 (Pentacon). For the measurement of P/I curves light intensities were adjusted by varying the distance between projector and electrode.

The cultures of the above mentioned strain were purged with gas mixtures containing 21%, 70% and 80% (v/v) oxygen in nitrogen. 21% oxygen in nitrogen corresponds to air. Purging with 21% oxygen resulted in oxygen concentration of approximately 200 µmol/L. Purging with 70% oxygen resulted in oxygen concentration of >650 µmol/L during the day period and >300 µmol/L during the "night". Purging with 80% oxygen resulted in a reading during the day of >900 µmol/L (in some cases >1000 µmol/L) and >600 µmol/L during the "night". The extremely high oxygen concentrations are caused by a high photosynthetic oxygen production.

The growth rates for the parameters $A_{750}$, ethanol production rates and chlorophyll comet were calculated. The results are summarized in table CCC. For these calculations the measured data were fitted to a regression line, and the slope was used to calculate the increase per 24 h. The quantitative analysis shows that even for the extremely high oxygen concentrations the measurable effect on ethanol production and growth was rather small.

TABLE CCC

| | 21% oxygen | 70% oxygen | 80% oxygen |
|---|---|---|---|
| Ethanol | 0.0236%/d | 0.0202%/d | 0.0213%/d |
| | 100% | 85% | 90% |
| Growth | 0.614 OD750/d | 0.583 OD750/d | 0.581 OD750/d |
| | 100% | 95% | 95% |
| Chlorophyll | 3.446 Chl/d | 2.878 Chl/d | 2.791 Chl/d |
| | 100% | 84% | 81% |

In order to ensure comparability to ABICyanol growth and ethanol production measurements were repeated in the same way with *Synechococcus* PCC7002 also including the ethanologenic genes pyruvate decarboxylase and SynADH. Significant effects were found for this strain when purged with the different oxygen concentrations similar to ABICyanol. A quantitative analysis (table XXX) shows that purging with 80% oxygen decreased the ethanol production rate by 28%, decreased the cell growth by 36% (A'), and decreased chlorophyll by 51%, respectively during the course of the experiment. The inhibitory effect of high oxygen concentrations especially on growth is therefore significantly higher for *Synechococcus* PCC7002 than for *Cyanobacterium* ABICyanol.

TABLE XXX

|  | 21% oxygen | 70% oxygen | 80% oxygen |
| --- | --- | --- | --- |
| Ethanol | 0.00646%/d | 0.00499%/d | 0.00466%/d |
|  | 100% | 77% | 72% |
| Growth | 0.959 OD750/d | 0.797 OD750/d | 0.612 OD750/d |
|  | 100% | 83% | 64% |
| Chlorophyll | 3.710 Chl/d | 2.455 Chl/d | 1.800 Chl/d |
|  | 100% | 66% | 49% |

The above results show that ABICyanol is much less sensitive to oxygen, than the ethanol producing Synechococcus PCC7002, which Was tested in parallel under comparable conditions. For the latter strain 70% (v/v) oxygen in nitrogen was sufficient to significantly inhibit growth and ethanol production.

Example 10

Isolation and Characterization of the Endogenous Vector(s) from *Cyanobacterium* ABICyanol One endogenous plasmid having a size of about 6.8 kb was found to be present in *Cyanobacterium* strain ABICyanol. To isolate, characterize, and identify this plasmid, the following method was used. Genomic DNA was prepared from exponentially growing ABICyanol cells, using QIAGEN Genomic-tip DNA extraction kit. The cyanobacterial plasmid DNA was prepared either using plasmid-safe ATP-dependent DNase (Epicentre) according to the manufacturer's instructions, or extracted from bands excised from agarose gel-electrophoresis. The ABICyanol endogenous plasmid was captured by in vitro transposition reaction with EZ-Tn5 R6K γ Ori/Kan-2 transposition kit, following the manufacturer's protocol. The cyanobacterial plasmid was rescued in surrogate *E. coli* host cells.

The sequence and size of the captured plasmid was confirmed and validated by PCR, as well as by comparison with available genome sequence data. Preliminary sequence analysis and annotation was performed using DNAStar and NCBI Blast tools. A map of the entire 6.8 kb endogenous plasmid is shown in FIG. 3.

The plasmid was found to have five putative open reading frames. ORF1 encodes a replication protein necessary for replicating the plasmid in the host cyanobacterial cell. This sequence was found to be similar to the hypothetical protein slr7037 of plasmid pSYSA (103 kb) from *Synechocystis* sp. PCC6803.

ORF4 from the 6.8 kb plasmid is a putative recombinase. Sequence analysis shows that the sequence appears to be similar to a site-specific recombinase of *Bacillus thuringiensis* serovar israelensis ATCC 35646.

Three other putative protein regions (ORF2, ORF3, ORF5) were found in the new plasmid, although their function has not yet been determined by blast searches and comparative sequence analysis.

Example 11

Construction of a Shuttle Vector Based on ABICyanol for the Transformation of *Cyanobacterium* ABICyanol The *Cyanobacterium* endogenous 6.8 kb plasmid can be used as a means of shuttling foreign DNA to cyanobacterial host cells. By inserting an origin of replication that is effective in *E. coli* (such as R6KOri), the plasmid DNA can be easily manipulated in bacteria such as *E. coli* to add genes and sequences of interest to the plasmid. For example, modifications to lessen the effect of endogenous restriction systems that present in *Cyanobacterium* sp., such as methylation, can be performed. The presence of the origin of replication that is already on *Cyanobacterium* sp., can assist with replication of the modified plasmid once it is transferred to a *Cyanobacterium* sp. host cell. Multiple cloning sites can be added to allow for several different antibiotic resistance clews to be added, if desired. Multiple cloning sites can also be inserted to allow for ease of insertion of various expression cassettes, such as the pdc/adh gene cassette for ethanol production. In this way, various sequence segments of the plasmid can be easily replaced with other sequence segments as needed.

Example 12

Detection of Endogenous Restriction Endonucleases

Restriction endonucleases (REN) expressed by cyanobacteria can be a major barrier for successful transformation. Accordingly, the presence of REN in *Cyanobacterium* ABICyanol has been analyzed. Bioinformatics approaches predicted the following REN for ABICyanol: HgiDI (AcyI), AvaI, AvaIII, BstEII, and HpaII (Table 5, below). in particular, automatic prediction of Restriction Endonucleases (REs) was conducted by comparing a query set of all the encoded amino acid (AA) sequences in the ABICyanol draft genome against the REBASE, the world's largest restriction enzyme database maintained by the New England Biolabs (NEB) using the basic local alignment search tool (BLAST). Significant hits were pooled and manually examined for the presence of the Restriction-Modification motifs, based on the previous result of BLAST against NR, and SMART, which can be found on the worldwide web. These bioinformatically predicted REs were further verified through biochemical assay of crude cellular extract.

In FIG. 55 lane 3, it is shown that plasmids intended for transformation were cleaved by a crude extract of ABICyanol. In order to improve transformation efficiency, protection against the damaging effects of RENs is needed. This can be achieved by methylation using the commercial CpG methylase M.SssI (FIG. 55, lane 4).

TABLE 5

REN Analysis

| Strain | Predicted RENs (bioinformatics) | Detected RENs (by biochemical methods) |
| --- | --- | --- |
| *Cyanobacterium* sp. ABICyano1 | HgiDI (AcyI), AvaI, AvaIII, BstEII, HpaII | HgiDI (AcyI), AvaI |

The preparation of crude extract and the subsequent analysis for REN activity is described below. Restriction analysis on plasmids followed by sequencing was used.

Preparation of crude extract. From a liquid pre-culture 50 ml were inoculated to an $OD_{750nm}$ 0.5-1. After 10 days, 30 ml of that culture of Cyanobacterium strains were pelleted (5 minutes at 3000×g at room temperature), washed once with lysis buffer (40 mM sodium hydrogenphosphate pH 7.4, 1 mM EDTA, 5% (v/v) glycerol) and resuspended in 1 ml lysis buffer. Cells were disrupted by glass beads using a tissue lysis apparatus at full speed for 4 minutes. The supernatant was then withdrawn and centrifuged twice at 14000×g at room temperature. One 1 U of RNase per ml volume was added to the final supernatant. ABICyanol Example 13

Protection from Restriction Endonucleases by Methylation

Enzymes whose recognition sites contain a CG stretch might be impaired or blocked in cleavage by use of the CG-methylase M.SssI, which methylates cytosine at the C5 position. AcyI and AvaI, which were detected in the ABICyanol crude extract recognize GRCGYC and CYCGRG, respectively. For example, pRL528, a helper plasmid for conjugal transfer, as described in Elhai and Wolk, 1988, can be used for in vivo methylation of the vectors to be transferred to Cyanobacterium sp. in particular Cyanobacterium sp. ABICyanol. This plasmid includes the M. AvaI gene coding for the methyltransferase protecting against the restriction endonuclease AvaI and the respective gene coding for M. AvaII. The latter is not required for transformation of ABICyanol, as it lacks any endonuclease activity of AvaII.

Example 14

Codon Optimization of the Foreign Genes

Codon optimization can be performed to increase the expression level of the foreign genes, such as the antibiotic resistance genes, the ethanologenic (or other product) cassette, and any other expressed genes on the plasmid. Codon optimization of the heterologously-derived genes (such as the genes encoding antibiotic resistance genes, and the recombinant production genes, such as genes in the ethanologenic cassette) was conducted using the software Gene Designer (DNA 2.0, Menlo Park, Calif.), guided by the Cyanobacterium ABICyanol codon usage table derived from ribosomal proteins and highly expressed genes (such as photosynthesis genes). In particular; to improve heterologous gene expression, original sequences of interest (such as ZmPdc and SynAdh) were assessed with the online software OPTIMIZER (Puigbò P. Guzmán E, Romeu A, & Garcia-Vallvé S (2007) OPTIMIZER: a web server for optimizing the codon usage of DNA sequences, Nucleic Acids Research 35(suppl 2):W126-W131) based on the codon-usage table derived from ABICyanol genome. The pre-optimized sequences were further modified with Gene Designer 2.0 to ensure that their codon adaptation index (CAI) (Sharp PM & Li W-H (1987) The codon adaptation index-a measure of directional synonymous codon usage bias, and its potential applications. Nucleic Acids Research 15(3):1281-1295) and effective number of codons (ENc) (Wright F (1990) The effective number of codons used in a gene. Gene 87(1):23-29) match those of highly expressed genes (such as ribosomal proteins) in the ABICyanol genome, and that there is no site of restriction endonucleases bioinformatically and biochemically identified from the ABICyanol strain. The resulting improved sequences were further modified and optimized to avoid the presence of the following: 1) any known or predicted putative Cyanobacterium ABICyanol endonuclease restriction sites (AvaI, BsaHI, KasI, XhoI etc.); 2) internal Shine-Dalgarno sequence and RNA destabilizing sequences; 3) internal terminator sequence; 4) repeat sequence (>10 bp) (Welch et al., PLoS One 4, e7002; 2009; and Welch et al., Journal of the Royal Society; Interface 6 (Suppl 4), S467-S476; 2009).

The GC% of the optimized antibiotic resistance genes decreased from 40-53% to 33-40%, which is similar to that of the cyanobacterial strain Cyanobacterium ABICyanol coding genes (about 36% on average). The codon adaptation index (CAI) of the codon-optimized antibiotic resistance genes is significantly improved from less than 0.4 to greater than 0.7, which is similar to that of ABICyanol native genes.

Example 15

Construction of Ethanologenic Cassette

As the GC content of the ABICyanol genome is rather low (ca. 36%), the ethanologenic gene cassette was codon-optimized for ABICyanol. Basically, two different versions were used i) a maximal codon-optimized gene cassette hereinafter referred as to pdcopt1-synadhopt1 iii) another maximal codon-optimized gene cassette, hereinafter referred as to pdcopt3-synadhopt3. The pdc genes were derived from the Zymomonas mobilis pdc and the adh genes from the Synechocystis adh. Optimization of the opt1 version was "manually codon optimized by replacing all rare codons for one amino acid were by the most frequently occurring codon for that aa—based on the ABICyanol codon usage The ethanologenic gene cassette opt3 was optimized using a two-step process which involved two programs (Optimizer and GENE designer DNA 2.0). which led to "less drastic codon-optimization"—which rather reflects the codon-usage of ABICyanol Example 16

Construction of Ethanologenic Plasmid Vectors for Transformation of ABICyanol

The table below lists several plasmids that were prepared based on the endogenous 6.8 kb plasmid from Cyanobacterium ABICyanol. These plasmids contain various configurations of ethanologenic cassettes, having a gene encoding PDC and a gene encoding ADH. Various promoters, as listed below, were used. Also, the genes were optimized for expression in ABICyanol by modifying the DNA content without modifying the protein sequence. Different origins of the genes are also noted. The ethanol production for cultures harboring the plasmids is indicated in the third column.

TABLE 7

Plasmids for Transformation of ABICyano1 with the Ethanologenic Cassette and Demonstration of Ethanol Production in ABICyano1 (in GC vials) and plasmids used for transformation of ABICyano1

| Plasmid No. | Construct | % EtOH/OD*d (GC Vial) |
|---|---|---|
| pRL528 | Helper plasmid for conjugal transfer, M. AvaI, M. AvaII (Elhai & Wolk, 1988) | Used for conjugation |
| TK225 | pABICyano1-6.8::PnirA$_{ABICyano1}$-PDC(opt1)-synADH(opt1)-Prbc$_{ABICyano1}$-Km** | ~0.007 |

TABLE 7-continued

Plasmids for Transformation of ABICyano1 with the Ethanologenic Cassette and Demonstration of Ethanol Production in ABICyano1 (in GC vials) and plasmids used for transformation of ABICyano1

| Plasmid No. | Construct | % EtOH/OD*d (GC Vial) |
|---|---|---|
| TK293 | pABICyano1-6.8::PnirA$_{ABICyano1}$-PDC(opt1)-PrpsL$_{ABICyano1}$-synADH(opt1)-Prbc$_{ABICyano1}$-Km** | 0.024 |
| TK295 | pABICyano1-6.8::PnirA$_{ABICyano1}$-PDC(opt1)-PpsbA$_{ABICyano1}$-synADH(opt1)-Prbc$_{ABICyano1}$-Km** | 0.005-0.01 |
| TK229 | pABICyano1-6.8::PpetE$_{ABICyano1}$-PDC(opt1)-synADH(opt1)-Prbc$_{ABICyano1}$-Km** | 0.002 |
| TK368 | pABICyano1-6.8::PpetE$_{ABICyano1}$-PDC(opt1)- PrpsL$_{ABICyano1}$-synADH(opt1)-Prbc$_{ABICyano1}$-Km** | >>0.02 (not inducible but constitutive) |
| #1536 | pABICyano1-6.8::smtB-PsmtA(ABCC1535)-PDC(opt1)-PrpsL$_{ABICyano1}$-synADH(opt1)-Prbc$_{ABICyano1}$-Km** | ~0.006 ($Zn^{2+}$ inducible) |
| #1495 | P$_{ABICyano1}$-6.8::PnirA$_{ABICyano1}$-zmPDC$_{ABICyano1}$(opt3)-PrpsL$_{ABICyano1}$-ADH ABICyano1 (opt3)_ter-PrbcABICyano1-Km** | 0.023 |
| #1578 | pABICyano1-6.8::PnirA ABICyano1-zmPDC ABICyano1 (opt3)-dsrA-Prbc*(optRBS)-synADH\oop-Prbc ABICyano1-Km** | 0.031 |
| #1581 | pABICyano1-6.8::PnirA ABICyano1-zmPDC ABICyano1 (opt3)-dsrA-PrpsL ABICyano1-ADH ABICyano1 (opt3)_ter-Prbc ABICyano1-Km** | 0.030 |
| TK441 | pABICyano1-6.8::PpetJ ABICyano1-PDCopt1-PrpsL ABICyano1-synADHopt1-Prbc ABICyano1-Km**-oriVT | 0.017 |

Example 17

Pre-treatment of *Cyanobacterium* ABICyano1 Cells for Transformation

Many cyanobacteria produce extracellular polymeric substances (EPS), however, the appearance and composition of the EPS layer are strain-specific and dependent on environmental condition. EPS can be associated to the cell surface or released to the surrounding medium (Pereira et al., 2009. Microbiol. Rev. 33:917-941). While the released substances can in some cases easy to remove, it can be seen from LM-micrographs that the EPS attached to the cell might can represent a major barrier for transformation (FIG. 1B).

The *Cyanobacterium* sp. ABICyano1 strain was stained for EPS using scribtol black (drawing Ink for calligraphy, Pelican). This stain cannot penetrate EPS. The cells stained with the dye have a wide white/yellowish layer around the cells. (FIG. 1B).

The *Cyanobacterium* sp. ABICyano1 has a significant layer of EPS outside the cell. This layer may decrease or hamper the ability for the cell to accept foreign DNA during the conjugation process for transformation. The following method was used to decrease the excess extracellular (EPS) layer prior to conjugation. The method involves several steps: treatment of cells with N-acetylcysteine (NAC); washing steps that utilize NaCl; a treatment with lysozyme and subsequent washing; followed by the conjugation procedure.

200 ml of an exponentially growing culture ($OD_{750nm}$>0.5<1) was incubated with N-acetylcysteine (NAC) for 2 days at 16° C. (end concentration: 0.1 mg/ml) without shaking. This pre-treatment was followed by several steps to degrade the EPS and to weaken the cell wall: the pretreated culture was pelleted at 4400 rpm and washed with 0.9% NaCl containing 8 mM EDTA.

For further treatment with lysozyme the cell pellet was resuspended in 0.5 M sucrose and incubated 60 minutes at room temperature (RT) with slow shaking (85 rpm). Then, cells were centrifuged and resuspended in 40 ml of a solution containing 50 mM Tris (pH 8.0), 10 mM EDTA (pH 8.0), 4% sucrose, and 20-40 µg/ml lysozyme. After incubation at RT for 10-15 minutes, cells were centrifuged and washed 3 times using different washing solutions. i) with 30 mM Tris containing 4% sucrose and 1 mM EDTA, ii) with 100 mM Tris containing 2% sucrose and iii) with BG11 medium All centrifugation steps before lysozyme treatment were performed at 4400 rpm for 10 mm at 10° C., all centrifugations after the lysozyme treatment were performed at 2400 rpm for 5 minutes at 4° C. Resuspended cells were used for conjugation.

Example 18

Transformation of Pre-treated *Cyanobacterium* Strain ABICyano1 using Conjugation Gene transfer to ABICyano1 was performed using conjugation. The generated plasmids with oriVT were used for conjugation. The shuttle vectors could be successfully transformed into ABICyano1 following a modified conjugation protocol which includes, as critical step, the pre-treatment of ABICyano1 to reduce its EPS layer as described in Example 27, above. Briefly, pretreatment of ABICyano1 with N-Acetylcysteine fir at least 2 days, followed by treatment with lysozyme, respectively, led to the generation of ABICyano1 transformants.

Triparental mating, was performed as follows. *E. coli* strain J53 bearing a conjugative RP4 plasmid and *E. coli* strain HB101 bearing the cargo to be introduced into ABICyano1 and the pRL528 helper plasmid (for in vivo methylation) were used. *E. coli* strains were grown in LB broth supplemented with the appropriate antibiotics overnight at 37° C. with shaking at 100 rpm. An aliquot of 3-5 ml of each culture was centrifuged, washed twice with LB medium and resuspended in 200 µl LB medium. Subsequently, the *E. coli* strains were mixed, centrifuged and resuspended in 100 µl BG11 medium. 200 ml of exponentially growing cyanobacterial culture ($OD_{750nm}$>0.5<1) was centrifuged (3000 rpm, 10 minutes), pretreated to degrade the EPS layer as described above, and subsequently washed and resuspended in 400 µl BG11 culture medium containing Tris/sucrose buffer (described above). A 100 µl aliquot of resuspended cyanobacterial and *E. coli* cultures was mixed and applied onto a membrane filter (Millipore GVWP, 0.22 µm pore size) placed on the surface of solid BG11 medium supplemented with 5% LB. Petri dishes were incubated under dim light (5 µmol photons/m2/s1) for 2 days. Cells were then resuspended in fresh BG11 medium and plated onto selective medium containing 10 and 15 µg/ml kanamycin, respectively. The following selection conditions were used: light intensity approximately 20-40 µmol photons/$m^2$/sec at a temperature of approximately 28° C. Transformants were visible after approximately 10-14 days. The transformant colonies were then plated on BG11 medium containing 15 µg/ml kanamycin and then stepwise transferred to higher kanamycin concentrations (up to kanamycin 60 µg/ml) to aid in the selection process.

Example 19

Electro-Transformation of *Cyanobacterium* strain ABICyano1

Although the transformation of *Cyanobacterium* strain ABICyano1 has been performed using conjugation, for the most part, electroporation can also be used for successful transformation using e.g. the same plasmids as for the conjugation, however, so far, with lower efficiency.

As for the conjugation protocol, strain-specific adaptations of standard electroporation procotols need to be made, in particular to avoid DNA digestion by endogenous restriction enzymes and to allow DNA entry through the EPS layer. To achieve successful electroporation, DNA is protected against endogenous restriction enzymes by methylation and cells are pretreated prior to electroporation with positively charged polyaminoacids such as Poly-L-lysine hydrobromide or Poly-L-ornithine hydrochloride or combinations thereof, in particular Poly-L-lysine hydrobromide in order to increase the DNA uptake efficiency.

In particular, 100 ml of exponential growing ABICyano1 cultures (corresponding to a cell density of approx $2 \times 10^7$ cells/mL), were harvested, washed and resuspended in 0.9% NaCl containing 25 mM Tris-HCl (pH 8.0). Poly-L-lysine hydrobromide was added at a final concentration of 50 µg/ml to the cells. Cells were incubated for several hours or overnight before electroporation.]

In a typical procedure, 50 mL of Poly-L-lysine hydrobromide treated ABICyano1 cells, are harvested and treated with 30 ml ice-cold BG11 containing 6% DMSO. After incubation on ice for 20 min, cells are harvested and frozen in liquid nitrogen for 15 min. These pre-frozen cells are thawed by adding 15 mL ice-cold buffer containing 1 mM HEPES (pH7.5) 0.2 mM K2HPO4 and 0.2 mM MgCl2. The cells are washed sequentially once more with 1 mM HEPES and ETMT buffer containing. 0.1 mM HEPES, 0.2 mM $K_2HPO_4$ and 0.2 mM $MgCl_2$. The cells are harvested by centrifugation at 15000 g for 5 minutes. All of the washes and centrifugations are carried out on ice or in a pre-chilled centrifuge (4° C.). For each electroporation procedure 3 µg methylated DNA is added to 100 µl concentrated cells. Cells are electroporated in a cuvette with a 2-mm gap between the electrodes and pulsed once in a Gene Pulse X-cell (Bio-Rad) using exponential decay protocol (electric field strength 8 kV/cm, capacitance 25 µF; resistance of 400 ohms, time of approximately 8-9 ms), After electroporation, 1-2 ml BG11 medium were immediately added to the cyanobacterial suspension, which was subsequently transferred to a 50 ml flask containing 15 ml fresh BG11 medium. After incubation for 1-2 days under normal light (30-40 µmol photons/m$^2$/s$^1$) with gentle shaking at 30° C., recovered cultures were centrifuged, resuspended in 500 µl BG11 medium and placed onto selective media (BG11 containing 20 µg/ml Km or Spectinomycin of 40-60 µg/ml).

Example 20

Confirmation of Transformants using Colony PCR and Plasmid Rescue

Colony PCR methods were used to confirm transformants. For this procedure, three primer sets were used, which were directed against parts of the $p_{ABICyano1}$-6.8 shuttle vectors to detect specific fragments of the shuttle vector. Transformants which were proven to be correct by colony PCR were analyzed further by plasmid rescue. For plasmid rescue a 25 ml liquid culture was subjected to DNA isolation, 500 ng-1 µg of isolated DNA from transformants ABICyano1 containing the transformed plasmids were re-transformed into *E. coli* resulting usually in approx. 10-20 transformants per transformation. Plasmid DNA of 10 *E. coli* colonies was isolated and analyzed by PCR using specific primers for the transformed plasmids. The plasmid DNA was further analyzed with specific restriction enzymes and sequenced, respectively.

Example 21

Identification of Potential Metal Inducible Promoters Endogenous to *Cyanobacterium* ABICyano1

RNA-Seq experiments were conducted in order to identify potential metal-ion inducible promoters in ABICyano1. The upstream regions of metal ion responding/inducible genes in ABICyano1, listed in the below, were selected to drive/control expression of the ethanologenic gene cassette in ABICyano1. The nucleic acid sequences are given in the Figures as listed in this table. All of the below potential inducible promoters are prime candidates for the transcriptional control of the at least one recombinant gene. Especially, petJ was characterized in more detail. Expression of petJ is tightly repressed under high copper (1-3 µM) conditions and induced under copper depletion (FIG. 52A). ABICyano1: TK441 hybrids carrying the endogenous petJ promoter upstream of an ethanologenic gene cassette, produce the same amount of ethanol (%v/v) under copper depletion conditions compared to an ABICyano1: TK293 hybrid strain grown in marine BG11 (FIGS. 52A and 52B).

The plasmid map of plasmid TK441 is shown in FIG. 53 and its nucleic acid sequence is depicted in FIG. 54.

| gene_id | DNA Sequence | homology | Inducible by |
|---|---|---|---|
| ABICyano1_orf0128 | FIG. 51A | hypothetical protein | nickel |
| ABICyano1_orf1486 | FIG. 51B | putative nickel-containing superoxide dismutase | nickel |
| ABICyano1_orf3164 | FIG. 51C | ferrochelatase | nickel |
| ABICyano1_orf3293 | FIG. 51D | hypothetical protein L8106_16134 | nickel |
| ABICyano1_orf3621 | FIG. 51E | hypothetical protein Cyan7822_1798 | nickel |
| ABICyano1_orf3635 | FIG. 51F | carbohydrate-selective porin | nickel |
| ABICyano1_orf3858 | FIG. 51G | manganese/iron superoxide dismutase-like protein | nickel |
| ABICyano1_orf1071 | FIG. 51H | Mn transporter | zinc |
| ABICyano1_orf1072 | FIG. 51I | ABC transporter family protein | zinc |
| ABICyano1_orf1074 | FIG. 51J | ABC 3 transport family | zinc |
| ABICyano1_orf1075 | FIG. 51K | No hits found -I- KEGG: -I- CyanoBase | zinc |

-continued

| gene_id | DNA Sequence | homology | Inducible by |
|---|---|---|---|
| ABICyano1_orf1542 | FIG. 51L | hypothetical protein PCC8801_4423 | zinc |
| ABICyano1_orf1823 | FIG. 51M | RNA polymerase sigma factor | zinc |
| ABICyano1_orf1824 | FIG. 51N | No hits found -\|- KEGG: -\|- CyanoBase | zinc |
| ABICyano1_orf3126 | FIG. 51O | Metallothionein | zinc |
| ABICyano1_orf3389 | FIG. 51P | HtrA2 peptidase | zinc |
| ABICyano1_orf0221 | FIG. 51Q | CopA family copper-resistance protein | copper |
| ABICyano1_orf0222 | FIG. 51R | copper resistance B | copper |
| ABICyano1_orf0223 | FIG. 51S | No hits found -\|- KEGG: -\|- CyanoBase | copper |
| ABICyano1_orf0316 | FIG. 51T | hypothetical protein CY0110_11047 | copper |
| ABICyano1_orf3232 | FIG. 51U | cation-transporting ATPase | copper |
| ABICyano1_orf3461 | FIG. 51V | petJ | copper |
| ABICyano1_orf3749 | FIG. 51W | conserved hypothetical protein | cobalt |

Example 22

Construction and Transformation for Integration into the Chromosomal DNA of *Cyanobacterium* ABICyanol Integration of target genes into the genome of ABICyanol will be conducted with the help of plasmid TK471, which was generated to integrate a kanamycin resistance gene in the pilT/pilC region, resulting in a pilT/pilC minus strain. The TK180 based plasmid contains a pilT flanking region of ABI-Cyanol upstream as well as a pilC flanking region of ABICyanol downstream of the kanamycin resistance gene to generate a double crossover event in ABICyanol. Moreover, sacB from *Bacillus subtilis* is encoded on TK471. Expression of sacB in gram negative bacteria grown on media supplemented with sucrose is toxic for the bacteria. Hence, only the bacteria which lose the sacB gene are able to grow on sucrose plates. ABICyanol: TK471 hybrids grown on sucrose/kanamycin plates are therefore forced to induce homologous recombination to flip the kanamycin resistance gene into the genome and to lose the plasmid TK471 due to the presence of the sacB gene. In order to integrate the EtOH cassette into the genome, plasmid TK471 will be modified carrying the EtOH cassette adjacent to the Km gene (also within the pilT and pilC flanking region).

Figure 26:
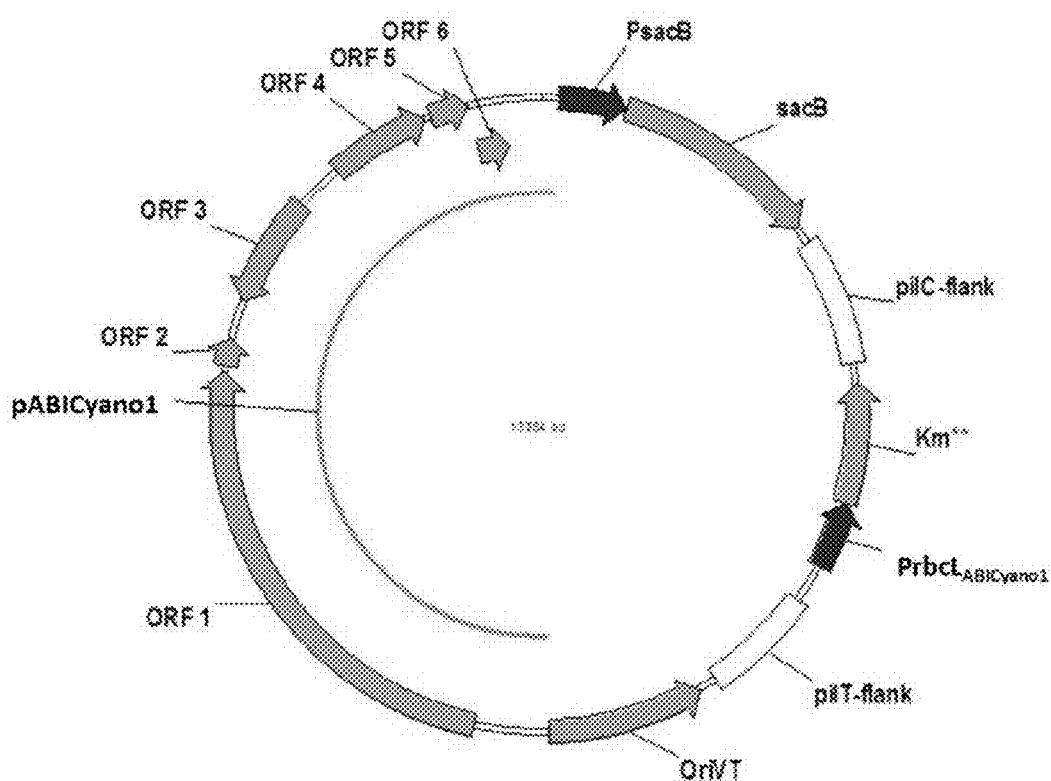
FIG. 26 is a map of the plasmid construct TK471. Its nucleotide sequence (SEQ ID NO: 18) is depicted in FIG. 27 including the annotation of the genes and promoters done with the program vector NTI.
Figure 28:
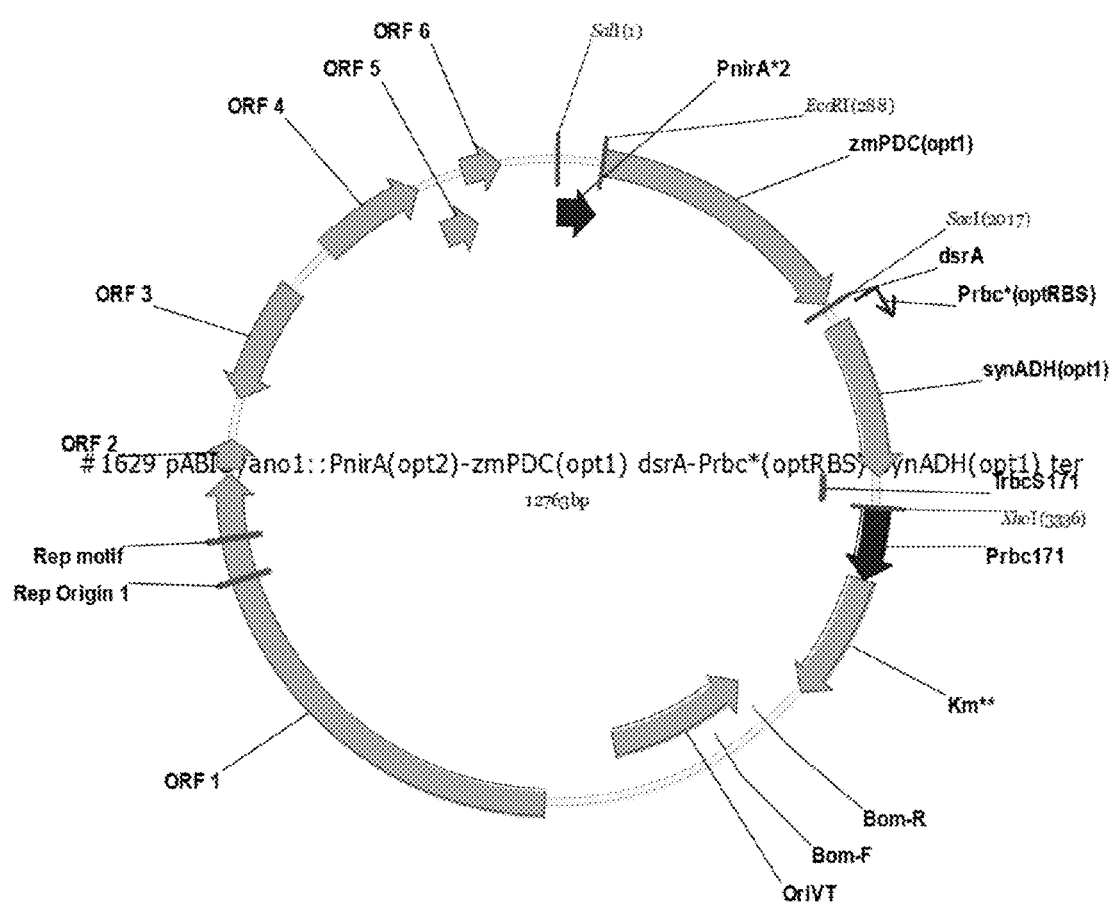
FIG. 28 is a map of the plasmid construct #1629 including the endogenous nirA promoter from ABICyanol with an improved ribosomal binding site in comparison to the respective native promoter. This modified promoter controls the transcription of a pdc gene, which can be codon improved, The nucleotide sequence (SEQ ID NO: 19) of the plasmid is depicted in FIG. 29 including the annotation of the genes and promoters done with the program vector NTI.
Figure 30:
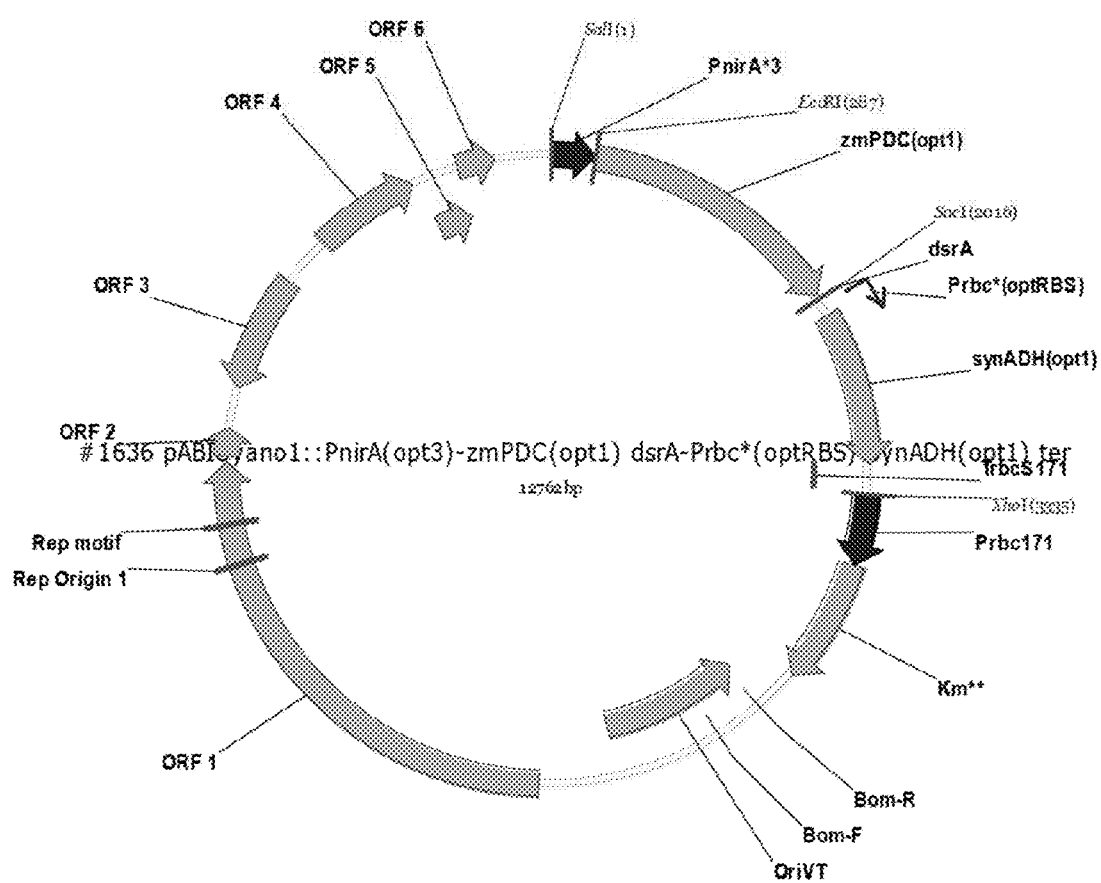
FIG. 30 is a map of the plasmid construct #1636 including the endogenous nirA promoter from ABICyanol with an improved binding site for the regulators NtcA and NtcB and an improved TATA box in comparison to the respective native promoter. This modified promoter controls the transcription of a pdc gene, which can be codon improved. The nucleotide sequence (SEQ ID NO: 20) of the plasmid is depicted in FIG. 31 including the annotation of the genes and promoters done with the program vector NTI.
Figure 32:
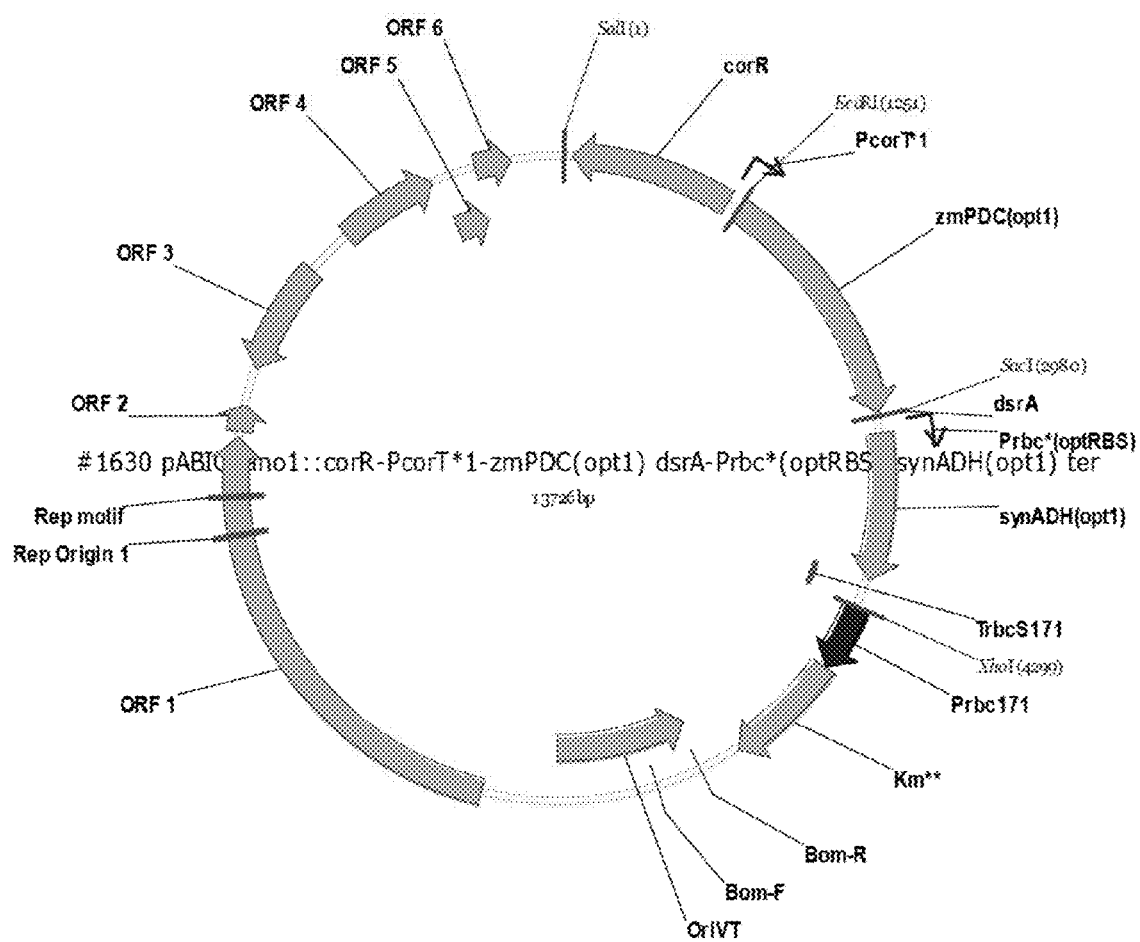
FIG. 32 is a map of the plasmid construct #1630 including the endogenous corT promoter from *Synechocystis* PCC6803 with an improved ribosomal binding site in comparison to the respective native promoter. This modified promoter controls the transcription of a pdc gene, which can be codon improved. The nucleotide sequence (SEQ ID NO: 21) of the plasmid is depicted in FIG. 33 including the annotation of the genes and promoters done with the program vector NTI.
Figure 34:
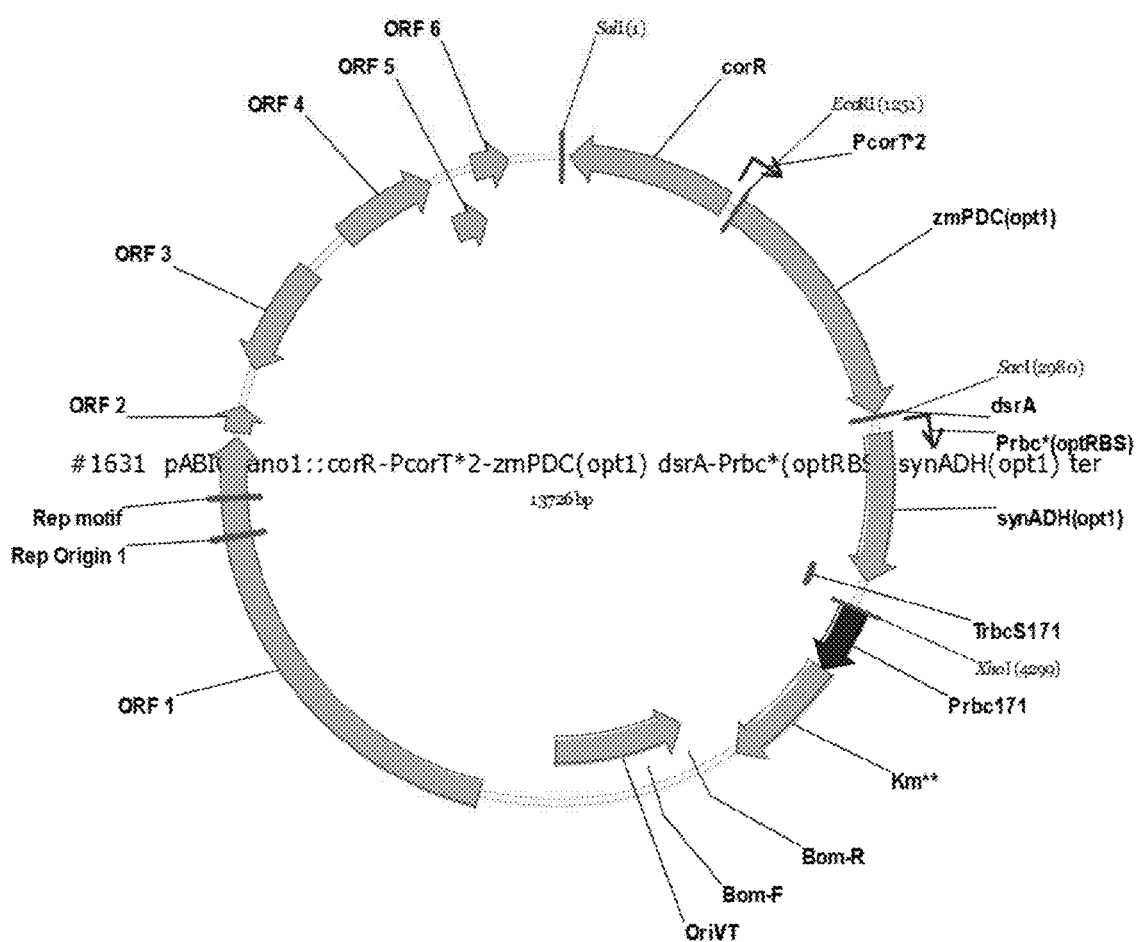
FIG. 34 is a map of the plasmid construct #1631 including the endogenous corT promoter from *Synechocystis* PCC6803 with an improved TATA box in comparison to the respective native promoter. This modified promoter controls the transcription of a pdc gene, which can be codon improved. The nucleotide sequence (SEQ ID NO: 22) of the plasmid is depicted in FIG. 35 including the annotation of the genes and promoters done with the program vector NTI.
Figure 36:
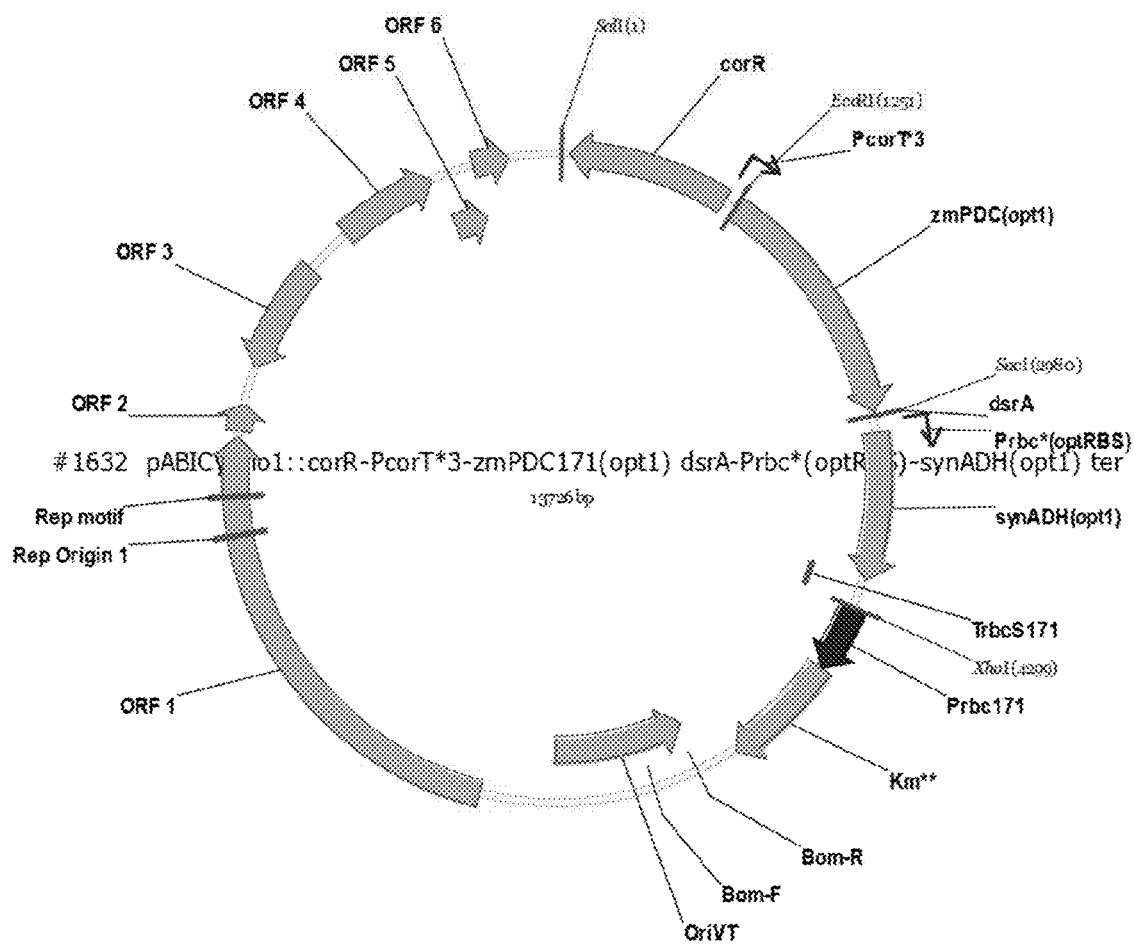
FIG. 36 is a map of the plasmid construct #1632 including the endogenous corT promoter from *Synechocystis* PCC6803 with an improved TATA box and ribosomal binding site in comparison to the respective native promoter. This modified promoter controls the transcription of a pdc gene, which can be codon improved. The nucleotide sequence (SEQ ID NO: 23) of the plasmid is depicted in FIG. 37 including the annotation of the genes and promoters done with the program vector NTI.
Figure 38:
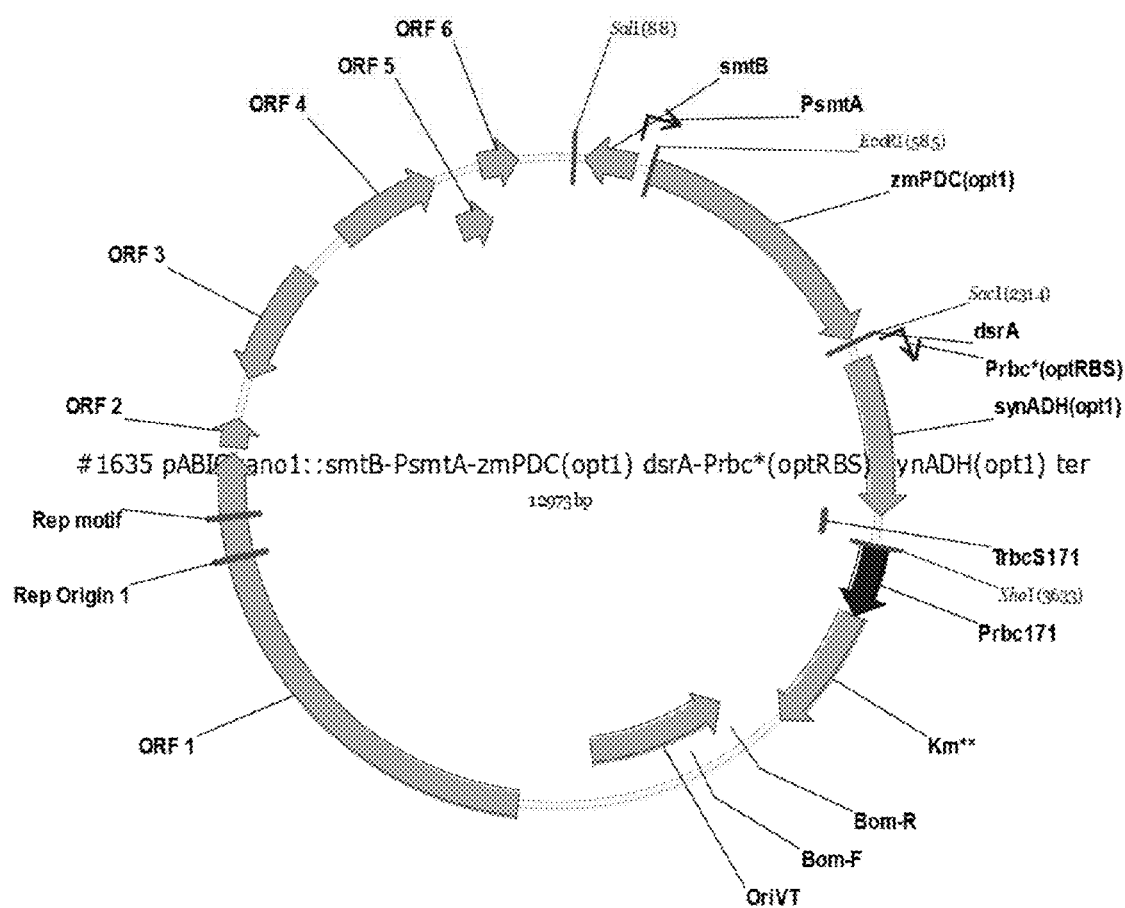
FIG. 38 is a map of the plasmid construct if #1635 including the native smtA promoter from Synechococcus PCC7002. This modified promoter controls the transcription of a pdc gene, which can be codon improved. The nucleotide sequence (SEQ ID NO: 24) of the plasmid is depicted in FIG. 39 including the annotation of the genes and promoters done with the program vector NTI.
Figure 40:
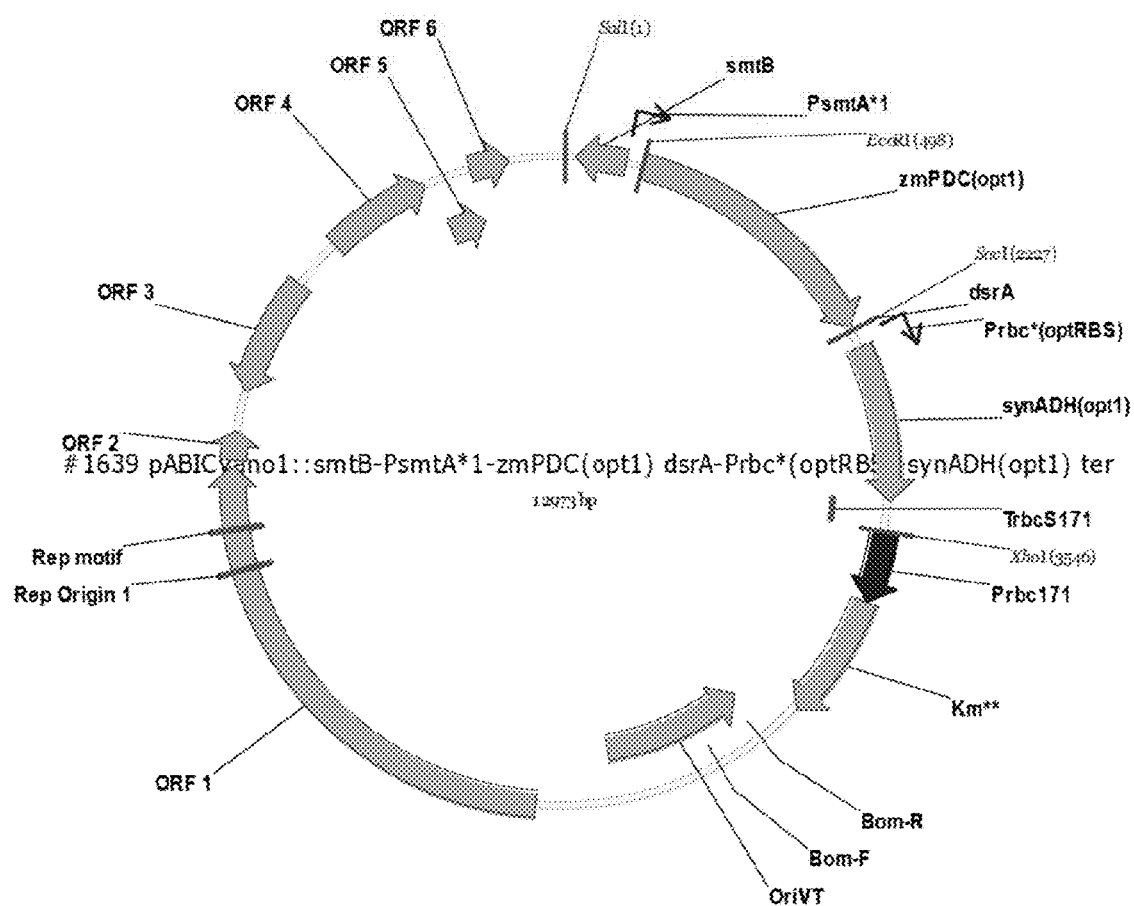
FIG. 40 is a map of the plasmid construct #1639 including a modified smtA promoter from Synechococcus PCC7002 which includes a modified RBS in comparison to the native promoter. This modified promoter controls the transcription of a pdc gene, which can be codon improved. The nucleotide sequence (SEQ ID NO: 25) of the plasmid is depicted in FIG. 41 including the annotation of the genes and promoters done with the program vector NTI.
Figure 42:
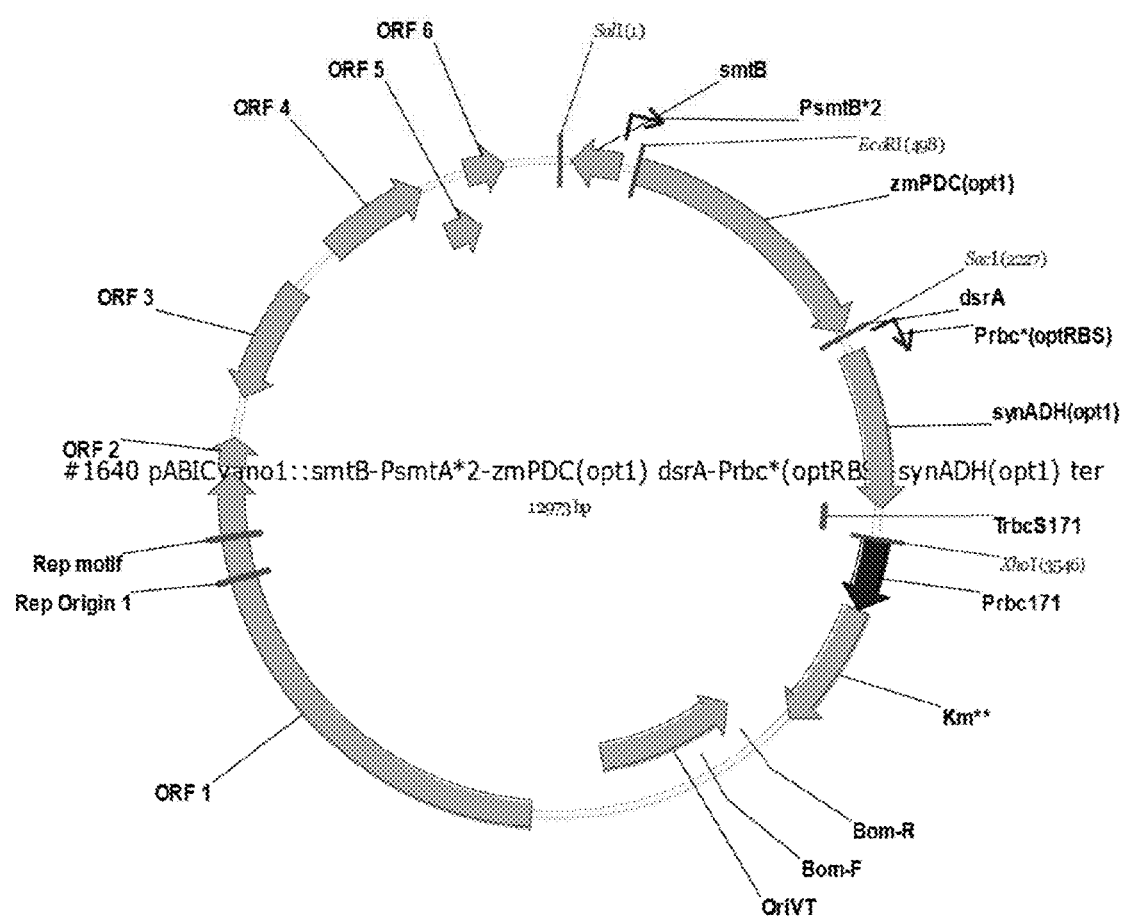
FIG. 42 is a map of the plasmid construct #1640 including a modified smtA promoter from Synechococcus PCC7002 which includes another modified RBS in comparison to the native promoter. This modified promoter controls the transcription of a pdc gene, which can be codon improved. The nucleotide sequence (SEQ ID NO: 26) of the plasmid is depicted in FIG. 43 including the annotation of the genes and promoters done with the program vector NTI.

The plasmid map of plasmid TK471 is shown in FIG. 26 and its nucleotide sequence including the annotations of the genes and regulatory elements in shown in FIG. 27.

Example 23

Production of Ethanol from Genetically Enhanced *Cyanobacterium* ABICyanol

The transformed cells containing the ethanologenic cassettes were then grown under inducing conditions, (in marine BG11 medium), and tested for ethanol production ABICyanol harboring the plasmids TK293 and TK225 were found to produce 0.086% (v/v) and 0.019% (v/v) ethanol, respectively, over a 50 hour period in an online GC vial system (FIG. 56A). Cultivation of ethanologenic ABICyanol cells was performed in 0.5 L round PBR glass vessels containing marine BG11 culture medium. pH is controlled via CO2 flux. In such an experiment ethanologenic ABICyanol, harboring the ethanologenic plasmid TK225, was characterized. Cell growths and ethanol production is shown in FIG. 57 Similarly, ABICyanol harboring TK293 was characterized with respect to EtOH productivity (FIG. 58).

Example 24

Characterization of Different Ethanologenic Strains of ABICyanol Harboring an Ethanologenic Cassette Under the Control of Different Inducible Native and Modified Promoters Genetically enhanced *Cyanobacterium* ABICyanol strains including extrachromosomal plasmids all harboring a pdc gene under the transcriptional control of either the native nirA promoter or modified variants thereof, were cultured in 0.51 photobioreactors. These strains included the plasmids #1606, #1629 and #1636, which were already described earlier. FIG. 47 shows the ethanol production normalized to the growth ($OD_{750nm}$) determined by the CG vial method for ABICyanol strains transformed with the plasmids #1606 (pdc gene under the control of the native PnirA), plasmid #1629 (pdc gene under the control of a modified variant of PnirA with changes in the RBS) and plasmid #1636 (pdc gene under the control of a modified variant of PnirA with changes in the operator sequence and the TATA box) for a period of time of at least 20 days after induction was realized by transition of the pre-culture to usual mBG11 medium (containing nitrate for induction) at the beginning of the cultivation experiment. The graph clearly shows that the normalized ethanol production is higher for the strains including the plasmids with the modified promoters. FIGS. 48A and 48B show the specific activity of PDC enzyme and ADH enzyme during the course of the above mentioned cultivation. It is evident that the inducible modified nirA promoter variants PnirA*2 (#1629) and PnirA*3 (#1636) result in a higher activity of PDC enzyme compared to the native promoter (#1606).

FIG. 49 shows the ethanol production normalized to the growth ($OD_{750nm}$) determined by the CC vial method for ABICyanol strains transformed with the plasmids #1606 (pdc gene under the control of the native PnirA), plasmid #1631 (pdc gene under the control of a modified PcorT with modifications in the TATA box) and plasmid #1632 (pdc gene under the control of a modified PcorT with modifications in the TATA box and the RBS) for a period of time of at least 20 days cultured in 0.51 photobioreactors. The ethanol production of the strain transformed with the plasmid containing the native PnirA with pdc gene is comparable to the ethanol production of the strain containing the plasmid with the pdc gene controlled by the modified corT promoter variants PcorT*3 (#1632) with modifications in the TATA box and RBS, whereas the ethanol production of the strain containing the plasmid with PcorT with modifications only in the TATA box PcorT*2 (#1631) exhibits a lower ethanol production rate, especially in the time period starting from the $10^{th}$ day of cultivation on.

FIGS. 50A and 50B show the specific activity of PDC enzyme and ADH enzyme during the course of the above mentioned cultivation. The strains with the native PnirA as well as the PcorT with modifications in the TATA box and the RBS show higher reactivity of PDC enzyme than the other strain.

FIG. 50C to 50D show the ethanol production rates of the ABICyanol strains transformed with the plasmids '1535, #1539 and #1540 including the native PsmtA promoter from *Synechococcus* PCC7002 as well as modified versions of PsmtA. It can clearly be seen that all promoters are repressed in the absence of Zn2+ and can be induced upon addition of Zn2+.

Example 25

Determination of Ethanol Production using Headspace Gas Chromatography with Flame Ionization Detection Experimental Setup GC headspace measurements are performed on a Shimadzu GC-2010 gas chromatograph with Flame Ionization Detector. The instrument is connected in-line with a Shimadzu PAL LHS2-SHIM/AOC-5000 autosampler, comprising a gas-tight syringe for transfer of headspace aliquots from the culture samples to the analytical unit. Culture amples in the autosampler are illuminated with NARVA fluorescence lamps (BIO vital LT24WT5/958HQ) of 24 Watt. Mixing of the samples in the autosampler is accomplished with the IKA RO5 power magnetic stirrer. A heating mat KM-SM3 of Mohr & Co in combination with the JUMO dTRON 316 temperature regulator is used for thermostatisation of the culture samples in the autosampler. The gas chromatograph is connected to helium carrier gas as well as hydrogen and artificial air as fuel gas and oxidizer gas, respectively, for the flame ionization detector. Oxidizer air is generated with the generator WGAZA50 from Science Support. The gas chromatograph is equipped with a FS-CS-624 medium bore capillary with a length of 30 m, internal diameter of 0.32 mm and film thickness of 1.8 µm from the GC supplier Chromatographic Service GmbH.

Sample Preparation:

Hybrid clones are raised on BG11 plates containing inducing agent or without supplementation of the inducing agent. A sample is prepared by scratching an individual clone from the BG11 plate and resuspending the corresponding clone in marine BG11 liquid medium (mBG11). Addition of inducing agent triggers ethanol production in the sample by induction of the inducible promoter driving over-expression of the recombinant pyruvate decarboxylase and alcohol dehydrogenase gene. The cell density in the sample is then adjusted to an optical density at 750 nm of approximately 1.0. Two millilitres of sample are then filled into a gas-tight GC vial for headspace autosampling with a nominal volume of 20 millilitres. The sample headspace is supplemented with 3 millilitres $CO_2$. The vial is tightly closed with a cap with self-sealing silicone septum and placed into the autosampler rack which is temperature controlled at a given temperature for example 37° C.

If necessary, reference samples can be prepared as 2 millilitre aliquots with 0.005, 0.01, 0.02, 0.05, 0.1, 0.2, 0.5, 1, 2, 5 and 10 mg/ml ethanol in 35 psu sodium cloride. Reference samples are placed into the same 20 ml sample containers with self-sealing silicon septum caps for headspace autosampling. For each reference sample at least six measurements are applied. After the measurements, the resulting peak areas of the reference samples are used for generating two calibration curves, the first in the concentration range from 0.005 to 0.5 mg/ml ethanol and the second one for the concentration range from 0.5 to 10 mg/ml ethanol. The calibration curves have to fulfil linearity.

General Procedure:

The sample incubation temperature in the autosampler is adjusted to a given temperature for example 37° C. The illumination is set at 90 µE to 150 µE, preferably 100 µE. The magnetic stirrer is configured for interval mixing of the samples, with cycles of 2 minutes mixing at 400 rpm, followed by 90 minutes without mixing. An automated process follows, wherein after given periods aliquots of 500 µl of the headspace of the samples are automatically drawn with the gas-tight headspace syringe and injected via the injection port into the gas chromatograph for analysis. Before each headspace autosampling, the mixing is changed for 10 min to continuous mixing with 750 rpm at 37° C. incubation temperature. The syringe temperature is set at 70° C. The fill speed is 250 µl per second, following an initial lag time of 1 second after the septum of the samples has been pierced by the syringe needle. The injection of the aliquot into the gas chromatograph happens with an injection speed of 500 µl per second. Afterwards, the syringe flushes for 3 minutes with air to prevent sample carryover between two injections. The gas chromatograph runtime is 4 minutes and 30 seconds. The injection temperature on the gas chromatograph is 230° C. The column temperature is 60° C. Detection is accomplished with the flame ionization detector at 250° C. process temperature. The makeup gas is nitrogen at 30 ml per minute, the fuel gas is hydrogen at 35 ml per minute and the oxidizer gas is artificial air at 400 ml per minute.

After the final measurement, the final optical density at 750 nm of the samples is measured and an average cell density for each sample is determined by calculating the arithmetic mean of the optical density at the starting point and the optical density at the end point of the process divided by two. Afterwards, the average ethanol production rate per cell density is calculated.

Concrete Examples:

Two kinds of measurements were performed. a) GC online measurements (applied for clone testing and short-term characterizations, single GC measurements (applied for measurements of EtOH production for PBR cultivations)

In a typical experiment for the quantitative determination of acetaldehyde and/or ethanol content in growth media by headspace gas chromatography (GC), the ethanol production of the respective cyanobacterial culture has to be induced 1-3 days prior to the GC measurement to trigger the overexpression of the pdc and Synadh production genes. For instance, to repress the PnirA promoter (e.g. in TK225, TK293) hybrids were grown in mBG11 (artificial seawater) depleted of $NO_3$, with 2 mM Urea and 2 mM $NH_4Cl$. To induce the nirA promoter, cells were transferred prior to the GC measurement into mBG11 (artificial seawater salts) with nitrate. For GC measurements cells were harvested from liquid cultures by centrifugation and then resuspended in the appropriate fresh marine medium ensuring that the induction conditions were maintained. The medium was timber supplemented with 50 mM TES, pH 7.3 and 20 mM $NaHCO_3$. The sample was adjusted to an $OD_{750nm}$. 1.2 mL samples were then aliquoted per 20 mL GC vial loaded with 3 ml pure $CO_2$. The tightly closed GC vials were placed onto an illuminated (150 µE $m^{-2}$ $s^{-1}$) headspace auto sampler and were analyzed on the same day on a Shimadzu GC-2010 gas chromatograph equipped with a medium-bore capillary column (FS-CS-624, length 30 m; I.D. 0.32 mm; film 1.8 µm) and a flame ionisation detector.

The culture was stirred once in an hour under constant light (approximately 100 µE) in GC vials (temperature 35° C.) on the GC sampling tray. Acetaldehyde and ethanol content were measured online at four different time points during 18-24 hours. Measurements could be extended to 72 hours.

After completion of the GC measurements, the final $OD_{750nm}$ was determined to normalise the ethanol production rate according to the average $OD_{750nm}$ of the bacterial sample. The average $OD_{750nm}$ was calculated as the arithmetic mean of the OD750nm at the time of sample preparation and the $OD_{750nm}$ after completion of the GC measurement.

The results of the ethanol quantitation are shown in FIG. 56. Briefly, ABICyanol with TK293 produced a high amount of ethanol (~0.02% (v/v)/OD*d), which is 2-4 fold higher than with plasmids TK225/TK295.

Example 26

Transformation of a Modified Vector Based on the Endogenous 6.8 kb Plasmid from *Cyanobacterium* to Other Cyanobacterial Cells The modified plasmid vector based on the endogenous 6.8 kb plasmid backbone from *Cyanobacterium* ABICyanol, in addition to being useful for transformation to other *Cyanobacterium* host cells, can also be used to transform other cyanobacterial species. In particular, it was shown that a shuttle vector containing the 6.8 kb endogenous plasmid from *Cyanobacterium* sp. ABICyanol including a kanamycin resistance cassette (KmR) and the oriVT for replication in *E. coli* could be transformed into *Synechococcus* PCC7002 by natural uptake.

In a prophetic example, the modified vectors such as TK293, and #1536 as described herein, each containing an ethanologenic cassette and an antibiotic resistance gene under the transcriptional control of an ABICyanol and/or an endogenous promoter of *Synechococcus* PCC7002, respectively, are transformed to *Synechococcus* PCC7002 using electroporation, conjugation or natural uptake. The transformants are selected for on an agar plate using the appropriate antibiotic. The putative transformants are they confirmed by PCR analysis. Positive cells are streaked and scaled up to grow as a culture. Ethanol production is measured. By use of this method, ethanol is produced in the transformed. cells.

Although the present invention has been described in considerable detail with reference to certain embodiments thereof, other embodiments are possible. Therefore, the spirit and scope of the appended claims should not be limited to the description of the embodiments contained therein.

What is claimed is:

1. A genetically enhanced ethanologenic *Cyanobacterium* sp. ABICyanol host cell comprising *Cyanobacterium* sp. ABICyanol deposited in the American Type Culture Collection (ATCC) under ATCC accession number PTA-13311 comprising a genetically enhanced plasmid derived from a plasmid that is endogenous to *Cyanobacterium* sp. ABICyanol, and wherein said plasmid comprises a heterologous alcohol dehydrogenase gene and a heterologous pyruvate decarboxylase gene, and
   wherein said alcohol dehydrogenase gene is operably linked to a constitutive promoter, and
   wherein said pyruvate decarboxylase gene is operably linked to an inducible promoter, and
   wherein said *Cyanobacterium* sp. ABICyanol can tolerate salinities ranging up to about 35 practical salinity units, and
   can tolerate temperatures ranging up to about 55 degrees Celsius, and
   can tolerate dissolved oxygen concentrations ranging up to about 1000 μmol/L, and
   can tolerate ethanol. concentrations ranging up to about one percent for 16 weeks, and
   wherein production of ethanol by said ethanologenic *Cyanobacterium* sp. ABICyanol host cell is from about 0.017 percent ethanol (vol/vol) per $OD_{750}$ per day to about 0.031 percent ethanol (vol/vol) per $OD_{750}$ per day.

2. The host cell of claim 1 wherein said constitutive promoter and said inducible promoter are endogenous to *Cyanobacterium* sp. ABICyanol.

3. The host cell of claim 1 wherein said constitutive promoter is heterologous to *Cyanobacterium* sp. ABICyanol.

* * * * *